(12) United States Patent
Freier

(10) Patent No.: US 12,180,479 B2
(45) Date of Patent: Dec. 31, 2024

(54) COMPOUNDS AND METHODS FOR MODULATING ATXN1

(71) Applicant: Ionis Pharmaceuticals, Inc., Carlsbad, CA (US)

(72) Inventor: Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 18/047,973

(22) Filed: Oct. 19, 2022

(65) Prior Publication Data

US 2024/0067962 A1 Feb. 29, 2024

Related U.S. Application Data

(63) Continuation of application No. 17/751,450, filed on May 23, 2022, now Pat. No. 11,542,504, which is a continuation of application No. PCT/US2021/030203, filed on Apr. 30, 2021.

(60) Provisional application No. 63/019,089, filed on May 1, 2020.

(51) Int. Cl.
| | |
|---|---|
| C07H 21/04 | (2006.01) |
| A61K 31/712 | (2006.01) |
| A61K 35/30 | (2015.01) |
| A61K 47/02 | (2006.01) |
| A61P 25/00 | (2006.01) |
| C12N 15/113 | (2010.01) |

(52) U.S. Cl.
CPC .......... *C12N 15/113* (2013.01); *A61K 31/712* (2013.01); *A61K 35/30* (2013.01); *A61K 47/02* (2013.01); *A61P 25/00* (2018.01); *C12N 2310/11* (2013.01); *C12N 2310/315* (2013.01); *C12N 2310/3231* (2013.01); *C12N 2310/3341* (2013.01); *C12N 2310/341* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |

(Continued)

FOREIGN PATENT DOCUMENTS

| | | |
|---|---|---|
| WO | WO 2002/058626 | 8/2002 |
| WO | WO 2004/044123 | 5/2004 |

(Continued)

OTHER PUBLICATIONS

Branch et al., "A good antisense molecule is hard to find," TIBS (1998) 23:45-50.

(Continued)

*Primary Examiner* — Kimberly Chong

(74) *Attorney, Agent, or Firm* — McNeill Baur PLLC

(57) ABSTRACT

Provided are compounds, methods, and pharmaceutical compositions for reducing the amount or activity of ATXN1 RNA in a cell or subject, and in certain instances reducing the amount of ATXN1 in a cell or subject. Such compounds, methods, and pharmaceutical compositions are useful to ameliorate at least one symptom or hallmark of a neurodegenerative disease. Such symptoms and hallmarks include gait and limb ataxia, cognitive impairments, difficulty with speaking and swallowing, atrophy of the cerebellum and brainstem in magnetic resonance imaging (MRI), neurochemical abnormalities in the cerebellum and brainstem detected via magnetic resonance spectroscopy (MRS), and death within 10-15 years of symptom onset. Such neurodegenerative diseases include Spinocerebellar ataxia type 1.

30 Claims, No Drawings

Specification includes a Sequence Listing.

(56) References Cited

U.S. PATENT DOCUMENTS

| | | |
|---|---|---|
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,691,997 B2 | 4/2010 | Khvorova et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 11,542,504 B2 | 1/2023 | Zhou |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2005/0244851 A1 | 11/2005 | Blume et al. |
| 2006/0148740 A1 | 7/2006 | Platenburg |
| 2007/0031844 A1 | 2/2007 | Khvorova et al. |
| 2008/0039618 A1 | 2/2008 | Allerson et al. |
| 2010/0190837 A1 | 7/2010 | Migawa et al. |
| 2010/0197762 A1 | 8/2010 | Swayze et al. |
| 2011/0111491 A1 | 5/2011 | Davidson et al. |
| 2013/0130378 A1 | 5/2013 | Manoharan et al. |

(56) References Cited

U.S. PATENT DOCUMENTS

| | | |
|---|---|---|
| 2014/0107330 A1 | 4/2014 | Freier et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2019/0330639 A1 | 10/2019 | Brown et al. |
| 2022/0290146 A1 | 9/2022 | Zhou |

FOREIGN PATENT DOCUMENTS

| | | |
|---|---|---|
| WO | WO 2004/047872 | 6/2004 |
| WO | WO 2012/012467 | 1/2012 |
| WO | WO 2018/154439 | 8/2018 |
| WO | WO 2021/222768 | 11/2021 |

OTHER PUBLICATIONS

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Crooke, St., et al., "Antisense Drug Technology" Second Edition, CRC Press (2008) Chapters 1-28.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Evers et al., "Targeting Several CAG Expansion Diseases by a Single Antisense Oligonucleotide" PLOS One (2011) 6: e24308.

Friedrich et al., "Antisense oligonucleotide-mediated ataxin-1 reduction prolongs survival in SCA1 mice and reveals disease-associated transcriptome profiles" JCI Insight (2018) 3: e123193.

Friedrich et al., "Antisense Oligonucleotides as a Potential Therapeutic for SCA1" Presentation for 6th Ataxia Investigators Meeting (AIM 2016) Orlando, FL (Mar. 29-Apr. 1).

Gao et al., "Antisense RNA Sequences Modulating the Ataxin-1 Message: Molecular Model of Gene Therapy for Spinocerebellar Ataxia Type 1, a Dominant-Acting Unstable Trinucleotide Repeat Disease" Cell Transplantation (2008) 17: 723-734.

Gautschi et al., "Activity of a novel bcl-2/bcl-xLbispecific antisense oligonucleotide against tumors of diverse histologic origins" J. Natl. Cancer Inst. (2001) 93:463-471.

International Search Report for PCT/US21/030203 dated Oct. 27, 2021.

Ju et al., "Beyond the glutamine expansion: influence of post-translational modifications of ataxin-1 in the pathogenesis of spinocerebellar ataxia type 1" Mol Neurobiol (2014) 50: 866-874.

Keiser et al., "RNAi Prevents and Reverses Phenotypes Induced by Mutant Human Ataxin-1" Ann Neurol (2016) 80: 754-765.

Keiser et al., "RNAi of overexpression: Alternative therapies for Spinocerebellar Ataxia Type 1" Neurobiology of Disease (2013) 56: 6-13.

Maher et al., "Comparative hybrid arrest by tandem antisense oligodeoxyribonucleotides or oligodeoxyribonucleoside methylphosphonates in a cell-free system" Nucl. Acid. Res. (1988) 16(8): 3341-3358.

O'Callaghan et al. "Antisense Oligonucleotide Therapeutic Approach for Suppression of Ataxin-1 Expression: A Safety Assessment" Mol Ther Nucl Acids (2020) 21: 1006-1016.

Ortiz et al., "Spinocerebellar Ataxia Type 1: Molecular Mechanisms of Neurodegeneration and Preclinical Studies" Adv Exp Med Biol (2018) 1049: 135-145.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Woolf et al., "Specificity of antisense oligonucleotides in vivo" PNAS (1992) 89: 7305-7309.

COMPOUNDS AND METHODS FOR MODULATING ATXN1

SEQUENCE LISTING

The present application is being filed along with a Sequence Listing in electronic format. The Sequence Listing is provided as a file entitled BIOL0355USC2SEQ.xml, created on Aug. 22, 2022, which is 3,707 KB in size. The information in the electronic format of the sequence listing is incorporated herein by reference in its entirety.

FIELD

Provided are compounds, methods, and pharmaceutical compositions for reducing the amount or activity of ATXN1 RNA in a cell or subject, and in certain instances reducing the amount of ATXN1 protein in a cell or subject. Such compounds, methods, and pharmaceutical compositions are useful to ameliorate at least one symptom or hallmark of a neurodegenerative disease. Such symptoms and hallmarks include gait and limb ataxia, cognitive impairments, difficulty with speaking and swallowing, atrophy of the cerebellum and brainstem in magnetic resonance imaging (MRI), neurochemical abnormalities in the cerebellum and brainstem detected via magnetic resonance spectroscopy (MRS), and death within 10-15 years of symptom onset. Such neurodegenerative diseases include Spinocerebellar ataxia type 1.

BACKGROUND

Spinocerebellar ataxia type 1 (SCA1) is a progressive and fatal neurodegenerative disorder that affects 1-2/100,000 individuals worldwide. SCA1 is caused by an expanded CAG repeat in the coding region of gene encoding Ataxin-1, ATXN1. Accumulation of mutant Ataxin-1 protein leads to the degeneration of Purkinje cells and brainstem nuclei. Symptoms and hallmarks of SCA1 include gait and limb ataxia, cognitive impairments, difficulty with speaking and swallowing, atrophy of the cerebellum and brainstem in magnetic resonance imaging (MRI), neurochemical abnormalities in the cerebellum and brainstem detected via magnetic resonance spectroscopy (MRS), and death within years of symptom onset (see, e.g., Ju, H., Kokubu, H., and Lim, J., *Mol. Neurobiol.* 50:866-874, 2014; Ortiz, J. P., Orr, H. T., in Polyglutamine Disorders, Nóbrega, C. and Almeida, L., eds., *Advances in Exp. Med. And Biol.*, 1049: 135-145, 2018).

There are no specific therapies for SCA1, with current treatments being limited to supportive treatments for individual symptoms.

Currently there is a lack of acceptable options for treating neurodegenerative diseases such as SCA1. It is therefore an object herein to provide compounds, methods, and pharmaceutical compositions for the treatment of such diseases.

SUMMARY OF THE INVENTION

Provided herein are compounds, methods and pharmaceutical compositions for reducing the amount or activity of ATXN1 RNA, and in certain embodiments reducing the expression of ATXN1 protein in a cell or subject. In certain embodiments, the subject has a neurodegenerative disease. In certain embodiments, the subject has Spinocerebellar ataxia type 1 (SCA1). In certain embodiments, compounds useful for reducing the amount or activity of ATXN1 RNA are oligomeric compounds. In certain embodiments, compounds useful for reducing the amount or activity of ATXN1 RNA are modified oligonucleotides. In certain embodiments, compounds useful for decreasing expression of ATXN1 protein are oligomeric compounds. In certain embodiments, compounds useful for decreasing expression of ATXN1 protein are modified oligonucleotides.

Also provided are methods useful for ameliorating at least one symptom or hallmark of a neurodegenerative disease. In certain embodiments, the neurodegenerative disease is Spinocerebellar ataxia type 1. In certain embodiments, the symptom or hallmark includes gait and limb ataxia, cognitive impairments, difficulty with speaking and swallowing, atrophy of the cerebellum and brainstem in magnetic resonance imaging (MRI), neurochemical abnormalities in the cerebellum and brainstem detected via magnetic resonance spectroscopy (MRS), and death within years of symptom onset.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, treatises, and GenBank, ENSEMBL, and NCBI reference sequence records, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising a 2'-H(H) deoxyfuranosyl sugar moiety. In certain embodiments, a 2'-deoxynucleoside is a 2'-β-D-deoxynucleoside and comprises a 2'-β-D-deoxyribosyl sugar moiety, which has the 13-D ribosyl configuration as found in naturally occurring deoxyribonucleic acids (DNA). In certain embodiments, a 2'-deoxynucleoside may comprise a modified nucleobase or may comprise an RNA nucleobase (uracil).

As used herein, "2'-MOE" means a 2'-OCH$_2$CH$_2$OCH$_3$ group in place of the 2'-OH group of a furanosyl sugar moiety. A "2'-MOE sugar moiety" means a sugar moiety with a 2'-OCH$_2$CH$_2$OCH$_3$ group in place of the 2'-OH group of a furanosyl sugar moiety. Unless otherwise indicated, a 2'-MOE sugar moiety is in the 0-D-ribosyl configuration. "MOE" means O-methoxyethyl.

As used herein, "2'-MOE nucleoside" means a nucleoside comprising a 2'-MOE sugar moiety.

As used herein, "2'-OMe" means a 2'-OCH$_3$ group in place of the 2'-OH group of a furanosyl sugar moiety. A "2'-O-methyl sugar moiety" or "2'-OMe sugar moiety" means a sugar moiety with a 2'-OCH$_3$ group in place of the 2'-OH group of a furanosyl sugar moiety. Unless otherwise indicated, a 2'-OMe sugar moiety is in the 0-D-ribosyl configuration.

As used herein, "2'-OMe nucleoside" means a nucleoside comprising a 2'-OMe sugar moiety.

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "5-methyl cytosine" means a cytosine modified with a methyl group attached to the 5 position. A 5-methyl cytosine is a modified nucleobase.

As used herein, "administering" means providing a pharmaceutical agent to a subject.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means an oligomeric compound capable of achieving at least one antisense activity.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom. In certain embodiments, the symptom or hallmark is gait and limb ataxia, cognitive impairments, difficulty with speaking and swallowing, atrophy of the cerebellum and brainstem in magnetic resonance imaging (MRI), neurochemical abnormalities in the cerebellum and brainstem detected via magnetic resonance spectroscopy (MRS), and death within years of symptom onset.

As used herein, "bicyclic nucleoside" or "BNA" means a nucleoside comprising a bicyclic sugar moiety.

As used herein, "bicyclic sugar" or "bicyclic sugar moiety" means a modified sugar moiety comprising two rings, wherein the second ring is formed via a bridge connecting two of the atoms of the first ring thereby forming a bicyclic structure. In certain embodiments, the first ring of the bicyclic sugar moiety is a furanosyl moiety. In certain embodiments, the furanosyl sugar moiety is a ribosyl moiety. In certain embodiments, the bicyclic sugar moiety does not comprise a furanosyl moiety.

As used herein, "cleavable moiety" means a bond or group of atoms that is cleaved under physiological conditions, for example, inside a cell, an animal, or a human.

As used herein, "complementary" in reference to an oligonucleotide means that at least 70% of the nucleobases of the oligonucleotide or one or more portions thereof and the nucleobases of another nucleic acid or one or more portions thereof are capable of hydrogen bonding with one another when the nucleobase sequence of the oligonucleotide and the other nucleic acid are aligned in opposing directions. As used herein, complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methyl cytosine (mC) and guanine (G). Complementary oligonucleotides and/or target nucleic acids need not have nucleobase complementarity at each nucleoside. Rather, some mismatches are tolerated. As used herein, "fully complementary" or "100% complementary" in reference to an oligonucleotide, or portion thereof, means that the oligonucleotide, or a portion thereof, is complementary to another oligonucleotide or target nucleic acid at each nucleobase of the shorter of the two oligonucleotides, or at each nucleoside if the oligonucleotides are the same length.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a single bond or a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "cEt" means a 4' to 2' bridge in place of the 2'OH-group of a ribosyl sugar moiety, wherein the bridge has the formula of 4'-CH(CH$_3$)—O-2', and wherein the methyl group of the bridge is in the S configuration. A "cEt sugar moiety" is a bicyclic sugar moiety with a 4' to 2' bridge in place of the 2'OH-group of a ribosyl sugar moiety, wherein the bridge has the formula of 4'-CH(CH$_3$)—O-2', and wherein the methyl group of the bridge is in the S configuration. "cEt" means constrained ethyl.

As used herein, "cEt nucleoside" means a nucleoside comprising a cEt sugar moiety. As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "chirally controlled" in reference to an internucleoside linkage means chirality at that linkage is enriched for a particular stereochemical configuration.

As used herein, "deoxy region" means a region of 5-12 contiguous nucleotides, wherein at least 70% of the nucleosides are 2'-β-D-deoxynucleosides. In certain embodiments, each nucleoside is selected from a 2'-β-D-deoxynucleoside, a bicyclic nucleoside, and a 2'-substituted nucleoside. In certain embodiments, a deoxy region supports RNase H activity. In certain embodiments, a deoxy region is the gap or internal region of a gapmer.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." The internal region is a deoxy region. The positions of the internal region or gap refer to the order of the nucleosides of the internal region and are counted starting from the 5'-end of the internal region. Unless otherwise indicated, "gapmer" refers to a sugar motif. In certain embodiments, each nucleoside of the gap is a 2'-β-D-deoxynucleoside. In certain embodiments, the gap comprises one 2'-substituted nucleoside at position 1, 2, 3, 4, or 5 of the gap, and the remainder of the nucleosides of the gap are 2'-β-D-deoxynucleosides. As used herein, the term "MOE gapmer" indicates a gapmer having a gap comprising 2'-β-D-deoxynucleosides and wings comprising 2'-MOE nucleosides. As used herein, the term "mixed wing gapmer" indicates a gapmer having wings comprising modified nucleosides comprising at least two different sugar modifications. Unless otherwise indicated, a gapmer may comprise one or more modified internucleoside linkages and/or modified nucleobases and such modifications do not necessarily follow the gapmer pattern of the sugar modifications.

As used herein, "hotspot region" is a range of nucleobases on a target nucleic acid that is amenable to oligomeric compound-mediated reduction of the amount or activity of the target nucleic acid.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "internucleoside linkage" means the covalent linkage between contiguous nucleosides in an oligonucleotide. As used herein, "modified internucleoside linkage" means any internucleoside linkage other than a phosphodiester internucleoside linkage. "Phosphorothioate internucleoside linkage" is a modified internucleoside linkage in which one of the non-bridging oxygen atoms of a phosphodiester internucleoside linkage is replaced with a sulfur atom.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar moiety" means a modified sugar moiety that comprises a modification, such as a substituent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "motif" means the pattern of unmodified and/or modified sugar moieties, nucleobases, and/or internucleoside linkages, in an oligonucleotide.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a target nucleic acid or oligonucleotide independent of any sugar or internucleoside linkage modification.

As used herein, "nucleoside" means a compound or a fragment of a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to a subject. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water, sterile saline, sterile buffer solution or sterile artificial cerebrospinal fluid.

As used herein, "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein, "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein, "prodrug" means a therapeutic agent in a form outside the body that is converted to a different form within a subject or cells thereof. Typically, conversion of a prodrug within the subject is facilitated by the action of an enzymes (e.g., endogenous or viral enzyme) or chemicals present in cells or tissues and/or by physiologic conditions.

As used herein, "reducing the amount or activity" refers to a reduction or blockade of the transcriptional expression or activity relative to the transcriptional expression or activity in an untreated or control sample and does not necessarily indicate a total elimination of transcriptional expression or activity.

As used herein, "RNA" means an RNA transcript and includes pre-mRNA and mature mRNA unless otherwise specified.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "standard in vitro assay" or "standard cell assay" means the assay described in Example 1 and reasonable variations thereof.

As used herein, "standard in vivo assay" means the assay described in Example 6 and reasonable variations thereof.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

As used herein, "subject" means a human or non-human animal.

As used herein, "sugar moiety" means an unmodified sugar moiety or a modified sugar moiety. As used herein, "unmodified sugar moiety" means a 2'-OH(H) 0-D-ribosyl moiety, as found in RNA (an "unmodified RNA sugar moiety"), or a 2'-H(H) 0-D-deoxyribosyl sugar moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or target nucleic acids.

As used herein, "symptom or hallmark" means any physical feature or test result that indicates the existence or extent of a disease or disorder. In certain embodiments, a symptom is apparent to a subject or to a medical professional examining or testing said subject. In certain embodiments, a hallmark is apparent upon invasive diagnostic testing, including, but not limited to, post-mortem tests. In certain embodiments, a hallmark is apparent on a brain MRI scan.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to a subject. For example, a therapeutically effective amount improves a symptom or hallmark of a disease.

Certain Embodiments

The present disclosure provides the following non-limiting numbered embodiments:

Embodiment 1. An oligomeric compound comprising a modified oligonucleotide consisting of 12 to 30 linked nucleosides wherein the nucleobase sequence of the modified oligonucleotide is at least 90% complementary to an equal length portion of an ATXN1 nucleic acid, and wherein the modified oligonucleotide comprises at least one modification selected from a modified sugar moiety and a modified internucleoside linkage.

Embodiment 2. An oligomeric compound comprising a modified oligonucleotide consisting of 12 to 30 linked nucleosides and having a nucleobase sequence comprising at least 12, 13, 14, 15, 16, 17, 18, 19, or 20 contiguous nucleobases of any of SEQ ID NOs: 22-3624 or 3655.

Embodiment 3. An oligomeric compound comprising a modified oligonucleotide consisting of 12 to 30 linked nucleosides and having a nucleobase sequence comprising at least 12, 13, 14, 15, 16, or 17 contiguous nucleobases of any of SEQ ID NOs: 3625-3654 or 3656-3669.

Embodiment 4. An oligomeric compound comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 contiguous nucleobases complementary to:

an equal length portion of nucleobases 5472-5552 of SEQ ID NO: 1;

an equal length portion of nucleobases 5906-6005 of SEQ ID NO: 1;

an equal length portion of nucleobases 7868-7911 of SEQ ID NO: 1;

an equal length portion of nucleobases 8481-8514 of SEQ ID NO: 1; or an equal length portion of nucleobases 446679-446706 of SEQ ID NO: 2.

Embodiment 5. An oligomeric compound comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, or at least 17 contiguous nucleobases of a sequence selected from:

SEQ ID NOs: 196, 274, 352, 430, 508, 2578, 2655, 2732, 2809, 2886, 2963, 3121, 3122, 3190, 3191, 3192, 3262, 3330, 3331, 3332, 3401, 3402, 3575, 3577, 3620, 3624, 3638-3640, 3653-3655, 3662, 3665, 3669;

SEQ ID Nos: 42, 120, 198, 276, 509, 587, 2502, 2579, 2656, 2733, 2810, 2887, 2964, 3585, 3588-3590, 3615, 3618, 3622, 3657, 3660, 3661, 3663, 3664, 3666-3668;

SEQ ID Nos: 48, 126, 2044, 2121;

SEQ ID Nos: 128, 206, 284, 1045, 1122, 1199, and 1276; or

SEQ ID Nos: 2475, 2552, 2629, 2706, 2783, 3627-3630, 3644.

Embodiment 6. The oligomeric compound of any of embodiments 1-5, wherein the modified oligonucleotide has a nucleobase sequence that is at least 80%, 85%, 90%, 95%, or 100% complementary to the nucleobase sequence of SEQ ID NO: 1, SEQ ID NO: 2, SEQ ID NO: 3, SEQ ID NO: 4, SEQ ID NO: 5, or SEQ ID NO: 6 when measured across the entire nucleobase sequence of the modified oligonucleotide.

Embodiment 7. The oligomeric compound of any of embodiments 1-6, wherein the modified oligonucleotide comprises at least one modified nucleoside.

Embodiment 8. The oligomeric compound of embodiment 7, wherein the modified oligonucleotide comprises at least one modified nucleoside comprising a modified sugar moiety.

Embodiment 9. The oligomeric compound of embodiment 8, wherein the modified oligonucleotide comprises at least one modified nucleoside comprising a bicyclic sugar moiety.

Embodiment 10. The oligomeric compound of embodiment 9, wherein the modified oligonucleotide comprises at least one modified nucleoside comprising a bicyclic sugar moiety having a 2'-4' bridge, wherein the 2'-4' bridge is selected from —O—CH$_2$—; and —O—CH(CH$_3$)—.

Embodiment 11. The oligomeric compound of any of embodiments 7-10, wherein the modified oligonucleotide comprises at least one modified nucleoside comprising a non-bicyclic modified sugar moiety.

Embodiment 12. The oligomeric compound of embodiment 11, wherein the non-bicyclic modified sugar moiety is a 2'-MOE sugar moiety or 2'-OMe modified sugar moiety.

Embodiment 13. The oligomeric compound of any of embodiments 7-8, wherein the modified oligonucleotide comprises at least one modified nucleoside comprising a sugar surrogate.

Embodiment 14. The oligomeric compound of embodiment 13, wherein the modified oligonucleotide comprises at least one modified nucleoside comprising a sugar surrogate selected from morpholino and PNA.

Embodiment 15. The oligomeric compound of any of embodiments 1-8 or 11-14, wherein the modified oligonucleotide does not comprise a bicyclic sugar moiety.

Embodiment 16. The oligomeric compound of any of embodiments 1-15, wherein the modified oligonucleotide is a gapmer.

Embodiment 17. The oligomeric compound of any of embodiments 1-16, wherein the modified oligonucleotide has a sugar motif comprising:

a 5'-region consisting of 1-6 linked 5'-region nucleosides;

a central region consisting of 6-10 linked central region nucleosides; and a 3'-region consisting of 1-6 linked 3'-region nucleosides; wherein each of the 5'-region nucleosides and each of the 3'-region nucleosides comprises a modified sugar moiety and each of the central region nucleosides comprises a 2'-deoxyfuranosyl sugar moiety.

Embodiment 18. The oligomeric compound of embodiment 17, wherein the modified oligonucleotide has a sugar motif comprising:

a 5'-region consisting of 6 linked 5'-region nucleosides;

a central region consisting of 10 linked central region nucleosides; and a 3'-region consisting of 4 linked 3'-region nucleosides; wherein each of the 5'-region nucleosides and each of the 3'-region nucleosides is a 2'-MOE nucleoside, and each of the central region nucleosides is a 2'-β-D-deoxynucleoside.

Embodiment 19. The oligomeric compound of embodiment 17, wherein the modified oligonucleotide has a sugar motif comprising:

a 5'-region consisting of 5 linked 5'-region nucleosides;

a central region consisting of 10 linked central region nucleosides; and a 3'-region consisting of 5 linked 3'-region nucleosides; wherein each of the 5'-region nucleosides and each of the 3'-region nucleosides is a 2'-MOE nucleoside, and each of the central region nucleosides is a 2'-β-D-deoxynucleoside.

Embodiment 20. The oligomeric compound of embodiment 17, wherein the modified oligonucleotide has a 5'-region consisting of 5 linked 5'-region nucleosides;

a central region consisting of 8 linked central region nucleosides; and a 3'-region consisting of 4 linked 3'-region nucleosides; wherein each of the 5'-region nucleosides and each of the 3'-region nucleosides comprises a is a 2'-MOE nucleoside, and each of the central region nucleosides is a 2'-β-D-deoxynucleoside.

Embodiment 21. The oligomeric compound of embodiment 17, wherein the modified oligonucleotide has a 5'-region consisting of 5 linked 5'-region nucleosides;

a central region consisting of 8 linked central region nucleosides; and a 3'-region consisting of 4 linked 3'-region nucleosides; wherein each of the 5'-region nucleosides comprises a 2'-MOE sugar moiety, each of the 3'-region nucleosides is selected from a 2'-MOE nucleoside and a cEt nucleoside, and each of the central region nucleosides comprises a 2'-β-D-deoxynucleoside.

Embodiment 22. The oligomeric compound of any of embodiments 1-16, wherein the modified oligonucleotide has a sugar motif comprising:

a 5'-region consisting of 1-6 linked 5'-region nucleosides;

a central region consisting of 6-10 linked central region nucleosides; and a 3'-region consisting of 1-6 linked 3'-region nucleosides; wherein each of the 5'-region nucleosides and each of the 3'-region nucleosides comprises a modified sugar moiety, and the central region has the following formula:

(N$d$)(N$x$)(N$d$)$n$ wherein Nx is a 2'-OMe nucleoside and each Nd is a 2'-O-D-deoxynucleoside;

and n is from 6 to 8.

Embodiment 23. The oligomeric compound of any of embodiments 1-16, wherein the modified oligonucleotide has a sugar motif comprising:

a 5'-region consisting of 5 linked 5'-region nucleosides;

a central region consisting of 6-10 linked central region nucleosides; and a 3'-region consisting of 4 linked 3'-region nucleosides; wherein each of the 5'-region nucleosides and each of the 3'-region nucleosides is selected from a 2'-MOE nucleoside and a cEt nucleoside, and the central region has the following formula:

(N$d$)(N$x$)(N$d$)$n$ wherein Nx is a 2'-OMe nucleoside and each Nd is a 2'-O-D-deoxynucleoside;

and n is 7.

Embodiment 24. The oligomeric compound of any of embodiments 1-23, wherein the modified oligonucleotide comprises at least one modified internucleoside linkage.

Embodiment 25. The oligomeric compound of embodiment 24, wherein each internucleoside linkage of the modified oligonucleotide is a modified internucleoside linkage.

Embodiment 26. The oligomeric compound of embodiment 24 or 25 wherein the modified internucleoside linkage is a phosphorothioate internucleoside linkage.

Embodiment 27. The oligomeric compound of embodiment 24 or 26 wherein the modified oligonucleotide comprises at least one phosphodiester internucleoside linkage.

Embodiment 28. The oligomeric compound of any of embodiments 24, 26, or 27, wherein each internucleoside linkage is independently selected from a phosphodiester internucleoside linkage or a phosphorothioate internucleoside linkage.

Embodiment 29. The oligomeric compound of embodiments 1-24 or 26-28, wherein the modified oligonucleotide has an internucleoside linkage motif selected from among: sooossssssssssssooss, sssosssssssssssssosss, sssosssssssssssoss, or sooooosssssssssssoss; wherein, s=a phosphorothioate internucleoside linkage and o=a phosphodiester internucleoside linkage.

Embodiment 30. The oligomeric compound of any of embodiments 1-29, wherein the modified oligonucleotide comprises a modified nucleobase.

Embodiment 31. The oligomeric compound of embodiment 30, wherein the modified nucleobase is a 5-methyl cytosine.

Embodiment 32. The oligomeric compound of any of embodiments 1-31, wherein the modified oligonucleotide consists of 12-30, 12-22, 12-20, 14-18, 16-18, 14-20, 15-17, 15-25, 16-20, or 17-20 linked nucleosides.

Embodiment 33. The oligomeric compound of any of embodiments 1-2, 4-19, 22 or 24-31, wherein the modified oligonucleotide consists of 18-22 or 18-20 linked nucleosides.

Embodiment 34. The oligomeric compound of any of embodiments 1-17 or 20-32, wherein the modified oligonucleotide consists of 17 linked nucleosides.

Embodiment 35. The oligomeric compound of any of embodiments 1-2, 4-19, 22 or 24-31, wherein the modified oligonucleotide consists of 20 linked nucleosides.

Embodiment 36. The oligomeric compound of any of embodiments 1-35, consisting of the modified oligonucleotide.

Embodiment 37. The oligomeric compound of any of embodiments 1-35, comprising a conjugate group comprising a conjugate moiety and a conjugate linker.

Embodiment 38. The oligomeric compound of embodiment 37, wherein the conjugate linker consists of a single bond.

Embodiment 39. The oligomeric compound of embodiment 37, wherein the conjugate linker is cleavable.

Embodiment 40. The oligomeric compound of embodiment 37, wherein the conjugate linker comprises 1-3 linker-nucleosides.

Embodiment 41. The oligomeric compound of any of embodiments 37-40, wherein the conjugate group is attached to the modified oligonucleotide at the 5'-end of the modified oligonucleotide.

Embodiment 42. The oligomeric compound of any of embodiments 37-40, wherein the conjugate group is attached to the modified oligonucleotide at the 3'-end of the modified oligonucleotide.

Embodiment 43. The oligomeric compound of any of embodiments 1-35 or 37-42, comprising a terminal group.

Embodiment 44. The oligomeric compound of any of embodiments 1-43 wherein the oligomeric compound is a singled-stranded oligomeric compound.

Embodiment 45. The oligomeric compound of any of embodiments 1-39 or 41-42, wherein the oligomeric compound does not comprise linker-nucleosides.

Embodiment 46. An oligomeric duplex comprising an oligomeric compound of any of embodiments 1-43 or 45.

Embodiment 47. An antisense compound comprising or consisting of an oligomeric compound of any of embodiments 1-45 or an oligomeric duplex of embodiment 46.

Embodiment 48. A pharmaceutical composition comprising an oligomeric compound of any of embodiments 1-45 or an oligomeric duplex of embodiment 46 and a pharmaceutically acceptable carrier or diluent.

Embodiment 49. The pharmaceutical composition of embodiment 48, wherein the pharmaceutically acceptable diluent is artificial cerebral spinal fluid.

Embodiment 50. The pharmaceutical composition of embodiment 49, wherein the pharmaceutical composition consists essentially of the modified oligonucleotide and artificial cerebral spinal fluid.

Embodiment 51. A method comprising administering to a subject a pharmaceutical composition of any of embodiments 48-50.

Embodiment 52. A method of treating a disease associated with ATXN1 comprising administering to an individual having or at risk for developing a disease associated with ATXN1 a therapeutically effective amount of a pharmaceutical composition according to any of embodiments 48-50; and thereby treating the disease associated with ATXN1.

Embodiment 53. The method of embodiment 52, wherein the ATXN1-associated disease is Spinocerebellar ataxia type 1.

Embodiment 54. The method of any of embodiments 51-52, wherein at least one symptom or hallmark of the ATXN1-associated disease is ameliorated.

Embodiment 55. The method of embodiment 54, wherein the symptom or hallmark is gait or limb ataxia, cognitive impairments, difficulty with speaking or swallowing, atrophy of the cerebellum and/or brainstem in magnetic resonance imaging (MRI), neurochemical abnormalities in the cerebellum and/or brainstem detected via magnetic resonance spectroscopy (MRS), or death within 10-15 years of symptom onset.

Embodiment 56. The method of any of embodiments 51-53, wherein ATXN1 levels in the individual are reduced.

Embodiment 57. A modified oligonucleotide according to the following chemical structure:

(SEQ ID NO: 3671)

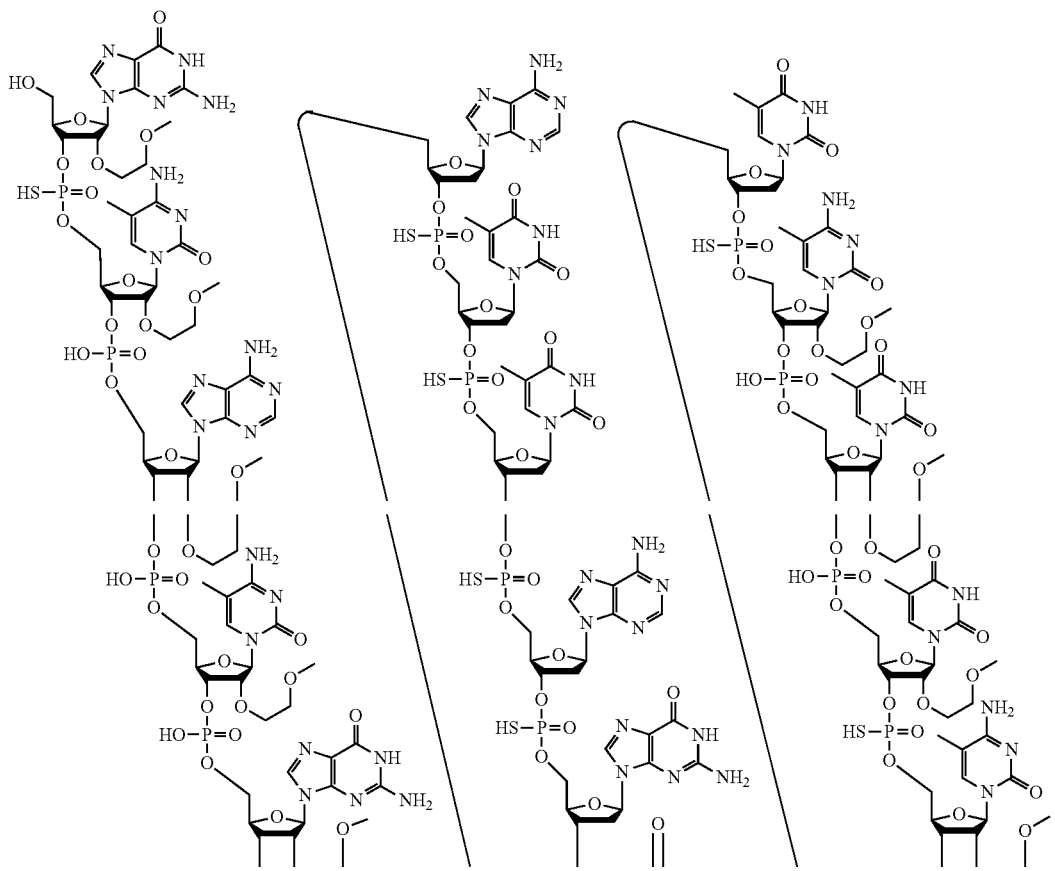

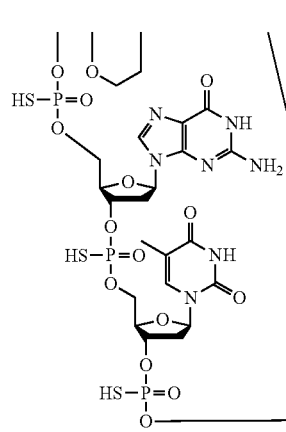
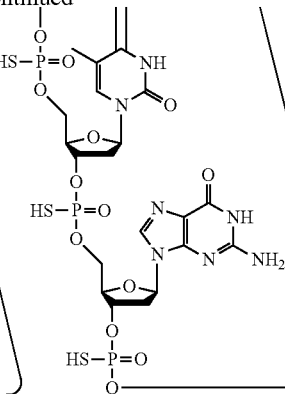
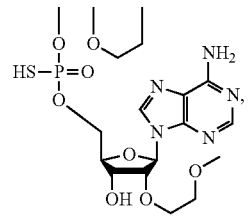
or a salt thereof.
Embodiment 58. A modified oligonucleotide according to the following chemical structure:
(SEQ ID NO: 3672)
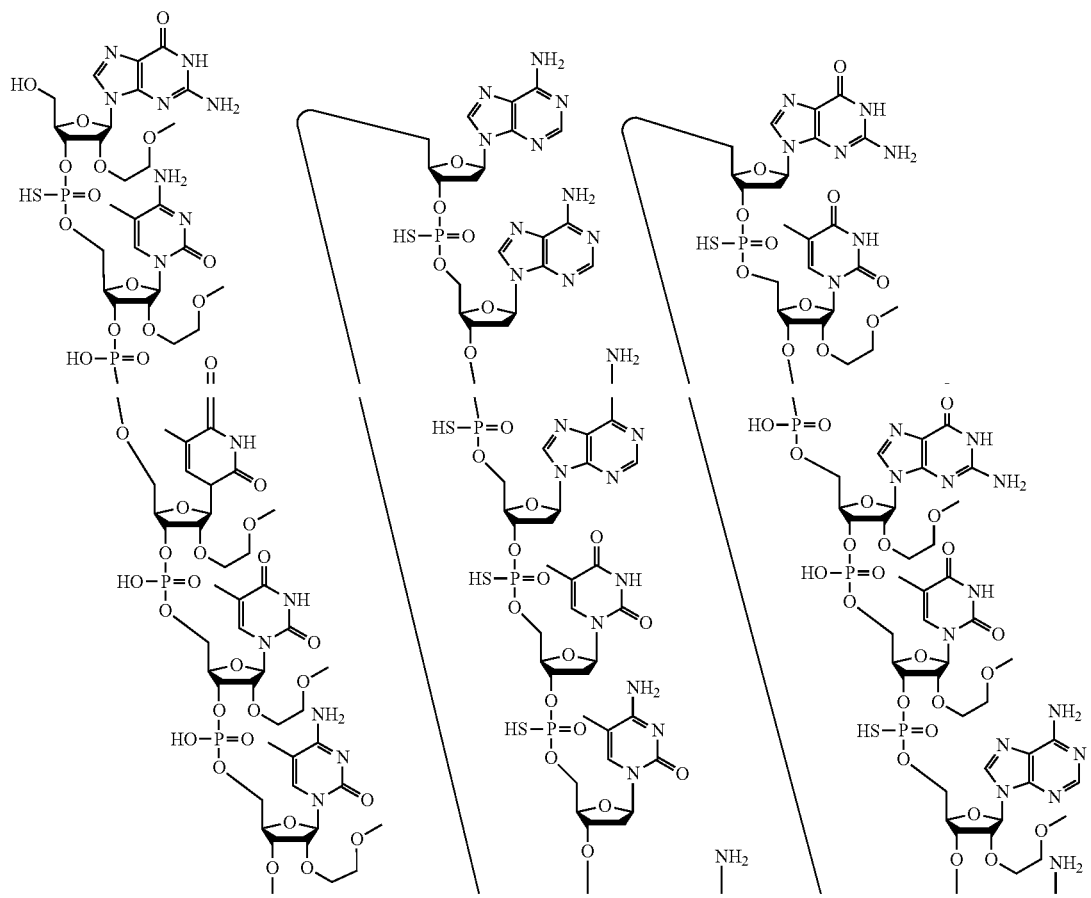

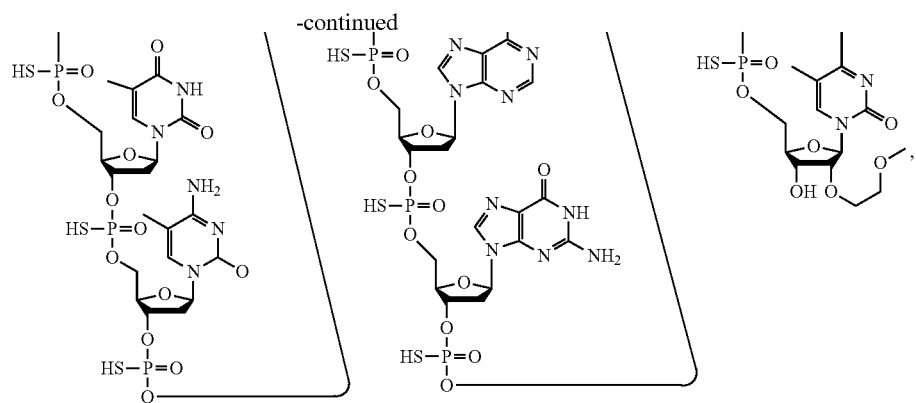
or a salt thereof.
Embodiment 59. A modified oligonucleotide according to the following chemical structure:
(SEQ ID NO: 3673)
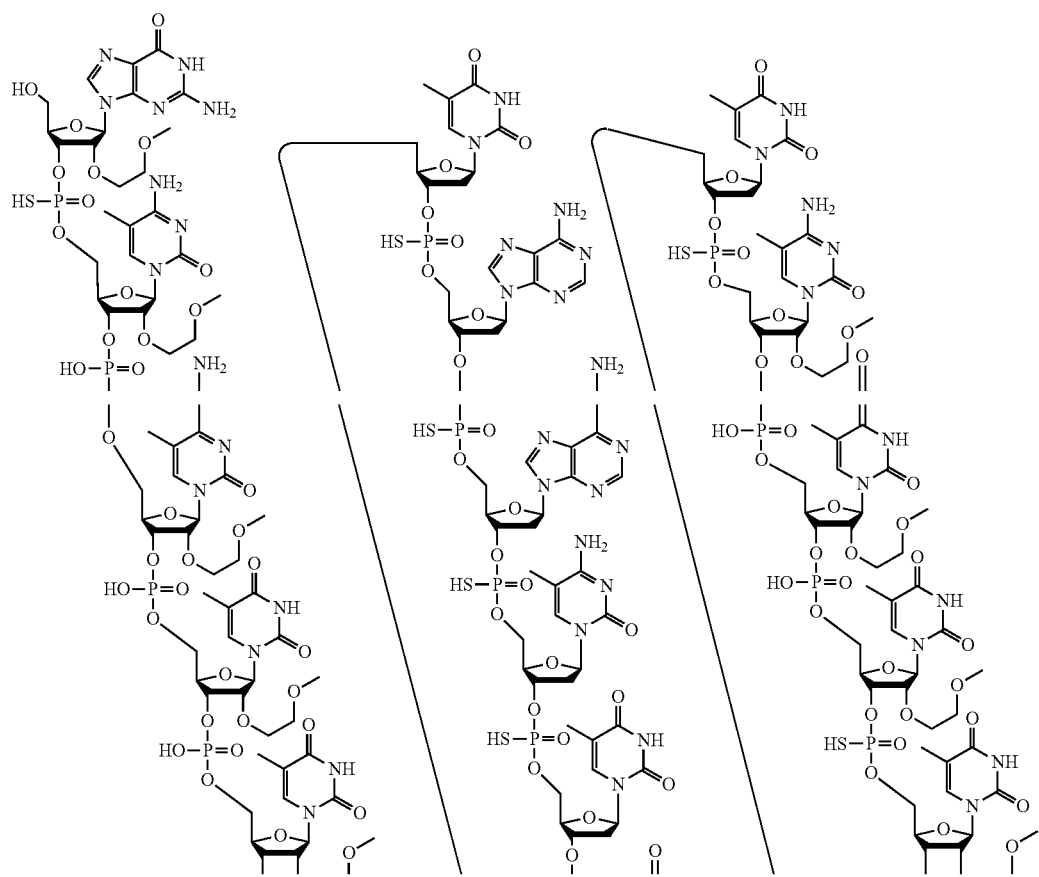

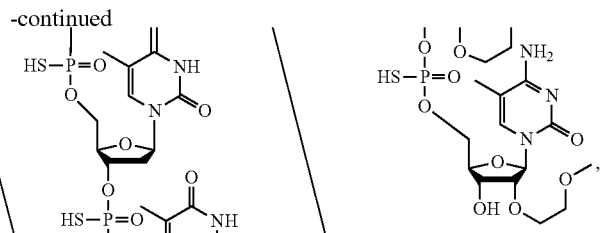
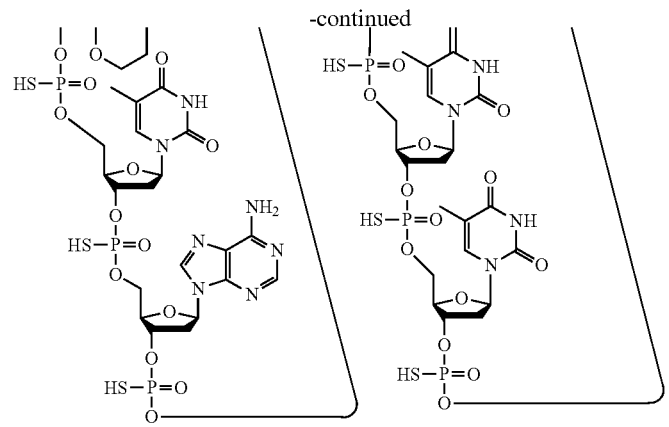
or a salt thereof.
Embodiment 60. A modified oligonucleotide according to the following chemical structure:
(SEQ ID NO: 3674)
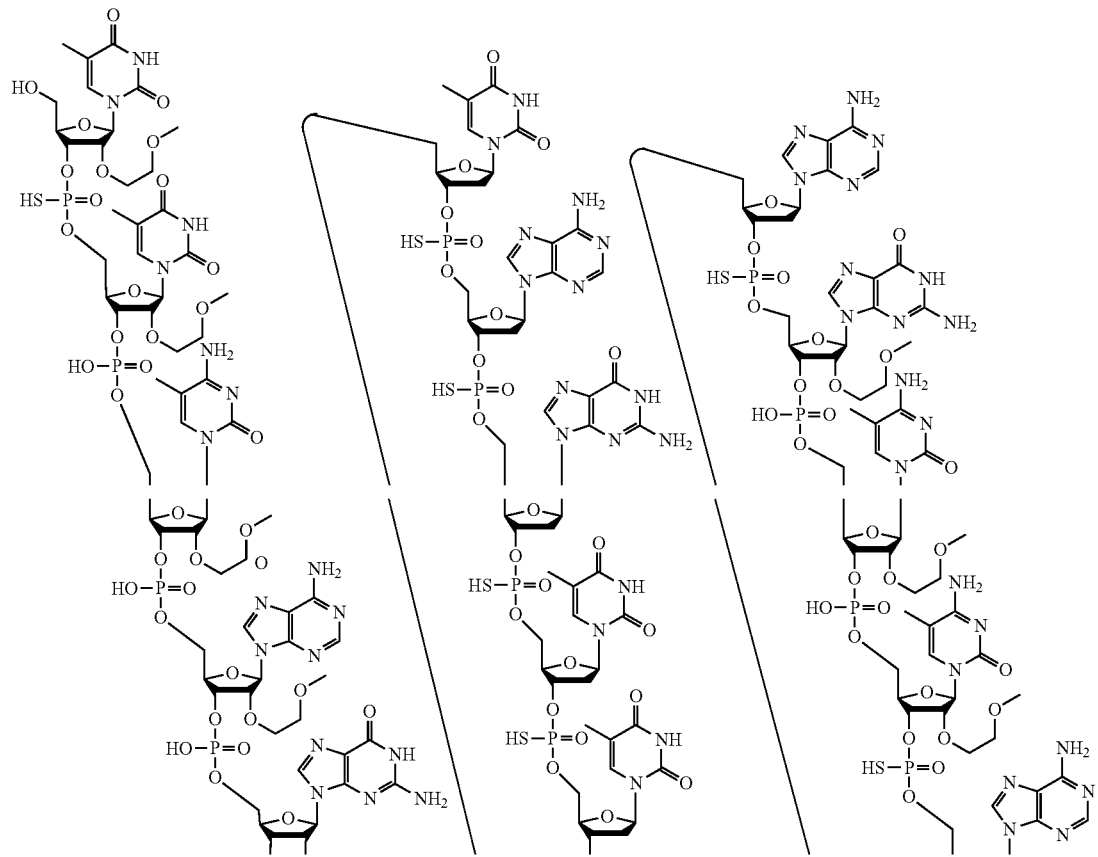

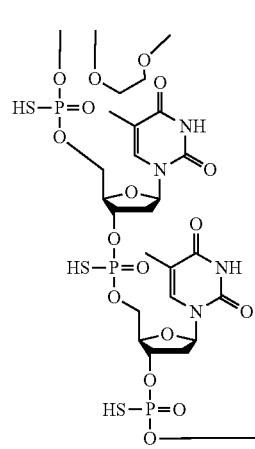
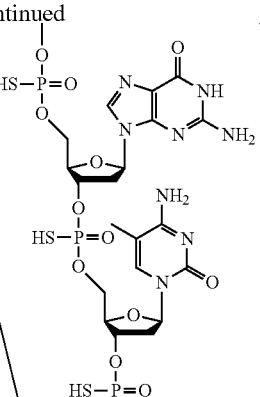
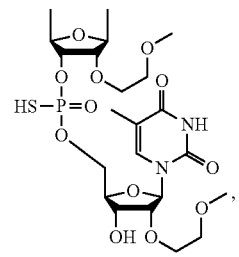
or a salt thereof.
Embodiment 61. A modified oligonucleotide according to the following chemical structure:
(SEQ ID NO: 3670)
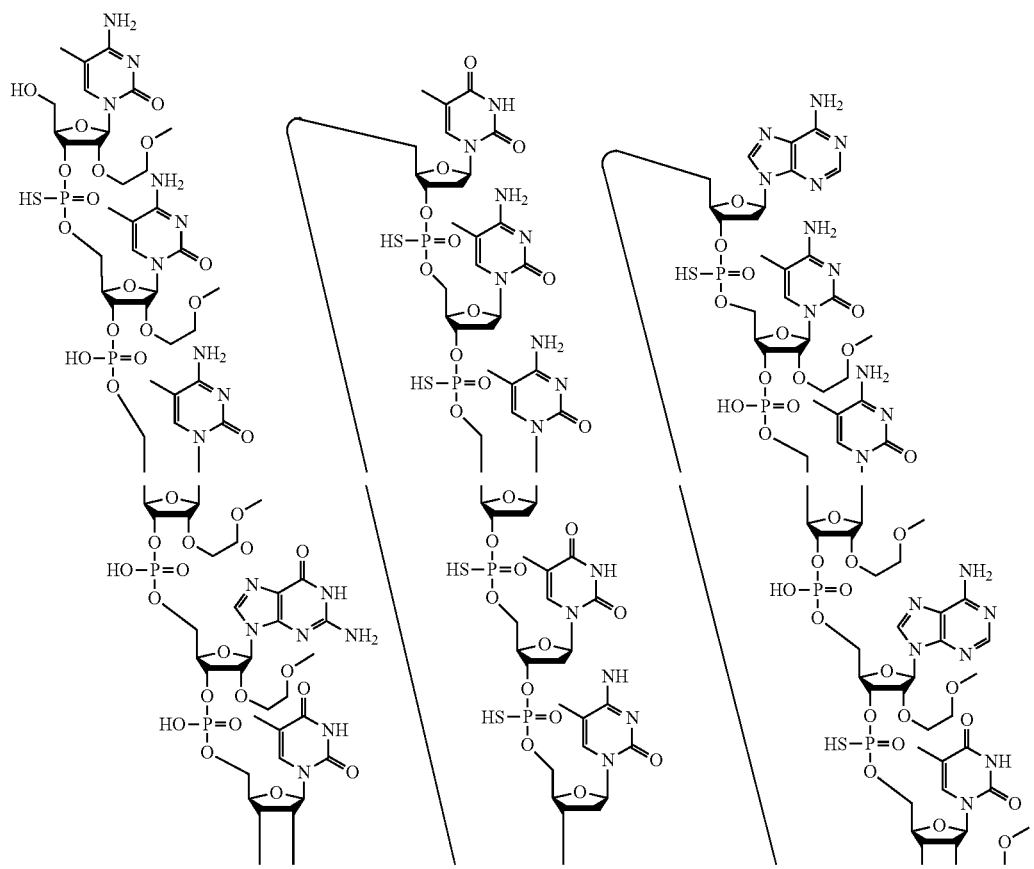

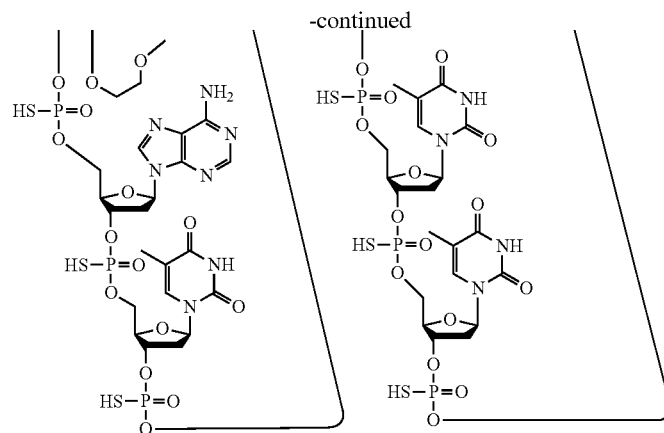
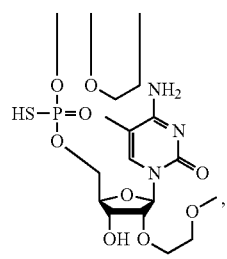
or a salt thereof.
Embodiment 62. A modified oligonucleotide according to the following chemical structure:
(SEQ ID NO: 3675)
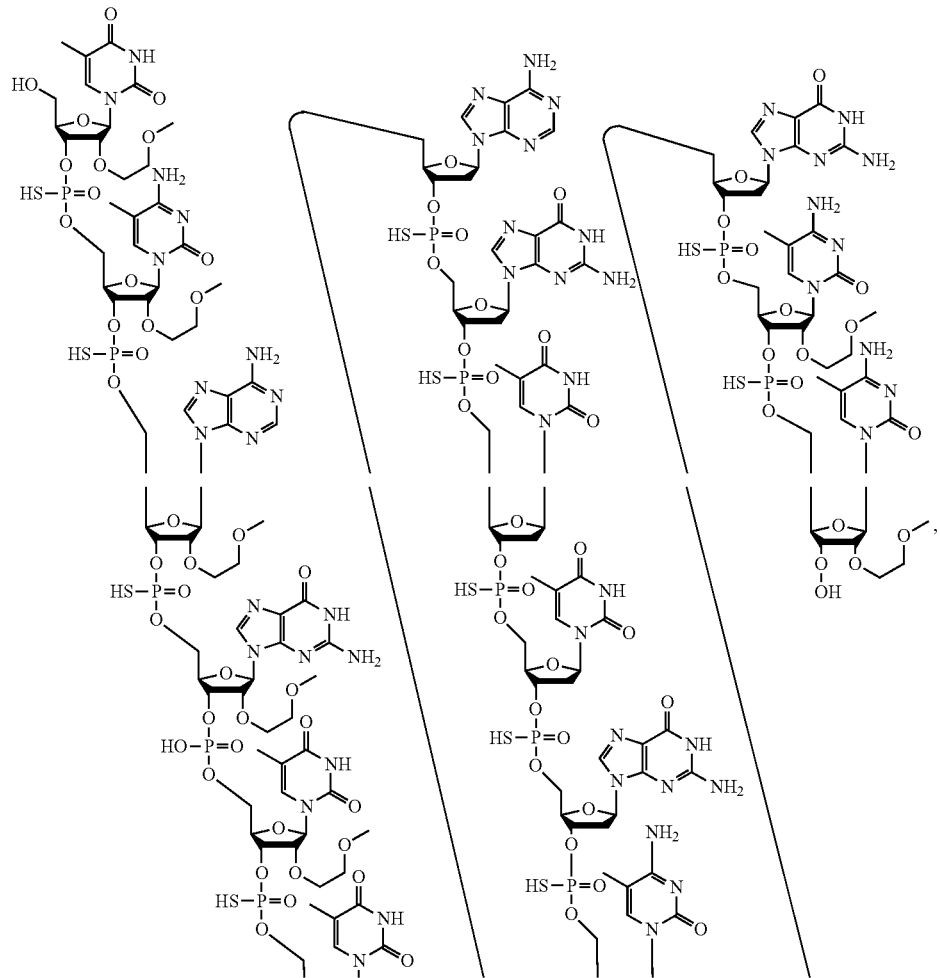

-continued
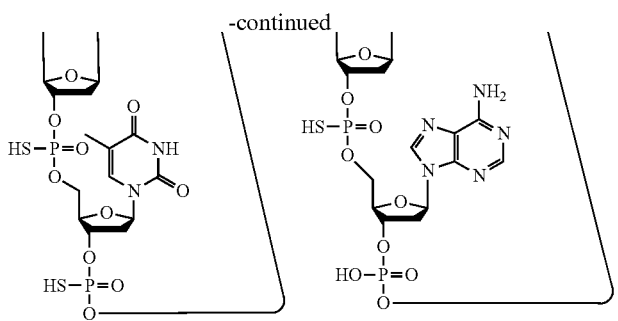
or a salt thereof.
Embodiment 63. A modified oligonucleotide according to the following chemical structure:
(SEQ ID NO: 3671)
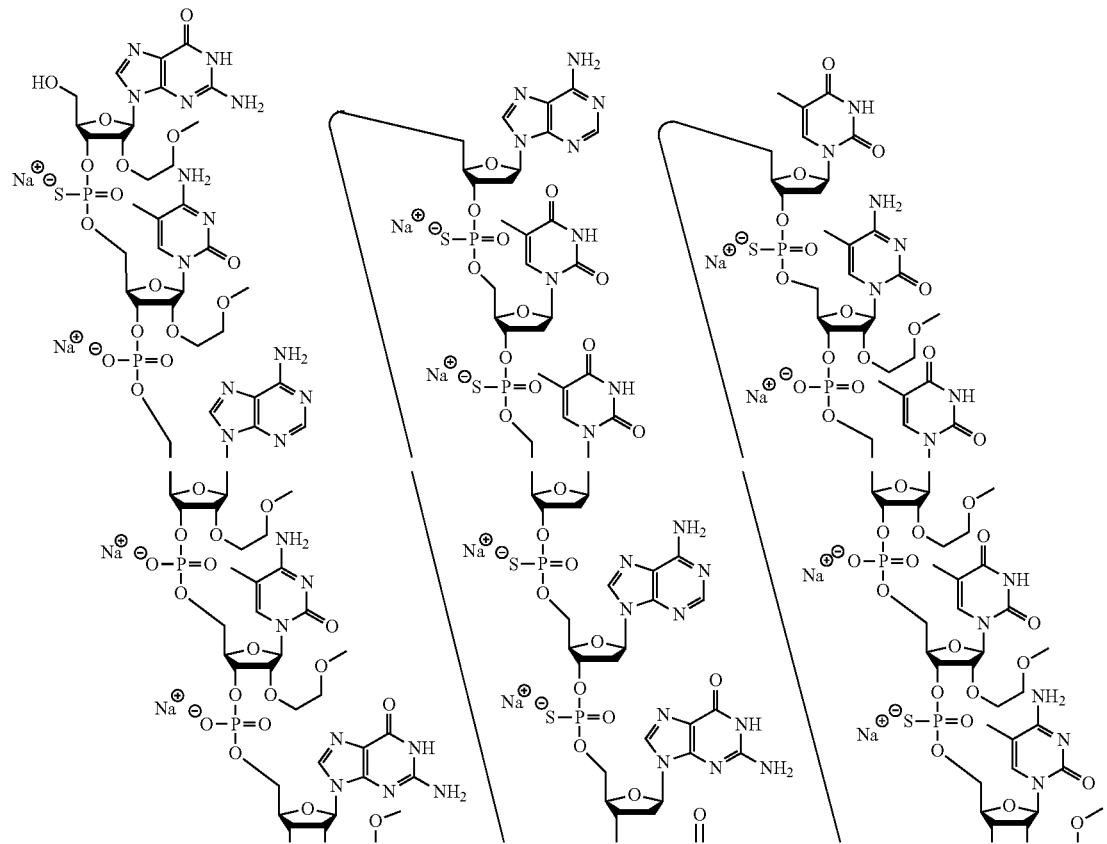

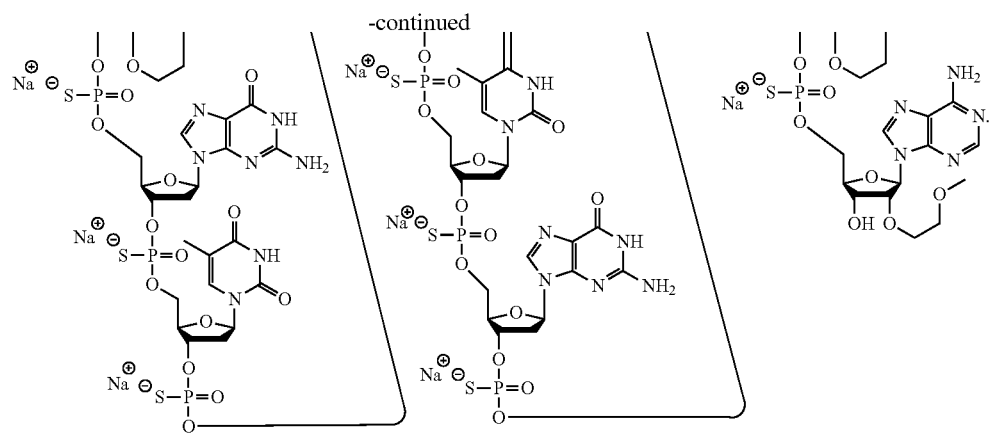
Embodiment 64. A modified oligonucleotide according to the following chemical structure:
(SEQ ID NO: 3672)
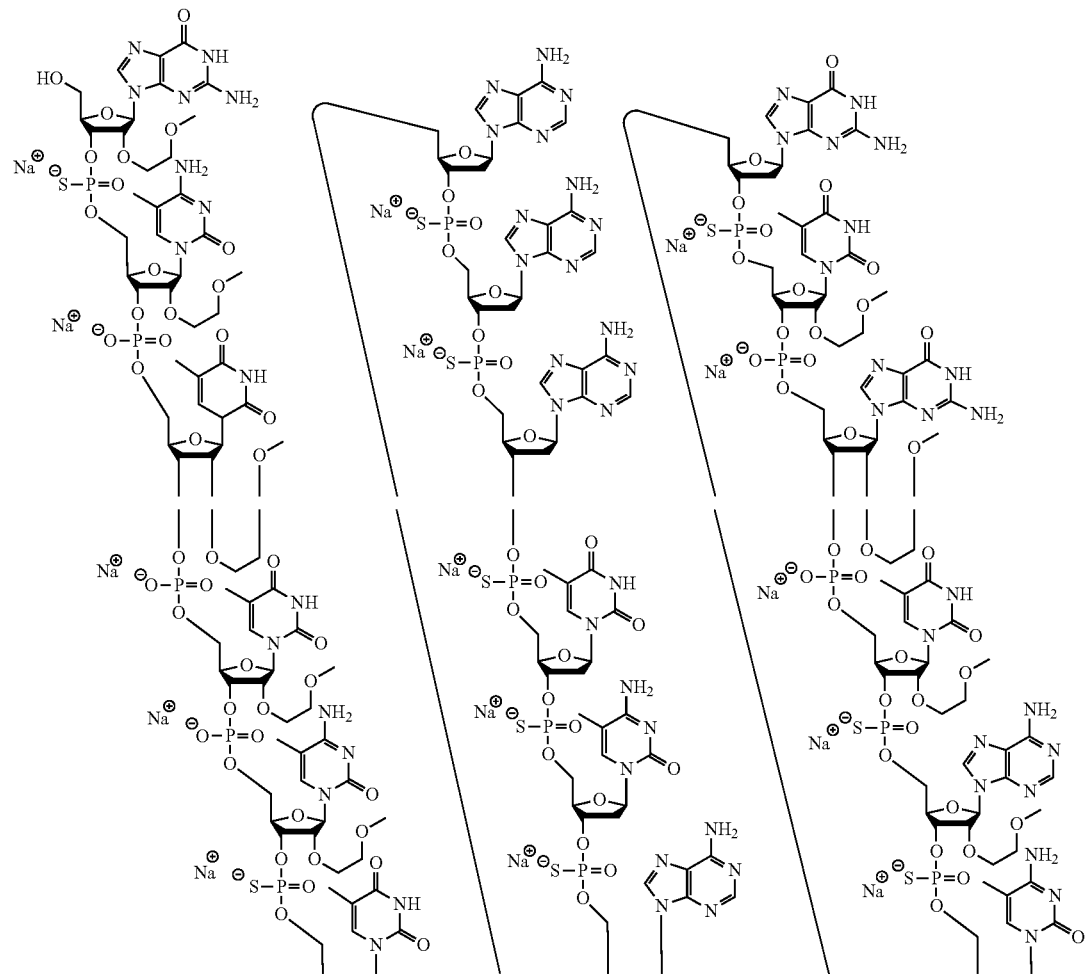

-continued
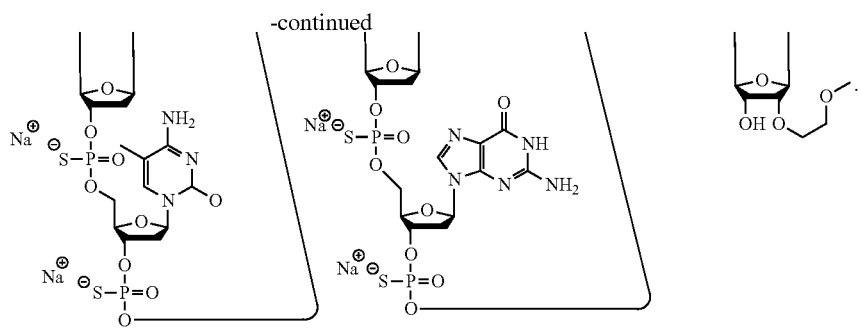
Embodiment 65. A modified oligonucleotide according to the following chemical structure:
(SEQ ID NO: 3673)
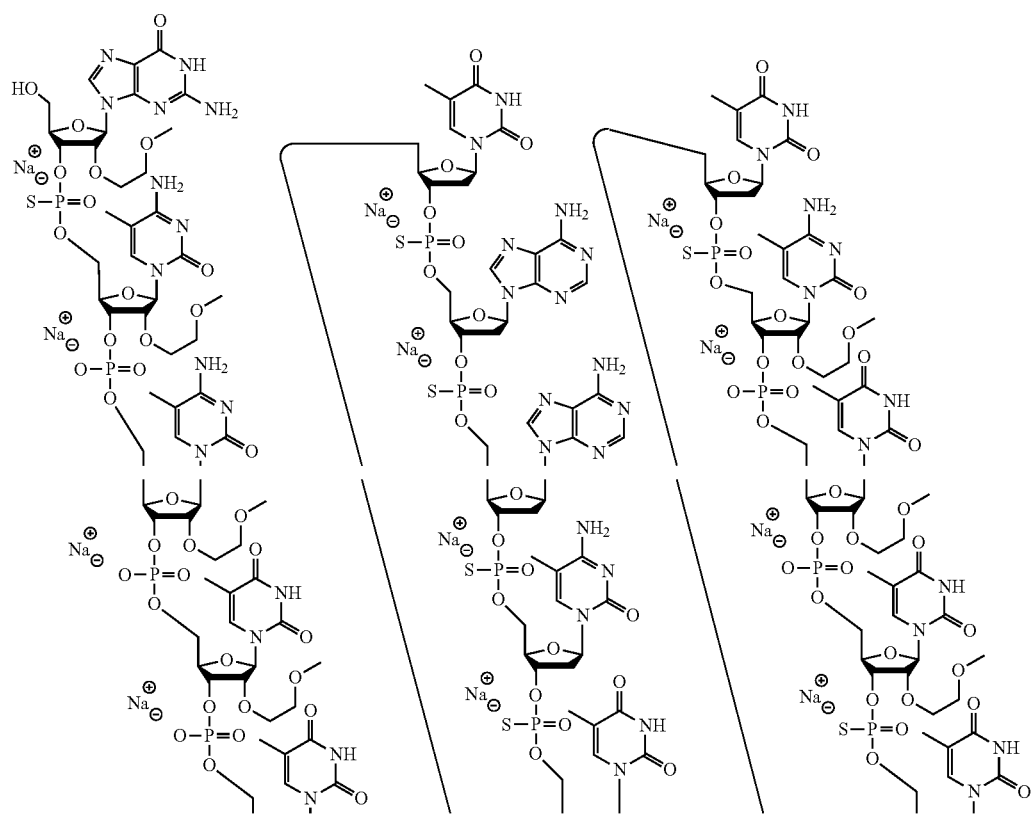

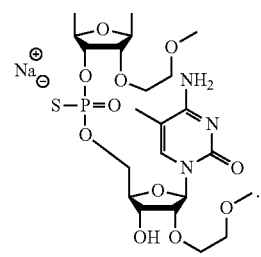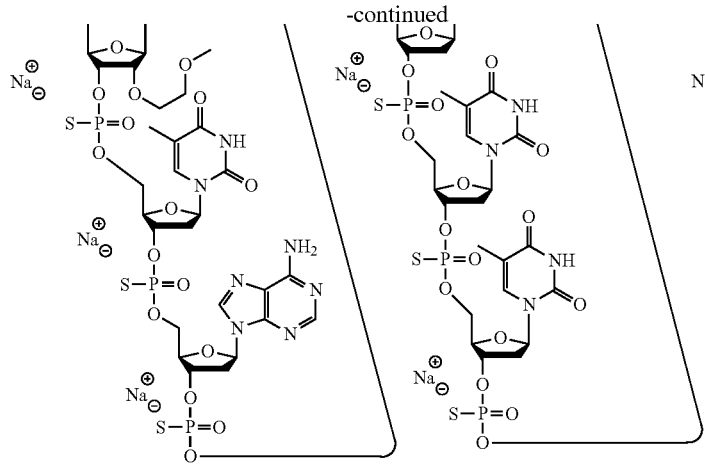
Embodiment 66. A modified oligonucleotide according to the following chemical structure:
(SEQ ID NO: 3674)
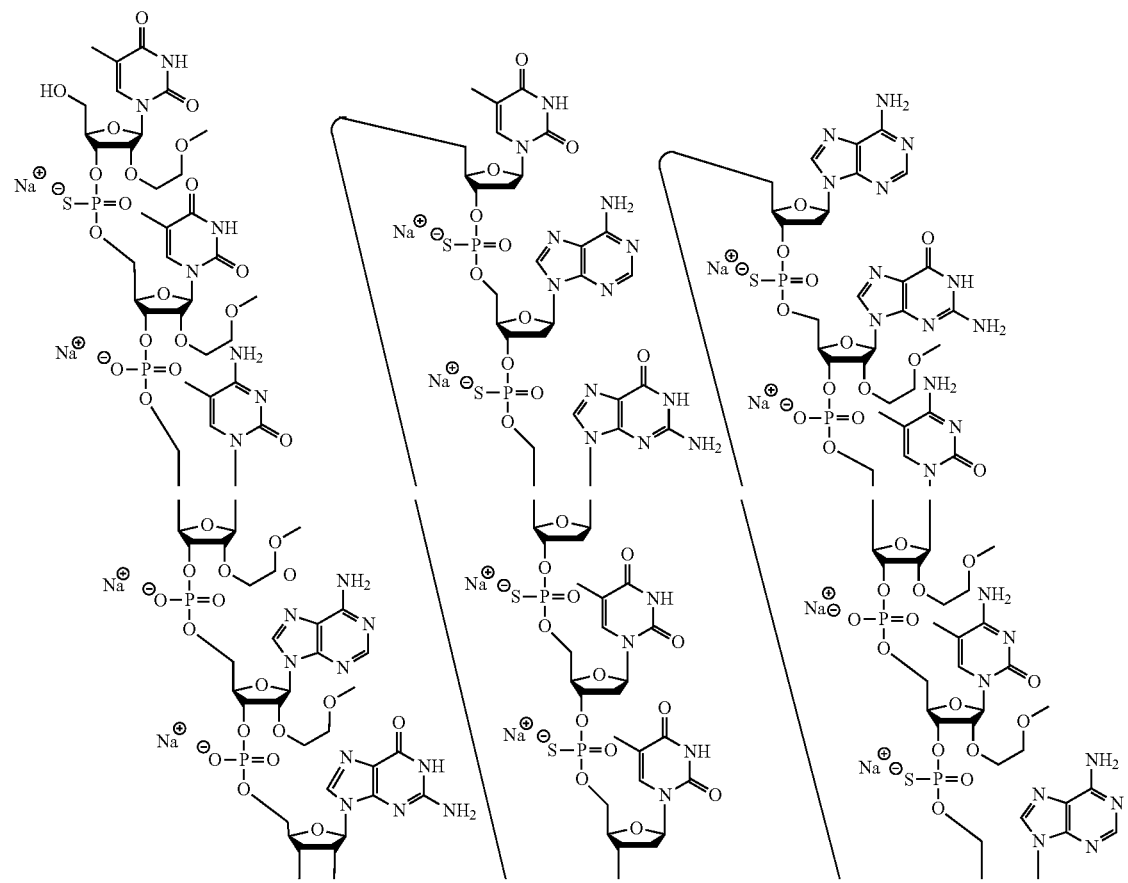

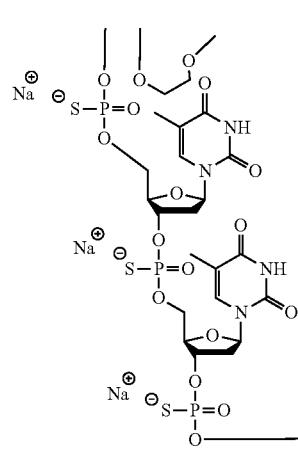
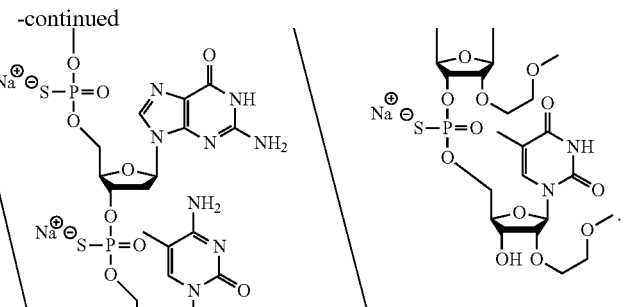
Embodiment 67. A modified oligonucleotide according to the following chemical structure:
(SEQ ID NO: 3670)
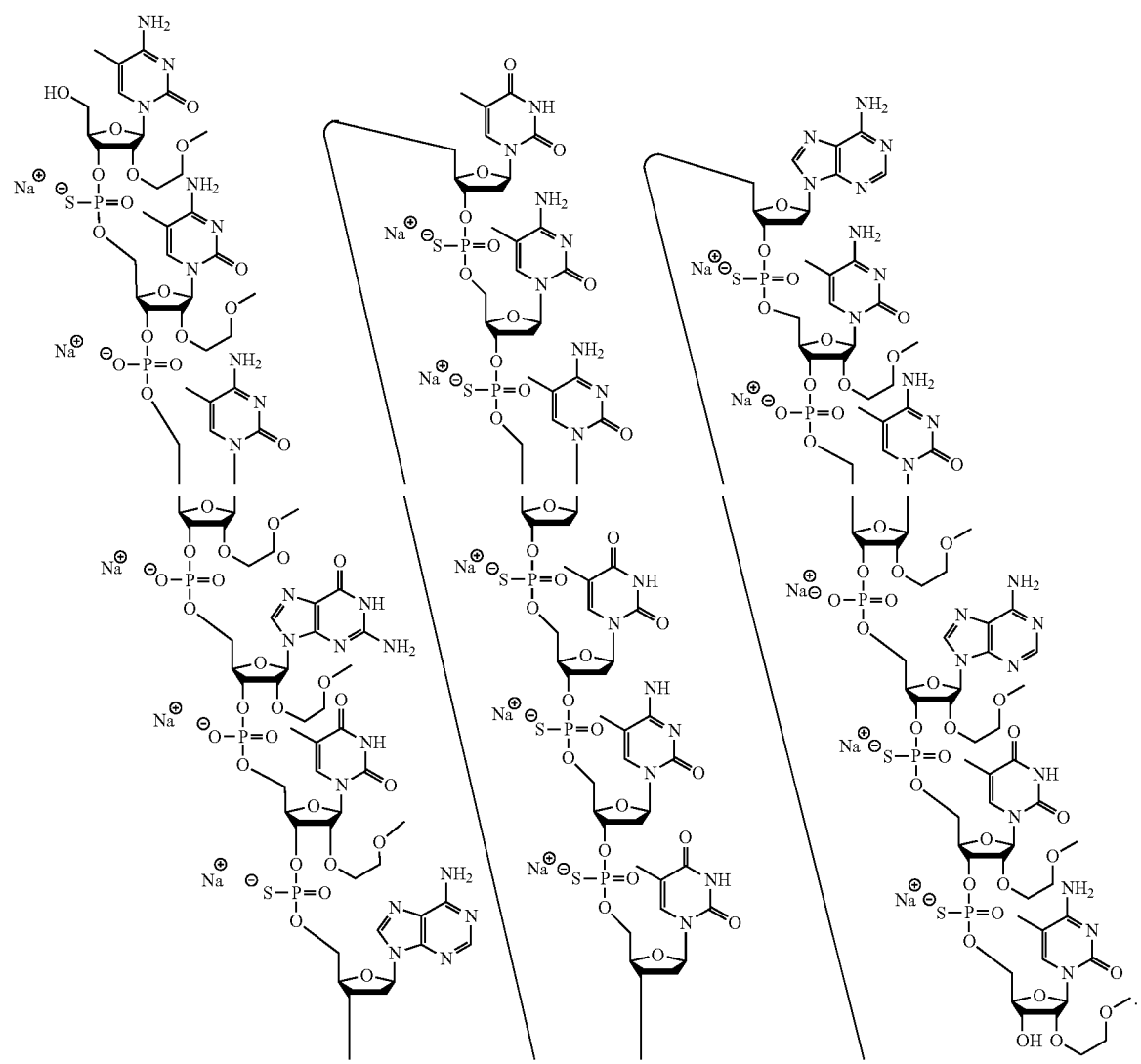

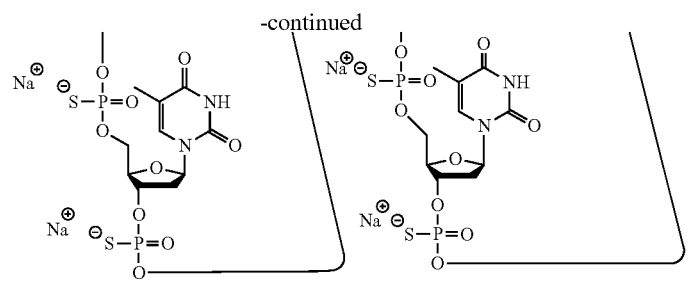
Embodiment 68. A modified oligonucleotide according to the following chemical structure:
(SEQ ID NO: 3675)
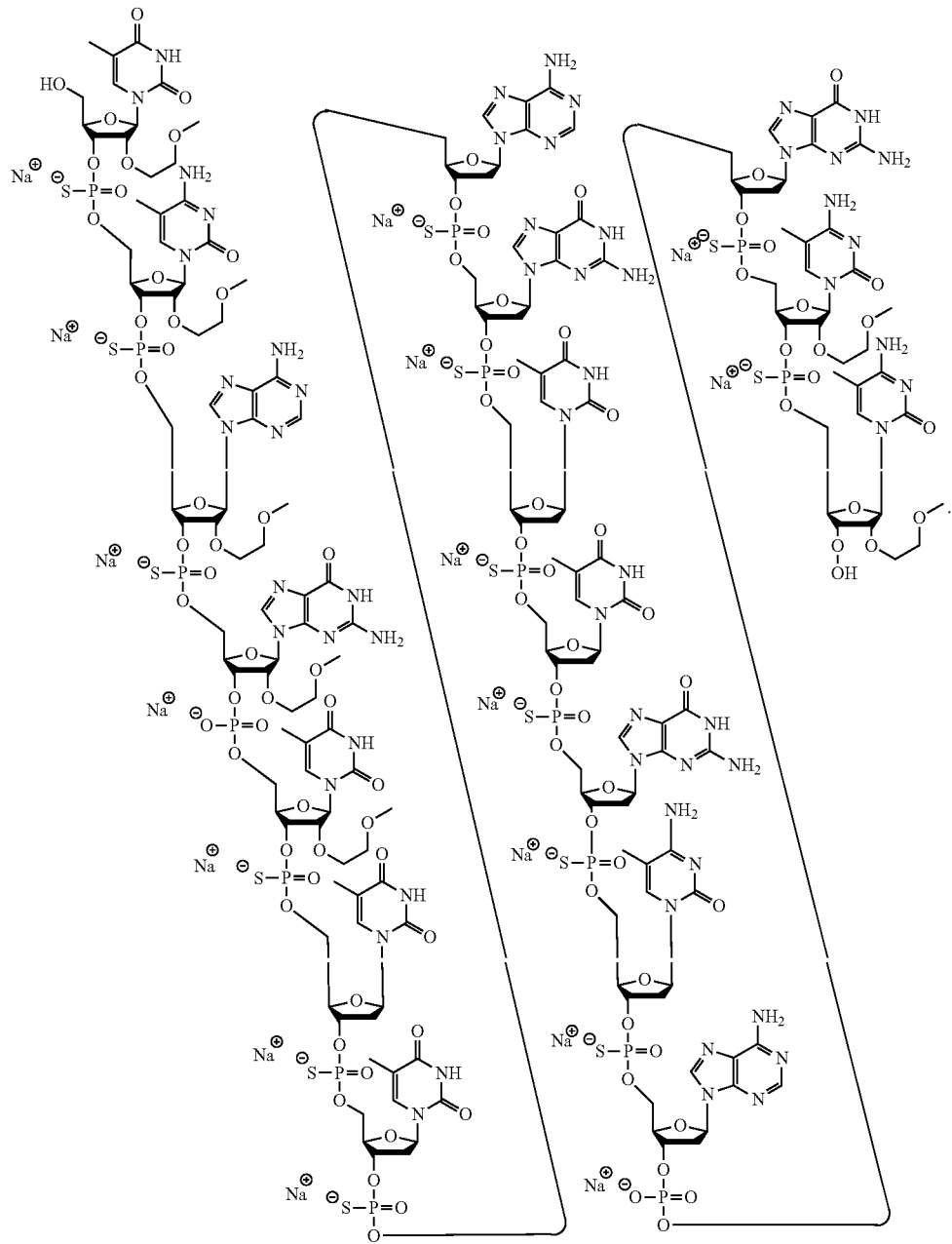

Embodiment 69. The modified oligonucleotide of embodiment 57-62, which is a sodium salt or a potassium salt.

Embodiment 70. A compound comprising a modified oligonucleotide according to the following chemical notation:

(SEQ ID NO: 3671)
Ges $^m$Ceo Aeo $^m$Ceo Ges Gds Tds Ads Tds Tds Ads Gds Tds Gds Tds $^m$Ceo Teo Tes $^m$Ces Ae, wherein,
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D deoxyribosyl sugar moiety,
s=a phosphorothioate internucleoside linkage, and
o=a phosphodiester internucleoside linkage.

Embodiment 71. A compound comprising a modified oligonucleotide according to the following chemical notation:

(SEQ ID NO: 3672)
Ges $^m$Ceo Teo Teo $^m$Ces Tds $^m$Cds Ads Ads Ads Tds $^m$Cds Ads Gds Gds Teo Geo Tes Aes mCe, wherein,
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D deoxyribosyl sugar moiety,
s=a phosphorothioate internucleoside linkage, and
o=a phosphodiester internucleoside linkage.

Embodiment 72. A compound comprising a modified oligonucleotide according to the following chemical notation:

(SEQ ID NO: 3673)
Ges $^m$Ceo $^m$Ceo Teo Tes Tds Ads Tds Ads Ads $^m$Cds Tds Tds Tds Tds $^m$Ceo Teo Tes Tes $^m$Ce, wherein,
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D deoxyribosyl sugar moiety,
s=a phosphorothioate internucleoside linkage, and
o=a phosphodiester internucleoside linkage.

Embodiment 73. A compound comprising a modified oligonucleotide according to the following chemical notation:

(SEQ ID NO: 3674)
Tes Teo $^m$Ceo Aeo Ges Tds Tds Tds Ads Gds Tds Tds Gds $^m$Cds Ads Geo $^m$Ceo $^m$Ces Aes Te, wherein,
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D deoxyribosyl sugar moiety,
s=a phosphorothioate internucleoside linkage, and
o=a phosphodiester internucleoside linkage.

Embodiment 74. A compound comprising a modified oligonucleotide according to the following chemical notation:

(SEQ ID NO: 3670)
$^m$Ces $^m$Ceo $^m$Ceo Geo Tes Ads Tds Tds Tds $^m$Cds $^m$Cds Tds $^m$Cds Tds Tds Ads $^m$Ceo $^m$Ceo Aes Tes $^m$Ce, wherein,
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D deoxyribosyl sugar moiety,
s=a phosphorothioate internucleoside linkage, and
o=a phosphodiester internucleoside linkage.

Embodiment 75. A compound comprising a modified oligonucleotide according to the following chemical notation:

(SEQ ID NO: 3675)
Tes $^m$Ces Aes Geo Tes Tds Tds Ads Gds Tds Tds Gds $^m$Cds Aeo Ges $^m$Ces $^m$Ce, wherein,
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D deoxyribosyl sugar moiety,
s=a phosphorothioate internucleoside linkage, and
o=a phosphodiester internucleoside linkage.

Embodiment 76. The compound of any of embodiments 73-78, comprising the modified oligonucleotide covalently linked to a conjugate group.

Embodiment 77. A chirally enriched population of modified oligonucleotides of any of embodiments 57-68, wherein the population is enriched for modified oligonucleotides comprising at least one particular phosphorothioate internucleoside linkage having a particular stereochemical configuration.

Embodiment 78. The chirally enriched population of embodiment 77, wherein the population is enriched for modified oligonucleotides comprising at least one particular phosphorothioate internucleoside linkage having the (Sp) or (Rp) configuration.

Embodiment 79. The chirally enriched population of embodiment 77, wherein the population is enriched for modified oligonucleotides having a particular, independently selected stereochemical configuration at each phosphorothioate internucleoside linkage.

Embodiment 80. The chirally enriched population of embodiment 77, wherein the population is enriched for modified oligonucleotides having the (Rp) configuration at one particular phosphorothioate internucleoside linkage and the (Sp) configuration at each of the remaining phosphorothioate internucleoside linkages.

Embodiment 81. The chirally enriched population of embodiment 77 wherein the population is enriched for modified oligonucleotides having at least 3 contiguous phosphorothioate internucleoside linkages in the Sp, Sp, and Rp configurations, in the 5' to 3' direction.

Embodiment 82. A population of modified oligonucleotides of any of embodiments 57-68, wherein all of the phosphorothioate internucleoside linkages of the modified oligonucleotide are stereorandom.

Embodiment 83. A pharmaceutical composition comprising the population of modified oligonucleotides of any of embodiments 77-82 and a pharmaceutically acceptable diluent or carrier.

Embodiment 84. A pharmaceutical composition of any of embodiments 62-75, and a pharmaceutically acceptable diluent or carrier.

Embodiment 85. The pharmaceutical composition of embodiment 84, wherein the pharmaceutically acceptable diluent is artificial cerebrospinal fluid or phosphate-buffered saline.

Embodiment 86. The pharmaceutical composition of embodiment 85, wherein the pharmaceutical composition consists essentially of the modified oligonucleotide and artificial cerebrospinal fluid or phosphate-buffered saline.

Embodiment 87. An oligomeric compound comprising a modified oligonucleotide consisting of 12 to 30 linked nucleosides wherein the nucleobase sequence of the modified oligonucleotide is at least 80% complementary to an equal length portion of an ATXN1 nucleic acid, and wherein the modified oligonucleotide comprises at least one modification selected from a modified sugar moiety and a modified internucleoside linkage.

Embodiment 88. The oligomeric compound of embodiment 87, wherein the ATXN1 nucleic acid has the nucleobase sequence of any of SEQ ID NO: 1, SEQ ID NO: 2, SEQ ID NO: 3, SEQ ID NO: 4, SEQ ID NO: 5, or SEQ ID NO: 6.

Embodiment 89. The oligomeric compound of embodiment 87 or embodiment 88, wherein the nucleobase sequence of the modified oligonucleotide is at least 80% complementary to an equal length portion within nucleobases:
an equal length portion of nucleobases 5472-5552 of SEQ ID NO: 1;
an equal length portion of nucleobases 5906-6005 of SEQ ID NO: 1;
an equal length portion of nucleobases 7868-7911 of SEQ ID NO: 1;
an equal length portion of nucleobases 8481-8514 of SEQ ID NO: 1; or
an equal length portion of nucleobases 446679-446706 of SEQ ID NO: 2.

Embodiment 90. The oligomeric compound of any of embodiments 87-89, wherein the nucleobase sequence of the modified oligonucleotide is at least 80% complementary to an equal length portion within nucleobases:
an equal length portion of nucleobases 5489-5508 of SEQ ID NO: 1;
an equal length portion of nucleobases 5491-5507 of SEQ ID NO: 1;
an equal length portion of nucleobases 5912-5931 of SEQ ID NO: 1;
an equal length portion of nucleobases 7892-7911 of SEQ ID NO: 1;
an equal length portion of nucleobases 8481-8500 of SEQ ID NO: 1; or
an equal length portion of nucleobases 446680-446699 of SEQ ID NO: 2.

Embodiment 91. The oligomeric compound of any of embodiments 87-90, wherein the nucleobase sequence of the modified oligonucleotide is at least 85%, at least 90%, at least 95%, or 100% complementary to an equal length portion of the ATXN1 nucleic acid.

Embodiment 92. An oligomeric compound comprising a modified oligonucleotide consisting of 12 to 30 linked nucleosides, wherein the modified oligonucleotide has a nucleobase sequence comprising at least 12, 13, 14, 16, 17, 18, 19, or 20 contiguous nucleobases of any of SEQ ID NOs: 22-3624 or 3655.

Embodiment 93. An oligomeric compound comprising a modified oligonucleotide consisting of 12 to 30 linked nucleosides, wherein the modified oligonucleotide has a nucleobase sequence comprising at least 12, 13, 14, 16, or 17 contiguous nucleobases of any of SEQ ID NOs: 3625-3654 or 3656-3669.

Embodiment 94. The oligomeric compound of embodiment 92 or 93, wherein the modified oligonucleotide has a nucleobase sequence comprising the nucleobase sequence of any of SEQ ID NO: 22-3669.

Embodiment 95. The oligomeric compound of embodiment 94, wherein the modified oligonucleotide has a nucleobase sequence consisting of the nucleobase sequence of any of SEQ ID NO: 22-3669.

Embodiment 96. The oligomeric compound of any of embodiments 92-95, wherein the modified oligonucleotide has a nucleobase sequence comprising at least 8, at least 9, at least 10, at least 11, at least 12, at least 13, at least 14, at least 15, at least 16, or at least 17 contiguous nucleobases of a sequence selected from:
SEQ ID NOs: 196, 274, 352, 430, 508, 2578, 2655, 2732, 2809, 2886, 2963, 3121, 3122, 3190, 3191, 3192, 3262, 3330, 3331, 3332, 3401, 3402, 3575, 3577, 3620, 3624, 3638-3640, 3653-3655, 3662, 3665, 3669;
SEQ ID Nos: 42, 120, 198, 276, 509, 587, 2502, 2579, 2656, 2733, 2810, 2887, 2964, 3585, 3588-3590, 3615, 3618, 3622, 3657, 3660, 3661, 3663, 3664, 3666-3668;
SEQ ID Nos: 48, 126, 2044, 2121;
SEQ ID Nos: 128, 206, 284, 1045, 1122, 1199, and 1276; or SEQ ID Nos: 2475, 2552, 2629, 2706, 2783, 3627-3630, 3644.

Embodiment 97. The oligomeric compound of any of embodiments 92-95, wherein the modified oligonucleotide has a nucleobase sequence comprising at least 8, at least 9, at least 10, at least 11, at least 12, at least 13, at least 14, at least 15, at least 16, or 17 contiguous nucleobases of any of the nucleobase sequences of SEQ ID NO: 3638.

Embodiment 98. The oligomeric compound of any of embodiments 92-95, wherein the modified oligonucleotide has a nucleobase sequence comprising at least 8, at least 9, at least 10, at least 11, at least 12, at least 13, at least 14, at least 15, at least 16, at least 17, at least 18, at least 19, or 20 contiguous nucleobases of any of the nucleobase sequences of SEQ ID NO: 126, 1045, 2552, 3190, or 3590.

Embodiment 99. The oligomeric compound of embodiment 97 or 98, wherein the modified oligonucleotide consists of 17 to 30 linked nucleosides and has a nucleobase sequence comprising the nucleobase sequence of any of 126, 1045, 2552, 3190, 3590, or 3638.

Embodiment 100. The oligomeric compound of embodiment 99, wherein the modified oligonucleotide has a nucleobase sequence consisting of the nucleobase sequence of any one of 126, 1045, 2552, 3190, 3590, or 3638.

Embodiment 101. The oligomeric compound of any of embodiments 92-100, wherein the nucleobase sequence of the modified oligonucleotide is at least 85%, at least 90%, at least 95%, or 100% complementary to an equal length portion of the ATXN1 nucleic acid, wherein the ATXN1 nucleic acid has the nucleobase sequence of SEQ ID NO: 1, SEQ ID NO: 2, SEQ ID NO: 3, SEQ ID NO: 4, SEQ ID NO: 5, or SEQ ID NO: 6.

Embodiment 102. The oligomeric compound of any of embodiments 87-101, wherein at least one nucleoside of the modified oligonucleotide comprises a modified sugar moiety.

Embodiment 103. The oligomeric compound of embodiment 102, wherein the modified sugar moiety comprises a bicyclic sugar moiety.

Embodiment 104. The oligomeric compound of embodiment 103, wherein the bicyclic sugar moiety comprises a 2'-4' bridge selected from —O—CH$_2$—; and —O—CH(CH$_3$)—.

Embodiment 105. The oligomeric compound of any of embodiments 102-104, wherein the modified nucleoside comprises a non-bicyclic modified sugar moiety.

Embodiment 106. The oligomeric compound of embodiment 105, wherein the non-bicyclic modified sugar moiety is a 2'-MOE sugar moiety or 2'-OMe modified sugar moiety.

Embodiment 107. The oligomeric compound of any of embodiments 102-106, wherein at least one nucleoside of the modified oligonucleotide comprises a sugar surrogate.

Embodiment 108. The oligomeric compound of embodiment 107, wherein the sugar surrogate is selected from morpholino and PNA.

Embodiment 109. The oligomeric compound of any of embodiments 87-102 or 105-108, wherein the modified oligonucleotide does not comprise a bicyclic sugar moiety.

Embodiment 110. The oligomeric compound of any of embodiments 87-109, wherein the modified oligonucleotide comprises at least one modified internucleoside linkage.

Embodiment 111. The oligomeric compound of embodiment 110, wherein at least one modified internucleoside linkage is a phosphorothioate internucleoside linkage.

Embodiment 112. The oligomeric compound of embodiment 110 or 111, wherein each internucleoside linkage is a modified internucleoside linkage.

Embodiment 113. The oligomeric compound of embodiment 112, wherein each internucleoside linkage is a phosphorothioate internucleoside linkage.

Embodiment 114. The oligomeric compound of any of embodiments 110-111, wherein at least one internucleoside linkage of the modified oligonucleotide is a phosphodiester internucleoside linkage.

Embodiment 115. The oligomeric compound of any of embodiments 87-109, wherein each internucleoside linkage of the modified oligonucleotide is independently selected from a phosphodiester or a phosphorothioate internucleoside linkage.

Embodiment 116. The oligomeric compound of any of embodiments 87-115, wherein at least 10, at least 11, at least 12, at least 13, at least 14, at least 15, at least 16, at least 17, or at least 18 internucleoside linkages of the modified oligonucleotide are phosphorothioate internucleoside linkages.

Embodiment 117. The oligomeric compound of embodiment 116, wherein the modified oligonucleotide has an internucleoside linkage motif selected from: sooosssssssssssoooss, sssosssssssssssosss, sssossssssssssoss, or sooooosssssssssssoss; wherein,
s=a phosphorothioate internucleoside linkage and o=a phosphodiester internucleoside linkage.

Embodiment 118. The oligomeric compound of any of embodiments 87-117, wherein the modified oligonucleotide comprises a modified nucleobase.

Embodiment 119. The oligomeric compound of embodiment 118, wherein the modified nucleobase is a 5-methyl cytosine.

Embodiment 120. The oligomeric compound of any of embodiments 1-33, wherein the modified oligonucleotide comprises a deoxy region consisting of 5-12 contiguous 2'-deoxynucleosides.

Embodiment 121. The oligomeric compound of embodiment 120, wherein each nucleoside of the deoxy region is a 2'-β-D-deoxynucleoside.

Embodiment 122. The oligomeric compound of embodiment 120 or 121 wherein the deoxy region consists of 6, 7, 8, 9, 10, or 6-10 linked nucleosides.

Embodiment 123. The oligomeric compound of any of embodiments 120-122, wherein each nucleoside immediately adjacent to the deoxy region comprises a modified sugar moiety.

Embodiment 124. The oligomeric compound of any of embodiments 120-122, wherein the deoxy region is flanked on the 5'-side by a 5'-region consisting of 1-6 linked 5'-region nucleosides and on the 3'-side by a 3' external region consisting of 1-6 linked 3'-region nucleosides; wherein
the 3'-most nucleoside of the 5'-region comprises a modified sugar moiety; and
the 5'-most nucleoside of the 3'-region comprises a modified sugar moiety.

Embodiment 125. The oligomeric compound of embodiment 124, wherein each nucleoside of the 3'-region comprises a modified sugar moiety.

Embodiment 126. The oligomeric compound of embodiment 124 or 125, wherein each nucleoside of the 5'-region comprises a modified sugar moiety.

Embodiment 127. The oligomeric compound of embodiment 120-126, wherein the modified oligonucleotide has
a 5'-region consisting of 1-6 linked nucleosides;
a deoxy region consisting of 6-10 linked nucleosides; and
a 3'-region consisting of 1-6 linked nucleosides; wherein
each of the 5'-region nucleosides and each of the 3'-region nucleosides comprises a modified sugar moiety.

Embodiment 128. The oligomeric compound of embodiment 127, wherein the modified oligonucleotide has
a 5'-region consisting of 6 linked nucleosides;
a deoxy region consisting of 10 linked nucleosides; and
a 3'-region consisting of 4 linked nucleosides; wherein
each of the 5'-region nucleosides and each of the 3'-region nucleosides is a 2'-MOE nucleoside, and
each of the deoxy region nucleosides is a 2'-β-D-deoxynucleoside.

Embodiment 129. The oligomeric compound of embodiment 127, wherein the modified oligonucleotide has
a 5'-region consisting of 5 linked nucleosides;
a central region consisting of 10 linked nucleosides; and a 3'-region consisting of 5 linked nucleosides; wherein each of the 5'-region nucleosides and each of the 3'-region nucleosides is a 2'-MOE nucleoside, and each of the deoxy region nucleosides is a 2'-β-D-deoxynucleoside.

Embodiment 130. The oligomeric compound of embodiment 127, wherein the modified oligonucleotide has
a 5'-region consisting of 5 linked nucleosides;
a deoxy region consisting of 8 linked nucleosides; and
a 3'-region consisting of 4 linked nucleosides; wherein each of the 5'-region nucleosides and each of the 3'-region nucleosides is a 2'-MOE nucleoside, and each of the deoxy region nucleosides is a 2'-β-D-deoxynucleoside.

Embodiment 131. The oligomeric compound of embodiment 127, wherein the modified oligonucleotide has
a 5'-region consisting of 5 linked nucleosides;
a deoxy region consisting of 8 linked nucleosides; and
a 3'-region consisting of 4 linked nucleosides; wherein each of the 5'-region nucleosides is a 2'-MOE nucleoside, each of the 3'-region nucleosides is selected from a 2'-MOE nucleoside and a cEt nucleoside, and each of the deoxy region nucleosides is a 2'-β-D-deoxynucleoside.

Embodiment 132. The oligomeric compound of any of embodiments 87-119, wherein the modified oligonucleotide has
a 5' region consisting of 3-7 linked nucleosides;
a deoxy region consisting of 6-8 linked nucleosides; and
a 3' region consisting of 3-6 linked nucleosides; wherein
each of the 3' region nucleosides is selected from a 2'-MOE nucleoside and a cEt nucleoside, and the region has the following formula:

(N$k$)$n$(N$d$)(N$x$)

wherein each Nk is a bicyclic nucleoside, Nx is a 2'-OMe nucleoside and Nd is a 2'-β-D-deoxynucleoside;
and n is from 1-5.

Embodiment 133. The oligomeric compound of any of embodiments 87-119, wherein the modified oligonucleotide has
a 5' region consisting of 7 linked nucleosides;
a deoxy region consisting of 6 linked nucleosides; and
a 3' region consisting of 4 linked nucleosides; wherein each of the 3' region nucleosides is selected from a 2'-MOE nucleoside and a cEt nucleoside, and the region has the following formula:

(N$k$)$n$(N$d$)(N$x$)

wherein each Nk is a bicyclic nucleoside, Nx is a 2'-OMe nucleoside and Nd is a 2'-β-D-deoxynucleoside;
and n is from 5.

Embodiment 134. The oligomeric compound of any of embodiments 87-133, wherein the modified oligonucleotide consists of 12-30, 12-22, 12-20, 14-18, 16-18, 14-20, 15-17, 15-25, 16-20, or 17-20 linked nucleosides.

Embodiment 135. The oligomeric compound of any of embodiments 87-132, wherein the modified oligonucleotide consists of 18-22 or 18-20 linked nucleosides.

Embodiment 136. The oligomeric compound of any of embodiments 87-133, wherein the modified oligonucleotide consists of 17 linked nucleosides.

Embodiment 137. The oligomeric compound of any of embodiments 87-132, wherein the modified oligonucleotide consists of 20 linked nucleosides.

Embodiment 138. A compound comprising a modified oligonucleotide according to the following chemical notation:

(SEQ ID NO: 3671)
Ges $^m$Ceo Aeo $^m$Ceo Ges Gds Tds Ads Tds Tds Ads Gds

Tds Gds Tds $^m$Ceo Teo Tes $^m$Ces Ae, wherein,
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D deoxyribosyl sugar moiety,
s=a phosphorothioate internucleoside linkage, and
o=a phosphodiester internucleoside linkage.

Embodiment 139. A compound comprising a modified oligonucleotide according to the following chemical notation:

(SEQ ID NO: 3672)
Ges $^m$Ceo Teo Teo $^m$Ces Tds $^m$Cds Ads Ads Ads Tds $^m$Cds Ads Gds Gds Teo Geo Tes Aes $^m$Ce, wherein,
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D deoxyribosyl sugar moiety,
s=a phosphorothioate internucleoside linkage, and
o=a phosphodiester internucleoside linkage.

Embodiment 140. A compound comprising a modified oligonucleotide according to the following chemical notation:

(SEQ ID NO: 3673)
Ges $^m$Ceo $^m$Ceo Teo Tes Tds Ads Tds Ads Ads $^m$Cds

Tds Tds Tds Tds $^m$Ceo Teo Tes Tes $^m$Ce, wherein,
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D deoxyribosyl sugar moiety,
s=a phosphorothioate internucleoside linkage, and
o=a phosphodiester internucleoside linkage.

Embodiment 141. A compound comprising a modified oligonucleotide according to the following chemical notation:

(SEQ ID NO: 3674)
Tes Teo $^m$Ceo Aeo Ges Tds Tds Tds Ads Gds Tds Tds

Gds $^m$Cds Ads Geo $^m$Ceo $^m$Ces Aes Te, wherein,
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D deoxyribosyl sugar moiety,
s=a phosphorothioate internucleoside linkage, and
o=a phosphodiester internucleoside linkage.

Embodiment 142. A compound comprising a modified oligonucleotide according to the following chemical notation:

(SEQ ID NO: 3670)
$^m$Ces $^m$Ceo $^m$Ceo Geo Tes Ads Tds Tds $^m$Cds $^m$Cds Tds $^m$Cds Tds Tds Ads $^m$Ceo $^m$Ceo Aes Tes $^m$Ce, wherein,
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D deoxyribosyl sugar moiety,
s=a phosphorothioate internucleoside linkage, and
o=a phosphodiester internucleoside linkage.

Embodiment 143. A compound comprising a modified oligonucleotide according to the following chemical notation:

(SEQ ID NO: 3675)
Tes $^m$Ces Aes Geo Tes Tds Tds Ads Gds Tds Tds Gds $^m$Cds Aeo Ges $^m$Ces $^m$Ce, wherein,
A=an adenine nucleobase,
$^m$=a 5-methyl cytosine nucleobase,
G=a guanine nucleobase,
T=a thymine nucleobase,
e=a 2'-MOE sugar moiety,
d=a 2'-β-D deoxyribosyl sugar moiety,
s=a phosphorothioate internucleoside linkage, and
o=a phosphodiester internucleoside linkage.

Embodiment 144. The oligomeric compound of any of embodiments 87-143, consisting of the modified oligonucleotide.

Embodiment 145. The oligomeric compound of any of embodiments 87-144, comprising a conjugate group comprising a conjugate moiety and a conjugate linker.

Embodiment 146. The oligomeric compound of embodiment 145, wherein the conjugate linker consists of a single bond.

Embodiment 147. The oligomeric compound of embodiment 145, wherein the conjugate linker is cleavable.

Embodiment 148. The oligomeric compound of embodiment 145, wherein the conjugate linker comprises 1-3 linker nucleosides.

Embodiment 149. The oligomeric compound of any of embodiments 145-148, wherein the conjugate linker does not comprise any linker nucleosides.

Embodiment 150. The oligomeric compound of any of embodiments 145-148, wherein the conjugate group is attached to the modified oligonucleotide at the 5'-end of the modified oligonucleotide.

Embodiment 151. The oligomeric compound of any of embodiments 145-148, wherein the conjugate group is attached to the modified oligonucleotide at the 3'-end of the modified oligonucleotide.

Embodiment 152. The oligomeric compound of any of embodiments 87-143 or 146-148, comprising a terminal group.

Embodiment 153. The oligomeric compound of embodiment 152, wherein the terminal group is an abasic sugar moiety.

Embodiment 154. The oligomeric compound of any of embodiments 87-153 wherein the oligomeric compound is a singled-stranded oligomeric compound.

Embodiment 155. A modified oligonucleotide according to the following chemical structure:

(SEQ ID NO: 3671)

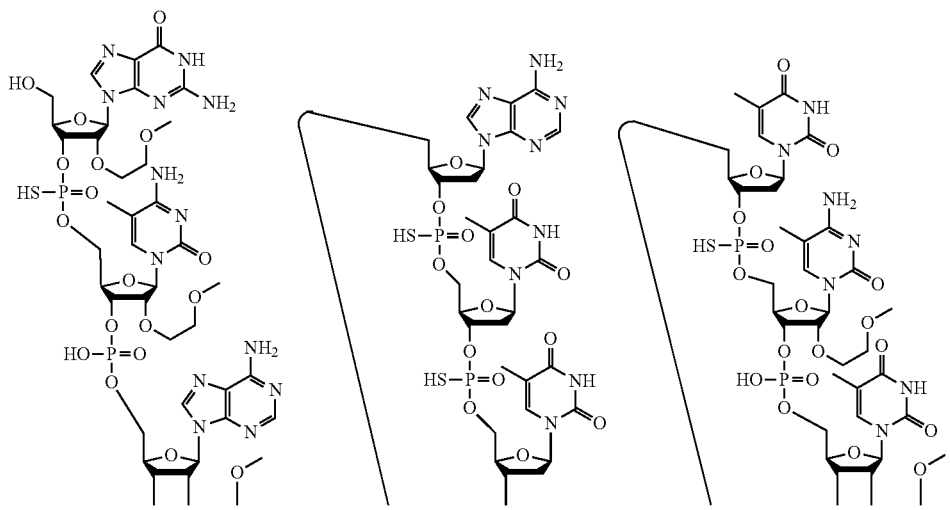

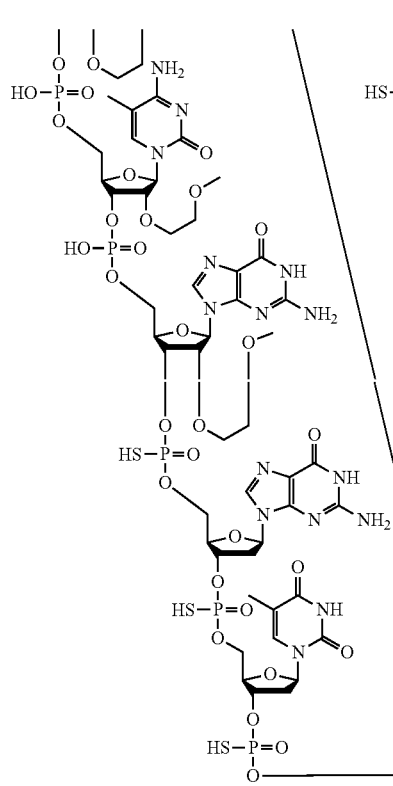
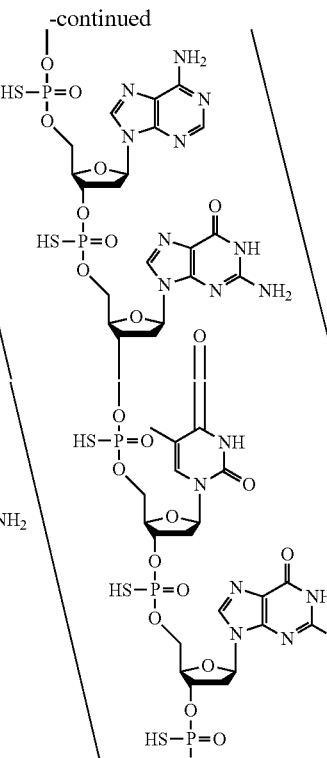
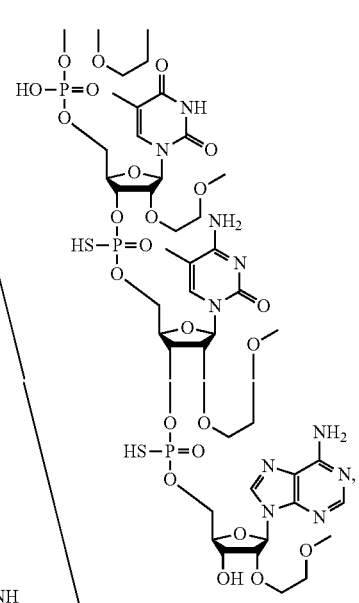
or a salt thereof.
Embodiment 156. A modified oligonucleotide according to the following chemical structure:
(SEQ ID NO: 3672)
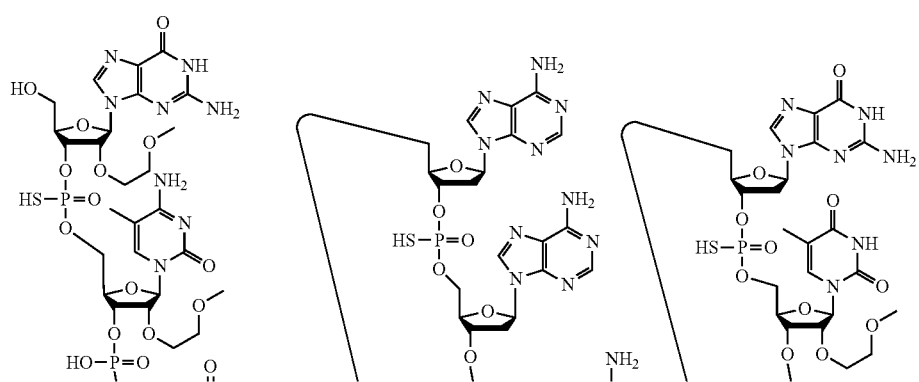

49
50
-continued
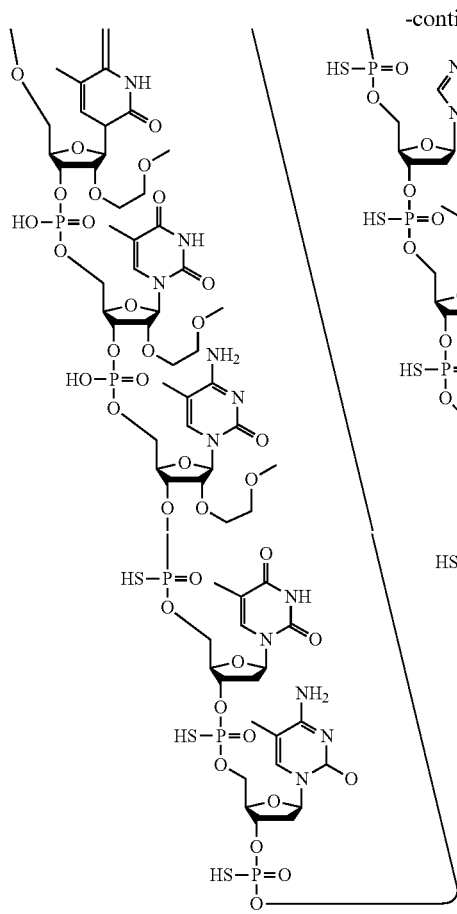
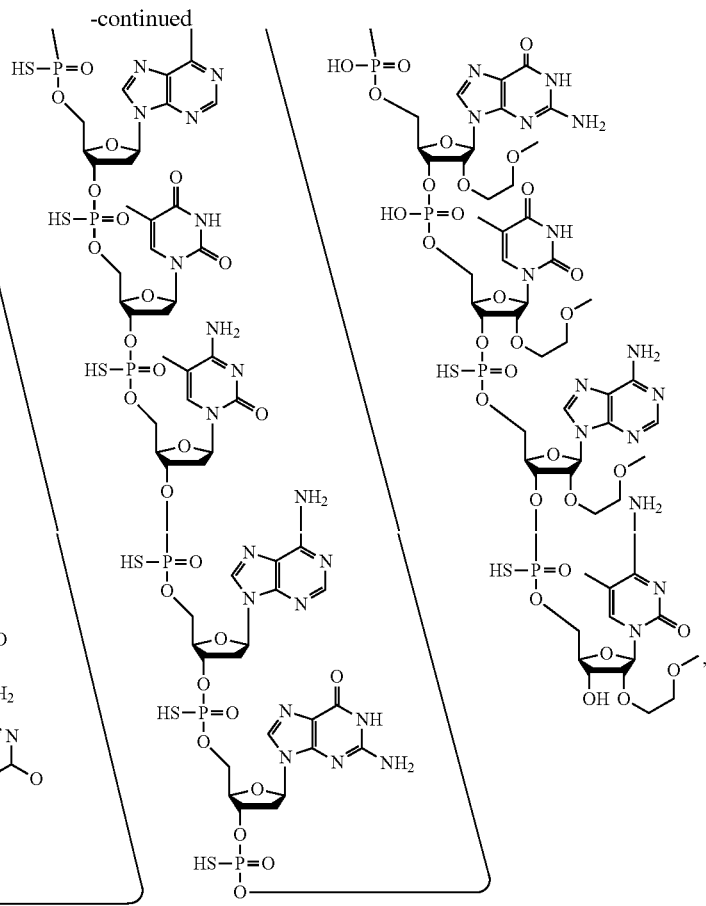
or a salt thereof.
Embodiment 157. A modified oligonucleotide according to the following chemical structure:
(SEQ ID NO: 3673)
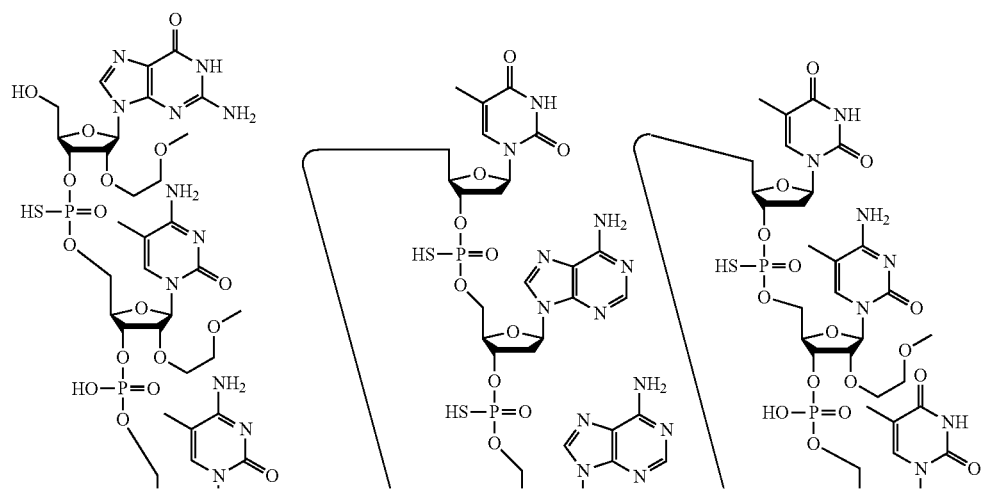

51
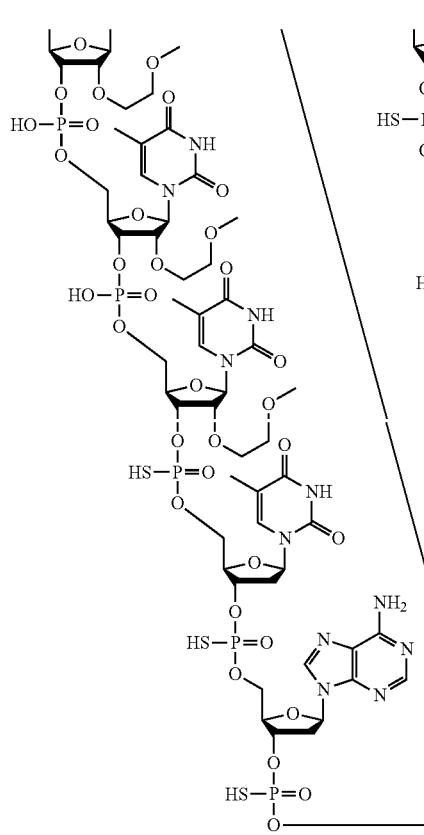
-continued
52
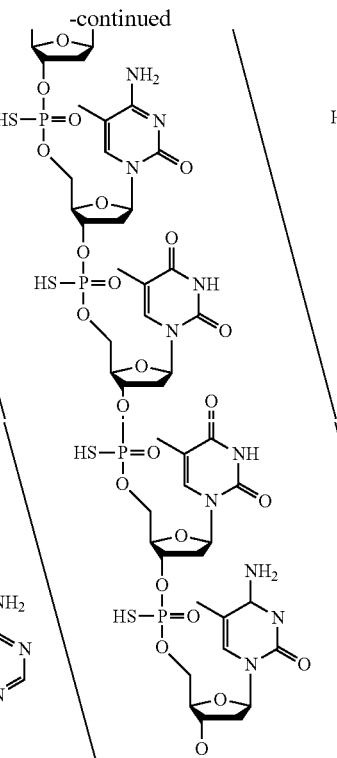
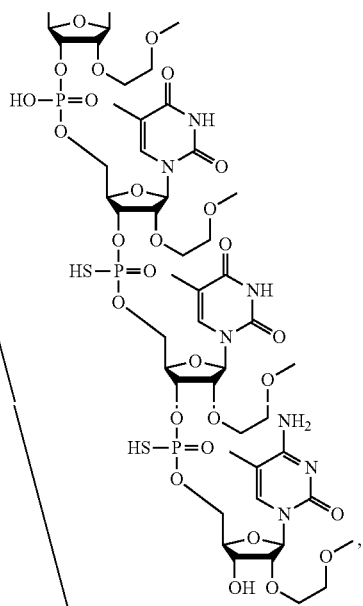
or a salt thereof.
Embodiment 158. A modified oligonucleotide according to the following chemical structure:
(SEQ ID NO: 3674)
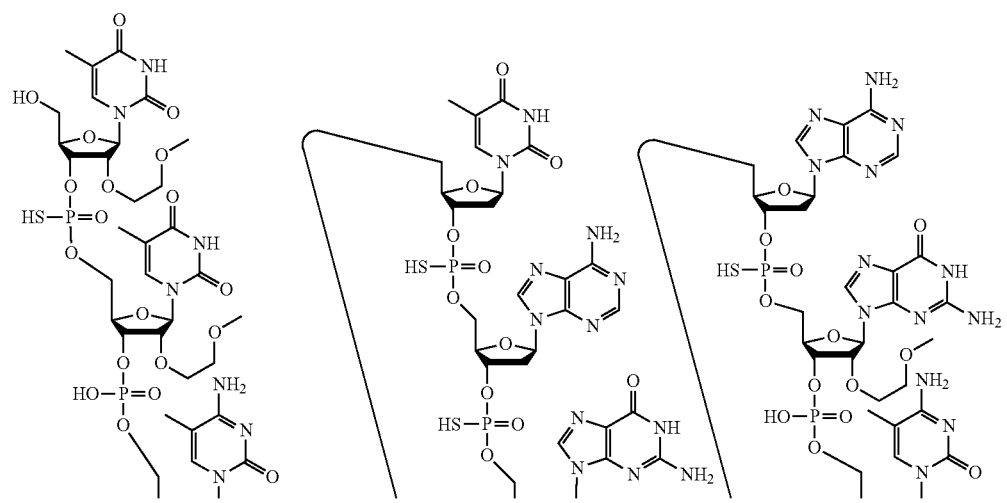

-continued
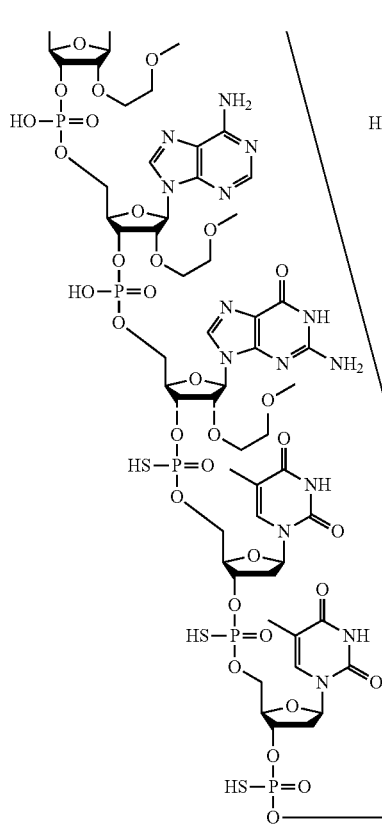
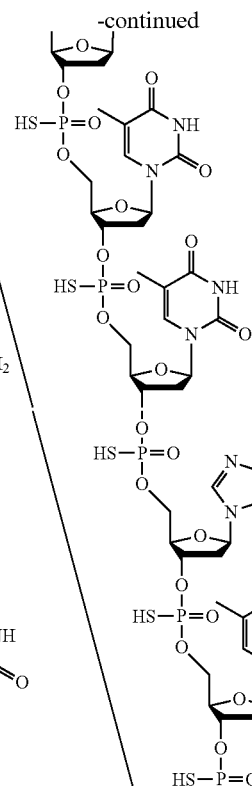
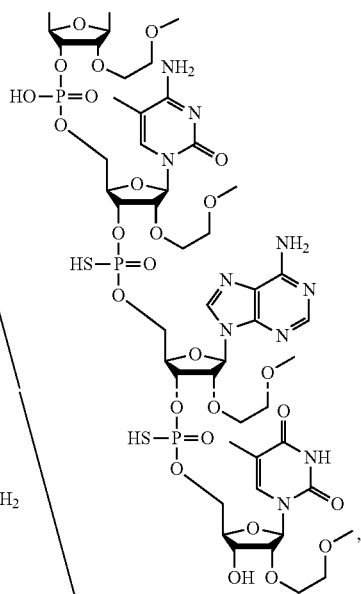
or a salt thereof.
Embodiment 159. A modified oligonucleotide according to the following chemical structure:
(SEQ ID NO: 3670)
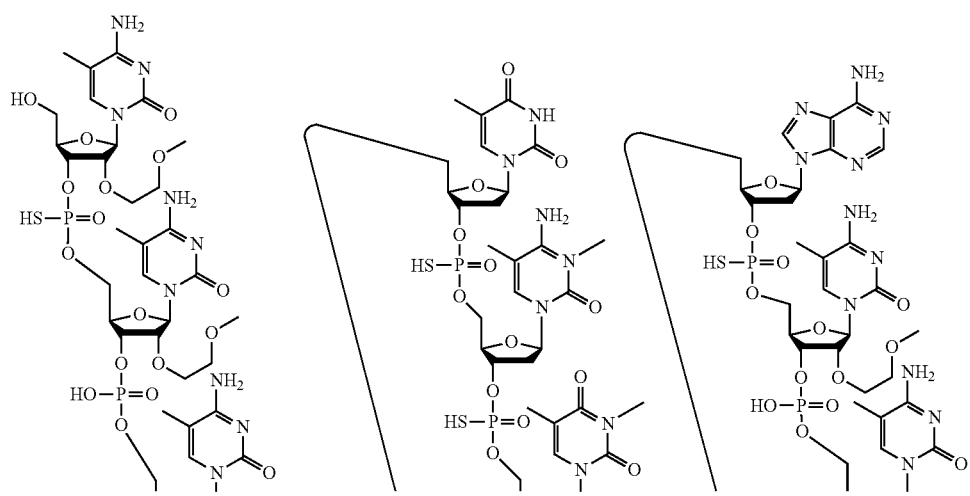

-continued
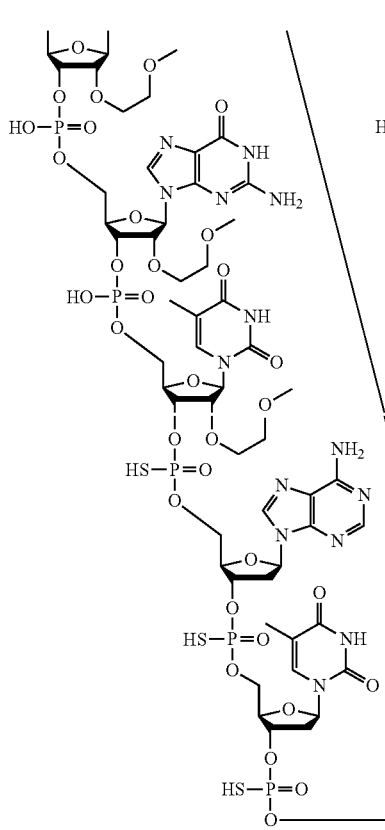
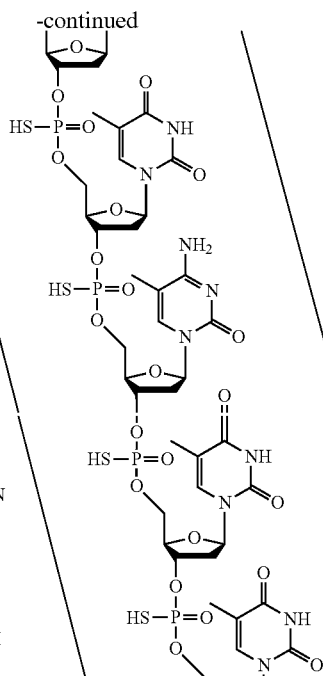
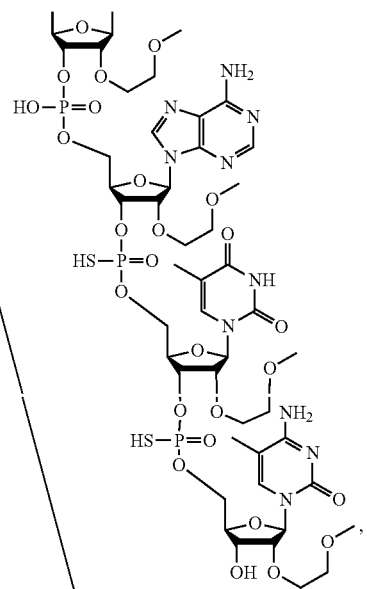
or a salt thereof.
Embodiment 160. A modified oligonucleotide according to the following chemical structure:
(SEQ ID NO: 3675)
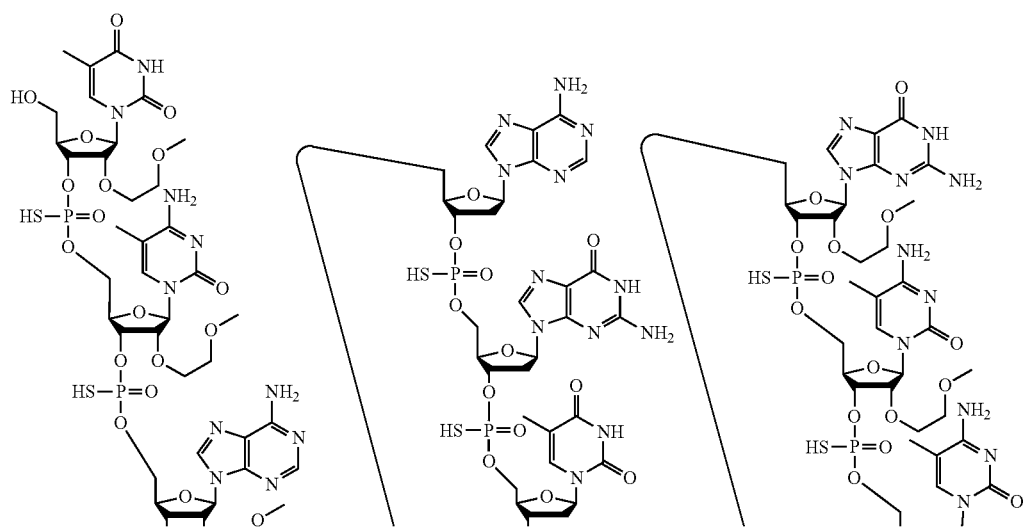

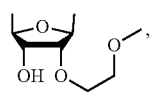
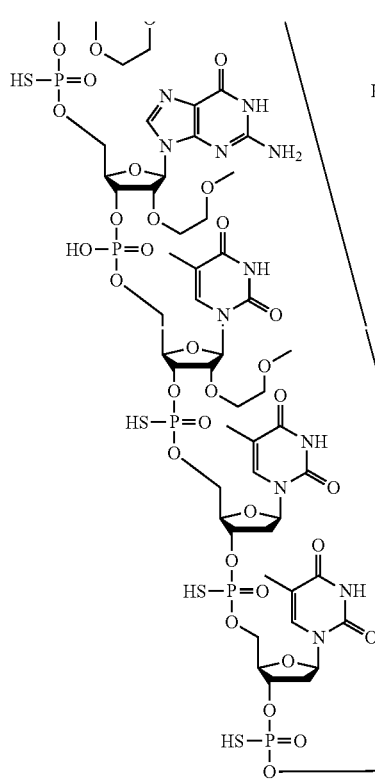
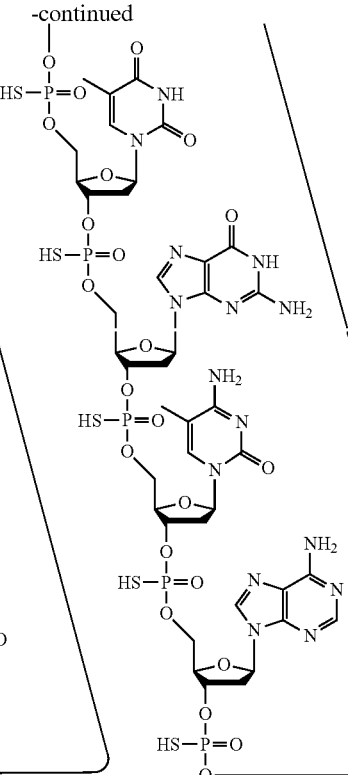
or a salt thereof.
Embodiment 161. The modified oligonucleotide of any of embodiments 155-160, which is the sodium salt or the potassium salt.
Embodiment 162. A modified oligonucleotide according to the following chemical structure:
(SEQ ID NO: 3671)
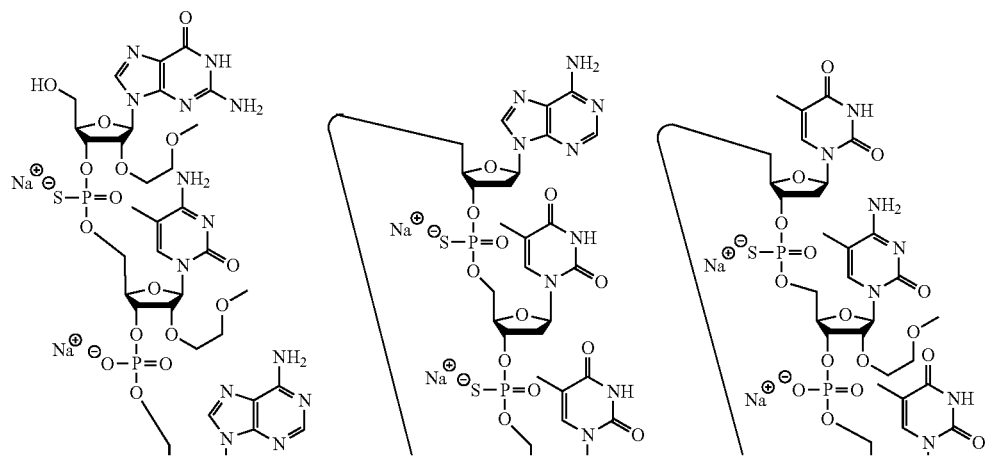

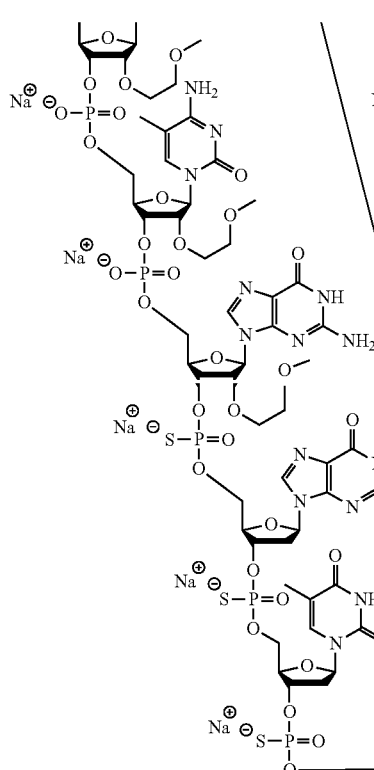
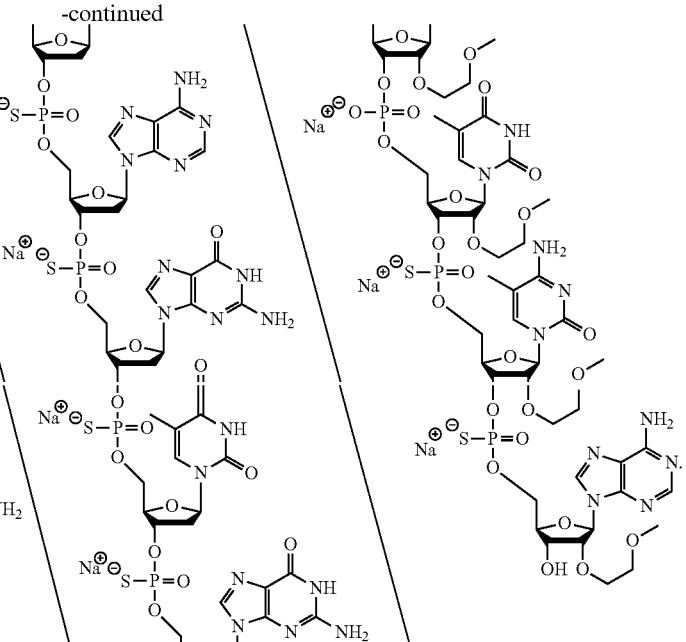
Embodiment 163. A modified oligonucleotide according to the following chemical structure:
(SEQ ID NO: 3672)
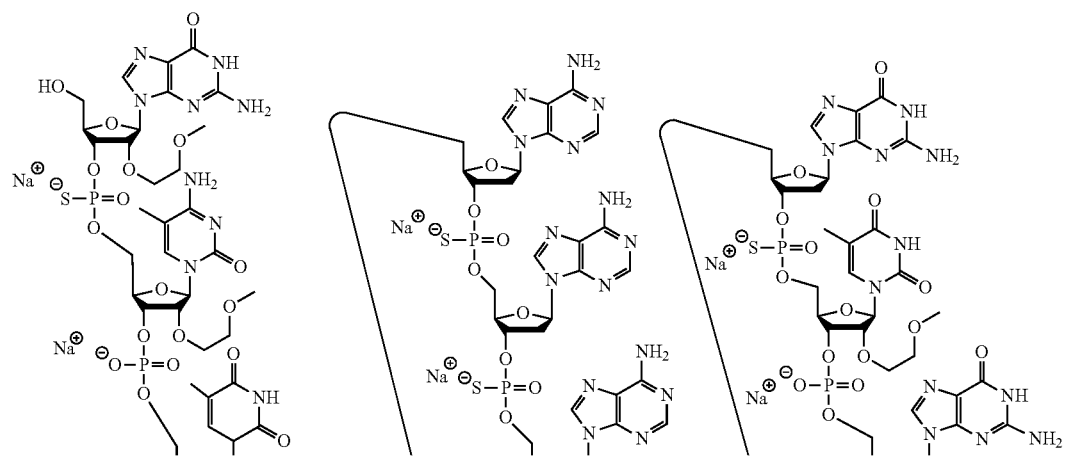

61
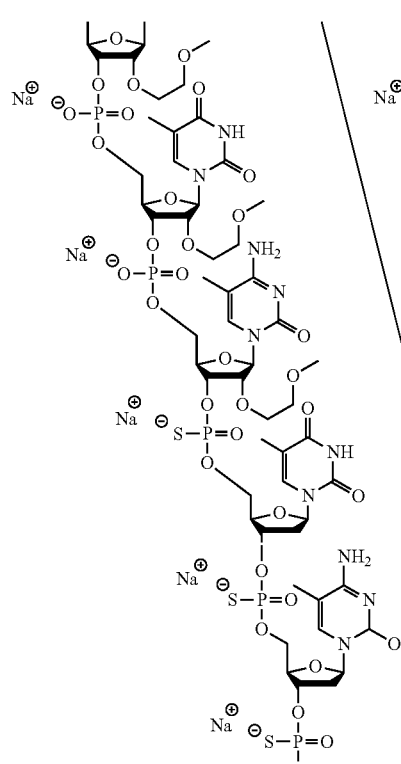
-continued
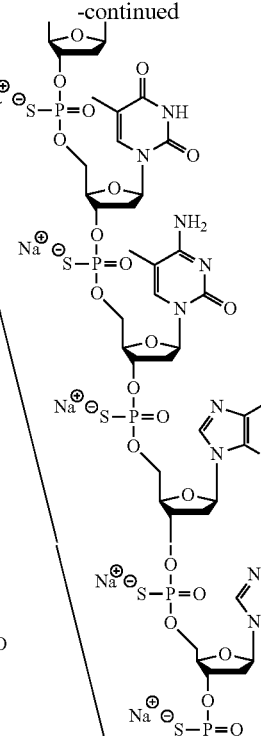
62
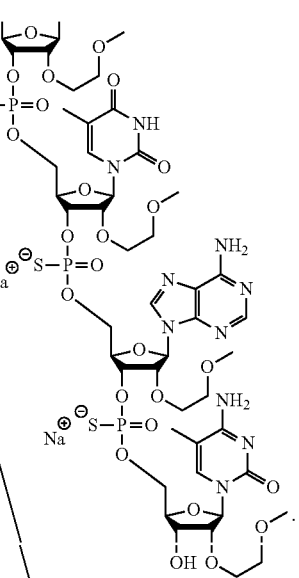
Embodiment 164. A modified oligonucleotide according to the following chemical structure:
(SEQ ID NO: 3673)
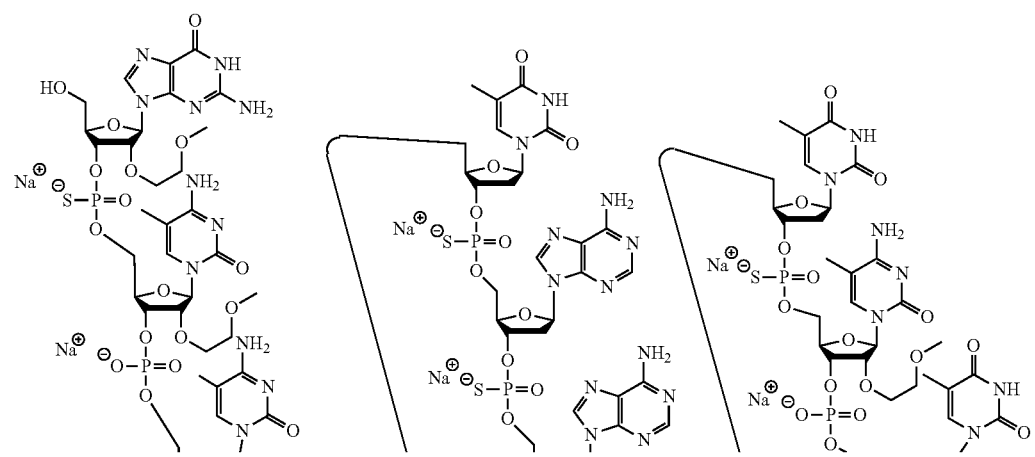

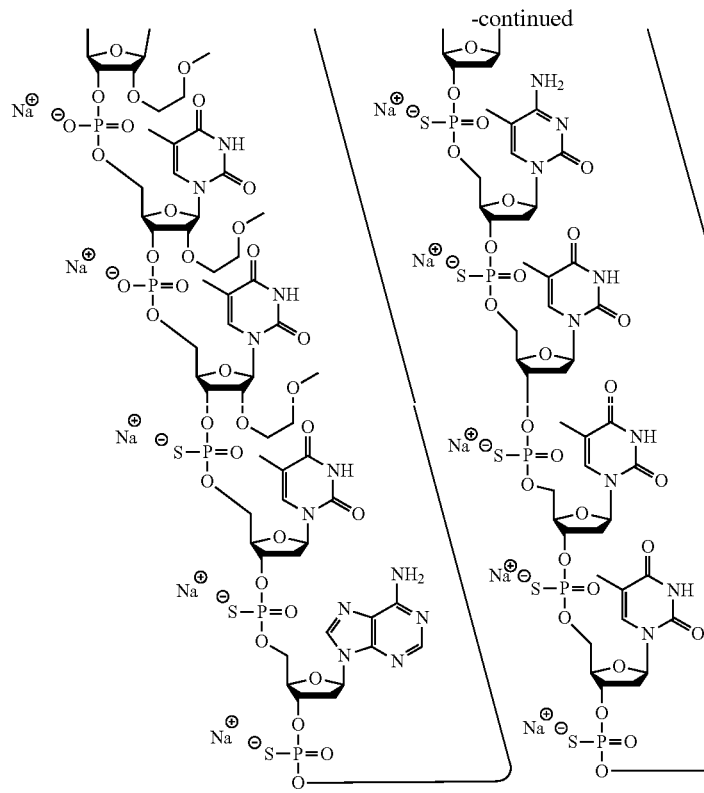
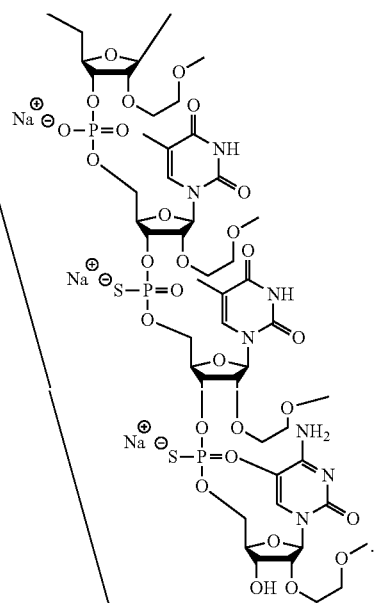
Embodiment 165. A modified oligonucleotide according to the following chemical structure:
(SEQ ID NO: 3674)
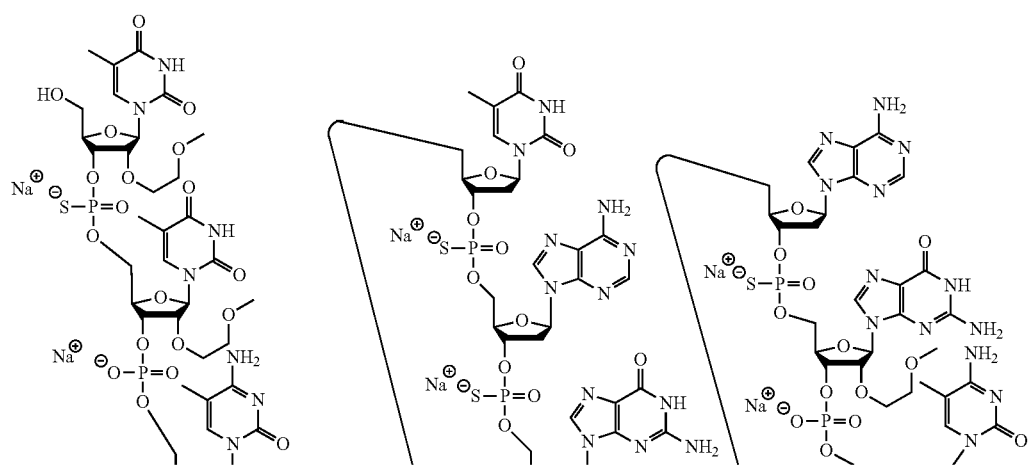

65 66
-continued
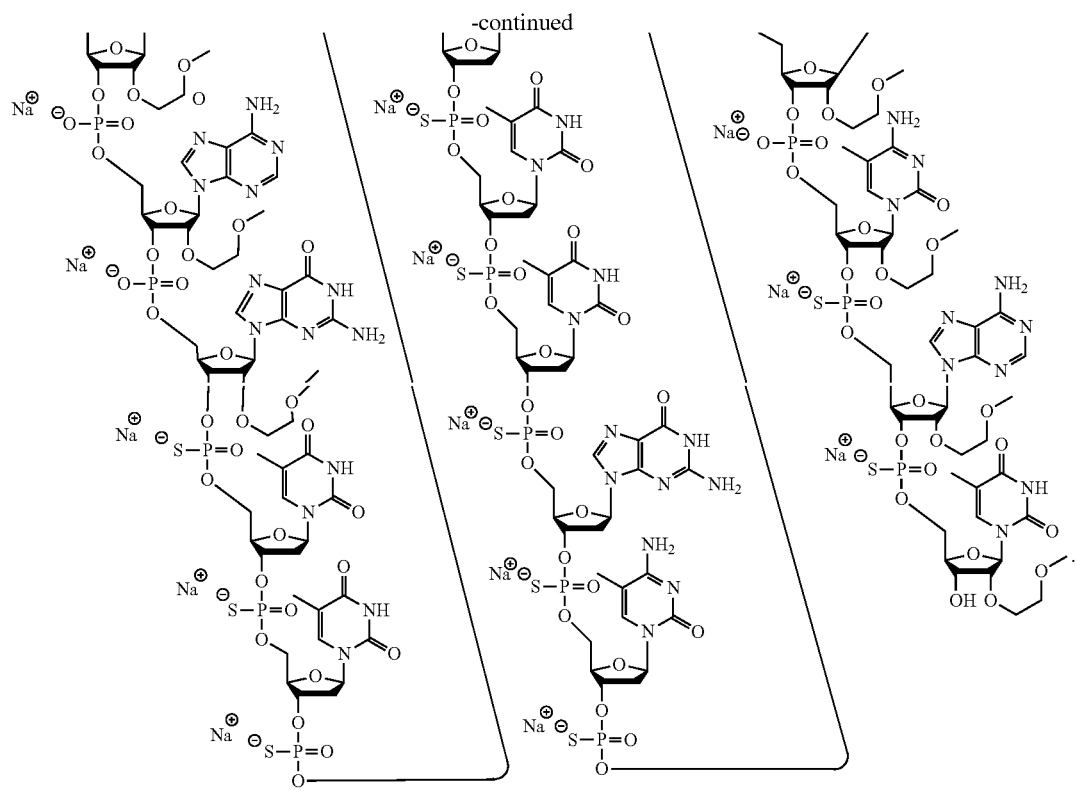
Embodiment 166. A modified oligonucleotide according to the following chemical structure:
(SEQ ID NO: 3670)
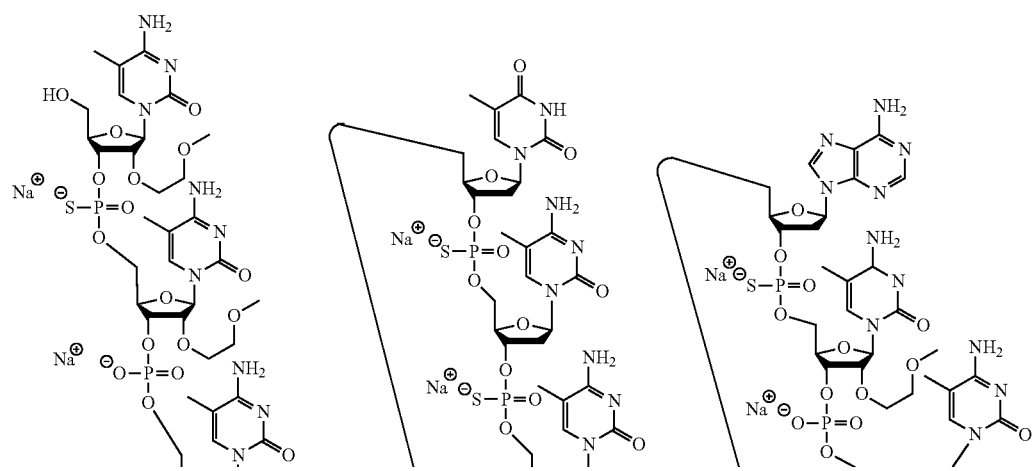

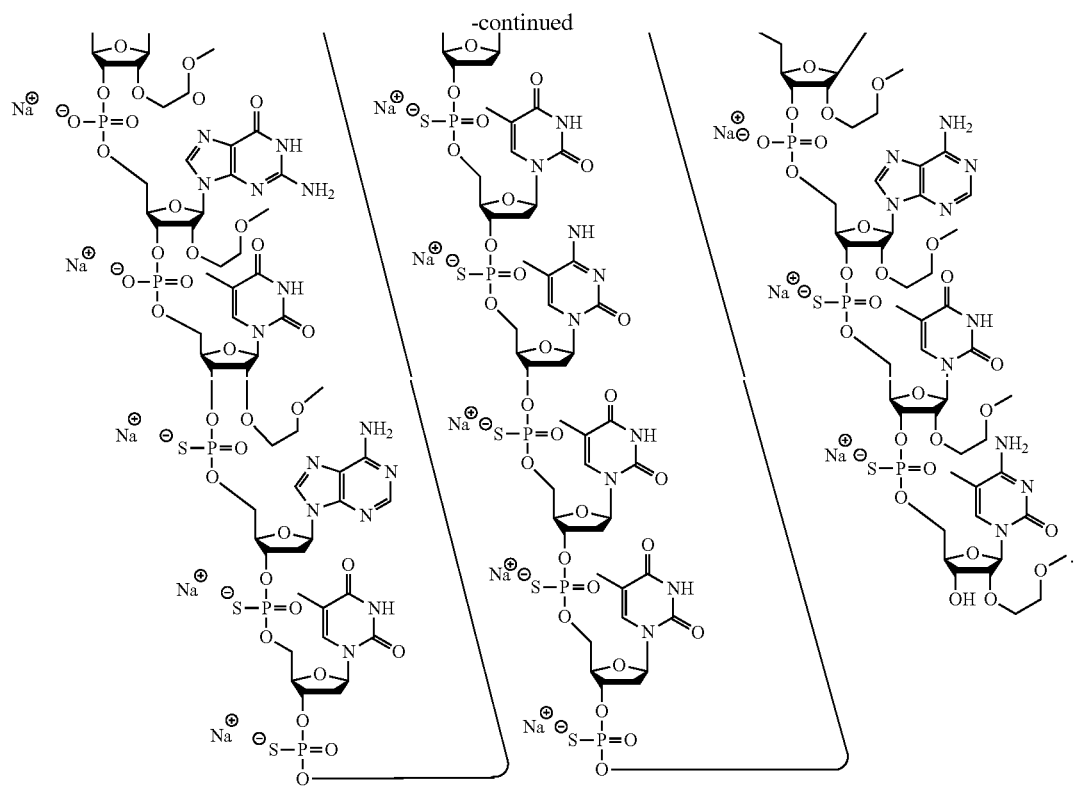
Embodiment 167. A modified oligonucleotide according to the following chemical structure:
(SEQ ID NO: 3675)
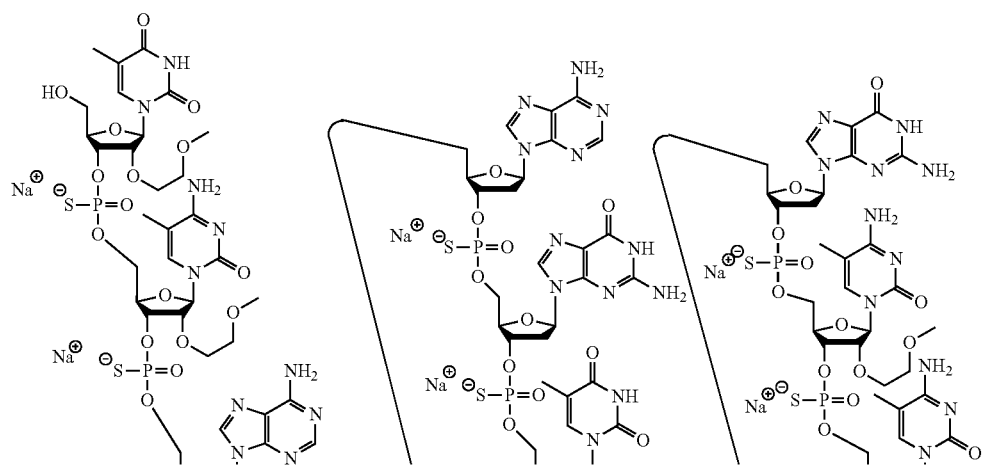

-continued

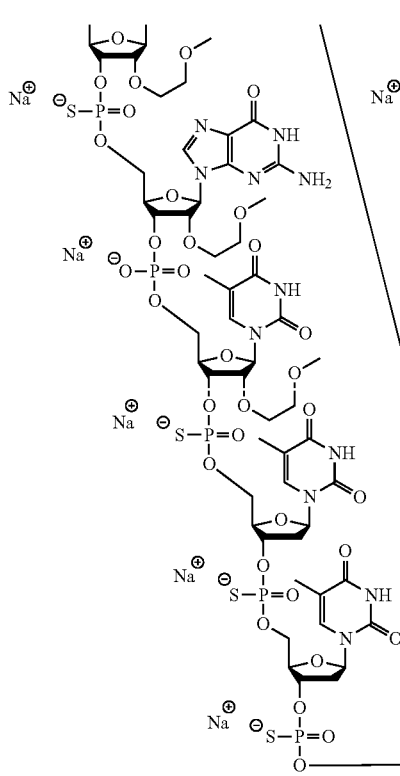
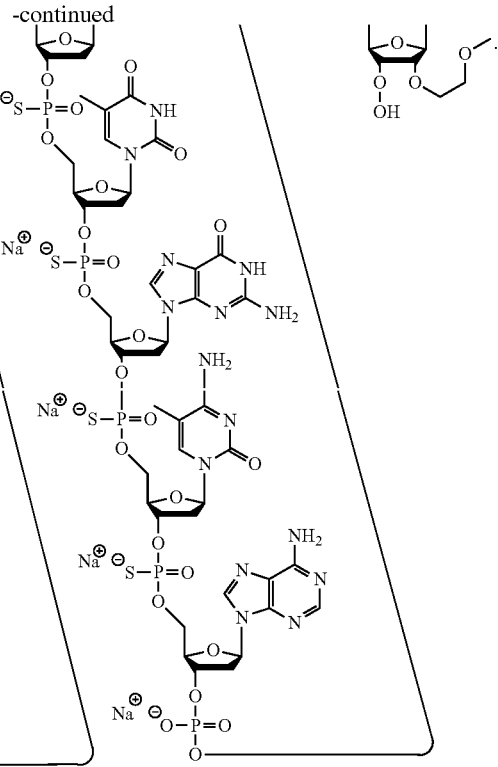

Embodiment 168. A chirally enriched population of oligomeric compounds of any of embodiments 87-154 or modified oligonucleotide of embodiments 155-167, wherein the population is enriched for modified oligonucleotides comprising at least one particular phosphorothioate internucleoside linkage having a particular stereochemical configuration.

Embodiment 169. The chirally enriched population of embodiment 168, wherein the population is enriched for modified oligonucleotides comprising at least one particular phosphorothioate internucleoside linkage having the (Sp) or (Rp) configuration.

Embodiment 170. The chirally enriched population of embodiment 169, wherein the population is enriched for modified oligonucleotides having a particular, independently selected stereochemical configuration at each phosphorothioate internucleoside linkage.

Embodiment 171. The chirally enriched population of embodiment 170, wherein the population is enriched for modified oligonucleotides having the (Rp) configuration at one particular phosphorothioate internucleoside linkage and the (Sp) configuration at each of the remaining phosphorothioate internucleoside linkages.

Embodiment 172. The chirally enriched population of embodiment 171, wherein the population is enriched for modified oligonucleotides having at least 3 contiguous phosphorothioate internucleoside linkages in the Sp, Sp, and Rp configurations, in the 5' to 3' direction.

Embodiment 173. A population of oligomeric compounds comprising modified oligonucleotides of any of embodiments 87-154, or a population of modified oligonucleotides of embodiments 155-167, wherein all of the phosphorothioate internucleoside linkages of the modified oligonucleotide are stereorandom.

Embodiment 174. An oligomeric duplex, comprising a first oligomeric compound and a second oligomeric compound comprising a second modified oligonucleotide, wherein the first oligomeric compound is an oligomeric compound of any of embodiments 87-154.

Embodiment 175. The oligomeric duplex of embodiment 174, wherein the second oligomeric compound comprises a second modified oligonucleotide consisting of 12 to 30 linked nucleosides, and wherein the nucleobase sequence of the second modified oligonucleotide comprises a complementary region of at least 8 nucleobases that is at least 90% complementary to an equal length portion of the first modified oligonucleotide.

Embodiment 176. The oligomeric duplex of embodiment 174 or 175, wherein the modified oligonucleotide of the first oligomeric compound comprises a 5'-stabilized phosphate group.

Embodiment 177. The oligomeric duplex of embodiment 176, wherein the stabilized phosphate group comprises a cyclopropyl phosphonate or a vinyl phosphonate.

Embodiment 178. The oligomeric duplex of any of embodiments 174-177, wherein the modified oligonucleotide of the first oligomeric compound comprises a glycol nucleic acid (GNA) sugar surrogate.

Embodiment 179. The oligomeric duplex of any of embodiments 174-178, wherein the modified oligonucleotide of the first oligomeric compound comprises a 2'-NMA sugar moiety.

Embodiment 180. The oligomeric duplex of any of embodiments 174-179, wherein at least one nucleoside of the second modified oligonucleotide comprises a modified sugar moiety.

Embodiment 181. The oligomeric duplex of embodiment 180, wherein the modified sugar moiety of the second modified oligonucleotide comprises a bicyclic sugar moiety.

Embodiment 182. The oligomeric duplex of embodiment 181, wherein the bicyclic sugar moiety of the second modified oligonucleotide comprises a 2'-4' bridge selected from —O—CH$_2$—; and —O—CH(CH$_3$)—.

Embodiment 183. The oligomeric duplex of embodiment 182, wherein the modified sugar moiety of the second modified oligonucleotide comprises a non-bicyclic modified sugar moiety.

Embodiment 184. The oligomeric duplex of embodiment 183, wherein the non-bicyclic modified sugar moiety of the second modified oligonucleotide is a 2'-MOE sugar moiety, a 2'-F sugar moiety, or 2'-OMe sugar moiety.

Embodiment 185. The oligomeric duplex of any of embodiments 174-184, wherein at least one nucleoside of the second modified oligonucleotide comprises a sugar surrogate.

Embodiment 186. The oligomeric duplex of any of embodiments 174-185, wherein at least one internucleoside linkage of the second modified oligonucleotide is a modified internucleoside linkage.

Embodiment 187. The oligomeric duplex of embodiment 186, wherein at least one modified internucleoside linkage of the second modified oligonucleotide is a phosphorothioate internucleoside linkage.

Embodiment 188. The oligomeric duplex of any of embodiments 174-187, wherein at least one internucleoside linkage of the second modified oligonucleotide is a phosphodiester internucleoside linkage.

Embodiment 189. The oligomeric duplex of any of embodiments 174-188, wherein each internucleoside linkage of the second modified oligonucleotide is independently selected from a phosphodiester or a phosphorothioate internucleoside linkage.

Embodiment 190. The oligomeric duplex of any of embodiments 174-189, wherein each internucleoside linkage of the second modified oligonucleotide is independently selected from a phosphodiester internucleoside linkage, a phosphorothioate internucleoside linkage, or a mesyl phosphoramidate internucleoside linkage.

Embodiment 191. The oligomeric duplex of any of embodiments 174-190, wherein the second modified oligonucleotide comprises at least one modified nucleobase.

Embodiment 192. The oligomeric duplex of embodiment 191, wherein the modified nucleobase of the second modified oligonucleotide is 5-methylcytosine.

Embodiment 193. The oligomeric duplex of any of embodiments 174-192, wherein the second modified oligonucleotide comprises a conjugate group.

Embodiment 194. The oligomeric duplex of embodiment 193, wherein the conjugate group comprises a conjugate linker and a conjugate moiety.

Embodiment 195. The oligomeric duplex of embodiment 193 or 194, wherein the conjugate group is attached to the second modified oligonucleotide at the 5'-end of the second modified oligonucleotide.

Embodiment 196. The oligomeric duplex of embodiment 193 or 194, wherein the conjugate group is attached to the second modified oligonucleotide at the 3'-end of the modified oligonucleotide.

Embodiment 197. The oligomeric duplex of any of embodiments 193-196, wherein the second modified oligonucleotide comprises a terminal group.

Embodiment 198. The oligomeric duplex of embodiment 197, wherein the terminal group is an abasic sugar moiety.

Embodiment 199. The oligomeric duplex of any of embodiments 174-198, wherein the second modified oligonucleotide consists of 10 to 25, 10 to 30, 10 to 50, 12 to 20, 12 to 25, 12 to 30, 12 to 50, 13 to 20, 13 to 25, 13 to 30, 13 to 50, 14 to 20, 14 to 25, 14 to 30, 14 to 50, 15 to 20, 15 to 25, 15 to 30, 15 to 50, 16 to 18, 16 to 20, 16 to 25, 16 to 30, 16 to 50, 17 to 20, 17 to 25, 17 to 30, 17 to 50, 18 to 20, 18 to 25, 18 to 30, 18 to 50, 19 to 19 to 25, 19 to 30, 19 to 50, 20 to 25, 20 to 30, 20 to 50, 21 to 25, 21 to 30, 21 to 50, 22 to 25, 22 to 30, 22 to 50, 23 to 25, 23 to 30, or 23 to 50 linked nucleosides.

Embodiment 200. An antisense agent comprising an antisense compound, wherein the antisense compound is the oligomeric compound of any of embodiments 87-154 or the modified oligonucleotide of any of embodiments 155-167.

Embodiment 201. The antisense agent of embodiment 200, wherein the antisense agent is the oligomeric duplex of any of embodiments 174-199.

Embodiment 202. The antisense agent of embodiment 200 or 201, wherein the antisense agent is an RNase H agent capable of reducing the amount of ATXN1 nucleic acid through the activation of RNase H.

Embodiment 203. The antisense agent of any of embodiments 200-202, wherein the conjugate group comprises a cell-targeting moiety.

Embodiment 204. A pharmaceutical composition comprising an oligomeric compound of any of embodiments 87-154, the modified oligonucleotide of any of embodiments 155-167, the population of any of embodiments 168-173, an oligomeric duplex of any of embodiments 174-199, or an antisense agent of any of embodiments 200-203, and a pharmaceutically acceptable carrier or diluent.

Embodiment 205. The pharmaceutical composition of embodiment 204, wherein the pharmaceutically acceptable diluent is water, phosphate-buffered saline, or artificial cerebral spinal fluid.

Embodiment 206. The pharmaceutical composition of embodiment 205, wherein the pharmaceutical composition consists essentially of the modified oligonucleotide and artificial cerebral spinal fluid.

Embodiment 207. A method comprising administering to a subject the oligomeric compound of any of embodiments 87-154, the modified oligonucleotide of any of embodiments 155-167, the population of any of embodiments 168-173, the oligomeric duplex of any of embodiments 174-199, the antisense agent of any of embodiments 200-203, or the pharmaceutical composition of any of embodiments 204-206.

Embodiment 208. A method of treating a disease associated with ATXN1 comprising administering to a subject having a disease associated with ATXN1 a therapeutically effective amount of the oligomeric compound of any of embodiments 87-154, the modified oligonucleotide of any of embodiments 155-167, the population of any of embodiments 168-173, the oligomeric duplex of any of embodiments 174-199, the antisense agent of any of embodiments 200-203, or the pharmaceutical composition of any of embodiments 204-206; thereby treating the disease associated with ATXN1.

Embodiment 209. The method of embodiment 208, wherein the ATXN1-associated disease is Spinocerebellar ataxia type 1.

Embodiment 210. The method of any of embodiments 208-209, wherein at least one symptom or hallmark of the ATXN1-associated disease is ameliorated.

Embodiment 211. The method of embodiment 210, wherein the symptom or hallmark is gait or limb ataxia, cognitive impairments, difficulty with speaking or swallowing, atrophy of the cerebellum and/or brainstem in magnetic resonance imaging (MRI), neurochemical abnormalities in the cerebellum and/or brainstem detected via magnetic resonance spectroscopy (MRS), or death within 10-15 years of symptom onset.

Embodiment 212. The method of any of embodiments 208-211, wherein ATXN1 levels in the subject are reduced.

Embodiment 213. A method of reducing expression of ATXN1 in a cell comprising contacting the cell with the oligomeric compound of any of embodiments 87-154, the modified oligonucleotide of any of embodiments 155-167, the population of any of embodiments 168-173, the oligomeric duplex of any of embodiments 174-199, the antisense agent of any of embodiments 200-203, or the pharmaceutical composition of any of embodiments 204-206.

Embodiment 214. The method of embodiment 213, wherein the cell is a CNS cell.

Embodiment 215. Use of the oligomeric compound of any of embodiments 87-154, the modified oligonucleotide of any of embodiments 155-167, the population of any of embodiments 168-173, the oligomeric duplex of any of embodiments 174-199, the antisense agent of any of embodiments 200-203, or the pharmaceutical composition of any of embodiments 204-206 for treating a disease associated with ATXN1.

Embodiment 216. Use of the oligomeric compound of any of embodiments 87-154, the modified oligonucleotide of any of embodiments 155-167, the population of any of embodiments 168-173, the oligomeric duplex of any of embodiments 174-199, the antisense agent of any of embodiments 200-203, or the pharmaceutical composition of any of embodiments 204-206 in the manufacture of a medicament for treating a disease associated with ATXN1.

Embodiment 217. The use of embodiment 215 or 216, wherein the disease associated with ATXN1 is Spinocerebellar ataxia type 1.

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE" or "O-methoxyethyl"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside comprises a sugar moiety comprising a non-bridging 2'-substituent group selected from: F, OCH$_3$, and OCH$_2$CH$_2$OCH$_3$.

In certain embodiments, modified furanosyl sugar moieties and nucleosides incorporating such modified furanosyl sugar moieties are further defined by isomeric configuration. For example, a 2'-deoxyfuranosyl sugar moiety may be in seven isomeric configurations other than the naturally occurring β-D-deoxyribosyl configuration. Such modified sugar moieties are described in, e.g., WO 2019/157531, incorporated by reference herein. A 2'-modified sugar moiety has an additional stereocenter at the 2'-position relative to a 2'-deoxyfuranosyl sugar moiety; therefore, such sugar moieties have a total of sixteen possible isomeric configurations. 2'-modified sugar moieties described herein are in the β-D-ribosyl isomeric configuration unless otherwise specified.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt"), 4'-CH$_2$—O—CH$_2$-2', 4'- CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., *J. Org. Chem.*, 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O- 2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129, 8362-8379; Wengel et al., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

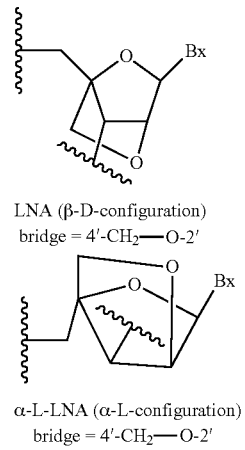

LNA (β-D-configuration)
bridge = 4'-CH$_2$—O-2'

α-L-LNA (α-L-configuration)
bridge = 4'-CH$_2$—O-2'

α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("NINA") (see, e.g., Leumann, CJ. *Bioorg. & Med. Chem.* 2002, 10, 841-854), fluoro HNA:

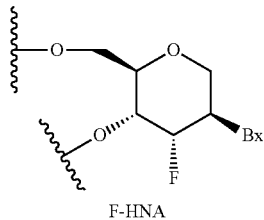

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

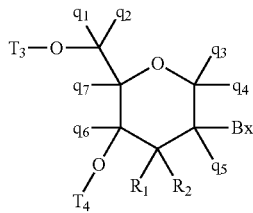

wherein, independently, for each of the modified THP nucleosides:
  Bx is a nucleobase moiety;
  $T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;
  $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and
    each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

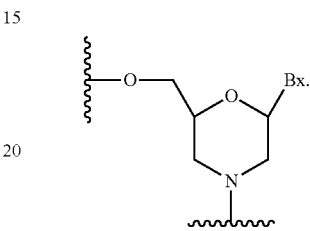

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Certain Modified Nucleobases

In certain embodiments, modified oligonucleotides comprise one or more nucleosides comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH₃) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphodiesters, which contain a phosphodiester bond ("P(O$_2$)=O") (also referred to as unmodified or naturally occurring linkages), phosphotriesters, methylphosphonates, phosphoramidates, and phosphorothioates ("P(O$_2$)=S"), and phosphorodithioates ("HS—P=S"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphodiester internucleoside linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkage in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACCS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

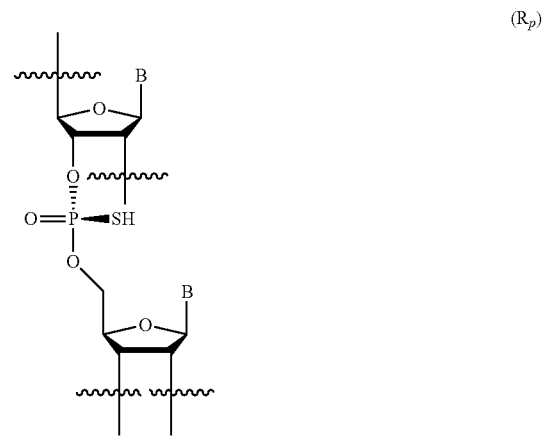

(R$_p$)

-continued

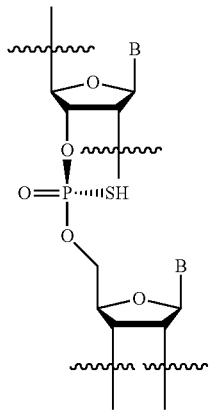

(S$_p$)

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl (MOP), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts. In certain embodiments, a neutral internucleoside linkage is any of those described in WO 2021/030778, incorporated by reference herein.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or portion thereof in a defined pattern or sugar motif. In certain instances, such sugar motifs include but are not limited to any of the sugar modifications discussed herein.

In certain embodiments, modified oligonucleotides have a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-6 nucleosides. In certain embodiments, each nucleoside of each wing of a gapmer comprises a modified sugar moiety. In certain embodiments, at least one nucleoside of each wing of a gapmer comprises a modified sugar moiety. In certain embodiments, at least two nucleosides of each wing of a gapmer comprises a modified sugar moiety. In certain embodiments, at least three nucleosides of each wing of a gapmer comprises a modified sugar moiety. In certain embodiments, at least four nucleosides of each wing of a gapmer comprises a modified sugar moiety. In certain embodiments, at least five nucleosides of each wing of a gapmer comprises a modified sugar moiety.

In certain embodiments, the gap of a gapmer comprises 7-12 nucleosides. In certain embodiments, each nucleoside of the gap of a gapmer comprises a 2'-deoxyribosyl sugar moiety. In certain embodiments, each nucleoside of the gap of a gapmer comprises a 2'-β-D-deoxyribosyl sugar moiety. In certain embodiments, at least one nucleoside of the gap of a gapmer comprises a modified sugar moiety. In certain embodiments, at least one nucleoside of the gap of a gapmer comprises a 2'-OMe sugar moiety.

In certain embodiments, the gapmer is a deoxy gapmer. In certain embodiments, the nucleosides on the gap side of each wing/gap junction comprise 2'-deoxyribosyl sugar moieties and the nucleosides on the wing sides of each wing/gap junction comprise modified sugar moieties. In certain embodiments, each nucleoside of the gap comprises a 2'-deoxyribosyl sugar moiety. In certain embodiments, each nucleoside of each wing of a gapmer comprises a modified sugar moiety. In certain embodiments, one nucleoside of the gap comprises a modified sugar moiety and each remaining nucleoside of the gap comprises a 2'-deoxyribosyl sugar moiety.

In certain embodiments, modified oligonucleotides comprise or consist of a portion having a fully modified sugar motif. In such embodiments, each nucleoside of the fully modified portion of the modified oligonucleotide comprises a modified sugar moiety. In certain embodiments, each nucleoside of the entire modified oligonucleotide comprises a modified sugar moiety. In certain embodiments, modified oligonucleotides comprise or consist of a portion having a fully modified sugar motif, wherein each nucleoside within the fully modified portion comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified oligonucleotide comprises the same 2'-modification.

Herein, the lengths (number of nucleosides) of the three regions of a gapmer may be provided using the notation [#of nucleosides in the 5'-wing]–[#of nucleosides in the gap]–[#of nucleosides in the 3'-wing]. Thus, a 5-10-5 gapmer consists of 5 linked nucleosides in each wing and 10 linked nucleosides in the gap. Where such nomenclature is followed by a specific modification, that modification is the modification in each sugar moiety of each wing and the gap nucleosides comprises a 2'-β-D-deoxyribosyl sugar moiety. Thus, a 5-10-5 MOE gapmer consists of 5 linked 2'-MOE nucleosides in the 5'-wing, 10 linked a 2'-β-D-deoxynucleosides in the gap, and 5 linked 2'-MOE nucleosides in the 3'-wing. A 3-10-3 cEt gapmer consists of 3 linked cEt nucleosides in the 5'-wing, 10 linked 2'-β-D-deoxynucleosides in the gap, and 3 linked cEt nucleosides in the 3'-wing. A 5-8-5 gapmer consists of 5 linked nucleosides comprising a modified sugar moiety in the 5'-wing, 8 linked a 2'-β-D-deoxynucleosides in the gap, and 5 linked nucleosides comprising a modified sugar moiety in the 3'-wing. A 5-8-5 or 5-8-4 mixed wing gapmer has at least two different modified sugar moieties in the 5'- and/or the 3'-wing.

In certain embodiments, modified oligonucleotides are 5-10-5 MOE gapmers. In certain embodiments, modified oligonucleotides are 6-10-4 MOE gapmers. In certain embodiments, modified oligonucleotides are 5-8-4 MOE gapmers. In certain embodiments, modified oligonucleotides are X—Y—Z MOE gapmers, wherein X and Z are independently selected from 1, 2, 3, 4, 5, 6, or 7 linked 2'-MOE nucleosides and Y is selected from 7, 8, 9, 10, or 11. linked deoxynucleosides.

In certain embodiments, modified oligonucleotides have a sugar motif selected from the following (5' to 3'): eeeeeddddddddkkee or eeeeedyddddddkkee, wherein 'd' represents a 2'-deoxyribosyl sugar moiety, 'e' represents a 2'-MOE sugar moiety, 'k' represents a cEt sugar moiety, and 'y' represents a 2'-OMe sugar moiety.

2. Certain Nucleobase Motifs

In certain embodiments, oligonucleotides comprise modified and/or unmodified nucleobases arranged along the oligonucleotide or portion thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl sugar moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or portion thereof in a defined pattern or motif. In certain embodiments, each internucleoside linking group is a phosphodiester internucleoside linkage ($P(O_2)=O$). In certain embodiments, each internucleoside linking group of a modified oligonucleotide is a phosphorothioate internucleoside linkage ($P(O_2)=S$). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, all of the internucleoside linkages are either phosphodiester internucleoside linkages or phosphorothioate internucleoside linkages, and the chiral motif is (5' to 3'): Sp-o-o-o-Sp-Sp-Sp-Rp-Sp-Sp-Rp-Sp-Sp-Sp-Sp-Sp-Sp-Sp-Sp or Sp-o-o-o-Sp-Sp-Sp-Rp-Sp-Sp-Sp-Sp-Sp-Sp-Sp-Sp-Sp-Sp, wherein each 'Sp' represents a (Sp) phosphorothioate internucleoside linkage, each 'Rp' is a Rp internucleoside linkage, and each 'o' represents a phosphodiester internucleoside linkage. In certain embodiments, populations of modified oligonucleotides are enriched for modified oligonucleotides comprising such internucleoside linkage motifs.

In certain embodiments, modified oligonucleotides have an internucleoside linkage motif of sooossssssssssssooss, wherein each "s" represents a phosphorothioate internucleoside linkage and each "o" represents a phosphodiester internucleoside linkage. In certain embodiments, modified oligonucleotides have an internucleoside linkage motif of (5' to 3'): sooooossssssssssoss, wherein each "s" represents a phosphorothioate internucleoside linkage and each "o" represents a phosphodiester internucleoside linkage. In certain embodiments, modified oligonucleotides have an internucleoside linkage motif of (5' to 3'): sssosssssssssssosss, wherein each "s" represents a phosphorothioate internucleoside linkage and each "o" represents a phosphodiester internucleoside linkage. In certain embodiments, modified oligonucleotides have an internucleoside linkage motif of (5' to 3'): sssosssssssssssoss, wherein each "s" represents a phosphorothioate internucleoside linkage and each "o" represents a phosphodiester internucleoside linkage.

C. Certain Lengths

It is possible to increase or decrease the length of an oligonucleotide without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target nucleic acid in an oocyte injection model. Oligonucleotides 25 nucleobases in length with 8 or 11 mismatch bases near the ends of the oligonucleotides were able to direct specific cleavage of the target nucleic acid, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

D. Certain Modified Oligonucleotides

In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a portion of an oligonucleotide has a nucleobase sequence that is complementary to a second oligonucleotide or an identified reference nucleic acid, such as a target nucleic acid. In certain embodiments, the nucleobase sequence of a portion or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, lipophilic groups, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate or phosphodiester linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxynucleoside that is attached to either the 3' or 5'-terminal nucleoside of an oligonucleotide by a phosphodiester internucleoside linkage and covalently attached to the remainder of the conjugate linker or conjugate moiety by a phosphate or phosphorothioate linkage. In certain such embodiments, the cleavable moiety is 2'-deoxyadenosine.

3. Cell-Targeting Moieties

In certain embodiments, a conjugate group comprises a cell-targeting moiety. In certain embodiments, a conjugate group has the general formula:

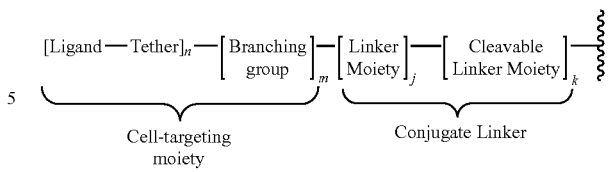

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

B. Certain Terminal Groups

In certain embodiments, oligomeric compounds comprise one or more terminal groups. In certain such embodiments, oligomeric compounds comprise a stabilized 5'-phosphate. Stabilized 5'-phosphates include, but are not limited to 5'-phosphonates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a portion complementary to a target nucleic acid and a second oligomeric compound having a portion complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or subject.

V. Certain Target Nucleic Acids

In certain embodiments, oligomeric compounds comprise or consist of an oligonucleotide comprising a portion that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target nucleic acid is a mature mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a portion that is 100% or fully complementary to a target nucleic acid. In certain embodiments, the portion of full complementarity is 6, 7, 8, 9, 10, 11, 12, 13, 14, 15, 16, 17, 18, 19, 20, 21, 22, 23, or 24 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligonucleotide is improved. In certain embodiments, the mismatch is specifically positioned within an oligonucleotide having a gapmer motif. In certain embodiments, the mismatch is at position 1, 2, 3, 4, 5, 6, 7, 8, 9, 10, or 11 from the 5'-end of the gap region. In certain embodiments, the mismatch is at position 1, 2, 3, 4, 5, or 6 from the 5'-end of the 5' wing region or the 3' wing region.

B. ATXN1

In certain embodiments, oligomeric compounds comprise or consist of an oligonucleotide that is complementary to a target nucleic acid, wherein the target nucleic acid is an ATXN1 nucleic acid. In certain embodiments, ATXN1 nucleic acid has the sequence set forth in SEQ ID NO: 1 (GENBANK Accession No. NM_000332.3), SEQ ID NO: 2 (the complement of GENBANK Accession No. NC_000006.12 truncated from nucleotides 16296001 to 16764000), SEQ ID NO: 3 (GENBANK Accession No. NM_001128164.1), SEQ ID NO: 4 (GENBANK Accession No. BC011026.1), SEQ ID NO: 5 (GENBANK Accession No. BC029401.1), or SEQ ID NO: 6 (GENBANK Accession No. BC047894.1).

In certain embodiments, contacting a cell with an oligomeric compound complementary to any of SEQ ID NO: 1-6 reduces the amount of ATXN1 RNA in a cell. In certain embodiments, contacting a cell with an oligomeric compound complementary to any of SEQ ID NO: 1-6 reduces the amount of ATXN1 in a cell. In certain embodiments, the cell is in vitro. In certain embodiments, the cell is in a subject. In certain embodiments, the oligomeric compound consists of a modified oligonucleotide. In certain embodiments, contacting a cell in a subject with an oligomeric compound complementary to any of SEQ ID NO: 1-6 ameliorates one or more symptom or hallmark of a neurodegenerative disease. In certain embodiments, the neurodegenerative disease is SCA1. In certain embodiments, the symptom or hallmark is selected from gait and limb ataxia, cognitive impairments, difficulty with speaking and swallowing, atrophy of the cerebellum and brainstem in magnetic resonance imaging (MRI), neurochemical abnormalities in the cerebellum and brainstem detected via magnetic resonance spectroscopy (MRS), and death within 10-15 years of symptom onset.

In certain embodiments, an oligomeric compound complementary to any of SEQ ID NO: 1-6 is capable of reducing the detectable amount of ATXN1 RNA in vitro by at least 10%, at least 20%, at least 30%, at least 40%, at least 50%, at least 60%, at least 70%, at least 80%, or at least 90% when administered according to the standard cell assay. In certain embodiments, an oligomeric compound complementary to SEQ ID NO: 1, SEQ ID NO: 2, SEQ ID NO: 3, SEQ ID NO: 4, SEQ ID NO: 5, or SEQ ID NO: 6 is capable of decreasing the amount of ATXN1 in vitro by at least 10%, at least 20%, at least 30%, at least 40%, at least 50%, at least 60%, at least 70%, at least 80%, or at least 90% when administered according to the standard cell assay. In certain embodiments, an oligomeric compound complementary to SEQ ID NO: 1, SEQ ID NO: 2, SEQ ID NO: 3, SEQ ID NO: 4, SEQ ID NO: 5, or SEQ ID NO: 6 is capable of reducing the detectable amount of ATXN1 RNA in the CSF of a subject by at least 10%, at least 20%, at least 30%, at least 40%, at least 50%, at least 60%, at least 70%, at least 80%, or at least 90%. In certain embodiments, an oligomeric compound complementary to SEQ ID NO: 1, SEQ ID NO: 2, SEQ ID NO: 3, SEQ ID NO: 4, SEQ ID NO: 5, or SEQ ID NO: 6 is capable of decreasing the detectable amount of ATXN1 in the CSF of a subject by at least 10%, at least 20%, at least 30%, at least 40%, at least 50%, at least 60%, at least 70%, at least 80%, or at least 90%.

C. Certain Target Nucleic Acids in Certain Tissues

In certain embodiments, oligomeric compounds comprise or consist of an oligonucleotide comprising a portion that is complementary to a target nucleic acid, wherein the target nucleic acid is expressed in a pharmacologically relevant tissue. In certain embodiments, the pharmacologically relevant tissues are the cells and tissues that comprise the central nervous system. Such tissues include the cortex, cerebellum, and brainstem.

VI. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid. In certain embodiments, the artificial cerebrospinal fluid is pharmaceutical grade.

In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to a subject, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents comprising an oligomeric compound provided herein to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

VII. Certain Compositions

1. Compound No. 994509

In certain embodiments, Compound No. 994509 is characterized as a 5-10-5 MOE gapmer having a sequence of (from 5' to 3') GCACGGTATTAGTGTCTTCA (SEQ ID NO: 126), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 994509 is represented by the following chemical notation (5' to 3'):

(SEQ ID NO: 3671)
Ges ᵐCeo Aeo ᵐCeo Ges Gds Tds Ads Tds Tds Ads Gds Tds Gds Tds ᵐCeo Teo Tes ᵐCes Ae, wherein,
 A=an adenine nucleobase,
 ᵐC=a 5-methyl cytosine nucleobase,
 G=a guanine nucleobase,
 T=a thymine nucleobase,
 e=a 2'-MOE sugar moiety,
 d=a 2'-β-D deoxyribosyl sugar moiety,
 s=a phosphorothioate internucleoside linkage, and
 o=a phosphodiester internucleoside linkage.

In certain embodiments, Compound No. 994509 is represented by the following chemical structure:

(SEQ ID NO: 3671)

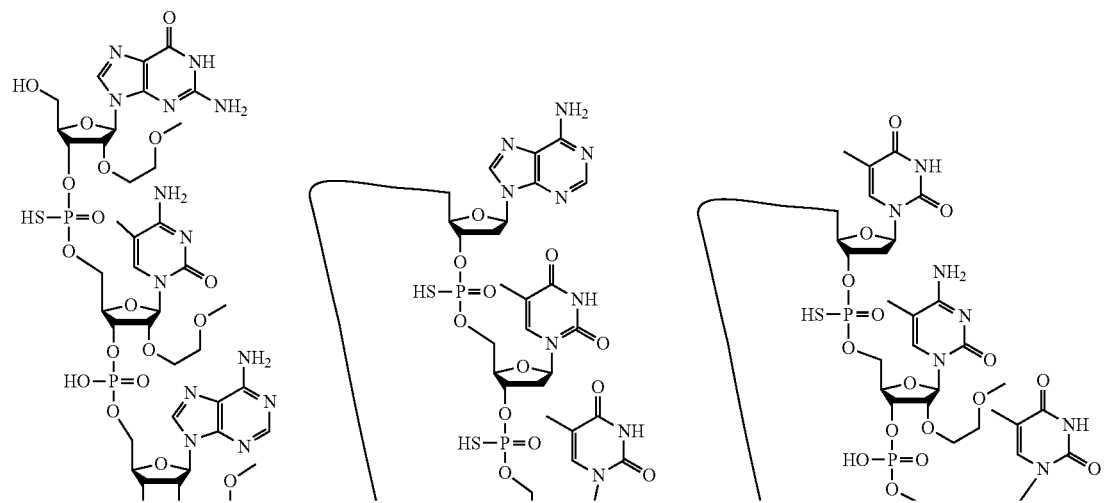

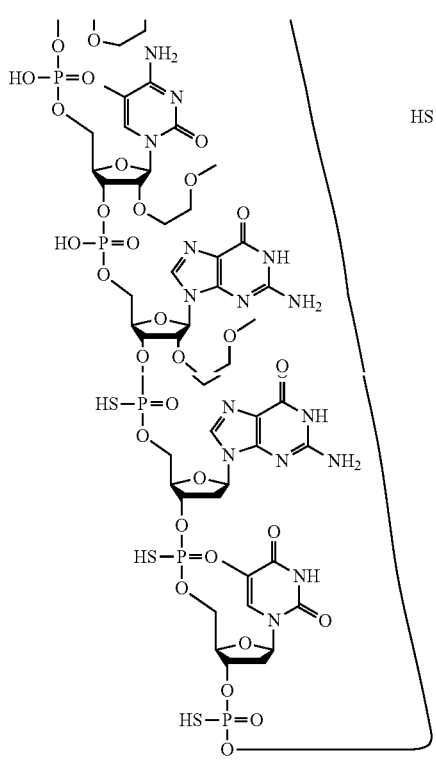
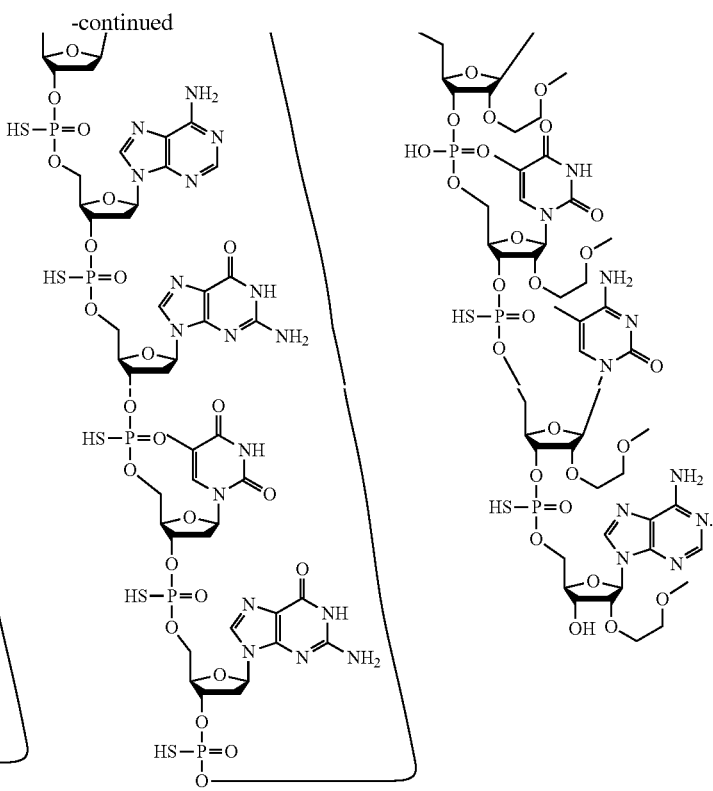
Structure 1. Compound No. 994509
In certain embodiments, the sodium salt of Compound No. 994509 is represented by the following chemical structure:
(SEQ ID NO: 3671)
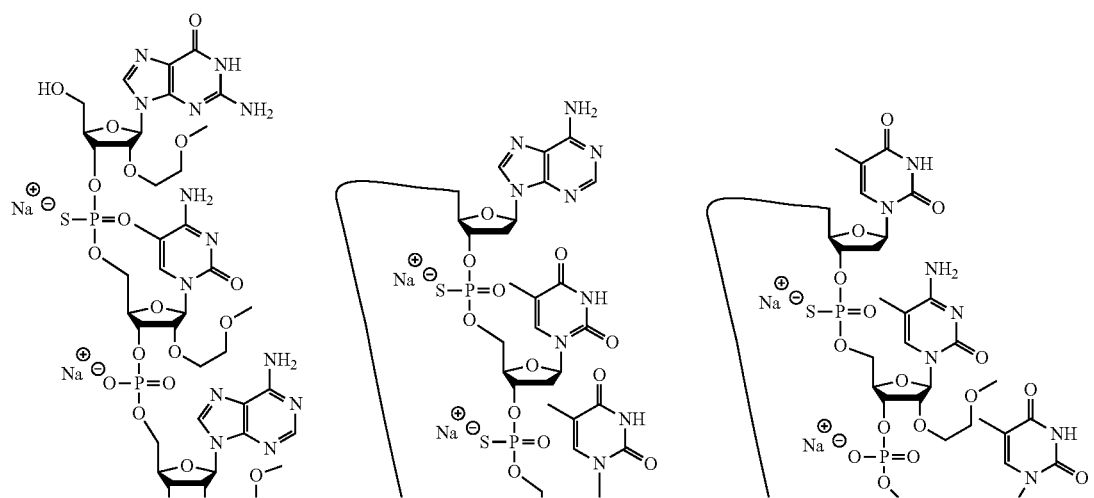

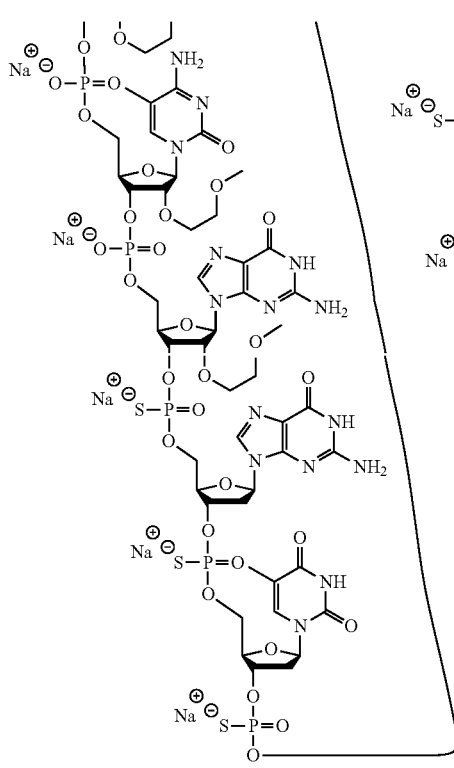
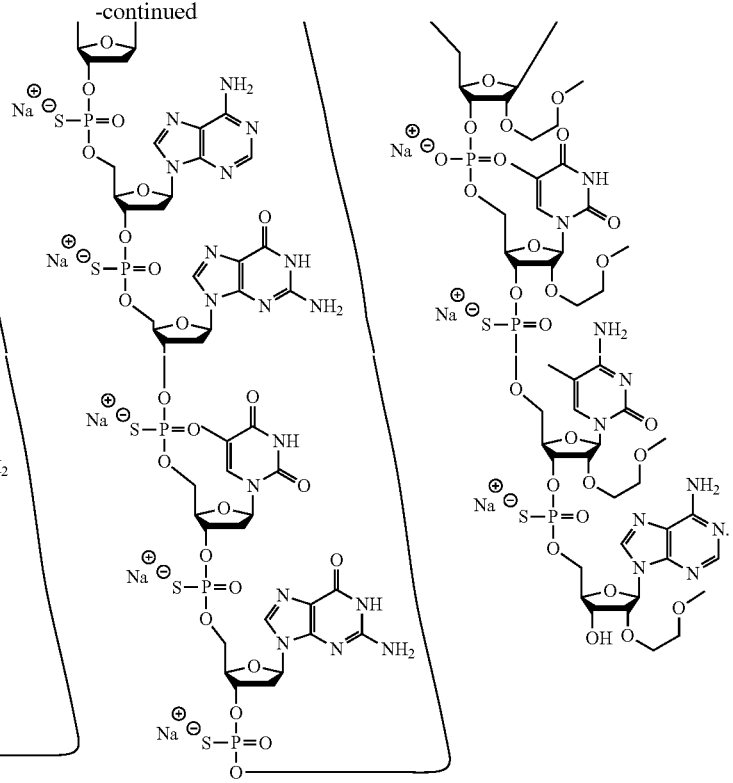

Structure 2. The Sodium Salt of Compound No. 994509

2. Compound No. 1040500

In certain embodiments, Compound No. 1040500 is characterized as a 5-10-5 MOE gapmer having a sequence of (from 5' to 3') GCTTCTCAAATCAGGTGTAC (SEQ ID NO: 1045), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1040500 is represented by the following chemical notation (5' to 3'):

(SEQ ID NO: 3672)
Ges $^m$Ceo Teo Teo $^m$Ces Tds $^m$Cds Ads Ads Ads Tds $^m$Cds Ads Gds Gds Teo Geo Tes Aes mCe, wherein, A=an adenine nucleobase, $^m$C=a 5-methyl cytosine nucleobase, G=a guanine nucleobase, T=a thymine nucleobase, e=a 2'-MOE sugar moiety, d=a 2'-β-D deoxyribosyl sugar moiety, s=a phosphorothioate internucleoside linkage, and o=a phosphodiester internucleoside linkage.

In certain embodiments, Compound No. 1040500 is represented by the following chemical structure:

(SEQ ID NO: 3672)
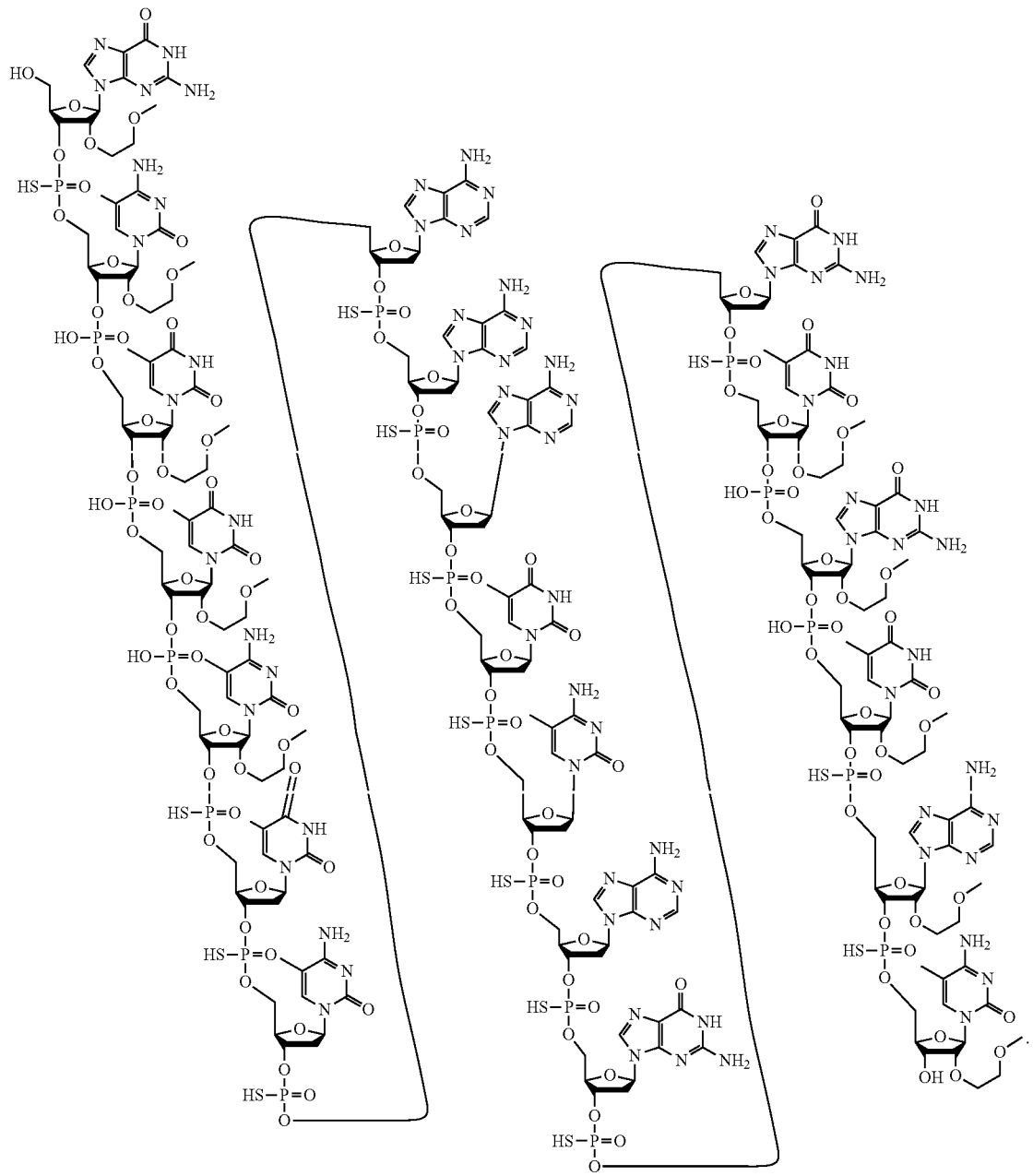
Structure 3. Compound No. 1040500
In certain embodiments, the sodium salt of Compound No. 1040500 is represented by the following chemical structure:

(SEQ ID NO: 3672)

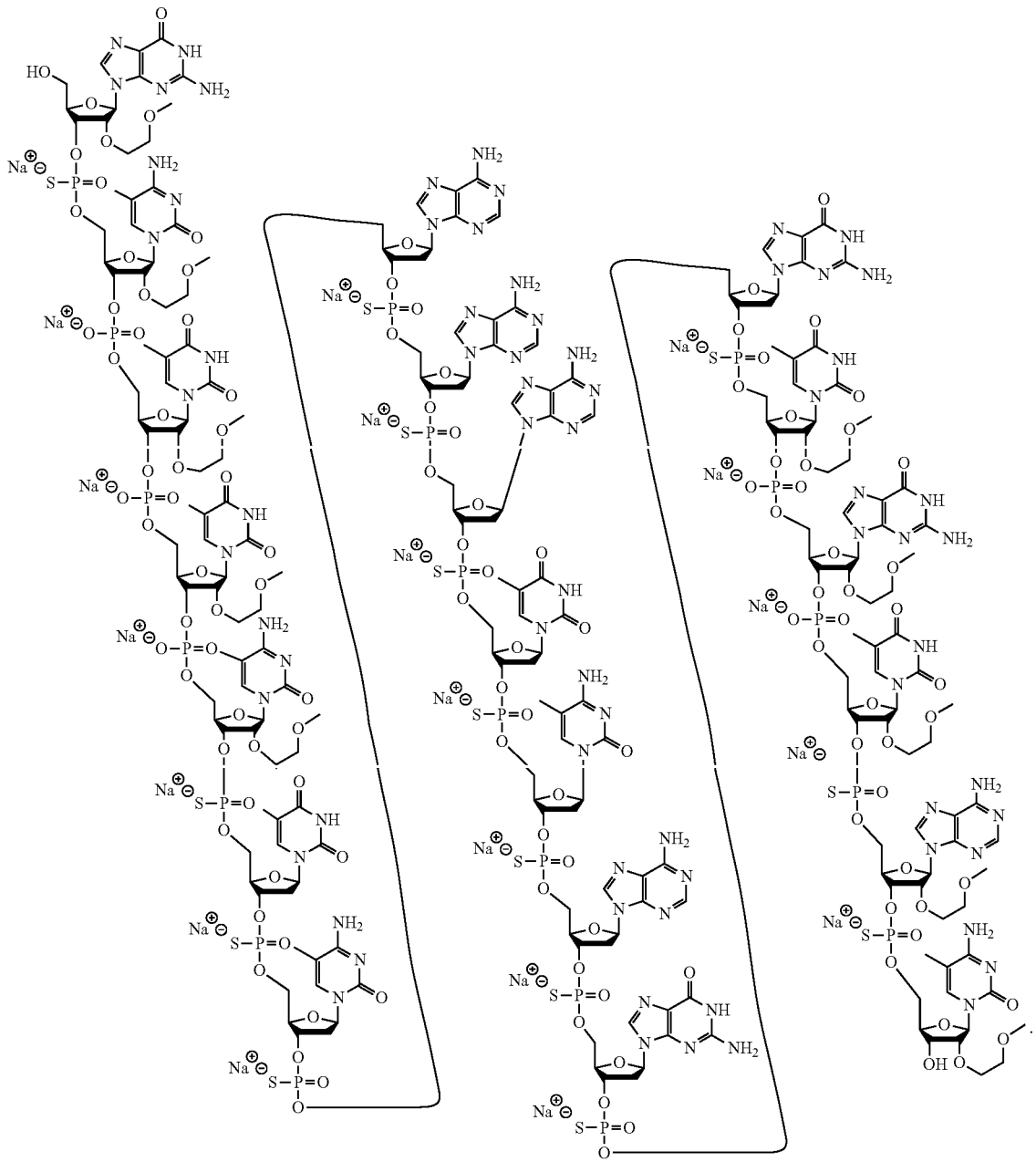

Structure 4. The Sodium Salt of Compound No. 1040500

3. Compound No. 1041927

In certain embodiments, Compound No. 1041927 is characterized as a 5-10-5 MOE gapmer having a sequence of (from 5' to 3') GCCTTTATAACTTTCTTTC (SEQ ID NO: 2552), wherein each of nucleosides 1-5 and 16-20 (from 5' to 3') are 2'-MOE nucleosides and each of nucleosides 6-15 are 2'-$3-D-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1041927 is represented by the following chemical notation (5' to 3'):

(SEQ ID NO: 3673)
Ges ᵐCeo ᵐCeo Teo Tes Tds Ads Tds Ads Ads ᵐCds

Tds Tds Tds Tds ᵐCeo Teo Tes Tes ᵐCe, wherein,
A=an adenine nucleobase,
ᵐC=a 5-methyl cytosine nucleobase,
G=a guanine nucleobase,
T=a thymine nucleobase,
e=a 2'-MOE sugar moiety, d=a 2'-β-D deoxyribosyl sugar moiety,
s=a phosphorothioate internucleoside linkage, and
o=a phosphodiester internucleoside linkage.

In certain embodiments, Compound No. 1041927 is represented by the following chemical structure:

(SEQ ID NO: 3673)

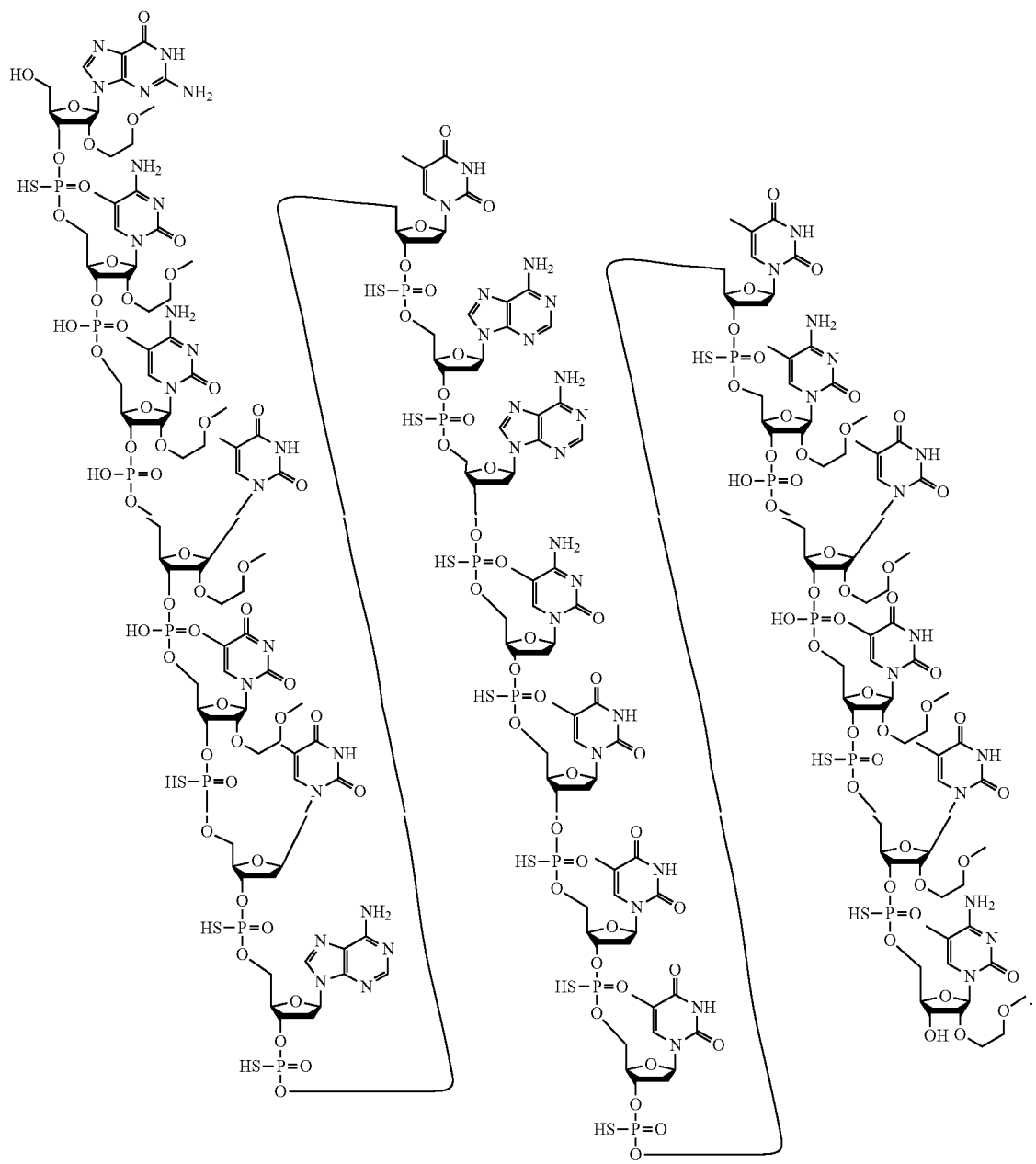

Structure 5. Compound No. 1041927

In certain embodiments, the sodium salt of Compound No. 1041927 is represented by the following chemical structure:

(SEQ ID NO: 3673)

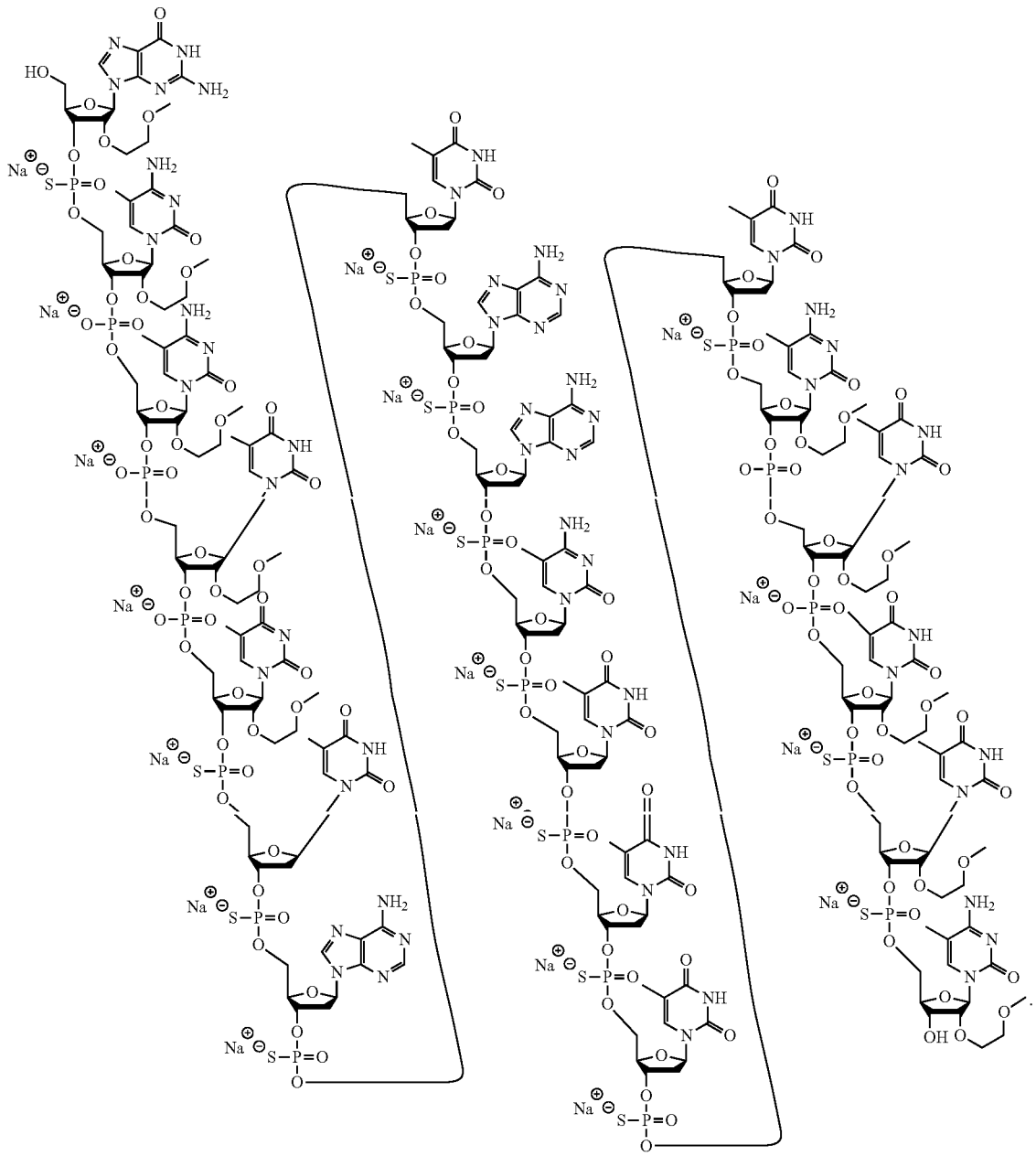

Structure 6. The Sodium Salt of Compound No. 1041927

4. Compound No. 1055001

In certain embodiments, Compound No. 1055001 is characterized as a 5-10-5 MOE gapmer having a sequence of (from 5' to 3') TTCAGTTTAGTTGCAGCCAT (SEQ ID NO: 3190), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1055001 is represented by the following chemical notation (5' to 3'):

(SEQ ID NO: 3674)
Tes Teo $^m$Ceo Aeo Ges Tds Tds Tds Ads Gds Tds Tds Gds $^m$Cds Ads Geo $^m$Ceo $^m$Ces Aes Te, wherein,
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D deoxyribosyl sugar moiety, s=a phosphorothioate internucleoside linkage, and
o=a phosphodiester internucleoside linkage.
In certain embodiments, Compound No. 1055001 is represented by the following chemical structure:
(SEQ ID NO: 3674)
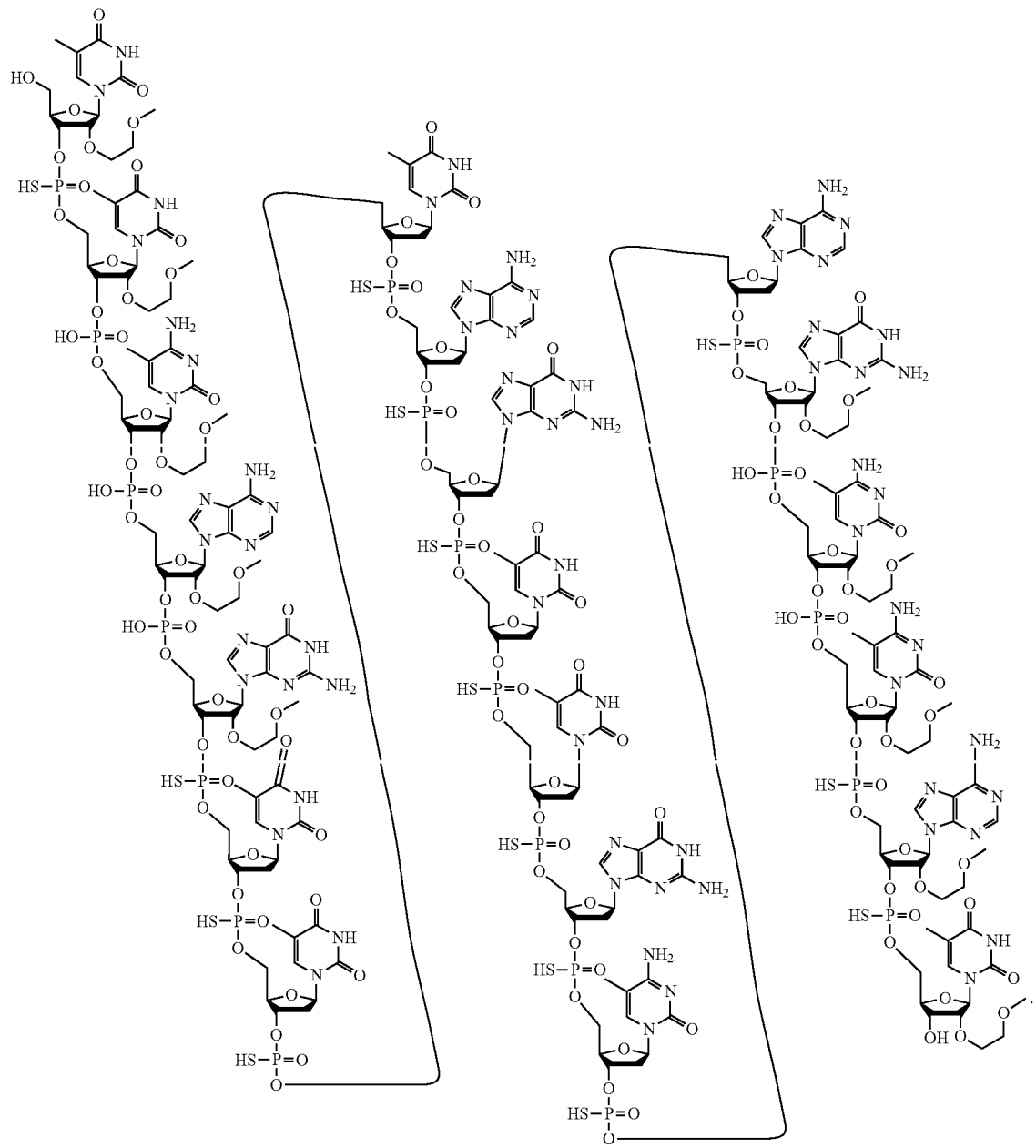
Structure 7. Compound No. 1055001
In certain embodiments, the sodium salt of Compound No. 1055001 is represented by the following chemical structure:

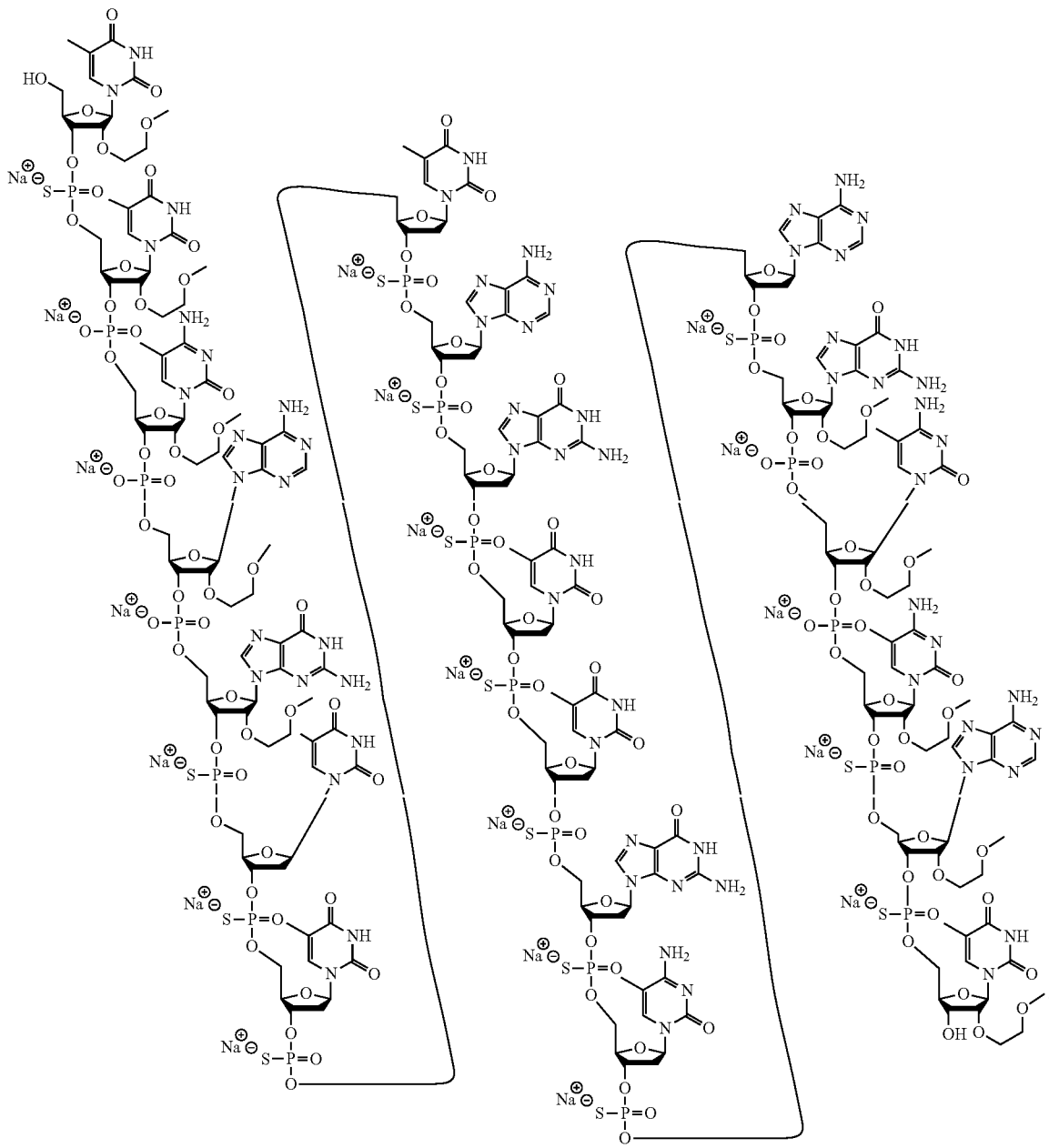

(SEQ ID NO: 3674)

Structure 8. The Sodium Salt of Compound No. 1055001

5. Compound No. 1371311

In certain embodiments, Compound No. 1371311 is characterized as a 5-10-5 MOE gapmer having a sequence of (from 5' to 3') CCCGTATTCCTCTTACCATC (SEQ ID NO: 3590), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1371311 is represented by the following chemical notation (5' to 3'):

(SEQ ID NO: 3670)
$^m$Ces $^m$Ceo $^m$Ceo Geo Tes Ads Tds Tds $^m$Cds $^m$Cds Tds $^m$Cds Tds Tds Ads $^m$Ceo $^m$Ceo Aes Tes $^m$Ce, wherein, A=an adenine nucleobase, $^m$C=a 5-methyl cytosine nucleobase, G=a guanine nucleobase, T=a thymine nucleobase, e=a 2'-MOE sugar moiety, d=a 2'-β-D deoxyribosyl sugar moiety, s=a phosphorothioate internucleoside linkage, and o=a phosphodiester internucleoside linkage.

In certain embodiments, Compound No. 1371311 is represented by the following chemical structure:
(SEQ ID NO: 3670)
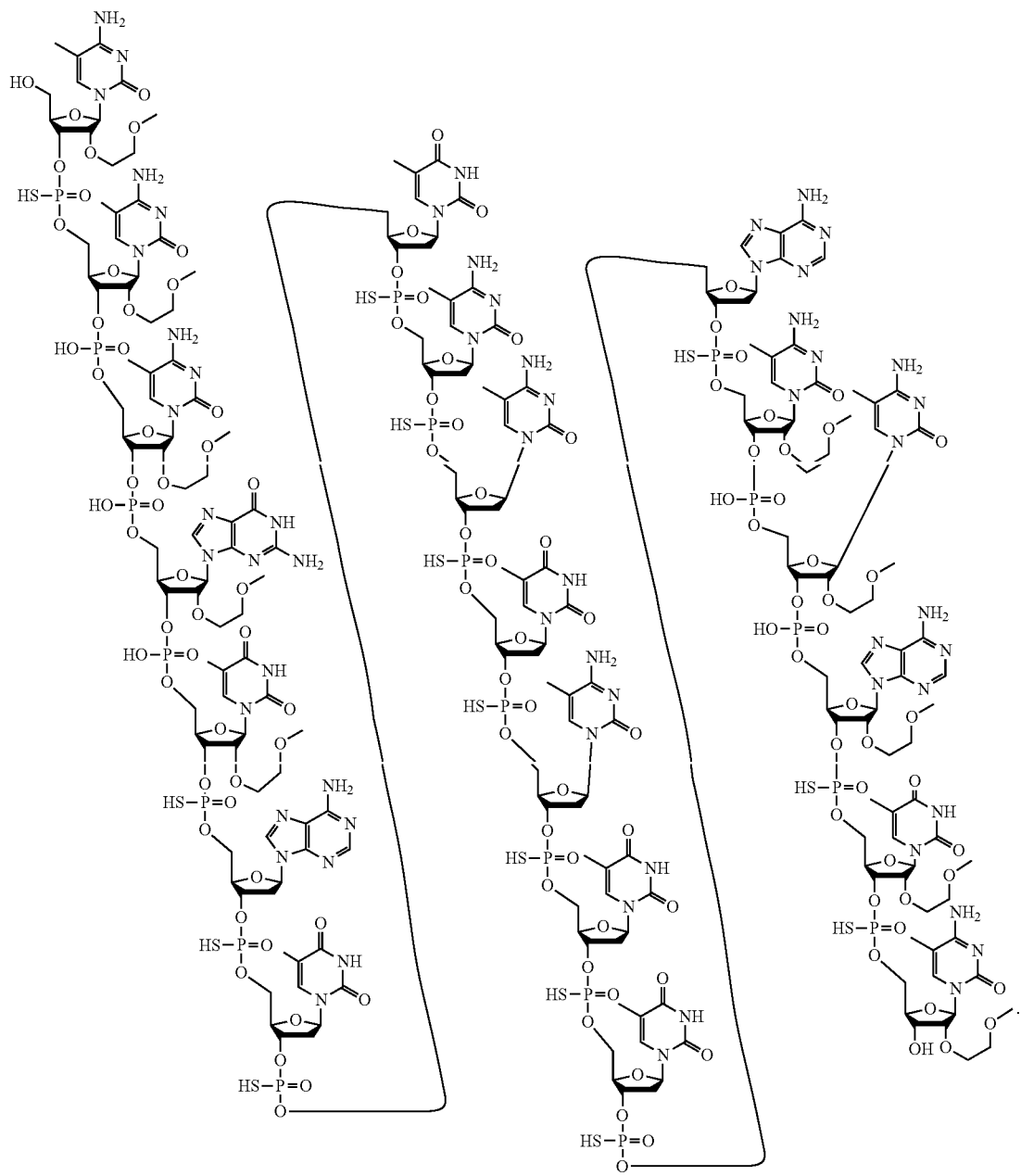
Structure 9. Compound No. 1371311
In certain embodiments, the sodium salt of Compound No. 1371311 is represented by the following chemical structure:

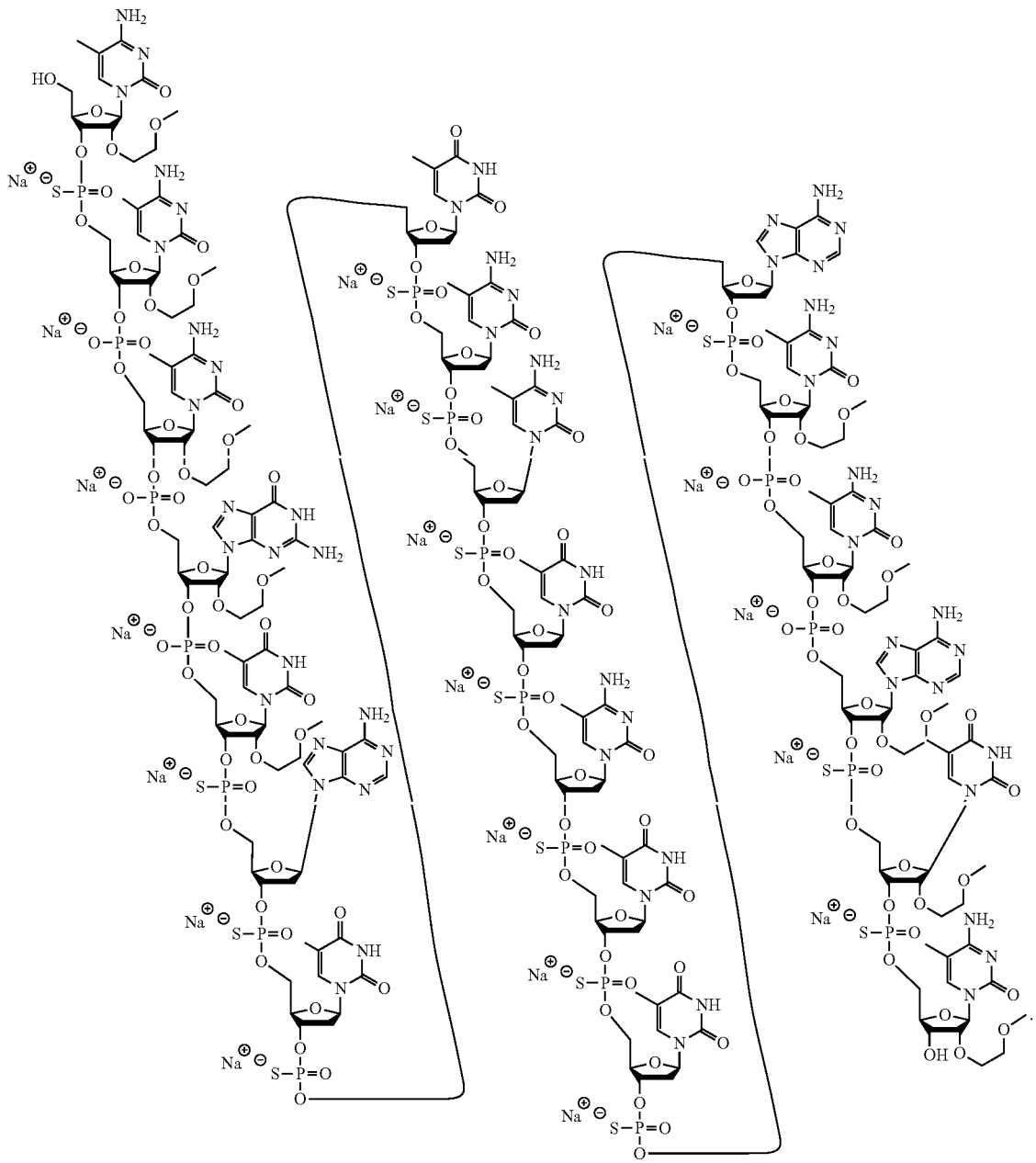

Structure 10. The Sodium Salt of Compound 13711

6. Compound No. 138529

In certain embodiments, Compound No. 1385293 is characterized as ah 5-8-4 MOE gapmer having a sequence of (from 5' to 3') TCAGTTTAGTTGCAGCC (SEQ ID NO: 3638), wherein each of nucleosides 1-5 and 14-17 (from 5' to 3') are 2'-MOE nucleosides and each of nucleosides 6-13 are 2'-β-D-deoxynucleosides, wherein the internucleoside linkages between nucleosides 4 to 5 and 14 to 15 are phosphodiester internucleoside linkages and the internucleoside linkages between nucleosides to 2, 3 to 4, 5 to 6, 6 to 7, 7 to 8, 8 to 9, 9 to 10, 10 to 11, 11 to 12, 12 to 13, 13 to 14, 15 to 16, and 16 to 17 are phosphorothioate internucleoside linkages, and wherein each cytosine is a 5-methyl cytosine.

In certain embodiments, Compound No. 1385293 is represented by the following chemical notation (5' to 3'):

(SEQ ID NO: 3675)
Tes $^m$Ces Aes Geo Tes Tds Tds Ads Gds Tds Tds Gds $^m$Cds Aeo Ges $^m$Ces $^m$Ce, wherein,
A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D deoxyribosyl sugar moiety,
s=a phosphorothioate internucleoside linkage, and
o=a phosphodiester internucleoside linkage.

In certain embodiments, Compound No. 1385293 is represented by the following chemical structure:
(SEQ ID NO: 3675)
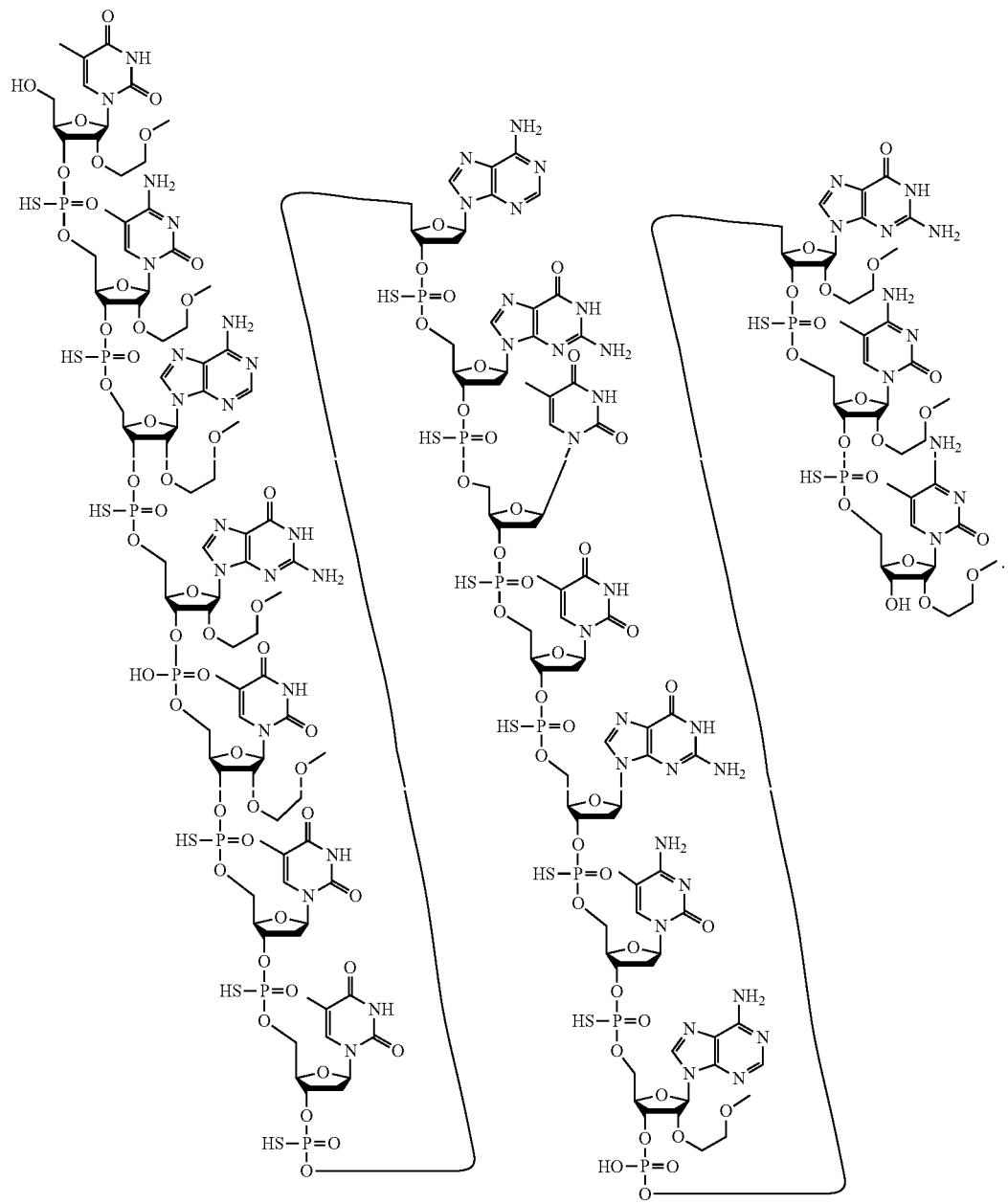
Structure 11. Compound No. 1385293
In certain embodiments, the sodium salt of Compound No. 1385293 is represented by the following chemical structure:

(SEQ ID NO: 3675)

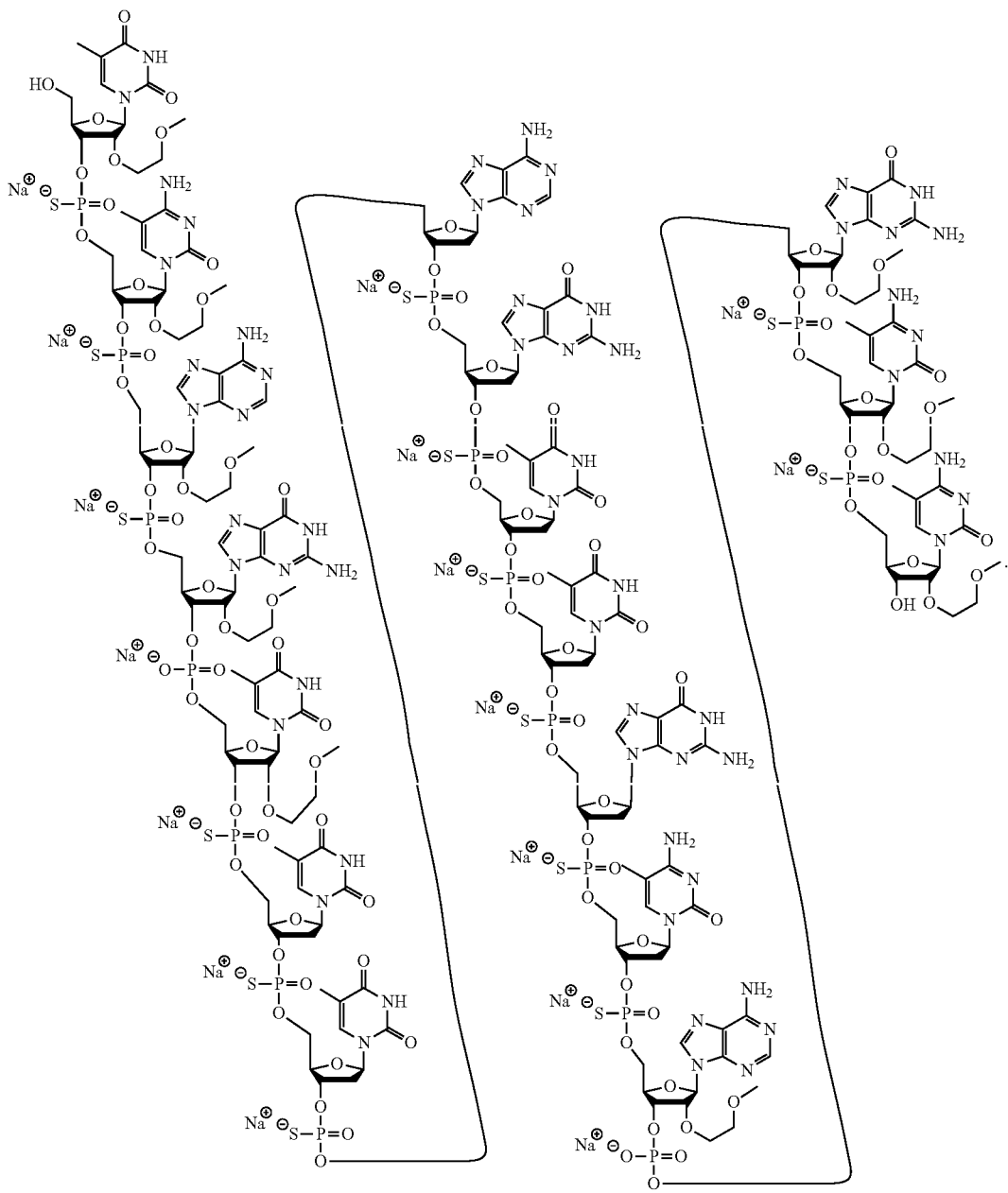

Structure 12. The Sodium Salt of Compound No. 1385293

VIII. Certain Hotspot Regions

In certain embodiments, nucleobases in the ranges specified below comprise a hotspot region of ATXN1 nucleic acid. In certain embodiments, modified oligonucleotides that are complementary within a hotspot region of ATXN1 nucleic acid achieve an average of more than 75% reduction of ATXN1 RNA in vitro in the standard cell assay. In certain embodiments, modified oligonucleotides that are complementary within a hotspot region of ATXN1 nucleic acid achieve an average of 24% or greater reduction of ATXN1 RNA in vivo in the standard in vivo assay. In certain embodiments, modified oligonucleotides that are complementary within a hotspot region of ATXN1 nucleic acid achieve an average of 45% or greater reduction of ATXN1 RNA in vivo in the standard in vivo assay.

1. Nucleobases 5472-5552 of SEQ ID NO: 1 or 459725-459805 of SEQ ID NO: 2

In certain embodiments, nucleobases 5472-5552 of SEQ TD NO: 1 or 459725-459805 of SEQ ID NO: 2 comprise a hotspot region. In certain embodiments, modified oligonucleotides are complementary within nucleobases 5472-5552 of SEQ TD NO: 1 or 459725-459805 of SEQ TD NO: 2. In certain embodiments, modified oligonucleotides are 20 nucleobases in length. In certain embodiments, modified oligonucleotides are 17 nucleobases in length. In certain embodiments, modified oligonucleotides are gapmers. In certain embodiments, modified oligonucleotides are mixed wing gapmers.

In certain embodiments, the gapmers are 5-10-5 MOE gapmers. In certain embodiments, the gapmers are 6-10-4 MOE gapmers. In certain embodiments, the gapmers are 5-8-4 MOE gapmers or 5-8-4 mixed MOE/cEt gapmers. In certain embodiments, the mixed wing gapmers have the sugar motif in order from 5' to 3': eeeeedddddddkkee; wherein 'd' represents a 2'-β-D-deoxyribosyl sugar moiety, 'k' represents a cEt sugar moiety, and 'e' represents a 2'-MOE sugar moiety. In certain embodiments, the gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3'). In certain embodiments, the gapmers have the sugar motif in order from 5' to 3': eeeeedyddddddddeeeee or eeeeedyddddddkkee; wherein 'd' represents a 2'-β-D-deoxyribosyl sugar moiety, 'k' represents a cEt sugar moiety, 'e' represents a 2'-MOE sugar moiety, and "y" represents a 2'-OMe sugar moiety.

In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in order from 5' to 3': In certain embodiments, modified nucleotides have an internucleoside linkage motif of sooosssssssssssooss, sssosssssssssssosss, sssosssssssss-soss, or sooooosssssssssssoss wherein each "s" represents a phosphorothioate internucleoside linkage and each "o" represents a phosphodiester internucleoside linkage.

The nucleobase sequences of SEQ ID Nos: 196, 274, 352, 430, 508, 2578, 2655, 2732, 2809, 2886, 2963, 3121, 3122, 3190, 3191, 3192, 3262, 3330, 3331, 3332, 3401, 3402, 3575, 3577, 3620, 3624, 3638-3640, 3653-3655, 3662, 3665, and 3669 are complementary within nucleobases 5472-5552 of SEQ ID NO: 1 or 459725-459805 of SEQ ID NO: 2.

The nucleobase sequence of Compound Nos.: 994446-994450, 1040296-1040301, 1055001-1055011, 1342062, 1342063, 1342067, 1342068, 1365271, 1365272, 1365274, 1365294, 1365299, 1365300, 1371818, 1371821, 1371827, 1371829, 1371837, 1371843, 1371866, 1371869, 1371871, 1371876, 1385293, 1394156-1394160, 1394162, 1394164, 1394166-1394168, 1394533, 1394544, 1394546, 1394549, and 1394553 are complementary within nucleobases 5472-5552 of SEQ ID NO: 1 or 459725-459805 of SEQ ID NO: 2.

In certain embodiments, modified oligonucleotides complementary within nucleobases 5472-5552 of SEQ ID NO: 1 or 459725-459805 of SEQ ID NO: 2 achieve at least 58% reduction of ATXN1 RNA in vitro in the standard cell assay. In certain embodiments, modified oligonucleotides complementary within nucleobases 5472-5552 of SEQ ID NO: 1 or 459725-459805 of SEQ ID NO: 2 achieve an average of 90% reduction of ATXN1 RNA in vitro in the standard cell assay. In certain embodiments, modified oligonucleotides complementary within nucleobases 5472-5552 of SEQ ID NO: 1 or 459725-459805 of SEQ ID NO: 2 achieve an average of 52% reduction of ATXN1 RNA in vivo in the standard in vivo assay.

2. Nucleobases 5906-6005 of SEQ ID NO: 1 or 460159-460258 of SEQ ID NO: 2

In certain embodiments, nucleobases 5906-6005 of SEQ ID NO: 1 or 460159-460258 of SEQ ID NO: 2 comprise a hotspot region. In certain embodiments, modified oligonucleotides are complementary to nucleobases 5906-6005 of SEQ ID NO: 1 or 460159-460258 of SEQ ID NO: 2. In certain embodiments, modified oligonucleotides are 20 nucleobases in length. In certain embodiments, modified oligonucleotides are 17 nucleobases in length. In certain embodiments, modified oligonucleotides are mixed wing gapmers.

In certain embodiments, the gapmers are 5-10-5 MOE gapmers. In certain embodiments, the gapmers are 6-10-4 MOE gapmers. In certain embodiments, the gapmers are 5-8-4 MOE gapmers or 5-8-4 mixed MOE/cEt gapmers. In certain embodiments, the mixed wing gapmers have the sugar motif in order from 5' to 3': eeeeedddddddkkee; wherein 'd' represents a 2'-β-D-deoxyribosyl sugar moiety, 'k' represents a cEt sugar moiety, and 'e' represents a 2'-MOE sugar moiety.

In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in order from 5' to 3': In certain embodiments, modified nucleotides have an internucleoside linkage motif of sooosssssssssssooss, sssosssssssssssosss, sssosssssssss-soss, or sooooosssssssssssoss wherein each "s" represents a phosphorothioate internucleoside linkage and each "o" represents a phosphodiester internucleoside linkage.

The nucleobase sequences of SEQ ID Nos: 42, 120, 198, 276, 509, 587, 2502, 2579, 2656, 2733, 2810, 2887, 2964, 3585, 3588-3590, 3615, 3618, 3622, 3657, 3660, 3661, 3663, 3664, and 3666-3668 are complementary within nucleobases 5906-6005 of SEQ ID NO: 1 or 460159-460258 of SEQ ID NO: 2.

The nucleobase sequence of Compound Nos.: 994458-994463, 1040327-1040333, 1367569, 1367580-1367581, 1367589-1367591, 1371311, 1371820, 1371823, 1371825, 1371842, 1371865, 1371868, 1371870, 1371873, 1371875, 1371877, 1394161, 1394163, 1394165, 1394524, 1394538, 1394541, 1394543, 1394545, 1394548, and 1394550-1394552 are complementary within nucleobases 5906-6005 of SEQ ID NO: 1 or 460159-460258 of SEQ ID NO: 2.

In certain embodiments, modified oligonucleotides complementary within 5906-6005 of SEQ ID NO: 1 or 460159-460258 of SEQ ID NO: 2 achieve at least 26% reduction of ATXN1 RNA in vitro in the standard cell assay. In certain embodiments, modified oligonucleotides complementary within nucleobases 5906-6005 of SEQ ID NO: 1 or 460159-460258 of SEQ ID NO: 2 achieve an average of 78% reduction of ATXN1 RNA in vitro in the standard cell assay. In certain embodiments, modified oligonucleotides complementary within nucleobases 5906-6005 of SEQ ID NO: 1 or 460159-460258 of SEQ ID NO: 2 achieve an average of 51% reduction of ATXN1 RNA in vivo in the standard in vivo assay.

3. Nucleobases 7868-7911 of SEQ ID NO: 1 or 462121-462164 of SEQ ID NO: 2

In certain embodiments, nucleobases 7868-7911 of SEQ ID NO: 1 or 462121-462164 of SEQ ID NO: 2 comprise a hotspot region. In certain embodiments, modified oligonucleotides are complementary to nucleobases 7868-7911 of SEQ ID NO: 1 or 462121-462164 of SEQ ID NO: 2. In certain embodiments, modified oligonucleotides are 20 nucleobases in length. In certain embodiments, modified oligonucleotides are gapmers.

In certain embodiments, the gapmers are 5-10-5 MOE gapmers. In certain embodiments, the gapmers are 6-10-4 MOE gapmers.

In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in order from 5' to 3': In certain embodiments, modified nucleotides have an internucleoside linkage motif of sooosssssssssssooss, sssosssssssssssosss, or sooooosssssssssssoss wherein each "s" represents a phosphorothioate internucleoside linkage and each "o" represents a phosphodiester internucleoside linkage.

The nucleobase sequences of SEQ ID Nos: 48, 126, 2044, and 2121 are complementary within nucleobases 7868-7911 of SEQ ID NO: 1 or 462121-462164 of SEQ ID NO: 2.

The nucleobase sequence of Compound Nos.: 994508, 994509, 1040499, 1040450, 1394513, and 1394529 are complementary within nucleobases 7868-7911 of SEQ ID NO: 1 or 462121-462164 of SEQ ID NO: 2.

In certain embodiments, modified oligonucleotides complementary within 7868-7911 of SEQ ID NO: 1 or 462121-462145 of SEQ ID NO: 2 achieve at least 61% reduction of ATXN1 RNA in vitro in the standard cell assay. In certain embodiments, modified oligonucleotides complementary within nucleobases 7868-7911 of SEQ ID NO: 1 or 462121-462145 of SEQ ID NO: 2 an average of 79% reduction of ATXN1 RNA in vitro in the standard cell assay. In certain embodiments, modified oligonucleotides complementary within nucleobases 7868-7911 of SEQ ID NO: 1 or 462121-462164 of SEQ ID NO: 2 achieve an average of 53% reduction of ATXN1 RNA in vivo in the standard in vivo assay.

4. Nucleobases 8481-8514 of SEQ ID NO: 1 or 462734-462767 of SEQ ID NO: 2

In certain embodiments, nucleobases 8481-8514 of SEQ ID NO: 1 or 462734-462767 of SEQ ID NO: 2 comprise a hotspot region. In certain embodiments, modified oligonucleotides are complementary to nucleobases 8481-8514 of SEQ ID NO: 1 or 462734-462767 of SEQ ID NO: 2. In certain embodiments, modified oligonucleotides are 20 nucleobases in length. In certain embodiments, modified oligonucleotides are gapmers.

In certain embodiments, the gapmers are 5-10-5 MOE gapmers. In certain embodiments, the gapmers are 6-10-4 MOE gapmers.

In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in order from 5' to 3': In certain embodiments, modified nucleotides have an internucleoside linkage motif of sooosssssssssssooss, sssosssssssssssosss, or sooooosssssssssssoss wherein each "s" represents a phosphorothioate internucleoside linkage and each "o" represents a phosphodiester internucleoside linkage.

The nucleobase sequences of SEQ ID Nos: 128, 206, 284, 1045, 1122, 1199, and 1276 are complementary within nucleobases 8481-8514 of SEQ ID NO: 1 or 462734-462767 of SEQ ID NO: 2.

The nucleobase sequence of Compound Nos.: 994525-994527, 1040500-1040503, 1394514, and 1394525 are complementary within nucleobases 8481-8514 of SEQ ID NO: 1 or 462734-462767 of SEQ ID NO: 2.

In certain embodiments, modified oligonucleotides complementary within 8481-8514 of SEQ ID NO: 1 or 462734-462767 of SEQ ID NO: 2 achieve at least 54% reduction of ATXN1 RNA in vitro in the standard cell assay. In certain embodiments, modified oligonucleotides complementary within nucleobases 8481-8514 of SEQ ID NO: 1 or 462734-462767 of SEQ ID NO: 2 achieve an average of 79% reduction of ATXN1 RNA in vitro in the standard cell assay. In certain embodiments, modified oligonucleotides complementary within nucleobases 8481-8514 of SEQ ID NO: 1 or 462734-462767 of SEQ ID NO: 2 achieve an average of 48% reduction of ATXN1 RNA in vivo in the standard in vivo assay.

5. Nucleobases 446679-446706 of SEQ ID NO: 2

In certain embodiments, nucleobases 446679-446706 of SEQ ID NO: 2 comprise a hotspot region. In certain embodiments, modified oligonucleotides are complementary to nucleobases 446679-446706 of SEQ ID NO: 2. In certain embodiments, modified oligonucleotides are 20 nucleobases in length. In certain embodiments, modified oligonucleotides are gapmers.

In certain embodiments, the gapmers are 5-10-5 MOE gapmers. In certain embodiments, the gapmers are 6-10-4 MOE gapmers.

In certain embodiments, 446679-446706 of SEQ ID NO: 2 comprise a hotspot region. In certain embodiments, modified oligonucleotides are complementary within 446679-446706 of SEQ ID NO: 2. In certain embodiments, modified oligonucleotides are 20 nucleobases in length. In certain embodiments, modified oligonucleotides are 17 nucleobases in length. In certain embodiments, modified oligonucleotides are gapmers. In certain embodiments, the gapmers are MOE gapmers. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in order from 5' to 3': In certain embodiments, modified nucleotides have an internucleoside linkage motif of sooosssssssssssooss, sssosssssssssssosss, or sooooosssssssssssoss wherein each "s" represents a phosphorothioate internucleoside linkage and each "o" represents a phosphodiester internucleoside linkage.

The nucleobase sequences of SEQ ID Nos: 2475, 2552, 2629, 2706, 2783, 3627-3630, and 3644 are complementary within nucleobases 446679-446706 of SEQ ID NO: 2.

The nucleobase sequence of Compound Nos.: 1041926-1041930, 1364282, 1365258-1365261, 1365282-1365284, 1365287, and 1394522 are complementary within nucleobases 446679-446706 of SEQ ID NO: 2.

In certain embodiments, modified oligonucleotides complementary within nucleobases 446679-446706 of SEQ ID NO: 2 achieve at least 67% reduction of ATXN1 RNA in vitro in the standard cell assay. In certain embodiments, modified oligonucleotides complementary within nucleobases 446679-446706 of SEQ ID NO: 2. achieve an average of 81% reduction of ATXN1 RNA in vitro in the standard cell assay.

6. Additional Hotspot Regions

In certain embodiments, the ranges described in the Table below comprise hotspot regions. Each hotspot region begins with the nucleobase of SEQ ID NO:1 identified in the "Start Site SEQ ID NO: 1" column and ends with the nucleobase of SEQ ID NO: 1 identified in the "Stop Site SEQ ID NO: 1" column. In certain embodiments, modified oligonucleotides are complementary within any of the hotspot regions 1-53, as defined in the table below. In certain embodiments, modified oligonucleotides are 17 nucleobases in length. In certain embodiments, modified oligonucleotides are 20 nucleobases in length.

In certain embodiments, the gapmers are 5-10-5 MOE gapmers. In certain embodiments, the gapmers are 6-10-4 MOE gapmers. In certain embodiments, the gapmers are 5-8-4 MOE gapmers or 5-8-4 mixed MOE/cEt gapmers. In certain embodiments, the mixed wing gapmers have the sugar motif in order from 5' to 3': eeeeeddddddddkkee; wherein 'd' represents a 2'-β-D-deoxyribosyl sugar moiety, 'k' represents a cEt sugar moiety, and 'e' represents a 2'-MOE sugar moiety. In certain embodiments, gapmers comprise a 2'-substituted nucleoside in the gap. In certain embodiments, the 2'-substituted nucleoside comprises a 2'-OMe sugar moiety. In certain embodiments, the 2'-substituted nucleoside is at position 2 of the gap (5' to 3'). In certain embodiments, the gapmers have the sugar motif in order from 5' to 3': eeeeedydddddddeeeee or eeeeedyddddddkkee; wherein 'd' represents a 2'-β-D-deoxyribosyl sugar moiety, 'k' represents a cEt sugar moiety, 'e' represents a 2'-MOE sugar moiety, and "y" represents a 2'-OMe sugar moiety.

In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in order from 5' to 3': In certain embodiments, modified nucleotides have an internucleoside linkage motif of sooosssssssssssooss, sssosssssssssssosss, sssosssssssssoss, or sooooossssssssssoss wherein each "s" represents a phosphorothioate internucleoside linkage and each "o" represents a phosphodiester internucleoside linkage.

The nucleobase sequence of compounds listed in the "Compound No. in range" column in the table below are complementary to SEQ ID NO: 2 within the specified hotspot region. The nucleobase sequence of the oligonucleotides listed in the "SEQ ID NO: in range" column in the table below are complementary to the target sequence, SEQ ID NO: 2, within the specified hotspot region.

In certain embodiments, modified oligonucleotides complementary to nucleobases within the hotspot region achieve at least "Min. % Red. in vitro" (minimum % reduction, relative to untreated control cells) of ATXN1 RNA in vitro in the standard cell assay, as indicated in the table below. In certain embodiments, modified oligonucleotides complementary to nucleobases within the hotspot region achieve an average of "Avg. % Red. in vitro" (average % reduction, relative to untreated control cells) of ATXN1 RNA in vitro in the standard cell assay, as indicated in the table below. In certain embodiments, modified oligonucleotides complementary to nucleobases within the hotspot region achieve a maximum of "Max. % Red. in vitro" (maximum % reduction, relative to untreated control cells) of ATXN1 RNA in vitro in the standard cell assay, as indicated in the table below. In certain embodiments, modified oligonucleotides complementary to nucleobases within the hotspot region achieve an average of "Avg. % Red. in vivo" (average % reduction, relative to PBS-treated animals) of ATXN1 RNA in vivo in the standard in vivo assay in cortical tissue, as indicated in the table below. Note that due to the transgenic mouse model used, only compounds targeting nucleosides 435531-464889 of SEQ ID NO: 2 were tested in vivo; "n.d." indicates that no in vivo data are available for compounds within that range. In other cases, average reduction in vivo includes a subset of the compounds in any given hotspot, as not all compounds were tested in vivo.

TABLE 1

ATXN1 Hotspots

| Hotspot ID | SEQ ID NO: 1 Start Site | SEQ ID NO: 1 Stop Site | SEQ ID NO: 2 Start Site | SEQ ID NO: 2 Stop Site | Min. % Red. in vitro | Max. % Red. in vitro | Avg. % Red. in vitro | Avg. % Red. in vivo (ctx) | Compound No. in range | SEQ ID NO in range |
|---|---|---|---|---|---|---|---|---|---|---|
| 1 | 5477 | 5552 | 459730 | 459805 | 58 | 96 | 90 | 54 | 994446-994450, 1040296-1040301, 1055001-1055011, 1342062, 1342067, 1365271, 1365272, 1365274, 1365294, 1365299-1365300, 1371818, 1371827, 1371829, 1371837, 1371843, 1371871, 1371876, 1385293, 1394156-1394160, 1394162, 1394164, 1394166-1394168, 1394533, 1394544, 1394546, 1394549, 1394553 | 196, 274, 352, 430, 508, 2578, 2655, 2732, 2809, 2886, 2963, 3121, 3122, 3190-3192, 3262, 3330-3332, 3401, 3402, 3575, 3577, 3620, 3624, 3638-3640, 3653-3655, 3662, 3665, 3669 |
| 2 | 5906 | 6005 | 460159 | 460258 | 26 | 97 | 78 | 51 | 994458-994463, 1040327-1040333, 1367569, 1367580-1367581, 1367589-1367591, 1371311, 1371820, 1371823, 1371825, 1371842, 1371865, 1371868, 1371870, 1371873, 1371875, 1371877, 1394161, 1394163, 1394165, 1394524, 1394538, 1394541, 1394543, 1394545, | 42, 120, 198, 276, 509, 587, 2502, 2579, 2656, 2733, 2810, 2887, 2964, 3585, 3588-3590, 3615, 3618, 3622, 3657, 3660, 3661, 3663, 3664, 3666-3668 |

TABLE 1-continued

ATXN1 Hotspots

| Hot spot ID | SEQ ID NO: 1 Start Site | SEQ ID NO: 1 Stop Site | SEQ ID NO: 2 Start Site | SEQ ID NO: 2 Stop Site | Min. % Red. in vitro | Max. % Red. in vitro | Avg. % Red. in vitro | Avg. % Red. in vivo (ctx) | Compound No. in range | SEQ ID NO in range |
|---|---|---|---|---|---|---|---|---|---|---|
| 3 | 7868 | 7911 | 462121 | 462145 | 61 | 94 | 79 | 53 | 1394548, 1394550-1394552 994508, 994509, 1040499, 1040450, 1394513, 1394529 | 48, 126, 2044, 2121 |
| 4 | 8481 | 8514 | 462734 | 462767 | 54 | 89 | 79 | 48 | 994525-994527, 1040500-1040503, 1394514, 1394525 | 128, 206, 284, 1045, 1122, 1199, 1276 |
| 5 | N/A | N/A | 446679 | 446706 | 67 | 89 | 81 | 24 | 1041926-1041930, 1364282, 1365258-1365261, 1365282-1365284, 1365287, 1394522 | 2475, 2552, 2629, 2706, 2783, 3627-3630, 3644 |
| 6 | 99 | 140 | 2609 | 2650 | 43 | 90 | 76 | n.d. | 994310-994313, 1054946-1054957 | 179, 257, 335, 413, 3111-3113, 3183, 3253-3254, 3321-3322, 3394-3395, 3464-3465 |
| 7 | 195 | 227 | 9911 | 9943 | 64 | 92 | 78 | n.d. | 994597-994601, 1055055-1055061 | 137, 215, 293, 371, 449, 3131-3132, 3201, 3341-3342, 3410, 3478 |
| 8 | 243 | 275 | 10654 | 10686 | 75 | 93 | 85 | n.d. | 994314, 1054962-1054971 | 491, 3114, 3184-3185, 3255-3256, 3323-3324, 3396, 3466-3467 |
| 9 | 413 | 454 | 106155 | 106196 | 68 | 95 | 86 | n.d. | 994318-994324 | 25, 180, 258, 336, 414, 492, 570 |
| 10 | 500 | 589 | 178110 | 178199 | 60 | 98 | 88 | n.d. | 994325-994328, 1054972-1054984 | 103, 181, 259, 337, 3115-3117, 3186-3187, 3257-3258, 3325-3326, 3397-3398, 3468-3469 |
| 11 | 587 | 619 | N/A | N/A | 80 | 99 | 94 | n.d. | 994329, 1054990-1054999 | 415, 3119, 3188-3189, 3260-3261, 3328-3329, 3400, 3471-3472 |
| 12 | 3984 | 4031 | 458237 | 458284 | 77 | 95 | 83 | 24 | 994408-994409, 1040170-1040173 | 347, 425, 2728, 2805, 2882, 2959, 3036 |
| 13 | 4434 | 4457 | 458687 | 458710 | 88* | 88* | 88* | 49 | 994419, 1342032, 1364280, 1365267, 1365268, 1365270, 1365290-1365292, 1365298, 1371322, 1371325, 1371809, 1371824, 1371851, 1371854, 1371872, 1385295, 1394153-1394155, 1394534, 1394537, 1394539, 1394540, 1394547 | 582, 3563, 3593, 3605, 3621, 3635-3637, 3648-3649, 3652, 3656, 3658-3659 |
| 14 | 4497 | 4553 | 458750 | 458806 | 48 | 91 | 78 | 25 | 1040205-1040211 | 651, 728, 805, 882, 959, 2960, 3037 |
| 15 | 4586 | 4640 | 458839 | 458893 | 63 | 99 | 87 | 50 | 994420-994422, 1040212-1040215 | 37, 115, 193, 1036, 1113, 1190, 1267 |

TABLE 1-continued

| ATXN1 Hotspots | | | | | | | | | | |
|---|---|---|---|---|---|---|---|---|---|---|
| Hot spot ID | SEQ ID NO: 1 Start Site | SEQ ID NO: 1 Stop Site | SEQ ID NO: 2 Start Site | SEQ ID NO: 2 Stop Site | Min. % Red. in vitro | Max. % Red. in vitro | Avg. % Red. in vitro | Avg. % Red. in vivo (ctx) | Compound No. in range | SEQ ID NO in range |
| 16 | 4725 | 4786 | 458978 | 459039 | 24 | 98 | 77 | 33 | 994429-994430, 1040222-1040239, 1342061, 1342064, 1342069, 1342071, 1342074-1342076, 1364283, 1365262-1356265, 1365285-1365286, 1365288-1365289, 1371808, 1371810, 1371813, 1371815-1371816, 1371819, 1371822, 1371844-1371845, 1371848, 1371853, 1385294, 1394507, 1394511, 1394518, 1394523, 1394527 | 116, 194, 652, 1806, 1883, 1960, 2037, 2114, 2191, 2268, 2345, 2422, 2499, 2576, 2653, 2730, 2807, 2884, 2961, 3038, 3558, 3560-3562, 3574, 3576, 3578, 3592, 3594, 3597, 3604, 3631-3635, 3645, 3646-3647 |
| 17 | 6015 | 6099 | 460268 | 460352 | 58 | 94 | 78 | 34 | 994464-994469, 1040334-1040344, 1055012-1055023, 1342039, 1342041, 1342044, 1342046, 1342048 | 43, 121, 354, 1432, 510, 588, 655, 732, 809, 886, 963, 1040, 1117, 1194, 1271, 1348, 3041, 3123-3125, 3193-3194, 3263-3264, 3333-3334, 3403, 3473-3474, 3541, 3543, 3545, 3565, 3569 |
| 18 | 6919 | 6960 | 461172 | 461213 | 90 | 96 | 93 | 50 | 994484, 1040382-1040384 | 45, 1811, 1888, 1965 |
| 19 | 7076 | 7114 | 461329 | 461367 | 76 | 98 | 89 | 58 | 994490-994496, 1040393-1040395, 1394166-1394167, 1394516, 1394530 | 46, 124, 202, 280, 358, 513, 591, 2658, 2735, 2812 |
| 20 | 7696 | 7741 | 461949 | 461994 | 74 | 94 | 87 | 29 | 994506, 1040435-1040438 | 515, 966, 1043, 1120, 1197 |
| 21 | 8194 | 8257 | 462447 | 462510 | 58 | 97 | 82 | 37 | 994516-994521, 1040472-1040482, 1394512, 1394517, 1394528, 1394531 | 49, 127, 205, 283, 361, 439, 1352, 1429, 1506, 1583, 1660, 1737, 1814, 1891, 1968, 2045, 2122 |
| 22 | 9181 | 9214 | 463434 | 463467 | 68 | 97 | 82 | 51 | 994549-994551, 1040566-1040567 | 131, 209, 287, 1201, 1278 |
| 23 | 9472 | 9513 | 463725 | 463766 | 79 | 91 | 84 | 25 | 994559-994561, 1055024-1055036 | 288, 366, 444, 3126-3127, 3195-3197, 3265-3266, 3335-3336, 3404-3405, 3475-3476 |
| 24 | 9667 | 9730 | 463920 | 463983 | 75 | 94 | 86 | 35 | 994562-994564, 1040612-1040613 | 55, 522, 600, 2280, 2357 |
| 25 | 10095 | 10121 | 464348 | 464374 | 66 | 95 | 84 | 13 | 994571, 1055043-1055048 | 601, 3129, 3199, 3268, 3339, 3407, 3408 |
| 26 | 10133 | 10158 | 464386 | 464411 | 84 | 92 | 88 | n.d. | 994572-994574, 1040633 | 56, 134, 212, 1434 |
| 27 | 10237 | 10277 | 464490 | 464530 | 72 | 90 | 82 | n.d. | 994579-994580, 1040653-1040658 | 57, 602, 665, 742, 819, 896, 2974, 3051 |

TABLE 1-continued

| | ATXN1 Hotspots | | | | | | | | | |
|---|---|---|---|---|---|---|---|---|---|---|
| Hot spot ID | SEQ ID NO: 1 Start Site | SEQ ID NO: 1 Stop Site | SEQ ID NO: 2 Start Site | SEQ ID NO: 2 Stop Site | Min. % Red. in vitro | Max. % Red. in vitro | Avg. % Red. in vitro | Avg. % Red. in vivo (ctx) | Compound No. in range | SEQ ID NO in range |
| 28 | 10311 | 10353 | 464564 | 464606 | 80 | 95 | 89 | n.d. | 994581-994583 1040663-1040666 | 135, 213, 291, 1281, 1358, 1435, 1512 |
| 29 | N/A | N/A | 439072 | 439126 | 69 | 99 | 87 | 47 | 994809-994811, 1041407-1041414, 1364281, 1365254-1365255, 1365278, 1365281, 1394526 | 475, 553, 631, 1920, 1997, 2074, 2151, 2228, 2305, 2382, 2459, 3625-3626, 3642-3643 |
| 30 | N/A | N/A | 17722 | 17748 | 72 | 99 | 87 | n.d. | 994605, 1055065-1055071 | 138, 3134, 3202-3203, 3270, 3343, 3412, 3480 |
| 31 | N/A | N/A | 85512 | 85545 | 64 | 92 | 76 | n.d. | 994630, 1055084-1055094 | 219, 3137, 3206-3207, 3273-3274, 3346-3347, 3415-3416, 3483-3484 |
| 32 | N/A | N/A | 179779 | 179809 | 43 | 96 | 81 | n.d. | 994690, 1055106-1055113 | 538, 3140, 3210, 3276-3277, 3350, 3419-3420, 3487 |
| 33 | N/A | N/A | 184181 | 184213 | 85 | 99 | 94 | n.d. | 994693, 1055123-1055132 | 149, 3143, 3212-3213, 3280, 3352-3353, 3422-3423, 3490-3491 |
| 34 | N/A | N/A | 203033 | 203066 | 48 | 94 | 76 | n.d. | 994700, 1055137-1055147 | 72, 3144-3145, 3214-3215, 3282-3283, 3355-3356, 3425, 3493-3494 |
| 35 | N/A | N/A | 203889 | 203914 | 81 | 98 | 92 | n.d. | 994701, 1055151-1055156 | 150, 3147, 3285, 3357-3358, 3426, 3495 |
| 36 | N/A | N/A | 210720 | 210755 | 47 | 96 | 80 | n.d. | 994702, 1055157-1055168 | 228, 3148-3149, 3217-3218, 3286-3287, 3359-3360, 3427-3429, 3496 |
| 37 | N/A | N/A | 212027 | 212056 | 69 | 90 | 80 | n.d. | 994703, 1055174-1055182 | 306, 3151-3152, 3220-3221, 3362, 3430-3431, 3498-3499 |
| 38 | N/A | N/A | 217274 | 217309 | 40 | 97 | 73 | n.d. | 994706, 1055186-1055197 | 540, 3153, 3222-3223, 3290-3291, 3364-3365, 3433-3434, 3500-3502 |
| 39 | N/A | N/A | 226995 | 227019 | 75 | 90 | 81 | n.d. | 994713, 1055208-1055212 | 463, 3156, 3226, 3294, 3368, 3436 |
| 40 | N/A | N/A | 251500 | 251533 | 68 | 94 | 83 | n.d. | 994717, 1055224-1055234 | 152, 3159-3160, 3229, 3297-3298, 3370-3371, 3439-3440, 3506-3507 |
| 41 | N/A | N/A | 284223 | 284260 | 96 | 99 | 98 | n.d. | 994731, 1055240-1055252 | 621, 3162, 3163, 3231, 3232, 3299, 3300, 3374, |

TABLE 1-continued

| ATXN1 Hotspots | | | | | | | | | |
|---|---|---|---|---|---|---|---|---|---|
| Hot spot ID | SEQ ID NO: 1 Start Site | SEQ ID NO: 1 Stop Site | SEQ ID NO: 2 Start Site | SEQ ID NO: 2 Stop Site | Min. % Red. in vitro | Max. % Red. in vitro | Avg. % Red. in vitro | Avg. % Red. in vivo (ctx) | Compound No. in range | SEQ ID NO in range |
| 42 | N/A | N/A | 284331 | 284370 | 39 | 98 | 88 | n.d. | 994732, 1055253-1055266 | 3375, 3442, 3443, 3509, 3510 76, 3164-3166, 3233-3234, 3301-3302. 3376-3377, 3444-3446, 3511-3512 |
| 43 | N/A | N/A | 291004 | 291043 | 93 | 99 | 97 | n.d. | 994734, 1055268-1055281 | 232, 3167-3168, 3236-3237, 3303-3305, 3378-3379, 3447-3449, 3513-3514 |
| 44 | N/A | N/A | 296997 | 297034 | 73 | 99 | 95 | n.d. | 994735, 1055283-1055295 | 310, 3169-3170, 3238-3240, 3306-3307, 3380-3381, 3450-3451, 3516-3517 |
| 45 | N/A | N/A | 306737 | 306769 | 78 | 98 | 92 | n.d. | 994740, 1055300-1055305 | 77, 3171, 3241, 3309, 3383, 3453, 3519 |
| 46 | N/A | N/A | 318484 | 318519 | 88 | 99 | 96 | n.d. | 994743, 1041154, 1055310-1055317 | 311, 2143, 3173-3174, 3243, 3311, 3385, 3454-3455, 3520 |
| 47 | N/A | N/A | 332352 | 332391 | 54 | 99 | 90 | n.d. | 994756, 1055321-1055334 | 79, 3175-3177, 3245-3246, 3313-3314, 3387-3388, 3456-3458, 3521-3522 |
| 48 | N/A | N/A | 347813 | 347852 | 57 | 99 | 84 | n.d. | 994761, 1055337-1055350 | 469, 3178-3179, 3248-3249, 3316-3317, 3389-3391, 3459-3460, 3523-3525 |
| 49 | N/A | N/A | 437786 | 437815 | 74 | 97 | 91 | 12 | 1041316-1041322 | 2302, 2379, 2456, 2533, 2610, 2687, 2764 |
| 50 | N/A | N/A | 439429 | 439463 | 81 | 96 | 87 | 14 | 1041438-1041443, 1342051, 1342058, 1342043, 1342040 | 1844, 1921, 1998, 2075, 2152, 2229, 3547, 3572 |
| 51 | N/A | N/A | 442680 | 442711 | 78 | 93 | 87 | 30 | 1041636-1041639 | 2312, 2389, 2466, 2543 |
| 52 | N/A | N/A | 446727 | 446761 | 74 | 93 | 84 | n.d. | 1041936-1041941 | 782, 859, 936, 1013, 1090, 1167 |
| 53 | N/A | N/A | 446925 | 446970 | 59 | 91 | 77 | n.d. | 994871-994873, 1041961-1041966 | 327, 405, 483, 2707, 2784, 2861, 2938, 3015, 3092 |
| 54 | N/A | N/A | 451523 | 451560 | 82 | 95 | 89 | n.d. | 1042239-1042244 | 1946, 2023, 2100, 2177, 2254, 2331 |
| 55 | N/A | N/A | 451681 | 451718 | 72 | 91 | 83 | 0 | 1042253-1042258 | 715, 792, 869, 946, 3024, 3101 |

TABLE 1-continued

ATXN1 Hotspots

| Hot spot ID | SEQ ID NO: 1 Start Site | SEQ ID NO: 1 Stop Site | SEQ ID NO: 2 Start Site | SEQ ID NO: 2 Stop Site | Min. % Red. in vitro | Max. % Red. in vitro | Avg. % Red. in vitro | Avg. % Red. in vivo (ctx) | Compound No. in range | SEQ ID NO in range |
|---|---|---|---|---|---|---|---|---|---|---|
| 6 | 99 | 140 | 2609 | 2650 | 43 | 90 | 76 | n.d. | 994310-994313, 1054946-1054957 | 179, 257, 335, 413, 3111-3113, 3183, 3253-3254, 3321-3322, 3394-3395, 3464-3465 |

*Only a single compound tested in vitro; see in vivo column for average % reduction.

NONLIMITING DISCLOSURE AND INCORPORATION BY REFERENCE

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of an uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, tautomeric forms of the compounds herein are also included unless otherwise indicated. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1H$ hydrogen atoms. Isotopic substitutions encompassed by the compounds herein include but are not limited to: $^2H$ or 3H in place of $^1H$, $^{13}C$ or $^{14}C$ in place of $^{12}C$, $^{15}N$ in place of $^{14}N$, $^{17}O$ or $^{18}O$ in place of $^{16}O$, and $^{33}S$, $^{34}S$, $^{35}S$, or $^{36}S$ in place of $^{32}S$. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

Under certain conditions, certain compounds disclosed herein act as acids. Although such compounds may be drawn or described in protonated (free acid) form, or ionized and in association with a cation (salt) form, aqueous solutions of such compounds exist in equilibrium among such forms. For example, a phosphodiester linkage of an oligonucleotide in aqueous solution exists in equilibrium among free acid, anion and salt forms. Unless otherwise indicated, compounds described herein are intended to include all such forms. Moreover, certain oligonucleotides have several such linkages, each of which is in equilibrium. Thus, oligonucleotides in solution exist in an ensemble of forms at multiple positions all at equilibrium. The term "oligonucleotide" is intended to include all such forms. Drawn structures necessarily depict a single form. Nevertheless, unless otherwise indicated, such drawings are likewise intended to include corresponding forms. Herein, a structure depicting the free acid of a compound followed by the term "or a salt thereof" expressly includes all such forms that may be fully or partially protonated/de-protonated/in association with a cation. In certain instances, one or more specific cation is identified. In certain embodiments, modified oligonucleotides or oligomeric compounds are in aqueous solution with sodium. In certain embodiments, modified oligonucleotides or oligomeric compounds are in aqueous solution with potassium. In certain embodiments, modified oligonucleotides or oligomeric compounds are in PBS. In certain embodiments, modified oligonucleotides or oligomeric compounds are in water. In certain such embodiments, the pH of the solution is adjusted with NaOH and/or HCl to achieve a desired pH.

Herein, certain specific doses are described. A dose may be in the form of a dosage unit. For clarity, a dose (or dosage unit) of a modified oligonucleotide or an oligomeric compound in milligrams indicates the mass of the free acid form of the modified oligonucleotide or oligomeric compound. As described above, in aqueous solution, the free acid is in equilibrium with anionic and salt forms. However, for the purpose of calculating dose, it is assumed that the modified oligonucleotide or oligomeric compound exists as a solvent-free, sodium-acetate free, anhydrous, free acid. For example, where a modified oligonucleotide or an oligomeric compound is in solution comprising sodium (e.g., saline), the modified oligonucleotide or oligomeric compound may be partially or fully de-protonated and in association with Na+ ions. However, the mass of the protons are nevertheless counted toward the weight of the dose, and the mass of the Na+ ions are not counted toward the weight of the dose. Thus, for example, a dose, or dosage unit, of 10 mg of Compound No. 1371311, equals the number of fully protonated molecules that weighs 10 mg. This would be equivalent to 10.59 mg of solvent-free, sodium acetate-free, anhydrous sodiated Compound No. 1371311. When an oligomeric compound comprises a conjugate group, the mass of the conjugate group is included in calculating the dose of such oligomeric compound. If the conjugate group also has an acid, the conjugate group is likewise assumed to be fully protonated for the purpose of calculating dose.

EXAMPLES

Example 1: Effect of 5-10-5 MOE Gapmer Modified Oligonucleotides on Human ATXN1 RNA In Vitro, Single Dose Modified oligonucleotides complementary to human ATXN1 nucleic acid were designed and tested for their single dose effects on ATXN1 mRNA in vitro. The modified oligonucleotides were tested in a series of experiments that had similar culture conditions.

The modified oligonucleotides in the tables below are 5-10-5 MOE gapmers with mixed PO/PS internucleoside linkages. The gapmers are 20 nucleosides in length, wherein the central gap segment consists of ten 2'-β-D-deoxynucleosides and the 3' and 5' wings each consist of five 2'-MOE modified nucleosides. The motif for the gapmers is (from 5' to 3'): eeeeedddddddddddeeeee; wherein "d" represents a 2'-β-D-deoxyribosyl sugar, and 'e' represents a 2'-MOE modified ribosyl sugar. The internucleoside linkage motif for the gapmers is (from 5' to 3'): sooossssssssssssooss; wherein 'o' represents a phosphodiester internucleoside linkage and 's' represents a phosphorothioate internucleoside linkage. Each cytosine residue is a 5-methyl cytosine.

"Start site" indicates the 5'-most nucleoside to which the modified oligonucleotide is complementary in the human gene sequence. "Stop site" indicates the 3'-most nucleoside to which the modified oligonucleotide is complementary in the human gene sequence. Each modified oligonucleotide listed in the Tables below is 100% complementary to SEQ ID NO: 1 (GENBANK Accession No. NM_000332.3), or SEQ ID NO: 2 (the complement of GENBANK Accession No. NC_000006.12 truncated from nucleotides 16296001 to 16764000). 'N/A' indicates that the modified oligonucleotide is not 100% complementary to that particular gene sequence.

Cultured A-431 cells were treated with modified oligonucleotide at a concentration of 4,000 nM by free uptake at a density of 10,000 cells per well for a treatment period of 48 hours. At the end of their treatment period, total RNA was isolated from the cells and ATXN1 RNA levels were measured by quantitative real-time RTPCR. ATXN1 RNA levels were measured by Human ATXN1 primer probe set RTS37573 (forward sequence CATCCAGAGTGCAGAGATAAGC, designated herein as SEQ ID NO: 11; reverse sequence ACTCTACCAAAACTTCAACGCT, designated herein as SEQ ID NO: 12; probe sequence AGAGGATTGAAGACAGCCATAGCCC, designated herein as SEQ ID NO: 13). ATXN1 RNA levels were normalized to total RNA content, as measured by RIBOGREEN® fluorescent RNA assay. Results are presented in the tables below as percent ATXN1 RNA levels relative to untreated control cells (% control). Each table represents results from an individual assay plate. The Compound No. marked with an asterisk (*) indicates that the modified oligonucleotide is complementary to the amplicon region of the primer probe set. Additional assays may be used to measure the potency and efficacy of the modified oligonucleotides complementary to the amplicon region.

TABLE 2

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994308 | 6 | 25 | 2516 | 2535 | CTGCGGTATACTCTGCTCTC | 96 | 23 |
| 994316 | 305 | 324 | 1076 | 10735 | GGAGGAGGAGATTGCTGTAC | 13 | 24 |
| 994324 | 435 | 454 | 106177 | 106196 | GTGCAGGCTGAAATCCACTC | 32 | 25 |
| 994332 | 691 | 710 | 277909 | 277928 | GTGTTCTTTCTTCCTTTCAC | 37 | 26 |
| 994340 | 959 | 978 | 435678 | 435697 | ATTTCATTTTTCGCCGTCCC | 53 | 27 |
| 994348 | 1190 | 1209 | 435909 | 435928 | CTTTGTGTAAACCTATTCCC | 29 | 28 |
| 994356 | 1881 | 1900 | 436600 | 436619 | TCAGCTTTCTTGGTGGCCTC | 103 | 29 |
| 994364 | 2264 | 2283 | 436983 | 437002 | GTGTGGTCTGAATGACCGTG | 76 | 30 |

TABLE 2-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994372 | 2728 | 2747 | 437447 | 437466 | GTCTTCCACCTTCTTTAGCT | 65 | 31 |
| 994380* | 2816 | 2835 | 437535 | 437554 | GGCTGTCTTCAATCCTCTCT | 4 | 32 |
| 994388 | 3139 | 3158 | 457392 | 457411 | TCCGTTTTCCTGCTCGGCAT | 32 | 33 |
| 994396 | 3398 | 3417 | 457651 | 457670 | ACTTGCCTACATTAGACCGG | 30 | 34 |
| 994404 | 3630 | 3649 | 457883 | 457902 | ACCGCTCCTGCTGTGCCCTT | 35 | 35 |
| 994412 | 4246 | 4265 | 458499 | 458518 | CGCTCTCTCCCTCTCCCCCA | 55 | 36 |
| 994420 | 4617 | 4636 | 458870 | 458889 | TGTTTTTGTTTTTTCCCCAA | 2 | 37 |
| 994428 | 4708 | 4727 | 458961 | 458980 | ATTGAAACTTTCAATATCTT | 50 | 38 |
| 994436 | 4858 | 4877 | 459111 | 459130 | CCCTTTTCTCTCAGTTTCTC | 37 | 39 |
| 994444 | 5428 | 5447 | 459681 | 459700 | TTTTTTTTAAAGCACTTTAA | 73 | 40 |
| 994452 | 5560 | 5579 | 459813 | 459832 | GATTTTTTTTTAATTTGTG | 72 | 41 |
| 994460 | 5980 | 5999 | 460233 | 460252 | TGTGTGTTTTTCTGAGTCCA | 4 | 42 |
| 994468 | 6050 | 6069 | 460303 | 460322 | GTGTTTTCCCATCTTAGTGT | 7 | 43 |
| 994476 | 6324 | 6343 | 460577 | 460596 | TGGGAGGCTCTCTCCCTCCT | 86 | 44 |
| 994484 | 6937 | 6956 | 461190 | 461209 | CGGTAAATATTGCAAAGTGG | 4 | 45 |
| 994492 | 7083 | 7102 | 461336 | 461355 | GTTTGTTGGTTTCTTATTAA | 5 | 46 |
| 994500 | 7217 | 7236 | 461470 | 461489 | GGCATCCATCTCTGTATCCC | 34 | 47 |
| 994508 | 7868 | 7887 | 462121 | 462140 | CATTGGAGATTTTCTCTCT | 17 | 48 |
| 994516 | 8196 | 8215 | 462449 | 462468 | TCTCTATTTCAGAAATTCTG | 34 | 49 |
| 994524 | 8379 | 8398 | 462632 | 462651 | ATCTATGTAAAAGAAATCTC | 58 | 50 |
| 994532 | 8542 | 8561 | 462795 | 462814 | AATTTTTTAAAACATTACCT | 57 | 51 |
| 994540 | 8764 | 8783 | 463017 | 463036 | GGTATAGTTTAAGAGCCTTT | 10 | 52 |
| 994548 | 9176 | 9195 | 463429 | 463448 | GCCTCTTTATATTAAATAAA | 76 | 53 |
| 994556 | 9296 | 9315 | 463549 | 463568 | TCTGAATTTAAGAATTGTAA | 52 | 54 |
| 994564 | 9707 | 9726 | 463960 | 463979 | ACCTAATACTTGGTATTCTG | 17 | 55 |
| 994572 | 10133 | 10152 | 464386 | 464405 | GTGTCTGTTTTCCCTTGGCC | 9 | 56 |
| 994580 | 10241 | 10260 | 464494 | 464513 | GTATGCACTTAAAATTTTCT | 11 | 57 |
| 994588 | 10381 | 10400 | 464634 | 464653 | ATAGAATATGAATTCTTCCA | 30 | 58 |
| 994596 | 10613 | 10632 | 464866 | 464885 | ATTGGCACTGTTATTTTATT | 48 | 59 |
| 994604 | N/A | N/A | 15633 | 15652 | GGCTCTTTAAATATTACTCC | 63 | 60 |
| 994612 | N/A | N/A | 31191 | 31210 | GTTTGACTAGATGTGCTTCT | 7 | 61 |
| 994620 | N/A | N/A | 41645 | 41664 | TCTTGAGCTTTTAATTTTAC | 22 | 62 |
| 994628 | N/A | N/A | 72785 | 72804 | TGCTCCTTTTATCATTGTCA | 16 | 63 |
| 994636 | N/A | N/A | 94229 | 94248 | CGGTGGTTTGTTGTACCCTT | 62 | 64 |

TABLE 2-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994644 | N/A | N/A | 111441 | 111460 | TGTACTCTATAATTTTTAA | 82 | 65 |
| 994652 | N/A | N/A | 134750 | 134769 | TGAGCTGCTTTTCATATTCT | 28 | 66 |
| 994660 | N/A | N/A | 148412<br>149523 | 148431<br>149542 | CAATAGACAAAAATTATCAT | 78 | 67 |
| 994668 | N/A | N/A | 148748<br>149859 | 148767<br>149878 | TTTCCGAAGCTGCTATATGT | 63 | 68 |
| 994676 | N/A | N/A | 155724 | 155743 | GTCTCTCTTTTTCTAAGTCA | 46 | 69 |
| 994684 | N/A | N/A | 169830<br>170088 | 169849<br>170107 | AGACTAATATATATATATAT | 52 | 70 |
| 994692 | N/A | N/A | 180504 | 180523 | GGGTCTCTTCATCTACCTTC | 61 | 71 |
| 994700 | N/A | N/A | 203037 | 203056 | TGTTCCTTTCTTCTTTGTTC | 21 | 72 |
| 994708 | N/A | N/A | 219463 | 219482 | GGGTGTGTATTCAATTCTCT | 59 | 73 |
| 994716 | N/A | N/A | 250181 | 250200 | GTGACTTTAAAGCTTTCCTG | 53 | 74 |
| 994724 | N/A | N/A | 269848<br>269877 | 269867<br>269896 | ACTGAGAGGCATCTCCAGTG | 86 | 75 |
| 994732 | N/A | N/A | 284341 | 284360 | TGTCAACTAGTTCTTATCAC | 7 | 76 |
| 994740 | N/A | N/A | 306740<br>306826 | 306759<br>306845 | GGTAAGGGCCACTAAATCTG | 5 | 77 |
| 994748 | N/A | N/A | 322467<br>323729 | 322486<br>323748 | CTTACCACAGAGACATGCCC | 56 | 78 |
| 994756 | N/A | N/A | 332362 | 332381 | GGAGTATTATAACAATTTGC | 5 | 79 |
| 994764 | N/A | N/A | 354092 | 354111 | GTCTGGGCTGATGATGCTGG | 16 | 80 |
| 994772 | N/A | N/A | 369873 | 369892 | GTCTGCCTTTAACATTTTTC | 25 | 81 |
| 994780 | N/A | N/A | 386759 | 386778 | TGTTGTTTATAAGTTTACGG | 12 | 82 |
| 994788 | N/A | N/A | 406846 | 406865 | TGCAGCTTATTTTATAGGTG | 8 | 83 |
| 994796 | N/A | N/A | 422947 | 422966 | CGGTGTCTTAATATCCTCAG | 32 | 84 |
| 994804 | N/A | N/A | 437891 | 437910 | GTTCCTCATCTTAATCACAG | 24 | 85 |
| 994812 | N/A | N/A | 439175 | 439194 | GTGACTCATCTTGGCTACAG | 32 | 86 |
| 994820 | N/A | N/A | 440213 | 440232 | ATTTTCCATGTGTCACCTGG | 34 | 87 |
| 994828 | N/A | N/A | 441396 | 441415 | GTGCAGTGTCAGCAGTGCCT | 44 | 88 |
| 994836 | N/A | N/A | 443271 | 443290 | GTTGTCTTACTGATCTGGAG | 12 | 89 |
| 994844 | N/A | N/A | 444292 | 444311 | TGAGACCTCTCTCTACTTGC | 43 | 90 |
| 994852 | N/A | N/A | 445329 | 445348 | TCAGTCCTTGGTGGAAGTGT | 50 | 91 |
| 994860 | N/A | N/A | 445809 | 445828 | TCTGTTGTTTAAATATGTCT | 49 | 92 |
| 994868 | N/A | N/A | 446320 | 446339 | TCTTTCATCTCTGGATGCCC | 42 | 93 |
| 994876 | N/A | N/A | 447587 | 447606 | GTGTTCTATCTCCAGAGTCT | 20 | 94 |
| 994884 | N/A | N/A | 448144 | 448163 | TGGTGAAGATAATGATGATC | 28 | 95 |
| 994892 | N/A | N/A | 449029 | 449048 | TCCAGTTTTAATAAAAGTTC | 61 | 96 |
| 994900 | N/A | N/A | 451116 | 451135 | ATTTTACTTAATTTTTACAA | 77 | 97 |
| 994908 | N/A | N/A | 452370 | 452389 | ATGTGCATATATACATAGAC | 23 | 98 |

TABLE 2-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994916 | N/A | N/A | 453097 | 453116 | CTTTTCTACTTCATCTTCTT | 61 | 99 |
| 994924 | N/A | N/A | 455432 | 455451 | GTGTTCTCTGGTGAGCCCCA | 59 | 100 |

TABLE 3

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994309 | 23 | 42 | 2533 | 2552 | TGTAGTAGAAATGATGTCTG | 75 | 101 |
| 994317 | 368 | 387 | 106110 | 106129 | AAATAGACTCTTTCACTATG | 41 | 102 |
| 994325 | 500 | 519 | 178110 | 178129 | GTGGCAGTGGAGAATCTCAG | 10 | 103 |
| 994333 | 761 | 780 | 277979 | 277998 | TCAGCCTATACTTCACCATG | 40 | 104 |
| 994341 | 965 | 984 | 435684 | 435703 | GGTTGGATTTCATTTTTCGC | 17 | 105 |
| 994349 | 1363 | 1382 | 436082 | 436101 | TCCACTGTATTGGGAGGACC | 73 | 106 |
| 994357 | 1882 | 1901 | 436601 | 436620 | CTCAGCTTTCTTGGTGGCCT | 93 | 107 |
| 994365 | 2455 | 2474 | 437174 | 437193 | CGCTTCCATGTCAGTGCTGC | 62 | 108 |
| 994373 | 2739 | 2758 | 437458 | 437477 | TCTGTTTTAAGTCTTCCAC | 35 | 109 |
| 994381* | 2848 | 2867 | 437567 | 437586 | GGCGAACTGTATCACGGCCA | 49 | 110 |
| 994389 | 3147 | 3166 | 457400 | 457419 | TGGTTGATTCCGTTTTCCTG | 63 | 111 |
| 994397 | 3467 | 3486 | 457720 | 457739 | CCTACAGTACAGTAATCTGG | 32 | 112 |
| 994405 | 3750 | 3769 | 458003 | 458022 | CACGGGACTTTTCTCCTGAC | 49 | 113 |
| 994413 | 4249 | 4268 | 458502 | 458521 | GTTCGCTCTCTCCCTCTCCC | 13 | 114 |
| 994421 | 4618 | 4637 | 458871 | 458890 | TTGTTTTTGTTTTTTCCCCA | 1 | 115 |
| 994429 | 4759 | 4778 | 459012 | 459031 | CATTTATTGTCACATACTAG | 19 | 116 |
| 994437 | 4922 | 4941 | 459175 | 459194 | GGTTCTTTAAAAGTTCATCT | 2 | 117 |
| 994445 | 5429 | 5448 | 459682 | 459701 | CTTTTTTTTAAAGCACTTTA | 37 | 118 |
| 994453 | 5571 | 5590 | 459824 | 459843 | GGTTGATACCAGATTTTTTT | 19 | 119 |
| 994461 | 5981 | 6000 | 460234 | 460253 | GTGTGTGTTTTTCTGAGTCC | 6 | 120 |
| 994469 | 6054 | 6073 | 460307 | 460326 | ATGTGTGTTTTCCCATCTTA | 8 | 121 |
| 994477 | 6421 | 6440 | 460674 | 460693 | GTCTCCTTGGCTGGCTCTTT | 21 | 122 |
| 994485 | 7018 | 7037 | 461271 | 461290 | GTGTTCCATTGTAAACGCAA | 36 | 123 |
| 994493 | 7087 | 7106 | 461340 | 461359 | TCTTGTTTGTTGGTTTCTTA | 3 | 124 |
| 994501 | 7243 | 7262 | 461496 | 461515 | TCCACTTTAAAAGATCTGAG | 18 | 125 |
| 994509 | 7892 | 7911 | 462145 | 462164 | GCACGGTATTAGTGTCTTCA | 6 | 126 |
| 994517 | 8204 | 8223 | 462457 | 462476 | TCTTAAATTCTCTATTTCAG | 34 | 127 |
| 994525 | 8487 | 8506 | 462740 | 462759 | TCTTCAGCTTCTCAAATCAG | 46 | 128 |

TABLE 3-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994533 | 8648 | 8667 | 462901 | 462920 | TCTGCTTTTTTTTTTTACA | 45 | 129 |
| 994541 | 8867 | 8886 | 463120 | 463139 | AAGTACTTTCAGCATAGGAA | 13 | 130 |
| 994549 | 9189 | 9208 | 463442 | 463461 | CGTATTTATTCTGGCCTCTT | 14 | 131 |
| 994557 | 9428 | 9447 | 463681 | 463700 | AATACAGTTGAACCATTTGT | 28 | 132 |
| 994565 | 9725 | 9744 | 463978 | 463997 | ACAGCTTGAGCTAGTGTCAC | 32 | 133 |
| 994573 | 10135 | 10154 | 464388 | 464407 | TGGTGTCTGTTTTCCCTTGG | 16 | 134 |
| 994581 | 10311 | 10330 | 464564 | 464583 | GGAATTACAGAGAGTATGCA | 11 | 135 |
| 994589 | 10506 | 10525 | 464759 | 464778 | GTTTTATTATAATAATGAAA | 76 | 136 |
| 994597 | 198 | 217 | 9914 | 9933 | GTAGTAGTTTTGTGAGGTA | 14 | 137 |
| 994605 | N/A | N/A | 17726 | 17745 | GTCACCTTTTCTATTTGCAC | 6 | 138 |
| 994613 | N/A | N/A | 33070 | 33089 | ATTTTGACTTTTGATTGGTG | 12 | 139 |
| 994621 | N/A | N/A | 44962 44984 | 44981 45003 | GGGACTCTGTCTTTATTTCC | 75 | 140 |
| 994629 | N/A | N/A | 77141 | 77160 | ATGTTTCTATCTAAGTCCCA | 40 | 141 |
| 994637 | N/A | N/A | 98148 | 98167 | GTGTGCATTTTTAATTTTGT | 55 | 142 |
| 994645 | N/A | N/A | 112180 | 112199 | TGAGGACATCATGATGGTGC | 20 | 143 |
| 994653 | N/A | N/A | 139451 | 139470 | GTTTTGTTTCAGTATTAGGT | 3 | 144 |
| 994661 | N/A | N/A | 148441 149552 | 148460 149571 | TACATCCTGAAAATCACAGC | 42 | 145 |
| 994669 | N/A | N/A | 148797 149908 | 148816 149927 | CTCTCACTTTTCTTCTCCTT | 59 | 146 |
| 994677 | N/A | N/A | 157700 | 157719 | GTCTCCTTACATAGTGCTGC | 42 | 147 |
| 994685 | N/A | N/A | 169837 169922 | 169856 169941 | ATATATTAGACTAATATATA | 86 | 148 |
| 994693 | N/A | N/A | 184184 | 184203 | TCAGGTTTATATGTATACAA | 7 | 149 |
| 994701 | N/A | N/A | 203893 | 203912 | GTTTGTTTAGATTTATCCTC | 5 | 150 |
| 994709 | N/A | N/A | 219913 | 219932 | GTCATAGCTCTCCTCTGCAC | 46 | 151 |
| 994717 | N/A | N/A | 251504 | 251523 | GTCAGCATACTTAGCTTTTC | 16 | 152 |
| 994725 | N/A | N/A | 269857 269886 | 269876 269905 | CAGGGCTGGACTGAGAGGCA | 58 | 153 |
| 994733 | N/A | N/A | 288893 | 288912 | TGAGACTATTATAGTTTCCA | 12 | 154 |
| 994741 | N/A | N/A | 308086 308110 | 308105 308129 | TAAAATGCACCAATCAACGC | 38 | 155 |
| 994749 | N/A | N/A | 328172 | 328191 | GTTACTTTATTTCTCTAGGG | 10 | 156 |
| 994757 | N/A | N/A | 333463 | 333482 | ATTTGTCTTGTTGTATGTTG | 15 | 157 |
| 994765 | N/A | N/A | 355633 | 355652 | GTTATTTAAATAGTGGCCT | 65 | 158 |
| 994773 | N/A | N/A | 369913 | 369932 | TCTTTGGCTTTTAGACCTGT | 35 | 159 |
| 994781 | N/A | N/A | 390011 | 390030 | ATGTTATATCAATGTTCTGT | 6 | 160 |
| 994789 | N/A | N/A | 413612 | 413631 | GTCTCAGCTCAAGAGTCTGT | 75 | 161 |
| 994797 | N/A | N/A | 430371 | 430390 | TGGCCTGTATATCTATGGAC | 75 | 162 |

TABLE 3-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
| --- | --- | --- | --- | --- | --- | --- | --- |
| 994805 | N/A | N/A | 438153 | 438172 | TCAGCCATAGCTCACTACAG | 26 | 163 |
| 994813 | N/A | N/A | 439396 | 439415 | GTCCCATTTGAATGTTTTCA | 15 | 164 |
| 994821 | N/A | N/A | 440225 | 440244 | TCACTCATGTTTATTTTCCA | 58 | 165 |
| 994829 | N/A | N/A | 441413 | 441432 | TCTGAATTTCTCTGTGGGTG | 11 | 166 |
| 994837 | N/A | N/A | 443454 | 443473 | TGTACTCTTCAGAGAAGCTG | 64 | 167 |
| 994845 | N/A | N/A | 444302 | 444321 | GTTAGGTGTGTGAGACCTCT | 61 | 168 |
| 994853 | N/A | N/A | 445380 | 445399 | TCTGTGAGTGTTCTATTTAA | 27 | 169 |
| 994861 | N/A | N/A | 445876 | 445895 | TGGTGCTATGTCTATATACA | 25 | 170 |
| 994869 | N/A | N/A | 446356 | 446375 | TGGCCTTTATACTTTTGTAA | 92 | 171 |
| 994877 | N/A | N/A | 447624 | 447643 | TGTATATTTGTCTGTTTTGC | 9 | 172 |
| 994885 | N/A | N/A | 448318 | 448337 | CTTCCTTTTTTATTTTGAG | 17 | 173 |
| 994893 | N/A | N/A | 449699 | 449718 | TCTTTATTTTATAATTAGGT | 63 | 174 |
| 994901 | N/A | N/A | 451209 | 451228 | TCTATGGTCCTCAGTCTCCT | 57 | 175 |
| 994909 | N/A | N/A | 452421 | 452440 | GTGACACTATTTGGTTTCAA | 59 | 176 |
| 994917 | N/A | N/A | 453098 | 453117 | GCTTTTCTACTTCATCTTCT | 59 | 177 |
| 994925 | N/A | N/A | 455497 | 455516 | TGGGCTTTTGATAGTGTTAA | 20 | 178 |

TABLE 4

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
| --- | --- | --- | --- | --- | --- | --- | --- |
| 994310 | 99 | 118 | 2609 | 2628 | GTTGCTCTGGCTGCTGCTCC | 23 | 179 |
| 994318 | 413 | 432 | 106155 | 106174 | TCTCTCTTGTTCCTGGTCTG | 9 | 180 |
| 994326 | 515 | 534 | 178125 | 178144 | GCTTGAGTAGAAAGGGTGGC | 40 | 181 |
| 994334 | 879 | 898 | 435598 | 435617 | GTCACATTTGATTTCTGTAG | 12 | 182 |
| 994342 | 966 | 985 | 435685 | 435704 | TGGTTGGATTTCATTTTTCG | 24 | 183 |
| 994350 | 1550 | 1569 | 436269 | 436288 | GCTGCTGCTGCTCAGCCTTG | 62 | 184 |
| 994358 | 1889 | 1908 | 436608 | 436627 | GGCTGCTCTCAGCTTTCTTG | 89 | 185 |
| 994366 | 2554 | 2573 | 437273 | 437292 | GTTGAAGTTCTCGCTCTTGG | 23 | 186 |
| 994374 | 2740 | 2759 | 437459 | 437478 | TTCTGTTTTTAAGTCTTCCA | 30 | 187 |
| 994382* | 2849 | 2868 | 437568 | 437587 | CGGCGAACTGTATCACGGCC | 30 | 188 |
| 994390 | 3154 | 3173 | 457407 | 457426 | ACTCCCCTGGTTGATTCCGT | 54 | 189 |
| 994398 | 3481 | 3500 | 457734 | 457753 | CTGTGTTATTTTAGCCTACA | 5 | 190 |
| 994406 | 3932 | 3951 | 458185 | 458204 | GTTCCTGATGTTGATTTTGC | 27 | 191 |
| 994414 | 4251 | 4270 | 458504 | 458523 | GTGTTCGCTCTCTCCCTCTC | 24 | 192 |

TABLE 4-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994422 | 4621 | 4640 | 458874 | 458893 | TTTTTGTTTTTGTTTTTCC | 14 | 193 |
| 994430 | 4762 | 4781 | 459015 | 459034 | GGTCATTTATTGTCACATAC | 2 | 194 |
| 994438 | 4971 | 4990 | 459224 | 459243 | ACTGCAGGAATATCACACAA | 54 | 195 |
| 994446 | 5485 | 5504 | 459738 | 459757 | GTTTAGTTGCAGCCATCCAA | 8 | 196 |
| 994454 | 5572 | 5591 | 459825 | 459844 | GGGTTGATACCAGATTTTTT | 29 | 197 |
| 994462 | 5983 | 6002 | 460236 | 460255 | TGGTGTGTGTTTTCTGAGT | 7 | 198 |
| 994470 | 6121 | 6140 | 460374 | 460393 | ATTTTATAATTCCTATACCT | 74 | 199 |
| 994478 | 6470 | 6489 | 460723 | 460742 | CATTCACTATTCCGTGTGGT | 41 | 200 |
| 994486 | 7024 | 7043 | 461277 | 461296 | GTGATTGTGTTCCATTGTAA | 5 | 201 |
| 994494 | 7088 | 7107 | 461341 | 461360 | TTCTTGTTTGTTGGTTTCTT | 5 | 202 |
| 994502 | 7384 | 7403 | 461637 | 461656 | TCACAATTCCAAGTTAGAAA | 16 | 203 |
| 994510 | 7930 | 7949 | 462183 | 462202 | GTACCGAGAGCTCTGCTTCC | 54 | 204 |
| 994518 | 8208 | 8227 | 462461 | 462480 | GTGTTCTTAAATTCTCTATT | 3 | 205 |
| 994526 | 8492 | 8511 | 462745 | 462764 | TGTTTTCTTCAGCTTCTCAA | 18 | 206 |
| 994534 | 8649 | 8668 | 462902 | 462921 | CTCTGCTTTTTTTTTTTAC | 45 | 207 |
| 994542 | 8893 | 8912 | 463146 | 463165 | GTTTAGACTAAGAAGGGAGC | 22 | 208 |
| 994550 | 9191 | 9210 | 463444 | 463463 | TCCGTATTTATTCTGGCCTC | 32 | 209 |
| 994558 | 9462 | 9481 | 463715 | 463734 | AGATACTACCTATTGGCCAA | 63 | 210 |
| 994566 | 9758 | 9777 | 464011 | 464030 | GCACCGAGCTTCTTGGTAAC | 60 | 211 |
| 994574 | 10139 | 10158 | 464392 | 464411 | GTTCTGGTGTCTGTTTTCCC | 8 | 212 |
| 994582 | 10328 | 10347 | 464581 | 464600 | GTACAATATTTTACACTGGA | 5 | 213 |
| 994590 | 10548 | 10567 | 464801 | 464820 | ATTTATTTAAAACAATTTTG | 86 | 214 |
| 994598 | 201 | 220 | 9917 | 9936 | CTTGTAGTAGTTTTTGTGAG | 36 | 215 |
| 994606 | N/A | N/A | 18215 18273 | 18234 18292 | GGAGGGTGCTTAGTCCTTCC | 69 | 216 |
| 994614 | N/A | N/A | 34101 355035 | 34120 355054 | GTTTGGCACACAGTAGGTGC | 29 | 217 |
| 994622 | N/A | N/A | 46490 | 46509 | GTGACTGCTGCTGATACCTG | 39 | 218 |
| 994630 | N/A | N/A | 85516 | 85535 | GTTTGATATGCTATGCTCAC | 26 | 219 |
| 994638 | N/A | N/A | 98883 | 98902 | TGTTTGGTTGAAGTATGTGG | 30 | 220 |
| 994646 | N/A | N/A | 115266 | 115285 | ATGTGGGTATTTAATGTTTC | 17 | 221 |
| 994654 | N/A | N/A | 140695 | 140714 | GTCTTTCTAAATGGTTGTAC | 31 | 222 |
| 994662 | N/A | N/A | 148489 149600 | 148508 149619 | TTCAGCATGATCTCAGTTCT | 25 | 223 |
| 994670 | N/A | N/A | 148889 150000 | 148908 150019 | ATGACATAATTCTAATAACT | 58 | 224 |
| 994678 | N/A | N/A | 159922 | 159941 | TCTCCTTATCTTGTCCTCTC | 47 | 225 |
| 994686 | N/A | N/A | 169926 170006 | 169945 170025 | TATTATATATTAGACTAATA | 81 | 226 |

TABLE 4-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994694 | N/A | N/A | 185906 | 185925 | GTTCTATTTTATAATAGTAG | 70 | 227 |
| 994702 | N/A | N/A | 210730 | 210749 | TGTGTAATACTCCATTTTTC | 18 | 228 |
| 994710 | N/A | N/A | 223261 | 223280 | GTTTGTGTTGTGTTTTACAG | 19 | 229 |
| 994718 | N/A | N/A | 251771 | 251790 | GTTTTCATACACAGTTCTTC | 23 | 230 |
| 994726 | N/A | N/A | 270287 | 270306 | ATTATATTACATTATACTTG | 100 | 231 |
| 994734 | N/A | N/A | 291014 | 291033 | TCCTGGGTTTTAGTTTTCC | 4 | 232 |
| 994742 | N/A | N/A | 310465 | 310484 | TGAGGATTACATCAGTGTAA | 4 | 233 |
| 994750 | N/A | N/A | 328842 | 328861 | TCTTGGGTAGATGAGGTTTG | 11 | 234 |
| 994758 | N/A | N/A | 337233 | 337252 | TCTTGTTTTTCCTTTCTTG | 25 | 235 |
| 994766 | N/A | N/A | 357070 | 357089 | GTCTCCTTTGTTCCGTGTAC | 21 | 236 |
| 994774 | N/A | N/A | 372154 | 372173 | GTCTTTTTATTTCTCTGCCC | 11 | 237 |
| 994782 | N/A | N/A | 396255<br>396277 | 396274<br>396296 | TTGCAAGAAGGTATGCCTAG | 61 | 238 |
| 994790 | N/A | N/A | 413815 | 413834 | TCCTGTTTACAACAAAGCTC | 66 | 239 |
| 994798 | N/A | N/A | 430661 | 430680 | TCTTTCTTTGCTATAATTTC | 84 | 240 |
| 994806 | N/A | N/A | 438267 | 438286 | GTCTGCTGATCTATCTGTTG | 20 | 241 |
| 994814 | N/A | N/A | 439492 | 439511 | ATTAGTTTATCTTTTTTTC | 78 | 242 |
| 994822 | N/A | N/A | 440914 | 440933 | CTGTCAGTAGAGAGATTTAG | 41 | 243 |
| 994830 | N/A | N/A | 441421 | 441440 | TGCACATTTCTGAATTTCTC | 13 | 244 |
| 994838 | N/A | N/A | 443819 | 443838 | GTACCAGCTAATCCATTCAA | 43 | 245 |
| 994846 | N/A | N/A | 444486 | 444505 | TGTTCTGTATAATAATGTAA | 60 | 246 |
| 994854 | N/A | N/A | 445456 | 445475 | CGAGAGACCCATTTACTGCA | 16 | 247 |
| 994862 | N/A | N/A | 446068 | 446087 | TGGGCTCATAATTATTTTT | 71 | 248 |
| 994870 | N/A | N/A | 446878 | 446897 | AAGTCATTTTATGATCTTGC | 55 | 249 |
| 994878 | N/A | N/A | 447631 | 447650 | ATTTACTTGTATATTTGTCT | 12 | 250 |
| 994886 | N/A | N/A | 448328 | 448347 | GTTTCCATAGCTTCCTTTTT | 37 | 251 |
| 994894 | N/A | N/A | 449737 | 449756 | TCTCAAATAGGTACACTCAA | 40 | 252 |
| 994902 | N/A | N/A | 451578 | 451597 | TTTTGTTTAAAGGGTTTTAC | 85 | 253 |
| 994910 | N/A | N/A | 452423 | 452442 | GTGTGACACTATTTGGTTTC | 49 | 254 |
| 994918 | N/A | N/A | 453104 | 453123 | ATTGTTGCTTTTCTACTTCA | 73 | 255 |
| 994926 | N/A | N/A | 455500 | 455519 | AAGTGGGCTTTTGATAGTGT | 20 | 256 |

TABLE 5

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994311 | 103 | 122 | 2613 | 2632 | TGCTGTTGCTCTGGCTGCTG | 62 | 257 |
| 994319 | 417 | 436 | 106159 | 106178 | TCTTTCTCTCTTGTTCCTGG | 5 | 258 |
| 994327 | 533 | 552 | 178143 | 178162 | TCTTTTCACGAAGATTTTGC | 22 | 259 |
| 994335 | 881 | 900 | 435600 | 435619 | AAGTCACATTTGATTTCTGT | 31 | 260 |
| 994343 | 969 | 988 | 435688 | 435707 | TCTTGGTTGGATTTCATTTT | 31 | 261 |
| 994351 | 1634 | 1653 | 436353 | 436372 | TGAGGTGCTGCTGCTGCTGC | 15 | 262 |
| 994359 | 1904 | 1923 | 436623 | 436642 | TGGCCTGCTGCAGCCGGCTG | 82 | 263 |
| 994367 | 2555 | 2574 | 437274 | 437293 | GGTTGAAGTTCTCGCTCTTG | 14 | 264 |
| 994375 | 2742 | 2761 | 437461 | 437480 | TCTTCTGTTTTAAGTCTTC | 30 | 265 |
| 994383 | 2952 | 2971 | 457205 | 457224 | TGGCTGGTTCTCTCCGGACA | 71 | 266 |
| 994391 | 3245 | 3264 | 457498 | 457517 | TGCTGGGTTCTATTTTGGTG | 38 | 267 |
| 994399 | 3490 | 3509 | 457743 | 457762 | ATGTAAATACTGTGTTATTT | 32 | 268 |
| 994407 | 3933 | 3952 | 458186 | 458205 | GGTTCCTGATGTTGATTTG | 33 | 269 |
| 994415 | 4254 | 4273 | 458507 | 458526 | TGGGTGTTCGCTCTCTCCCT | 37 | 270 |
| 994423 | 4636 | 4655 | 458889 | 458908 | AAAGCAACTTAGTTTTTTTT | 46 | 271 |
| 994431 | 4774 | 4793 | 459027 | 459046 | GTAGTACTTGGTGGTCATTT | 67 | 272 |
| 994439 | 5033 | 5052 | 459286 | 459305 | TGCTACATTTATTTATGCTC | 36 | 273 |
| 994447 | 5491 | 5510 | 459744 | 459763 | TGTTCAGTTTAGTTGCAGCC | 4 | 274 |
| 994455 | 5593 | 5612 | 459846 | 459865 | AATACTAGACAGCCAAAATG | 34 | 275 |
| 994463 | 5986 | 6005 | 460239 | 460258 | AGGTGGTGTGTGTTTTTCTG | 4 | 276 |
| 994471 | 6124 | 6143 | 460377 | 460396 | ATTATTTTATAATTCCTATA | 79 | 277 |
| 994479 | 6535 | 6554 | 460788 | 460807 | TCCAGGCTACATGGCTCCAG | 27 | 278 |
| 994487 | 7056 | 7075 | 461309 | 461328 | ATTTTTTTCTTTTCGCCCTG | 21 | 279 |
| 994495 | 7091 | 7110 | 461344 | 461363 | AGGTTCTTGTTTGTTGGTTT | 2 | 280 |
| 994503 | 7392 | 7411 | 461645 | 461664 | ATAGAGGCTCACAATTCCAA | 12 | 281 |
| 994511 | 8000 | 8019 | 462253 | 462272 | TGTTGAGCTGCTTGTGGTTC | 63 | 282 |
| 994519 | 8212 | 8231 | 462465 | 462484 | TGATGTGTTCTTAAATTCTC | 24 | 283 |
| 994527 | 8495 | 8514 | 462748 | 462767 | TTTTGTTTTCTTCAGCTTCT | 19 | 284 |
| 994535 | 8651 | 8670 | 462904 | 462923 | TTCTCTGCTTTTTTTTTTTT | 44 | 285 |
| 994543 | 8984 | 9003 | 463237 | 463256 | CAAGATTATATTCTTTGGGT | 11 | 286 |
| 994551 | 9194 | 9213 | 463447 | 463466 | TGCTCCGTATTTATTCTGGC | 3 | 287 |
| 994559 | 9472 | 9491 | 463725 | 463744 | GTTATTGTATAGATACTACC | 17 | 288 |
| 994567 | 9841 | 9860 | 464094 | 464113 | GCACTAACTAAAGGATTTAC | 14 | 289 |
| 994575 | 10146 | 10165 | 464399 | 464418 | AACCCAAGTTCTGGTGTCTG | 32 | 290 |
| 994583 | 10334 | 10353 | 464587 | 464606 | GTGCAAGTACAATATTTTAC | 5 | 291 |
| 994591 | 10601 | 10620 | 464854 | 464873 | ATTTTATTAGTACGAGTATA | 41 | 292 |
| 994599 | 204 | 223 | 9920 | 9939 | GTGCTTGTAGTAGTTTTTGT | 30 | 293 |

TABLE 5-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994607 | N/A | N/A | 18221 18279 | 18240 18298 | GTTAGTGGAGGGTGCTTAGT | 24 | 294 |
| 994615 | N/A | N/A | 39140 | 39159 | TCCTGTTATTTTGGTACTGG | 24 | 295 |
| 994623 | N/A | N/A | 47154 | 47173 | GTTTGCCTACTCCTGGTCTG | 28 | 296 |
| 994631 | N/A | N/A | 85766 | 85785 | GTTGACTATCTTATTTTTTC | 20 | 297 |
| 994639 | N/A | N/A | 99612 | 99631 | TCTTGCTTTTAATTTTTTTG | 37 | 298 |
| 994647 | N/A | N/A | 117178 | 117197 | GTTCACCTACATGTTTCCCC | 16 | 299 |
| 994655 | N/A | N/A | 144856 | 144875 | TCTTTTTTTTTAATTACAG | 79 | 300 |
| 994663 | N/A | N/A | 148529 149640 | 148548 149659 | TGGTGCACTCAGCTCTACCT | 62 | 301 |
| 994671 | N/A | N/A | 148965 150076 | 148984 150095 | AAAAATCCTGATCAAAAAAA | 76 | 302 |
| 994679 | N/A | N/A | 160587 | 160606 | GGCTCCATACTCCATTCTGT | 40 | 303 |
| 994687 | N/A | N/A | 170194 | 170213 | TGTATAATATTCCATTCTGT | 48 | 304 |
| 994695 | N/A | N/A | 185938 | 185957 | ATTTTATTACATTTTTCTTG | 77 | 305 |
| 994703 | N/A | N/A | 212031 | 212050 | TCTATGTTAGTCATTTCTCT | 98 | 306 |
| 994711 | N/A | N/A | 223958 | 223977 | TCTTGACATGATGTTTCCCT | 60 | 307 |
| 994719 | N/A | N/A | 256280 | 256299 | ATTACCTTAAAACTACCTTG | 54 | 308 |
| 994727 | N/A | N/A | 271835 271877 | 271854 271896 | TAAGCCATGCCTGGACTTCG | 55 | 309 |
| 994735 | N/A | N/A | 297005 | 297024 | GTTTGCATTAAATGACTGTG | 2 | 310 |
| 994743 | N/A | N/A | 318485 | 318504 | TGTTTGATATTTCTTTTTTT | 10 | 311 |
| 994751 | N/A | N/A | 328883 | 328902 | TCTTGGGTAACTAGATGATG | 15 | 312 |
| 994759 | N/A | N/A | 341935 | 341954 | GTTTTTTTTTTATTTGCCT | 4 | 313 |
| 994767 | N/A | N/A | 357089 | 357108 | GTCAGGTTATAATGACCCTG | 49 | 314 |
| 994775 | N/A | N/A | 376249 | 376268 | TCTTCTGTATTTAATTCTTC | 11 | 315 |
| 994783 | N/A | N/A | 396693 | 396712 | GTTATTGTGTTTATATTCAG | 10 | 316 |
| 994791 | N/A | N/A | 414662 | 414681 | TGGTGACATCTTGTTTCTAC | 15 | 317 |
| 994799 | N/A | N/A | 433785 | 433804 | TGAGCCACTGTGTGTAGCCA | 52 | 318 |
| 994807 | N/A | N/A | 438269 | 438288 | TTGTCTGCTGATCTATCTGT | 25 | 319 |
| 994815 | N/A | N/A | 439696 | 439715 | GTTTTTATTTTAAATTAG | 62 | 320 |
| 994823 | N/A | N/A | 441090 | 441109 | CCTTGCACTTTGTTTCTAC | 7 | 321 |
| 994831 | N/A | N/A | 442195 | 442214 | TCAGTACATGTTCATCTTAA | 10 | 322 |
| 994839 | N/A | N/A | 443918 | 443937 | CGGCATGTTCAATGTTGGCA | 14 | 323 |
| 994847 | N/A | N/A | 444822 | 444841 | GTGAGCTATTATGGTGTCAC | 101 | 324 |
| 994855 | N/A | N/A | 445546 | 445565 | GTCTGCTTTCCTGGAAGGCT | 37 | 325 |
| 994863 | N/A | N/A | 446159 | 446178 | ATCCCCTAAATCGACTCCT | 63 | 326 |
| 994871 | N/A | N/A | 446925 | 446944 | GTTATTTTCTCTCCACTCTC | 33 | 327 |

TABLE 5-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994879 | N/A | N/A | 447641 | 447660 | ATTCTTTTTATTTACTTGT | 43 | 328 |
| 994887 | N/A | N/A | 448332 | 448351 | TCTAGTTTCCATAGCTTCCT | 17 | 329 |
| 994895 | N/A | N/A | 450049 | 450068 | TCTTTGTTTCTTTTTGCCTA | 9 | 330 |
| 994903 | N/A | N/A | 451583 | 451602 | TCCATTTTGTTTAAAGGGT | 25 | 331 |
| 994911 | N/A | N/A | 452493 | 452512 | TGGTACAGATAATTGTGATG | 29 | 332 |
| 994919 | N/A | N/A | 453190 | 453209 | TGGATTTTATACACATTCAG | 49 | 333 |
| 994927 | N/A | N/A | 456737 | 456756 | CTTAGATTTTATGAGCTCAA | 21 | 334 |

TABLE 6

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994312 | 105 | 124 | 2615 | 2634 | GCTGCTGTTGCTCTGGCTGC | 46 | 335 |
| 994320 | 418 | 437 | 106160 | 106179 | CTCTTTCTCTCTTGTTCCTG | 7 | 336 |
| 994328 | 562 | 581 | 178172 | 178191 | ACCATAAGCTATCAGTTCCT | 8 | 337 |
| 994336 | 916 | 935 | 435635 | 435654 | GTCTGGATGGCTCTGATTTT | 39 | 338 |
| 994344 | 974 | 993 | 435693 | 435712 | TCCGCTCTTGGTTGGATTTC | 63 | 339 |
| 994352 | 1637 | 1656 | 436356 | 436375 | TGCTGAGGTGCTGCTGCTGC | 31 | 340 |
| 994360 | 1927 | 1946 | 436646 | 436665 | GTTCAGGACCTCCTTGGCCT | 69 | 341 |
| 994368 | 2560 | 2579 | 437279 | 437298 | CTCAGGGTTGAAGTTCTCGC | 36 | 342 |
| 994376* | 2758 | 2777 | 437477 | 437496 | TGCACTCTGGATGAAATCTT | 34 | 343 |
| 994384 | 3025 | 3044 | 457278 | 457297 | CTTCAGGTTCTTGAGGGTAA | 33 | 344 |
| 994392 | 3248 | 3267 | 457501 | 457520 | GCTTGCTGGGTTCTATTTTG | 93 | 345 |
| 994400 | 3546 | 3565 | 457799 | 457818 | CCTGCTGTAACTCTAATGAC | 40 | 346 |
| 994408 | 3987 | 4006 | 458240 | 458259 | TGGTTAACTTTCCAAATCTG | 16 | 347 |
| 994416 | 4283 | 4302 | 458536 | 458555 | GTTTTCCTAACACTGCACAG | 23 | 348 |
| 994424 | 4661 | 4680 | 458914 | 458933 | ATGTAGTTACAGTGTTGAAA | 5 | 349 |
| 994432 | 4777 | 4796 | 459030 | 459049 | CAGGTAGTACTTGGTGGTCA | 76 | 350 |
| 994440 | 5037 | 5056 | 459290 | 459309 | ATTTGCTACATTTATTTAT | 53 | 351 |
| 994448 | 5496 | 5515 | 459749 | 459768 | GTATTTGTTCAGTTTAGTTG | 5 | 352 |
| 994456 | 5682 | 5701 | 459935 | 459954 | GCTATTCTAAACCTATTCAA | 75 | 353 |
| 994464 | 6029 | 6048 | 460282 | 460301 | GGTTTAGTGGATCCAGTCAA | 7 | 354 |
| 994472 | 6143 | 6162 | 460396 | 460415 | AAGTGTTTAGAAAGAACCAA | 41 | 355 |
| 994480 | 6702 | 6721 | 460955 | 460974 | TGGCAGGTGGTCCCCTCCAC | 68 | 356 |
| 994488 | 7064 | 7083 | 461317 | 461336 | ATAGTATTATTTTTTCTTT | 68 | 357 |
| 994496 | 7095 | 7114 | 461348 | 461367 | AGAGAGGTTCTTGTTTGTTG | 6 | 358 |

TABLE 6-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994504 | 7447 | 7466 | 461700 | 461719 | TGCTGCCACTTCCTGGTGGG | 87 | 359 |
| 994512 | 8003 | 8022 | 462256 | 462275 | GTCTGTTGAGCTGCTTGTGG | 32 | 360 |
| 994520 | 8230 | 8249 | 462483 | 462502 | CTCTGTATATTTATTACTTG | 5 | 361 |
| 994528 | 8496 | 8515 | 462749 | 462768 | ATTTTGTTTTCTTCAGCTTC | 34 | 362 |
| 994536 | 8653 | 8672 | 462906 | 462925 | CCTTCTCTGCTTTTTTTTTT | 73 | 363 |
| 994544 | 8987 | 9006 | 463240 | 463259 | GTTCAAGATTATATTCTTTG | 21 | 364 |
| 994552 | 9235 | 9254 | 463488 | 463507 | GTCCGGCTTGATTTTTGGAC | 78 | 365 |
| 994560 | 9477 | 9496 | 463730 | 463749 | TTGTTGTTATTGTATAGATA | 21 | 366 |
| 994568 | 9935 | 9954 | 464188 | 464207 | TTTAGAGTTGAGCAGTTCAG | 20 | 367 |
| 994576 | 10167 | 10186 | 464420 | 464439 | TGTCAGTCTGGTAGTGCCCT | 18 | 368 |
| 994584 | 10362 | 10381 | 464615 | 464634 | ATTTTTTAATATTTGTTTAA | 75 | 369 |
| 994592 | 10604 | 10623 | 464857 | 464876 | GTTATTTTATTAGTACGAGT | 25 | 370 |
| 994600 | 205 | 224 | 9921 | 9940 | GGTGCTTGTAGTAGTTTTTG | 27 | 371 |
| 994608 | N/A | N/A | 22131 | 22150 | TCCTCCTTTTATATCTGTTT | 72 | 372 |
| 994616 | N/A | N/A | 39208 | 39227 | GTTTGATTACTGTCATGACT | 36 | 373 |
| 994624 | N/A | N/A | 51696 51749 | 51715 51768 | GTGAAAAGAAAGATGTACTT | 82 | 374 |
| 994632 | N/A | N/A | 85767 | 85786 | CGTTGACTATCTTATTTTTT | 26 | 375 |
| 994640 | N/A | N/A | 103358 | 103377 | TCTCAATTATAATTTGTTTT | 71 | 376 |
| 994648 | N/A | N/A | 118549 | 118568 | GTTTCCTTAAAAGCAACTGT | 24 | 377 |
| 994656 | N/A | N/A | 148250 149361 | 148269 149380 | AGAGTCAATGATTAAATTCA | 29 | 378 |
| 994664 | N/A | N/A | 148584 149695 | 148603 149714 | CATGACTCTTTCTTAAGAAT | 49 | 379 |
| 994672 | N/A | N/A | 149011 150122 | 149030 150141 | AAATTTTCTAGAAACATTAA | 60 | 380 |
| 994680 | N/A | N/A | 160737 | 160756 | GTTACCATTCTCCTTTCCCC | 50 | 381 |
| 994688 | N/A | N/A | 170872 170939 | 170891 170958 | TGCTAGCTACAGAGCACTGA | 122 | 382 |
| 994696 | N/A | N/A | 188547 | 188566 | CGTTGGATATTTTATTCTTT | 2 | 383 |
| 994704 | N/A | N/A | 213149 | 213168 | ATGTTTGTATTCCATATTTG | 20 | 384 |
| 994712 | N/A | N/A | 224696 | 224715 | TCTTTTCATCTTCAGCTCTG | 50 | 385 |
| 994720 | N/A | N/A | 264945 | 264964 | GTTTGTGCTTTTGGTGTCAC | 14 | 386 |
| 994728 | N/A | N/A | 275360 | 275379 | GTTTGCTTTCTTCATCCTAC | 45 | 387 |
| 994736 | N/A | N/A | 299651 308026 | 299670 308045 | AATCGCAGGGAGGATTGAAA | 47 | 388 |
| 994744 | N/A | N/A | 318885 | 318904 | TGACCTTTATTTGGATCTTG | 26 | 389 |
| 994752 | N/A | N/A | 329899 | 329918 | TGGCATTTATAATATTTGTG | 2 | 390 |
| 994760 | N/A | N/A | 347724 | 347743 | ATTTTCTTAGAAGGATCTCT | 10 | 391 |

TABLE 6-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994768 | N/A | N/A | 359649 | 359668 | GTTTGAACTGAGCATGTTTT | 17 | 392 |
| 994776 | N/A | N/A | 380393 | 380412 | TGGTCATTAGATCATGCTAC | 31 | 393 |
| 994784 | N/A | N/A | 396974 | 396993 | TGTAGCTTTTAGTGACTTTG | 11 | 394 |
| 994792 | N/A | N/A | 415670 | 415689 | ATTTTGGCTTTCCATAGTGT | 44 | 395 |
| 994800 | N/A | N/A | 434146 | 434165 | GTTACTGCTGCTGTGTGGGC | 64 | 396 |
| 994808 | N/A | N/A | 439027 | 439046 | CTAGGATTAGCTAATTCCTA | 78 | 397 |
| 994816 | N/A | N/A | 439709 | 439728 | TCTCTACTAAAATGTTTTTT | 43 | 398 |
| 994824 | N/A | N/A | 441169 | 441188 | GGAGTATTTTAGCTGTGATG | 6 | 399 |
| 994832 | N/A | N/A | 442536 | 442555 | GCTTCCTTTGGTGCACGCAG | 34 | 400 |
| 994840 | N/A | N/A | 444077 | 444096 | GTTTGACATAGTTTCTCTGT | 15 | 401 |
| 994848 | N/A | N/A | 444899 | 444918 | TGGTGTGTACTTGTGGTCCC | 49 | 402 |
| 994856 | N/A | N/A | 445653 | 445672 | GTTTCAGTAAGTATGTCTTG | 11 | 403 |
| 994864 | N/A | N/A | 446193 | 446212 | GTTATAAGAGATCTGCCTAC | 70 | 404 |
| 994872 | N/A | N/A | 446936 | 446955 | ATCACACTTCAGTTATTTTC | 31 | 405 |
| 994880 | N/A | N/A | 447652 | 447671 | TCTTCTTATGCATTCTTTTT | 29 | 406 |
| 994888 | N/A | N/A | 448391 | 448410 | CCACCCACTGTCCTTTTCAG | 58 | 407 |
| 994896 | N/A | N/A | 450077 | 450096 | ATTCTTCTTTAATCACTTCA | 55 | 408 |
| 994904 | N/A | N/A | 452108 | 452127 | GTTTGCTTATTCTTGCCCAA | 11 | 409 |
| 994912 | N/A | N/A | 452497 | 452516 | TCCATGGTACAGATAATTGT | 53 | 410 |
| 994920 | N/A | N/A | 453505 | 453524 | GTTGGATTCTTTTTTTCTTT | 5 | 411 |
| 994928 | N/A | N/A | 456851 | 456870 | TCTATAGCTGGTCTCTGTTA | 54 | 412 |

TABLE 7

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994313 | 111 | 130 | 2621 | 2640 | CTTGCGGCTGCTGTTGCTCT | 28 | 413 |
| 994321 | 419 | 438 | 106161 | 106180 | ACTCTTTCTCTCTTGTTCCT | 7 | 414 |
| 994329 | 590 | 609 | 178200 | 178219 | GTACCATGTGCTTTCATCAC | 11 | 415 |
| 994337 | 924 | 943 | 435643 | 435662 | GTTTCACTGTCTGGATGGCT | 21 | 416 |
| 994345 | 977 | 996 | 435696 | 435715 | TGCTCCGCTCTTGGTTGGAT | 57 | 417 |
| 994353 | 1693 | 1712 | 436412 | 436431 | GTACTGGTTCTGCTGGGCTG | 32 | 418 |
| 994361 | 1949 | 1968 | 436668 | 436687 | GCCGGCTCTTCTCCATCTCA | 87 | 419 |
| 994369 | 2720 | 2739 | 437439 | 437458 | CCTTCTTTAGCTCCCCGTTG | 48 | 420 |
| 994377* | 2768 | 2787 | 437487 | 437506 | TGCTTATCTCTGCACTCTGG | 6 | 421 |
| 994385 | 3034 | 3053 | 457287 | 457306 | AGAGCCGTTCTTCAGGTTCT | 90 | 422 |

TABLE 7-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994393 | 3279 | 3298 | 457532 | 457551 | GCCGACCACCTCCTCTTCCT | 89 | 423 |
| 994401 | 3568 | 3587 | 457821 | 457840 | TGCACCAGTCTCCTGCGACA | 41 | 424 |
| 994409 | 3999 | 4018 | 458252 | 458271 | TGTTCTTTTAAATGGTTAAC | 17 | 425 |
| 994417 | 4330 | 4349 | 458583 | 458602 | GTTTGCATCTACCTCTTGGG | 14 | 426 |
| 994425 | 4673 | 4692 | 458926 | 458945 | TGCAGAGCTGAAATGTAGTT | 38 | 427 |
| 994433 | 4780 | 4799 | 459033 | 459052 | CGTCAGGTAGTACTTGGTGG | 55 | 428 |
| 994441 | 5069 | 5088 | 459322 | 459341 | AATGGCCTAGAGTTTAGGCA | 81 | 429 |
| 994449 | 5499 | 5518 | 459752 | 459771 | CAGGTATTTGTTCAGTTTAG | 3 | 430 |
| 994457 | 5905 | 5924 | 460158 | 460177 | TCCTCTTACCATCAAAGGCT | 45 | 431 |
| 994465 | 6033 | 6052 | 460286 | 460305 | TGTTGGTTTAGTGGATCCAG | 13 | 432 |
| 994473 | 6194 | 6213 | 460447 | 460466 | TGGCACAGAAAGTATTGCAC | 34 | 433 |
| 994481 | 6716 | 6735 | 460969 | 460988 | GTGGTGACCGTGGGTGGCAG | 84 | 434 |
| 994489 | 7075 | 7094 | 461328 | 461347 | GTTTCTTATTAATAGTATTA | 38 | 435 |
| 994497 | 7125 | 7144 | 461378 | 461397 | GTCATTTTATATATTTAGAA | 74 | 436 |
| 994505 | 7454 | 7473 | 461707 | 461726 | GGAGGGATGCTGCCACTTCC | 67 | 437 |
| 994513 | 8005 | 8024 | 462258 | 462277 | CAGTCTGTTGAGCTGCTTGT | 55 | 438 |
| 994521 | 8232 | 8251 | 462485 | 462504 | TTCTCTGTATATTTATTACT | 42 | 439 |
| 994529 | 8503 | 8522 | 462756 | 462775 | CTTCAAAATTTTGTTTTCTT | 38 | 440 |
| 994537 | 8693 | 8712 | 462946 | 462965 | TGACAAATTTCTATATACAA | 66 | 441 |
| 994545 | 9036 | 9055 | 463289 | 463308 | TGAGTCCTGTTTGATTGGTA | 8 | 442 |
| 994553 | 9244 | 9263 | 463497 | 463516 | GTTTCCACTGTCCGGCTTGA | 29 | 443 |
| 994561 | 9486 | 9505 | 463739 | 463758 | TCTTAGAGATTGTTGTTATT | 12 | 444 |
| 994569 | 9942 | 9961 | 464195 | 464214 | ATTTGGGTTTAGAGTTGAGC | 6 | 445 |
| 994577 | 10193 | 10212 | 464446 | 464465 | TCCCTAGTTCTCCTCTGTAC | 74 | 446 |
| 994585 | 10365 | 10384 | 464618 | 464637 | TCCATTTTTAATATTTGTT | 27 | 447 |
| 994593 | 10606 | 10625 | 464859 | 464878 | CTGTTATTTTATTAGTACGA | 42 | 448 |
| 994601 | 206 | 225 | 9922 | 9941 | TGGTGCTTGTAGTAGTTTTT | 33 | 449 |
| 994609 | N/A | N/A | 22231 | 22250 | TCTTCATTTTAATGTTGTTT | 13 | 450 |
| 994617 | N/A | N/A | 39411 | 39430 | TCTGCTCTAAAACTTTCTAC | 55 | 451 |
| 994625 | N/A | N/A | 51702 51755 | 51721 51774 | TTATTAGTGAAAAGAAAGAT | 43 | 452 |
| 994633 | N/A | N/A | 86196 | 86215 | ATTCAGATATAATTGTTTAC | 69 | 453 |
| 994641 | N/A | N/A | 105012 | 105031 | GTGTGAATAACTAATTCCTT | 53 | 454 |
| 994649 | N/A | N/A | 120191 | 120210 | TGTTTGATAAATGTTATTCT | 11 | 455 |
| 994657 | N/A | N/A | 148273 149384 | 148292 149403 | TATTATATTAAAAGTTAAAA | 62 | 456 |
| 994665 | N/A | N/A | 148615 149726 | 148634 149745 | AGAGGCTTCTGGAAATCCCC | 49 | 457 |

TABLE 7-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994673 | N/A | N/A | 149065 150161 | 149084 150180 | CCTGTCTTGATAAAATAAAA | 96 | 458 |
| 994681 | N/A | N/A | 162490 | 162509 | TGCATCTATTTTCTATTCTG | 96 | 459 |
| 994689 | N/A | N/A | 176036 176352 | 176055 176371 | GAAAATTCCTACTCATTTTT | 99 | 460 |
| 994697 | N/A | N/A | 189098 | 189117 | GTTTCTGCTAATCTGTGACA | 31 | 461 |
| 994705 | N/A | N/A | 214840 | 214859 | GTTTGCAGTTAACTTTTTTT | 34 | 462 |
| 994713 | N/A | N/A | 226996 | 227015 | TGGTTATTTACTCATTCTAC | 19 | 463 |
| 994721 | N/A | N/A | 265218 | 265237 | TCTTTTCATAAGCTTATTGG | 71 | 464 |
| 994729 | N/A | N/A | 279331 | 279350 | GTCTGCTTTCAATGAAGCAC | 69 | 465 |
| 994737 | N/A | N/A | 299784 299827 | 299803 299846 | ACTTTCCTGTCTTACAAGAG | 19 | 466 |
| 994745 | N/A | N/A | 320275 | 320294 | GTGAGAACTGCTATTTTCAG | 7 | 467 |
| 994753 | N/A | N/A | 330357 | 330376 | TCAGCTGTACAGCTCCTTAC | 55 | 468 |
| 994761 | N/A | N/A | 347823 | 347842 | TGGTCATTATCTAGTTTCTG | 5 | 469 |
| 994769 | N/A | N/A | 365364 | 365383 | GTGTGTCTAGTTTGTTTTTC | 20 | 470 |
| 994777 | N/A | N/A | 380610 | 380629 | GTTATATATTTCCTATTTTC | 34 | 471 |
| 994785 | N/A | N/A | 398119 | 398138 | TCTATATATTAATCATTTCC | 68 | 472 |
| 994793 | N/A | N/A | 417738 | 417757 | GGGTTATATCATGTTGGCCA | 67 | 473 |
| 994801 | N/A | N/A | 437630 | 437649 | CGGTGTGGTGTCCCATCCCT | 71 | 474 |
| 994809 | N/A | N/A | 439072 | 439091 | CTTTGATATTTAGTGTCTT | 12 | 475 |
| 994817 | N/A | N/A | 440059 | 440078 | TCCTGATTTTCTTTTTTTTT | 49 | 476 |
| 994825 | N/A | N/A | 441229 | 441248 | TGCTCTCTGTCTGAGTCTCC | 68 | 477 |
| 994833 | N/A | N/A | 442847 | 442866 | GTGCCAGTTCCTGCATTTTC | 43 | 478 |
| 994841 | N/A | N/A | 444080 | 444099 | GTGGTTTGACATAGTTTCTC | 6 | 479 |
| 994849 | N/A | N/A | 445236 | 445255 | GTTTTTCTTACACATGGTAG | 23 | 480 |
| 994857 | N/A | N/A | 445654 | 445673 | GGTTTCAGTAAGTATGTCTT | 8 | 481 |
| 994865 | N/A | N/A | 446197 | 446216 | TGTGGTTATAAGAGATCTGC | 28 | 482 |
| 994873 | N/A | N/A | 446951 | 446970 | TCATGATTTTATTGAATCAC | 26 | 483 |
| 994881 | N/A | N/A | 447992 | 448011 | TCTTTATACCAGGGATCCCC | 154 | 484 |
| 994889 | N/A | N/A | 448705 | 448724 | TCATACTTTCTTCCGCTCTT | 38 | 485 |
| 994897 | N/A | N/A | 450234 | 450253 | GGGTTTCATTCACCATGTTG | 47 | 486 |
| 994905 | N/A | N/A | 452110 | 452129 | CGGTTTGCTTATTCTTGCCC | 43 | 487 |
| 994913 | N/A | N/A | 452653 | 452672 | ATTTTCTTTTTCTGTGCCT | 9 | 488 |
| 994921 | N/A | N/A | 453506 | 453525 | TGTTGGATTCTTTTTTCTT | 12 | 489 |
| 994929 | N/A | N/A | 456930 | 456949 | TGGGTTGTACCTCTACTTGC | 69 | 490 |

TABLE 8

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994314 | 246 | 265 | 10657 | 10676 | TGGTGACTTGATGCACGATG | 10 | 491 |
| 994322 | 422 | 441 | 106164 | 106183 | TCCACTCTTTCTCTCTTGTT | 17 | 492 |
| 994330 | 687 | 706 | 277905 | 277924 | TCTTTCTTCCTTTCACAGAG | 35 | 493 |
| 994338 | 930 | 949 | 435649 | 435668 | GTGACTGTTTCACTGTCTGG | 79 | 494 |
| 994346 | 980 | 999 | 435699 | 435718 | CGTTGCTCCGCTCTTGGTTG | 47 | 495 |
| 994354 | 1870 | 1889 | 436589 | 436608 | GGTGGCCTCCCGAGGGACAA | 76 | 496 |
| 994362 | 2074 | 2093 | 436793 | 436812 | ATCACGACTGCTGTAGTCTG | 42 | 497 |
| 994370 | 2724 | 2743 | 437443 | 437462 | TCCACCTTCTTTAGCTCCCC | 71 | 498 |
| 994378* | 2771 | 2790 | 437490 | 437509 | CGTTGCTTATCTCTGCACTC | 16 | 499 |
| 994386 | 3115 | 3134 | 457368 | 457387 | GTGTCTGCTGCCCGCCAGGC | 77 | 500 |
| 994394 | 3310 | 3329 | 457563 | 457582 | TTCTGACTTCTCCAGTTTGC | 75 | 501 |
| 994402 | 3618 | 3637 | 457871 | 457890 | GTGCCCTTCCTCCCGCCCGC | 77 | 502 |
| 994410 | 4028 | 4047 | 458281 | 458300 | TTTATTGTAAAATATGTTGG | 71 | 503 |
| 994418 | 4334 | 4353 | 458587 | 458606 | GGCAGTTTGCATCTACCTCT | 19 | 504 |
| 994426 | 4691 | 4710 | 458944 | 458963 | CTTGCTCTTCAGCAATTCTG | 52 | 505 |
| 994434 | 4824 | 4843 | 459077 | 459096 | ATGCCTTGAACTGATTCTCA | 13 | 506 |
| 994442 | 5218 | 5237 | 459471 | 459490 | CTCACATATATAAATGTCTT | 17 | 507 |
| 994450 | 5532 | 5551 | 459785 | 459804 | AAAGTACTATTTTCAATGGG | 23 | 508 |
| 994458 | 5915 | 5934 | 460168 | 460187 | CAGCCCGTATTCCTCTTACC | 19 | 509 |
| 994466 | 6034 | 6053 | 460287 | 460306 | GTGTTGGTTTAGTGGATCCA | 22 | 510 |
| 994474 | 6208 | 6227 | 460461 | 460480 | TGGTCAGACTCTATTGGCAC | 36 | 511 |
| 994482 | 6842 | 6861 | 461095 | 461114 | TGTTTGCTACACAGAAGCGG | 61 | 512 |
| 994490 | 7077 | 7096 | 461330 | 461349 | TGGTTTCTTATTAATAGTAT | 24 | 513 |
| 994498 | 7127 | 7146 | 461380 | 461399 | CAGTCATTTTATATATTTAG | 44 | 514 |
| 994506 | 7707 | 7726 | 461960 | 461979 | GTGCAAAGAGTGGATTTTAT | 6 | 515 |
| 994514 | 8063 | 8082 | 462316 | 462335 | TGGCCCTGTTTTCACCTGGT | 76 | 516 |
| 994522 | 8333 | 8352 | 462586 | 462605 | GTTTGGAGTTTCCCTATGCC | 13 | 517 |
| 994530 | 8509 | 8528 | 462762 | 462781 | TGAGTGCTTCAAAATTTTGT | 42 | 518 |
| 994538 | 8741 | 8760 | 462994 | 463013 | GTAGTAATTCTTCCAGGCCA | 25 | 519 |
| 994546 | 9047 | 9066 | 463300 | 463319 | TGTCCCCATAATGAGTCCTG | 32 | 520 |
| 994554 | 9249 | 9268 | 463502 | 463521 | GTCCAGTTTCCACTGTCCGG | 49 | 521 |
| 994562 | 9685 | 9704 | 463938 | 463957 | GGACAGTATGTTATCTTGGT | 8 | 522 |
| 994570 | 9953 | 9972 | 464206 | 464225 | GGCTGACACTAATTTGGGTT | 22 | 523 |
| 994578 | 10196 | 10215 | 464449 | 464468 | CCTTCCCTAGTTCTCCTCTG | 24 | 524 |
| 994586 | 10367 | 10386 | 464620 | 464639 | CTTCCATTTTTTAATATTTG | 38 | 525 |

TABLE 8-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994594 | 10608 | 10627 | 464861 | 464880 | CACTGTTATTTTATTAGTAC | 77 | 526 |
| 994602 | N/A | N/A | 5488 6515 | 5507 6534 | ATAAAAGTTGAGTAGCTAGA | 68 | 527 |
| 994610 | N/A | N/A | 28064 | 28083 | TCCGCATTATTTTCCCTGC | 9 | 528 |
| 994618 | N/A | N/A | 40728 | 40747 | TCCTACTTTTAAGTTTCCAG | 10 | 529 |
| 994626 | N/A | N/A | 51710 51763 | 51729 51782 | AAACTAATTTATTAGTGAAA | 94 | 530 |
| 994634 | N/A | N/A | 86436 | 86455 | TGTATAGTAGAATTTTTTT | 77 | 531 |
| 994642 | N/A | N/A | 106495 | 106514 | GTGTGTTTAGTTGTTGGGT | 3 | 532 |
| 994650 | N/A | N/A | 122443 | 122462 | GTTGAGACTTAATTGCTCAG | 67 | 533 |
| 994658 | N/A | N/A | 149437 148326 | 149456 148345 | GAATACTATGTATTTGCCAC | 14 | 534 |
| 994666 | N/A | N/A | 149806 148695 | 149825 148714 | TTTTGACAAGTCAGTCTTTT | 87 | 535 |
| 994674 | N/A | N/A | 155493 | 155512 | GTTTCCTTAAAATATGTTGG | 9 | 536 |
| 994682 | N/A | N/A | 163871 | 163890 | TCCATTGTATATGTATCTGT | 26 | 537 |
| 994690 | N/A | N/A | 179789 | 179808 | GTTATATTTAATCATGTTCC | 13 | 538 |
| 994698 | N/A | N/A | 189111 | 189130 | GTCATATTTCTTAGTTTCTG | 4 | 539 |
| 994706 | N/A | N/A | 217284 | 217303 | GTTATGTTTAAGGTATTTTC | 21 | 540 |
| 994714 | N/A | N/A | 234290 | 234309 | CGTCGGATAAATTTATCCAC | 80 | 541 |
| 994722 | N/A | N/A | 265414 | 265433 | GTTTTCTATAGTGATTGCAC | 44 | 542 |
| 994730 | N/A | N/A | 281189 | 281208 | TCTTTTTTTCTTTTAACCCT | 6 | 543 |
| 994738 | N/A | N/A | 299793 308168 | 299812 308187 | CAATCAGGAACTTTCCTGTC | 65 | 544 |
| 994746 | N/A | N/A | 322234 323496 | 322253 323515 | AGGAACACAAGAGGGAATAC | 53 | 545 |
| 994754 | N/A | N/A | 331549 | 331568 | TCTTTCCTAAAGCTTATTAG | 52 | 546 |
| 994762 | N/A | N/A | 352034 | 352053 | GTTTTAACTCAGCTCTCTCT | 53 | 547 |
| 994770 | N/A | N/A | 366558 | 366577 | CGGCTAGTATTTATATTTTT | 48 | 548 |
| 994778 | N/A | N/A | 382060 | 382079 | GTCTACATTTATAGATTTAG | 11 | 549 |
| 994786 | N/A | N/A | 400669 | 400688 | GTGTTACATAAATTAATTCC | 14 | 550 |
| 994794 | N/A | N/A | 418949 | 418968 | GTTACTGTTCTTATCTTGTG | 47 | 551 |
| 994802 | N/A | N/A | 437850 | 437869 | GGTGAGTTTCTGGATTGTCT | 7 | 552 |
| 994810 | N/A | N/A | 439073 | 439092 | GCTTTGATATTTTAGTGTCT | 6 | 553 |
| 994818 | N/A | N/A | 440092 | 440111 | TGAGCTGTATTATTATGCCA | 68 | 554 |
| 994826 | N/A | N/A | 441272 | 441291 | TCCAGATATGAGTTCTCTCT | 28 | 555 |
| 994834 | N/A | N/A | 442868 | 442887 | GTTCAGACTCAGATCTCTTC | 27 | 556 |
| 994842 | N/A | N/A | 444247 | 444266 | ATAGTCTTTAATTTTTTTCT | 88 | 557 |
| 994850 | N/A | N/A | 445319 | 445338 | GTGGAAGTGTTTCAGGGTTG | 14 | 558 |
| 994858 | N/A | N/A | 445807 | 445826 | TGTTGTTTAAATATGTCTCC | 23 | 559 |

TABLE 8-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994866 | N/A | N/A | 446198 | 446217 | GTGTGGTTATAAGAGATCTG | 27 | 560 |
| 994874 | N/A | N/A | 447042 | 447061 | CAGTGCTTTCTCCAGGGTGT | 3 | 561 |
| 994882 | N/A | N/A | 447995 | 448014 | TCCTCTTTATACCAGGGATC | 47 | 562 |
| 994890 | N/A | N/A | 448758 | 448777 | ATCTCCATAAATGGTATCCC | 37 | 563 |
| 994898 | N/A | N/A | 450475 | 450494 | GGAGAGAGAGAATATTTGAG | 22 | 564 |
| 994906 | N/A | N/A | 452112 | 452131 | TGCGGTTTGCTTATTCTTGC | 14 | 565 |
| 994914 | N/A | N/A | 452981 | 453000 | ACTTGAGTACATTCATATGG | 57 | 566 |
| 994922 | N/A | N/A | 453610 | 453629 | ATCTAGATTGAAGTTTGTAC | 94 | 567 |
| 994930 | N/A | N/A | 456945 | 456964 | TGAGGCTCTTCTCTTTGGGT | 35 | 568 |

TABLE 9

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994315 | 295 | 314 | 10706 | 10725 | ATTGCTGTACAAGGATGACA | 16 | 569 |
| 994323 | 433 | 452 | 106175 | 106194 | GCAGGCTGAAATCCACTCTT | 20 | 570 |
| 994331 | 690 | 709 | 277908 | 277927 | TGTTCTTTCTTCCTTTCACA | 29 | 571 |
| 994339 | 932 | 951 | 435651 | 435670 | CGGTGACTGTTTCACTGTCT | 70 | 572 |
| 994347 | 1068 | 1087 | 435787 | 435806 | CGGTGGTTGTCGCTGGGCAG | 24 | 573 |
| 994355 | 1879 | 1898 | 436598 | 436617 | AGCTTTCTTGGTGGCCTCCC | 91 | 574 |
| 994363 | 2213 | 2232 | 436932 | 436951 | GCTTCCCTAAATGCAGGCCA | 64 | 575 |
| 994371 | 2727 | 2746 | 437446 | 437465 | TCTTCCACCTTCTTTAGCTC | 96 | 576 |
| 994379* | 2812 | 2831 | 437531 | 437550 | GTCTTCAATCCTCTCTACGG | 3 | 577 |
| 994387 | 3127 | 3146 | 457380 | 457399 | CTCGGCATACCTGTGTCTGC | 58 | 578 |
| 994395 | 3313 | 3332 | 457566 | 457585 | GTCTTCTGACTTCTCCAGTT | 47 | 579 |
| 994403 | 3627 | 3646 | 457880 | 457899 | GCTCCTGCTGTGCCCTTCCT | 34 | 580 |
| 994411 | 4046 | 4065 | 458299 | 458318 | ATACAATTAAAAGTTGCTTT | 98 | 581 |
| 994419 | 4436 | 4455 | 458689 | 458708 | ACCCGAGTTGTCCATAGTCA | 12 | 582 |
| 994427 | 4701 | 4720 | 458954 | 458973 | CTTTCAATATCTTGCTCTTC | 25 | 583 |
| 994435 | 4856 | 4875 | 459109 | 459128 | CTTTTCTCTCAGTTTCTCTG | 23 | 584 |
| 994443 | 5219 | 5238 | 459472 | 459491 | GCTCACATATATAAATGTCT | 14 | 585 |
| 994451 | 5557 | 5576 | 459810 | 459829 | TTTTTTTTAATTTGTGAAA | 95 | 586 |
| 994459 | 5979 | 5998 | 460232 | 460251 | GTGTGTTTTCTGAGTCCAC | 3 | 587 |
| 994467 | 6040 | 6059 | 460293 | 460312 | ATCTTAGTGTTGGTTTAGTG | 14 | 588 |
| 994475 | 6231 | 6250 | 460484 | 460503 | TGAGCTTTAACTATATAGCA | 52 | 589 |

TABLE 9-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994483 | 6899 | 6918 | 461152 | 461171 | TGGCTGATCCTTGTAAGCTG | 64 | 590 |
| 994491 | 7080 | 7099 | 461333 | 461352 | TGTTGGTTTCTTATTAATAG | 12 | 591 |
| 994499 | 7151 | 7170 | 461404 | 461423 | TCTTAAGTTAAACATTCTAA | 49 | 592 |
| 994507 | 7839 | 7858 | 462092 | 462111 | ATAGGTTTCCTTAGTAGTCA | 17 | 593 |
| 994515 | 8068 | 8087 | 462321 | 462340 | TCTGCTGGCCCTGTTTTCAC | 23 | 594 |
| 994523 | 8356 | 8375 | 462609 | 462628 | TCCGGAGTAGAGGTGTGCAA | 68 | 595 |
| 994531 | 8510 | 8529 | 462763 | 462782 | GTGAGTGCTTCAAAATTTTG | 34 | 596 |
| 994539 | 8763 | 8782 | 463016 | 463035 | GTATAGTTTAAGAGCCTTTT | 8 | 597 |
| 994547 | 9121 | 9140 | 463374 | 463393 | CATTGAAATCATGTTTTTAC | 23 | 598 |
| 994555 | 9258 | 9277 | 463511 | 463530 | CCCACAGCTGTCCAGTTTCC | 62 | 599 |
| 994563 | 9700 | 9719 | 463953 | 463972 | ACTTGGTATTCTGGAGGACA | 6 | 600 |
| 994571 | 10096 | 10115 | 464349 | 464368 | GGGTAATGATCTGATATTAA | 5 | 601 |
| 994579 | 10239 | 10258 | 464492 | 464511 | ATGCACTTAAAATTTTCTTT | 10 | 602 |
| 994587 | 10368 | 10387 | 464621 | 464640 | TCTTCCATTTTTAATATTT | 22 | 603 |
| 994595 | 10611 | 10630 | 464864 | 464883 | TGGCACTGTTATTTTATTAG | 41 | 604 |
| 994603 | N/A | N/A | 15303 | 15322 | TGCTCATTAAATAATTGCAG | 57 | 605 |
| 994611 | N/A | N/A | 28526 | 28545 | GTGTCACTAGAAGATGCCCA | 39 | 606 |
| 994619 | N/A | N/A | 41522 | 41541 | GTGCTCACTAATAATAGTCT | 21 | 607 |
| 994627 | N/A | N/A | 71054 | 71073 | TCTCCTCTACTTAAGCTCAG | 42 | 608 |
| 994635 | N/A | N/A | 87298 | 87317 | GTTTCCTATCCTGATTCCCA | 43 | 609 |
| 994643 | N/A | N/A | 106499 | 106518 | GTTTGTGTGTTTAGTTGTTT | 10 | 610 |
| 994651 | N/A | N/A | 127663 | 127682 | GTGACCACTCTCCTCCTCCC | 55 | 611 |
| 994659 | N/A | N/A | 148376 149487 | 148395 149506 | AAGGTTTTCTCTTAAATATT | 54 | 612 |
| 994667 | N/A | N/A | 148746 149857 | 148765 149876 | TCCGAAGCTGCTATATGTCA | 51 | 613 |
| 994675 | N/A | N/A | 155513 | 155532 | GTGTGACACTATTATTCTTT | 27 | 614 |
| 994683 | N/A | N/A | 169801 | 169820 | CGACCTTTAAAATTTTTCA | 63 | 615 |
| 994691 | N/A | N/A | 180049 | 180068 | ATTTGTTTACTTCTATATTG | 65 | 616 |
| 994699 | N/A | N/A | 198910 | 198929 | GCTTCTTTAAATCTTAGCTC | 72 | 617 |
| 994707 | N/A | N/A | 218665 | 218684 | GTTTGAGTCCAGTGACTTCT | 44 | 618 |
| 994715 | N/A | N/A | 244999 | 245018 | TCTTGAGTTTATCTTTTCTT | 36 | 619 |
| 994723 | N/A | N/A | 269836 269865 269894 | 269855 269884 269913 | CTCCAGTGCAGGGCTGGACT | 86 | 620 |
| 994731 | N/A | N/A | 284231 | 284250 | GTTTGGGTTTTTCTGTACAA | 2 | 621 |
| 994739 | N/A | N/A | 305998 | 306017 | TGGTAGGTATATAGATGTCC | 3 | 622 |
| 994747 | N/A | N/A | 322370 323632 | 322389 323651 | ATCCCAATAAAAACATTCAG | 61 | 623 |

TABLE 9-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994755 | N/A | N/A | 331619 | 331638 | TGTTCCATAGCTCATTTGCA | 8 | 624 |
| 994763 | N/A | N/A | 353740 | 353759 | TGCTGTGTACTTAATTGACA | 41 | 625 |
| 994771 | N/A | N/A | 369407 | 369426 | TCTTGTCTAGTTTTCTGCAG | 54 | 626 |
| 994779 | N/A | N/A | 384151 | 384170 | GTCATTTTTGAACATATCCT | 11 | 627 |
| 994787 | N/A | N/A | 404260 | 404279 | GTCTGTGTACCTCATTCTTT | 13 | 628 |
| 994795 | N/A | N/A | 420137 | 420156 | GTGTGGGTGGCTGTGTCCTG | 70 | 629 |
| 994803 | N/A | N/A | 437851 | 437870 | TGGTGAGTTTCTGGATTGTC | 6 | 630 |
| 994811 | N/A | N/A | 439088 | 439107 | CTTTTATTTTCTGATGCTTT | 7 | 631 |
| 994819 | N/A | N/A | 440165 | 440184 | GTAGTTCATTTCTTTCTCC | 6 | 632 |
| 994827 | N/A | N/A | 441275 | 441294 | AAGTCCAGATATGAGTTCTC | 25 | 633 |
| 994835 | N/A | N/A | 442870 | 442889 | ATGTTCAGACTCAGATCTCT | 26 | 634 |
| 994843 | N/A | N/A | 444248 | 444267 | AATAGTCTTTAATTTTTTC | 88 | 635 |
| 994851 | N/A | N/A | 445325 | 445344 | TCCTTGGTGGAAGTGTTTCA | 57 | 636 |
| 994859 | N/A | N/A | 445808 | 445827 | CTGTTGTTTAAATATGTCTC | 15 | 637 |
| 994867 | N/A | N/A | 446255 | 446274 | TCCTCCACTCTTTCCCTCCC | 98 | 638 |
| 994875 | N/A | N/A | 447189 | 447208 | GTTTGCCTTCTGTATGGAAA | 12 | 639 |
| 994883 | N/A | N/A | 448112 | 448131 | TGGAGCCTTGCTATGTTGGC | 59 | 640 |
| 994891 | N/A | N/A | 448954 | 448973 | TGGTTAAGACCTAGTTTCTT | 42 | 641 |
| 994899 | N/A | N/A | 451089 | 451108 | ATTTCTTGAGATGGATTCTC | 24 | 642 |
| 994907 | N/A | N/A | 452123 | 452142 | TCTACCAGAGTTGCGGTTTG | 53 | 643 |
| 994915 | N/A | N/A | 453089 | 453108 | CTTCATCTTCTTTGTTTCCT | 36 | 644 |
| 994923 | N/A | N/A | 455414 | 455433 | CATTCTTTTGAGTTGTGACC | 31 | 645 |
| 994931 | N/A | N/A | 457057 | 457076 | GTTTGATTTATGCACACAC | 63 | 646 |

Example 2: Effect of 5-10-5 MOE Gapmer Modified Oligonucleotides on Human ATXN1 RNA In Vitro, Single Dose Modified oligonucleotides complementary to human ATXN1 nucleic acid were designed and tested for their single dose effects on ATXN1 mRNA in vitro. The modified oligonucleotides were tested in a series of experiments that had similar culture conditions.

The modified oligonucleotides in the tables below are 5-10-5 MOE gapmers with mixed internucleoside linkages. The gapmers are 20 nucleosides in length, wherein the central gap segment consists of ten 2'-β-D-deoxynucleosides and the 3' and 5' wings each consist of five 2'-MOE modified nucleosides. The motif for the gapmers is (from 5' to 3'): eeeeedddddddddeeeee; wherein "d" represents a 2'-β-D-deoxyribosyl sugar, and 'e' represents a 2'-MOE modified ribosyl sugar. The internucleoside linkage motif for the gapmers is (from 5' to 3'): sooossssssssssooss; wherein 'o' represents a phosphodiester internucleoside linkage and 's' represents a phosphorothioate internucleoside linkage. Each cytosine residue is a 5-methyl cytosine.

"Start site" indicates the 5'-most nucleoside to which the modified oligonucleotide is complementary in the human gene sequence. "Stop site" indicates the 3'-most nucleoside to which the modified oligonucleotide is complementary in the human gene sequence. Each modified oligonucleotide listed in the Tables below is 100% complementary to SEQ ID NO: 1, SEQ ID NO: 2, or SEQ ID NO: 3 (GENBANK Accession No. NM_001128164.1). 'N/A' indicates that the modified oligonucleotide is not 100% complementary to that particular gene sequence.

Cultured A-431 cells were treated with modified oligonucleotide at a concentration of 4,000 nM by free uptake at a density of 10,000 cells per well for a treatment period of 48 hours. At the end of their treatment period, total RNA was isolated from the cells and ATXN1 RNA levels were measured by quantitative real-time RTPCR. ATXN1 RNA levels were measured by Human ATXN1 primer probe set RTS37575 (forward sequence GTATAGGCTGAGGC-TACCTGT, designated herein as SEQ ID NO: 14; reverse sequence GATCCAGGCTCTTCATGAGG, designated herein as SEQ ID NO: 15; probe sequence ACAGCAGCTCTGGATGAACATTCACT, designated herein as SEQ ID NO: 16). ATXN1 RNA levels were normalized to total RNA content, as measured by RIBOGREEN® fluorescent RNA assay. Results are presented in the tables below as percent ATXN1 RNA levels relative to untreated control cells (% Control). The Compound No. marked with an asterisk (*) indicates that the modified oligonucleotide is complementary to the amplicon region of the primer probe set. Additional assays may be used to measure the potency and efficacy of the modified oligonucleotides complementary to the amplicon region.

TABLE 10

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 4 | 138 |
| 1040079 | 468 | 487 | N/A | N/A | AGACCAAAAACCATTTGTGT | 9 | 647 |
| 1040111 | 2755 | 2774 | 437474 | 437493 | ACTCTGGATGAAATCTTCTG | 71 | 648 |
| 1040143 | 3244 | 3263 | 457497 | 457516 | GCTGGGTTCTATTTTGGTGA | 46 | 649 |
| 1040175 | 4029 | 4048 | 458282 | 458301 | TTTTATTGTAAAATATGTTG | 90 | 650 |
| 1040207 | 4510 | 4529 | 458763 | 458782 | GATAGTAATATATGCTCATC | 9 | 651 |
| 1040239 | 4767 | 4786 | 459020 | 459039 | TTGGTGGTCATTTATTGTCA | 8 | 652 |
| 1040271 | 5224 | 5243 | 459477 | 459496 | ATCTTGCTCACATATATAAA | 33 | 653 |
| 1040303 | 5589 | 5608 | 459842 | 459861 | CTAGACAGCCAAAATGTGGG | 29 | 654 |
| 1040335 | 6017 | 6036 | 460270 | 460289 | CCAGTCAATTCAATACTCGA | 14 | 655 |
| 1040367 | 6475 | 6494 | 460728 | 460747 | CTCCACATTCACTATTCCGT | 13 | 656 |
| 1040399 | 7152 | 7171 | 461405 | 461424 | TTCTTAAGTTAAACATTCTA | 75 | 657 |
| 1040431 | 7622 | 7641 | 461875 | 461894 | GGAGTAATCCACAAGATGCA | 48 | 658 |
| 1040463 | 8111 | 8130 | 462364 | 462383 | TCCTTTCACATCACCACCGA | 42 | 659 |
| 1040495 | 8375 | 8394 | 462628 | 462647 | ATGTAAAAGAAATCTCAGCT | 42 | 660 |
| 1040527 | 8696 | 8715 | 462949 | 462968 | ACATGACAAATTTCTATATA | 79 | 661 |
| 1040559 | 9109 | 9128 | 463362 | 463381 | GTTTTTACTCCCCCCATTTA | 106 | 662 |
| 1040591 | 9441 | 9460 | 463694 | 463713 | TGCACTTAATTTTAATACAG | 24 | 663 |
| 1040623 | 9885 | 9904 | 464138 | 464157 | GGGCAGTATTCACAGAACTG | 27 | 664 |
| 1040655 | 10254 | 10273 | 464507 | 464526 | TCTTAACTATTATGTATGCA | 18 | 665 |
| 1040687 | 10527 | 10546 | 464780 | 464799 | TCAAATTTTGAATCAAACAT | 88 | 666 |
| 1040719 | N/A | N/A | 17960 | 17979 | TGAGTGCACATTTAATCTTT | 11 | 667 |
| 1040751 | N/A | N/A | 31937 | 31956 | TTGTCATATTTTTATAGCAT | 76 | 668 |
| 1040783 | N/A | N/A | 51100 | 51119 | TGTTCATTCCCTTAGTAACT | 21 | 669 |
| 1040815 | N/A | N/A | 77282 | 77301 | GGCAAGATCTTTTAAAGTCC | 18 | 670 |
| 1040847 | N/A | N/A | 94809 | 94828 | AGACTGTTTCTTTACCACAT | 14 | 671 |
| 1040879 | N/A | N/A | 118132 | 118151 | TCCACCAGTATTTATGGAGT | 119 | 672 |
| 1040911 | N/A | N/A | 151437 | 151456 | CTTTAGTATTTTTATCATTA | 40 | 673 |
| 1040943 | N/A | N/A | 179378 | 179397 | AACAGTACAATTTACTTGAC | 56 | 674 |
| 1040975 | N/A | N/A | 195960 | 195979 | CCTTTAAAAACCAACACAGT | 84 | 675 |
| 1041007 | N/A | N/A | 216607 | 216626 | TCTTGTCATTTTTAACATCC | 28 | 676 |
| 1041039 | N/A | N/A | 237165 | 237184 | ACTCAATTTTAAAGACTCGG | 38 | 677 |
| 1041071 | N/A | N/A | 258705 | 258724 | ATGTGTTGAATTTAACCAGC | 22 | 678 |

TABLE 10-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041103 | N/A | N/A | 276428 | 276447 | CTCATTAATTAAATCATTCG | 105 | 679 |
| 1041135 | N/A | N/A | 295010 | 295029 | CACCTAAAAATACAGGAAGT | 76 | 680 |
| 1041167 | N/A | N/A | 324809 | 324828 | CCAAGAATTTAAAAGGACA | 42 | 681 |
| 1041199 | N/A | N/A | 345760 | 345779 | TGTCTCAAACTATTCCCATT | 26 | 682 |
| 1041231 | N/A | N/A | 371655 | 371674 | TTAACAATCTTTTAGACCTG | 24 | 683 |
| 1041263 | N/A | N/A | 393703 | 393722 | GACATATTTCAAAAATGCAA | 68 | 684 |
| 1041295 | N/A | N/A | 426181 | 426200 | AACTTGTTTCAAAGTGAGAG | 88 | 685 |
| 1041327 | N/A | N/A | 437896 | 437915 | TCAGGGTTCCTCATCTTAAT | 24 | 686 |
| 1041359 | N/A | N/A | 438301 | 438320 | AGAGAGTATAAAAATTATCT | 72 | 687 |
| 1041391 | N/A | N/A | 438910 | 438929 | GCAGCCTCCTATATTGGTCC | 40 | 688 |
| 1041423 | N/A | N/A | 439178 | 439197 | CCAGTGACTCATCTTGGCTA | 48 | 689 |
| 1041455 | N/A | N/A | 439863 | 439882 | TGGTCCTTTCCTCACTTGGG | 27 | 690 |
| 1041487 | N/A | N/A | 440220 | 440239 | CATGTTTATTTTCCATGTGT | 8 | 691 |
| 1041519 | N/A | N/A | 440788 | 440807 | ACACACCTAGATCTTCCTCC | 49 | 692 |
| 1041551 | N/A | N/A | 441387 | 441406 | CAGCAGTGCCTAACCAGTTG | 43 | 693 |
| 1041583 | N/A | N/A | 441652 | 441671 | TGCCAGAGACCCAAATCCGC | 64 | 694 |
| 1041615 | N/A | N/A | 442276 | 442295 | TCATCCCCAAACTAAACACC | 100 | 695 |
| 1041647 | N/A | N/A | 442821 | 442840 | GCTAACCTACTTCCTACCCA | 59 | 696 |
| 1041679 | N/A | N/A | 443177 | 443196 | CATGACATCATTTAGCCTTA | 12 | 697 |
| 1041711 | N/A | N/A | 443557 | 443576 | GGCCCTAATAACACAGAGCC | 113 | 698 |
| 1041743 | N/A | N/A | 444006 | 444025 | GCGGCACAAATCCAGGGCTG | 71 | 699 |
| 1041775 | N/A | N/A | 444407 | 444426 | GTAGTATAAACTATGGACTT | 26 | 700 |
| 1041807 | N/A | N/A | 445306 | 445325 | AGGGTTGTTCAGTAAACCCA | 134 | 701 |
| 1041839 | N/A | N/A | 445658 | 445677 | GCTAGGTTTCAGTAAGTATG | 9 | 702 |
| 1041871 | N/A | N/A | 445920 | 445939 | ACACGCATATTTATGCTGTT | 64 | 703 |
| 1041903 | N/A | N/A | 446128 | 446147 | ACCTCCAACTCCCATTTTGG | 54 | 704 |
| 1041935 | N/A | N/A | 446724 | 446743 | GTAAATATATCCTGTTTCAA | 59 | 705 |
| 1041967 | N/A | N/A | 446975 | 446994 | TCACCTTGTCAGATGCTGAG | 45 | 706 |
| 1041999 | N/A | N/A | 447909 | 447928 | GGTGAGCAACCATTCCAGAC | 74 | 707 |
| 1042031 | N/A | N/A | 448558 | 448577 | CTCGGTCACCACATGCAAGC | 102 | 708 |
| 1042063 | N/A | N/A | 448821 | 448840 | GACCTAAAACACACCAGACC | 78 | 709 |
| 1042095 | N/A | N/A | 449388 | 449407 | ATAGCTTCAAAATATTGTTA | 31 | 710 |
| 1042127 | N/A | N/A | 449700 | 449719 | ATCTTTATTTTATAATTAGG | 87 | 711 |
| 1042159 | N/A | N/A | 449981 | 450000 | GATGCCACGACCAGATATCA | 73 | 712 |
| 1042191 | N/A | N/A | 450575 | 450594 | ACCAAACTCCAAATCTCCAA | 38 | 713 |
| 1042223 | N/A | N/A | 451243 | 451262 | TCAACCTTCTTGAACCCTCA | 62 | 714 |

TABLE 10-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
| --- | --- | --- | --- | --- | --- | --- | --- |
| 1042255 | N/A | N/A | 451690 | 451709 | TCATTATTTCCGCATCTCAA | 13 | 715 |
| 1042287 | N/A | N/A | 451970 | 451989 | CCGGACACCTACCCATGGAG | 82 | 716 |
| 1042319 | N/A | N/A | 452312 | 452331 | CACTGTATTCTAAGTAGGAG | 81 | 717 |
| 1042351 | N/A | N/A | 452637 | 452656 | GCCTCCTGACCTCTACCCTT | 56 | 718 |
| 1042383 | N/A | N/A | 453119 | 453138 | AGTAGATTTCCACAGATTGT | 26 | 719 |
| 1042415 | N/A | N/A | 453901 | 453920 | AGCCTCTAGAACAAAATACA | 97 | 720 |
| 1042447 | N/A | N/A | 455088 | 455107 | AGCTTGAGAATTTTGATAGG | 22 | 721 |
| 1042479 | N/A | N/A | 455365 | 455384 | GAACCACAAGCCAACAGGCC | 89 | 722 |
| 1042511 | N/A | N/A | 456665 | 456684 | ACTGTGAGTTCCAAGAAGCA | 49 | 723 |

TABLE 11

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
| --- | --- | --- | --- | --- | --- | --- | --- |
| 994605 | N/A | N/A | 17726 | 17745 | GTCACCTTTTCTATTTGCAC | 3 | 138 |
| 1040080* | 824 | 843 | 435543 | 435562 | TGGGTACAATCCGCCAACAG | 32 | 724 |
| 1040112 | 2813 | 2832 | 437532 | 437551 | TGTCTTCAATCCTCTCTACG | 65 | 725 |
| 1040144 | 3334 | 3353 | 457587 | 457606 | AGGAAGAGTCAAAGGTGGTT | 41 | 726 |
| 1040176 | 4034 | 4053 | 458287 | 458306 | GTTGCTTTTATTGTAAAATA | 29 | 727 |
| 1040208 | 4512 | 4531 | 458765 | 458784 | AAGATAGTAATATATGCTCA | 11 | 728 |
| 1040240 | 4802 | 4821 | 459055 | 459074 | CATCAAAGTGAAAAGTGCCT | 48 | 729 |
| 1040272 | 5278 | 5297 | 459531 | 459550 | CCATTCTGAAAATAACATTA | 15 | 730 |
| 1040304 | 5614 | 5633 | 459867 | 459886 | GGTGAACCCTAAATGTAAAT | 40 | 731 |
| 1040336 | 6018 | 6037 | 460271 | 460290 | TCCAGTCAATTCAATACTCG | 26 | 732 |
| 1040368 | 6478 | 6497 | 460731 | 460750 | ACACTCCACATTCACTATTC | 55 | 733 |
| 1040400 | 7162 | 7181 | 461415 | 461434 | ACTGAAATAATTCTTAAGTT | 108 | 734 |
| 1040432 | 7653 | 7672 | 461906 | 461925 | AGCATTATATTGCAATCTAT | 31 | 735 |
| 1040464 | 8113 | 8132 | 462366 | 462385 | TCTCCTTTCACATCACCACC | 27 | 736 |
| 1040496 | 8385 | 8404 | 462638 | 462657 | GAGGTCATCTATGTAAAAGA | 15 | 737 |
| 1040528 | 8697 | 8716 | 462950 | 462969 | GACATGACAAATTCTATAT | 12 | 738 |
| 1040560 | 9114 | 9133 | 463367 | 463386 | ATCATGTTTTTACTCCCCCC | 48 | 739 |
| 1040592 | 9454 | 9473 | 463707 | 463726 | CCTATTGGCCAAATGCACTT | 46 | 740 |
| 1040624 | 9970 | 9989 | 464223 | 464242 | TCTTGAAACCTCCTTTCGGC | 74 | 741 |
| 1040656 | 10255 | 10274 | 464508 | 464527 | CTCTTAACTATTATGTATGC | 25 | 742 |
| 1040688 | 10529 | 10548 | 464782 | 464801 | GTTCAAATTTTGAATCAAAC | 39 | 743 |
| 1040720 | N/A | N/A | 18197 | 18216 | CCCAAATTTCAAGGTCCTT | 6 | 744 |

TABLE 11-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040752 | N/A | N/A | 32181 | 32200 | GTGGTCAAAGAATCTGTTTC | 10 | 745 |
| 1040784 | N/A | N/A | 51766 | 51785 | TAGAAACTAATTTATTAGTG | 119 | 746 |
| 1040816 | N/A | N/A | 77793 | 77812 | ACACAGATTATTTATAGTCA | 13 | 747 |
| 1040848 | N/A | N/A | 96129 | 96148 | CACTTTCTAGATTATTCTTA | 84 | 748 |
| 1040880 | N/A | N/A | 118292 | 118311 | ACTCTCTACCTTTAAGATTT | 28 | 749 |
| 1040912 | N/A | N/A | 153619 | 153638 | CATCTATTTATTTACCTTCT | 30 | 750 |
| 1040944 | N/A | N/A | 179493 | 179512 | GAACTTAAAATTCCCTAGGA | 111 | 751 |
| 1040976 | N/A | N/A | 195968 | 195987 | TCTTTTAACCTTTAAAAACC | 53 | 752 |
| 1041008 | N/A | N/A | 216637 | 216656 | ACCTGCTTTCAAAAGTCAAA | 72 | 753 |
| 1041040 | N/A | N/A | 238066 | 238085 | CAAGTAATACAAATCCACAG | 65 | 754 |
| 1041072 | N/A | N/A | 259575 | 259594 | CAGGACTTATTTTATATATG | 32 | 755 |
| 1041104 | N/A | N/A | 276769 | 276788 | CTTCCCAAATACATCATCGA | 101 | 756 |
| 1041136 | N/A | N/A | 295238 | 295257 | CATTTAAAAACTGTACATGG | 20 | 757 |
| 1041168 | N/A | N/A | 324921 | 324940 | ATCTAAATTTAAACTGCACA | 31 | 758 |
| 1041200 | N/A | N/A | 347770 | 347789 | TGGTCAATAATTTATATGGC | 2 | 759 |
| 1041232 | N/A | N/A | 372753 | 372772 | AACTATTATATTTATAGATT | 108 | 760 |
| 1041264 | N/A | N/A | 395038 | 395057 | AGCTGTAAAATATATCCCTG | 8 | 761 |
| 1041296 | N/A | N/A | 427897 | 427916 | AACCTTACTTAAATATCTCA | 62 | 762 |
| 1041328 | N/A | N/A | 437897 | 437916 | ATCAGGGTTCCTCATCTTAA | 11 | 763 |
| 1041360 | N/A | N/A | 438322 | 438341 | GTGCCCTTTCCTCTTGGGAT | 58 | 764 |
| 1041392 | N/A | N/A | 438914 | 438933 | CCCAGCAGCCTCCTATATTG | 91 | 765 |
| 1041424 | N/A | N/A | 439182 | 439201 | ACTTCCAGTGACTCATCTTG | 34 | 766 |
| 1041456 | N/A | N/A | 439866 | 439885 | ATTTGGTCCTTTCCTCACTT | 28 | 767 |
| 1041488 | N/A | N/A | 440222 | 440241 | CTCATGTTTATTTTCCATGT | 31 | 768 |
| 1041520 | N/A | N/A | 440796 | 440815 | AGGGAAAAACACACCTAGAT | 39 | 769 |
| 1041552 | N/A | N/A | 441389 | 441408 | GTCAGCAGTGCCTAACCAGT | 41 | 770 |
| 1041584 | N/A | N/A | 441726 | 441745 | ACAGAAAAACAAAACTCATT | 105 | 771 |
| 1041616 | N/A | N/A | 442285 | 442304 | CCTTAAAAATCATCCCCAAA | 99 | 772 |
| 1041648 | N/A | N/A | 442823 | 442842 | CAGCTAACCTACTTCCTACC | 90 | 773 |
| 1041680 | N/A | N/A | 443212 | 443231 | TCAGAAATACAGATTGATAT | 44 | 774 |
| 1041712 | N/A | N/A | 443559 | 443578 | ACGGCCCTAATAACACAGAG | 94 | 775 |
| 1041744 | N/A | N/A | 444009 | 444028 | ACTGCGGCACAAATCCAGGG | 32 | 776 |
| 1041776 | N/A | N/A | 444408 | 444427 | TGTAGTATAAACTATGGACT | 23 | 777 |
| 1041808 | N/A | N/A | 445316 | 445335 | GAAGTGTTTCAGGGTTGTTC | 8 | 778 |
| 1041840 | N/A | N/A | 445659 | 445678 | AGCTAGGTTTCAGTAAGTAT | 7 | 779 |
| 1041872 | N/A | N/A | 445921 | 445940 | TACACGCATATTTATGCTGT | 98 | 780 |

TABLE 11-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041904 | N/A | N/A | 446135 | 446154 | AACTGTCACCTCCAACTCCC | 57 | 781 |
| 1041936 | N/A | N/A | 446727 | 446746 | CCAGTAAATATATCCTGTTT | 26 | 782 |
| 1041968 | N/A | N/A | 446985 | 447004 | CATAGCCACCTCACCTTGTC | 72 | 783 |
| 1042000 | N/A | N/A | 447963 | 447982 | GCAACAGACCAGTAGCAGTC | 79 | 784 |
| 1042032 | N/A | N/A | 448600 | 448619 | TACCTCCACCACCTTTGTCC | 63 | 785 |
| 1042064 | N/A | N/A | 448823 | 448842 | GTGACCTAAAACACACCAGA | 37 | 786 |
| 1042096 | N/A | N/A | 449389 | 449408 | GATAGCTTCAAAATATTGTT | 20 | 787 |
| 1042128 | N/A | N/A | 449708 | 449727 | GCAAATCTATCTTTATTTTA | 79 | 788 |
| 1042160 | N/A | N/A | 449991 | 450010 | CCTGCGAAAAGATGCCACGA | 117 | 789 |
| 1042192 | N/A | N/A | 450674 | 450693 | AAGTTCAGTTACAGAGGTGC | 19 | 790 |
| 1042224 | N/A | N/A | 451247 | 451266 | GTTCTCAACCTTCTTGAACC | 110 | 791 |
| 1042256 | N/A | N/A | 451693 | 451712 | CTTTCATTATTTCCGCATCT | 14 | 792 |
| 1042288 | N/A | N/A | 451971 | 451990 | GCCGGACACCTACCCATGGA | 132 | 793 |
| 1042320 | N/A | N/A | 452314 | 452333 | CCCACTGTATTCTAAGTAGG | 82 | 794 |
| 1042352 | N/A | N/A | 452646 | 452665 | TTTTTCTGTGCCTCCTGACC | 59 | 795 |
| 1042384 | N/A | N/A | 453143 | 453162 | AAGTACCAAAAAAACTTTAA | 77 | 796 |
| 1042416 | N/A | N/A | 454243 | 454262 | AGCCTCTAGAACAGGCTGGG | 131 | 797 |
| 1042448 | N/A | N/A | 455090 | 455109 | ACAGCTTGAGAATTTTGATA | 21 | 798 |
| 1042480 | N/A | N/A | 455370 | 455389 | ACAGTGAACCACAAGCCAAC | 107 | 799 |
| 1042512 | N/A | N/A | 456692 | 456711 | ACAGGACTAAACATGGATCA | 39 | 800 |

TABLE 12

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 1 | 138 |
| 1040081* | 856 | 875 | 435575 | 435594 | ATCCAGGCTCTTCATGAGGA | 5 | 801 |
| 1040113 | 2819 | 2838 | 437538 | 437557 | TATGGCTGTCTTCAATCCTC | 53 | 802 |
| 1040145 | 3369 | 3388 | 457622 | 457641 | CAAATCTTAACCTCCTGAGG | 48 | 803 |
| 1040177 | 4047 | 4066 | 458300 | 458319 | TATACAATTAAAAGTTGCTT | 110 | 804 |
| 1040209 | 4531 | 4550 | 458784 | 458803 | CAGTATTTTAAATGCTTAA | 35 | 805 |
| 1040241 | 4815 | 4834 | 459068 | 459087 | ACTGATTCTCAGACATCAAA | 40 | 806 |
| 1040273 | 5279 | 5298 | 459532 | 459551 | GCCATTCTGAAAATAACATT | 9 | 807 |
| 1040305 | 5616 | 5635 | 459869 | 459888 | CTGGTGAACCCTAAATGTAA | 43 | 808 |
| 1040337 | 6019 | 6038 | 460272 | 460291 | ATCCAGTCAATTCAATACTC | 10 | 809 |
| 1040369 | 6480 | 6499 | 460733 | 460752 | CCACACTCCACATTCACTAT | 35 | 810 |

TABLE 12-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040401 | 7190 | 7209 | 461443 | 461462 | CCCCTCTGCCCCAGTGTGGC | 96 | 811 |
| 1040433 | 7656 | 7675 | 461909 | 461928 | TGCAGCATTATATTGCAATC | 74 | 812 |
| 1040465 | 8114 | 8133 | 462367 | 462386 | CTCTCCTTTCACATCACCAC | 30 | 813 |
| 1040497 | 8417 | 8436 | 462670 | 462689 | TCCTATCATCAGTAAGGTAA | 92 | 814 |
| 1040529 | 8711 | 8730 | 462964 | 462983 | AATCTGATCATTTAGACATG | 42 | 815 |
| 1040561 | 9115 | 9134 | 463368 | 463387 | AATCATGTTTTACTCCCCC | 76 | 816 |
| 1040593 | 9464 | 9483 | 463717 | 463736 | ATAGATACTACCTATTGGCC | 39 | 817 |
| 1040625 | 9971 | 9990 | 464224 | 464243 | ATCTTGAAACCTCCTTTCGG | 55 | 818 |
| 1040657 | 10257 | 10276 | 464510 | 464529 | AGCTCTTAACTATTATGTAT | 16 | 819 |
| 1040689 | 10559 | 10578 | 464812 | 464831 | GTATACAGACAATTTATTTA | 83 | 820 |
| 1040721 | N/A | N/A | 18359 | 18378 | ACATGGTATTTTATCAGTC | 3 | 821 |
| 1040753 | N/A | N/A | 33291 | 33310 | CCTAACAAAATTTCCCTTCA | 73 | 822 |
| 1040785 | N/A | N/A | 53624 | 53643 | GTGAATTTTCCTTAAATTTC | 23 | 823 |
| 1040817 | N/A | N/A | 77899 | 77918 | TGCAAATTCTAAAAATTACT | 101 | 824 |
| 1040849 | N/A | N/A | 96635 | 96654 | TTCTTGTTTCAAAGTGAGGA | 121 | 825 |
| 1040881 | N/A | N/A | 118343 | 118362 | GACCTCATCCATTATAATAT | 52 | 826 |
| 1040913 | N/A | N/A | 153709 | 153728 | CCAACCAACCAAAAACTCAC | 101 | 827 |
| 1040945 | N/A | N/A | 179793 | 179812 | CATAGTTATATTTAATCATG | 64 | 828 |
| 1040977 | N/A | N/A | 196970 | 196989 | ATGCCTCACCTTTAAATAGT | 82 | 829 |
| 1041009 | N/A | N/A | 217125 | 217144 | GACAAGTTTATTTATTTTTC | 25 | 830 |
| 1041041 | N/A | N/A | 239500 | 239519 | AACTGATTTCAAAGTCAGAC | 131 | 831 |
| 1041073 | N/A | N/A | 260025 | 260044 | ACTGAAACTTTTTAACATAC | 37 | 832 |
| 1041105 | N/A | N/A | 278198 | 278217 | CAGCAAATACAAACAGGACC | 3 | 833 |
| 1041137 | N/A | N/A | 295336 | 295355 | ACACAGTTACAAATCAATGC | 1 | 834 |
| 1041169 | N/A | N/A | 324924 | 324943 | TGGATCTAAATTTAAACTGC | 6 | 835 |
| 1041201 | N/A | N/A | 348183 | 348202 | ATGCTCAAACCTCATTCATT | 23 | 836 |
| 1041233 | N/A | N/A | 373954 | 373973 | TACTCCTTATTTTAAATATA | 114 | 837 |
| 1041265 | N/A | N/A | 395428 | 395447 | AAGGTTCTATTTTATATGCC | 24 | 838 |
| 1041297 | N/A | N/A | 428019 | 428038 | AGTGTTAGAGAATACTTTTC | 33 | 839 |
| 1041329 | N/A | N/A | 437898 | 437917 | AATCAGGGTTCCTCATCTTA | 26 | 840 |
| 1041361 | N/A | N/A | 438362 | 438381 | TGCCCCCACTTTACGGTGT | 98 | 841 |
| 1041393 | N/A | N/A | 438931 | 438950 | CAGTCCAGAGCCCACTCCCC | 96 | 842 |
| 1041425 | N/A | N/A | 439188 | 439207 | AACCATACTTCCAGTGACTC | 10 | 843 |
| 1041457 | N/A | N/A | 439897 | 439916 | CCAGTCATTCACGAGTGGTT | 60 | 844 |
| 1041489 | N/A | N/A | 440232 | 440251 | TGACTCTTCACTCATGTTTA | 67 | 845 |
| 1041521 | N/A | N/A | 440798 | 440817 | GTAGGGAAAAACACACCTAG | 87 | 846 |

TABLE 12-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041553 | N/A | N/A | 441417 | 441436 | CATTTCTGAATTTCTCTGTG | 15 | 847 |
| 1041585 | N/A | N/A | 441728 | 441747 | CCACAGAAAAACAAAACTCA | 100 | 848 |
| 1041617 | N/A | N/A | 442286 | 442305 | CCCTTAAAAATCATCCCCAA | 103 | 849 |
| 1041649 | N/A | N/A | 442824 | 442843 | GCAGCTAACCTACTTCCTAC | 24 | 850 |
| 1041681 | N/A | N/A | 443215 | 443234 | TACTCAGAAATACAGATTGA | 62 | 851 |
| 1041713 | N/A | N/A | 443563 | 443582 | ACAGACGGCCCTAATAACAC | 106 | 852 |
| 1041745 | N/A | N/A | 444022 | 444041 | TGTATTACCAACAACTGCGG | 37 | 853 |
| 1041777 | N/A | N/A | 444419 | 444438 | ACAGAGTGAACTGTAGTATA | 3 | 854 |
| 1041809 | N/A | N/A | 445337 | 445356 | AGCCTGACTCAGTCCTTGGT | 122 | 855 |
| 1041841 | N/A | N/A | 445672 | 445691 | GAATTCTCTCATAAGCTAGG | 51 | 856 |
| 1041873 | N/A | N/A | 445928 | 445947 | ATGCACATACACGCATATTT | 57 | 857 |
| 1041905 | N/A | N/A | 446161 | 446180 | CCATCCCCCTAAATCGACTC | 84 | 858 |
| 1041937 | N/A | N/A | 446729 | 446748 | ATCCAGTAAATATATCCTGT | 15 | 859 |
| 1041969 | N/A | N/A | 447005 | 447024 | GGCAGCTTTCTCAGCGGAGC | 65 | 860 |
| 1042001 | N/A | N/A | 447978 | 447997 | ATCCCCAACCCCCAGGCAAC | 110 | 861 |
| 1042033 | N/A | N/A | 448602 | 448621 | ACTACCTCCACCACCTTTGT | 57 | 862 |
| 1042065 | N/A | N/A | 448825 | 448844 | AAGTGACCTAAAACACACCA | 88 | 863 |
| 1042097 | N/A | N/A | 449390 | 449409 | TGATAGCTTCAAAATATTGT | 30 | 864 |
| 1042129 | N/A | N/A | 449710 | 449729 | TAGCAAATCTATCTTTATTT | 70 | 865 |
| 1042161 | N/A | N/A | 450005 | 450024 | AGGAGCTGTGTCACCCTGCG | 71 | 866 |
| 1042193 | N/A | N/A | 450685 | 450704 | CAGCCAAACCTAAGTTCAGT | 32 | 867 |
| 1042225 | N/A | N/A | 451248 | 451267 | AGTTCTCAACCTTCTTGAAC | 78 | 868 |
| 1042257 | N/A | N/A | 451698 | 451717 | AAAGCCTTTCATTATTTCCG | 9 | 869 |
| 1042289 | N/A | N/A | 452004 | 452023 | CCGGATAACTCCCTGTCTCC | 80 | 870 |
| 1042321 | N/A | N/A | 452315 | 452334 | ACCCACTGTATTCTAAGTAG | 23 | 871 |
| 1042353 | N/A | N/A | 452658 | 452677 | AACCCATTTTCTTTTTTCTG | 119 | 872 |
| 1042385 | N/A | N/A | 453188 | 453207 | GATTTATACACATTCAGAC | 58 | 873 |
| 1042417 | N/A | N/A | 454279 | 454298 | CATCTTGTAAACTAAACAGG | 58 | 874 |
| 1042449 | N/A | N/A | 455116 | 455135 | GCTTACAATAATTAAGAAGA | 60 | 875 |
| 1042481 | N/A | N/A | 455372 | 455391 | AGACAGTGAACCACAAGCCA | 95 | 876 |
| 1042513 | N/A | N/A | 456694 | 456713 | GGACAGGACTAAACATGGAT | 23 | 877 |

TABLE 13

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 2 | 138 |
| 1040082 | 896 | 915 | 435615 | 435634 | AGTCTGATAAACGGAAAGTC | 58 | 878 |
| 1040114 | 2839 | 2858 | 437558 | 437577 | TATCACGGCCACGCCCGGGC | 149 | 879 |
| 1040146 | 3372 | 3391 | 457625 | 457644 | ATGCAAATCTTAACCTCCTG | 12 | 880 |
| 1040178 | 4048 | 4067 | 458301 | 458320 | CTATACAATTAAAAGTTGCT | 111 | 881 |
| 1040210 | 4532 | 4551 | 458785 | 458804 | ACAGTATTTTAAATGCTTA | 52 | 882 |
| 1040242 | 4816 | 4835 | 459069 | 459088 | AACTGATTCTCAGACATCAA | 39 | 883 |
| 1040274 | 5306 | 5325 | 459559 | 459578 | GATTTGATTTTGAATAGAAA | 64 | 884 |
| 1040306 | 5617 | 5636 | 459870 | 459889 | CCTGGTGAACCCTAAATGTA | 66 | 885 |
| 1040338 | 6025 | 6044 | 460278 | 460297 | TAGTGGATCCAGTCAATTCA | 22 | 886 |
| 1040370 | 6483 | 6502 | 460736 | 460755 | TCTCCACACTCCACATTCAC | 87 | 887 |
| 1040402 | 7241 | 7260 | 461494 | 461513 | CACTTTAAAGATCTGAGGT | 51 | 888 |
| 1040434 | 7676 | 7695 | 461929 | 461948 | GCTACTGTTCATCTTGAACA | 76 | 889 |
| 1040466 | 8123 | 8142 | 462376 | 462395 | AGTGTAATTCTCTCCTTTCA | 17 | 890 |
| 1040498 | 8426 | 8445 | 462679 | 462698 | AAGAAAAGATCCTATCATCA | 76 | 891 |
| 1040530 | 8716 | 8735 | 462969 | 462988 | ATACAAATCTGATCATTTAG | 60 | 892 |
| 1040562 | 9116 | 9135 | 463369 | 463388 | AAATCATGTTTTTACTCCCC | 81 | 893 |
| 1040594 | 9466 | 9485 | 463719 | 463738 | GTATAGATACTACCTATTGG | 27 | 894 |
| 1040626 | 9991 | 10010 | 464244 | 464263 | CCACAAATACTGACAGGACT | 18 | 895 |
| 1040658 | 10258 | 10277 | 464511 | 464530 | AAGCTCTTAACTATTATGTA | 28 | 896 |
| 1040690 | 10561 | 10580 | 464814 | 464833 | TGGTATACAGACAATTTATT | 58 | 897 |
| 1040722 | N/A | N/A | 18895 | 18914 | AACTTTAAAACCAAAGAGCC | 89 | 898 |
| 1040754 | N/A | N/A | 33435 | 33454 | TGTACAATAATATATTTCTT | 63 | 899 |
| 1040786 | N/A | N/A | 53693 | 53712 | GCAGAAATTCATTAAAAAGG | 44 | 900 |
| 1040818 | N/A | N/A | 78103 | 78122 | TACTGGTATATTTATTTGTT | 25 | 901 |
| 1040850 | N/A | N/A | 96906 | 96925 | CTTGAGTTTCATTATCTCCT | 62 | 902 |
| 1040882 | N/A | N/A | 122955 | 122974 | CATACATTCCCTTAAGCCAA | 45 | 903 |
| 1040914 | N/A | N/A | 154008 | 154027 | AGTATTATTTAAAACTACAT | 107 | 904 |
| 1040946 | N/A | N/A | 180271 | 180290 | CCATGGTTTCAAAGCTCTGT | 68 | 905 |
| 1040978 | N/A | N/A | 198120 | 198139 | AGCTATAAAATATAAACTTC | 116 | 906 |
| 1041010 | N/A | N/A | 218069 | 218088 | AGCTTTTGAATTTATTATGA | 63 | 907 |
| 1041042 | N/A | N/A | 240054 | 240073 | CAGAGACTATTTAAAGACG | 67 | 908 |
| 1041074 | N/A | N/A | 262925 | 262944 | CTCTTATTTTAAACTGGTGC | 17 | 909 |
| 1041106 | N/A | N/A | 279276 | 279295 | TTACTGATTATTTAACCCTG | 1 | 910 |
| 1041138 | N/A | N/A | 296194 | 296213 | AGTTCATTTTAAACTGTATT | 1 | 911 |
| 1041170 | N/A | N/A | 326365 | 326384 | TGTATTATTTTCTAACAGAA | 17 | 912 |
| 1041202 | N/A | N/A | 349100 | 349119 | AAGTATACAATTTAAGGATC | 18 | 913 |

TABLE 13-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041234 | N/A | N/A | 374001 | 374020 | ATTAGATTTCCTTACTGCAA | 16 | 914 |
| 1041266 | N/A | N/A | 395704 | 395723 | CCTCTCAAAACCACTTTTAT | 123 | 915 |
| 1041298 | N/A | N/A | 428253 | 428272 | CCCTCAATTCAAAGACAAAT | 128 | 916 |
| 1041330 | N/A | N/A | 437904 | 437923 | TTTCCTAATCAGGGTTCCTC | 24 | 917 |
| 1041362 | N/A | N/A | 438363 | 438382 | GTGCCCCCACTTTACGGTG | 35 | 918 |
| 1041394 | N/A | N/A | 438955 | 438974 | CCTGACTTTCATATGCAAAC | 23 | 919 |
| 1041426 | N/A | N/A | 439190 | 439209 | TTAACCATACTTCCAGTGAC | 49 | 920 |
| 1041458 | N/A | N/A | 439905 | 439924 | CCCCATATCCAGTCATTCAC | 91 | 921 |
| 1041490 | N/A | N/A | 440236 | 440255 | GCAATGACTCTTCACTCATG | 49 | 922 |
| 1041522 | N/A | N/A | 440800 | 440819 | GAGTAGGGAAAAACACACCT | 49 | 923 |
| 1041554 | N/A | N/A | 441434 | 441453 | AAGCTCAACAATTTGCACAT | 37 | 924 |
| 1041586 | N/A | N/A | 441742 | 441761 | ACGAACACAAAAACCCACAG | 65 | 925 |
| 1041618 | N/A | N/A | 442287 | 442306 | CCCCTTAAAAATCATCCCCA | 84 | 926 |
| 1041650 | N/A | N/A | 442825 | 442844 | AGCAGCTAACCTACTTCCTA | 34 | 927 |
| 1041682 | N/A | N/A | 443218 | 443237 | TCATACTCAGAAATACAGAT | 19 | 928 |
| 1041714 | N/A | N/A | 443616 | 443635 | TTAAGCAGCCACCGAGTCAG | 94 | 929 |
| 1041746 | N/A | N/A | 444023 | 444042 | GTGTATTACCAACAACTGCG | 8 | 930 |
| 1041778 | N/A | N/A | 444443 | 444462 | TTCATCAAAAACAGCATGTA | 85 | 931 |
| 1041810 | N/A | N/A | 445344 | 445363 | CACGCAAAGCCTGACTCAGT | 50 | 932 |
| 1041842 | N/A | N/A | 445673 | 445692 | TGAATTCTCTCATAAGCTAG | 96 | 933 |
| 1041874 | N/A | N/A | 445931 | 445950 | ACTATGCACATACACGCATA | 108 | 934 |
| 1041906 | N/A | N/A | 446163 | 446182 | ATCCATCCCCCTAAATCGAC | 54 | 935 |
| 1041938 | N/A | N/A | 446730 | 446749 | CATCCAGTAAATATATCCTG | 17 | 936 |
| 1041970 | N/A | N/A | 447020 | 447039 | CTTTACCGCCTAACAGGCAG | 123 | 937 |
| 1042002 | N/A | N/A | 447979 | 447998 | GATCCCCAACCCCCAGGCAA | 94 | 938 |
| 1042034 | N/A | N/A | 448606 | 448625 | TTTTACTACCTCCACCACCT | 61 | 939 |
| 1042066 | N/A | N/A | 448836 | 448855 | ACTCAAACTTAAAGTGACCT | 66 | 940 |
| 1042098 | N/A | N/A | 449409 | 449428 | TGGGTATTCTCTATGATGCT | 26 | 941 |
| 1042130 | N/A | N/A | 449713 | 449732 | TCATAGCAAATCTATCTTTA | 74 | 942 |
| 1042162 | N/A | N/A | 450017 | 450036 | GCTTCCTACCAAAGGAGCTG | 128 | 943 |
| 1042194 | N/A | N/A | 450686 | 450705 | GCAGCCAAACCTAAGTTCAG | 78 | 944 |
| 1042226 | N/A | N/A | 451252 | 451271 | AAGAAGTTCTCAACCTTCTT | 91 | 945 |
| 1042258 | N/A | N/A | 451699 | 451718 | GAAAGCCTTTCATTATTTCC | 29 | 946 |
| 1042290 | N/A | N/A | 452046 | 452065 | TAGTTCCAAACATGTCAGCC | 29 | 947 |
| 1042322 | N/A | N/A | 452353 | 452372 | GACAAATATACTTACAAGTG | 17 | 948 |
| 1042354 | N/A | N/A | 452664 | 452683 | CCCCCAAACCCATTTTCTTT | 121 | 949 |

TABLE 13-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042386 | N/A | N/A | 453191 | 453210 | TTGGATTTTATACACATTCA | 45 | 950 |
| 1042418 | N/A | N/A | 454294 | 454313 | GCTATAAATCAAAGACATCT | 61 | 951 |
| 1042450 | N/A | N/A | 455117 | 455136 | TGCTTACAATAATTAAGAAG | 75 | 952 |
| 1042482 | N/A | N/A | 455402 | 455421 | TTGTGACCCCAAAGCACTGT | 100 | 953 |
| 1042514 | N/A | N/A | 456708 | 456727 | GCTATTATCATACAGGACAG | 20 | 954 |

TABLE 14

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 3 | 138 |
| 1040083 | 902 | 921 | 435621 | 435640 | GATTTTAGTCTGATAAACGG | 32 | 955 |
| 1040115 | 2852 | 2871 | 437571 | 437590 | CGACGGCGAACTGTATCACG | 120 | 956 |
| 1040147 | 3386 | 3405 | 457639 | 457658 | TAGACCGGCCTTCAATGCAA | 41 | 957 |
| 1040179 | 4050 | 4069 | 458303 | 458322 | ATCTATACAATTAAAAGTTG | 116 | 958 |
| 1040211 | 4534 | 4553 | 458787 | 458806 | GAACAGTATTTTTAAATGCT | 13 | 959 |
| 1040243 | 4817 | 4836 | 459070 | 459089 | GAACTGATTCTCAGACATCA | 15 | 960 |
| 1040275 | 5323 | 5342 | 459576 | 459595 | ACCAAACATTAAATCTCGAT | 36 | 961 |
| 1040307 | 5636 | 5655 | 459889 | 459908 | GTTTATAAAAATCATTAGTC | 76 | 962 |
| 1040339 | 6064 | 6083 | 460317 | 460336 | GCTCCAAACCATGTGTGTTT | 23 | 963 |
| 1040371 | 6493 | 6512 | 460746 | 460765 | GCCTCCTTCCTCTCCACACT | 54 | 964 |
| 1040403 | 7244 | 7263 | 461497 | 461516 | TTCCACTTTAAAAGATCTGA | 34 | 965 |
| 1040435 | 7696 | 7715 | 461949 | 461968 | GGATTTTATGATTACTAGGA | 9 | 966 |
| 1040467 | 8151 | 8170 | 462404 | 462423 | GGCCTCCACGCCACTTAAAA | 144 | 967 |
| 1040499 | 8432 | 8451 | 462685 | 462704 | TGCTACAAGAAAAGATCCTA | 63 | 968 |
| 1040531 | 8722 | 8741 | 462975 | 462994 | ATAACCATACAAATCTGATC | 61 | 969 |
| 1040563 | 9124 | 9143 | 463377 | 463396 | TTACATTGAAATCATGTTTT | 48 | 970 |
| 1040595 | 9467 | 9486 | 463720 | 463739 | TGTATAGATACTACCTATTG | 53 | 971 |
| 1040627 | 9996 | 10015 | 464249 | 464268 | GGTCACCACAAATACTGACA | 29 | 972 |
| 1040659 | 10269 | 10288 | 464522 | 464541 | TGTCACAATAAAAGCTCTTA | 47 | 973 |
| 1040691 | 10563 | 10582 | 464816 | 464835 | ACTGGTATACAGACAATTTA | 80 | 974 |
| 1040723 | N/A | N/A | 19256 | 19275 | CCCAGCAAAGCCATCCAGTG | 80 | 975 |
| 1040755 | N/A | N/A | 33606 | 33625 | TTGATTACAATTTAAATTCA | 90 | 976 |
| 1040787 | N/A | N/A | 54456 | 54475 | AAGGGAATATTTTACTTTAT | 13 | 977 |
| 1040819 | N/A | N/A | 78391 | 78410 | CTATTATTATTTTACTGGCA | 7 | 978 |
| 1040851 | N/A | N/A | 97882 | 97901 | TTTTATAGCCACTAACCAAC | 96 | 979 |

TABLE 14-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040883 | N/A | N/A | 125349 | 125368 | AACATATTTCATTATAATTC | 100 | 980 |
| 1040915 | N/A | N/A | 154957 | 154976 | ACCCAGCATTTTAACATTA | 63 | 981 |
| 1040947 | N/A | N/A | 180483 | 180502 | CTTTCATTTATTTAGTGAAA | 116 | 982 |
| 1040979 | N/A | N/A | 200076 | 200095 | TTCCTTACTTTTTAGGATAC | 119 | 983 |
| 1041011 | N/A | N/A | 218138 | 218157 | GATTTATTTTAAAGTACTCT | 83 | 984 |
| 1041043 | N/A | N/A | 241942 | 241961 | GATTCCAAAACCAGACTTGT | 143 | 985 |
| 1041075 | N/A | N/A | 263175 | 263194 | CCATATATAGATTACAAAGC | 39 | 986 |
| 1041107 | N/A | N/A | 281181 | 281200 | TCTTTTAACCCTAAGACTGT | 67 | 987 |
| 1041139 | N/A | N/A | 296440 | 296459 | TGACAGTATTTTTAAAGACT | 2 | 988 |
| 1041171 | N/A | N/A | 326617 | 326636 | ACTGGCAAACCCAAAAGCTA | 103 | 989 |
| 1041203 | N/A | N/A | 349644 | 349663 | ACTGTTAAAACCCATCCAAC | 63 | 990 |
| 1041235 | N/A | N/A | 374559 | 374578 | ATGCAGTTCTAAAAGAAAGC | 66 | 991 |
| 1041267 | N/A | N/A | 397171 | 397190 | AGGCCCAAACCTCTAATCAA | 123 | 992 |
| 1041299 | N/A | N/A | 429792 | 429811 | AAGATTCAAATATATCTTAA | 130 | 993 |
| 1041331 | N/A | N/A | 437924 | 437943 | GGACCTGAAGTCCAGCAGCG | 60 | 994 |
| 1041363 | N/A | N/A | 438401 | 438420 | ACTCCCTCCACCTCCTGACC | 101 | 995 |
| 1041395 | N/A | N/A | 438956 | 438975 | GCCTGACTTTCATATGCAAA | 45 | 996 |
| 1041427 | N/A | N/A | 439210 | 439229 | GCCTGTGGAAATTAAGAGCG | 101 | 997 |
| 1041459 | N/A | N/A | 439912 | 439931 | TGCAAGCCCCCATATCCAGT | 45 | 998 |
| 1041491 | N/A | N/A | 440261 | 440280 | TTAAGGATTCTAAGTACCAT | 20 | 999 |
| 1041523 | N/A | N/A | 440821 | 440840 | TCATTAATTTTGCAAAGTTT | 19 | 1000 |
| 1041555 | N/A | N/A | 441445 | 441464 | TTTTGCTTATTAAGCTCAAC | 49 | 1001 |
| 1041587 | N/A | N/A | 441743 | 441762 | AACGAACACAAAAACCCACA | 105 | 1002 |
| 1041619 | N/A | N/A | 442289 | 442308 | AGCCCCTTAAAAATCATCCC | 116 | 1003 |
| 1041651 | N/A | N/A | 442826 | 442845 | AAGCAGCTAACCTACTTCCT | 53 | 1004 |
| 1041683 | N/A | N/A | 443220 | 443239 | GTTCATACTCAGAAATACAG | 33 | 1005 |
| 1041715 | N/A | N/A | 443625 | 443644 | CACTGAATATTAAGCAGCCA | 76 | 1006 |
| 1041747 | N/A | N/A | 444024 | 444043 | TGTGTATTACCAACAACTGC | 69 | 1007 |
| 1041779 | N/A | N/A | 444458 | 444477 | ACATGACATCATAAATTCAT | 38 | 1008 |
| 1041811 | N/A | N/A | 445353 | 445372 | AATCATGTTCACGCAAAGCC | 41 | 1009 |
| 1041843 | N/A | N/A | 445675 | 445694 | AATGAATTCTCTCATAAGCT | 69 | 1010 |
| 1041875 | N/A | N/A | 445943 | 445962 | CTATATCTAAACACTATGCA | 79 | 1011 |
| 1041907 | N/A | N/A | 446164 | 446183 | CATCCATCCCCCTAAATCGA | 100 | 1012 |
| 1041939 | N/A | N/A | 446731 | 446750 | TCATCCAGTAAATATATCCT | 21 | 1013 |
| 1041971 | N/A | N/A | 447021 | 447040 | GCTTTACCGCCTAACAGGCA | 92 | 1014 |
| 1042003 | N/A | N/A | 447994 | 448013 | CCTCTTTATACCAGGGATCC | 83 | 1015 |

TABLE 14-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042035 | N/A | N/A | 448607 | 448626 | TTTTTACTACCTCCACCACC | 93 | 1016 |
| 1042067 | N/A | N/A | 448839 | 448858 | GCAACTCAAACTTAAAGTGA | 46 | 1017 |
| 1042099 | N/A | N/A | 449410 | 449429 | ATGGGTATTCTCTATGATGC | 22 | 1018 |
| 1042131 | N/A | N/A | 449715 | 449734 | ATTCATAGCAAATCTATCTT | 102 | 1019 |
| 1042163 | N/A | N/A | 450018 | 450037 | TGCTTCCTACCAAAGGAGCT | 129 | 1020 |
| 1042195 | N/A | N/A | 450687 | 450706 | AGCAGCCAAACCTAAGTTCA | 61 | 1021 |
| 1042227 | N/A | N/A | 451307 | 451326 | ACCCTCTATTAAAAATACTA | 113 | 1022 |
| 1042259 | N/A | N/A | 451702 | 451721 | TTTGAAAGCCTTTCATTATT | 85 | 1023 |
| 1042291 | N/A | N/A | 452049 | 452068 | CCTTAGTTCCAAACATGTCA | 42 | 1024 |
| 1042323 | N/A | N/A | 452358 | 452377 | ACATAGACAAATATACTTAC | 31 | 1025 |
| 1042355 | N/A | N/A | 452665 | 452684 | GCCCCCAAACCCATTTTCTT | 113 | 1026 |
| 1042387 | N/A | N/A | 453354 | 453373 | ATGCACCACCACCACCACGC | 79 | 1027 |
| 1042419 | N/A | N/A | 454295 | 454314 | TGCTATAAATCAAAGACATC | 93 | 1028 |
| 1042451 | N/A | N/A | 455129 | 455148 | TTACAAAGACTATGCTTACA | 68 | 1029 |
| 1042483 | N/A | N/A | 455404 | 455423 | AGTTGTGACCCCAAAGCACT | 94 | 1030 |
| 1042515 | N/A | N/A | 456709 | 456728 | TGCTATTATCATACAGGACA | 21 | 1031 |

TABLE 15

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 2 | 138 |
| 1040084 | 909 | 928 | 435628 | 435647 | TGGCTCTGATTTTAGTCTGA | 34 | 1032 |
| 1040116 | 2895 | 2914 | 457148 | 457167 | TACTCTACCAAAACTTCAAC | 75 | 1033 |
| 1040148 | 3387 | 3406 | 457640 | 457659 | TTAGACCGGCCTTCAATGCA | 39 | 1034 |
| 1040180 | 4134 | 4153 | 458387 | 458406 | GCAGAAATGAAATCCCGCAT | 31 | 1035 |
| 1040212 | 4586 | 4605 | 458839 | 458858 | TGAGATACAGTACTTGTTGA | 12 | 1036 |
| 1040244 | 4866 | 4885 | 459119 | 459138 | TTCTCCATCCCTTTTCTCTC | 25 | 1037 |
| 1040276 | 5325 | 5344 | 459578 | 459597 | GTACCAAACATTAAATCTCG | 43 | 1038 |
| 1040308 | 5638 | 5657 | 459891 | 459910 | CGGTTTATAAAAATCATTAG | 80 | 1039 |
| 1040340 | 6065 | 6084 | 460318 | 460337 | TGCTCCAAACCATGTGTGTT | 42 | 1040 |
| 1040372 | 6500 | 6519 | 460753 | 460772 | TGAATCTGCCTCCTTCCTCT | 29 | 1041 |
| 1040404 | 7245 | 7264 | 461498 | 461517 | TTTCCACTTTAAAAGATCTG | 51 | 1042 |
| 1040436 | 7699 | 7718 | 461952 | 461971 | AGTGGATTTTATGATTACTA | 9 | 1043 |
| 1040468 | 8176 | 8195 | 462429 | 462448 | GGTTAAAAACAAATGTGGAA | 132 | 1044 |
| 1040500 | 8481 | 8500 | 462734 | 462753 | GCTTCTCAAATCAGGTGTAC | 11 | 1045 |

TABLE 15-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040532 | 8726 | 8745 | 462979 | 462998 | GGCCATAACCATACAAATCT | 74 | 1046 |
| 1040564 | 9177 | 9196 | 463430 | 463449 | GGCCTCTTTATATTAAATAA | 135 | 1047 |
| 1040596 | 9510 | 9529 | 463763 | 463782 | TCAGATAAGAAAAGTTATGG | 54 | 1048 |
| 1040628 | 9997 | 10016 | 464250 | 464269 | AGGTCACCACAAATACTGAC | 36 | 1049 |
| 1040660 | 10275 | 10294 | 464528 | 464547 | TTCTCCTGTCACAATAAAAG | 93 | 1050 |
| 1040692 | 10565 | 10584 | 464818 | 464837 | GTACTGGTATACAGACAATT | 95 | 1051 |
| 1040724 | N/A | N/A | 20058 | 20077 | GTCCTCAAAACCTATGGAGC | 127 | 1052 |
| 1040756 | N/A | N/A | 34396 | 34415 | TGGCTTAACCAGGGAGATGT | 13 | 1053 |
| 1040788 | N/A | N/A | 56211 | 56230 | ACTGATAATTTTTAGACATA | 41 | 1054 |
| 1040820 | N/A | N/A | 79273 | 79292 | ACCTCAATCATTTACTCTCT | 22 | 1055 |
| 1040852 | N/A | N/A | 99200 | 99219 | ACTCCTAAAATTTATTGAGG | 124 | 1056 |
| 1040884 | N/A | N/A | 127408 | 127427 | CCCTGAATAGTCTATGCCAT | 37 | 1057 |
| 1040916 | N/A | N/A | 155491 | 155510 | TTCCTTAAAATATGTTGGCA | 43 | 1058 |
| 1040948 | N/A | N/A | 181346 | 181365 | GGAAACAACCAAAAACTGCT | 32 | 1059 |
| 1040980 | N/A | N/A | 202475 | 202494 | TGACACAATATTTACTGTGT | 99 | 1060 |
| 1041012 | N/A | N/A | 218314 | 218333 | TCTCAGTTTCAAAATAGGAC | 32 | 1061 |
| 1041044 | N/A | N/A | 241960 | 241979 | CCTCAAAAAGAATCTGCAGA | 102 | 1062 |
| 1041076 | N/A | N/A | 263468 | 263487 | TCGGTTACTATTTACCTTTC | 60 | 1063 |
| 1041108 | N/A | N/A | 281316 | 281335 | GGACCCTAAATTTAAACAGC | 2 | 1064 |
| 1041140 | N/A | N/A | 296918 | 296937 | TGGAAATTTCAAAAGCTAA | 32 | 1065 |
| 1041172 | N/A | N/A | 327619 | 327638 | AACAACAAATAATTACCTAT | 114 | 1066 |
| 1041204 | N/A | N/A | 350026 | 350045 | AAGGAAAATCAAACATTGCT | 7 | 1067 |
| 1041236 | N/A | N/A | 375439 | 375458 | AGGTCTAGTATTTATCTTCT | 1 | 1068 |
| 1041268 | N/A | N/A | 398360 | 398379 | GAAACATTATTTTACTTTTC | 65 | 1069 |
| 1041300 | N/A | N/A | 430468 | 430487 | TCCTAAAAATACATCTTAAA | 102 | 1070 |
| 1041332 | N/A | N/A | 437957 | 437976 | CTGGTAAGAAAAGTGCCGA | 120 | 1071 |
| 1041364 | N/A | N/A | 438416 | 438435 | GCCACATTTCCCCTCACTCC | 23 | 1072 |
| 1041396 | N/A | N/A | 438957 | 438976 | AGCCTGACTTTCATATGCAA | 56 | 1073 |
| 1041428 | N/A | N/A | 439250 | 439269 | GTAATCGATCTAAGAACCTG | 21 | 1074 |
| 1041460 | N/A | N/A | 439916 | 439935 | TTTGTGCAAGCCCCCATATC | 103 | 1075 |
| 1041492 | N/A | N/A | 440277 | 440296 | TGTTCACAAAAATGTGTTAA | 71 | 1076 |
| 1041524 | N/A | N/A | 440828 | 440847 | CATTTAATCATTAATTTTGC | 63 | 1077 |
| 1041556 | N/A | N/A | 441446 | 441465 | ATTTTGCTTATTAAGCTCAA | 38 | 1078 |
| 1041588 | N/A | N/A | 441811 | 441830 | CCAATGATCCCATCACTGCA | 103 | 1079 |
| 1041620 | N/A | N/A | 442290 | 442309 | CAGCCCCTTAAAAATCATCC | 105 | 1080 |
| 1041652 | N/A | N/A | 442846 | 442865 | TGCCAGTTCCTGCATTTTCC | 8 | 1081 |

TABLE 15-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041684 | N/A | N/A | 443222 | 443241 | CAGTTCATACTCAGAAATAC | 50 | 1082 |
| 1041716 | N/A | N/A | 443626 | 443645 | GCACTGAATATTAAGCAGCC | 93 | 1083 |
| 1041748 | N/A | N/A | 444025 | 444044 | GTGTGTATTACCAACAACTG | 16 | 1084 |
| 1041780 | N/A | N/A | 444459 | 444478 | TACATGACATCATAAATTCA | 56 | 1085 |
| 1041812 | N/A | N/A | 445359 | 445378 | ACACTGAATCATGTTCACGC | 7 | 1086 |
| 1041844 | N/A | N/A | 445679 | 445698 | GAGCAATGAATTCTCTCATA | 27 | 1087 |
| 1041876 | N/A | N/A | 445945 | 445964 | TACTATATCTAAACACTATG | 115 | 1088 |
| 1041908 | N/A | N/A | 446169 | 446188 | TCCTCCATCCATCCCCCTAA | 75 | 1089 |
| 1041940 | N/A | N/A | 446740 | 446759 | CCCATTTTTTCATCCAGTAA | 12 | 1090 |
| 1041972 | N/A | N/A | 447022 | 447041 | GGCTTTACCGCCTAACAGGC | 107 | 1091 |
| 1042004 | N/A | N/A | 447996 | 448015 | CTCCTCTTTATACCAGGGAT | 85 | 1092 |
| 1042036 | N/A | N/A | 448608 | 448627 | TTTTTTACTACCTCCACCAC | 105 | 1093 |
| 1042068 | N/A | N/A | 448842 | 448861 | TGGGCAACTCAAACTTAAAG | 57 | 1094 |
| 1042100 | N/A | N/A | 449424 | 449443 | AATTTAAAACCCATATGGGT | 115 | 1095 |
| 1042132 | N/A | N/A | 449743 | 449762 | CACACATCTCAAATAGGTAC | 54 | 1096 |
| 1042164 | N/A | N/A | 450034 | 450053 | GCCTAAATTCTGCCTTTGCT | 35 | 1097 |
| 1042196 | N/A | N/A | 450690 | 450709 | GTGAGCAGCCAAACCTAAGT | 45 | 1098 |
| 1042228 | N/A | N/A | 451308 | 451327 | AACCCTCTATTAAAAATACT | 111 | 1099 |
| 1042260 | N/A | N/A | 451730 | 451749 | CTAAAGACTTCATAATGTTA | 58 | 1100 |
| 1042292 | N/A | N/A | 452051 | 452070 | AGCCTTAGTTCCAAACATGT | 107 | 1101 |
| 1042324 | N/A | N/A | 452368 | 452387 | GTGCATATATACATAGACAA | 8 | 1102 |
| 1042356 | N/A | N/A | 452666 | 452685 | GGCCCCCAAACCCATTTTCT | 114 | 1103 |
| 1042388 | N/A | N/A | 453520 | 453539 | AATATTTAAAATATTGTTGG | 120 | 1104 |
| 1042420 | N/A | N/A | 454296 | 454315 | CTGCTATAAATCAAAGACAT | 74 | 1105 |
| 1042452 | N/A | N/A | 455135 | 455154 | TAGACTTTACAAAGACTATG | 46 | 1106 |
| 1042484 | N/A | N/A | 455425 | 455444 | CTGGTGAGCCCCATTCTTTT | 39 | 1107 |
| 1042516 | N/A | N/A | 456710 | 456729 | CTGCTATTATCATACAGGAC | 18 | 1108 |

TABLE 16

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 3 | 138 |
| 1040085 | 964 | 983 | 435683 | 435702 | GTTGGATTTCATTTTTCGCC | 21 | 1109 |
| 1040117 | 2896 | 2915 | 457149 | 457168 | ATACTCTACCAAAACTTCAA | 90 | 1110 |
| 1040149 | 3411 | 3430 | 457664 | 457683 | CCACGCTGCCTCTACTTGCC | 49 | 1111 |

TABLE 16-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040181 | 4135 | 4154 | 458388 | 458407 | AGCAGAAATGAAATCCCGCA | 33 | 1112 |
| 1040213 | 4588 | 4607 | 458841 | 458860 | AGTGAGATACAGTACTTGTT | 11 | 1113 |
| 1040245 | 4889 | 4908 | 459142 | 459161 | ACTGGACAAAAATGAGTATT | 39 | 1114 |
| 1040277 | 5326 | 5345 | 459579 | 459598 | TGTACCAAACATTAAATCTC | 53 | 1115 |
| 1040309 | 5639 | 5658 | 459892 | 459911 | ACGGTTTATAAAAATCATTA | 71 | 1116 |
| 1040341 | 6066 | 6085 | 460319 | 460338 | TTGCTCCAAACCATGTGTGT | 37 | 1117 |
| 1040373 | 6641 | 6660 | 460894 | 460913 | CCACACTTCCCGTCCAGGCT | 19 | 1118 |
| 1040405 | 7293 | 7312 | 461546 | 461565 | CCAACATAGAAAATTATCCT | 27 | 1119 |
| 1040437 | 7702 | 7721 | 461955 | 461974 | AAGAGTGGATTTTATGATTA | 26 | 1120 |
| 1040469 | 8177 | 8196 | 462430 | 462449 | GGGTTAAAAACAAATGTGGA | 67 | 1121 |
| 1040501 | 8482 | 8501 | 462735 | 462754 | AGCTTCTCAAATCAGGTGTA | 14 | 1122 |
| 1040533 | 8732 | 8751 | 462985 | 463004 | CTTCCAGGCCATAACCATAC | 23 | 1123 |
| 1040565 | 9179 | 9198 | 463432 | 463451 | CTGGCCTCTTTATATTAAAT | 83 | 1124 |
| 1040597 | 9518 | 9537 | 463771 | 463790 | GAGTCCTTTCAGATAAGAAA | 18 | 1125 |
| 1040629 | 10046 | 10065 | 464299 | 464318 | CTCTGGAGCCAGGACTCCAC | 111 | 1126 |
| 1040661 | 10289 | 10308 | 464542 | 464561 | CATATGGAAAAAGTTCTCC | 69 | 1127 |
| 1040693 | 10566 | 10585 | 464819 | 464838 | TGTACTGGTATACAGACAAT | 79 | 1128 |
| 1040725 | N/A | N/A | 21690 | 21709 | CCAATAAAAGCCACAACTTG | 101 | 1129 |
| 1040757 | N/A | N/A | 34751 | 34770 | AAGGTGTATATTTATATGTT | 9 | 1130 |
| 1040789 | N/A | N/A | 56964 | 56983 | GCTCAAATTCAAAAGATGAA | 44 | 1131 |
| 1040821 | N/A | N/A | 79281 | 79300 | TCAGTAAAACCTCAATCATT | 51 | 1132 |
| 1040853 | N/A | N/A | 100126 | 100145 | TGGAATATTCTTTATTTTGG | 68 | 1133 |
| 1040885 | N/A | N/A | 127831 | 127850 | TTACTCTTTCAAATGCAAAA | 124 | 1134 |
| 1040917 | N/A | N/A | 157778 | 157797 | AGGTTCTATATTTAGAACAC | 143 | 1135 |
| 1040949 | N/A | N/A | 181515 | 181534 | CTCACAATTCAAAAGTTGTG | 93 | 1136 |
| 1040981 | N/A | N/A | 203086 | 203105 | TTAGTCAAACATATCAACCT | 52 | 1137 |
| 1041013 | N/A | N/A | 218395 | 218414 | GGCTGCAAACTATTCAAGTA | 99 | 1138 |
| 1041045 | N/A | N/A | 242013 | 242032 | TCATTATTAGATTACCAAGA | 36 | 1139 |
| 1041077 | N/A | N/A | 263601 | 263620 | CAGTAATTTCAAAAGGGCCA | 139 | 1140 |
| 1041109 | N/A | N/A | 281523 | 281542 | TGGATGCTATTTTATGTAGA | 3 | 1141 |
| 1041141 | N/A | N/A | 304301 | 304320 | GACCACAAAACCCAACTTAC | 41 | 1142 |
| 1041173 | N/A | N/A | 329293 | 329312 | TCAACAAATCAAATACTGAT | 94 | 1143 |
| 1041205 | N/A | N/A | 350846 | 350865 | TGCTGCATATTTTATATTTA | 21 | 1144 |
| 1041237 | N/A | N/A | 375452 | 375471 | AGTGTATTAGATTAGGTCTA | 3 | 1145 |
| 1041269 | N/A | N/A | 399227 | 399246 | CTCCTTAAACCCCATTTTAT | 79 | 1146 |
| 1041301 | N/A | N/A | 430469 | 430488 | CTCCTAAAAATACATCTTAA | 129 | 1147 |

TABLE 16-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041333 | N/A | N/A | 437958 | 437977 | CCTGGTAAGAAAAAGTGCCG | 126 | 1148 |
| 1041365 | N/A | N/A | 438420 | 438439 | GTTTGCCACATTTCCCCTCA | 20 | 1149 |
| 1041397 | N/A | N/A | 438974 | 438993 | CAGAGCTAATTCCTAGGAGC | 35 | 1150 |
| 1041429 | N/A | N/A | 439254 | 439273 | GCATGTAATCGATCTAAGAA | 16 | 1151 |
| 1041461 | N/A | N/A | 439954 | 439973 | TTCAGGGCTAAAAGCTCTCG | 113 | 1152 |
| 1041493 | N/A | N/A | 440278 | 440297 | CTGTTCACAAAAATGTGTTA | 54 | 1153 |
| 1041525 | N/A | N/A | 440829 | 440848 | TCATTTAATCATTAATTTTG | 109 | 1154 |
| 1041557 | N/A | N/A | 441447 | 441466 | GATTTTGCTTATTAAGCTCA | 23 | 1155 |
| 1041589 | N/A | N/A | 441816 | 441835 | GTGAGCCAATGATCCCATCA | 68 | 1156 |
| 1041621 | N/A | N/A | 442291 | 442310 | TCAGCCCCTTAAAAATCATC | 127 | 1157 |
| 1041653 | N/A | N/A | 442874 | 442893 | GGATATGTTCAGACTCAGAT | 7 | 1158 |
| 1041685 | N/A | N/A | 443223 | 443242 | CCAGTTCATACTCAGAAATA | 61 | 1159 |
| 1041717 | N/A | N/A | 443628 | 443647 | TGGCACTGAATATTAAGCAG | 52 | 1160 |
| 1041749 | N/A | N/A | 444026 | 444045 | AGTGTGTATTACCAACAACT | 13 | 1161 |
| 1041781 | N/A | N/A | 444482 | 444501 | CTGTATAATAATGTAATGCT | 6 | 1162 |
| 1041813 | N/A | N/A | 445369 | 445388 | TCTATTTAAAACACTGAATC | 88 | 1163 |
| 1041845 | N/A | N/A | 445681 | 445700 | GGGAGCAATGAATTCTCTCA | 111 | 1164 |
| 1041877 | N/A | N/A | 445946 | 445965 | CTACTATATCTAAACACTAT | 121 | 1165 |
| 1041909 | N/A | N/A | 446170 | 446189 | TTCCTCCATCCATCCCCCTA | 108 | 1166 |
| 1041941 | N/A | N/A | 446742 | 446761 | AGCCCATTTTTTCATCCAGT | 7 | 1167 |
| 1041973 | N/A | N/A | 447025 | 447044 | TGTGGCTTTACCGCCTAACA | 106 | 1168 |
| 1042005 | N/A | N/A | 447997 | 448016 | TCTCCTCTTTATACCAGGGA | 47 | 1169 |
| 1042037 | N/A | N/A | 448611 | 448630 | TATTTTTTACTACCTCCAC | 72 | 1170 |
| 1042069 | N/A | N/A | 448882 | 448901 | AGTGACCACACTATCCGATG | 28 | 1171 |
| 1042101 | N/A | N/A | 449428 | 449447 | CTTGAATTTAAAACCCATAT | 83 | 1172 |
| 1042133 | N/A | N/A | 449745 | 449764 | TGCACACATCTCAAATAGGT | 40 | 1173 |
| 1042165 | N/A | N/A | 450037 | 450056 | TTTGCCTAAATTCTGCCTTT | 68 | 1174 |
| 1042197 | N/A | N/A | 450727 | 450746 | CTCACCAACCTCATCTCTCG | 98 | 1175 |
| 1042229 | N/A | N/A | 451449 | 451468 | ACAACTAACTATATATTGTT | 97 | 1176 |
| 1042261 | N/A | N/A | 451738 | 451757 | GTTTCCCTCTAAAGACTTCA | 17 | 1177 |
| 1042293 | N/A | N/A | 452058 | 452077 | GACCAGAAGCCTTAGTTCCA | 26 | 1178 |
| 1042325 | N/A | N/A | 452384 | 452403 | ACACAGAAACATATATGTGC | 87 | 1179 |
| 1042357 | N/A | N/A | 452669 | 452688 | ATTGGCCCCAAACCCATTT | 83 | 1180 |
| 1042389 | N/A | N/A | 453547 | 453566 | TCTGAATGAATATTGGCTAT | 21 | 1181 |

TABLE 16-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042421 | N/A | N/A | 454309 | 454328 | GATGAGAATTAAACTGCTAT | 66 | 1182 |
| 1042453 | N/A | N/A | 455147 | 455166 | GAGTCATACATATAGACTTT | 132 | 1183 |
| 1042485 | N/A | N/A | 455452 | 455471 | TCAGGATACACCAAGGGAGG | 82 | 1184 |
| 1042517 | N/A | N/A | 456712 | 456731 | AACTGCTATTATCATACAGG | 57 | 1185 |

TABLE 17

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 3 | 138 |
| 1040086 | 1112 | 1131 | 435831 | 435850 | CCCGGCCACCAGGGTTGCCC | 110 | 1186 |
| 1040118 | 2897 | 2916 | 457150 | 457169 | GATACTCTACCAAAACTTCA | 64 | 1187 |
| 1040150 | 3412 | 3431 | 457665 | 457684 | CCCACGCTGCCTCTACTTGC | 56 | 1188 |
| 1040182 | 4147 | 4166 | 458400 | 458419 | GCACTAGTAAAAGCAGAAA | 72 | 1189 |
| 1040214 | 4594 | 4613 | 458847 | 458866 | GTTTAAAGTGAGATACAGTA | 15 | 1190 |
| 1040246 | 4923 | 4942 | 459176 | 459195 | AGGTTCTTTAAAAGTTCATC | 12 | 1191 |
| 1040278 | 5330 | 5349 | 459583 | 459602 | GGTTTGTACCAAACATTAAA | 106 | 1192 |
| 1040310 | 5652 | 5671 | 459905 | 459924 | TACACCCCAGAAAACGGTTT | 124 | 1193 |
| 1040342 | 6069 | 6088 | 460322 | 460341 | CTATTGCTCCAAACCATGTG | 39 | 1194 |
| 1040374 | 6678 | 6697 | 460931 | 460950 | ACTGGCCAACACGCTCAGAA | 102 | 1195 |
| 1040406 | 7294 | 7313 | 461547 | 461566 | ACCAACATAGAAAATTATCC | 30 | 1196 |
| 1040438 | 7722 | 7741 | 461975 | 461994 | AGTAAAGATCAAACTGTGCA | 14 | 1197 |
| 1040470 | 8178 | 8197 | 462431 | 462450 | TGGGTTAAAAACAAATGTGG | 81 | 1198 |
| 1040502 | 8484 | 8503 | 462737 | 462756 | TCAGCTTCTCAAATCAGGTG | 13 | 1199 |
| 1040534 | 8740 | 8759 | 462993 | 463012 | TAGTAATTCTTCCAGGCCAT | 23 | 1200 |
| 1040566 | 9181 | 9200 | 463434 | 463453 | TTCTGGCCTCTTTATATTAA | 30 | 1201 |
| 1040598 | 9521 | 9540 | 463774 | 463793 | CTTGAGTCCTTTCAGATAAG | 28 | 1202 |
| 1040630 | 10087 | 10106 | 464340 | 464359 | TCTGATATTAAAACATCCAG | 34 | 1203 |
| 1040662 | 10290 | 10309 | 464543 | 464562 | GCATATGGAAAAAGTTCTC | 24 | 1204 |
| 1040694 | 10583 | 10602 | 464836 | 464855 | TACTGAAACAATAAACTTGT | 102 | 1205 |
| 1040726 | N/A | N/A | 22134 | 22153 | TCTTCCTCCTTTTATATCTG | 30 | 1206 |
| 1040758 | N/A | N/A | 34802 | 34821 | GGATTAAAAATTATGACCTC | 57 | 1207 |
| 1040790 | N/A | N/A | 59689 | 59708 | GGAGCAGTTCCTTAACTATC | 20 | 1208 |
| 1040822 | N/A | N/A | 79548 | 79567 | CCCCTTACCCAAACCCTTGG | 124 | 1209 |
| 1040854 | N/A | N/A | 102583 | 102602 | AGAGATAATTTTTAATGCAG | 34 | 1210 |
| 1040886 | N/A | N/A | 129211 | 129230 | CCATTAAACATTTATTTTGC | 11 | 1211 |

TABLE 17-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040918 | N/A | N/A | 158178 | 158197 | TCTATATTCCCTTAACCGTA | 32 | 1212 |
| 1040950 | N/A | N/A | 182959 | 182978 | CATTTTCAACCTTATGATAT | 42 | 1213 |
| 1040982 | N/A | N/A | 203492 | 203511 | CAGACATTCCTTTAATATGC | 17 | 1214 |
| 1041014 | N/A | N/A | 218412 | 218431 | TAGAACTTTTAAAGCAAGGC | 52 | 1215 |
| 1041046 | N/A | N/A | 242061 | 242080 | AGTCAAATAGTCTATCAGTA | 11 | 1216 |
| 1041078 | N/A | N/A | 263847 | 263866 | ACATGATTTTAAAAGTCTTA | 73 | 1217 |
| 1041110 | N/A | N/A | 281874 | 281893 | TCCCCACACCCTTAAACTGC | 115 | 1218 |
| 1041142 | N/A | N/A | 310242 | 310261 | TACACATAAATTTATATCTG | 78 | 1219 |
| 1041174 | N/A | N/A | 329490 | 329509 | TGGTTCTATATTTATGTACC | 25 | 1220 |
| 1041206 | N/A | N/A | 353449 | 353468 | TTGTCTAAACCTGTTTGAGG | 6 | 1221 |
| 1041238 | N/A | N/A | 375665 | 375684 | GCTACCAAAATACAGAACTT | 66 | 1222 |
| 1041270 | N/A | N/A | 399709 | 399728 | GCACCATTTTAAAAATGGCT | 123 | 1223 |
| 1041302 | N/A | N/A | 430826 | 430845 | TCATCTAAACCTAATACGGC | 99 | 1224 |
| 1041334 | N/A | N/A | 437968 | 437987 | TCTGTCTTTTCCTGGTAAGA | 11 | 1225 |
| 1041366 | N/A | N/A | 438425 | 438444 | CTGTTGTTTGCCACATTTCC | 9 | 1226 |
| 1041398 | N/A | N/A | 438975 | 438994 | CCAGAGCTAATTCCTAGGAG | 4 | 1227 |
| 1041430 | N/A | N/A | 439288 | 439307 | TTGGGCAGTGAAAGAAATGG | 74 | 1228 |
| 1041462 | N/A | N/A | 439989 | 440008 | ACCTACAGTGACATCTCATA | 63 | 1229 |
| 1041494 | N/A | N/A | 440279 | 440298 | TCTGTTCACAAAAATGTGTT | 94 | 1230 |
| 1041526 | N/A | N/A | 440834 | 440853 | CTCTTTCATTTAATCATTAA | 47 | 1231 |
| 1041558 | N/A | N/A | 441464 | 441483 | TCCCCAATCAAATTTGTGAT | 62 | 1232 |
| 1041590 | N/A | N/A | 441897 | 441916 | GTAGTGGTACACACCCATAG | 77 | 1233 |
| 1041622 | N/A | N/A | 442320 | 442339 | GGCATCTTTCCACAGTCTTA | 43 | 1234 |
| 1041654 | N/A | N/A | 442947 | 442966 | CCGAGCCATCTAAGTTGAAG | 30 | 1235 |
| 1041686 | N/A | N/A | 443225 | 443244 | ATCCAGTTCATACTCAGAAA | 29 | 1236 |
| 1041718 | N/A | N/A | 443659 | 443678 | CACCCACGCCAGGACAGTCG | 128 | 1237 |
| 1041750 | N/A | N/A | 444049 | 444068 | TTCCAGCACCAGAACAGACA | 116 | 1238 |
| 1041782 | N/A | N/A | 444483 | 444502 | TCTGTATAATAATGTAATGC | 11 | 1239 |
| 1041814 | N/A | N/A | 445371 | 445390 | GTTCTATTTAAAACACTGAA | 25 | 1240 |
| 1041846 | N/A | N/A | 445703 | 445722 | CATACAAATTTCGCCTGTTG | 55 | 1241 |
| 1041878 | N/A | N/A | 445947 | 445966 | ACTACTATATCTAAACACTA | 109 | 1242 |
| 1041910 | N/A | N/A | 446176 | 446195 | TACCCCTTCCTCCATCCATC | 88 | 1243 |
| 1041942 | N/A | N/A | 446750 | 446769 | CTCAATATAGCCCATTTTTT | 47 | 1244 |
| 1041974 | N/A | N/A | 447063 | 447082 | GACCTCCCCAGGGAGAGGA | 75 | 1245 |
| 1042006 | N/A | N/A | 447998 | 448017 | TTCTCCTCTTTATACCAGGG | 12 | 1246 |
| 1042038 | N/A | N/A | 448613 | 448632 | ACTATTTTTTACTACCTCC | 54 | 1247 |

TABLE 17-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042070 | N/A | N/A | 448885 | 448904 | ACCAGTGACCACACTATCCG | 45 | 1248 |
| 1042102 | N/A | N/A | 449429 | 449448 | CCTTGAATTTAAAACCCATA | 42 | 1249 |
| 1042134 | N/A | N/A | 449762 | 449781 | GAAAGTTAAAATCTTGTTGC | 57 | 1250 |
| 1042166 | N/A | N/A | 450040 | 450059 | CTTTTTGCCTAAATTCTGCC | 70 | 1251 |
| 1042198 | N/A | N/A | 450728 | 450747 | TCTCACCAACCTCATCTCTC | 77 | 1252 |
| 1042230 | N/A | N/A | 451450 | 451469 | AACAACTAACTATATATTGT | 112 | 1253 |
| 1042262 | N/A | N/A | 451767 | 451786 | AGTGCAAAAGTCAGGATACA | 12 | 1254 |
| 1042294 | N/A | N/A | 452064 | 452083 | TCAGAAGACCAGAAGCCTTA | 62 | 1255 |
| 1042326 | N/A | N/A | 452397 | 452416 | ACATTTACATCACACACAGA | 104 | 1256 |
| 1042358 | N/A | N/A | 452685 | 452704 | GGATTTTATCCCAGTCATTG | 57 | 1257 |
| 1042390 | N/A | N/A | 453577 | 453596 | GAGGAATGAAAATGGTAGAT | 25 | 1258 |
| 1042422 | N/A | N/A | 454311 | 454330 | CAGATGAGAATTAAACTGCT | 62 | 1259 |
| 1042454 | N/A | N/A | 455148 | 455167 | AGAGTCATACATATAGACTT | 129 | 1260 |
| 1042486 | N/A | N/A | 455459 | 455478 | ATGGAGTTCAGGATACACCA | 54 | 1261 |
| 1042518 | N/A | N/A | 456740 | 456759 | GGTCTTAGATTTTATGAGCT | 16 | 1262 |

TABLE 18

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 3 | 138 |
| 1040087 | 1115 | 1134 | 435834 | 435853 | GGCCCCGGCCACCAGGGTTG | 104 | 1263 |
| 1040119 | 2898 | 2917 | 457151 | 457170 | GGATACTCTACCAAAACTTC | 20 | 1264 |
| 1040151 | 3423 | 3442 | 457676 | 457695 | GTTTCCTTTCCCCCACGCTG | 23 | 1265 |
| 1040183 | 4148 | 4167 | 458401 | 458420 | TGCACTAGTAAAAAGCAGAA | 99 | 1266 |
| 1040215 | 4609 | 4628 | 458862 | 458881 | TTTTTTCCCCAAAGAGTTTA | 37 | 1267 |
| 1040247 | 4924 | 4943 | 459177 | 459196 | AAGGTTCTTTAAAAGTTCAT | 20 | 1268 |
| 1040279 | 5332 | 5351 | 459585 | 459604 | TGGGTTTGTACCAAACATTA | 59 | 1269 |
| 1040311 | 5676 | 5695 | 459929 | 459948 | CTAAACCTATTCAAATGTTT | 90 | 1270 |
| 1040343 | 6078 | 6097 | 460331 | 460350 | ATGATGTTCCTATTGCTCCA | 11 | 1271 |
| 1040375 | 6750 | 6769 | 461003 | 461022 | TCTTCCTATTTGAAGAGAAA | 64 | 1272 |
| 1040407 | 7311 | 7330 | 461564 | 461583 | GGGAAAACGAAAAGTTGACC | 29 | 1273 |
| 1040439 | 7724 | 7743 | 461977 | 461996 | TCAGTAAAGATCAAACTGTG | 103 | 1274 |
| 1040471 | 8180 | 8199 | 462433 | 462452 | TCTGGGTTAAAAACAAATGT | 69 | 1275 |
| 1040503 | 8486 | 8505 | 462739 | 462758 | CTTCAGCTTCTCAAATCAGG | 26 | 1276 |
| 1040535 | 8767 | 8786 | 463020 | 463039 | ATAGGTATAGTTTAAGAGCC | 22 | 1277 |

TABLE 18 -continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040567 | 9195 | 9214 | 463448 | 463467 | ATGCTCCGTATTTATTCTGG | 9 | 1278 |
| 1040599 | 9523 | 9542 | 463776 | 463795 | GACTTGAGTCCTTTCAGATA | 32 | 1279 |
| 1040631 | 10088 | 10107 | 464341 | 464360 | ATCTGATATTAAAACATCCA | 33 | 1280 |
| 1040663 | 10327 | 10346 | 464580 | 464599 | TACAATATTTTACACTGGAA | 11 | 1281 |
| 1040695 | 10609 | 10628 | 464862 | 464881 | GCACTGTTATTTTATTAGTA | 41 | 1282 |
| 1040727 | N/A | N/A | 22675 | 22694 | CTGTGGTTTTAAAGGCTGTA | 4 | 1283 |
| 1040759 | N/A | N/A | 34869 | 34888 | GGTTTTAAAAACATCCTCCT | 41 | 1284 |
| 1040791 | N/A | N/A | 63051 | 63070 | TTTTAGCACCTTTAAACTCT | 85 | 1285 |
| 1040823 | N/A | N/A | 79759 | 79778 | CTCTCATTTTAAAGTTTTCT | 44 | 1286 |
| 1040855 | N/A | N/A | 103256 | 103275 | ATCTTTATTCAAAAATGCAA | 88 | 1287 |
| 1040887 | N/A | N/A | 132848 | 132867 | TTCATGTTTTAAAGCTGAGA | 11 | 1288 |
| 1040919 | N/A | N/A | 158451 | 158470 | CTCACAATTCAAAATTATTC | 44 | 1289 |
| 1040951 | N/A | N/A | 182994 | 183013 | AACCTTAGAAATGTACATTT | 29 | 1290 |
| 1040983 | N/A | N/A | 204258 | 204277 | CTAGCAATTCAAAACAATAT | 45 | 1291 |
| 1041015 | N/A | N/A | 219043 | 219062 | CTTCTCCTTCCTTAATAGAT | 65 | 1292 |
| 1041047 | N/A | N/A | 243398 | 243417 | TCTCAAGGCCCTTAATTGCC | 67 | 1293 |
| 1041079 | N/A | N/A | 264140 | 264159 | ACTTTTAAATCCCCCTAAAG | 105 | 1294 |
| 1041111 | N/A | N/A | 281939 | 281958 | CTCACATTTCTTTATACACA | 2 | 1295 |
| 1041143 | N/A | N/A | 311352 | 311371 | GTGAGATTTTAAAGACATTC | 1 | 1296 |
| 1041175 | N/A | N/A | 330016 | 330035 | GATGCCAAACTATTATCTCA | 7 | 1297 |
| 1041207 | N/A | N/A | 354249 | 354268 | AGACAATTTTAAAAGCTTCC | 8 | 1298 |
| 1041239 | N/A | N/A | 375816 | 375835 | TCTCTTAACCAAAGAATCTG | 132 | 1299 |
| 1041271 | N/A | N/A | 400962 | 400981 | ATGCTGTTCCTTTATAACGG | 16 | 1300 |
| 1041303 | N/A | N/A | 431185 | 431204 | AATTTCTAAATTTAGCCCAG | 55 | 1301 |
| 1041335 | N/A | N/A | 437990 | 438009 | TCCCCTCACTCCAACGGCAT | 80 | 1302 |
| 1041367 | N/A | N/A | 438448 | 438467 | CTCCCATGAAACCACAATAA | 142 | 1303 |
| 1041399 | N/A | N/A | 439002 | 439021 | CTGACTTTATATGCAAACC | 25 | 1304 |
| 1041431 | N/A | N/A | 439344 | 439363 | CTCGATAGCCAGGAAAGCTC | 64 | 1305 |
| 1041463 | N/A | N/A | 439996 | 440015 | ACTGTAAACCTACAGTGACA | 130 | 1306 |
| 1041495 | N/A | N/A | 440280 | 440299 | CTCTGTTCACAAAAATGTGT | 95 | 1307 |
| 1041527 | N/A | N/A | 440836 | 440855 | TTCTCTTTCATTTAATCATT | 16 | 1308 |
| 1041559 | N/A | N/A | 441465 | 441484 | TTCCCCAATCAAATTTGTGA | 83 | 1309 |
| 1041591 | N/A | N/A | 442071 | 442090 | GAGATTATCTCCTATGAAGA | 50 | 1310 |
| 1041623 | N/A | N/A | 442374 | 442393 | AGCATTTTCTCCTACATTG | 14 | 1311 |
| 1041655 | N/A | N/A | 442950 | 442969 | GGCCCGAGCCATCTAAGTTG | 129 | 1312 |
| 1041687 | N/A | N/A | 443226 | 443245 | AATCCAGTTCATACTCAGAA | 47 | 1313 |

TABLE 18 -continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041719 | N/A | N/A | 443664 | 443683 | ACTCACACCCACGCCAGGAC | 109 | 1314 |
| 1041751 | N/A | N/A | 444094 | 444113 | CCACAAACAAAAATGTGGTT | 79 | 1315 |
| 1041783 | N/A | N/A | 444487 | 444506 | CTGTTCTGTATAATAATGTA | 48 | 1316 |
| 1041815 | N/A | N/A | 445372 | 445391 | TGTTCTATTTAAAACACTGA | 62 | 1317 |
| 1041847 | N/A | N/A | 445705 | 445724 | GACATACAAATTTCGCCTGT | 22 | 1318 |
| 1041879 | N/A | N/A | 445948 | 445967 | AACTACTATATCTAAACACT | 95 | 1319 |
| 1041911 | N/A | N/A | 446181 | 446200 | CTGCCTACCCCTTCCTCCAT | 80 | 1320 |
| 1041943 | N/A | N/A | 446755 | 446774 | GACAGCTAATATAGCCCAT | 28 | 1321 |
| 1041975 | N/A | N/A | 447085 | 447104 | AGCCAGAACTAAAGTGGGCT | 74 | 1322 |
| 1042007 | N/A | N/A | 448000 | 448019 | CCTTCTCCTCTTTATACCAG | 35 | 1323 |
| 1042039 | N/A | N/A | 448615 | 448634 | ATACTATTTTTTTACTACCT | 65 | 1324 |
| 1042071 | N/A | N/A | 448888 | 448907 | GACACCAGTGACCACACTAT | 46 | 1325 |
| 1042103 | N/A | N/A | 449430 | 449449 | TCCTTGAATTTAAAACCCAT | 55 | 1326 |
| 1042135 | N/A | N/A | 449763 | 449782 | TGAAAGTTAAAATCTTGTTG | 75 | 1327 |
| 1042167 | N/A | N/A | 450041 | 450060 | TCTTTTTGCCTAAATTCTGC | 43 | 1328 |
| 1042199 | N/A | N/A | 450731 | 450750 | TCCTCTCACCAACCTCATCT | 77 | 1329 |
| 1042231 | N/A | N/A | 451490 | 451509 | CTTTTAGAAACTAACTCTGG | 107 | 1330 |
| 1042263 | N/A | N/A | 451782 | 451801 | GTACTATAATTGATTAGTGC | 50 | 1331 |
| 1042295 | N/A | N/A | 452071 | 452090 | GTGACATTCAGAAGACCAGA | 15 | 1332 |
| 1042327 | N/A | N/A | 452400 | 452419 | ACTACATTTACATCACACAC | 83 | 1333 |
| 1042359 | N/A | N/A | 452688 | 452707 | TTAGGATTTTATCCCAGTCA | 28 | 1334 |
| 1042391 | N/A | N/A | 453658 | 453677 | GCATTATAGAAAATACTAAA | 85 | 1335 |
| 1042423 | N/A | N/A | 454312 | 454331 | GCAGATGAGAATTAAACTGC | 100 | 1336 |
| 1042455 | N/A | N/A | 455154 | 455173 | TCATATAGAGTCATACATAT | 45 | 1337 |
| 1042487 | N/A | N/A | 455532 | 455551 | TGAACATTCCAAAGTGGAGC | 44 | 1338 |
| 1042519 | N/A | N/A | 456742 | 456761 | GCGGTCTTAGATTTTATGAG | 24 | 1339 |

TABLE 19

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 3 | 138 |
| 1040088 | 1144 | 1163 | 435863 | 435882 | CCCTGCCGGCCCATGCCTCC | 159 | 1340 |
| 1040120 | 2908 | 2927 | 457161 | 457180 | CACAAAAAAGGATACTCTA | 104 | 1341 |
| 1040152 | 3453 | 3472 | 457706 | 457725 | ATCTGGATACAAATGATAAG | 50 | 1342 |
| 1040184 | 4176 | 4195 | 458429 | 458448 | GTCCACCACAACACCCTGGT | 78 | 1343 |

TABLE 19-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040216 | 4671 | 4690 | 458924 | 458943 | CAGAGCTGAAATGTAGTTAC | 12 | 1344 |
| 1040248 | 4926 | 4945 | 459179 | 459198 | GCAAGGTTCTTTAAAAGTTC | 11 | 1345 |
| 1040280 | 5347 | 5366 | 459600 | 459619 | ATGAAATACCCTTTCTGGGT | 124 | 1346 |
| 1040312 | 5684 | 5703 | 459937 | 459956 | TAGCTATTCTAAACCTATTC | 140 | 1347 |
| 1040344 | 6080 | 6099 | 460333 | 460352 | TGATGATGTTCCTATTGCTC | 15 | 1348 |
| 1040376 | 6870 | 6889 | 461123 | 461142 | GAAGAATTTCTACCCCTGTC | 39 | 1349 |
| 1040408 | 7336 | 7355 | 461589 | 461608 | ATCCCAAACTAAACTGGGTG | 105 | 1350 |
| 1040440 | 7732 | 7751 | 461985 | 462004 | AACATATTTCAGTAAAGATC | 13 | 1351 |
| 1040472 | 8194 | 8213 | 462447 | 462466 | TCTATTTCAGAAATTCTGGG | 11 | 1352 |
| 1040504 | 8505 | 8524 | 462758 | 462777 | TGCTTCAAAATTTTGTTTTC | 40 | 1353 |
| 1040536 | 8815 | 8834 | 463068 | 463087 | TTCCCCTCCCTCAGACGAGG | 109 | 1354 |
| 1040568 | 9206 | 9225 | 463459 | 463478 | ATTCTGAGAAGATGCTCCGT | 35 | 1355 |
| 1040600 | 9525 | 9544 | 463778 | 463797 | AAGACTTGAGTCCTTTCAGA | 26 | 1356 |
| 1040632 | 10089 | 10108 | 464342 | 464361 | GATCTGATATTAAAACATCC | 20 | 1357 |
| 1040664 | 10329 | 10348 | 464582 | 464601 | AGTACAATATTTTACACTGG | 14 | 1358 |
| 1040696 | N/A | N/A | 5825 | 5844 | GTCAAGTTTTAAAATGTGAC | 68 | 1359 |
| 1040728 | N/A | N/A | 22774 | 22793 | ACTGAAACAATTTATCTAAG | 83 | 1360 |
| 1040760 | N/A | N/A | 36098 | 36117 | ACAAAAATAATTTAAGCCAC | 106 | 1361 |
| 1040792 | N/A | N/A | 63073 | 63092 | TACTATCACCTTTAAACTTT | 71 | 1362 |
| 1040824 | N/A | N/A | 80953 | 80972 | ACCGCCAAAACCAACCAGGG | 65 | 1363 |
| 1040856 | N/A | N/A | 103405 | 103424 | CTAATCTATCAAATAAAGGA | 105 | 1364 |
| 1040888 | N/A | N/A | 133117 | 133136 | GAGAGGTTTCATTATGTAAA | 5 | 1365 |
| 1040920 | N/A | N/A | 158507 | 158526 | GCACTTAGACAATGCTGCAG | 106 | 1366 |
| 1040952 | N/A | N/A | 183278 | 183297 | GGTAAGTTATTTTAAAACTT | 76 | 1367 |
| 1040984 | N/A | N/A | 205648 | 205667 | AGTTTTACGATATATGAATC | 81 | 1368 |
| 1041016 | N/A | N/A | 219199 | 219218 | TACCATTATTTTTAGCTTTT | 18 | 1369 |
| 1041048 | N/A | N/A | 243460 | 243479 | CAGTTTATTCTTTACCCAAA | 10 | 1370 |
| 1041080 | N/A | N/A | 264569 | 264588 | CCCACATTTTAAAGATGCAG | 46 | 1371 |
| 1041112 | N/A | N/A | 282392 | 282411 | TCCAGAAACCTTTATTATTG | 1 | 1372 |
| 1041144 | N/A | N/A | 311667 | 311686 | AACAGGTTACAAATACGGTT | 1 | 1373 |
| 1041176 | N/A | N/A | 330322 | 330341 | ATTCTGTTTTAAATTCCTTT | 1 | 1374 |
| 1041208 | N/A | N/A | 354293 | 354312 | ATGCAATTTCAAAAGCTGGC | 10 | 1375 |
| 1041240 | N/A | N/A | 376063 | 376082 | GTGGATACTTTTTAAAACTC | 2 | 1376 |
| 1041272 | N/A | N/A | 401167 | 401186 | GTCGCAAACCTTTATGGAGT | 6 | 1377 |
| 1041304 | N/A | N/A | 431998 | 432017 | CAAATCCAAATTTATTCTTC | 76 | 1378 |
| 1041336 | N/A | N/A | 437997 | 438016 | CATCTAATCCCCTCACTCCA | 92 | 1379 |

TABLE 19-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041368 | N/A | N/A | 438450 | 438469 | GCCTCCCATGAAACCACAAT | 122 | 1380 |
| 1041400 | N/A | N/A | 439003 | 439022 | CCTGACTTTTATATGCAAAC | 11 | 1381 |
| 1041432 | N/A | N/A | 439351 | 439370 | AAGTACGCTCGATAGCCAGG | 22 | 1382 |
| 1041464 | N/A | N/A | 439999 | 440018 | AAGACTGTAAACCTACAGTG | 101 | 1383 |
| 1041496 | N/A | N/A | 440281 | 440300 | CCTCTGTTCACAAAAATGTG | 121 | 1384 |
| 1041528 | N/A | N/A | 440838 | 440857 | ATTTCTCTTTCATTTAATCA | 33 | 1385 |
| 1041560 | N/A | N/A | 441466 | 441485 | CTTCCCCAATCAAATTTGTG | 87 | 1386 |
| 1041592 | N/A | N/A | 442072 | 442091 | AGAGATTATCTCCTATGAAG | 70 | 1387 |
| 1041624 | N/A | N/A | 442397 | 442416 | AGGGATAGTGACAAACACGG | 8 | 1388 |
| 1041656 | N/A | N/A | 442952 | 442971 | AGGGCCCGAGCCATCTAAGT | 122 | 1389 |
| 1041688 | N/A | N/A | 443233 | 443252 | CCCCTCAAATCCAGTTCATA | 111 | 1390 |
| 1041720 | N/A | N/A | 443705 | 443724 | CATCATGATAACAACTGCTG | 47 | 1391 |
| 1041752 | N/A | N/A | 444095 | 444114 | CCCACAAACAAAAATGTGGT | 100 | 1392 |
| 1041784 | N/A | N/A | 444575 | 444594 | GAGTAAAATGATCAGTGGGT | 15 | 1393 |
| 1041816 | N/A | N/A | 445373 | 445392 | GTGTTCTATTTAAAACACTG | 107 | 1394 |
| 1041848 | N/A | N/A | 445706 | 445725 | AGACATACAAATTTCGCCTG | 45 | 1395 |
| 1041880 | N/A | N/A | 445954 | 445973 | GTCAATAACTACTATATCTA | 54 | 1396 |
| 1041912 | N/A | N/A | 446182 | 446201 | TCTGCCTACCCCTTCCTCCA | 61 | 1397 |
| 1041944 | N/A | N/A | 446788 | 446807 | CCACAGATAACCAAAGCACG | 37 | 1398 |
| 1041976 | N/A | N/A | 447087 | 447106 | CCAGCCAGAACTAAAGTGGG | 75 | 1399 |
| 1042008 | N/A | N/A | 448004 | 448023 | GGCCCCTTCTCCTCTTTATA | 118 | 1400 |
| 1042040 | N/A | N/A | 448617 | 448636 | TGATACTATTTTTTTACTAC | 97 | 1401 |
| 1042072 | N/A | N/A | 448922 | 448941 | GAGACAGAACATACACGCAA | 35 | 1402 |
| 1042104 | N/A | N/A | 449432 | 449451 | ATTCCTTGAATTTAAAACCC | 51 | 1403 |
| 1042136 | N/A | N/A | 449764 | 449783 | GTGAAAGTTAAAATCTTGTT | 47 | 1404 |
| 1042168 | N/A | N/A | 450045 | 450064 | TGTTTCTTTTTGCCTAAATT | 13 | 1405 |
| 1042200 | N/A | N/A | 450734 | 450753 | TTTTCCTCTCACCAACCTCA | 67 | 1406 |
| 1042232 | N/A | N/A | 451491 | 451510 | ACTTTTAGAAACTAACTCTG | 71 | 1407 |
| 1042264 | N/A | N/A | 451796 | 451815 | GCCCTTTATAACAGGTACTA | 44 | 1408 |
| 1042296 | N/A | N/A | 452072 | 452091 | TGTGACATTCAGAAGACCAG | 27 | 1409 |
| 1042328 | N/A | N/A | 452405 | 452424 | TCAAAACTACATTTACATCA | 118 | 1410 |
| 1042360 | N/A | N/A | 452691 | 452710 | GGTTTAGGATTTTATCCCAG | 25 | 1411 |
| 1042392 | N/A | N/A | 453659 | 453678 | TGCATTATAGAAAATACTAA | 121 | 1412 |
| 1042424 | N/A | N/A | 454313 | 454332 | GGCAGATGAGAATTAAACTG | 38 | 1413 |

TABLE 19-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042456 | N/A | N/A | 455163 | 455182 | CAGGGCTTCTCATATAGAGT | 31 | 1414 |
| 1042488 | N/A | N/A | 455538 | 455557 | GGCACTTGAACATTCCAAAG | 10 | 1415 |
| 1042520 | N/A | N/A | 456757 | 456776 | GCTCACAAGCCCAGCGCGGT | 90 | 1416 |

TABLE 20

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 3 | 138 |
| 1040089 | 1170 | 1189 | 435889 | 435908 | TGTTGTAAACCAAGCTCCAC | 56 | 1417 |
| 1040121 | 2915 | 2934 | 457168 | 457187 | GTCCAAACACAAAAAAGGA | 90 | 1418 |
| 1040153 | 3475 | 3494 | 457728 | 457747 | TATTTTAGCCTACAGTACAG | 70 | 1419 |
| 1040185 | 4179 | 4198 | 458432 | 458451 | CCTGTCCACCACAACACCCT | 80 | 1420 |
| 1040217 | 4683 | 4702 | 458936 | 458955 | TCAGCAATTCTGCAGAGCTG | 103 | 1421 |
| 1040249 | 4953 | 4972 | 459206 | 459225 | AAGTTATAAACTCAATATGT | 38 | 1422 |
| 1040281 | 5348 | 5367 | 459601 | 459620 | TATGAAATACCCTTTCTGGG | 106 | 1423 |
| 1040313 | 5686 | 5705 | 459939 | 459958 | TCTAGCTATTCTAAACCTAT | 80 | 1424 |
| 1040345 | 6092 | 6111 | 460345 | 460364 | CCACAAAAATTATGATGATG | 45 | 1425 |
| 1040377 | 6871 | 6890 | 461124 | 461143 | CGAAGAATTTCTACCCCTGT | 47 | 1426 |
| 1040409 | 7338 | 7357 | 461591 | 461610 | TCATCCCAAACTAAACTGGG | 87 | 1427 |
| 1040441 | 7734 | 7753 | 461987 | 462006 | GCAACATATTTCAGTAAAGA | 13 | 1428 |
| 1040473 | 8203 | 8222 | 462456 | 462475 | CTTAAATTCTCTATTTCAGA | 30 | 1429 |
| 1040505 | 8506 | 8525 | 462759 | 462778 | GTGCTTCAAAATTTTGTTTT | 27 | 1430 |
| 1040537 | 8821 | 8840 | 463074 | 463093 | ACCGAGTTCCCCTCCCTCAG | 106 | 1431 |
| 1040569 | 9217 | 9236 | 463470 | 463489 | ACAGGAATACTATTCTGAGA | 38 | 1432 |
| 1040601 | 9550 | 9569 | 463803 | 463822 | GAAGCTCCAATGTATCTGC | 17 | 1433 |
| 1040633 | 10134 | 10153 | 464387 | 464406 | GGTGTCTGTTTTCCCTTGGC | 14 | 1434 |
| 1040665 | 10330 | 10349 | 464583 | 464602 | AAGTACAATATTTTACACTG | 20 | 1435 |
| 1040697 | N/A | N/A | 6321 | 6340 | GGCCATAAAATTGTAAACTG | 44 | 1436 |
| 1040729 | N/A | N/A | 23146 | 23165 | AACATCTAAATTTATAATGA | 113 | 1437 |
| 1040761 | N/A | N/A | 36881 | 36900 | AGGTGGTTACAAACATAAAT | 35 | 1438 |
| 1040793 | N/A | N/A | 63098 | 63117 | AGCTAAAAACCCAACATGGG | 81 | 1439 |
| 1040825 | N/A | N/A | 81039 | 81058 | GACAGTTATTTTAAGAGGC | 7 | 1440 |
| 1040857 | N/A | N/A | 103451 | 103470 | TTGGACTTTTAAATGTAAGT | 83 | 1441 |
| 1040889 | N/A | N/A | 135046 | 135065 | TGTGTCTAAATTTATGGTAG | 13 | 1442 |
| 1040921 | N/A | N/A | 160360 | 160379 | GTTGAATTTCAAAAATCAAA | 59 | 1443 |

TABLE 20-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040953 | N/A | N/A | 184290 | 184309 | CAGGAAAAAATACAGGGTGT | 19 | 1444 |
| 1040985 | N/A | N/A | 206209 | 206228 | ACCTAAAAAAATATAGATCC | 142 | 1445 |
| 1041017 | N/A | N/A | 223097 | 223116 | CTAATTAATCCTTAAATTGC | 109 | 1446 |
| 1041049 | N/A | N/A | 244961 | 244980 | TTTCAATATATTTACACACT | 63 | 1447 |
| 1041081 | N/A | N/A | 266459 | 266478 | CTCACACAAATTTACATTCT | 89 | 1448 |
| 1041113 | N/A | N/A | 284256 | 284275 | ACCTAAAAAATACATCTTTA | 94 | 1449 |
| 1041145 | N/A | N/A | 313344 | 313363 | CTGAAGATTCCTTAATATCT | 1 | 1450 |
| 1041177 | N/A | N/A | 331091 | 331110 | CTAATGTTTTAAAACTCTTG | 35 | 1451 |
| 1041209 | N/A | N/A | 355246 | 355265 | TTCCAATTTTAAAAAACCTG | 44 | 1452 |
| 1041241 | N/A | N/A | 376190 | 376209 | CTGTCAAAAATATAATACCT | 81 | 1453 |
| 1041273 | N/A | N/A | 401168 | 401187 | TGTCGCAAACCTTTATGGAG | 33 | 1454 |
| 1041305 | N/A | N/A | 432296 | 432315 | AAGTCCTTTCAAAGCCAAGT | 38 | 1455 |
| 1041337 | N/A | N/A | 437999 | 438018 | AGCATCTAATCCCCTCACTC | 42 | 1456 |
| 1041369 | N/A | N/A | 438464 | 438483 | AACCCGTTTACCCTGCCTCC | 77 | 1457 |
| 1041401 | N/A | N/A | 439004 | 439023 | GCCTGACTTTTATATGCAAA | 13 | 1458 |
| 1041433 | N/A | N/A | 439362 | 439381 | ACACTTGTAGAAAGTACGCT | 8 | 1459 |
| 1041465 | N/A | N/A | 440005 | 440024 | CTTCCAAAGACTGTAAACCT | 65 | 1460 |
| 1041497 | N/A | N/A | 440282 | 440301 | GCCTCTGTTCACAAAAATGT | 99 | 1461 |
| 1041529 | N/A | N/A | 440844 | 440863 | AAGCCAATTTCTCTTTCATT | 57 | 1462 |
| 1041561 | N/A | N/A | 441471 | 441490 | CACAACTTCCCCAATCAAAT | 70 | 1463 |
| 1041593 | N/A | N/A | 442076 | 442095 | CTCAAGAGATTATCTCCTAT | 30 | 1464 |
| 1041625 | N/A | N/A | 442399 | 442418 | ACAGGGATAGTGACAAACAC | 24 | 1465 |
| 1041657 | N/A | N/A | 442969 | 442988 | CTGTGAATCACTTTCTCAGG | 73 | 1466 |
| 1041689 | N/A | N/A | 443234 | 443253 | ACCCCTCAAATCCAGTTCAT | 129 | 1467 |
| 1041721 | N/A | N/A | 443723 | 443742 | GTAGACAGCCAGTAAGTACA | 62 | 1468 |
| 1041753 | N/A | N/A | 444096 | 444115 | ACCCACAAACAAAATGTGG | 132 | 1469 |
| 1041785 | N/A | N/A | 444648 | 444667 | CGCCAATGTGAAAAGGCGAC |  | 1470 |
| 1041817 | N/A | N/A | 445374 | 445393 | AGTGTTCTATTTAAAACACT | 131 | 1471 |
| 1041849 | N/A | N/A | 445708 | 445727 | CCAGACATACAAATTTCGCC | 40 | 1472 |
| 1041881 | N/A | N/A | 445955 | 445974 | AGTCAATAACTACTATATCT | 46 | 1473 |
| 1041913 | N/A | N/A | 446221 | 446240 | CCAGCAAGCCCATGTGCTCA | 109 | 1474 |
| 1041945 | N/A | N/A | 446792 | 446811 | AGTACCACAGATAACCAAAG | 52 | 1475 |
| 1041977 | N/A | N/A | 447180 | 447199 | CTGTATGGAAAACATTGCA | 29 | 1476 |
| 1042009 | N/A | N/A | 448133 | 448152 | ATGATGATCATTATGTAGAG | 24 | 1477 |
| 1042041 | N/A | N/A | 448619 | 448638 | AATGATACTATTTTTTACT | 77 | 1478 |
| 1042073 | N/A | N/A | 448923 | 448942 | GGAGACAGAACATACACGCA | 44 | 1479 |

TABLE 20-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042105 | N/A | N/A | 449439 | 449458 | TCTGTGAATTCCTTGAATTT | 41 | 1480 |
| 1042137 | N/A | N/A | 449765 | 449784 | GGTGAAAGTTAAAATCTTGT | 60 | 1481 |
| 1042169 | N/A | N/A | 450072 | 450091 | TCTTTAATCACTTCAAAGGC | 54 | 1482 |
| 1042201 | N/A | N/A | 450754 | 450773 | GGCTTTCCCAATAAACCTGC | 37 | 1483 |
| 1042233 | N/A | N/A | 451493 | 451512 | GTACTTTTAGAAACTAACTC | 47 | 1484 |
| 1042265 | N/A | N/A | 451798 | 451817 | AAGCCCTTTATAACAGGTAC | 38 | 1485 |
| 1042297 | N/A | N/A | 452094 | 452113 | GCCCAACACCAGGCAGAGGT | 82 | 1486 |
| 1042329 | N/A | N/A | 452407 | 452426 | TTTCAAAACTACATTTACAT | 117 | 1487 |
| 1042361 | N/A | N/A | 452759 | 452778 | TTGTAAATTTTACGAATAGT | 63 | 1488 |
| 1042393 | N/A | N/A | 453673 | 453692 | ACCATCAACAGATCTGCATT | 62 | 1489 |
| 1042425 | N/A | N/A | 454359 | 454378 | GCCTAGCCCCAAACAGGAAA | 117 | 1490 |
| 1042457 | N/A | N/A | 455172 | 455191 | AGGATGCACCAGGGCTTCTC | 79 | 1491 |
| 1042489 | N/A | N/A | 455557 | 455576 | GGGCCTGTTTTCTCCTGAAG | 116 | 1492 |
| 1042521 | N/A | N/A | 456758 | 456777 | GGCTCACAAGCCCAGCGCGG | 132 | 1493 |

TABLE 21

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 3 | 138 |
| 1040090 | 1171 | 1190 | 435890 | 435909 | CTGTTGTAAACCAAGCTCCA | 64 | 1494 |
| 1040122 | 2927 | 2946 | 457180 | 457199 | ATGACCAGCCCTGTCCAAAC | 73 | 1495 |
| 1040154 | 3482 | 3501 | 457735 | 457754 | ACTGTGTTATTTTAGCCTAC | 11 | 1496 |
| 1040186 | 4224 | 4243 | 458477 | 458496 | CCCAACCCCCCTTACCCCAT | 82 | 1497 |
| 1040218 | 4709 | 4728 | 458962 | 458981 | CATTGAAACTTTCAATATCT | 43 | 1498 |
| 1040250 | 4967 | 4986 | 459220 | 459239 | CAGGAATATCACACAAGTTA | 17 | 1499 |
| 1040282 | 5349 | 5368 | 459602 | 459621 | CTATGAAATACCCTTTCTGG | 79 | 1500 |
| 1040314 | 5687 | 5706 | 459940 | 459959 | TTCTAGCTATTCTAAACCTA | 75 | 1501 |
| 1040346 | 6094 | 6113 | 460347 | 460366 | AACCACAAAAATTATGATGA | 59 | 1502 |
| 1040378 | 6872 | 6891 | 461125 | 461144 | CCGAAGAATTTCTACCCCTG | 31 | 1503 |
| 1040410 | 7339 | 7358 | 461592 | 461611 | ATCATCCCAAACTAAACTGG | 71 | 1504 |
| 1040442 | 7739 | 7758 | 461992 | 462011 | TTTTGGCAACATATTTCAGT | 16 | 1505 |
| 1040474 | 8207 | 8226 | 462460 | 462479 | TGTTCTTAAATTCTCTATTT | 18 | 1506 |
| 1040506 | 8508 | 8527 | 462761 | 462780 | GAGTGCTTCAAAATTTTGTT | 20 | 1507 |
| 1040538 | 8843 | 8862 | 463096 | 463115 | CAGTATTCTCAAATCGCAGA | 58 | 1508 |
| 1040570 | 9219 | 9238 | 463472 | 463491 | GGACAGGAATACTATTCTGA | 45 | 1509 |

TABLE 21-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040602 | 9554 | 9573 | 463807 | 463826 | GGGTGAAGCCTCCAATGTAT | 29 | 1510 |
| 1040634 | 10151 | 10170 | 464404 | 464423 | CCCTCAACCCAAGTTCTGGT | 78 | 1511 |
| 1040666 | 10332 | 10351 | 464585 | 464604 | GCAAGTACAATATTTTACAC | 13 | 1512 |
| 1040698 | N/A | N/A | 6643 | 6662 | CACTGAAAAATATATGTTCA | 28 | 1513 |
| 1040730 | N/A | N/A | 23318 | 23337 | CACTATAAAAACATCTAACA | 98 | 1514 |
| 1040762 | N/A | N/A | 38292 | 38311 | TTCAACAATATTTATGCCCA | 5 | 1515 |
| 1040794 | N/A | N/A | 63099 | 63118 | CAGCTAAAAACCCAACATGG | 109 | 1516 |
| 1040826 | N/A | N/A | 81067 | 81086 | AGTTATATATTTTAGCTGAA | 58 | 1517 |
| 1040858 | N/A | N/A | 103630 | 103649 | GCTATATTTTAAAAGGATC | 89 | 1518 |
| 1040890 | N/A | N/A | 137052 | 137071 | CTTTCATTTCAAACTTACTG | 59 | 1519 |
| 1040922 | N/A | N/A | 161567 | 161586 | ACTTTCTTTTAAATTCTAAC | 69 | 1520 |
| 1040954 | N/A | N/A | 184602 | 184621 | GATGGTAATTTTTAGAGGTG | 4 | 1521 |
| 1040986 | N/A | N/A | 206522 | 206541 | TCTTTCTATATTTATCTATA | 51 | 1522 |
| 1041018 | N/A | N/A | 223242 | 223261 | GTTTACAAAATATTTGCACA | 37 | 1523 |
| 1041050 | N/A | N/A | 245286 | 245305 | TCTATCAAACCTAATCTATC | 53 | 1524 |
| 1041082 | N/A | N/A | 267260 | 267279 | AAGGAATTTCTTTACACCAT | 27 | 1525 |
| 1041114 | N/A | N/A | 284274 | 284293 | GCACTTCGAATTTATACCAC | 2 | 1526 |
| 1041146 | N/A | N/A | 314135 | 314154 | AACATAAAAATATACCTAA | 109 | 1527 |
| 1041178 | N/A | N/A | 331394 | 331413 | GCTGTTAAAATATGCTTTCC | 2 | 1528 |
| 1041210 | N/A | N/A | 356766 | 356785 | GGGCACTACCCTTATCTTAA | 38 | 1529 |
| 1041242 | N/A | N/A | 376191 | 376210 | CCTGTCAAAAATATAATACC | 89 | 1530 |
| 1041274 | N/A | N/A | 402544 | 402563 | CCTTTAAAAATATGCCTTTT | 46 | 1531 |
| 1041306 | N/A | N/A | 432451 | 432470 | CCAATAAAACCCCACAGGGT | 109 | 1532 |
| 1041338 | N/A | N/A | 438003 | 438022 | CTTTAGCATCTAATCCCCTC | 59 | 1533 |
| 1041370 | N/A | N/A | 438465 | 438484 | AAACCCGTTTACCCTGCCTC | 76 | 1534 |
| 1041402 | N/A | N/A | 439005 | 439024 | GGCCTGACTTTTATATGCAA | 117 | 1535 |
| 1041434 | N/A | N/A | 439383 | 439402 | GTTTTCAAATCCTAGATGGA | 26 | 1536 |
| 1041466 | N/A | N/A | 440010 | 440029 | GGGCCCTTCCAAAGACTGTA | 124 | 1537 |
| 1041498 | N/A | N/A | 440298 | 440317 | ACCTCTTTTCACACCTGCCT | 22 | 1538 |
| 1041530 | N/A | N/A | 440851 | 440870 | CACAGGGAAGCCAATTTCTC | 76 | 1539 |
| 1041562 | N/A | N/A | 441483 | 441502 | CATCTCTTCTTCCACAACTT | 52 | 1540 |
| 1041594 | N/A | N/A | 442078 | 442097 | CTCTCAAGAGATTATCTCCT | 104 | 1541 |
| 1041626 | N/A | N/A | 442489 | 442508 | CTTTCCTCCCACAGCACCTA | 49 | 1542 |
| 1041658 | N/A | N/A | 442983 | 443002 | GATTTATTTTCAGCTGTGA | 6 | 1543 |
| 1041690 | N/A | N/A | 443237 | 443256 | TGCACCCCTCAAATCCAGTT | 99 | 1544 |
| 1041722 | N/A | N/A | 443729 | 443748 | CCATCGGTAGACAGCCAGTA | 39 | 1545 |

TABLE 21-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041754 | N/A | N/A | 444105 | 444124 | GGTACAAAGACCCACAAACA | 51 | 1546 |
| 1041786 | N/A | N/A | 444737 | 444756 | AACATAATATTCAGTGCTAA | 40 | 1547 |
| 1041818 | N/A | N/A | 445375 | 445394 | GAGTGTTCTATTTAAAACAC | 82 | 1548 |
| 1041850 | N/A | N/A | 445710 | 445729 | TCCCAGACATACAAATTTCG | 90 | 1549 |
| 1041882 | N/A | N/A | 445956 | 445975 | TAGTCAATAACTACTATATC | 148 | 1550 |
| 1041914 | N/A | N/A | 446222 | 446241 | GCCAGCAAGCCCATGTGCTC | 121 | 1551 |
| 1041946 | N/A | N/A | 446793 | 446812 | CAGTACCACAGATAACCAAA | 30 | 1552 |
| 1041978 | N/A | N/A | 447541 | 447560 | GCTCAGTTAAAATCTGAAAG | 38 | 1553 |
| 1042010 | N/A | N/A | 448228 | 448247 | GTGGGCTCAAGATATCTTCC | 113 | 1554 |
| 1042042 | N/A | N/A | 448621 | 448640 | AGAATGATACTATTTTTTTA | 92 | 1555 |
| 1042074 | N/A | N/A | 448934 | 448953 | GCCTCCCACCAGGAGACAGA | 115 | 1556 |
| 1042106 | N/A | N/A | 449466 | 449485 | GATGTCATCTTCAACTGGAA | 28 | 1557 |
| 1042138 | N/A | N/A | 449771 | 449790 | TTCTTTGGTGAAAGTTAAAA | 91 | 1558 |
| 1042170 | N/A | N/A | 450076 | 450095 | TTCTTCTTTAATCACTTCAA | 35 | 1559 |
| 1042202 | N/A | N/A | 450757 | 450776 | TCTGGCTTTCCCAATAAACC | 62 | 1560 |
| 1042234 | N/A | N/A | 451505 | 451524 | AACAACAATCATGTACTTTT | 36 | 1561 |
| 1042266 | N/A | N/A | 451800 | 451819 | ACAAGCCCTTTATAACAGGT | 16 | 1562 |
| 1042298 | N/A | N/A | 452096 | 452115 | TTGCCCAACACCAGGCAGAG | 104 | 1563 |
| 1042330 | N/A | N/A | 452408 | 452427 | GTTTCAAAACTACATTTACA | 100 | 1564 |
| 1042362 | N/A | N/A | 452769 | 452788 | TCTTCCAATTTTGTAAATTT | 35 | 1565 |
| 1042394 | N/A | N/A | 453674 | 453693 | CACCATCAACAGATCTGCAT | 88 | 1566 |
| 1042426 | N/A | N/A | 454361 | 454380 | AGGCCTAGCCCCAAACAGGA | 145 | 1567 |
| 1042458 | N/A | N/A | 455185 | 455204 | CAGATCTTAAAAAAGGATGC | 59 | 1568 |
| 1042490 | N/A | N/A | 455600 | 455619 | ATCAGGAAAAGATGATGGCC | 111 | 1569 |
| 1042522 | N/A | N/A | 456802 | 456821 | AGAGCACCCACTTAGCTTTC | 98 | 1570 |

TABLE 22

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 2 | 138 |
| 1040091 | 1181 | 1200 | 435900 | 435919 | AACCTATTCCCTGTTGTAAA | 23 | 1571 |
| 1040123 | 2969 | 2988 | 457222 | 457241 | ACGGCAAATCAAAGAGCTGG | 130 | 1572 |
| 1040155 | 3517 | 3536 | 457770 | 457789 | ACAGAAACCTAAAATTAAGA | 116 | 1573 |
| 1040187 | 4227 | 4246 | 458480 | 458499 | ACCCCCAACCCCCCTTACCC | 102 | 1574 |
| 1040219 | 4720 | 4739 | 458973 | 458992 | CCTTTAAACCACATTGAAAC | 69 | 1575 |

TABLE 22-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040251 | 4968 | 4987 | 459221 | 459240 | GCAGGAATATCACACAAGTT | 14 | 1576 |
| 1040283 | 5351 | 5370 | 459604 | 459623 | AACTATGAAATACCCTTTCT | 130 | 1577 |
| 1040315 | 5696 | 5715 | 459949 | 459968 | AAGGAACTATTCTAGCTATT | 43 | 1578 |
| 1040347 | 6097 | 6116 | 460350 | 460369 | TAGAACCACAAAAATTATGA | 65 | 1579 |
| 1040379 | 6873 | 6892 | 461126 | 461145 | ACCGAAGAATTTCTACCCCT | 37 | 1580 |
| 1040411 | 7351 | 7370 | 461604 | 461623 | AACAGAAATCAAATCATCCC | 58 | 1581 |
| 1040443 | 7751 | 7770 | 462004 | 462023 | AACAAAAATAAATTTTGGCA | 103 | 1582 |
| 1040475 | 8210 | 8229 | 462463 | 462482 | ATGTGTTCTTAAATTCTCTA | 9 | 1583 |
| 1040507 | 8523 | 8542 | 462776 | 462795 | TGTACTCCTCAAAGTGAGTG | 126 | 1584 |
| 1040539 | 8844 | 8863 | 463097 | 463116 | ACAGTATTCTCAAATCGCAG | 67 | 1585 |
| 1040571 | 9251 | 9270 | 463504 | 463523 | CTGTCCAGTTTCCACTGTCC | 31 | 1586 |
| 1040603 | 9584 | 9603 | 463837 | 463856 | CAGCAAACAAACTAAAGGGA | 29 | 1587 |
| 1040635 | 10152 | 10171 | 464405 | 464424 | GCCCTCAACCCAAGTTCTGG | 129 | 1588 |
| 1040667 | 10375 | 10394 | 464628 | 464647 | TATGAATTCTTCCATTTTTT | 92 | 1589 |
| 1040699 | N/A | N/A | 7015 | 7034 | AACATTATTCAAAGAAATGT | 108 | 1590 |
| 1040731 | N/A | N/A | 24365 | 24384 | AGGCAGAACATTTAACATCG | 29 | 1591 |
| 1040763 | N/A | N/A | 38732 | 38751 | TCTGTGTTTATTTAGGTTTC | 3 | 1592 |
| 1040795 | N/A | N/A | 64787 | 64806 | ACTGCATTTCAAAACCTACA | 25 | 1593 |
| 1040827 | N/A | N/A | 81310 | 81329 | TTGAAGTTTTAAAGTACATG | 87 | 1594 |
| 1040859 | N/A | N/A | 105462 | 105481 | ATGTTTAAAATATGCATGCC | 152 | 1595 |
| 1040891 | N/A | N/A | 137270 | 137289 | TTTCTCAGAATATAACTGTA | 44 | 1596 |
| 1040923 | N/A | N/A | 162773 | 162792 | GTGTAATTTCAAAATAGGGT | 10 | 1597 |
| 1040955 | N/A | N/A | 185622 | 185641 | AGCTTTCAAATTTATCCACT | 9 | 1598 |
| 1040987 | N/A | N/A | 207222 | 207241 | ACTTAGCCAATTTAACTGCA | 26 | 1599 |
| 1041019 | N/A | N/A | 224367 | 224386 | TCTTTAAAACTATTAGTCAC | 81 | 1600 |
| 1041051 | N/A | N/A | 245290 | 245309 | CTAATCTATCAAACCTAATC | 142 | 1601 |
| 1041083 | N/A | N/A | 267301 | 267320 | TCAGTTAAAATACCTGATGA | 94 | 1602 |
| 1041115 | N/A | N/A | 284506 | 284525 | GGTTAATATTTTTATGGTAT | 1 | 1603 |
| 1041147 | N/A | N/A | 314443 | 314462 | GTTATAATTTAAAAGTGTT | 100 | 1604 |
| 1041179 | N/A | N/A | 332631 | 332650 | CCGTTTTATTTTTAAACTCG | 9 | 1605 |
| 1041211 | N/A | N/A | 356791 | 356810 | GCTTCATTTTAAAAGATTGT | 7 | 1606 |
| 1041243 | N/A | N/A | 376226 | 376245 | CCACATAAAATATCGAATCA | 40 | 1607 |
| 1041275 | N/A | N/A | 407589 | 407608 | CAGGGCTGTATTTAATTCTG | 14 | 1608 |
| 1041307 | N/A | N/A | 433208 | 433227 | GTTCTCAATCCTTAATGATT | 55 | 1609 |
| 1041339 | N/A | N/A | 438044 | 438063 | GACATATTTTAAAACATGGA | 13 | 1610 |
| 1041371 | N/A | N/A | 438475 | 438494 | AACCAATCCTAAACCCGTTT | 62 | 1611 |

TABLE 22-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041403 | N/A | N/A | 439006 | 439025 | AGGCCTGACTTTTATATGCA | 137 | 1612 |
| 1041435 | N/A | N/A | 439384 | 439403 | TGTTTTCAAATCCTAGATGG | 43 | 1613 |
| 1041467 | N/A | N/A | 440042 | 440061 | TTTTAAATAAGATCTTTGGG | 62 | 1614 |
| 1041499 | N/A | N/A | 440299 | 440318 | AACCTCTTTTCACACCTGCC | 26 | 1615 |
| 1041531 | N/A | N/A | 440909 | 440928 | AGTAGAGAGATTTAGTGATC | 16 | 1616 |
| 1041563 | N/A | N/A | 441492 | 441511 | GGAGAAAACCATCTCTTCTT | 76 | 1617 |
| 1041595 | N/A | N/A | 442096 | 442115 | GCATTAAAAAACGGAACCCT | 103 | 1618 |
| 1041627 | N/A | N/A | 442494 | 442513 | TTCCCCTTTCCTCCCACAGC | 99 | 1619 |
| 1041659 | N/A | N/A | 442984 | 443003 | TGATTTATTTTCAGCTGTG | 5 | 1620 |
| 1041691 | N/A | N/A | 443239 | 443258 | AATGCACCCCTCAAATCCAG | 109 | 1621 |
| 1041723 | N/A | N/A | 443762 | 443781 | AGTCAACCAAAAATAGTAG | 40 | 1622 |
| 1041755 | N/A | N/A | 444110 | 444129 | AGAGAGGTACAAAGACCCAC | 52 | 1623 |
| 1041787 | N/A | N/A | 444740 | 444759 | AACAACATAATATTCAGTGC | 27 | 1624 |
| 1041819 | N/A | N/A | 445394 | 445413 | TGAGTGTAAGAATCTCTGTG | 119 | 1625 |
| 1041851 | N/A | N/A | 445716 | 445735 | ACACTATCCCAGACATACAA | 57 | 1626 |
| 1041883 | N/A | N/A | 445961 | 445980 | CCACTTAGTCAATAACTACT | 34 | 1627 |
| 1041915 | N/A | N/A | 446223 | 446242 | TGCCAGCAAGCCCATGTGCT | 98 | 1628 |
| 1041947 | N/A | N/A | 446796 | 446815 | GAGCAGTACCACAGATAACC | 22 | 1629 |
| 1041979 | N/A | N/A | 447542 | 447561 | TGCTCAGTTAAAATCTGAAA | 49 | 1630 |
| 1042011 | N/A | N/A | 448333 | 448352 | CTCTAGTTTCCATAGCTTCC | 42 | 1631 |
| 1042043 | N/A | N/A | 448635 | 448654 | TTCCAAATACACCTAGAATG | 68 | 1632 |
| 1042075 | N/A | N/A | 448937 | 448956 | CTTGCCTCCCACCAGGAGAC | 100 | 1633 |
| 1042107 | N/A | N/A | 449467 | 449486 | TGATGTCATCTTCAACTGGA | 27 | 1634 |
| 1042139 | N/A | N/A | 449783 | 449802 | GGTTTTTTCCCTTCTTTGG | 8 | 1635 |
| 1042171 | N/A | N/A | 450078 | 450097 | GATTCTTCTTTAATCACTTC | 31 | 1636 |
| 1042203 | N/A | N/A | 450777 | 450796 | CTCATCATCTTCTCAATTTC | 86 | 1637 |
| 1042235 | N/A | N/A | 451509 | 451528 | CACAAACAACAATCATGTAC | 47 | 1638 |
| 1042267 | N/A | N/A | 451802 | 451821 | CTACAAGCCCTTTATAACAG | 26 | 1639 |
| 1042299 | N/A | N/A | 452101 | 452120 | TATTCTTGCCCAACACCAGG | 80 | 1640 |
| 1042331 | N/A | N/A | 452409 | 452428 | GGTTTCAAAACTACATTTAC | 58 | 1641 |
| 1042363 | N/A | N/A | 452840 | 452859 | TCTCAGGTACAAACTTTACA | 26 | 1642 |
| 1042395 | N/A | N/A | 453676 | 453695 | TTCACCATCAACAGATCTGC | 80 | 1643 |
| 1042427 | N/A | N/A | 454375 | 454394 | AGACAGTTTCAAGAAGGCCT | 111 | 1644 |
| 1042459 | N/A | N/A | 455186 | 455205 | TCAGATCTTAAAAAAGGATG | 102 | 1645 |
| 1042491 | N/A | N/A | 456123 | 456142 | AAGATAGTAAAAAGGCCAGG | 135 | 1646 |
| 1042523 | N/A | N/A | 456821 | 456840 | ATCGAACCCAGTAATGACA | 38 | 1647 |

TABLE 23

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 3 | 138 |
| 1040092 | 1188 | 1207 | 435907 | 435926 | TTGTGTAAACCTATTCCCTG | 17 | 1648 |
| 1040124 | 2971 | 2990 | 457224 | 457243 | ACACGGCAAATCAAAGAGCT | 93 | 1649 |
| 1040156 | 3526 | 3545 | 457779 | 457798 | AAGGTTAGAACAGAAACCTA | 94 | 1650 |
| 1040188 | 4228 | 4247 | 458481 | 458500 | CACCCCCAACCCCCCTTACC | 112 | 1651 |
| 1040220 | 4721 | 4740 | 458974 | 458993 | CCCTTTAAACCACATTGAAA | 59 | 1652 |
| 1040252 | 5005 | 5024 | 459258 | 459277 | CCCCAAACCTTTCCCACAAT | 53 | 1653 |
| 1040284 | 5387 | 5406 | 459640 | 459659 | ATGATATTTCGGATCTCTGG | 11 | 1654 |
| 1040316 | 5699 | 5718 | 459952 | 459971 | GTCAAGGAACTATTCTAGCT | 22 | 1655 |
| 1040348 | 6113 | 6132 | 460366 | 460385 | ATTCCTATACCTGAAATAGA | 51 | 1656 |
| 1040380 | 6874 | 6893 | 461127 | 461146 | CACCGAAGAATTTCTACCCC | 54 | 1657 |
| 1040412 | 7385 | 7404 | 461638 | 461657 | CTCACAATTCCAAGTTAGAA | 23 | 1658 |
| 1040444 | 7827 | 7846 | 462080 | 462099 | AGTAGTCACAGATGTTAAAG | 16 | 1659 |
| 1040476 | 8211 | 8230 | 462464 | 462483 | GATGTGTTCTTAAATTCTCT | 14 | 1660 |
| 1040508 | 8526 | 8545 | 462779 | 462798 | ACCTGTACTCCTCAAAGTGA | 58 | 1661 |
| 1040540 | 8845 | 8864 | 463098 | 463117 | AACAGTATTCTCAAATCGCA | 73 | 1662 |
| 1040572 | 9267 | 9286 | 463520 | 463539 | CTTAATATCCCCACAGCTGT | 108 | 1663 |
| 1040604 | 9597 | 9616 | 463850 | 463869 | TTGGCCATCCAGACAGCAAA | 96 | 1664 |
| 1040636 | 10153 | 10172 | 464406 | 464425 | TGCCCTCAACCCAAGTTCTG | 82 | 1665 |
| 1040668 | 10376 | 10395 | 464629 | 464648 | ATATGAATTCTTCCATTTTT | 91 | 1666 |
| 1040700 | N/A | N/A | 7886 | 7905 | CGTTATAAAATATATTACTA | 97 | 1667 |
| 1040732 | N/A | N/A | 24555 | 24574 | GCAAGATGAATTTATCCTCC | 11 | 1668 |
| 1040764 | N/A | N/A | 38983 | 39002 | CACAACTTATTTAATGTCA | 13 | 1669 |
| 1040796 | N/A | N/A | 66238 | 66257 | TGAGTATTTTAAACTCTTCT | 138 | 1670 |
| 1040828 | N/A | N/A | 83133 | 83152 | ATTCCATTATTTTAGAAAGC | 50 | 1671 |
| 1040860 | N/A | N/A | 105795 | 105814 | ACTTGCAAAATTTCAAGTTT | 131 | 1672 |
| 1040892 | N/A | N/A | 138729 | 138748 | AGCAAGTTAATTTATGGCCA | 101 | 1673 |
| 1040924 | N/A | N/A | 163155 | 163174 | GATTGAATCATTTACCTCGC | 49 | 1674 |
| 1040956 | N/A | N/A | 185759 | 185778 | ATCTGCTTTCTTTATTCCCT | 9 | 1675 |
| 1040988 | N/A | N/A | 207251 | 207270 | ATCTCTGTTATTTAACACTG | 70 | 1676 |
| 1041020 | N/A | N/A | 224368 | 224387 | TTCTTTAAAACTATTAGTCA | 122 | 1677 |
| 1041052 | N/A | N/A | 245320 | 245339 | GACCTCAAAACCAAATTAGG | 119 | 1678 |
| 1041084 | N/A | N/A | 268039 | 268058 | TCTGAAATTCAAAATCAGTG | 122 | 1679 |
| 1041116 | N/A | N/A | 284543 | 284562 | CCACTGGAAATTTAACATGA | 18 | 1680 |
| 1041148 | N/A | N/A | 315438 | 315457 | TGTATCACCCATTAACTGAC | 2 | 1681 |
| 1041180 | N/A | N/A | 332732 | 332751 | GACTAAAAAATATACATCTC | 57 | 1682 |
| 1041212 | N/A | N/A | 356967 | 356986 | GGTCTATTTCTTTACAGCAC | 2 | 1683 |

TABLE 23-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041244 | N/A | N/A | 376250 | 376269 | TTCTTCTGTATTTAATTCTT | 18 | 1684 |
| 1041276 | N/A | N/A | 407619 | 407638 | ACTGAGTTTCAAAGCAAAGA | 30 | 1685 |
| 1041308 | N/A | N/A | 433762 | 433781 | ATCCGATTTTAAAACAAACA | 64 | 1686 |
| 1041340 | N/A | N/A | 438045 | 438064 | AGACATATTTTAAAACATGG | 29 | 1687 |
| 1041372 | N/A | N/A | 438476 | 438495 | TAACCAATCCTAAACCCGTT | 97 | 1688 |
| 1041404 | N/A | N/A | 439022 | 439041 | ATTAGCTAATTCCTAGAGGC | 60 | 1689 |
| 1041436 | N/A | N/A | 439388 | 439407 | TGAATGTTTTCAAATCCTAG | 31 | 1690 |
| 1041468 | N/A | N/A | 440075 | 440094 | CCATTTATTTTAAAAATCCT | 69 | 1691 |
| 1041500 | N/A | N/A | 440312 | 440331 | CATTTCTAAACAAACCTCT | 95 | 1692 |
| 1041532 | N/A | N/A | 440910 | 440929 | CAGTAGAGAGATTTAGTGAT | 15 | 1693 |
| 1041564 | N/A | N/A | 441493 | 441512 | TGGAGAAAACCATCTCTTCT | 126 | 1694 |
| 1041596 | N/A | N/A | 442101 | 442120 | GTGAAGCATTAAAAAACGGA | 28 | 1695 |
| 1041628 | N/A | N/A | 442500 | 442519 | CTGGCATTCCCCTTTCCTCC | 92 | 1696 |
| 1041660 | N/A | N/A | 442985 | 443004 | TTGATTTATTTTCAGCTGT | 30 | 1697 |
| 1041692 | N/A | N/A | 443241 | 443260 | CCAATGCACCCCTCAAATCC | 147 | 1698 |
| 1041724 | N/A | N/A | 443784 | 443803 | CCGATGACTCACAGCTCACA | 46 | 1699 |
| 1041756 | N/A | N/A | 444141 | 444160 | GAGAGCATTTTTCTCCTTTT | 25 | 1700 |
| 1041788 | N/A | N/A | 444741 | 444760 | GAACAACATAATATTCAGTG | 10 | 1701 |
| 1041820 | N/A | N/A | 445425 | 445444 | TCATTAATAAAAACAGTCAA | 102 | 1702 |
| 1041852 | N/A | N/A | 445718 | 445737 | TGACACTATCCCAGACATAC | 34 | 1703 |
| 1041884 | N/A | N/A | 445963 | 445982 | CACCACTTAGTCAATAACTA | 38 | 1704 |
| 1041916 | N/A | N/A | 446261 | 446280 | CCACCCTCCTCCACTCTTTC | 138 | 1705 |
| 1041948 | N/A | N/A | 446798 | 446817 | GGGAGCAGTACCACAGATAA | 34 | 1706 |
| 1041980 | N/A | N/A | 447543 | 447562 | GTGCTCAGTTAAAATCTGAA | 29 | 1707 |
| 1042012 | N/A | N/A | 448335 | 448354 | CCCTCTAGTTTCCATAGCTT | 60 | 1708 |
| 1042044 | N/A | N/A | 448638 | 448657 | CTTTTCCAAATACACCTAGA | 46 | 1709 |
| 1042076 | N/A | N/A | 448955 | 448974 | TTGGTTAAGACCTAGTTTCT | 52 | 1710 |
| 1042108 | N/A | N/A | 449502 | 449521 | TGGATGTGAAACAGAGACGG | 17 | 1711 |
| 1042140 | N/A | N/A | 449787 | 449806 | ATAAGGTTTTTTCCCTTCT | 48 | 1712 |
| 1042172 | N/A | N/A | 450079 | 450098 | AGATTCTTCTTTAATCACTT | 39 | 1713 |
| 1042204 | N/A | N/A | 450800 | 450819 | GAGATGGTACTTTAGAAGGC | 14 | 1714 |
| 1042236 | N/A | N/A | 451510 | 451529 | ACACAAACAACAATCATGTA | 56 | 1715 |
| 1042268 | N/A | N/A | 451805 | 451824 | TGTCTACAAGCCCTTTATAA | 50 | 1716 |
| 1042300 | N/A | N/A | 452105 | 452124 | TGCTTATTCTTGCCCAACAC | 35 | 1717 |
| 1042332 | N/A | N/A | 452410 | 452429 | TGGTTTCAAAACTACATTTA | 105 | 1718 |
| 1042364 | N/A | N/A | 452899 | 452918 | GGCTATTTTTATAATGTGAA | 25 | 1719 |

TABLE 23-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042396 | N/A | N/A | 453692 | 453711 | ACAGTAATTAAAAGAATTCA | 88 | 1720 |
| 1042428 | N/A | N/A | 454436 | 454455 | CAGAAGTTAATACTTGAGGA | 71 | 1721 |
| 1042460 | N/A | N/A | 455194 | 455213 | GCAAAATATCAGATCTTAAA | 65 | 1722 |
| 1042492 | N/A | N/A | 456134 | 456153 | GGACAGCAAATAAGATAGTA | 48 | 1723 |
| 1042524 | N/A | N/A | 456828 | 456847 | CCAGTCAATCGAACCCCAGT | 85 | 1724 |

TABLE 24

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 1 | 138 |
| 1040093 | 1189 | 1208 | 435908 | 435927 | TTTGTGTAAACCTATTCCCT | 23 | 1725 |
| 1040125 | 2998 | 3017 | 457251 | 457270 | GCAGACATCCCCAACTGAGA | 41 | 1726 |
| 1040157 | 3559 | 3578 | 457812 | 457831 | CTCCTGCGACACACCTGCTG | 58 | 1727 |
| 1040189 | 4287 | 4306 | 458540 | 458559 | ATTGGTTTTCCTAACACTGC | 54 | 1728 |
| 1040221 | 4722 | 4741 | 458975 | 458994 | TCCCTTTAAACCACATTGAA | 65 | 1729 |
| 1040253 | 5006 | 5025 | 459259 | 459278 | CCCCCAAACCTTTCCCACAA | 61 | 1730 |
| 1040285 | 5394 | 5413 | 459647 | 459666 | CCCACAAATGATATTTCGGA | 20 | 1731 |
| 1040317 | 5719 | 5738 | 459972 | 459991 | GGTAATGAAATTCGAGGAAA | 12 | 1732 |
| 1040349 | 6120 | 6139 | 460373 | 460392 | TTTTATAATTCCTATACCTG | 61 | 1733 |
| 1040381 | 6876 | 6895 | 461129 | 461148 | GGCACCGAAGAATTTCTACC | 28 | 1734 |
| 1040413 | 7386 | 7405 | 461639 | 461658 | GCTCACAATTCCAAGTTAGA | 17 | 1735 |
| 1040445 | 7830 | 7849 | 462083 | 462102 | CTTAGTAGTCACAGATGTTA | 27 | 1736 |
| 1040477 | 8225 | 8244 | 462478 | 462497 | TATATTTATTACTTGATGTG | 24 | 1737 |
| 1040509 | 8541 | 8560 | 462794 | 462813 | ATTTTTTAAAACATTACCTG | 112 | 1738 |
| 1040541 | 8869 | 8888 | 463122 | 463141 | AGAAGTACTTTCAGCATAGG | 12 | 1739 |
| 1040573 | 9268 | 9287 | 463521 | 463540 | GCTTAATATCCCCACAGCTG | 120 | 1740 |
| 1040605 | 9624 | 9643 | 463877 | 463896 | TTGGCCACAGAAAAGGAGAC | 110 | 1741 |
| 1040637 | 10159 | 10178 | 464412 | 464431 | TGGTAGTGCCCTCAACCCAA | 43 | 1742 |
| 1040669 | 10394 | 10413 | 464647 | 464666 | CCACGATTAGAAAATAGAAT | 108 | 1743 |
| 1040701 | N/A | N/A | 8020 | 8039 | TCAAACAAAATATAATGCTT | 87 | 1744 |
| 1040733 | N/A | N/A | 24636 | 24655 | CTACACAAAACCAATCACTT | 78 | 1745 |
| 1040765 | N/A | N/A | 39292 | 39311 | CGCCTTAATTTTTATTATAG | 83 | 1746 |
| 1040797 | N/A | N/A | 66579 | 66598 | CCATTTAGAATATAGCTGTT | 25 | 1747 |
| 1040829 | N/A | N/A | 83570 | 83589 | ATTCTCATCCATTATACTTT | 48 | 1748 |
| 1040861 | N/A | N/A | 106210 | 106229 | TTACCAAAAACCATTTGTGT | 21 | 1749 |

TABLE 24 -continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040893 | N/A | N/A | 138831 | 138850 | TCCTTCTTTCAAAGTTCACC | 26 | 1750 |
| 1040925 | N/A | N/A | 163322 | 163341 | CTGCCACTATTTTATGTCTG | 59 | 1751 |
| 1040957 | N/A | N/A | 185775 | 185794 | CCCAGGTTCCCTTATCATCT | 19 | 1752 |
| 1040989 | N/A | N/A | 207430 | 207449 | TTCTGCAAATAATTCCGTCA | 23 | 1753 |
| 1041021 | N/A | N/A | 224375 | 224394 | CCATCATTTCTTTAAAACTA | 67 | 1754 |
| 1041053 | N/A | N/A | 246302 | 246321 | AAGTACATACAAATACATAT | 146 | 1755 |
| 1041085 | N/A | N/A | 268505 | 268524 | CCTATCAAAGCCACAACTTC | 117 | 1756 |
| 1041117 | N/A | N/A | 284846 | 284865 | TTGTATACCATTTATGTTTC | 2 | 1757 |
| 1041149 | N/A | N/A | 315942 | 315961 | CCACTCAAACCTTTCAATGC | 20 | 1758 |
| 1041181 | N/A | N/A | 334092 | 334111 | GAGCTCAAACCCAAGTCTGT | 72 | 1759 |
| 1041213 | N/A | N/A | 357527 | 357546 | ACCCTATTTCCTTAATGTAA | 41 | 1760 |
| 1041245 | N/A | N/A | 377993 | 378012 | CTCCTTCACCCTTAAGGCTA | 68 | 1761 |
| 1041277 | N/A | N/A | 409360 | 409379 | ATCGAGTCCTTTTAAACAAA | 19 | 1762 |
| 1041309 | N/A | N/A | 434288 | 434307 | ACAACTCGCCATTAACACTA | 65 | 1763 |
| 1041341 | N/A | N/A | 438053 | 438072 | AGCTAATAAGACATATTTTA | 109 | 1764 |
| 1041373 | N/A | N/A | 438477 | 438496 | CTAACCAATCCTAAACCCGT | 101 | 1765 |
| 1041405 | N/A | N/A | 439023 | 439042 | GATTAGCTAATTCCTAGAGG | 42 | 1766 |
| 1041437 | N/A | N/A | 439389 | 439408 | TTGAATGTTTTCAAATCCTA | 41 | 1767 |
| 1041469 | N/A | N/A | 440076 | 440095 | GCCATTTATTTTAAAAATCC | 10 | 1768 |
| 1041501 | N/A | N/A | 440313 | 440332 | GCATTTCTAAACAAAACCTC | 62 | 1769 |
| 1041533 | N/A | N/A | 441017 | 441036 | TGAGGAAGCCCTTCCCGGCA | 115 | 1770 |
| 1041565 | N/A | N/A | 441494 | 441513 | TTGGAGAAAACCATCTCTTC | 108 | 1771 |
| 1041597 | N/A | N/A | 442114 | 442133 | GGAAAGTATAAAAGTGAAGC | 25 | 1772 |
| 1041629 | N/A | N/A | 442524 | 442543 | GCACGCAGTAACAATGGACA | 31 | 1773 |
| 1041661 | N/A | N/A | 442987 | 443006 | CTTTGATTATTTTTCAGCT | 11 | 1774 |
| 1041693 | N/A | N/A | 443288 | 443307 | CCCTTGTTTCTGCATTGGTT | 46 | 1775 |
| 1041725 | N/A | N/A | 443792 | 443811 | TGTTACCACCGATGACTCAC | 42 | 1776 |
| 1041757 | N/A | N/A | 444158 | 444177 | GCACATACAGTTTAAAGGAG | 12 | 1777 |
| 1041789 | N/A | N/A | 444885 | 444904 | GGTCCCTGTTCCTAGGGAGG | 143 | 1778 |
| 1041821 | N/A | N/A | 445439 | 445458 | GCAATGTTTAAAAATCATTA | 71 | 1779 |
| 1041853 | N/A | N/A | 445722 | 445741 | TTCATGACACTATCCCAGAC | 46 | 1780 |
| 1041885 | N/A | N/A | 445968 | 445987 | CCTTTCACCACTTAGTCAAT | 33 | 1781 |
| 1041917 | N/A | N/A | 446266 | 446285 | GCCTCCCACCCTCCTCCACT | 101 | 1782 |
| 1041949 | N/A | N/A | 446814 | 446833 | ATGAAAATAAACTCATGGGA | 84 | 1783 |
| 1041981 | N/A | N/A | 447571 | 447590 | GTCTAAAGACTTCCTAGCA | 78 | 1784 |
| 1042013 | N/A | N/A | 448352 | 448371 | TCTATTTAAAATAACAACCC | 107 | 1785 |

TABLE 24 -continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042045 | N/A | N/A | 448641 | 448660 | TTCCTTTTCCAAATACACCT | 59 | 1786 |
| 1042077 | N/A | N/A | 448969 | 448988 | TAGAAGAGTATCTATTGGTT | 32 | 1787 |
| 1042109 | N/A | N/A | 449541 | 449560 | CATCTCAAAACATGCTGTCA | 86 | 1788 |
| 1042141 | N/A | N/A | 449797 | 449816 | GAGAAGTAAAATAAGGTTTT | 62 | 1789 |
| 1042173 | N/A | N/A | 450080 | 450099 | GAGATTCTTCTTTAATCACT | 27 | 1790 |
| 1042205 | N/A | N/A | 451120 | 451139 | GGAGATTTTACTTAATTTTT | 8 | 1791 |
| 1042237 | N/A | N/A | 451511 | 451530 | TACACAAACAACAATCATGT | 54 | 1792 |
| 1042269 | N/A | N/A | 451817 | 451836 | CTCATTAAGAAATGTCTACA | 69 | 1793 |
| 1042301 | N/A | N/A | 452128 | 452147 | GACTCTCTACCAGAGTTGCG | 102 | 1794 |
| 1042333 | N/A | N/A | 452413 | 452432 | ATTTGGTTTCAAAACTACAT | 91 | 1795 |
| 1042365 | N/A | N/A | 452900 | 452919 | GGGCTATTTTTATAATGTGA | 20 | 1796 |
| 1042397 | N/A | N/A | 453702 | 453721 | GTTCAGACAAACAGTAATTA | 18 | 1797 |
| 1042429 | N/A | N/A | 454481 | 454500 | ACATAATTTGAATCCTAGGA | 135 | 1798 |
| 1042461 | N/A | N/A | 455196 | 455215 | TAGCAAAATATCAGATCTTA | 41 | 1799 |
| 1042493 | N/A | N/A | 456136 | 456155 | CTGGACAGCAAATAAGATAG | 35 | 1800 |
| 1042525 | N/A | N/A | 456836 | 456855 | TGTTAGAACCAGTCAATCGA | 116 | 1801 |

TABLE 25

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 2 | 138 |
| 1040094 | 1212 | 1231 | 435931 | 435950 | TAGTCCAGCCCTGTGGACAA | 47 | 1802 |
| 1040126 | 2999 | 3018 | 457252 | 457271 | TGCAGACATCCCCAACTGAG | 57 | 1803 |
| 1040158 | 3572 | 3591 | 457825 | 457844 | CATATGCACCAGTCTCCTGC | 65 | 1804 |
| 1040190 | 4299 | 4318 | 458552 | 458571 | TGCAATAACCTGATTGGTTT | 39 | 1805 |
| 1040222 | 4725 | 4744 | 458978 | 458997 | TCATCCCTTTAAACCACATT | 35 | 1806 |
| 1040254 | 5007 | 5026 | 459260 | 459279 | TCCCCCAAACCTTTCCCACA | 94 | 1807 |
| 1040286 | 5401 | 5420 | 459654 | 459673 | TTCAAAACCCACAAATGATA | 88 | 1808 |
| 1040318 | 5721 | 5740 | 459974 | 459993 | AGGGTAATGAAATTCGAGGA | 10 | 1809 |
| 1040350 | 6122 | 6141 | 460375 | 460394 | TATTTTATAATTCCTATACC | 108 | 1810 |
| 1040382 | 6919 | 6938 | 461172 | 461191 | GGACATAGTACAGAGGCACA | 8 | 1811 |
| 1040414 | 7387 | 7406 | 461640 | 461659 | GGCTCACAATTCCAAGTTAG | 32 | 1812 |
| 1040446 | 7840 | 7859 | 462093 | 462112 | AATAGGTTTCCTTAGTAGTC | 22 | 1813 |
| 1040478 | 8227 | 8246 | 462480 | 462499 | TGTATATTATTACTTGATG | 10 | 1814 |
| 1040510 | 8546 | 8565 | 462799 | 462818 | GTGCAATTTTTTAAAACATT | 18 | 1815 |

TABLE 25-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040542 | 8907 | 8926 | 463160 | 463179 | GCAATGGCTTAAGAGTTTAG | 9 | 1816 |
| 1040574 | 9269 | 9288 | 463522 | 463541 | TGCTTAATATCCCCACAGCT | 91 | 1817 |
| 1040606 | 9636 | 9655 | 463889 | 463908 | AAGGCCTTCAGATTGGCCAC | 125 | 1818 |
| 1040638 | 10161 | 10180 | 464414 | 464433 | TCTGGTAGTGCCCTCAACCC | 45 | 1819 |
| 1040670 | 10402 | 10421 | 464655 | 464674 | TAGACACACCACGATTAGAA | 68 | 1820 |
| 1040702 | N/A | N/A | 8570 | 8589 | ACTCAATATTTTAAAACCC | 28 | 1821 |
| 1040734 | N/A | N/A | 25367 | 25386 | GACTGAATTATTTATAGTTG | 42 | 1822 |
| 1040766 | N/A | N/A | 40104 | 40123 | ATGCAATTTTAAATTCATGT | 18 | 1823 |
| 1040798 | N/A | N/A | 66787 | 66806 | GGGAAAATTCCTTAGCATAT | 30 | 1824 |
| 1040830 | N/A | N/A | 83587 | 83606 | GCTGAGTTCCAAAGCAAATT | 35 | 1825 |
| 1040862 | N/A | N/A | 106215 | 106234 | ATGACTTACCAAAAACCATT | 105 | 1826 |
| 1040894 | N/A | N/A | 139215 | 139234 | AGGGCTTAAATTTAACTGAA | 28 | 1827 |
| 1040926 | N/A | N/A | 163369 | 163388 | AACGAAATTCCTTAAGGACA | 62 | 1828 |
| 1040958 | N/A | N/A | 185909 | 185928 | TTGGTTCTATTTTATAATAG | 66 | 1829 |
| 1040990 | N/A | N/A | 207479 | 207498 | AGACTACTATTTTATCACTG | 19 | 1830 |
| 1041022 | N/A | N/A | 225966 | 225985 | TCACTTAAACCCAGGTCAGC | 81 | 1831 |
| 1041054 | N/A | N/A | 247054 | 247073 | TTCCCCAAAATTTAGTTGTG | 85 | 1832 |
| 1041086 | N/A | N/A | 268668 | 268687 | CTTCAACTATTTTATTTGGC | 30 | 1833 |
| 1041118 | N/A | N/A | 284950 | 284969 | AGTAGAATTTAAAAGTAGAA | 110 | 1834 |
| 1041150 | N/A | N/A | 316219 | 316238 | GGATTTCTAATTTAATCTTT | 37 | 1835 |
| 1041182 | N/A | N/A | 334729 | 334748 | TAGTTCTTTCAAACTCCTTT | 2 | 1836 |
| 1041214 | N/A | N/A | 358497 | 358516 | GCTATAATTCAAAATGCTCT | 115 | 1837 |
| 1041246 | N/A | N/A | 380363 | 380382 | GCCTAAACAATTTATTCATT | 31 | 1838 |
| 1041278 | N/A | N/A | 409434 | 409453 | ACCCTTCTATTTTATAAAGC | 69 | 1839 |
| 1041310 | N/A | N/A | 434517 | 434536 | TGCAAGTTTCAAAAGAATTC | 133 | 1840 |
| 1041342 | N/A | N/A | 438074 | 438093 | AAGGCATATACCACTGTACC | 61 | 1841 |
| 1041374 | N/A | N/A | 438478 | 438497 | TCTAACCAATCCTAAACCCG | 107 | 1842 |
| 1041406 | N/A | N/A | 439043 | 439062 | AGAGGTATAGTCTCTCCTAG | 29 | 1843 |
| 1041438 | N/A | N/A | 439430 | 439449 | TGACTATTTTCAACTCAAGC | 16 | 1844 |
| 1041470 | N/A | N/A | 440085 | 440104 | TATTATTATGCCATTTATTT | 41 | 1845 |
| 1041502 | N/A | N/A | 440315 | 440334 | TCGCATTTCTAAACAAAACC | 52 | 1846 |
| 1041534 | N/A | N/A | 441019 | 441038 | TTTGAGGAAGCCCTTCCCGG | 119 | 1847 |
| 1041566 | N/A | N/A | 441497 | 441516 | GTTTTGGAGAAAACCATCTC | 69 | 1848 |
| 1041598 | N/A | N/A | 442146 | 442165 | CTAATAAATTTTTACAAGGG | 72 | 1849 |
| 1041630 | N/A | N/A | 442542 | 442561 | AAGGAGGCTTCCTTTGGTGC | 70 | 1850 |
| 1041662 | N/A | N/A | 442991 | 443010 | AGGCCTTTGATTTATTTTTC | 110 | 1851 |

TABLE 25-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041694 | N/A | N/A | 443385 | 443404 | GATGGAAGCCAAAGGCTCCC | 115 | 1852 |
| 1041726 | N/A | N/A | 443794 | 443813 | AATGTTACCACCGATGACTC | 71 | 1853 |
| 1041758 | N/A | N/A | 444206 | 444225 | TCTGAGAGAATCAAAACATA | 29 | 1854 |
| 1041790 | N/A | N/A | 445090 | 445109 | CTCACTTGCCTTCCTTTTCT | 46 | 1855 |
| 1041822 | N/A | N/A | 445440 | 445459 | TGCAATGTTTAAAAATCATT | 94 | 1856 |
| 1041854 | N/A | N/A | 445730 | 445749 | AACATTTTTTCATGACACTA | 10 | 1857 |
| 1041886 | N/A | N/A | 445969 | 445988 | TCCTTTCACCACTTAGTCAA | 47 | 1858 |
| 1041918 | N/A | N/A | 446324 | 446343 | TCTGTCTTTCATCTCTGGAT | 44 | 1859 |
| 1041950 | N/A | N/A | 446817 | 446836 | CCAATGAAAATAAACTCATG | 98 | 1860 |
| 1041982 | N/A | N/A | 447576 | 447595 | CCAGAGTCTAAAAGACTTCC | 110 | 1861 |
| 1042014 | N/A | N/A | 448353 | 448372 | TTCTATTTAAAATAACAACC | 116 | 1862 |
| 1042046 | N/A | N/A | 448648 | 448667 | GTATGGGTTCCTTTTCCAAA | 7 | 1863 |
| 1042078 | N/A | N/A | 449026 | 449045 | AGTTTTAATAAAGTTCAAC | 96 | 1864 |
| 1042110 | N/A | N/A | 449542 | 449561 | CCATCTCAAAACATGCTGTC | 78 | 1865 |
| 1042142 | N/A | N/A | 449830 | 449849 | ATGTACTTTTCCCCCTTGG | 65 | 1866 |
| 1042174 | N/A | N/A | 450083 | 450102 | TGGGAGATTCTTCTTTAATC | 19 | 1867 |
| 1042206 | N/A | N/A | 451121 | 451140 | TGGAGATTTTACTTAATTTT | 33 | 1868 |
| 1042238 | N/A | N/A | 451518 | 451537 | GATAATATACACAAACAACA | 86 | 1869 |
| 1042270 | N/A | N/A | 451821 | 451840 | TAGACTCATTAAGAAATGTC | 91 | 1870 |
| 1042302 | N/A | N/A | 452129 | 452148 | AGACTCTCTACCAGAGTTGC | 100 | 1871 |
| 1042334 | N/A | N/A | 452424 | 452443 | TGTGTGACACTATTTGGTTT | 74 | 1872 |
| 1042366 | N/A | N/A | 452902 | 452921 | CTGGGCTATTTTTATAATGT | 30 | 1873 |
| 1042398 | N/A | N/A | 453708 | 453727 | AGACATGTTCAGACAAACAG | 58 | 1874 |
| 1042430 | N/A | N/A | 454483 | 454502 | ACACATAATTTGAATCCTAG | 110 | 1875 |
| 1042462 | N/A | N/A | 455198 | 455217 | ACTAGCAAAATATCAGATCT | 49 | 1876 |
| 1042494 | N/A | N/A | 456154 | 456173 | ACTTTTTTCTTATAGTACT | 68 | 1877 |
| 1042526 | N/A | N/A | 456838 | 456857 | TCTGTTAGAACCAGTCAATC | 51 | 1878 |

TABLE 26

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 2 | 138 |
| 1040095 | 1514 | 1533 | 436233 | 436252 | TCAGACTGCCCATGTTGGCC | 71 | 1879 |
| 1040127 | 3033 | 3052 | 457286 | 457305 | GAGCCGTTCTTCAGGTTCTT | 93 | 1880 |
| 1040159 | 3643 | 3662 | 457896 | 457915 | GCCTGGAGCCCTGACCGCTC | 60 | 1881 |

TABLE 26-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040191 | 4300 | 4319 | 458553 | 458572 | ATGCAATAACCTGATTGGTT | 16 | 1882 |
| 1040223 | 4727 | 4746 | 458980 | 458999 | ATTCATCCCTTTAAACCACA | 15 | 1883 |
| 1040255 | 5011 | 5030 | 459264 | 459283 | TCAGTCCCCCAAACCTTTCC | 20 | 1884 |
| 1040287 | 5407 | 5426 | 459660 | 459679 | GATGCATTCAAAACCCACAA | 21 | 1885 |
| 1040319 | 5766 | 5785 | 460019 | 460038 | TGACTGCAAGAATGAGCCCA | 60 | 1886 |
| 1040351 | 6126 | 6145 | 460379 | 460398 | CAATTATTTTATAATTCCTA | 82 | 1887 |
| 1040383 | 6921 | 6940 | 461174 | 461193 | GTGGACATAGTACAGAGGCA | 7 | 1888 |
| 1040415 | 7388 | 7407 | 461641 | 461660 | AGGCTCACAATTCCAAGTTA | 26 | 1889 |
| 1040447 | 7865 | 7884 | 462118 | 462137 | TGGAGATTTTCTCTCTATG | 36 | 1890 |
| 1040479 | 8228 | 8247 | 462481 | 462500 | CTGTATATTTATTACTTGAT | 7 | 1891 |
| 1040511 | 8566 | 8585 | 462819 | 462838 | TCGACATTCATTTTTCTTTT | 10 | 1892 |
| 1040543 | 8940 | 8959 | 463193 | 463212 | ATGTCAAACATCATCTCTGA | 12 | 1893 |
| 1040575 | 9272 | 9291 | 463525 | 463544 | GGGTGCTTAATATCCCCACA | 115 | 1894 |
| 1040607 | 9637 | 9656 | 463890 | 463909 | GAAGGCCTTCAGATTGGCCA | 101 | 1895 |
| 1040639 | 10163 | 10182 | 464416 | 464435 | AGTCTGGTAGTGCCCTCAAC | 17 | 1896 |
| 1040671 | 10407 | 10426 | 464660 | 464679 | ACAAATAGACACACCACGAT | 77 | 1897 |
| 1040703 | N/A | N/A | 9147 | 9166 | GTTGAGTTACAAATATAAAT | 70 | 1898 |
| 1040735 | N/A | N/A | 25394 | 25413 | CCAGGATTTTAAAAAAGCA | 15 | 1899 |
| 1040767 | N/A | N/A | 40413 | 40432 | GCTAAATTTCCTTAAGCTTT | 42 | 1900 |
| 1040799 | N/A | N/A | 70441 | 70460 | CATCAGTTCCAAAACCTGGA | 83 | 1901 |
| 1040831 | N/A | N/A | 83929 | 83948 | CCAATACACCTTTATTTTTC | 22 | 1902 |
| 1040863 | N/A | N/A | 106559 | 106578 | CGATTAATCCCTTATGTTTT | 4 | 1903 |
| 1040895 | N/A | N/A | 140193 | 140212 | CTCTTCAAAAACATATCCGA | 55 | 1904 |
| 1040927 | N/A | N/A | 163438 | 163457 | TTCTAAATTTAAAACTCCAA | 101 | 1905 |
| 1040959 | N/A | N/A | 186773 | 186792 | ACAGGCAATATTTACTATAA | 1 | 1906 |
| 1040991 | N/A | N/A | 207544 | 207563 | GCCTTCTTCCTTTATAGCAC | 32 | 1907 |
| 1041023 | N/A | N/A | 227246 | 227265 | TTAGGCTATTAAATAATAGA | 124 | 1908 |
| 1041055 | N/A | N/A | 247203 | 247222 | CTCAGTATCTTTTAATTGCC | 29 | 1909 |
| 1041087 | N/A | N/A | 269929 | 269948 | TGGGCCAAAACACCCCTTT | 95 | 1910 |
| 1041119 | N/A | N/A | 284975 | 284994 | CTGTTTAAAAATGTATTGAG | 23 | 1911 |
| 1041151 | N/A | N/A | 316940 | 316959 | GTCCCTTATCCTTAACACAC | 2 | 1912 |
| 1041183 | N/A | N/A | 334783 | 334802 | CCCTAAATTTAAATTCTCTG | 62 | 1913 |
| 1041215 | N/A | N/A | 358611 | 358630 | ACCTTTATTTAAATTTTCCA | 22 | 1914 |
| 1041247 | N/A | N/A | 380517 | 380536 | GCTCAATATATTTATCTATT | 1 | 1915 |
| 1041279 | N/A | N/A | 410051 | 410070 | TCTGTATTTTAAAAATCTCT | 27 | 1916 |
| 1041311 | N/A | N/A | 437693 | 437712 | CGAGAACCCTTAATCCTGCC | 34 | 1917 |

TABLE 26-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041343 | N/A | N/A | 438076 | 438095 | CGAAGGCATATACCACTGTA | 48 | 1918 |
| 1041375 | N/A | N/A | 438482 | 438501 | CCACTCTAACCAATCCTAAA | 48 | 1919 |
| 1041407 | N/A | N/A | 439087 | 439106 | TTTTATTTTCTGATGCTTTG | 10 | 1920 |
| 1041439 | N/A | N/A | 439432 | 439451 | CATGACTATTTTCAACTCAA | 4 | 1921 |
| 1041471 | N/A | N/A | 440089 | 440108 | GCTGTATTATTATGCCATTT | 12 | 1922 |
| 1041503 | N/A | N/A | 440316 | 440335 | GTCGCATTTCTAAACAAAAC | 64 | 1923 |
| 1041535 | N/A | N/A | 441116 | 441135 | AGTGACAAATCATTGGTTGC | 28 | 1924 |
| 1041567 | N/A | N/A | 441513 | 441532 | AGTCACAATGCCATCTGTTT | 10 | 1925 |
| 1041599 | N/A | N/A | 442147 | 442166 | GCTAATAAATTTTTACAAGG | 56 | 1926 |
| 1041631 | N/A | N/A | 442566 | 442585 | TGCTATCACCCTCCACTGAA | 85 | 1927 |
| 1041663 | N/A | N/A | 443017 | 443036 | CTTCCATAAACTCTTTTTAG | 45 | 1928 |
| 1041695 | N/A | N/A | 443387 | 443406 | CAGATGGAAGCCAAAGGCTC | 117 | 1929 |
| 1041727 | N/A | N/A | 443815 | 443834 | CAGCTAATCCATTCAATGCA | 60 | 1930 |
| 1041759 | N/A | N/A | 444223 | 444242 | GCTATAAACAACAACAGTCT | 26 | 1931 |
| 1041791 | N/A | N/A | 445120 | 445139 | CACGGAAGCCCTTAGGCACA | 63 | 1932 |
| 1041823 | N/A | N/A | 445455 | 445474 | GAGAGACCCATTTACTGCAA | 8 | 1933 |
| 1041855 | N/A | N/A | 445739 | 445758 | GTTTTACAAAACATTTTTTC | 56 | 1934 |
| 1041887 | N/A | N/A | 445972 | 445991 | AATTCCTTTCACCACTTAGT | 16 | 1935 |
| 1041919 | N/A | N/A | 446325 | 446344 | CTCTGTCTTTCATCTCTGGA | 49 | 1936 |
| 1041951 | N/A | N/A | 446818 | 446837 | CCCAATGAAAATAAACTCAT | 77 | 1937 |
| 1041983 | N/A | N/A | 447604 | 447623 | CTCTTTCCCCAAACTCAGTG | 30 | 1938 |
| 1042015 | N/A | N/A | 448354 | 448373 | GTTCTATTTAAAATAACAAC | 109 | 1939 |
| 1042047 | N/A | N/A | 448660 | 448679 | TATAAGCAAACTGTATGGGT | 13 | 1940 |
| 1042079 | N/A | N/A | 449037 | 449056 | TCAGGCTTTCCAGTTTTAAT | 16 | 1941 |
| 1042111 | N/A | N/A | 449544 | 449563 | CTCCATCTCAAAACATGCTG | 82 | 1942 |
| 1042143 | N/A | N/A | 449832 | 449851 | CAATGTACTTTTTCCCCCTT | 32 | 1943 |
| 1042175 | N/A | N/A | 450112 | 450131 | AATGAAATTTATGTTAACCT | 75 | 1944 |
| 1042207 | N/A | N/A | 451122 | 451141 | TTGGAGATTTTACTTAATTT | 30 | 1945 |
| 1042239 | N/A | N/A | 451523 | 451542 | ACCGAGATAATATACACAAA | 5 | 1946 |
| 1042271 | N/A | N/A | 451863 | 451882 | TAGGTAAACTTATCTGAGGA | 15 | 1947 |
| 1042303 | N/A | N/A | 452153 | 452172 | TCAGGTGTTAACATCTGTCT | 99 | 1948 |
| 1042335 | N/A | N/A | 452453 | 452472 | CTCATACAATTCTAGTTACC | 45 | 1949 |
| 1042367 | N/A | N/A | 452919 | 452938 | GGGAAAGTTTCATTGTTCTG | 24 | 1950 |
| 1042399 | N/A | N/A | 453742 | 453761 | GCAAAAGATCCTTCCAGAA | 62 | 1951 |
| 1042431 | N/A | N/A | 454491 | 454510 | GCTAACAGACACATAATTTG | 111 | 1952 |

TABLE 26-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042463 | N/A | N/A | 455199 | 455218 | CACTAGCAAAATATCAGATC | 54 | 1953 |
| 1042495 | N/A | N/A | 456155 | 456174 | AACTTTTTTCTTATAGTAC | 66 | 1954 |
| 1042527 | N/A | N/A | 456877 | 456896 | TTCAAAATATTCCATCAAGT | 25 | 1955 |

TABLE 27

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 1 | 138 |
| 1040096 | 1932 | 1951 | 436651 | 436670 | TCACCGTTCAGGACCTCCTT | 70 | 1956 |
| 1040128 | 3046 | 3065 | 457299 | 457318 | GCCCTTTTTAACAGAGCCGT | 122 | 1957 |
| 1040160 | 3669 | 3688 | 457922 | 457941 | GCCCCGTTCCTTTCTTCCCC | 67 | 1958 |
| 1040192 | 4313 | 4332 | 458566 | 458585 | GGGAGTGAAGTCAATGCAAT | 17 | 1959 |
| 1040224 | 4728 | 4747 | 458981 | 459000 | CATTCATCCCTTTAAACCAC | 22 | 1960 |
| 1040256 | 5013 | 5032 | 459266 | 459285 | GTTCAGTCCCCCAAACCTTT | 16 | 1961 |
| 1040288 | 5408 | 5427 | 459661 | 459680 | AGATGCATTCAAAACCCACA | 21 | 1962 |
| 1040320 | 5785 | 5804 | 460038 | 460057 | CAGCACTAAATAAGCAGTAT | 11 | 1963 |
| 1040352 | 6128 | 6147 | 460381 | 460400 | ACCAATTATTTTATAATTCC | 59 | 1964 |
| 1040384 | 6941 | 6960 | 461194 | 461213 | CTGTCGGTAAATATTGCAAA | 10 | 1965 |
| 1040416 | 7404 | 7423 | 461657 | 461676 | CTAACAGAAAACATAGAGGC | 28 | 1966 |
| 1040448 | 7866 | 7885 | 462119 | 462138 | TTGGAGATTTTTCTCTCTAT | 54 | 1967 |
| 1040480 | 8229 | 8248 | 462482 | 462501 | TCTGTATATTTATTACTTGA | 10 | 1968 |
| 1040512 | 8597 | 8616 | 462850 | 462869 | GCCATATCTTTCAAACACTG | 8 | 1969 |
| 1040544 | 8941 | 8960 | 463194 | 463213 | AATGTCAAACATCATCTCTG | 13 | 1970 |
| 1040576 | 9292 | 9311 | 463545 | 463564 | AATTTAAGAATTGTAAGTGG | 123 | 1971 |
| 1040608 | 9640 | 9659 | 463893 | 463912 | AACGAAGGCCTTCAGATTGG | 107 | 1972 |
| 1040640 | 10189 | 10208 | 464442 | 464461 | TAGTTCTCCTCTGTACTGGC | 14 | 1973 |
| 1040672 | 10409 | 10428 | 464662 | 464681 | CTACAAATAGACACACCACG | 70 | 1974 |
| 1040704 | N/A | N/A | 9365 | 9384 | AACAGTAGCCAAAATGTTCT | 100 | 1975 |
| 1040736 | N/A | N/A | 25410 | 25429 | CTAGAATTTTAAAAAACCAG | 80 | 1976 |
| 1040768 | N/A | N/A | 40502 | 40521 | AGTACAATCTTTTATAGATA | 89 | 1977 |
| 1040800 | N/A | N/A | 70463 | 70482 | TGCCTGAGAATTTAATACTA | 72 | 1978 |
| 1040832 | N/A | N/A | 84147 | 84166 | AGTAAGCTTCTTTAACTTTA | 11 | 1979 |
| 1040864 | N/A | N/A | 107690 | 107709 | TGGATAATTATTTAATTCAT | 70 | 1980 |
| 1040896 | N/A | N/A | 140329 | 140348 | CCAAACTAAGAATAATCTAG | 89 | 1981 |
| 1040928 | N/A | N/A | 165500 | 165519 | GAGGAAATTATTTACTGGCT | 5 | 1982 |

TABLE 27-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040960 | N/A | N/A | 187228 | 187247 | ATGCACATACAAATAAGCTC | 51 | 1983 |
| 1040992 | N/A | N/A | 207564 | 207583 | GAGATTAAAATACAATTGCT | 36 | 1984 |
| 1041024 | N/A | N/A | 227353 | 227372 | GATTTCTCCTTTTAACCTCT | 23 | 1985 |
| 1041056 | N/A | N/A | 248796 | 248815 | TTCTCAAAACCTTATCTCCT | 92 | 1986 |
| 1041088 | N/A | N/A | 270452 | 270471 | CATTTTATTCCTTATCCTAC | 118 | 1987 |
| 1041120 | N/A | N/A | 285644 | 285663 | CATTTGCACCTTTAATTTGT | 24 | 1988 |
| 1041152 | N/A | N/A | 316955 | 316974 | TTCCAAAAGAATGTGTCCC | 16 | 1989 |
| 1041184 | N/A | N/A | 335393 | 335412 | GGTAGCTATCATTATTAAGC | 19 | 1990 |
| 1041216 | N/A | N/A | 358821 | 358840 | CGACAGAAAATATATCTGCT | 47 | 1991 |
| 1041248 | N/A | N/A | 382312 | 382331 | GACTGCAAAATTCCCATTGC | 28 | 1992 |
| 1041280 | N/A | N/A | 410115 | 410134 | CTGTAAAAATACACATCCTC | 38 | 1993 |
| 1041312 | N/A | N/A | 437695 | 437714 | CCCGAGAACCCTTAATCCTG | 37 | 1994 |
| 1041344 | N/A | N/A | 438160 | 438179 | CACAGGTTCAGCCATAGCTC | 21 | 1995 |
| 1041376 | N/A | N/A | 438483 | 438502 | TCCACTCTAACCAATCCTAA | 66 | 1996 |
| 1041408 | N/A | N/A | 439090 | 439109 | CGCTTTTATTTTCTGATGCT | 20 | 1997 |
| 1041440 | N/A | N/A | 439433 | 439452 | TCATGACTATTTTCAACTCA | 18 | 1998 |
| 1041472 | N/A | N/A | 440090 | 440109 | AGCTGTATTATTATGCCATT | 43 | 1999 |
| 1041504 | N/A | N/A | 440317 | 440336 | AGTCGCATTTCTAAACAAAA | 66 | 2000 |
| 1041536 | N/A | N/A | 441117 | 441136 | AAGTGACAAATCATTGGTTG | 21 | 2001 |
| 1041568 | N/A | N/A | 441519 | 441538 | GCCTAGAGTCACAATGCCAT | 33 | 2002 |
| 1041600 | N/A | N/A | 442148 | 442167 | CGCTAATAAATTTTTACAAG | 91 | 2003 |
| 1041632 | N/A | N/A | 442620 | 442639 | TCAACCAGAATCAAGGCATG | 66 | 2004 |
| 1041664 | N/A | N/A | 443022 | 443041 | CTCTCCTTCCATAAACTCTT | 69 | 2005 |
| 1041696 | N/A | N/A | 443410 | 443429 | GATGGGATAATATAGAACGC | 45 | 2006 |
| 1041728 | N/A | N/A | 443816 | 443835 | CCAGCTAATCCATTCAATGC | 34 | 2007 |
| 1041760 | N/A | N/A | 444225 | 444244 | ATGCTATAAACAACAACAGT | 47 | 2008 |
| 1041792 | N/A | N/A | 445122 | 445141 | GACACGGAAGCCCTTAGGCA | 46 | 2009 |
| 1041824 | N/A | N/A | 445457 | 445476 | GCGAGAGACCCATTTACTGC | 11 | 2010 |
| 1041856 | N/A | N/A | 445746 | 445765 | GGCATCTGTTTTACAAAACA | 9 | 2011 |
| 1041888 | N/A | N/A | 445977 | 445996 | AATAAAATTCCTTTCACCAC | 35 | 2012 |
| 1041920 | N/A | N/A | 446352 | 446371 | CTTTATACTTTTGTAAGCTT | 29 | 2013 |
| 1041952 | N/A | N/A | 446819 | 446838 | TCCCAATGAAAATAAACTCA | 108 | 2014 |
| 1041984 | N/A | N/A | 447606 | 447625 | GCCTCTTTCCCCAAACTCAG | 29 | 2015 |
| 1042016 | N/A | N/A | 448356 | 448375 | CAGTTCTATTTAAAATAACA | 117 | 2016 |
| 1042048 | N/A | N/A | 448668 | 448687 | ATCCCAATTATAAGCAAACT | 64 | 2017 |
| 1042080 | N/A | N/A | 449039 | 449058 | TTTCAGGCTTTCCAGTTTTA | 20 | 2018 |

TABLE 27-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042112 | N/A | N/A | 449545 | 449564 | TCTCCATCTCAAAACATGCT | 108 | 2019 |
| 1042144 | N/A | N/A | 449841 | 449860 | CTACCTAGACAATGTACTTT | 86 | 2020 |
| 1042176 | N/A | N/A | 450127 | 450146 | CCCACCTGGCCTGTTAATGA | 86 | 2021 |
| 1042208 | N/A | N/A | 451135 | 451154 | CCAGCCTAAAAAATTGGAGA | 94 | 2022 |
| 1042240 | N/A | N/A | 451524 | 451543 | CACCGAGATAATATACACAA | 18 | 2023 |
| 1042272 | N/A | N/A | 451875 | 451894 | ACTGTGTTCTCATAGGTAAA | 32 | 2024 |
| 1042304 | N/A | N/A | 452173 | 452192 | AAGTCATAAAAATAAAACTC | 99 | 2025 |
| 1042336 | N/A | N/A | 452454 | 452473 | ACTCATACAATTCTAGTTAC | 44 | 2026 |
| 1042368 | N/A | N/A | 452952 | 452971 | AGCATGAACCCCTTCTCCTG | 78 | 2027 |
| 1042400 | N/A | N/A | 453743 | 453762 | AGCAAAAGATCCTTCCAGA | 90 | 2028 |
| 1042432 | N/A | N/A | 454556 | 454575 | ATAGAGACAAAAGATGGTC | 104 | 2029 |
| 1042464 | N/A | N/A | 455200 | 455219 | GCACTAGCAAAATATCAGAT | 28 | 2030 |
| 1042496 | N/A | N/A | 456172 | 456191 | TCTGGACAAAATGTTTAAAC | 35 | 2031 |
| 1042528 | N/A | N/A | 456881 | 456900 | AATATTCAAAATATTCCATC | 64 | 2032 |

TABLE 28

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 2 | 138 |
| 1040097 | 1933 | 1952 | 436652 | 436671 | CTCACCGTTCAGGACCTCCT | 73 | 2033 |
| 1040129 | 3048 | 3067 | 457301 | 457320 | TGGCCCTTTTTAACAGAGCC | 113 | 2034 |
| 1040161 | 3670 | 3689 | 457923 | 457942 | AGCCCCGTTCCTTTCTTCCC | 46 | 2035 |
| 1040193 | 4328 | 4347 | 458581 | 458600 | TTGCATCTACCTCTTGGGAG | 44 | 2036 |
| 1040225 | 4729 | 4748 | 458982 | 459001 | ACATTCATCCCTTTAAACCA | 33 | 2037 |
| 1040257 | 5032 | 5051 | 459285 | 459304 | GCTACATTTATTTATGCTCG | 14 | 2038 |
| 1040289 | 5417 | 5436 | 459670 | 459689 | GCACTTTAAAGATGCATTCA | 29 | 2039 |
| 1040321 | 5786 | 5805 | 460039 | 460058 | ACAGCACTAAATAAGCAGTA | 28 | 2040 |
| 1040353 | 6129 | 6148 | 460382 | 460401 | AACCAATTATTTTATAATTC | 112 | 2041 |
| 1040385 | 6942 | 6961 | 461195 | 461214 | GCTGTCGGTAAATATTGCAA | 36 | 2042 |
| 1040417 | 7406 | 7425 | 461659 | 461678 | ACCTAACAGAAAACATAGAG | 36 | 2043 |
| 1040449 | 7882 | 7901 | 462135 | 462154 | AGTGTCTTCAAAAGCATTGG | 22 | 2044 |
| 1040481 | 8231 | 8250 | 462484 | 462503 | TCTCTGTATATTTATTACTT | 10 | 2045 |
| 1040513 | 8598 | 8617 | 462851 | 462870 | AGCCATATCTTTCAAACACT | 8 | 2046 |
| 1040545 | 8973 | 8992 | 463226 | 463245 | TCTTTGGGTTTATAGGAACA | 14 | 2047 |
| 1040577 | 9297 | 9316 | 463550 | 463569 | TTCTGAATTTAAGAATTGTA | 83 | 2048 |

TABLE 28-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040609 | 9647 | 9666 | 463900 | 463919 | CACTTCCAACGAAGGCCTTC | 100 | 2049 |
| 1040641 | 10192 | 10211 | 464445 | 464464 | CCCTAGTTCTCCTCTGTACT | 79 | 2050 |
| 1040673 | 10414 | 10433 | 464667 | 464686 | GTATCCTACAAATAGACACA | 56 | 2051 |
| 1040705 | N/A | N/A | 9443 | 9462 | ACTCACTATTTTAAGAGCA | 49 | 2052 |
| 1040737 | N/A | N/A | 25793 | 25812 | CTGGGAATTTAAAAACAAA | 77 | 2053 |
| 1040769 | N/A | N/A | 40905 | 40924 | TCCATAAACATTTATACAGA | 5 | 2054 |
| 1040801 | N/A | N/A | 71139 | 71158 | GGTTCAAAACCTTAGTCAGA | 69 | 2055 |
| 1040833 | N/A | N/A | 85391 | 85410 | ATAGAATATTTTATCATTC | 91 | 2056 |
| 1040865 | N/A | N/A | 108193 | 108212 | GAATAAATTATTTACTGCGG | 8 | 2057 |
| 1040897 | N/A | N/A | 140551 | 140570 | GGTCAATTTCAAACTGTTCT | 5 | 2058 |
| 1040929 | N/A | N/A | 166245 | 166264 | GGCCTAAAACTATTCTTGAT | 118 | 2059 |
| 1040961 | N/A | N/A | 187483 | 187502 | ACACTTAAACCTGTTAATAT | 78 | 2060 |
| 1040993 | N/A | N/A | 208043 | 208062 | GCTCATAAAATACCTCTCTA | 16 | 2061 |
| 1041025 | N/A | N/A | 227432 | 227451 | CCAGGAAAGATTTATTTAGC | 51 | 2062 |
| 1041057 | N/A | N/A | 250936 | 250955 | AGCACATTTCAAAAGTTCAG | 53 | 2063 |
| 1041089 | N/A | N/A | 270476 | 270495 | ATTCATTTTCCTTATGTTAC | 58 | 2064 |
| 1041121 | N/A | N/A | 286774 | 286793 | TCACCCAAACCCATTGCCTA | 77 | 2065 |
| 1041153 | N/A | N/A | 317256 | 317275 | TTCTGTAAAATATATCCTGT | 19 | 2066 |
| 1041185 | N/A | N/A | 335931 | 335950 | ATCTGTAAAATATGGTTGCA | 7 | 2067 |
| 1041217 | N/A | N/A | 362937 | 362956 | AACTTATTTTAAAGTGTCCA | 2 | 2068 |
| 1041249 | N/A | N/A | 385646 | 385665 | ACATTATACCCTTAATATCC | 39 | 2069 |
| 1041281 | N/A | N/A | 410116 | 410135 | GCTGTAAAAATACACATCCT | 18 | 2070 |
| 1041313 | N/A | N/A | 437751 | 437770 | GCTTATTTTTTCTAGAGAAC | 54 | 2071 |
| 1041345 | N/A | N/A | 438169 | 438188 | AGTGATAGTCACAGGTTCAG | 12 | 2072 |
| 1041377 | N/A | N/A | 438486 | 438505 | TTATCCACTCTAACCAATCC | 101 | 2073 |
| 1041409 | N/A | N/A | 439093 | 439112 | CCACGCTTTTATTTTCTGAT | 1 | 2074 |
| 1041441 | N/A | N/A | 439441 | 439460 | CAGCTATTTCATGACTATTT | 7 | 2075 |
| 1041473 | N/A | N/A | 440091 | 440110 | GAGCTGTATTATTATGCCAT | 107 | 2076 |
| 1041505 | N/A | N/A | 440318 | 440337 | CAGTCGCATTTCTAAACAAA | 76 | 2077 |
| 1041537 | N/A | N/A | 441122 | 441141 | CGGTAAAGTGACAAATCATT | 12 | 2078 |
| 1041569 | N/A | N/A | 441521 | 441540 | CTGCCTAGAGTCACAATGCC | 31 | 2079 |
| 1041601 | N/A | N/A | 442149 | 442168 | ACGCTAATAAATTTTTACAA | 109 | 2080 |
| 1041633 | N/A | N/A | 442624 | 442643 | ACTCTCAACCAGAATCAAGG | 86 | 2081 |
| 1041665 | N/A | N/A | 443023 | 443042 | CCTCTCCTTCCATAAACTCT | 85 | 2082 |
| 1041697 | N/A | N/A | 443457 | 443476 | CTGTGTACTCTTCAGAGAAG | 27 | 2083 |
| 1041729 | N/A | N/A | 443817 | 443836 | ACCAGCTAATCCATTCAATG | 17 | 2084 |

TABLE 28-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041761 | N/A | N/A | 444251 | 444270 | AACAATAGTCTTTAATTTTT | 109 | 2085 |
| 1041793 | N/A | N/A | 445143 | 445162 | GTGAGTGACCACAGCAGCTG | 110 | 2086 |
| 1041825 | N/A | N/A | 445458 | 445477 | AGCGAGAGACCCATTTACTG | 23 | 2087 |
| 1041857 | N/A | N/A | 445767 | 445786 | CTGTTTTCACAAATTGCGAA | 44 | 2088 |
| 1041889 | N/A | N/A | 445978 | 445997 | CAATAAAATTCCTTTCACCA | 37 | 2089 |
| 1041921 | N/A | N/A | 446354 | 446373 | GCCTTTATACTTTTGTAAGC | 73 | 2090 |
| 1041953 | N/A | N/A | 446832 | 446851 | GTTTCTGATTAAATCCCAAT | 18 | 2091 |
| 1041985 | N/A | N/A | 447607 | 447626 | TGCCTCTTTCCCCAAACTCA | 47 | 2092 |
| 1042017 | N/A | N/A | 448370 | 448389 | GAGAACTCCCCTGACAGTTC | 90 | 2093 |
| 1042049 | N/A | N/A | 448679 | 448698 | ACATCACAAACATCCCAATT | 71 | 2094 |
| 1042081 | N/A | N/A | 449045 | 449064 | GATACATTTCAGGCTTTCCA | 13 | 2095 |
| 1042113 | N/A | N/A | 449571 | 449590 | CTTGAAATTCCCTTGGAGAG | 42 | 2096 |
| 1042145 | N/A | N/A | 449843 | 449862 | AACTACCTAGACAATGTACT | 65 | 2097 |
| 1042177 | N/A | N/A | 450452 | 450471 | CGTACTAAAACAAGATGACG | 51 | 2098 |
| 1042209 | N/A | N/A | 451136 | 451155 | ACCAGCCTAAAAAATTGGAG | 72 | 2099 |
| 1042241 | N/A | N/A | 451525 | 451544 | GCACCGAGATAATATACACA | 13 | 2100 |
| 1042273 | N/A | N/A | 451891 | 451910 | TCTGAAAATAACATCTACTG | 43 | 2101 |
| 1042305 | N/A | N/A | 452175 | 452194 | CCAAGTCATAAAAATAAAAC | 104 | 2102 |
| 1042337 | N/A | N/A | 452460 | 452479 | ATAGCCACTCATACAATTCT | 34 | 2103 |
| 1042369 | N/A | N/A | 452953 | 452972 | AAGCATGAACCCCTTCTCCT | 66 | 2104 |
| 1042401 | N/A | N/A | 453745 | 453764 | GGAGCAAAAGATCCTTCCA | 91 | 2105 |
| 1042433 | N/A | N/A | 454600 | 454619 | GGATTCTCTAATTAGAGCTT | 41 | 2106 |
| 1042465 | N/A | N/A | 455224 | 455243 | GAGGAGACCAGATAGCTTGT | 79 | 2107 |
| 1042497 | N/A | N/A | 456173 | 456192 | CTCTGGACAAAATGTTTAAA | 82 | 2108 |
| 1042529 | N/A | N/A | 456883 | 456902 | TCAATATTCAAAATATTCCA | 98 | 2109 |

TABLE 29

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 3 | 138 |
| 1040098 | 2110 | 2129 | 436829 | 436848 | GGGCAGGACCATCACAGAGG | 60 | 2110 |
| 1040130 | 3049 | 3068 | 457302 | 457321 | CTGGCCCTTTTTAACAGAGC | 107 | 2111 |
| 1040162 | 3765 | 3784 | 458018 | 458037 | CTGCAGGACCCTTCCACGG | 118 | 2112 |
| 1040194 | 4393 | 4412 | 458646 | 458665 | TCAAAGACAAAAAGATTTCG | 75 | 2113 |

TABLE 29-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040226 | 4733 | 4752 | 458986 | 459005 | ATTCACATTCATCCCTTTAA | 35 | 2114 |
| 1040258 | 5048 | 5067 | 459301 | 459320 | GTTAGAAAGAAATTTTGCTA | 58 | 2115 |
| 1040290 | 5442 | 5461 | 459695 | 459714 | CCTACTTATAAAACTTTTTT | 114 | 2116 |
| 1040322 | 5787 | 5806 | 460040 | 460059 | TACAGCACTAAATAAGCAGT | 68 | 2117 |
| 1040354 | 6177 | 6196 | 460430 | 460449 | CACATGCTAAAAAGCAAGA | 86 | 2118 |
| 1040386 | 6960 | 6979 | 461213 | 461232 | AAGAAAGAACAAAAGACGGC | 66 | 2119 |
| 1040418 | 7407 | 7426 | 461660 | 461679 | CACCTAACAGAAAACATAGA | 118 | 2120 |
| 1040450 | 7883 | 7902 | 462136 | 462155 | TAGTGTCTTCAAAAGCATTG | 39 | 2121 |
| 1040482 | 8238 | 8257 | 462491 | 462510 | AGTATATTCTCTGTATATTT | 29 | 2122 |
| 1040514 | 8599 | 8618 | 462852 | 462871 | GAGCCATATCTTTCAAACAC | 25 | 2123 |
| 1040546 | 8986 | 9005 | 463239 | 463258 | TTCAAGATTATATTCTTTGG | 52 | 2124 |
| 1040578 | 9328 | 9347 | 463581 | 463600 | GTTGCCTTCAACGAGAAGGG | 62 | 2125 |
| 1040610 | 9658 | 9677 | 463911 | 463930 | ACTGTAAACAACACTTCCAA | 22 | 2126 |
| 1040642 | 10204 | 10223 | 464457 | 464476 | ACATCATTCCTTCCCTAGTT | 29 | 2127 |
| 1040674 | 10415 | 10434 | 464668 | 464687 | TGTATCCTACAAATAGACAC | 78 | 2128 |
| 1040706 | N/A | N/A | 9658 | 9677 | GGCTGATTTTAAACTTAGTT | 31 | 2129 |
| 1040738 | N/A | N/A | 26160 | 26179 | GTTTTATATTTTAAGTGCT | 7 | 2130 |
| 1040770 | N/A | N/A | 40931 | 40950 | ACATTTAAAATATTTCAGAC | 108 | 2131 |
| 1040802 | N/A | N/A | 71486 | 71505 | TGTCTATTTTAAAGACTCAA | 112 | 2132 |
| 1040834 | N/A | N/A | 85731 | 85750 | GGATATCTATTTTAATTCTT | 62 | 2133 |
| 1040866 | N/A | N/A | 108791 | 108810 | ACAGTATTTCAAAAGAAGCC | 73 | 2134 |
| 1040898 | N/A | N/A | 140712 | 140731 | CTGGATAATACCTAACTGTC | 58 | 2135 |
| 1040930 | N/A | N/A | 167395 | 167414 | AGTGACTTAGATTATCCTTT | 17 | 2136 |
| 1040962 | N/A | N/A | 187991 | 188010 | CACATCAAACCTCAAGGGCA | 64 | 2137 |
| 1040994 | N/A | N/A | 208238 | 208257 | GTTTCCCTAATTTATGGAGT | 52 | 2138 |
| 1041026 | N/A | N/A | 227529 | 227548 | ATTCTTACAATTTACTTGTA | 96 | 2139 |
| 1041058 | N/A | N/A | 251431 | 251450 | ATTCTCTTTTAAAGATAAAG | 119 | 2140 |
| 1041090 | N/A | N/A | 270489 | 270508 | CTATGGTTTTAAAATTCATT | 82 | 2141 |
| 1041122 | N/A | N/A | 287171 | 287190 | ACTACCAGCCCTTATTTCAG | 20 | 2142 |
| 1041154 | N/A | N/A | 318500 | 318519 | CTCTGCTTTCAAATGTGTTT | 6 | 2143 |
| 1041186 | N/A | N/A | 338862 | 338881 | TCTTTCATATTTTAAAGTGC | 3 | 2144 |
| 1041218 | N/A | N/A | 365191 | 365210 | TCCAGTAAAAACACAACACT | 44 | 2145 |
| 1041250 | N/A | N/A | 385654 | 385673 | TATAATATACATTATACCCT | 78 | 2146 |
| 1041282 | N/A | N/A | 410286 | 410305 | CCACAATTACAAACACACTT | 41 | 2147 |
| 1041314 | N/A | N/A | 437752 | 437771 | GGCTTATTTTTTCTAGAGAA | 18 | 2148 |
| 1041346 | N/A | N/A | 438171 | 438190 | GCAGTGATAGTCACAGGTTC | 19 | 2149 |

TABLE 29-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041378 | N/A | N/A | 438490 | 438509 | GGAATTATCCACTCTAACCA | 56 | 2150 |
| 1041410 | N/A | N/A | 439101 | 439120 | TGTATTAACCACGCTTTTAT | 31 | 2151 |
| 1041442 | N/A | N/A | 439443 | 439462 | AGCAGCTATTTCATGACTAT | 19 | 2152 |
| 1041474 | N/A | N/A | 440093 | 440112 | GTGAGCTGTATTATTATGCC | 62 | 2153 |
| 1041506 | N/A | N/A | 440327 | 440346 | GCAAGGAACCAGTCGCATTT | 56 | 2154 |
| 1041538 | N/A | N/A | 441144 | 441163 | AGCCGATTTCTGATAGGCTC | 78 | 2155 |
| 1041570 | N/A | N/A | 441530 | 441549 | GCAGGATTTCTGCCTAGAGT | 39 | 2156 |
| 1041602 | N/A | N/A | 442188 | 442207 | ATGTTCATCTTAATGCTCTT | 21 | 2157 |
| 1041634 | N/A | N/A | 442625 | 442644 | GACTCTCAACCAGAATCAAG | 111 | 2158 |
| 1041666 | N/A | N/A | 443025 | 443044 | TGCCTCTCCTTCCATAAACT | 89 | 2159 |
| 1041698 | N/A | N/A | 443481 | 443500 | TTTTACAACTCCACTGAGCA | 53 | 2160 |
| 1041730 | N/A | N/A | 443834 | 443853 | CTCGGCTATTTTTAGGTACC | 51 | 2161 |
| 1041762 | N/A | N/A | 444258 | 444277 | TGCTTTAAACAATAGTCTTT | 81 | 2162 |
| 1041794 | N/A | N/A | 445146 | 445165 | CCAGTGAGTGACCACAGCAG | 99 | 2163 |
| 1041826 | N/A | N/A | 445484 | 445503 | ACCCCGTCTCAAAGATGAAG | 102 | 2164 |
| 1041858 | N/A | N/A | 445769 | 445788 | CCCTGTTTTCACAAATTGCG | 62 | 2165 |
| 1041890 | N/A | N/A | 445979 | 445998 | TCAATAAAATTCCTTTCACC | 60 | 2166 |
| 1041922 | N/A | N/A | 446355 | 446374 | GGCCTTTATACTTTTGTAAG | 103 | 2167 |
| 1041954 | N/A | N/A | 446834 | 446853 | TGGTTTCTGATTAAATCCCA | 49 | 2168 |
| 1041986 | N/A | N/A | 447630 | 447649 | TTTACTTGTATATTTGTCTG | 15 | 2169 |
| 1042018 | N/A | N/A | 448384 | 448403 | CTGTCCTTTTCAGAGAGAAC | 88 | 2170 |
| 1042050 | N/A | N/A | 448680 | 448699 | TACATCACAAACATCCCAAT | 97 | 2171 |
| 1042082 | N/A | N/A | 449048 | 449067 | AATGATACATTTCAGGCTTT | 47 | 2172 |
| 1042114 | N/A | N/A | 449591 | 449610 | ATATATCATCAAATCTGTTG | 44 | 2173 |
| 1042146 | N/A | N/A | 449851 | 449870 | TTAGTGTGAACTACCTAGAC | 85 | 2174 |
| 1042178 | N/A | N/A | 450505 | 450524 | CTGCCGAAAAATTCACGAGA | 95 | 2175 |
| 1042210 | N/A | N/A | 451137 | 451156 | AACCAGCCTAAAAAATTGGA | 88 | 2176 |
| 1042242 | N/A | N/A | 451539 | 451558 | AGGATAATTTTATGGCACCG | 14 | 2177 |
| 1042274 | N/A | N/A | 451905 | 451924 | GCAATATTTAATTTTCTGAA | 36 | 2178 |
| 1042306 | N/A | N/A | 452185 | 452204 | TGCTGCAAATCCAAGTCATA | 51 | 2179 |
| 1042338 | N/A | N/A | 452464 | 452483 | CCTTATAGCCACTCTATACAA | 42 | 2180 |
| 1042370 | N/A | N/A | 452976 | 452995 | AGTACATTCATATGGCAGCT | 27 | 2181 |
| 1042402 | N/A | N/A | 453759 | 453778 | GGCGAATTCTATATGGACA | 98 | 2182 |
| 1042434 | N/A | N/A | 454604 | 454623 | AACTGGATTCTCTAATTAGA | 59 | 2183 |

TABLE 29-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042466 | N/A | N/A | 455257 | 455276 | GCATTCAATTTAAAAAGGG | 66 | 2184 |
| 1042498 | N/A | N/A | 456187 | 456206 | AATAAATTTAAAAACTCTGG | 108 | 2185 |
| 1042530 | N/A | N/A | 456884 | 456903 | ATCAATATTCAAAATATTCC | 89 | 2186 |

TABLE 30

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 2 | 138 |
| 1040099 | 2149 | 2168 | 436868 | 436887 | CTGTTGCACCTCCAGGTCAG | 77 | 2187 |
| 1040131 | 3050 | 3069 | 457303 | 457322 | GCTGGCCCTTTTTAACAGAG | 110 | 2188 |
| 1040163 | 3800 | 3819 | 458053 | 458072 | CCTGTGCACCCCCACATGCG | 107 | 2189 |
| 1040195 | 4416 | 4435 | 458669 | 458688 | TGAACTATAAACAGTACTAG | 69 | 2190 |
| 1040227 | 4734 | 4753 | 458987 | 459006 | AATTCACATTCATCCCTTTA | 34 | 2191 |
| 1040259 | 5079 | 5098 | 459332 | 459351 | AACCTTATAAAATGGCCTAG | 70 | 2192 |
| 1040291 | 5446 | 5465 | 459699 | 459718 | TCTCCCTACTTATAAAACTT | 31 | 2193 |
| 1040323 | 5788 | 5807 | 460041 | 460060 | ATACAGCACTAAATAAGCAG | 77 | 2194 |
| 1040355 | 6207 | 6226 | 460460 | 460479 | GGTCAGACTCTATTGGCACA | 10 | 2195 |
| 1040387 | 6987 | 7006 | 461240 | 461259 | TTACTAGTTTAAAAATGGAA | 100 | 2196 |
| 1040419 | 7414 | 7433 | 461667 | 461686 | ACACACTCACCTAACAGAAA | 68 | 2197 |
| 1040451 | 7915 | 7934 | 462168 | 462187 | CTTCCTCACCCATATCTGAA | 45 | 2198 |
| 1040483 | 8250 | 8269 | 462503 | 462522 | GCTTTATAAAAAAGTATATT | 139 | 2199 |
| 1040515 | 8600 | 8619 | 462853 | 462872 | AGAGCCATATCTTTCAAACA | 31 | 2200 |
| 1040547 | 8988 | 9007 | 463241 | 463260 | TGTTCAAGATTATATTCTTT | 73 | 2201 |
| 1040579 | 9332 | 9351 | 463585 | 463604 | AACAGTTGCCTTCAACGAGA | 29 | 2202 |
| 1040611 | 9661 | 9680 | 463914 | 463933 | ATTACTGTAAACAACACTTC | 52 | 2203 |
| 1040643 | 10205 | 10224 | 464458 | 464477 | AACATCATTCCTTCCCTAGT | 33 | 2204 |
| 1040675 | 10418 | 10437 | 464671 | 464690 | GAGTGTATCCTACAAATAGA | 53 | 2205 |
| 1040707 | N/A | N/A | 11372 | 11391 | TCTAGCAAACCTCTTTTTCC | 57 | 2206 |
| 1040739 | N/A | N/A | 27282 | 27301 | AGGTATAAATCCCCTTTCCA | 31 | 2207 |
| 1040771 | N/A | N/A | 41291 | 41310 | GATAGTAATCAAACCTGAGT | 43 | 2208 |
| 1040803 | N/A | N/A | 71489 | 71508 | ATTTGTCTATTTAAAGACT | 117 | 2209 |
| 1040835 | N/A | N/A | 87443 | 87462 | ATGAGTAAAATATGGTCCTT | 43 | 2210 |
| 1040867 | N/A | N/A | 109082 | 109101 | CACTTCATAATTTAATATTT | 92 | 2211 |
| 1040899 | N/A | N/A | 141267 | 141286 | GTGATATTTTAAAGACTTAC | 6 | 2212 |

TABLE 30-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040931 | N/A | N/A | 168114 | 168133 | AGGGCCTTATTTTAATCACA | 106 | 2213 |
| 1040963 | N/A | N/A | 188513 | 188532 | CATTTATTTCCTTACCCAGT | 6 | 2214 |
| 1040995 | N/A | N/A | 208356 | 208375 | GTGTCTAAAACCAACTGGGT | 28 | 2215 |
| 1041027 | N/A | N/A | 227703 | 227722 | AAGCCAATATTTTATTTTGA | 96 | 2216 |
| 1041059 | N/A | N/A | 251853 | 251872 | GGTGATAAAGATATCATTAC | 67 | 2217 |
| 1041091 | N/A | N/A | 270781 | 270800 | TTCGAAATTCTTTATTTGAT | 136 | 2218 |
| 1041123 | N/A | N/A | 287520 | 287539 | CACTATAAAGAATGATGAGT | 5 | 2219 |
| 1041155 | N/A | N/A | 318566 | 318585 | TAGAGAAAACGATGTTGGCT | 3 | 2220 |
| 1041187 | N/A | N/A | 339528 | 339547 | CCTTCGGCTATTTAATAATA | 75 | 2221 |
| 1041219 | N/A | N/A | 365605 | 365624 | AGGCATCTAATTTAAATTCA | 20 | 2222 |
| 1041251 | N/A | N/A | 386171 | 386190 | GCTTGTAAAACTATGGCGGC | 87 | 2223 |
| 1041283 | N/A | N/A | 413867 | 413886 | GGCAATAAAATATTTAATGG | 71 | 2224 |
| 1041315 | N/A | N/A | 437753 | 437772 | GGGCTTATTTTTCTAGAGA | 33 | 2225 |
| 1041347 | N/A | N/A | 438223 | 438242 | ACATTATATATATGTTGGAG | 16 | 2226 |
| 1041379 | N/A | N/A | 438493 | 438512 | ACTGGAATTATCCACTCTAA | 40 | 2227 |
| 1041411 | N/A | N/A | 439103 | 439122 | ATTGTATTAACCACGCTTTT | 29 | 2228 |
| 1041443 | N/A | N/A | 439444 | 439463 | TAGCAGCTATTTCATGACTA | 15 | 2229 |
| 1041475 | N/A | N/A | 440117 | 440136 | GTGAACAGCCACTACAGAGG | 76 | 2230 |
| 1041507 | N/A | N/A | 440360 | 440379 | CCTTCATTCTCAAGCTGAAG | 88 | 2231 |
| 1041539 | N/A | N/A | 441150 | 441169 | GATGTCAGCCGATTTCTGAT | 30 | 2232 |
| 1041571 | N/A | N/A | 441554 | 441573 | AGGCATCCTCAAGAGTCTGT | 32 | 2233 |
| 1041603 | N/A | N/A | 442192 | 442211 | GTACATGTTCATCTTAATGC | 12 | 2234 |
| 1041635 | N/A | N/A | 442626 | 442645 | GGACTCTCAACCAGAATCAA | 118 | 2235 |
| 1041667 | N/A | N/A | 443027 | 443046 | GCTGCCTCTCCTTCCATAAA | 64 | 2236 |
| 1041699 | N/A | N/A | 443488 | 443507 | CAATACATTTTACAACTCCA | 27 | 2237 |
| 1041731 | N/A | N/A | 443871 | 443890 | CTGACTCTACAGGCTCATGT | 51 | 2238 |
| 1041763 | N/A | N/A | 444259 | 444278 | CTGCTTTAAACAATAGTCTT | 70 | 2239 |
| 1041795 | N/A | N/A | 445170 | 445189 | AGGGATGGCCAGGAAGGACA | 96 | 2240 |
| 1041827 | N/A | N/A | 445492 | 445511 | ATCAGAAAACCCCGTCTCAA | 104 | 2241 |
| 1041859 | N/A | N/A | 445770 | 445789 | TCCCTGTTTTCACAAATTGC | 68 | 2242 |
| 1041891 | N/A | N/A | 445980 | 445999 | TTCAATAAAATTCCTTTCAC | 93 | 2243 |
| 1041923 | N/A | N/A | 446357 | 446376 | ATGGCCTTTATACTTTTGTA | 116 | 2244 |
| 1041955 | N/A | N/A | 446849 | 446868 | ACACATTTTCCAGAATGGTT | 16 | 2245 |
| 1041987 | N/A | N/A | 447638 | 447657 | CTTTTTTATTTACTTGTATA | 80 | 2246 |
| 1042019 | N/A | N/A | 448386 | 448405 | CACTGTCCTTTTCAGAGAGA | 68 | 2247 |
| 1042051 | N/A | N/A | 448682 | 448701 | CTTACATCACAAACATCCCA | 95 | 2248 |

TABLE 30-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
| --- | --- | --- | --- | --- | --- | --- | --- |
| 1042083 | N/A | N/A | 449050 | 449069 | CTAATGATACATTTCAGGCT | 46 | 2249 |
| 1042115 | N/A | N/A | 449593 | 449612 | ATATATATCATCAAATCTGT | 23 | 2250 |
| 1042147 | N/A | N/A | 449862 | 449881 | CTCCTCACTAATTAGTGTGA | 110 | 2251 |
| 1042179 | N/A | N/A | 450507 | 450526 | GCCTGCCGAAAAATTCACGA | 144 | 2252 |
| 1042211 | N/A | N/A | 451139 | 451158 | CCAACCAGCCTAAAAAATTG | 122 | 2253 |
| 1042243 | N/A | N/A | 451540 | 451559 | TAGGATAATTTTATGGCACC | 8 | 2254 |
| 1042275 | N/A | N/A | 451908 | 451927 | CAGGCAATATTTAATTTTCT | 11 | 2255 |
| 1042307 | N/A | N/A | 452186 | 452205 | TTGCTGCAAATCCAAGTCAT | 34 | 2256 |
| 1042339 | N/A | N/A | 452466 | 452485 | TGCCTTATAGCCACTCATAC | 33 | 2257 |
| 1042371 | N/A | N/A | 452978 | 452997 | TGAGTACATTCATATGGCAG | 13 | 2258 |
| 1042403 | N/A | N/A | 453760 | 453779 | TGGCGAATTCTATATGGAGC | 63 | 2259 |
| 1042435 | N/A | N/A | 454638 | 454657 | AGTTGAATAGACATGGATTA | 73 | 2260 |
| 1042467 | N/A | N/A | 455281 | 455300 | ACTTTCACAATTTTGCAAAT | 45 | 2261 |
| 1042499 | N/A | N/A | 456211 | 456230 | TCTGAACAAAAATATAAGCA | 106 | 2262 |
| 1042531 | N/A | N/A | 456890 | 456909 | AAGGTCATCAATATTCAAAA | 19 | 2263 |

TABLE 31

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
| --- | --- | --- | --- | --- | --- | --- | --- |
| 994605 | N/A | N/A | 17726 | 17745 | GTCACCTTTTCTATTTGCAC | 3 | 138 |
| 1040100 | 2215 | 2234 | 436934 | 436953 | AGGCTTCCCTAAATGCAGGC | 69 | 2264 |
| 1040132 | 3098 | 3117 | 457351 | 457370 | GGCCGTCGGCCTTTGAGTGC | 106 | 2265 |
| 1040164 | 3838 | 3857 | 458091 | 458110 | AGGCAGAGAAAAAGAGACCC | 72 | 2266 |
| 1040196 | 4421 | 4440 | 458674 | 458693 | AGTCATGAACTATAAACAGT | 34 | 2267 |
| 1040228 | 4736 | 4755 | 458989 | 459008 | ATAATTCACATTCATCCCTT | 28 | 2268 |
| 1040260 | 5084 | 5103 | 459337 | 459356 | AACATAACCTTATAAAATGG | 82 | 2269 |
| 1040292 | 5447 | 5466 | 459700 | 459719 | TTCTCCCTACTTATAAAACT | 48 | 2270 |
| 1040324 | 5798 | 5817 | 460051 | 460070 | CGTTTAAAAAATACAGCACT | 49 | 2271 |
| 1040356 | 6228 | 6247 | 460481 | 460500 | GCTTTAACTATATAGCACAC | 78 | 2272 |
| 1040388 | 6995 | 7014 | 461248 | 461267 | GCCTGCTGTTACTAGTTTAA | 31 | 2273 |
| 1040420 | 7415 | 7434 | 461668 | 461687 | AACACACTCACCTAACAGAA | 47 | 2274 |
| 1040452 | 7920 | 7939 | 462173 | 462192 | CTCTGCTTCCTCACCCATAT | 36 | 2275 |
| 1040484 | 8251 | 8270 | 462504 | 462523 | TGCTTTATAAAAAGTATAT | 128 | 2276 |

TABLE 31-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040516 | 8606 | 8625 | 462859 | 462878 | TTCAACAGAGCCATATCTTT | 65 | 2277 |
| 1040548 | 8989 | 9008 | 463242 | 463261 | GTGTTCAAGATTATATTCTT | 40 | 2278 |
| 1040580 | 9344 | 9363 | 463597 | 463616 | GTTAGCTACCAGAACAGTTG | 40 | 2279 |
| 1040612 | 9667 | 9686 | 463920 | 463939 | GTAAGGATTACTGTAAACAA | 12 | 2280 |
| 1040644 | 10208 | 10227 | 464461 | 464480 | CAAAACATCATTCCTTCCCT | 84 | 2281 |
| 1040676 | 10419 | 10438 | 464672 | 464691 | CGAGTGTATCCTACAAATAG | 56 | 2282 |
| 1040708 | N/A | N/A | 11914 | 11933 | TGCCAGAGAATTTATATGTA | 10 | 2283 |
| 1040740 | N/A | N/A | 27352 | 27371 | CCTGTCAAAACCAGTCACTC | 60 | 2284 |
| 1040772 | N/A | N/A | 41515 | 41534 | CTAATAATAGTCTAATTACA | 134 | 2285 |
| 1040804 | N/A | N/A | 71673 | 71692 | TTGTGCTTTTAAATTCAAAC | 10 | 2286 |
| 1040836 | N/A | N/A | 87528 | 87547 | ACATCCTTTTAAATGTTAGG | 31 | 2287 |
| 1040868 | N/A | N/A | 109301 | 109320 | TGTCTTAATCAAACCTCCCG | 50 | 2288 |
| 1040900 | N/A | N/A | 141437 | 141456 | CAGTTCTATTTTTAGTTATA | 10 | 2289 |
| 1040932 | N/A | N/A | 168436 | 168455 | ATTTACCTTCTTTAACACAA | 66 | 2290 |
| 1040964 | N/A | N/A | 188787 | 188806 | GGGATATTTTAAAATTCTAC | 54 | 2291 |
| 1040996 | N/A | N/A | 208934 | 208953 | CCTGGGTTTCAAAGATTCCT | 100 | 2292 |
| 1041028 | N/A | N/A | 229640 | 229659 | TAGAGAATTCAAAGCACCAA | 46 | 2293 |
| 1041060 | N/A | N/A | 253001 | 253020 | TCAAAGTTTTAAAGAGTTTT | 88 | 2294 |
| 1041092 | N/A | N/A | 271090 | 271109 | TGCTCCAAACCCAGCTCCTC | 132 | 2295 |
| 1041124 | N/A | N/A | 288911 | 288930 | CCCTACTCCTTTTATAGATG | 32 | 2296 |
| 1041156 | N/A | N/A | 319014 | 319033 | TCATCCAAACCCAGACGGGT | 120 | 2297 |
| 1041188 | N/A | N/A | 339984 | 340003 | ATAAAGTCCTTTTAACCCCT | 4 | 2298 |
| 1041220 | N/A | N/A | 367208 | 367227 | GTGCCCTTTTAAAATCTTTT | 6 | 2299 |
| 1041252 | N/A | N/A | 386698 | 386717 | AGCCAAAAATACATCCACCT | 24 | 2300 |
| 1041284 | N/A | N/A | 413882 | 413901 | ACTGTAATCTAAACAGGCAA | 87 | 2301 |
| 1041316 | N/A | N/A | 437786 | 437805 | TTCATTACACACAGCAGAGA | 26 | 2302 |
| 1041348 | N/A | N/A | 438225 | 438244 | AGACATTATATATATGTTGG | 27 | 2303 |
| 1041380 | N/A | N/A | 438512 | 438531 | CCCCTACACCCCAGAGCACA | 109 | 2304 |
| 1041412 | N/A | N/A | 439104 | 439123 | GATTGTATTAACCACGCTTT | 18 | 2305 |
| 1041444 | N/A | N/A | 439457 | 439476 | TGAATGTCCCAAATAGCAGC | 34 | 2306 |
| 1041476 | N/A | N/A | 440138 | 440157 | CACCCCTAATTCATGCAGGA | 72 | 2307 |
| 1041508 | N/A | N/A | 440361 | 440380 | GCCTTCATTCTCAAGCTGAA | 43 | 2308 |
| 1041540 | N/A | N/A | 441162 | 441181 | TTTAGCTGTGATGATGTCAG | 51 | 2309 |
| 1041572 | N/A | N/A | 441556 | 441575 | TCAGGCATCCTCAAGAGTCT | 68 | 2310 |
| 1041604 | N/A | N/A | 442235 | 442254 | CTTTAGTTCCCATGAGGTCT | 41 | 2311 |
| 1041636 | N/A | N/A | 442680 | 442699 | AAGTGGATTATATTTGGCAG | 7 | 2312 |

TABLE 31-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041668 | N/A | N/A | 443031 | 443050 | ATCAGCTGCCTCTCCTTCCA | 47 | 2313 |
| 1041700 | N/A | N/A | 443489 | 443508 | CCAATACATTTTACAACTCC | 57 | 2314 |
| 1041732 | N/A | N/A | 443874 | 443893 | GGACTGACTCTACAGGCTCA | 41 | 2315 |
| 1041764 | N/A | N/A | 444260 | 444279 | ACTGCTTTAAACAATAGTCT | 65 | 2316 |
| 1041796 | N/A | N/A | 445235 | 445254 | TTTTTCTTACACATGGTAGC | 28 | 2317 |
| 1041828 | N/A | N/A | 445506 | 445525 | TCAGCATGAAAAAAATCAGA | 76 | 2318 |
| 1041860 | N/A | N/A | 445772 | 445791 | AGTCCCTGTTTTCACAAATT | 45 | 2319 |
| 1041892 | N/A | N/A | 446016 | 446035 | GCTTTTAAGAAAAATTTTAG | 123 | 2320 |
| 1041924 | N/A | N/A | 446359 | 446378 | GGATGGCCTTTATACTTTTG | 52 | 2321 |
| 1041956 | N/A | N/A | 446875 | 446894 | TCATTTTATGATCTTGCTGG | 25 | 2322 |
| 1041988 | N/A | N/A | 447659 | 447678 | CTGGTTATCTTCTTATGCAT | 89 | 2323 |
| 1042020 | N/A | N/A | 448422 | 448441 | TTTGGAATCTTTTTTGCCTC | 44 | 2324 |
| 1042052 | N/A | N/A | 448684 | 448703 | CTCTTACATCACAAACATCC | 102 | 2325 |
| 1042084 | N/A | N/A | 449054 | 449073 | GTTCCTAATGATACATTTCA | 52 | 2326 |
| 1042116 | N/A | N/A | 449594 | 449613 | AATATATATCATCAAATCTG | 46 | 2327 |
| 1042148 | N/A | N/A | 449866 | 449885 | TTTTCTCCTCACTAATTAGT | 112 | 2328 |
| 1042180 | N/A | N/A | 450508 | 450527 | AGCCTGCCGAAAAATTCACG | 116 | 2329 |
| 1042212 | N/A | N/A | 451152 | 451171 | CCATAAAAACCCTCCAACCA | 112 | 2330 |
| 1042244 | N/A | N/A | 451541 | 451560 | CTAGGATAATTTTATGGCAC | 9 | 2331 |
| 1042276 | N/A | N/A | 451909 | 451928 | GCAGGCAATATTTAATTTTC | 37 | 2332 |
| 1042308 | N/A | N/A | 452218 | 452237 | GGAAACCAATCCCACATCAA | 78 | 2333 |
| 1042340 | N/A | N/A | 452472 | 452491 | AGTGTTTGCCTTATAGCCAC | 20 | 2334 |
| 1042372 | N/A | N/A | 452979 | 452998 | TTGAGTACATTCATATGGCA | 30 | 2335 |
| 1042404 | N/A | N/A | 453783 | 453802 | TGCTAAAGAAAAAGAATTGT | 111 | 2336 |
| 1042436 | N/A | N/A | 454643 | 454662 | TTTCCAGTTGAATAGACATG | 62 | 2337 |
| 1042468 | N/A | N/A | 455285 | 455304 | AATTACTTTCACAATTTTGC | 27 | 2338 |
| 1042500 | N/A | N/A | 456212 | 456231 | CTCTGAACAAAAATATAAGC | 87 | 2339 |
| 1042532 | N/A | N/A | 456957 | 456976 | ACACACTATAAATGAGGCTC | 46 | 2340 |

TABLE 32

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 3 | 138 |
| 1040101 | 2216 | 2235 | 436935 | 436954 | CAGGCTTCCCTAAATGCAGG | 70 | 2341 |

TABLE 32-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040133 | 3109 | 3128 | 457362 | 457381 | GCTGCCCGCCAGGCCGTCGG | 111 | 2342 |
| 1040165 | 3880 | 3899 | 458133 | 458152 | CCCCCCCGGCCCATGCCGAT | 108 | 2343 |
| 1040197 | 4422 | 4441 | 458675 | 458694 | TAGTCATGAACTATAAACAG | 46 | 2344 |
| 1040229 | 4738 | 4757 | 458991 | 459010 | TCATAATTCACATTCATCCC | 16 | 2345 |
| 1040261 | 5106 | 5125 | 459359 | 459378 | GACCAAAATGAATTTTCAAA | 26 | 2346 |
| 1040293 | 5458 | 5477 | 459711 | 459730 | TATTTAAAAATTTCTCCCTA | 95 | 2347 |
| 1040325 | 5902 | 5921 | 460155 | 460174 | TCTTACCATCAAAGGCTAAA | 60 | 2348 |
| 1040357 | 6229 | 6248 | 460482 | 460501 | AGCTTTAACTATATAGCACA | 107 | 2349 |
| 1040389 | 7040 | 7059 | 461293 | 461312 | CCTGACTAATTTCTTGGTGA | 46 | 2350 |
| 1040421 | 7422 | 7441 | 461675 | 461694 | AAAACCCAACACACTCACCT | 116 | 2351 |
| 1040453 | 7964 | 7983 | 462217 | 462236 | GACAACCAACACAGCTCAAG | 83 | 2352 |
| 1040485 | 8252 | 8271 | 462505 | 462524 | GTGCTTTATAAAAAGTATA | 94 | 2353 |
| 1040517 | 8613 | 8632 | 462866 | 462885 | TCATTGTTTCAACAGAGCCA | 12 | 2354 |
| 1040549 | 8990 | 9009 | 463243 | 463262 | CGTGTTCAAGATTATATTCT | 49 | 2355 |
| 1040581 | 9345 | 9364 | 463598 | 463617 | AGTTAGCTACCAGAACAGTT | 52 | 2356 |
| 1040613 | 9711 | 9730 | 463964 | 463983 | TGTCACCTAATACTTGGTAT | 25 | 2357 |
| 1040645 | 10211 | 10230 | 464464 | 464483 | GTGCAAAACATCATTCCTTC | 10 | 2358 |
| 1040677 | 10436 | 10455 | 464689 | 464708 | AATTCAATAAACAGACTCGA | 40 | 2359 |
| 1040709 | N/A | N/A | 12342 | 12361 | TTCAGAATTTAAAATTCAGC | 15 | 2360 |
| 1040741 | N/A | N/A | 27434 | 27453 | ACAATTAGCCAAAACTGAAT | 45 | 2361 |
| 1040773 | N/A | N/A | 42923 | 42942 | CGTTCCAAATTATTCCTGCT | 7 | 2362 |
| 1040805 | N/A | N/A | 72788 | 72807 | ATTTGCTCCTTTTATCATTG | 7 | 2363 |
| 1040837 | N/A | N/A | 87598 | 87617 | ACATTATTTCAAAACCCACA | 49 | 2364 |
| 1040869 | N/A | N/A | 110925 | 110944 | TAGTGGTTAGATTAACAGCT | 6 | 2365 |
| 1040901 | N/A | N/A | 141588 | 141607 | GTCTCATAACGATAACCAAA | 23 | 2366 |
| 1040933 | N/A | N/A | 169799 | 169818 | ACCTTTAAAATTTTTCAGC | 94 | 2367 |
| 1040965 | N/A | N/A | 189270 | 189289 | GCTTACAAAGCCATAGAACC | 67 | 2368 |
| 1040997 | N/A | N/A | 209089 | 209108 | GTCTACAGCCTTTAACGACT | 85 | 2369 |
| 1041029 | N/A | N/A | 229753 | 229772 | CCAGTTAACCAAAAAATTTT | 119 | 2370 |
| 1041061 | N/A | N/A | 255397 | 255416 | GGCTACTATCAAATACATTT | 9 | 2371 |
| 1041093 | N/A | N/A | 271117 | 271136 | TGTTTATTTCAAACTTTCCC | 55 | 2372 |
| 1041125 | N/A | N/A | 289433 | 289452 | GGTCTTGGCCCTTAACTGTT | 20 | 2373 |
| 1041157 | N/A | N/A | 319225 | 319244 | CCCTGATAAATTTATGAATT | 50 | 2374 |
| 1041189 | N/A | N/A | 341174 | 341193 | TTTGATCTGCCTTATCTCTG | 14 | 2375 |
| 1041221 | N/A | N/A | 367501 | 367520 | TTTGTATTTTAAACTGAGTG | 5 | 2376 |
| 1041253 | N/A | N/A | 386699 | 386718 | AAGCCAAAATACATCCACC | 46 | 2377 |

TABLE 32-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041285 | N/A | N/A | 414009 | 414028 | CTTTTTAGAATACCATGCCC | 95 | 2378 |
| 1041317 | N/A | N/A | 437788 | 437807 | AATTCATTACACACAGCAGA | 8 | 2379 |
| 1041349 | N/A | N/A | 438226 | 438245 | AAGACATTATATATATGTTG | 89 | 2380 |
| 1041381 | N/A | N/A | 438520 | 438539 | AAGGACAGCCCCTACACCCC | 97 | 2381 |
| 1041413 | N/A | N/A | 439106 | 439125 | CAGATTGTATTAACCACGCT | 5 | 2382 |
| 1041445 | N/A | N/A | 439471 | 439490 | TGTTTTATTTTATCTGAATG | 61 | 2383 |
| 1041477 | N/A | N/A | 440139 | 440158 | CCACCCCTAATTCATGCAGG | 67 | 2384 |
| 1041509 | N/A | N/A | 440364 | 440383 | GCTGCCTTCATTCTCAAGCT | 81 | 2385 |
| 1041541 | N/A | N/A | 441172 | 441191 | GGTGGAGTATTTTAGCTGTG | 10 | 2386 |
| 1041573 | N/A | N/A | 441564 | 441583 | TTATGAGTTCAGGCATCCTC | 15 | 2387 |
| 1041605 | N/A | N/A | 442237 | 442256 | GGCTTTAGTTCCCATGAGGT | 20 | 2388 |
| 1041637 | N/A | N/A | 442682 | 442701 | TTAAGTGGATTATATTTGGC | 11 | 2389 |
| 1041669 | N/A | N/A | 443041 | 443060 | CTAGACTTTCATCAGCTGCC | 53 | 2390 |
| 1041701 | N/A | N/A | 443490 | 443509 | ACCAATACATTTTACAACTC | 34 | 2391 |
| 1041733 | N/A | N/A | 443877 | 443896 | AAGGGACTGACTCTACAGGC | 16 | 2392 |
| 1041765 | N/A | N/A | 444289 | 444308 | GACCTCTCTCTACTTGCTGT | 30 | 2393 |
| 1041797 | N/A | N/A | 445239 | 445258 | TGGGTTTTTCTTACACATGG | 9 | 2394 |
| 1041829 | N/A | N/A | 445574 | 445593 | GTCTTGTTTTACCTGTAGAG | 6 | 2395 |
| 1041861 | N/A | N/A | 445787 | 445806 | CATTTCCTTCACAAGAGTCC | 78 | 2396 |
| 1041893 | N/A | N/A | 446036 | 446055 | CCTAATCTGACTAATGACTG | 94 | 2397 |
| 1041925 | N/A | N/A | 446361 | 446380 | AGGGATGGCCTTTATACTTT | 46 | 2398 |
| 1041957 | N/A | N/A | 446885 | 446904 | AATCATTAAGTCATTTTATG | 79 | 2399 |
| 1041989 | N/A | N/A | 447660 | 447679 | ACTGGTTATCTTCTTATGCA | 120 | 2400 |
| 1042021 | N/A | N/A | 448436 | 448455 | ACTCTCTCCATTCATTTGGA | 52 | 2401 |
| 1042053 | N/A | N/A | 448685 | 448704 | TCTCTTACATCACAAACATC | 94 | 2402 |
| 1042085 | N/A | N/A | 449059 | 449078 | TGAGGGTTCCTAATGATACA | 41 | 2403 |
| 1042117 | N/A | N/A | 449599 | 449618 | GTGAGAATATATATCATCAA | 100 | 2404 |
| 1042149 | N/A | N/A | 449885 | 449904 | CTTGCCAGCCCAATGCTAGT | 95 | 2405 |
| 1042181 | N/A | N/A | 450520 | 450539 | CATAGCTAGAACAGCCTGCC | 107 | 2406 |
| 1042213 | N/A | N/A | 451153 | 451172 | CCCATAAAAACCCTCCAACC | 102 | 2407 |
| 1042245 | N/A | N/A | 451542 | 451561 | GCTAGGATAATTTTATGGCA | 40 | 2408 |
| 1042277 | N/A | N/A | 451926 | 451945 | TATACACACTTCACAGGGCA | 56 | 2409 |
| 1042309 | N/A | N/A | 452223 | 452242 | CAGAAGGAAACCAATCCCAC | 80 | 2410 |
| 1042341 | N/A | N/A | 452473 | 452492 | CAGTGTTTGCCTTATAGCCA | 11 | 2411 |
| 1042373 | N/A | N/A | 452982 | 453001 | AACTTGAGTACATTCATATG | 72 | 2412 |
| 1042405 | N/A | N/A | 453799 | 453818 | TGGAATATCTTTACAGTGCT | 38 | 2413 |

TABLE 32-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042437 | N/A | N/A | 454668 | 454687 | CACTGAAATCAAGAATGCAA | 81 | 2414 |
| 1042469 | N/A | N/A | 455287 | 455306 | TGAATTACTTTCACAATTTT | 73 | 2415 |
| 1042501 | N/A | N/A | 456214 | 456233 | AACTCTGAACAAAAATATAA | 151 | 2416 |
| 1042533 | N/A | N/A | 456961 | 456980 | AGCCACACACTATAAATGAG | 99 | 2417 |

TABLE 33

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 3 | 138 |
| 1040102 | 2217 | 2236 | 436936 | 436955 | CCAGGCTTCCCTAAATGCAG | 92 | 2418 |
| 1040134 | 3141 | 3160 | 457394 | 457413 | ATTCCGTTTTCCTGCTCGGC | 32 | 2419 |
| 1040166 | 3890 | 3909 | 458143 | 458162 | CTGCTCTGAACCCCCCCGGC | 100 | 2420 |
| 1040198 | 4429 | 4448 | 458682 | 458701 | TTGTCCATAGTCATGAACTA | 78 | 2421 |
| 1040230 | 4739 | 4758 | 458992 | 459011 | TTCATAATTCACATTCATCC | 10 | 2422 |
| 1040262 | 5119 | 5138 | 459372 | 459391 | GATGTGGTAAAAAGACCAAA | 38 | 2423 |
| 1040294 | 5459 | 5478 | 459712 | 459731 | ATATTTAAAAATTTCTCCCT | 90 | 2424 |
| 1040326 | 5904 | 5923 | 460157 | 460176 | CCTCTTACCATCAAAGGCTA | 57 | 2425 |
| 1040358 | 6230 | 6249 | 460483 | 460502 | GAGCTTTAACTATATAGCAC | 44 | 2426 |
| 1040390 | 7045 | 7064 | 461298 | 461317 | TTCGCCCTGACTAATTTCTT | 25 | 2427 |
| 1040422 | 7450 | 7469 | 461703 | 461722 | GGATGCTGCCACTTCCTGGT | 66 | 2428 |
| 1040454 | 7968 | 7987 | 462221 | 462240 | CCATGACAACCAACACAGCT | 131 | 2429 |
| 1040486 | 8278 | 8297 | 462531 | 462550 | CCAACCCAACACAATAGCAG | 33 | 2430 |
| 1040518 | 8615 | 8634 | 462868 | 462887 | ACTCATTGTTTCAACAGAGC | 27 | 2431 |
| 1040550 | 9008 | 9027 | 463261 | 463280 | CCCTTGTTACAAACACTTCG | 65 | 2432 |
| 1040582 | 9369 | 9388 | 463622 | 463641 | CCCTCCCGCCATTACACAGG | 83 | 2433 |
| 1040614 | 9714 | 9733 | 463967 | 463986 | TAGTGTCACCTAATACTTGG | 59 | 2434 |
| 1040646 | 10212 | 10231 | 464465 | 464484 | GGTGCAAAACATCATTCCTT | 21 | 2435 |
| 1040678 | 10442 | 10461 | 464695 | 464714 | CCATAAAATTCAATAAACAG | 108 | 2436 |
| 1040710 | N/A | N/A | 13427 | 13446 | ATAAGCTTTCTTTAAATGCA | 9 | 2437 |
| 1040742 | N/A | N/A | 27656 | 27675 | GTGTTCTTTCTTTAACAGTT | 4 | 2438 |
| 1040774 | N/A | N/A | 42927 | 42946 | CCCCCGTTCCAAATTATTCC | 106 | 2439 |
| 1040806 | N/A | N/A | 74008 | 74027 | GTTTTTATCCATTACAAGAG | 22 | 2440 |
| 1040838 | N/A | N/A | 88730 | 88749 | ACCCGCAATCAAATACTGCC | 73 | 2441 |

TABLE 33-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040870 | N/A | N/A | 111213 | 111232 | CTAATGTGCCCTTAACATGG | 95 | 2442 |
| 1040902 | N/A | N/A | 141663 | 141682 | GCTCATAAACCATGTGCTC | 100 | 2443 |
| 1040934 | N/A | N/A | 170327 | 170346 | GCTTGATTTTAAACTTTATA | 40 | 2444 |
| 1040966 | N/A | N/A | 190544 | 190563 | ACCCTCAAACGAATAGGCTC | 145 | 2445 |
| 1040998 | N/A | N/A | 209796 | 209815 | TCCACACAAGAATAATCTAC | 86 | 2446 |
| 1041030 | N/A | N/A | 230401 | 230420 | GCTAGGAAAATTTACCATAC | 29 | 2447 |
| 1041062 | N/A | N/A | 255626 | 255645 | GATTAAATAATTTAAGCACA | 110 | 2448 |
| 1041094 | N/A | N/A | 271334 | 271353 | TCTTGGGTTCCTTATATTAC | 56 | 2449 |
| 1041126 | N/A | N/A | 290352 | 290371 | TAGGTGTTTATTTAGAACCC | 12 | 2450 |
| 1041158 | N/A | N/A | 319445 | 319464 | TCATGCTTTCAAAACACAGT | 11 | 2451 |
| 1041190 | N/A | N/A | 342628 | 342647 | AATGAAATCATTTACTGAAC | 85 | 2452 |
| 1041222 | N/A | N/A | 368463 | 368482 | AGTGTAATACATTACTCATA | 5 | 2453 |
| 1041254 | N/A | N/A | 387051 | 387070 | GTATACAAAGATATAACCTG | 76 | 2454 |
| 1041286 | N/A | N/A | 418439 | 418458 | TGTTTGTTTTAAAATTAGGG | 72 | 2455 |
| 1041318 | N/A | N/A | 437792 | 437811 | GGTTAATTCATTACACACAG | 3 | 2456 |
| 1041350 | N/A | N/A | 438237 | 438256 | ACCTAAATAATAAGACATTA | 141 | 2457 |
| 1041382 | N/A | N/A | 438532 | 438551 | AGCCAGACAACTAAGGACAG | 80 | 2458 |
| 1041414 | N/A | N/A | 439107 | 439126 | TCAGATTGTATTAACCACGC | 5 | 2459 |
| 1041446 | N/A | N/A | 439472 | 439491 | TTGTTTTATTTTATCTGAAT | 95 | 2460 |
| 1041478 | N/A | N/A | 440143 | 440162 | GTACCCACCCCTAATTCATG | 119 | 2461 |
| 1041510 | N/A | N/A | 440366 | 440385 | TGGCTGCCTTCATTCTCAAG | 106 | 2462 |
| 1041542 | N/A | N/A | 441188 | 441207 | TGTGGCAAACACAGCTGGTG | 45 | 2463 |
| 1041574 | N/A | N/A | 441611 | 441630 | ATACTATATCACACTGCTTT | 58 | 2464 |
| 1041606 | N/A | N/A | 442251 | 442270 | GTTTTATATGCCATGGCTTT | 58 | 2465 |
| 1041638 | N/A | N/A | 442691 | 442710 | TGGAGGATATTAAGTGGATT | 22 | 2466 |
| 1041670 | N/A | N/A | 443042 | 443061 | TCTAGACTTTCATCAGCTGC | 66 | 2467 |
| 1041702 | N/A | N/A | 443492 | 443511 | TTACCAATACATTTTACAAC | 72 | 2468 |
| 1041734 | N/A | N/A | 443917 | 443936 | GGCATGTTCAATGTTGGCAA | 16 | 2469 |
| 1041766 | N/A | N/A | 444314 | 444333 | ACAGGGAAAACTGTTAGGTG | 7 | 2470 |
| 1041798 | N/A | N/A | 445240 | 445259 | CTGGGTTTTCTTACACATG | 10 | 2471 |
| 1041830 | N/A | N/A | 445576 | 445595 | CAGTCTTGTTTTACCTGTAG | 6 | 2472 |
| 1041862 | N/A | N/A | 445791 | 445810 | CTCCCATTTCCTTCACAAGA | 53 | 2473 |
| 1041894 | N/A | N/A | 446044 | 446063 | GTCACCTTCCTAATCTGACT | 106 | 2474 |
| 1041926 | N/A | N/A | 446679 | 446698 | CCTTTATAACTTTTCTTTCT | 28 | 2475 |
| 1041958 | N/A | N/A | 446891 | 446910 | GTTAGTAATCATTAAGTCAT | 5 | 2476 |
| 1041990 | N/A | N/A | 447677 | 447696 | CCCTGGTGCCAAAAGGGACT | 100 | 2477 |

TABLE 33-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042022 | N/A | N/A | 448475 | 448494 | TCTTTAACCCCTCTTGCGCC | 123 | 2478 |
| 1042054 | N/A | N/A | 448687 | 448706 | TTTCTCTTACATCACAAACA | 116 | 2479 |
| 1042086 | N/A | N/A | 449060 | 449079 | TTGAGGGTTCCTAATGATAC | 54 | 2480 |
| 1042118 | N/A | N/A | 449600 | 449619 | AGTGAGAATATATATCATCA | 122 | 2481 |
| 1042150 | N/A | N/A | 449916 | 449935 | AATCTGATCATTGTAGGCAC | 12 | 2482 |
| 1042182 | N/A | N/A | 450530 | 450549 | TGGTGTGAACCATAGCTAGA | 120 | 2483 |
| 1042214 | N/A | N/A | 451161 | 451180 | ACCCCCCTCCCATAAAAACC | 117 | 2484 |
| 1042246 | N/A | N/A | 451566 | 451585 | GGTTTTACCCTTTCCTGCAC | 90 | 2485 |
| 1042278 | N/A | N/A | 451931 | 451950 | CACATTATACACACTTCACA | 78 | 2486 |
| 1042310 | N/A | N/A | 452244 | 452263 | TCATTAACAACATAAACTGA | 74 | 2487 |
| 1042342 | N/A | N/A | 452495 | 452514 | CATGGTACAGATAATTGTGA | 57 | 2488 |
| 1042374 | N/A | N/A | 453018 | 453037 | TACTGGATCCATACAAGGCA | 33 | 2489 |
| 1042406 | N/A | N/A | 453800 | 453819 | ATGGAATATCTTTACAGTGC | 17 | 2490 |
| 1042438 | N/A | N/A | 454669 | 454688 | CCACTGAAATCAAGAATGCA | 121 | 2491 |
| 1042470 | N/A | N/A | 455290 | 455309 | TCTTGAATTACTTTCACAAT | 24 | 2492 |
| 1042502 | N/A | N/A | 456227 | 456246 | GAGGACAACTAAAAACTCTG | 105 | 2493 |
| 1042534 | N/A | N/A | 456962 | 456981 | CAGCCACACACTATAAATGA | 112 | 2494 |

TABLE 34

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 2 | 138 |
| 1040103 | 2218 | 2237 | 436937 | 436956 | GCCAGGCTTCCCTAAATGCA | 135 | 2495 |
| 1040135 | 3180 | 3199 | 457433 | 457452 | TCGCCATTCTCAGAGAGCAT | 79 | 2496 |
| 1040167 | 3909 | 3928 | 458162 | 458181 | TGGGAACCCCAGGAGGACAC | 54 | 2497 |
| 1040199 | 4484 | 4503 | 458737 | 458756 | ATCTAATTCCTCATGTCACA | 15 | 2498 |
| 1040231 | 4740 | 4759 | 458993 | 459012 | GTTCATAATTCACATTCATC | 8 | 2499 |
| 1040263 | 5161 | 5180 | 459414 | 459433 | CAGAGTTTCTAAGAGCCCGC | 38 | 2500 |
| 1040295 | 5460 | 5479 | 459713 | 459732 | AATATTTAAAAATTTCTCCC | 110 | 2501 |
| 1040327 | 5906 | 5925 | 460159 | 460178 | TTCCTCTTACCATCAAAGGC | 38 | 2502 |
| 1040359 | 6232 | 6251 | 460485 | 460504 | ATGAGCTTTAACTATATAGC | 31 | 2503 |
| 1040391 | 7049 | 7068 | 461302 | 461321 | TCTTTTCGCCCTGACTAATT | 32 | 2504 |
| 1040423 | 7495 | 7514 | 461748 | 461767 | AAGAGGTGTGAAAGGTTCCG | 27 | 2505 |
| 1040455 | 7969 | 7988 | 462222 | 462241 | GCCATGACAACCAACACAGC | 96 | 2506 |

TABLE 34-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040487 | 8283 | 8302 | 462536 | 462555 | GGAAACCAACCCAACACAAT | 73 | 2507 |
| 1040519 | 8662 | 8681 | 462915 | 462934 | ACTTTCAACCCTTCTCTGCT | 53 | 2508 |
| 1040551 | 9010 | 9029 | 463263 | 463282 | ATCCCTTGTTACAAACACTT | 33 | 2509 |
| 1040583 | 9370 | 9389 | 463623 | 463642 | TCCCTCCCGCCATTACACAG | 94 | 2510 |
| 1040615 | 9719 | 9738 | 463972 | 463991 | TGAGCTAGTGTCACCTAATA | 12 | 2511 |
| 1040647 | 10213 | 10232 | 464466 | 464485 | AGGTGCAAAACATCATTCCT | 36 | 2512 |
| 1040679 | 10447 | 10466 | 464700 | 464719 | AGGGACCATAAAATTCAATA | 22 | 2513 |
| 1040711 | N/A | N/A | 14141 | 14160 | CTCCTCCAAATTTATCTTCA | 56 | 2514 |
| 1040743 | N/A | N/A | 28302 | 28321 | CACAAAATACATTAAGTCCT | 27 | 2515 |
| 1040775 | N/A | N/A | 43117 | 43136 | TCCAGCAAAATATTTCTTTA | 39 | 2516 |
| 1040807 | N/A | N/A | 74082 | 74101 | TTGATCAACCAAAGATGGCT | 39 | 2517 |
| 1040839 | N/A | N/A | 88777 | 88796 | CCAATGGCTTTTTAACAGAT | 27 | 2518 |
| 1040871 | N/A | N/A | 112988 | 113007 | AACACATTAGATTATGAGTA | 11 | 2519 |
| 1040903 | N/A | N/A | 141741 | 141760 | AGGGTGTTATTTTAGAGTAA | 13 | 2520 |
| 1040935 | N/A | N/A | 171157 | 171176 | GCTGGAAAAGAATCTGAGCA | 114 | 2521 |
| 1040967 | N/A | N/A | 190616 | 190635 | GTTATATTATTTTATCCCTT | 14 | 2522 |
| 1040999 | N/A | N/A | 209931 | 209950 | GAAGATATCTTTTATGACAC | 23 | 2523 |
| 1041031 | N/A | N/A | 231711 | 231730 | CACAGTAGCCAAAAGCAGTC | 95 | 2524 |
| 1041063 | N/A | N/A | 255652 | 255671 | GTATATATTATTTAAAATGT | 101 | 2525 |
| 1041095 | N/A | N/A | 273041 | 273060 | AGCTGGTTTCTTTAGCCACC | 81 | 2526 |
| 1041127 | N/A | N/A | 290740 | 290759 | GACTGAAAAATACCCAGCCA | 102 | 2527 |
| 1041159 | N/A | N/A | 322660 | 322679 | TAGGCCTTATTTTATTCCAT | 72 | 2528 |
| 1041191 | N/A | N/A | 342814 | 342833 | TGAGCTTTTTAAAAACAGTT | 4 | 2529 |
| 1041223 | N/A | N/A | 369251 | 369270 | TTTCTTAGCCAAAGAGATAT | 85 | 2530 |
| 1041255 | N/A | N/A | 387144 | 387163 | TGTTCAATTTAAAAGCCTTG | 5 | 2531 |
| 1041287 | N/A | N/A | 418795 | 418814 | ATCTGCAAAGAATCTGCCCC | 72 | 2532 |
| 1041319 | N/A | N/A | 437793 | 437812 | AGGTTAATTCATTACACACA | 5 | 2533 |
| 1041351 | N/A | N/A | 438241 | 438260 | TCATACCTAAATAATAAGAC | 102 | 2534 |
| 1041383 | N/A | N/A | 438533 | 438552 | CAGCCAGACAACTAAGGACA | 57 | 2535 |
| 1041415 | N/A | N/A | 439116 | 439135 | CCTGACTTCTCAGATTGTAT | 50 | 2536 |
| 1041447 | N/A | N/A | 439505 | 439524 | ATTCAAACCATTAATTAGTT | 73 | 2537 |
| 1041479 | N/A | N/A | 440144 | 440163 | AGTACCCACCCCTAATTCAT | 98 | 2538 |
| 1041511 | N/A | N/A | 440368 | 440387 | AGTGGCTGCCTTCATTCTCA | 52 | 2539 |
| 1041543 | N/A | N/A | 441206 | 441225 | GACTCTGAACCTGTCACTTG | 83 | 2540 |
| 1041575 | N/A | N/A | 441613 | 441632 | CCATACTATATCACACTGCT | 21 | 2541 |
| 1041607 | N/A | N/A | 442255 | 442274 | CTCAGTTTTATATGCCATGG | 44 | 2542 |

TABLE 34-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041639 | N/A | N/A | 442692 | 442711 | TTGGAGGATATTAAGTGGAT | 14 | 2543 |
| 1041671 | N/A | N/A | 443043 | 443062 | TTCTAGACTTTCATCAGCTG | 102 | 2544 |
| 1041703 | N/A | N/A | 443494 | 443513 | CTTTACCAATACATTTTACA | 61 | 2545 |
| 1041735 | N/A | N/A | 443936 | 443955 | ATTCATCGCCACCAAGCTCG | 48 | 2546 |
| 1041767 | N/A | N/A | 444343 | 444362 | ATCTATCACACCAATGCAAG | 29 | 2547 |
| 1041799 | N/A | N/A | 445241 | 445260 | GCTGGGTTTTCTTACACAT | 25 | 2548 |
| 1041831 | N/A | N/A | 445587 | 445606 | AGTGAAATTCTCAGTCTTGT | 37 | 2549 |
| 1041863 | N/A | N/A | 445806 | 445825 | GTTGTTTAAATATGTCTCCC | 8 | 2550 |
| 1041895 | N/A | N/A | 446045 | 446064 | TGTCACCTTCCTAATCTGAC | 51 | 2551 |
| 1041927 | N/A | N/A | 446680 | 446699 | GCCTTTATAACTTTTCTTTC | 11 | 2552 |
| 1041959 | N/A | N/A | 446892 | 446911 | TGTTAGTAATCATTAAGTCA | 12 | 2553 |
| 1041991 | N/A | N/A | 447705 | 447724 | CCAAAAAATCTTCTTCCATG | 45 | 2554 |
| 1042023 | N/A | N/A | 448476 | 448495 | TTCTTTAACCCCTCTTGCGC | 94 | 2555 |
| 1042055 | N/A | N/A | 448712 | 448731 | CTTGGAATCATACTTTCTTC | 55 | 2556 |
| 1042087 | N/A | N/A | 449061 | 449080 | ATTGAGGGTTCCTAATGATA | 46 | 2557 |
| 1042119 | N/A | N/A | 449602 | 449621 | TCAGTGAGAATATATATCAT | 98 | 2558 |
| 1042151 | N/A | N/A | 449921 | 449940 | CAGATAATCTGATCATTGTA | 45 | 2559 |
| 1042183 | N/A | N/A | 450531 | 450550 | GTGGTGTGAACCATAGCTAG | 97 | 2560 |
| 1042215 | N/A | N/A | 451169 | 451188 | CCCCCCATACCCCCCTCCCA | 92 | 2561 |
| 1042247 | N/A | N/A | 451567 | 451586 | GGGTTTTACCCTTTCCTGCA | 99 | 2562 |
| 1042279 | N/A | N/A | 451933 | 451952 | GCCACATTATACACACTTCA | 13 | 2563 |
| 1042311 | N/A | N/A | 452245 | 452264 | GTCATTAACAACATAAACTG | 21 | 2564 |
| 1042343 | N/A | N/A | 452496 | 452515 | CCATGGTACAGATAATTGTG | 105 | 2565 |
| 1042375 | N/A | N/A | 453045 | 453064 | CTGATACATTTCTAGAATGA | 28 | 2566 |
| 1042407 | N/A | N/A | 453852 | 453871 | TCACAGTTTACATCTCAACA | 28 | 2567 |
| 1042439 | N/A | N/A | 454686 | 454705 | TAGAATTAAAATATACACCA | 69 | 2568 |
| 1042471 | N/A | N/A | 455291 | 455310 | GTCTTGAATTACTTTCACAA | 9 | 2569 |
| 1042503 | N/A | N/A | 456245 | 456264 | TGGACCAACCCTCCTTCTGA | 81 | 2570 |
| 1042535 | N/A | N/A | 456967 | 456986 | TCCCCCAGCCACACACTATA | 102 | 2571 |

TABLE 35

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 1 | 138 |
| 1040104 | 2348 | 2367 | 437067 | 437086 | TCAGGTAGCCGATGACAGGG | 44 | 2572 |
| 1040136 | 3181 | 3200 | 457434 | 457453 | TTCGCCATTCTCAGAGAGCA | 57 | 2573 |
| 1040168 | 3937 | 3956 | 458190 | 458209 | GCTGGGTTCCTGATGTTGAT | 31 | 2574 |
| 1040200 | 4485 | 4504 | 458738 | 458757 | AATCTAATTCCTCATGTCAC | 21 | 2575 |
| 1040232 | 4741 | 4760 | 458994 | 459013 | AGTTCATAATTCACATTCAT | 13 | 2576 |
| 1040264 | 5162 | 5181 | 459415 | 459434 | TCAGAGTTTCTAAGAGCCCG | 17 | 2577 |
| 1040296 | 5477 | 5496 | 459730 | 459749 | GCAGCCATCCAAGTAAGAAT | 16 | 2578 |
| 1040328 | 5913 | 5932 | 460166 | 460185 | GCCCGTATTCCTCTTACCAT | 12 | 2579 |
| 1040360 | 6268 | 6287 | 460521 | 460540 | GGAAGATCAACCAAACAAGG | 46 | 2580 |
| 1040392 | 7061 | 7080 | 461314 | 461333 | GTATTATTTTTTCTTTTCG | 11 | 2581 |
| 1040424 | 7563 | 7582 | 461816 | 461835 | CAGAGCAGTCAAAGTGCTGC | 118 | 2582 |
| 1040456 | 7970 | 7989 | 462223 | 462242 | AGCCATGACAACCAACACAG | 63 | 2583 |
| 1040488 | 8289 | 8308 | 462542 | 462561 | AAGAGAGGAAACCAACCCAA | 50 | 2584 |
| 1040520 | 8663 | 8682 | 462916 | 462935 | AACTTTCAACCCTTCTCTGC | 37 | 2585 |
| 1040552 | 9040 | 9059 | 463293 | 463312 | ATAATGAGTCCTGTTTGATT | 20 | 2586 |
| 1040584 | 9377 | 9396 | 463630 | 463649 | CCGGTGTTCCCTCCCGCCAT | 85 | 2587 |
| 1040616 | 9772 | 9791 | 464025 | 464044 | CAGAGAAAACCTGTGCACCG | 71 | 2588 |
| 1040648 | 10214 | 10233 | 464467 | 464486 | AAGGTGCAAAACATCATTCC | 35 | 2589 |
| 1040680 | 10463 | 10482 | 464716 | 464735 | AAGCACCATCAAAGAAAGGG | 24 | 2590 |
| 1040712 | N/A | N/A | 14174 | 14193 | ACCCAATTTCAAAGATCACT | 29 | 2591 |
| 1040744 | N/A | N/A | 28305 | 28324 | GTTCACAAAATACATTAAGT | 6 | 2592 |
| 1040776 | N/A | N/A | 43918 | 43937 | AGATCAATTCAAAGGCTCCT | 62 | 2593 |
| 1040808 | N/A | N/A | 74369 | 74388 | GATTTGTATTTTTAATTGAC | 58 | 2594 |
| 1040840 | N/A | N/A | 89862 | 89881 | TTGACATTTTAAAACAGCTC | 40 | 2595 |
| 1040872 | N/A | N/A | 114285 | 114304 | AAGCTTATCCAAAAACATTT | 70 | 2596 |
| 1040904 | N/A | N/A | 143859 | 143878 | CCCCTCAACCAAACTTTTAC | 116 | 2597 |
| 1040936 | N/A | N/A | 172540 | 172559 | TATTAATTTCATTACCATGA | 92 | 2598 |
| 1040968 | N/A | N/A | 190768 | 190787 | CCTAGAATACATTATTCCTC | 56 | 2599 |
| 1041000 | N/A | N/A | 209947 | 209966 | AGCATATTTAAAGAAGAAG | 76 | 2600 |
| 1041032 | N/A | N/A | 233011 | 233030 | GTCCATACACCTTAATAAGT | 29 | 2601 |
| 1041064 | N/A | N/A | 256096 | 256115 | GATTACTTTTAAAAGCAACA | 54 | 2602 |
| 1041096 | N/A | N/A | 273624 | 273643 | CCTAAAAGAATTTATCCATA | 96 | 2603 |
| 1041128 | N/A | N/A | 290841 | 290860 | CTTGGCAAATTATTATCTGC | 12 | 2604 |
| 1041160 | N/A | N/A | 322672 | 322691 | GCTAAGAAAATATAGGCCTT | 73 | 2605 |
| 1041192 | N/A | N/A | 343258 | 343277 | GGCTTTATAGTCTAAGTTGC | 7 | 2606 |

TABLE 35-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041224 | N/A | N/A | 369453 | 369472 | ACTTCAAACCTTTATCAGTT | 3 | 2607 |
| 1041256 | N/A | N/A | 388260 | 388279 | CAAACCCAAATTTAGCTCTG | 41 | 2608 |
| 1041288 | N/A | N/A | 420471 | 420490 | CCTTTAAGCCCTTAAAGCTG | 110 | 2609 |
| 1041320 | N/A | N/A | 437794 | 437813 | GAGGTTAATTCATTACACAC | 5 | 2610 |
| 1041352 | N/A | N/A | 438248 | 438267 | GGCCTTATCATACCTAAATA | 61 | 2611 |
| 1041384 | N/A | N/A | 438538 | 438557 | ACCAGCAGCCAGACAACTAA | 66 | 2612 |
| 1041416 | N/A | N/A | 439148 | 439167 | TACCCCAAGCCCAGCAGGTC | 108 | 2613 |
| 1041448 | N/A | N/A | 439513 | 439532 | CCAAAACAATTCAAACCATT | 40 | 2614 |
| 1041480 | N/A | N/A | 440152 | 440171 | TTTCTCCTAGTACCCACCCC | 78 | 2615 |
| 1041512 | N/A | N/A | 440369 | 440388 | AAGTGGCTGCCTTCATTCTC | 44 | 2616 |
| 1041544 | N/A | N/A | 441287 | 441306 | GGAACCTCAATTAAGTCCAG | 38 | 2617 |
| 1041576 | N/A | N/A | 441615 | 441634 | CACCATACTATATCACACTG | 29 | 2618 |
| 1041608 | N/A | N/A | 442256 | 442275 | CCTCAGTTTTATATGCCATG | 6 | 2619 |
| 1041640 | N/A | N/A | 442706 | 442725 | TTATGGCCTCAAACTTGGAG | 53 | 2620 |
| 1041672 | N/A | N/A | 443046 | 443065 | TCTTTCTAGACTTTCATCAG | 33 | 2621 |
| 1041704 | N/A | N/A | 443496 | 443515 | CACTTTACCAATACATTTTA | 80 | 2622 |
| 1041736 | N/A | N/A | 443941 | 443960 | TTAGGATTCATCGCCACCAA | 19 | 2623 |
| 1041768 | N/A | N/A | 444346 | 444365 | CCAATCTATCACACCAATGC | 24 | 2624 |
| 1041800 | N/A | N/A | 445254 | 445273 | TCCCACATTAAAAGCTGGGT | 109 | 2625 |
| 1041832 | N/A | N/A | 445593 | 445612 | TCTGCAAGTGAAATTCTCAG | 66 | 2626 |
| 1041864 | N/A | N/A | 445849 | 445868 | GTACATATCACCAAAAACAA | 57 | 2627 |
| 1041896 | N/A | N/A | 446046 | 446065 | ATGTCACCTTCCTAATCTGA | 26 | 2628 |
| 1041928 | N/A | N/A | 446684 | 446703 | AATAGCCTTTATAACTTTTC | 18 | 2629 |
| 1041960 | N/A | N/A | 446894 | 446913 | TGTGTTAGTAATCATTAAGT | 19 | 2630 |
| 1041992 | N/A | N/A | 447708 | 447727 | CTGCCAAAAATCTTCTTCC | 50 | 2631 |
| 1042024 | N/A | N/A | 448482 | 448501 | TGCTGGTTCTTTAACCCCTC | 40 | 2632 |
| 1042056 | N/A | N/A | 448729 | 448748 | GCTGTTCAATCAAGCACCTT | 76 | 2633 |
| 1042088 | N/A | N/A | 449072 | 449091 | CTCAAAATATTATTGAGGGT | 35 | 2634 |
| 1042120 | N/A | N/A | 449604 | 449623 | TCTCAGTGAGAATATATATC | 103 | 2635 |
| 1042152 | N/A | N/A | 449922 | 449941 | TCAGATAATCTGATCATTGT | 54 | 2636 |
| 1042184 | N/A | N/A | 450547 | 450566 | CTTAGAATTAAATGCTGTGG | 63 | 2637 |
| 1042216 | N/A | N/A | 451173 | 451192 | GTCTCCCCCATACCCCCCT | 81 | 2638 |
| 1042248 | N/A | N/A | 451670 | 451689 | AACTCCAAAGACACCACTCT | 86 | 2639 |
| 1042280 | N/A | N/A | 451934 | 451953 | AGCCACATTATACACACTTC | 16 | 2640 |
| 1042312 | N/A | N/A | 452252 | 452271 | TCTTAGAGTCATTAACAACA | 15 | 2641 |
| 1042344 | N/A | N/A | 452506 | 452525 | TGGGCTTGTTCCATGGTACA | 42 | 2642 |

TABLE 35-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042376 | N/A | N/A | 453046 | 453065 | TCTGATACATTTCTAGAATG | 36 | 2643 |
| 1042408 | N/A | N/A | 453854 | 453873 | ACTCACAGTTTACATCTCAA | 16 | 2644 |
| 1042440 | N/A | N/A | 454687 | 454706 | GTAGAATTAAAATATACACC | 17 | 2645 |
| 1042472 | N/A | N/A | 455293 | 455312 | AGGTCTTGAATTACTTTCAC | 7 | 2646 |
| 1042504 | N/A | N/A | 456246 | 456265 | TTGGACCAACCCTCCTTCTG | 114 | 2647 |
| 1042536 | N/A | N/A | 456983 | 457002 | TTTGCAAACCTCCCTCTCCC | 106 | 2648 |

TABLE 36

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 2 | 138 |
| 1040105 | 2350 | 2369 | 437069 | 437088 | GCTCAGGTAGCCGATGACAG | 84 | 2649 |
| 1040137 | 3185 | 3204 | 457438 | 457457 | TCAGTTCGCCATTCTCAGAG | 68 | 2650 |
| 1040169 | 3938 | 3957 | 458191 | 458210 | AGCTGGGTTCCTGATGTTGA | 45 | 2651 |
| 1040201 | 4488 | 4507 | 458741 | 458760 | CAAAATCTAATTCCTCATGT | 61 | 2652 |
| 1040233 | 4742 | 4761 | 458995 | 459014 | TAGTTCATAATTCACATTCA | 19 | 2653 |
| 1040265 | 5163 | 5182 | 459416 | 459435 | CTCAGAGTTTCTAAGAGCCC | 27 | 2654 |
| 1040297 | 5481 | 5500 | 459734 | 459753 | AGTTGCAGCCATCCAAGTAA | 26 | 2655 |
| 1040329 | 5914 | 5933 | 460167 | 460186 | AGCCCGTATTCCTCTTACCA | 22 | 2656 |
| 1040361 | 6269 | 6288 | 460522 | 460541 | GGGAAGATCAACCAAACAAG | 37 | 2657 |
| 1040393 | 7076 | 7095 | 461329 | 461348 | GGTTTCTTATTAATAGTATT | 23 | 2658 |
| 1040425 | 7575 | 7594 | 461828 | 461847 | ACAACCCTACTCCAGAGCAG | 59 | 2659 |
| 1040457 | 7976 | 7995 | 462229 | 462248 | AACAGTAGCCATGACAACCA | 80 | 2660 |
| 1040489 | 8317 | 8336 | 462570 | 462589 | TGCCAGAAACACAACACTGT | 88 | 2661 |
| 1040521 | 8668 | 8687 | 462921 | 462940 | CATGTAACTTTCAACCCTTC | 28 | 2662 |
| 1040553 | 9050 | 9069 | 463303 | 463322 | TTTTGTCCCCATAATGAGTC | 47 | 2663 |
| 1040585 | 9393 | 9412 | 463646 | 463665 | ACATGAAAAACTGAAGCCGG | 67 | 2664 |
| 1040617 | 9815 | 9834 | 464068 | 464087 | CCTGGGCCAGAAAACTGAAA | 131 | 2665 |
| 1040649 | 10226 | 10245 | 464479 | 464498 | TTTCTTTTCAATAAGGTGCA | 14 | 2666 |
| 1040681 | 10476 | 10495 | 464729 | 464748 | CTAGAAAACCTGCAAGCACC | 32 | 2667 |
| 1040713 | N/A | N/A | 14562 | 14581 | GCTGAATTCAAACGCAGCA | 96 | 2668 |
| 1040745 | N/A | N/A | 28358 | 28377 | GCAGTAATTTAAAGTATGAA | 35 | 2669 |
| 1040777 | N/A | N/A | 44806 | 44825 | AACAAATTTTAAAGCTCTTT | 36 | 2670 |
| 1040809 | N/A | N/A | 75467 | 75486 | AGCATCAACCAAATTCAGTA | 20 | 2671 |

TABLE 36-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040841 | N/A | N/A | 91912 | 91931 | CCCTGACCTATTTAACATAC | 135 | 2672 |
| 1040873 | N/A | N/A | 114340 | 114359 | CTGTTTAACCAAAAACATCT | 85 | 2673 |
| 1040905 | N/A | N/A | 144629 | 144648 | ATCACTAAACGATAGCACAA | 102 | 2674 |
| 1040937 | N/A | N/A | 172695 | 172714 | AACTCCTTTTAAATTGAATT | 111 | 2675 |
| 1040969 | N/A | N/A | 193065 | 193084 | GGGATTAAATAATTATGTGC | 13 | 2676 |
| 1041001 | N/A | N/A | 209950 | 209969 | GCTAGCATATTTTAAAGAAG | 138 | 2677 |
| 1041033 | N/A | N/A | 233976 | 233995 | CCAGCATTTCAAAGAGCAAC | 69 | 2678 |
| 1041065 | N/A | N/A | 256246 | 256265 | GGCATGTTTATATAACAGCC | 124 | 2679 |
| 1041097 | N/A | N/A | 273626 | 273645 | TTCCTAAAAGAATTTATCCA | 108 | 2680 |
| 1041129 | N/A | N/A | 291710 | 291729 | GTTTCAATATTTTATGCAAA | 3 | 2681 |
| 1041161 | N/A | N/A | 322739 | 322758 | GCAGTAATAATTTAGCCAAA | 5 | 2682 |
| 1041193 | N/A | N/A | 343540 | 343559 | GCTATTAGACAATATAGAGT | 2 | 2683 |
| 1041225 | N/A | N/A | 369454 | 369473 | CACTTCAAACCTTTATCAGT | 30 | 2684 |
| 1041257 | N/A | N/A | 389567 | 389586 | AATCCTTTAATTTAACAACC | 111 | 2685 |
| 1041289 | N/A | N/A | 423903 | 423922 | CCATGAAGAATTTAACCTCA | 90 | 2686 |
| 1041321 | N/A | N/A | 437795 | 437814 | GGAGGTTAATTCATTACACA | 6 | 2687 |
| 1041353 | N/A | N/A | 438249 | 438268 | TGGCCTTATCATACCTAAAT | 80 | 2688 |
| 1041385 | N/A | N/A | 438553 | 438572 | ATTGATCACCCCAGCACCAG | 88 | 2689 |
| 1041417 | N/A | N/A | 439149 | 439168 | TTACCCCAAGCCCAGCAGGT | 95 | 2690 |
| 1041449 | N/A | N/A | 439514 | 439533 | CCCAAAACAATTCAAACCAT | 69 | 2691 |
| 1041481 | N/A | N/A | 440158 | 440177 | ATTTTCTTTCTCCTAGTACC | 69 | 2692 |
| 1041513 | N/A | N/A | 440406 | 440425 | AGAGGCTGCCAGGCCTGGGA | 106 | 2693 |
| 1041545 | N/A | N/A | 441288 | 441307 | TGGAACCTCAATTAAGTCCA | 75 | 2694 |
| 1041577 | N/A | N/A | 441617 | 441636 | ACCACCATACTATATCACAC | 37 | 2695 |
| 1041609 | N/A | N/A | 442257 | 442276 | CCCTCAGTTTTATATGCCAT | 17 | 2696 |
| 1041641 | N/A | N/A | 442708 | 442727 | ACTTATGGCCTCAAACTTGG | 63 | 2697 |
| 1041673 | N/A | N/A | 443057 | 443076 | AAGTTCAGCCTTCTTTCTAG | 28 | 2698 |
| 1041705 | N/A | N/A | 443498 | 443517 | AGCACTTTACCAATACATTT | 46 | 2699 |
| 1041737 | N/A | N/A | 443961 | 443980 | ACTATCTATTTTTGATACA | 63 | 2700 |
| 1041769 | N/A | N/A | 444350 | 444369 | GTAACCAATCTATCACACCA | 20 | 2701 |
| 1041801 | N/A | N/A | 445255 | 445274 | ATCCCACATTAAAAGCTGGG | 121 | 2702 |
| 1041833 | N/A | N/A | 445608 | 445627 | GCATTCTTAACTTTGTCTGC | 47 | 2703 |
| 1041865 | N/A | N/A | 445874 | 445893 | GTGCTATGTCTATATACACA | 71 | 2704 |
| 1041897 | N/A | N/A | 446067 | 446086 | GGGCTCATAATTATTTTTA | 103 | 2705 |
| 1041929 | N/A | N/A | 446685 | 446704 | GAATAGCCTTTATAACTTTT | 12 | 2706 |
| 1041961 | N/A | N/A | 446928 | 446947 | TCAGTTATTTTCTCTCCACT | 9 | 2707 |

TABLE 36-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041993 | N/A | N/A | 447709 | 447728 | CCTGCCAAAAAATCTTCTTC | 127 | 2708 |
| 1042025 | N/A | N/A | 448483 | 448502 | TTGCTGGTTCTTTAACCCCT | 31 | 2709 |
| 1042057 | N/A | N/A | 448731 | 448750 | CGGCTGTTCAATCAAGCACC | 85 | 2710 |
| 1042089 | N/A | N/A | 449073 | 449092 | CCTCAAATATTATTGAGGG | 153 | 2711 |
| 1042121 | N/A | N/A | 449627 | 449646 | TGAAGAAATCTCACTGAGGG | 149 | 2712 |
| 1042153 | N/A | N/A | 449929 | 449948 | AGATTATTCAGATAATCTGA | 125 | 2713 |
| 1042185 | N/A | N/A | 450548 | 450567 | CCTTAGAATTAAATGCTGTG | 84 | 2714 |
| 1042217 | N/A | N/A | 451193 | 451212 | TCCTCGATACTAACCCCTTC | 93 | 2715 |
| 1042249 | N/A | N/A | 451674 | 451693 | TCAAAACTCCAAAGACACCA | 67 | 2716 |
| 1042281 | N/A | N/A | 451935 | 451954 | GAGCCACATTATACACACTT | 30 | 2717 |
| 1042313 | N/A | N/A | 452254 | 452273 | CCTCTTAGAGTCATTAACAA | 62 | 2718 |
| 1042345 | N/A | N/A | 452531 | 452550 | AGTAGGATCCAAAGGCATGA | 29 | 2719 |
| 1042377 | N/A | N/A | 453048 | 453067 | GTTCTGATACATTTCTAGAA | 37 | 2720 |
| 1042409 | N/A | N/A | 453856 | 453875 | GAACTCACAGTTTACATCTC | 53 | 2721 |
| 1042441 | N/A | N/A | 454688 | 454707 | TGTAGAATTAAAATATACAC | 95 | 2722 |
| 1042473 | N/A | N/A | 455314 | 455333 | TGAGTCCCTAAAACTGGATT | 112 | 2723 |
| 1042505 | N/A | N/A | 456275 | 456294 | TCCTTTCTAGATGTAGTAGA | 25 | 2724 |
| 1042537 | N/A | N/A | 456984 | 457003 | GTTTGCAAACCTCCCTCTCC | 101 | 2725 |

TABLE 37

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 3 | 138 |
| 1040106 | 2686 | 2705 | 437405 | 437424 | GGAGCCTTTCATGAAGTAGG | 28 | 2726 |
| 1040138 | 3195 | 3214 | 457448 | 457467 | TCTGGAAACTTCAGTTCGCC | 91 | 2727 |
| 1040170 | 3984 | 4003 | 458237 | 458256 | TTAACTTTCCAAATCTGCCA | 21 | 2728 |
| 1040202 | 4491 | 4510 | 458744 | 458763 | CTTCAAAATCTAATTCCTCA | 43 | 2729 |
| 1040234 | 4745 | 4764 | 458998 | 459017 | TACTAGTTCATAATTCACAT | 29 | 2730 |
| 1040266 | 5164 | 5183 | 459417 | 459436 | TCTCAGAGTTTCTAAGAGCC | 28 | 2731 |
| 1040298 | 5494 | 5513 | 459747 | 459766 | ATTTGTTCAGTTTAGTTGCA | 10 | 2732 |
| 1040330 | 5934 | 5953 | 460187 | 460206 | GAGAACAAAGTCTATGTGGC | 19 | 2733 |
| 1040362 | 6304 | 6323 | 460557 | 460576 | GGCTCCTTCCCTCCAGCCCT | 115 | 2734 |
| 1040394 | 7078 | 7097 | 461331 | 461350 | TTGGTTTCTTATTAATAGTA | 11 | 2735 |

TABLE 37-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040426 | 7579 | 7598 | 461832 | 461851 | TTGTACAACCCTACTCCAGA | 78 | 2736 |
| 1040458 | 7985 | 8004 | 462238 | 462257 | GGTTCATGAAACAGTAGCCA | 93 | 2737 |
| 1040490 | 8319 | 8338 | 462572 | 462591 | TATGCCAGAAACACAACACT | 86 | 2738 |
| 1040522 | 8669 | 8688 | 462922 | 462941 | ACATGTAACTTTCAACCCTT | 29 | 2739 |
| 1040554 | 9051 | 9070 | 463304 | 463323 | TTTTTGTCCCCATAATGAGT | 34 | 2740 |
| 1040586 | 9396 | 9415 | 463649 | 463668 | GGGACATGAAAAACTGAAGC | 22 | 2741 |
| 1040618 | 9830 | 9849 | 464083 | 464102 | AGGATTTACCCCACTCCTGG | 82 | 2742 |
| 1040650 | 10228 | 10247 | 464481 | 464500 | ATTTTCTTTTCAATAAGGTG | 17 | 2743 |
| 1040682 | 10481 | 10500 | 464734 | 464753 | TCTACCTAGAAAACCTGCAA | 44 | 2744 |
| 1040714 | N/A | N/A | 14865 | 14884 | CTCACATTTTAAAGAGTCTG | 41 | 2745 |
| 1040746 | N/A | N/A | 29049 | 29068 | TCACTGAACCCTTATTTTTT | 30 | 2746 |
| 1040778 | N/A | N/A | 46649 | 46668 | ACTAGAAAAGCCACCCTTCT | 129 | 2747 |
| 1040810 | N/A | N/A | 76238 | 76257 | AGTCTGTATATTTATATTTA | 47 | 2748 |
| 1040842 | N/A | N/A | 92036 | 92055 | CCTTTGTTTTAAAATAGGTA | 122 | 2749 |
| 1040874 | N/A | N/A | 114410 | 114429 | AATGCCAAAGATATACGCCA | 6 | 2750 |
| 1040906 | N/A | N/A | 145082 | 145101 | AGTTAATATCCTTAATACAA | 44 | 2751 |
| 1040938 | N/A | N/A | 173470 | 173489 | AAGTACTATCATTATTGCAT | 113 | 2752 |
| 1040970 | N/A | N/A | 193239 | 193258 | TTCCCCTTATTTTATTCATA | 63 | 2753 |
| 1041002 | N/A | N/A | 210713 | 210732 | TTCCTTCTAGATTAAAGACT | 62 | 2754 |
| 1041034 | N/A | N/A | 234265 | 234284 | AACACAATTTAAATTGAGTT | 127 | 2755 |
| 1041066 | N/A | N/A | 256364 | 256383 | CCTAAGTACCCTTAATTTTT | 65 | 2756 |
| 1041098 | N/A | N/A | 273876 | 273895 | TGTCTATTTCAAAGAAGCGA | 80 | 2757 |
| 1041130 | N/A | N/A | 292765 | 292784 | CACACAATTCAAAACTTGAA | 93 | 2758 |
| 1041162 | N/A | N/A | 322761 | 322780 | AGCAGAATCTAAATCGAACA | 22 | 2759 |
| 1041194 | N/A | N/A | 343565 | 343584 | CGTGTTTTTATTTAACAATA | 2 | 2760 |
| 1041226 | N/A | N/A | 369541 | 369560 | ATTTCTTATATTTATGGGCT | 3 | 2761 |
| 1041258 | N/A | N/A | 391393 | 391412 | TATAGTAGTATTTATAGCTC | 28 | 2762 |
| 1041290 | N/A | N/A | 424357 | 424376 | ACCCCATTTCAAAGACAAGG | 59 | 2763 |
| 1041322 | N/A | N/A | 437796 | 437815 | TGGAGGTTAATTCATTACAC | 12 | 2764 |
| 1041354 | N/A | N/A | 438250 | 438269 | TTGGCCTTATCATACCTAAA | 34 | 2765 |
| 1041386 | N/A | N/A | 438574 | 438593 | GTGCCCAGCCCTTCCACCTG | 55 | 2766 |
| 1041418 | N/A | N/A | 439153 | 439172 | GACTTTACCCCAAGCCCAGC | 98 | 2767 |
| 1041450 | N/A | N/A | 439516 | 439535 | TGCCCAAAACAATTCAAACC | 94 | 2768 |
| 1041482 | N/A | N/A | 440163 | 440182 | AGTTCATTTTCTTTCTCCTA | 5 | 2769 |
| 1041514 | N/A | N/A | 440419 | 440438 | GTCTGGTTTCTGCAGAGGCT | 42 | 2770 |
| 1041546 | N/A | N/A | 441292 | 441311 | CCTTTGGAACCTCAATTAAG | 89 | 2771 |

TABLE 37-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
| --- | --- | --- | --- | --- | --- | --- | --- |
| 1041578 | N/A | N/A | 441621 | 441640 | TGTCACCACCATACTATATC | 26 | 2772 |
| 1041610 | N/A | N/A | 442258 | 442277 | CCCCTCAGTTTTATATGCCA | 45 | 2773 |
| 1041642 | N/A | N/A | 442717 | 442736 | GCGCCACAGACTTATGGCCT | 142 | 2774 |
| 1041674 | N/A | N/A | 443092 | 443111 | GGCAGGGTAAAAATGGCTTA | 52 | 2775 |
| 1041706 | N/A | N/A | 443499 | 443518 | GAGCACTTTACCAATACATT | 23 | 2776 |
| 1041738 | N/A | N/A | 443965 | 443984 | ACCAACTATCTATTTTTTGA | 51 | 2777 |
| 1041770 | N/A | N/A | 444351 | 444370 | TGTAACCAATCTATCACACC | 30 | 2778 |
| 1041802 | N/A | N/A | 445261 | 445280 | ACACAAATCCCACATTAAAA | 92 | 2779 |
| 1041834 | N/A | N/A | 445611 | 445630 | TGGGCATTCTTAACTTTGTC | 28 | 2780 |
| 1041866 | N/A | N/A | 445897 | 445916 | TTGTATATTTCAATCTTAGA | 26 | 2781 |
| 1041898 | N/A | N/A | 446071 | 446090 | TTCTGGGCTCATAATTATTT | 52 | 2782 |
| 1041930 | N/A | N/A | 446687 | 446706 | TAGAATAGCCTTTATAACTT | 33 | 2783 |
| 1041962 | N/A | N/A | 446929 | 446948 | TTCAGTTATTTTCTCTCCAC | 16 | 2784 |
| 1041994 | N/A | N/A | 447710 | 447729 | TCCTGCCAAAAAATCTTCTT | 118 | 2785 |
| 1042026 | N/A | N/A | 448513 | 448532 | ACTCCCTACACTGTAGCAAC | 97 | 2786 |
| 1042058 | N/A | N/A | 448749 | 448768 | AATGGTATCCCATTCTTCCG | 63 | 2787 |
| 1042090 | N/A | N/A | 449075 | 449094 | GGCCTCAAAATATTATTGAG | 107 | 2788 |
| 1042122 | N/A | N/A | 449649 | 449668 | TTAACTGATCATTAACCGTT | 49 | 2789 |
| 1042154 | N/A | N/A | 449930 | 449949 | AAGATTATTCAGATAATCTG | 178 | 2790 |
| 1042186 | N/A | N/A | 450550 | 450569 | GGCCTTAGAATTAAATGCTG | 145 | 2791 |
| 1042218 | N/A | N/A | 451194 | 451213 | CTCCTCGATACTAACCCCTT | 118 | 2792 |
| 1042250 | N/A | N/A | 451676 | 451695 | TCTCAAAACTCCAAAGACAC | 80 | 2793 |
| 1042282 | N/A | N/A | 451937 | 451956 | GTGAGCCACATTATACACAC | 69 | 2794 |
| 1042314 | N/A | N/A | 452263 | 452282 | TCTTGCAAACCTCTTAGAGT | 74 | 2795 |
| 1042346 | N/A | N/A | 452544 | 452563 | ATTGACTGAAATAAGTAGGA | 16 | 2796 |
| 1042378 | N/A | N/A | 453050 | 453069 | TAGTTCTGATACATTTCTAG | 47 | 2797 |
| 1042410 | N/A | N/A | 453883 | 453902 | CATATTATCTCCAAATAAGC | 124 | 2798 |
| 1042442 | N/A | N/A | 454701 | 454720 | GGTCTATGAGAATTGTAGAA | 32 | 2799 |
| 1042474 | N/A | N/A | 455315 | 455334 | CTGAGTCCCTAAAACTGGAT | 78 | 2800 |
| 1042506 | N/A | N/A | 456290 | 456309 | AGTCAATTTCCAATGTCCTT | 21 | 2801 |
| 1042538 | N/A | N/A | 456985 | 457004 | AGTTTGCAAACCTCCCTCTC | 117 | 2802 |

TABLE 38

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTCTATTTGCAC | 2 | 138 |
| 1040107 | 2687 | 2706 | 437406 | 437425 | TGGAGCCTTTCATGAAGTAG | 23 | 2803 |
| 1040139 | 3196 | 3215 | 457449 | 457468 | CTCTGGAAACTTCAGTTCGC | 87 | 2804 |
| 1040171 | 3985 | 4004 | 458238 | 458257 | GTTAACTTTCCAAATCTGCC | 23 | 2805 |
| 1040203 | 4493 | 4512 | 458746 | 458765 | ATCTTCAAAATCTAATTCCT | 45 | 2806 |
| 1040235 | 4746 | 4765 | 458999 | 459018 | ATACTAGTTCATAATTCACA | 35 | 2807 |
| 1040267 | 5172 | 5191 | 459425 | 459444 | AAGAAAATTCTCAGAGTTTC | 56 | 2808 |
| 1040299 | 5502 | 5521 | 459755 | 459774 | AGTCAGGTATTTGTTCAGTT | 5 | 2809 |
| 1040331 | 5952 | 5971 | 460205 | 460224 | GTAAATAGTGATATTAATGA | 53 | 2810 |
| 1040363 | 6365 | 6384 | 460618 | 460637 | GCTCCCCGCCCCAGCACTCA | 102 | 2811 |
| 1040395 | 7081 | 7100 | 461334 | 461353 | TTGTTGGTTTCTTATTAATA | 16 | 2812 |
| 1040427 | 7580 | 7599 | 461833 | 461852 | ATTGTACAACCCTACTCCAG | 70 | 2813 |
| 1040459 | 7987 | 8006 | 462240 | 462259 | GTGGTTCATGAAACAGTAGC | 88 | 2814 |
| 1040491 | 8321 | 8340 | 462574 | 462593 | CCTATGCCAGAAACACAACA | 72 | 2815 |
| 1040523 | 8683 | 8702 | 462936 | 462955 | CTATATACAAAAAAACATGT | 121 | 2816 |
| 1040555 | 9099 | 9118 | 463352 | 463371 | CCCCCATTTAAATGAGGTGT | 141 | 2817 |
| 1040587 | 9424 | 9443 | 463677 | 463696 | CAGTTGAACCATTTGTATGC | 22 | 2818 |
| 1040619 | 9842 | 9861 | 464095 | 464114 | TGCACTAACTAAAGGATTTA | 46 | 2819 |
| 1040651 | 10229 | 10248 | 464482 | 464501 | AATTTTCTTTTCAATAAGGT | 93 | 2820 |
| 1040683 | 10482 | 10501 | 464735 | 464754 | TTCTACCTAGAAAACCTGCA | 41 | 2821 |
| 1040715 | N/A | N/A | 16686 | 16705 | CTCGAAAACATATCCCCCA | 52 | 2822 |
| 1040747 | N/A | N/A | 29088 | 29107 | TGGTAATTTTAAAATATGGG | 15 | 2823 |
| 1040779 | N/A | N/A | 48578 | 48597 | GTGTTAATTCAAAAAATTTC | 119 | 2824 |
| 1040811 | N/A | N/A | 76251 | 76270 | TGCATACAAATTTAGTCTGT | 21 | 2825 |
| 1040843 | N/A | N/A | 93032 | 93051 | TCTAGATTACAAACCATCCT | 110 | 2826 |
| 1040875 | N/A | N/A | 114768 | 114787 | TTTCATTTTATTTAAGCCAA | 20 | 2827 |
| 1040907 | N/A | N/A | 146636 | 146655 | AAGATGTTTTAAAATCTGAC | 107 | 2828 |
| 1040939 | N/A | N/A | 174742 | 174761 | GTACTTGTTCCTTAACCAAG | 149 | 2829 |
| 1040971 | N/A | N/A | 193345 | 193364 | TCAGTTTACCTTTAATGGAA | 30 | 2830 |
| 1041003 | N/A | N/A | 211774 | 211793 | TGCTCAATATTTTAAACATT | 44 | 2831 |
| 1041035 | N/A | N/A | 234289 | 234308 | GTCGGATAAATTTATCCACA | 131 | 2832 |
| 1041067 | N/A | N/A | 256544 | 256563 | TTAGCAAACATTTATGAGCA | 45 | 2833 |
| 1041099 | N/A | N/A | 274538 | 274557 | CTTCCAATCCATTACATCTT | 81 | 2834 |
| 1041131 | N/A | N/A | 293124 | 293143 | CCTTCCAACCCTTAGCCTTT | 12 | 2835 |
| 1041163 | N/A | N/A | 323168 | 323187 | AGCCAAAAACCCATGGACCA | 120 | 2836 |
| 1041195 | N/A | N/A | 343967 | 343986 | ACAGTAATCTTTTATACAAG | 19 | 2837 |

TABLE 38-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041227 | N/A | N/A | 369669 | 369688 | TTCCCGAACCCTTAAGGATA | 99 | 2838 |
| 1041259 | N/A | N/A | 391405 | 391424 | AGTTGACACCTTTATAGTAG | 4 | 2839 |
| 1041291 | N/A | N/A | 424646 | 424665 | GTCTTAAAACTATTCACTGT | 81 | 2840 |
| 1041323 | N/A | N/A | 437820 | 437839 | ATAACTAGCCCCACTCTCCA | 98 | 2841 |
| 1041355 | N/A | N/A | 438251 | 438270 | GTTGGCCTTATCATACCTAA | 21 | 2842 |
| 1041387 | N/A | N/A | 438878 | 438897 | GCTGCCTTCCATCTGTTTTT | 90 | 2843 |
| 1041419 | N/A | N/A | 439154 | 439173 | TGACTTTACCCCAAGCCCAG | 109 | 2844 |
| 1041451 | N/A | N/A | 439554 | 439573 | GAGACAAGAAACACTGTCTC | 153 | 2845 |
| 1041483 | N/A | N/A | 440171 | 440190 | CTCAAGGTAGTTCATTTTCT | 10 | 2846 |
| 1041515 | N/A | N/A | 440723 | 440742 | GCCTACAATCCCAGCTTTAG | 88 | 2847 |
| 1041547 | N/A | N/A | 441337 | 441356 | GAGAAAACCCCTCAGGAAGG | 115 | 2848 |
| 1041579 | N/A | N/A | 441623 | 441642 | TCTGTCACCACCATACTATA | 57 | 2849 |
| 1041611 | N/A | N/A | 442265 | 442284 | CTAAACACCCCTCAGTTTTA | 100 | 2850 |
| 1041643 | N/A | N/A | 442722 | 442741 | TGGATGCGCCACAGACTTAT | 59 | 2851 |
| 1041675 | N/A | N/A | 443093 | 443112 | AGGCAGGGTAAAAATGGCTT | 66 | 2852 |
| 1041707 | N/A | N/A | 443502 | 443521 | CCAGAGCACTTTACCAATAC | 30 | 2853 |
| 1041739 | N/A | N/A | 443966 | 443985 | CACCAACTATCTATTTTTG | 47 | 2854 |
| 1041771 | N/A | N/A | 444355 | 444374 | CAGTTGTAACCAATCTATCA | 22 | 2855 |
| 1041803 | N/A | N/A | 445267 | 445286 | CTCCTAACACAAATCCCACA | 124 | 2856 |
| 1041835 | N/A | N/A | 445625 | 445644 | CGAAATTATTAAATTGGGCA | 36 | 2857 |
| 1041867 | N/A | N/A | 445899 | 445918 | GATTGTATATTTCAATCTTA | 55 | 2858 |
| 1041899 | N/A | N/A | 446086 | 446105 | ACAACACCGACTCACTTCTG | 41 | 2859 |
| 1041931 | N/A | N/A | 446708 | 446727 | TCAAACACCCTAAGCAGTAA | 74 | 2860 |
| 1041963 | N/A | N/A | 446930 | 446949 | CTTCAGTTATTTTCTCTCCA | 10 | 2861 |
| 1041995 | N/A | N/A | 447711 | 447730 | ATCCTGCCAAAAAATCTTCT | 100 | 2862 |
| 1042027 | N/A | N/A | 448517 | 448536 | CCTTACTCCCTACACTGTAG | 99 | 2863 |
| 1042059 | N/A | N/A | 448770 | 448789 | ATGTTCTTCCCCATCTCCAT | 36 | 2864 |
| 1042091 | N/A | N/A | 449076 | 449095 | CGGCCTCAAAATATTATTGA | 165 | 2865 |
| 1042123 | N/A | N/A | 449669 | 449688 | GATATAAACATTCTTAAAGG | 92 | 2866 |
| 1042155 | N/A | N/A | 449932 | 449951 | GGAAGATTATTCAGATAATC | 24 | 2867 |
| 1042187 | N/A | N/A | 450551 | 450570 | AGGCCTTAGAATTAAATGCT | 137 | 2868 |
| 1042219 | N/A | N/A | 451198 | 451217 | CAGTCTCCTCGATACTAACC | 67 | 2869 |
| 1042251 | N/A | N/A | 451677 | 451696 | ATCTCAAAACTCCAAAGACA | 87 | 2870 |
| 1042283 | N/A | N/A | 451938 | 451957 | TGTGAGCCACATTATACACA | 69 | 2871 |
| 1042315 | N/A | N/A | 452264 | 452283 | CTCTTGCAAACCTCTTAGAG | 99 | 2872 |
| 1042347 | N/A | N/A | 452571 | 452590 | TCCTGCTACCCCCAACAGT | 124 | 2873 |

TABLE 38-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042379 | N/A | N/A | 453088 | 453107 | TTCATCTTCTTTGTTTCCTT | 25 | 2874 |
| 1042411 | N/A | N/A | 453892 | 453911 | AACAAAATACATATTATCTC | 99 | 2875 |
| 1042443 | N/A | N/A | 454927 | 454946 | CCGTTTCTACAGAAATTTAA | 78 | 2876 |
| 1042475 | N/A | N/A | 455316 | 455335 | TCTGAGTCCCTAAAACTGGA | 90 | 2877 |
| 1042507 | N/A | N/A | 456620 | 456639 | CCCAGCCCCTAAAAGGATGC | 118 | 2878 |
| 1042539 | N/A | N/A | 457035 | 457054 | AGGTATGAACTCACACAGAC | 63 | 2879 |

TABLE 39

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 2 | 138 |
| 1040108 | 2725 | 2744 | 437444 | 437463 | TTCCACCTTCTTTAGCTCCC | 67 | 2880 |
| 1040140 | 3212 | 3231 | 457465 | 457484 | CAGGCAATCCCATTTTCTCT | 84 | 2881 |
| 1040172 | 4000 | 4019 | 458253 | 458272 | ATGTTCTTTTAAATGGTTAA | 15 | 2882 |
| 1040204 | 4494 | 4513 | 458747 | 458766 | CATCTTCAAAATCTAATTCC | 66 | 2883 |
| 1040236 | 4749 | 4768 | 459002 | 459021 | CACATACTAGTTCATAATTC | 20 | 2884 |
| 1040268 | 5188 | 5207 | 459441 | 459460 | TCTCTCAATGAATCTGAAGA | 26 | 2885 |
| 1040300 | 5514 | 5533 | 459767 | 459786 | GGGTAAAAGAAAAGTCAGGT | 10 | 2886 |
| 1040332 | 5954 | 5973 | 460207 | 460226 | TTGTAAATAGTGATATTAAT | 74 | 2887 |
| 1040364 | 6439 | 6458 | 460692 | 460711 | CTGCGGTTCCTCCCCCGGGT | 124 | 2888 |
| 1040396 | 7117 | 7136 | 461370 | 461389 | ATATATTTAGAAATCCCTAG | 82 | 2889 |
| 1040428 | 7581 | 7600 | 461834 | 461853 | AATTGTACAACCCTACTCCA | 98 | 2890 |
| 1040460 | 8014 | 8033 | 462267 | 462286 | GCAACAGACCAGTCTGTTGA | 113 | 2891 |
| 1040492 | 8323 | 8342 | 462576 | 462595 | TCCCTATGCCAGAAACACAA | 70 | 2892 |
| 1040524 | 8684 | 8703 | 462937 | 462956 | TCTATATACAAAAAACATG | 103 | 2893 |
| 1040556 | 9100 | 9119 | 463353 | 463372 | CCCCCCATTTAAATGAGGTG | 114 | 2894 |
| 1040588 | 9426 | 9445 | 463679 | 463698 | TACAGTTGAACCATTTGTAT | 67 | 2895 |
| 1040620 | 9862 | 9881 | 464115 | 464134 | GCACAGGTATCAAGTTCAAA | 17 | 2896 |
| 1040652 | 10235 | 10254 | 464488 | 464507 | ACTTAAAATTTCTTTTCAA | 109 | 2897 |
| 1040684 | 10493 | 10512 | 464746 | 464765 | AATGAAATAATTTCTACCTA | 55 | 2898 |
| 1040716 | N/A | N/A | 16822 | 16841 | GGCACATTTTAAAAGAAGC | 23 | 2899 |
| 1040748 | N/A | N/A | 30745 | 30764 | TGTTTGCTATTTTAAGAGCC | 24 | 2900 |
| 1040780 | N/A | N/A | 48620 | 48639 | GCTAGTAAAATTTAGGGCAG | 36 | 2901 |
| 1040812 | N/A | N/A | 76786 | 76805 | TCTGAAAACCTCTTCCTCT | 60 | 2902 |

TABLE 39-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040844 | N/A | N/A | 93297 | 93316 | GATGCATTTCATTACTGCTT | 41 | 2903 |
| 1040876 | N/A | N/A | 114844 | 114863 | ATGTAATATTAAATAGCATC | 70 | 2904 |
| 1040908 | N/A | N/A | 148861 149972 | 148880 149991 | AGGTAATTTCAAAGCTTCCA | 4 | 2905 |
| 1040940 | N/A | N/A | 175616 | 175635 | CTTTCAATTCCTTAAAAGGA | 101 | 2906 |
| 1040972 | N/A | N/A | 195063 | 195082 | ACACACAAAGAATGAACCAT | 57 | 2907 |
| 1041004 | N/A | N/A | 212966 | 212985 | ATCCTAATTCAAAAACTAGT | 131 | 2908 |
| 1041036 | N/A | N/A | 235568 | 235587 | AGCCATAAAACCATGCGGTT | 91 | 2909 |
| 1041068 | N/A | N/A | 256941 | 256960 | TTACCCAAATTATCACTGTA | 47 | 2910 |
| 1041100 | N/A | N/A | 274711 | 274730 | GGACTTAACCCTTACTCCAA | 84 | 2911 |
| 1041132 | N/A | N/A | 293412 | 293431 | TGTTAGCTATTTTATATGGA | 2 | 2912 |
| 1041164 | N/A | N/A | 323174 | 323193 | TTACACAGCCAAAAACCCAT | 100 | 2913 |
| 1041196 | N/A | N/A | 344505 | 344524 | TGAGTAATTTAAAATGCCCA | 43 | 2914 |
| 1041228 | N/A | N/A | 369876 | 369895 | AAGGTCTGCCTTTAACATTT | 14 | 2915 |
| 1041260 | N/A | N/A | 392003 | 392022 | GTAAAATTTCTTTATGTGTG | 4 | 2916 |
| 1041292 | N/A | N/A | 424647 | 424666 | AGTCTTAAAACTATTCACTG | 78 | 2917 |
| 1041324 | N/A | N/A | 437831 | 437850 | TCAAGGACTCCATAACTAGC | 111 | 2918 |
| 1041356 | N/A | N/A | 438263 | 438282 | GCTGATCTATCTGTTGGCCT | 58 | 2919 |
| 1041388 | N/A | N/A | 438882 | 438901 | TAGGGCTGCCTTCCATCTGT | 51 | 2920 |
| 1041420 | N/A | N/A | 439156 | 439175 | GCTGACTTTACCCCAAGCCC | 100 | 2921 |
| 1041452 | N/A | N/A | 439834 | 439853 | AATGCTCAAAAAGCCAGAC | 54 | 2922 |
| 1041484 | N/A | N/A | 440190 | 440209 | CTGTGAAGAGTCAACTTTGC | 65 | 2923 |
| 1041516 | N/A | N/A | 440724 | 440743 | CGCCTACAATCCCAGCTTTA | 93 | 2924 |
| 1041548 | N/A | N/A | 441358 | 441377 | GGAAGATTCTTCAGGCTAGG | 11 | 2925 |
| 1041580 | N/A | N/A | 441624 | 441643 | GTCTGTCACCACCATACTAT | 34 | 2926 |
| 1041612 | N/A | N/A | 442271 | 442290 | CCCAAACTAAACACCCCTCA | 97 | 2927 |
| 1041644 | N/A | N/A | 442787 | 442806 | AGCCCATCCTTCTTTTGAG | 88 | 2928 |
| 1041676 | N/A | N/A | 443103 | 443122 | CGAGGATTACAGGCAGGGTA | 15 | 2929 |
| 1041708 | N/A | N/A | 443511 | 443530 | CGTGTCAACCCAGAGCACTT | 120 | 2930 |
| 1041740 | N/A | N/A | 443969 | 443988 | AGTCACCAACTATCTATTTT | 53 | 2931 |
| 1041772 | N/A | N/A | 444356 | 444375 | TCAGTTGTAACCAATCTATC | 20 | 2932 |
| 1041804 | N/A | N/A | 445269 | 445288 | GCCTCCTAACACAAATCCCA | 93 | 2933 |
| 1041836 | N/A | N/A | 445626 | 445645 | GCGAAATTATTAAATTGGGC | 50 | 2934 |
| 1041868 | N/A | N/A | 445900 | 445919 | TGATTGTATATTTCAATCTT | 114 | 2935 |
| 1041900 | N/A | N/A | 446090 | 446109 | GGAGACAACACCGACTCACT | 81 | 2936 |
| 1041932 | N/A | N/A | 446710 | 446729 | TTTCAAACACCCTAAGCAGT | 92 | 2937 |

TABLE 39-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041964 | N/A | N/A | 446938 | 446957 | GAATCACACTTCAGTTATTT | 19 | 2938 |
| 1041996 | N/A | N/A | 447713 | 447732 | CCATCCTGCCAAAAAATCTT | 111 | 2939 |
| 1042028 | N/A | N/A | 448519 | 448538 | CCCCTTACTCCCTACACTGT | 95 | 2940 |
| 1042060 | N/A | N/A | 448773 | 448792 | CCCATGTTCTTCCCCATCTC | 70 | 2941 |
| 1042092 | N/A | N/A | 449077 | 449096 | CCGGCCTCAAAATATTATTG | 114 | 2942 |
| 1042124 | N/A | N/A | 449672 | 449691 | AAGGATATAAACATTCTTAA | 73 | 2943 |
| 1042156 | N/A | N/A | 449935 | 449954 | AGCGGAAGATTATTCAGATA | 18 | 2944 |
| 1042188 | N/A | N/A | 450567 | 450586 | CCAAATCTCCAAAGACAGGC | 54 | 2945 |
| 1042220 | N/A | N/A | 451224 | 451243 | ACTGGTGCCCAAATGTCTAT | 54 | 2946 |
| 1042252 | N/A | N/A | 451679 | 451698 | GCATCTCAAAACTCCAAAGA | 31 | 2947 |
| 1042284 | N/A | N/A | 451940 | 451959 | TGTGTGAGCCACATTATACA | 86 | 2948 |
| 1042316 | N/A | N/A | 452275 | 452294 | CTCCATAGATCCTCTTGCAA | 106 | 2949 |
| 1042348 | N/A | N/A | 452589 | 452608 | AAGAGATGAACTAAGCATTC | 52 | 2950 |
| 1042380 | N/A | N/A | 453101 | 453120 | GTTGCTTTTCTACTTCATCT | 21 | 2951 |
| 1042412 | N/A | N/A | 453897 | 453916 | TCTAGAACAAAATACATATT | 131 | 2952 |
| 1042444 | N/A | N/A | 455045 | 455064 | ATCCATGAAGCCAGGCATGG | 165 | 2953 |
| 1042476 | N/A | N/A | 455318 | 455337 | CATCTGAGTCCCTAAAACTG | 93 | 2954 |
| 1042508 | N/A | N/A | 456623 | 456642 | GTCCCCAGCCCCTAAAGGA | 101 | 2955 |
| 1042540 | N/A | N/A | 457036 | 457055 | CAGGTATGAACTCACACAGA | 56 | 2956 |

TABLE 40

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 3 | 138 |
| 1040109 | 2741 | 2760 | 437460 | 437479 | CTTCTGTTTTAAGTCTTCC | 30 | 2957 |
| 1040141 | 3213 | 3232 | 457466 | 457485 | GCAGGCAATCCCATTTTCTC | 78 | 2958 |
| 1040173 | 4010 | 4029 | 458263 | 458282 | GGAGAGAAAAATGTTCTTTT | 5 | 2959 |
| 1040205 | 4497 | 4516 | 458750 | 458769 | GCTCATCTTCAAAATCTAAT | 9 | 2960 |
| 1040237 | 4758 | 4777 | 459011 | 459030 | ATTTATTGTCACATACTAGT | 76 | 2961 |
| 1040269 | 5216 | 5235 | 459469 | 459488 | CACATATATAAATGTCTTTA | 28 | 2962 |
| 1040301 | 5533 | 5552 | 459786 | 459805 | GAAAGTACTATTTTCAATGG | 27 | 2963 |
| 1040333 | 5959 | 5978 | 460212 | 460231 | ATGAGTTGTAAATAGTGATA | 22 | 2964 |
| 1040365 | 6440 | 6459 | 460693 | 460712 | ACTGCGGTTCCTCCCCCGGG | 111 | 2965 |
| 1040397 | 7126 | 7145 | 461379 | 461398 | AGTCATTTTATATATTTAGA | 58 | 2966 |

TABLE 40-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1040429 | 7601 | 7620 | 461854 | 461873 | GAAATCCAAACATTCCTTGA | 51 | 2967 |
| 1040461 | 8061 | 8080 | 462314 | 462333 | GCCCTGTTTTCACCTGGTGC | 57 | 2968 |
| 1040493 | 8325 | 8344 | 462578 | 462597 | TTTCCCTATGCCAGAAACAC | 63 | 2969 |
| 1040525 | 8685 | 8704 | 462938 | 462957 | TTCTATATACAAAAAACAT | 107 | 2970 |
| 1040557 | 9101 | 9120 | 463354 | 463373 | TCCCCCCATTTAAATGAGGT | 145 | 2971 |
| 1040589 | 9439 | 9458 | 463692 | 463711 | CACTTAATTTTAATACAGTT | 44 | 2972 |
| 1040621 | 9883 | 9902 | 464136 | 464155 | GCAGTATTCACAGAACTGAA | 61 | 2973 |
| 1040653 | 10237 | 10256 | 464490 | 464509 | GCACTTAAAATTTTCTTTTC | 17 | 2974 |
| 1040685 | 10507 | 10526 | 464760 | 464779 | TGTTTTATTATAATAATGAA | 157 | 2975 |
| 1040717 | N/A | N/A | 17529 | 17548 | ACATCAAAACGATTTCTACT | 25 | 2976 |
| 1040749 | N/A | N/A | 31007 | 31026 | AACCAAAACCAAAAGCCTCT | 51 | 2977 |
| 1040781 | N/A | N/A | 48839 | 48858 | AATCTAAAATACATCTGCAT | 103 | 2978 |
| 1040813 | N/A | N/A | 77220 | 77239 | CAGTTTATTTAAAGATATAA | 119 | 2979 |
| 1040845 | N/A | N/A | 94390 | 94409 | ATCAGTAAAGAATTGATGTC | 115 | 2980 |
| 1040877 | N/A | N/A | 114917 | 114936 | CTTCATAAAATTCCATTCTG | 26 | 2981 |
| 1040909 | N/A | N/A | 148914 150025 | 148933 150044 | GCTTTCATAATATAACAACC | 6 | 2982 |
| 1040941 | N/A | N/A | 176494 | 176513 | ATCAACAAAATTATGTATGG | 124 | 2983 |
| 1040973 | N/A | N/A | 195332 | 195351 | GGAAACAACCAAAGTTTTTT | 58 | 2984 |
| 1041005 | N/A | N/A | 213451 | 213470 | CTGTAGTTTTAAAAGTGCCT | 15 | 2985 |
| 1041037 | N/A | N/A | 236934 | 236953 | ACCATATTTCTTTAGAAGGT | 70 | 2986 |
| 1041069 | N/A | N/A | 257007 | 257026 | GTGACCAAAATACATATACT | 47 | 2987 |
| 1041101 | N/A | N/A | 274862 | 274881 | ACTGGATTTATTTAAGTCTT | 96 | 2988 |
| 1041133 | N/A | N/A | 294752 | 294771 | GAGTCTTGCCCTTAAGAAGC | 4 | 2989 |
| 1041165 | N/A | N/A | 323691 | 323710 | TTGATATTTCAAAAGAGCTA | 45 | 2990 |
| 1041197 | N/A | N/A | 344706 | 344725 | ATGTAAATATTTTAGCACAG | 3 | 2991 |
| 1041229 | N/A | N/A | 370271 | 370290 | GACTAATTTTAAAATATGCT | 36 | 2992 |
| 1041261 | N/A | N/A | 392692 | 392711 | GAGATAAAATTATGTAGTT | 86 | 2993 |
| 1041293 | N/A | N/A | 425116 | 425135 | TGGGATAATATTTATAAGTG | 43 | 2994 |
| 1041325 | N/A | N/A | 437884 | 437903 | ATCTTAATCACAGAATTCAA | 46 | 2995 |
| 1041357 | N/A | N/A | 438268 | 438287 | TGTCTGCTGATCTATCTGTT | 14 | 2996 |
| 1041389 | N/A | N/A | 438883 | 438902 | TTAGGGCTGCCTTCCATCTG | 58 | 2997 |
| 1041421 | N/A | N/A | 439158 | 439177 | CAGCTGACTTTACCCCAAGC | 77 | 2998 |
| 1041453 | N/A | N/A | 439844 | 439863 | GCATTTAAGAAATGCTCAAA | 132 | 2999 |
| 1041485 | N/A | N/A | 440217 | 440236 | GTTTATTTTCCATGTGTCAC | 2 | 3000 |
| 1041517 | N/A | N/A | 440772 | 440791 | CTCCCCAAGAACAGAAGAGG | 149 | 3001 |

TABLE 40-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041549 | N/A | N/A | 441359 | 441378 | AGGAAGATTCTTCAGGCTAG | 17 | 3002 |
| 1041581 | N/A | N/A | 441646 | 441665 | AGACCCAAATCCGCACCCCT | 134 | 3003 |
| 1041613 | N/A | N/A | 442273 | 442292 | TCCCCAAACTAAACACCCCT | 106 | 3004 |
| 1041645 | N/A | N/A | 442814 | 442833 | TACTTCCTACCCAAGGAGGA | 124 | 3005 |
| 1041677 | N/A | N/A | 443114 | 443133 | GGATTCCACCCCGAGGATTA | 120 | 3006 |
| 1041709 | N/A | N/A | 443555 | 443574 | CCCTAATAACACAGAGCCTG | 113 | 3007 |
| 1041741 | N/A | N/A | 443971 | 443990 | GCAGTCACCAACTATCTATT | 47 | 3008 |
| 1041773 | N/A | N/A | 444357 | 444376 | ATCAGTTGTAACCAATCTAT | 16 | 3009 |
| 1041805 | N/A | N/A | 445298 | 445317 | TCAGTAAACCCACACCCTAG | 109 | 3010 |
| 1041837 | N/A | N/A | 445627 | 445646 | GGCGAAATTATTAAATTGGG | 100 | 3011 |
| 1041869 | N/A | N/A | 445902 | 445921 | TTTGATTGTATATTTCAATC | 85 | 3012 |
| 1041901 | N/A | N/A | 446109 | 446128 | GATGGACGAACCTAGACAGG | 54 | 3013 |
| 1041933 | N/A | N/A | 446716 | 446735 | ATCCTGTTTCAAACACCCTA | 27 | 3014 |
| 1041965 | N/A | N/A | 446945 | 446964 | TTTTATTGAATCACACTTCA | 41 | 3015 |
| 1041997 | N/A | N/A | 447722 | 447741 | TCCCTCTTCCCATCCTGCCA | 89 | 3016 |
| 1042029 | N/A | N/A | 448526 | 448545 | GCATGTGCCCCTTACTCCCT | 84 | 3017 |
| 1042061 | N/A | N/A | 448774 | 448793 | TCCCATGTTCTTCCCCATCT | 72 | 3018 |
| 1042093 | N/A | N/A | 449386 | 449405 | AGCTTCAAAATATTGTTATT | 53 | 3019 |
| 1042125 | N/A | N/A | 449674 | 449693 | ATAAGGATATAAACATTCTT | 59 | 3020 |
| 1042157 | N/A | N/A | 449937 | 449956 | GGAGCGGAAGATTATTCAGA | 33 | 3021 |
| 1042189 | N/A | N/A | 450569 | 450588 | CTCCAAATCTCCAAAGACAG | 86 | 3022 |
| 1042221 | N/A | N/A | 451237 | 451256 | TTCTTGAACCCTCACTGGTG | 100 | 3023 |
| 1042253 | N/A | N/A | 451681 | 451700 | CCGCATCTCAAAACTCCAAA | 9 | 3024 |
| 1042285 | N/A | N/A | 451942 | 451961 | GGTGTGTGAGCCACATTATA | 47 | 3025 |
| 1042317 | N/A | N/A | 452277 | 452296 | GGCTCCATAGATCCTCTTGC | 95 | 3026 |
| 1042349 | N/A | N/A | 452631 | 452650 | TGACCTCTACCCTTGTGAGC | 47 | 3027 |
| 1042381 | N/A | N/A | 453102 | 453121 | TGTTGCTTTTCTACTTCATC | 73 | 3028 |
| 1042413 | N/A | N/A | 453898 | 453917 | CTCTAGAACAAAATACATAT | 88 | 3029 |
| 1042445 | N/A | N/A | 455059 | 455078 | TCTGTTTTTAAAAGATCCAT | 36 | 3030 |
| 1042477 | N/A | N/A | 455353 | 455372 | AACAGGCCTTTCAAGGTCTG | 123 | 3031 |
| 1042509 | N/A | N/A | 456640 | 456659 | AGTGTGTTTATCACTGAGTC | 97 | 3032 |
| 1042541 | N/A | N/A | 457060 | 457079 | CTTGTTTGATTTATGCACA | 92 | 3033 |

TABLE 41

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 2 | 138 |
| 1040110 | 2743 | 2762 | 437462 | 437481 | ATCTTCTGTTTTTAAGTCTT | 41 | 3034 |
| 1040142 | 3214 | 3233 | 457467 | 457486 | TGCAGGCAATCCCATTTTCT | 99 | 3035 |
| 1040174 | 4012 | 4031 | 458265 | 458284 | TTGGAGAGAAAAATGTTCTT | 23 | 3036 |
| 1040206 | 4499 | 4518 | 458752 | 458771 | ATGCTCATCTTCAAAATCTA | 23 | 3037 |
| 1040238 | 4763 | 4782 | 459016 | 459035 | TGGTCATTTATTGTCACATA | 6 | 3038 |
| 1040270 | 5220 | 5239 | 459473 | 459492 | TGCTCACATATATAAATGTC | 36 | 3039 |
| 1040302 | 5570 | 5589 | 459823 | 459842 | GTTGATACCAGATTTTTTTT | 30 | 3040 |
| 1040334 | 6015 | 6034 | 460268 | 460287 | AGTCAATTCAATACTCGAAG | 6 | 3041 |
| 1040366 | 6474 | 6493 | 460727 | 460746 | TCCACATTCACTATTCCGTG | 17 | 3042 |
| 1040398 | 7128 | 7147 | 461381 | 461400 | ACAGTCATTTTATATATTTA | 34 | 3043 |
| 1040430 | 7604 | 7623 | 461857 | 461876 | CAGGAAATCCAAACATTCCT | 130 | 3044 |
| 1040462 | 8106 | 8125 | 462359 | 462378 | TCACATCACCACCGAAGAAA | 40 | 3045 |
| 1040494 | 8331 | 8350 | 462584 | 462603 | TTGGAGTTTCCCTATGCCAG | 17 | 3046 |
| 1040526 | 8692 | 8711 | 462945 | 462964 | GACAAATTTCTATATACAAA | 57 | 3047 |
| 1040558 | 9103 | 9122 | 463356 | 463375 | ACTCCCCCCATTTAAATGAG | 116 | 3048 |
| 1040590 | 9440 | 9459 | 463693 | 463712 | GCACTTAATTTTAATACAGT | 15 | 3049 |
| 1040622 | 9884 | 9903 | 464137 | 464156 | GGCAGTATTCACAGAACTGA | 41 | 3050 |
| 1040654 | 10253 | 10272 | 464506 | 464525 | CTTAACTATTATGTATGCAC | 17 | 3051 |
| 1040686 | 10508 | 10527 | 464761 | 464780 | TTGTTTTATTATAATAATGA | 195 | 3052 |
| 1040718 | N/A | N/A | 17546 | 17565 | GCAGGTAAAACCAAATGACA | 121 | 3053 |
| 1040750 | N/A | N/A | 31009 | 31028 | GCAACCAAAACCAAAAGCCT | 67 | 3054 |
| 1040782 | N/A | N/A | 49205 | 49224 | GGGCTATTAATTTATTAAAT | 123 | 3055 |
| 1040814 | N/A | N/A | 77279 | 77298 | AAGATCTTTTAAAGTCCTAC | 58 | 3056 |
| 1040846 | N/A | N/A | 94692 | 94711 | GTAAGCTCCATTTATAGAAT | 30 | 3057 |
| 1040878 | N/A | N/A | 117437 | 117456 | CCTCACACACCTTAACCCTG | 95 | 3058 |
| 1040910 | N/A | N/A | 151015 | 151034 | GAGATAAAAATTATTTTGGC | 108 | 3059 |
| 1040942 | N/A | N/A | 176706 | 176725 | GCTAAATTTCATTAGAAACA | 115 | 3060 |
| 1040974 | N/A | N/A | 195854 | 195873 | TTTTCTACAATTTATAGGCG | 27 | 3061 |
| 1041006 | N/A | N/A | 215585 | 215604 | CTGCACCAAATTTATTTTTG | 37 | 3062 |
| 1041038 | N/A | N/A | 237026 | 237045 | ACTGAAAAAACTGTATGATC | 99 | 3063 |
| 1041070 | N/A | N/A | 257572 | 257591 | CCTTTTAAAATTTCCAGAAA | 97 | 3064 |
| 1041102 | N/A | N/A | 276104 | 276123 | GAAGTTAGCCAGGCATCAGG | 77 | 3065 |
| 1041134 | N/A | N/A | 294914 | 294933 | GCAGAGTTTTAAAATGCACT | 14 | 3066 |
| 1041166 | N/A | N/A | 324245 | 324264 | AGGCATAGTATTTAGCAGAA | 2 | 3067 |
| 1041198 | N/A | N/A | 345616 | 345635 | TACTTCTTTCCTTAAGCACA | 6 | 3068 |

TABLE 41-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1041230 | N/A | N/A | 370434 | 370453 | TAGTTTAAAATATGTGACTC | 96 | 3069 |
| 1041262 | N/A | N/A | 393162 | 393181 | CCAGAAAAACCTTAAACTAC | 73 | 3070 |
| 1041294 | N/A | N/A | 425225 | 425244 | ACCTTCAAACTATCAATTCT | 105 | 3071 |
| 1041326 | N/A | N/A | 437890 | 437909 | TTCCTCATCTTAATCACAGA | 25 | 3072 |
| 1041358 | N/A | N/A | 438300 | 438319 | GAGAGTATAAAAATTATCTC | 102 | 3073 |
| 1041390 | N/A | N/A | 438894 | 438913 | GTCCATCACACTTAGGGCTG | 37 | 3074 |
| 1041422 | N/A | N/A | 439161 | 439180 | CTACAGCTGACTTTACCCCA | 50 | 3075 |
| 1041454 | N/A | N/A | 439848 | 439867 | TTGGGCATTTAAGAAATGCT | 116 | 3076 |
| 1041486 | N/A | N/A | 440219 | 440238 | ATGTTTATTTTCCATGTGTC | 3 | 3077 |
| 1041518 | N/A | N/A | 440776 | 440795 | CTTCCTCCCCAAGAACAGAA | 88 | 3078 |
| 1041550 | N/A | N/A | 441384 | 441403 | CAGTGCCTAACCAGTTGAGA | 28 | 3079 |
| 1041582 | N/A | N/A | 441650 | 441669 | CCAGAGACCCAAATCCGCAC | 65 | 3080 |
| 1041614 | N/A | N/A | 442275 | 442294 | CATCCCCAAACTAAACACCC | 95 | 3081 |
| 1041646 | N/A | N/A | 442820 | 442839 | CTAACCTACTTCCTACCCAA | 133 | 3082 |
| 1041678 | N/A | N/A | 443164 | 443183 | AGCCTTAGAAACAGGAACGG | 46 | 3083 |
| 1041710 | N/A | N/A | 443556 | 443575 | GCCCTAATAACACAGAGCCT | 142 | 3084 |
| 1041742 | N/A | N/A | 444005 | 444024 | CGGCACAAATCCAGGGCTGG | 87 | 3085 |
| 1041774 | N/A | N/A | 444387 | 444406 | TAGTTAAAAATAAGGTATCG | 87 | 3086 |
| 1041806 | N/A | N/A | 445299 | 445318 | TTCAGTAAACCCACACCCTA | 110 | 3087 |
| 1041838 | N/A | N/A | 445628 | 445647 | TGGCGAAATTATTAAATTGG | 102 | 3088 |
| 1041870 | N/A | N/A | 445919 | 445938 | CACGCATATTTATGCTGTTT | 86 | 3089 |
| 1041902 | N/A | N/A | 446110 | 446129 | GGATGGACGAACCTAGACAG | 34 | 3090 |
| 1041934 | N/A | N/A | 446718 | 446737 | ATATCCTGTTTCAAACACCC | 43 | 3091 |
| 1041966 | N/A | N/A | 446947 | 446966 | GATTTTATTGAATCACACTT | 19 | 3092 |
| 1041998 | N/A | N/A | 447903 | 447922 | CAACCATTCCAGACTGAGCT | 109 | 3093 |
| 1042030 | N/A | N/A | 448548 | 448567 | ACATGCAAGCCTGATGTGGT | 121 | 3094 |
| 1042062 | N/A | N/A | 448818 | 448837 | CTAAAACACACCAGACCTCC | 91 | 3095 |
| 1042094 | N/A | N/A | 449387 | 449406 | TAGCTTCAAAATATTGTTAT | 62 | 3096 |
| 1042126 | N/A | N/A | 449684 | 449703 | TAGGTTTGTCATAAGGATAT | 11 | 3097 |
| 1042158 | N/A | N/A | 449978 | 449997 | GCCACGACCAGATATCAGCT | 39 | 3098 |
| 1042190 | N/A | N/A | 450570 | 450589 | ACTCCAAATCTCCAAAGACA | 95 | 3099 |
| 1042222 | N/A | N/A | 451238 | 451257 | CTTCTTGAACCCTCACTGGT | 119 | 3100 |
| 1042254 | N/A | N/A | 451682 | 451701 | TCCGCATCTCAAAACTCCAA | 28 | 3101 |
| 1042286 | N/A | N/A | 451968 | 451987 | GGACACCTACCCATGGAGAG | 57 | 3102 |
| 1042318 | N/A | N/A | 452311 | 452330 | ACTGTATTCTAAGTAGGAGG | 23 | 3103 |
| 1042350 | N/A | N/A | 452636 | 452655 | CCTCCTGACCTCTACCCTTG | 77 | 3104 |

TABLE 41-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1042382 | N/A | N/A | 453115 | 453134 | GATTTCCACAGATTGTTGCT | 66 | 3105 |
| 1042414 | N/A | N/A | 453899 | 453918 | CCTCTAGAACAAAATACATA | 36 | 3106 |
| 1042446 | N/A | N/A | 455060 | 455079 | ATCTGTTTTAAAAGATCCA | 71 | 3107 |
| 1042478 | N/A | N/A | 455364 | 455383 | AACCACAAGCCAACAGGCCT | 114 | 3108 |
| 1042510 | N/A | N/A | 456663 | 456682 | TGTGAGTTCCAAGAAGCAGG | 54 | 3109 |
| 1042542 | N/A | N/A | 457069 | 457088 | CATTTTATTCTTGTTTGATT | 149 | 3110 |

TABLE 42

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 2 | 138 |
| 994630 | N/A | N/A | 85516 | 85535 | GTTTGATATGCTATGCTCAC | 12 | 219 |
| 994693 | N/A | N/A | 184184 | 184203 | TCAGGTTTATATGTATACAA | 2 | 149 |
| 994706 | N/A | N/A | 217284 | 217303 | GTTATGTTTAAGGTATTTTC | 5 | 540 |
| 994735 | N/A | N/A | 297005 | 297024 | GTTTGCATTAAATGACTGTG | 1 | 310 |
| 1054946 | 101 | 120 | 2611 | 2630 | CTGTTGCTCTGGCTGCTGCT | 10 | 3111 |
| 1054950 | 110 | 129 | 2620 | 2639 | TTGCGGCTGCTGTTGCTCTG | 14 | 3112 |
| 1054955 | 117 | 136 | 2627 | 2646 | CAATGTCTTGCGGCTGCTGT | 24 | 3113 |
| 1054966 | 248 | 267 | 10659 | 10678 | CCTGGTGACTTGATGCACGA | 25 | 3114 |
| 1054972 | 552 | 571 | 178162 | 178181 | ATCAGTTCCTTGCAGCAGAT | 3 | 3115 |
| 1054978 | 561 | 580 | 178171 | 178190 | CCATAAGCTATCAGTTCCTT | 2 | 3116 |
| 1054983 | 568 | 587 | 178178 | 178197 | TGGAGAACCATAAGCTATCA | 8 | 3117 |
| 1054989 | 586 | 605 | 178196 | 178215 | CATGTGCTTTCATCACAATG | 63 | 3118 |
| 1054994 | 592 | 611 | 178202 | 178221 | CTGTACCATGTGCTTTCATC | 2 | 3119 |
| 1055000 | 3487 | 3506 | 457740 | 457759 | TAAATACTGTGTTATTTTAG | 72 | 3120 |
| 1055004 | 5497 | 5516 | 459750 | 459769 | GGTATTTGTTCAGTTTAGTT | 6 | 3121 |
| 1055008 | 5503 | 5522 | 459756 | 459775 | AAGTCAGGTATTTGTTCAGT | 5 | 3122 |
| 1055014 | 6028 | 6047 | 460281 | 460300 | GTTTAGTGGATCCAGTCAAT | 16 | 3123 |
| 1055018 | 6035 | 6054 | 460288 | 460307 | AGTGTTGGTTTAGTGGATCC | 32 | 3124 |
| 1055023 | 6044 | 6063 | 460297 | 460316 | TCCCATCTTAGTGTTGGTTT | 28 | 3125 |
| 1055029 | 9484 | 9503 | 463737 | 463756 | TTAGAGATTGTTGTTATTGT | 13 | 3126 |
| 1055034 | 9490 | 9509 | 463743 | 463762 | AAATTCTTAGAGATTGTTGT | 14 | 3127 |
| 1055039 | 10090 | 10109 | 464343 | 464362 | TGATCTGATATTAAAACATC | 78 | 3128 |
| 1055044 | 10097 | 10116 | 464350 | 464369 | TGGGTAATGATCTGATATTA | 13 | 3129 |

TABLE 42-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1055050 | 10106 | 10125 | 464359 | 464378 | GGCATATGGTGGGTAATGAT | 12 | 3130 |
| 1055056 | 196 | 215 | 9912 | 9931 | AGTAGTTTTTGTGAGGTAAA | 11 | 3131 |
| 1055060 | 202 | 221 | 9918 | 9937 | GCTTGTAGTAGTTTTTGTGA | 29 | 3132 |
| 1055064 | N/A | N/A | 17720 | 17739 | TTTTCTATTTGCACTAGCTG | 65 | 3133 |
| 1055070 | N/A | N/A | 17728 | 17747 | ATGTCACCTTTTCTATTTGC | 3 | 3134 |
| 1055076 | N/A | N/A | 24689 | 24708 | AAACACTAGAAATCCAGGGA | 7 | 3135 |
| 1055082 | N/A | N/A | 85508 | 85527 | TGCTATGCTCACAGAGAACC | 78 | 3136 |
| 1055093 | N/A | N/A | 85524 | 85543 | TACAGTTAGTTTGATATGCT | 25 | 3137 |
| 1055098 | N/A | N/A | 108194 | 108213 | GGAATAAATTATTTACTGCG | 5 | 3138 |
| 1055104 | N/A | N/A | 148323 149434 | 148342 149453 | TACTATGTATTTGCCACAGT | 6 | 3139 |
| 1055110 | N/A | N/A | 179786 | 179805 | ATATTTAATCATGTTCCCGA | 13 | 3140 |
| 1055115 | N/A | N/A | 179792 | 179811 | ATAGTTATATTTAATCATGT | 67 | 3141 |
| 1055120 | N/A | N/A | 184176 | 184195 | ATATGTATACAATTCTGACA | 38 | 3142 |
| 1055131 | N/A | N/A | 184192 | 184211 | CAATGTTCTCAGGTTTATAT | 15 | 3143 |
| 1055137 | N/A | N/A | 203033 | 203052 | CCTTTCTTCTTTGTTCATAG | 6 | 3144 |
| 1055142 | N/A | N/A | 203039 | 203058 | CTTGTTCCTTTCTTCTTTGT | 31 | 3145 |
| 1055148 | N/A | N/A | 203883 | 203902 | ATTTATCCTCAGGATGCAAA | 55 | 3146 |
| 1055154 | N/A | N/A | 203892 | 203911 | TTTGTTTAGATTTATCCTCA | 6 | 3147 |
| 1055159 | N/A | N/A | 210724 | 210743 | ATACTCCATTTTTCCTTCTA | 19 | 3148 |
| 1055164 | N/A | N/A | 210731 | 210750 | ATGTGTAATACTCCATTTTT | 25 | 3149 |
| 1055170 | N/A | N/A | 210740 | 210759 | TTATTACAAATGTGTAATAC | 107 | 3150 |
| 1055176 | N/A | N/A | 212029 | 212048 | TATGTTAGTCATTTCTCTCT | 28 | 3151 |
| 1055181 | N/A | N/A | 212035 | 212054 | CAAGTCTATGTTAGTCATTT | 10 | 3152 |
| 1055187 | N/A | N/A | 217276 | 217295 | TAAGGTATTTTCATGGAGTT | 12 | 3153 |
| 1055198 | N/A | N/A | 217292 | 217311 | TTGTAACAGTTATGTTTAAG | 43 | 3154 |
| 1055204 | N/A | N/A | 226990 | 227009 | TTTACTCATTCTACCTTCAA | 66 | 3155 |
| 1055209 | N/A | N/A | 226997 | 227016 | TTGGTTATTTACTCATTCTA | 20 | 3156 |
| 1055215 | N/A | N/A | 227006 | 227025 | TCCATAAACTTGGTTATTTA | 25 | 3157 |
| 1055221 | N/A | N/A | 251494 | 251513 | TTAGCTTTTCAAATACTAAA | 91 | 3158 |
| 1055227 | N/A | N/A | 251503 | 251522 | TCAGCATACTTAGCTTTTCA | 11 | 3159 |
| 1055232 | N/A | N/A | 251510 | 251529 | GACAGTGTCAGCATACTTAG | 12 | 3160 |
| 1055238 | N/A | N/A | 273793 | 273812 | TACCCAGGTTATTACACTGT | 116 | 3161 |
| 1055244 | N/A | N/A | 284229 | 284248 | TTGGGTTTTTCTGTACAAAG | 1 | 3162 |
| 1055249 | N/A | N/A | 284235 | 284254 | TTTTGTTTGGGTTTTTCTGT | 1 | 3163 |
| 1055255 | N/A | N/A | 284335 | 284354 | CTAGTTCTTATCACTATTCA | 7 | 3164 |

TABLE 42-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1055260 | N/A | N/A | 284342 | 284361 | ATGTCAACTAGTTCTTATCA | 5 | 3165 |
| 1055266 | N/A | N/A | 284351 | 284370 | GACTAAACAATGTCAACTAG | 12 | 3166 |
| 1055272 | N/A | N/A | 291011 | 291030 | TGGGTTTTTAGTTTTCCTTC | 4 | 3167 |
| 1055277 | N/A | N/A | 291017 | 291036 | AGGTCCTGGGTTTTTAGTTT | 3 | 3168 |
| 1055283 | N/A | N/A | 296997 | 297016 | TAAATGACTGTGGTGCAGCC | 9 | 3169 |
| 1055294 | N/A | N/A | 297013 | 297032 | AAGCCAGTGTTTGCATTAAA | 1 | 3170 |
| 1055300 | N/A | N/A | 306737 | 306756 | AAGGGCCACTAAATCTGACC | 22 | 3171 |
| 1055306 | N/A | N/A | 318477 | 318496 | ATTTCTTTTTTTTTAAGTT | 103 | 3172 |
| 1055311 | N/A | N/A | 318486 | 318505 | GTGTTTGATATTTCTTTTTT | 1 | 3173 |
| 1055317 | N/A | N/A | 318495 | 318514 | CTTTCAAATGTGTTTGATAT | 3 | 3174 |
| 1055323 | N/A | N/A | 332356 | 332375 | TTATAACAATTTGCATAGTC | 4 | 3175 |
| 1055328 | N/A | N/A | 332363 | 332382 | GGGAGTATTATAACAATTTG | 1 | 3176 |
| 1055334 | N/A | N/A | 332372 | 332391 | TATTTTCCAGGGAGTATTAT | 36 | 3177 |
| 1055340 | N/A | N/A | 347819 | 347838 | CATTATCTAGTTTCTGGAAA | 28 | 3178 |
| 1055345 | N/A | N/A | 347825 | 347844 | AATGGTCATTATCTAGTTTC | 7 | 3179 |
| 1055351 | N/A | N/A | 353593 | 353612 | CTAAATCTGACTTACAAAGG | 121 | 3180 |
| 1055357 | N/A | N/A | 377459 | 377478 | TAAAACCAATACATTAACAT | 117 | 3181 |
| 1055363 | N/A | N/A | 410197 | 410216 | CATTATGCTTTAAGATCACA | 5 | 3182 |

TABLE 43

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994311 | 103 | 122 | 2613 | 2632 | TGCTGTTGCTCTGGCTGCTG | 33 | 257 |
| 994313 | 111 | 130 | 2621 | 2640 | CTTGCGGCTGCTGTTGCTCT | 14 | 413 |
| 994328 | 562 | 581 | 178172 | 178191 | ACCATAAGCTATCAGTTCCT | 2 | 337 |
| 994599 | 204 | 223 | 9920 | 9939 | GTGCTTGTAGTAGTTTTTGT | 23 | 293 |
| 994605 | N/A | N/A | 17726 | 17745 | GTCACCTTTTCTATTTGCAC | 1 | 138 |
| 994701 | N/A | N/A | 203893 | 203912 | GTTTGTTTAGATTTATCCTC | 2 | 150 |
| 994717 | N/A | N/A | 251504 | 251523 | GTCAGCATACTTAGCTTTTC | 8 | 152 |
| 1040945 | N/A | N/A | 179793 | 179812 | CATAGTTATATTTAATCATG | 52 | 828 |
| 1054956 | 119 | 138 | 2629 | 2648 | AACAATGTCTTGCGGCTGCT | 24 | 3183 |
| 1054962 | 243 | 262 | 10654 | 10673 | TGACTTGATGCACGATGCTC | 10 | 3184 |
| 1054967 | 249 | 268 | 10660 | 10679 | CCCTGGTGACTTGATGCACG | 23 | 3185 |
| 1054973 | 554 | 573 | 178164 | 178183 | CTATCAGTTCCTTGCAGCAG | 3 | 3186 |

TABLE 43-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1054984 | 570 | 589 | 178180 | 178199 | AATGGAGAACCATAAGCTAT | 26 | 3187 |
| 1054990 | 587 | 606 | 178197 | 178216 | CCATGTGCTTTCATCACAAT | 20 | 3188 |
| 1054995 | 593 | 612 | N/A | N/A | ACTGTACCATGTGCTTTCAT | 1 | 3189 |
| 1055001 | 5489 | 5508 | 459742 | 459761 | TTCAGTTTAGTTGCAGCCAT | 7 | 3190 |
| 1055005 | 5498 | 5517 | 459751 | 459770 | AGGTATTTGTTCAGTTTAGT | 7 | 3191 |
| 1055009 | 5505 | 5524 | 459758 | 459777 | AAAAGTCAGGTATTTGTTCA | 15 | 3192 |
| 1055015 | 6030 | 6049 | 460283 | 460302 | TGGTTTAGTGGATCCAGTCA | 18 | 3193 |
| 1055019 | 6036 | 6055 | 460289 | 460308 | TAGTGTTGGTTTAGTGGATC | 23 | 3194 |
| 1055024 | 9476 | 9495 | 463729 | 463748 | TGTTGTTATTGTATAGATAC | 9 | 3195 |
| 1055030 | 9485 | 9504 | 463738 | 463757 | CTTAGAGATTGTTGTTATTG | 15 | 3196 |
| 1055035 | 9492 | 9511 | 463745 | 463764 | GGAAATTCTTAGAGATTGTT | 12 | 3197 |
| 1055040 | 10092 | 10111 | 464345 | 464364 | AATGATCTGATATTAAAACA | 43 | 3198 |
| 1055045 | 10098 | 10117 | 464351 | 464370 | GTGGGTAATGATCTGATATT | 13 | 3199 |
| 1055051 | 188 | 207 | N/A | N/A | TTGTGAGGTAAAACTGTAAA | 137 | 3200 |
| 1055057 | 197 | 216 | 9913 | 9932 | TAGTAGTTTTGTGAGGTAA | 12 | 3201 |
| 1055065 | N/A | N/A | 17722 | 17741 | CCTTTTCTATTTGCACTAGC | 28 | 3202 |
| 1055071 | N/A | N/A | 17729 | 17748 | AATGTCACCTTTTCTATTTG | 16 | 3203 |
| 1055077 | N/A | N/A | 36482 | 36501 | AACTCTCTTAAGTACTTATA | 16 | 3204 |
| 1055083 | N/A | N/A | 85510 | 85529 | TATGCTATGCTCACAGAGAA | 55 | 3205 |
| 1055088 | N/A | N/A | 85517 | 85536 | AGTTTGATATGCTATGCTCA | 8 | 3206 |
| 1055094 | N/A | N/A | 85526 | 85545 | CTTACAGTTAGTTTGATATG | 26 | 3207 |
| 1055099 | N/A | N/A | 125427 | 125446 | AGCTTCCAGATAAAACCTCC | 61 | 3208 |
| 1055105 | N/A | N/A | 179272 | 179291 | TTCAAAATTCTCAGCATTGG | 5 | 3209 |
| 1055111 | N/A | N/A | 179787 | 179806 | TATATTTAATCATGTTCCCG | 13 | 3210 |
| 1055121 | N/A | N/A | 184178 | 184197 | TTATATGTATACAATTCTGA | 67 | 3211 |
| 1055126 | N/A | N/A | 184185 | 184204 | CTCAGGTTTATATGTATACA | 1 | 3212 |
| 1055132 | N/A | N/A | 184194 | 184213 | GGCAATGTTCTCAGGTTTAT | 1 | 3213 |
| 1055138 | N/A | N/A | 203034 | 203053 | TCCTTTCTTCTTTGTTCATA | 9 | 3214 |
| 1055143 | N/A | N/A | 203040 | 203059 | TCTTGTTCCTTTCTTCTTTG | 20 | 3215 |
| 1055149 | N/A | N/A | 203885 | 203904 | AGATTTATCCTCAGGATGCA | 26 | 3216 |
| 1055160 | N/A | N/A | 210726 | 210745 | TAATACTCCATTTTTCCTTC | 25 | 3217 |
| 1055165 | N/A | N/A | 210732 | 210751 | AATGTGTAATACTCCATTTT | 51 | 3218 |
| 1055171 | N/A | N/A | 212021 | 212040 | TCATTTCTCTCTGGCTGTGC | 27 | 3219 |
| 1055177 | N/A | N/A | 212030 | 212049 | CTATGTTAGTCATTTCTCTC | 15 | 3220 |
| 1055182 | N/A | N/A | 212037 | 212056 | ATCAAGTCTATGTTAGTCAT | 11 | 3221 |
| 1055188 | N/A | N/A | 217278 | 217297 | TTTAAGGTATTTTCATGGAG | 7 | 3222 |

TABLE 43-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1055193 | N/A | N/A | 217285 | 217304 | AGTTATGTTTAAGGTATTTT | 53 | 3223 |
| 1055199 | N/A | N/A | 217294 | 217313 | ACTTGTAACAGTTATGTTTA | 44 | 3224 |
| 1055205 | N/A | N/A | 226992 | 227011 | TATTTACTCATTCTACCTTC | 63 | 3225 |
| 1055210 | N/A | N/A | 226998 | 227017 | CTTGGTTATTTACTCATTCT | 21 | 3226 |
| 1055216 | N/A | N/A | 228677 | 228696 | GGCTGATTCTAGTACTGTGA | 51 | 3227 |
| 1055222 | N/A | N/A | 251496 | 251515 | ACTTAGCTTTTCAAATACTA | 30 | 3228 |
| 1055233 | N/A | N/A | 251512 | 251531 | AGGACAGTGTCAGCATACTT | 14 | 3229 |
| 1055239 | N/A | N/A | 284221 | 284240 | TTCTGTACAAAGTTCAGTTG | 54 | 3230 |
| 1055245 | N/A | N/A | 284230 | 284249 | TTTGGGTTTTTCTGTACAAA | <1 | 3231 |
| 1055250 | N/A | N/A | 284237 | 284256 | AGTTTTGTTTGGGTTTTTCT | <1 | 3232 |
| 1055256 | N/A | N/A | 284337 | 284356 | AACTAGTTCTTATCACTATT | 37 | 3233 |
| 1055261 | N/A | N/A | 284343 | 284362 | AATGTCAACTAGTTCTTATC | 2 | 3234 |
| 1055267 | N/A | N/A | 288842 | 288861 | TATAAAATTCACCTAAAATT | 110 | 3235 |
| 1055273 | N/A | N/A | 291012 | 291031 | CTGGGTTTTTAGTTTTCCTT | 1 | 3236 |
| 1055278 | N/A | N/A | 291018 | 291037 | TAGGTCCTGGGTTTTTAGTT | 3 | 3237 |
| 1055284 | N/A | N/A | 296999 | 297018 | ATTAAATGACTGTGGTGCAG | 3 | 3238 |
| 1055289 | N/A | N/A | 297006 | 297025 | TGTTTGCATTAAATGACTGT | 27 | 3239 |
| 1055295 | N/A | N/A | 297015 | 297034 | AAAAGCCAGTGTTTGCATTA | 2 | 3240 |
| 1055301 | N/A | N/A | 306738 306824 | 306757 306843 | TAAGGGCCACTAAATCTGAC | 12 | 3241 |
| 1055307 | N/A | N/A | 318479 | 318498 | ATATTTCTTTTTTTTTAAG | 134 | 3242 |
| 1055312 | N/A | N/A | 318487 | 318506 | TGTGTTTGATATTTCTTTTT | <1 | 3243 |
| 1055318 | N/A | N/A | 318632 | 318651 | ATGCAAGGTCCAGGGAATAC | 1 | 3244 |
| 1055324 | N/A | N/A | 332358 | 332377 | TATTATAACAATTTGCATAG | 46 | 3245 |
| 1055329 | N/A | N/A | 332364 | 332383 | AGGGAGTATTATAACAATTT | 1 | 3246 |
| 1055335 | N/A | N/A | 333552 | 333571 | TATGAGTAATTAGCACAAAG | 11 | 3247 |
| 1055341 | N/A | N/A | 347820 | 347839 | TCATTATCTAGTTTCTGGAA | 6 | 3248 |
| 1055346 | N/A | N/A | 347826 | 347845 | AAATGGTCATTATCTAGTTT | 5 | 3249 |
| 1055352 | N/A | N/A | 353767 | 353786 | ACTTCCAATTTTGAAATACT | 10 | 3250 |
| 1055358 | N/A | N/A | 389235 | 389254 | GAAAGCCCCAGCACATAAAT | 114 | 3251 |
| 1055364 | N/A | N/A | 420350 | 420369 | TGAAAGCTGGCCGATATCCC | 65 | 3252 |

TABLE 44

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994312 | 105 | 124 | 2615 | 2634 | GCTGCTGTTGCTCTGGCTGC | 48 | 335 |
| 994447 | 5491 | 5510 | 459744 | 459763 | TGTTCAGTTTAGTTGCAGCC | 12 | 274 |
| 994449 | 5499 | 5518 | 459752 | 459771 | CAGGTATTTGTTCAGTTTAG | 8 | 430 |
| 994561 | 9486 | 9505 | 463739 | 463758 | TCTTAGAGATTGTTGTTATT | 13 | 444 |
| 994597 | 198 | 217 | 9914 | 9933 | GTAGTAGTTTTTGTGAGGTA | 10 | 137 |
| 994601 | 206 | 225 | 9922 | 9941 | TGGTGCTTGTAGTAGTTTTT | 31 | 449 |
| 994605 | N/A | N/A | 17726 | 17745 | GTCACCTTTTCTATTTGCAC | 2 | 138 |
| 994703 | N/A | N/A | 212031 | 212050 | TCTATGTTAGTCATTTCTCT | 21 | 306 |
| 994731 | N/A | N/A | 284231 | 284250 | GTTTGGGTTTTTCTGTACAA | 2 | 621 |
| 1040848 | N/A | N/A | 96129 | 96148 | CACTTTCTAGATTATTCTTA | 102 | 748 |
| 1054951 | 112 | 131 | 2622 | 2641 | TCTTGCGGCTGCTGTTGCTC | 14 | 3253 |
| 1054957 | 121 | 140 | 2631 | 2650 | GAAACAATGTCTTGCGGCTG | 15 | 3254 |
| 1054963 | 244 | 263 | 10655 | 10674 | GTGACTTGATGCACGATGCT | 8 | 3255 |
| 1054968 | 250 | 269 | 10661 | 10680 | ACCCTGGTGACTTGATGCAC | 20 | 3256 |
| 1054974 | 556 | 575 | 178166 | 178185 | AGCTATCAGTTCCTTGCAGC | 11 | 3257 |
| 1054979 | 563 | 582 | 178173 | 178192 | AACCATAAGCTATCAGTTCC | 7 | 3258 |
| 1054985 | 572 | 591 | 178182 | 178201 | ACAATGGAGAACCATAAGCT | 101 | 3259 |
| 1054991 | 588 | 607 | 178198 | 178217 | ACCATGTGCTTTCATCACAA | 3 | 3260 |
| 1054996 | 594 | 613 | N/A | N/A | AACTGTACCATGTGCTTTCA | 3 | 3261 |
| 1055010 | 5507 | 5526 | 459760 | 459779 | AGAAAAGTCAGGTATTTGTT | 14 | 3262 |
| 1055016 | 6031 | 6050 | 460284 | 460303 | TTGGTTTAGTGGATCCAGTC | 31 | 3263 |
| 1055020 | 6037 | 6056 | 460290 | 460309 | TTAGTGTTGGTTTAGTGGAT | 20 | 3264 |
| 1055025 | 9478 | 9497 | 463731 | 463750 | ATTGTTGTTATTGTATAGAT | 18 | 3265 |
| 1055036 | 9494 | 9513 | 463747 | 463766 | ATGGAAATTCTTAGAGATTG | 16 | 3266 |
| 1055041 | 10093 | 10112 | 464346 | 464365 | TAATGATCTGATATTAAAAC | 111 | 3267 |
| 1055046 | 10099 | 10118 | 464352 | 464371 | GGTGGGTAATGATCTGATAT | 34 | 3268 |
| 1055052 | 190 | 209 | N/A | N/A | TTTTGTGAGGTAAAACTGTA | 136 | 3269 |
| 1055066 | N/A | N/A | 17723 | 17742 | ACCTTTTCTATTTGCACTAG | 19 | 3270 |
| 1055072 | N/A | N/A | 17730 | 17749 | AAATGTCACCTTTTCTATTT | 56 | 3271 |
| 1055078 | N/A | N/A | 36986 | 37005 | GCTATTTTTCCAGAAAGTC | 6 | 3272 |
| 1055084 | N/A | N/A | 85512 | 85531 | GATATGCTATGCTCACAGAG | 23 | 3273 |
| 1055089 | N/A | N/A | 85518 | 85537 | TAGTTTGATATGCTATGCTC | 33 | 3274 |
| 1055100 | N/A | N/A | 133992 | 134011 | AATTTTTTTAACATCTTGC | 88 | 3275 |
| 1055106 | N/A | N/A | 179779 | 179798 | ATCATGTTCCCGATATTGGA | 15 | 3276 |
| 1055112 | N/A | N/A | 179788 | 179807 | TTATATTTAATCATGTTCCC | 11 | 3277 |
| 1055116 | N/A | N/A | 179795 | 179814 | AACATAGTTATATTTAATCA | 132 | 3278 |

TABLE 44-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1055122 | N/A | N/A | 184180 | 184199 | GTTTATATGTATACAATTCT | 26 | 3279 |
| 1055127 | N/A | N/A | 184186 | 184205 | TCTCAGGTTTATATGTATAC | 4 | 3280 |
| 1055133 | N/A | N/A | 187811 | 187830 | TCACAGGGAATAATGAAGAG | 73 | 3281 |
| 1055139 | N/A | N/A | 203035 | 203054 | TTCCTTTCTTCTTTGTTCAT | 45 | 3282 |
| 1055144 | N/A | N/A | 203041 | 203060 | CTCTTGTTCCTTTCTTCTTT | 20 | 3283 |
| 1055150 | N/A | N/A | 203887 | 203906 | TTAGATTTATCCTCAGGATG | 51 | 3284 |
| 1055155 | N/A | N/A | 203894 | 203913 | GGTTTGTTTAGATTTATCCT | 11 | 3285 |
| 1055161 | N/A | N/A | 210727 | 210746 | GTAATACTCCATTTTCCTT | 4 | 3286 |
| 1055166 | N/A | N/A | 210733 | 210752 | AAATGTGTAATACTCCATTT | 53 | 3287 |
| 1055172 | N/A | N/A | 212023 | 212042 | AGTCATTTCTCTCTGGCTGT | 53 | 3288 |
| 1055183 | N/A | N/A | 212039 | 212058 | AAATCAAGTCTATGTTAGTC | 63 | 3289 |
| 1055189 | N/A | N/A | 217280 | 217299 | TGTTTAAGGTATTTTCATGG | 8 | 3290 |
| 1055194 | N/A | N/A | 217286 | 217305 | CAGTTATGTTTAAGGTATTT | 19 | 3291 |
| 1055200 | N/A | N/A | 222603 | 222622 | CTGTTCTTAGCTTCCCAGCT | 39 | 3292 |
| 1055206 | N/A | N/A | 226993 | 227012 | TTATTTACTCATTCTACCTT | 82 | 3293 |
| 1055211 | N/A | N/A | 226999 | 227018 | ACTTGGTTATTTACTCATTC | 17 | 3294 |
| 1055217 | N/A | N/A | 230285 | 230304 | AATCTCCAGTTATGAGTAAG | 82 | 3295 |
| 1055223 | N/A | N/A | 251498 | 251517 | ATACTTAGCTTTTCAAATAC | 83 | 3296 |
| 1055228 | N/A | N/A | 251505 | 251524 | TGTCAGCATACTTAGCTTTT | 32 | 3297 |
| 1055234 | N/A | N/A | 251514 | 251533 | CCAGGACAGTGTCAGCATAC | 29 | 3298 |
| 1055240 | N/A | N/A | 284223 | 284242 | TTTTCTGTACAAAGTTCAGT | 4 | 3299 |
| 1055251 | N/A | N/A | 284239 | 284258 | TTAGTTTTGTTTGGGTTTTT | 2 | 3300 |
| 1055257 | N/A | N/A | 284338 | 284357 | CAACTAGTTCTTATCACTAT | 15 | 3301 |
| 1055262 | N/A | N/A | 284344 | 284363 | CAATGTCAACTAGTTCTTAT | 4 | 3302 |
| 1055268 | N/A | N/A | 291004 | 291023 | TTAGTTTTCCTTCTTGTCTT | 7 | 3303 |
| 1055274 | N/A | N/A | 291013 | 291032 | CCTGGGTTTTAGTTTTCCT | 3 | 3304 |
| 1055279 | N/A | N/A | 291020 | 291039 | ATTAGGTCCTGGGTTTTTAG | 3 | 3305 |
| 1055285 | N/A | N/A | 297001 | 297020 | GCATTAAATGACTGTGGTGC | 5 | 3306 |
| 1055290 | N/A | N/A | 297007 | 297026 | GTGTTTGCATTAAATGACTG | 4 | 3307 |
| 1055296 | N/A | N/A | 306730 | 306749 | ACTAAATCTGACCTTCCTCA | 35 | 3308 |
| 1055302 | N/A | N/A | 306741 306827 | 306760 306846 | TGGTAAGGGCCACTAAATCT | 4 | 3309 |
| 1055308 | N/A | N/A | 318481 | 318500 | TGATATTTCTTTTTTTTTA | 104 | 3310 |
| 1055313 | N/A | N/A | 318488 | 318507 | ATGTGTTTGATATTTCTTTT | 1 | 3311 |
| 1055319 | N/A | N/A | 324476 | 324495 | TGATCTAAATTGTGTCTTTT | 17 | 3312 |
| 1055325 | N/A | N/A | 332359 | 332378 | GTATTATAACAATTTGCATA | 6 | 3313 |
| 1055330 | N/A | N/A | 332365 | 332384 | CAGGGAGTATTATAACAATT | 2 | 3314 |

TABLE 44-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1055336 | N/A | N/A | 334250 | 334269 | TCATAGAAGCATTCTGTGTT | 90 | 3315 |
| 1055342 | N/A | N/A | 347821 | 347840 | GTCATTATCTAGTTTCTGGA | 2 | 3316 |
| 1055347 | N/A | N/A | 347827 | 347846 | CAAATGGTCATTATCTAGTT | 10 | 3317 |
| 1055353 | N/A | N/A | 355980 | 355999 | ATCTGCTAGGCATGCGGGAT | 27 | 3318 |
| 1055359 | N/A | N/A | 396488 | 396507 | TGATTTGTACACACCCAGCA | 62 | 3319 |
| 1055365 | N/A | N/A | 432459 | 432478 | GCACTGATCCAATAAAACCC | 93 | 3320 |

TABLE 45

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994605 | N/A | N/A | 17726 | 17745 | GTCACCTTTTCTATTTGCAC | 2 | 138 |
| 994690 | N/A | N/A | 179789 | 179808 | GTTATATTTAATCATGTTCC | 4 | 538 |
| 994734 | N/A | N/A | 291014 | 291033 | TCCTGGGTTTTTAGTTTTCC | 2 | 232 |
| 1041358 | N/A | N/A | 438300 | 438319 | GAGAGTATAAAAATTATCTC | 93 | 3073 |
| 1054947 | 107 | 126 | 2617 | 2636 | CGGCTGCTGTTGCTCTGGCT | 25 | 3321 |
| 1054952 | 113 | 132 | 2623 | 2642 | GTCTTGCGGCTGCTGTTGCT | 16 | 3322 |
| 1054964 | 245 | 264 | 10656 | 10675 | GGTGACTTGATGCACGATGC | 7 | 3323 |
| 1054969 | 252 | 271 | 10663 | 10682 | CCACCCTGGTGACTTGATGC | 13 | 3324 |
| 1054975 | 558 | 577 | 178168 | 178187 | TAAGCTATCAGTTCCTTGCA | 5 | 3325 |
| 1054980 | 564 | 583 | 178174 | 178193 | GAACCATAAGCTATCAGTTC | 24 | 3326 |
| 1054986 | 580 | 599 | 178190 | 178209 | CTTTCATCACAATGGAGAAC | 101 | 3327 |
| 1054992 | 589 | 608 | 178199 | 178218 | TACCATGTGCTTTCATCACA | 6 | 3328 |
| 1054997 | 596 | 615 | N/A | N/A | AAAACTGTACCATGTGCTTT | 4 | 3329 |
| 1055002 | 5493 | 5512 | 459746 | 459765 | TTTGTTCAGTTTAGTTGCAG | 17 | 3330 |
| 1055006 | 5500 | 5519 | 459753 | 459772 | TCAGGTATTTGTTCAGTTTA | 6 | 3331 |
| 1055011 | 5509 | 5528 | 459762 | 459781 | AAAGAAAAGTCAGGTATTTG | 42 | 3332 |
| 1055017 | 6032 | 6051 | 460285 | 460304 | GTTGGTTTAGTGGATCCAGT | 42 | 3333 |
| 1055021 | 6038 | 6057 | 460291 | 460310 | CTTAGTGTTGGTTTAGTGGA | 28 | 3334 |
| 1055026 | 9480 | 9499 | 463733 | 463752 | AGATTGTTGTTATTGTATAG | 20 | 3335 |
| 1055031 | 9487 | 9506 | 463740 | 463759 | TTCTTAGAGATTGTTGTTAT | 20 | 3336 |
| 1055037 | 9496 | 9515 | 463749 | 463768 | TTATGGAAATTCTTAGAGAT | 67 | 3337 |
| 1055042 | 10094 | 10113 | 464347 | 464366 | GTAATGATCTGATATTAAAA | 54 | 3338 |
| 1055047 | 10100 | 10119 | 464353 | 464372 | TGGTGGGTAATGATCTGATA | 14 | 3339 |

TABLE 45-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1055053 | 192 | 211 | N/A | N/A | GTTTTTGTGAGGTAAAACTG | 111 | 3340 |
| 1055058 | 199 | 218 | 9915 | 9934 | TGTAGTAGTTTTTGTGAGGT | 19 | 3341 |
| 1055061 | 208 | 227 | 9924 | 9943 | CTTGGTGCTTGTAGTAGTTT | 25 | 3342 |
| 1055067 | N/A | N/A | 17724 | 17743 | CACCTTTTCTATTTGCACTA | 23 | 3343 |
| 1055073 | N/A | N/A | 17732 | 17751 | TCAAATGTCACCTTTTCTAT | 52 | 3344 |
| 1055079 | N/A | N/A | 49576 | 49595 | ATAGCAAGTCCCCTGAAGCT | 83 | 3345 |
| 1055085 | N/A | N/A | 85513 | 85532 | TGATATGCTATGCTCACAGA | 25 | 3346 |
| 1055090 | N/A | N/A | 85519 | 85538 | TTAGTTTGATATGCTATGCT | 36 | 3347 |
| 1055095 | N/A | N/A | 99353 | 99372 | CACAGAACACTTTTTCCAGA | 41 | 3348 |
| 1055101 | N/A | N/A | 144499 | 144518 | ATCACACAGCAGCATGTTTA | 72 | 3349 |
| 1055107 | N/A | N/A | 179781 | 179800 | TAATCATGTTCCCGATATTG | 21 | 3350 |
| 1055117 | N/A | N/A | 179797 | 179816 | CTAACATAGTTATATTTAAT | 121 | 3351 |
| 1055123 | N/A | N/A | 184181 | 184200 | GGTTTATATGTATACAATTC | 3 | 3352 |
| 1055128 | N/A | N/A | 184187 | 184206 | TTCTCAGGTTTATATGTATA | 5 | 3353 |
| 1055134 | N/A | N/A | 203027 | 203046 | TTCTTTGTTCATAGGAGAAC | 91 | 3354 |
| 1055140 | N/A | N/A | 203036 | 203055 | GTTCCTTTCTTCTTTGTTCA | 17 | 3355 |
| 1055145 | N/A | N/A | 203043 | 203062 | ACCTCTTGTTCCTTTCTTCT | 10 | 3356 |
| 1055151 | N/A | N/A | 203889 | 203908 | GTTTAGATTATCCTCAGGA | 3 | 3357 |
| 1055156 | N/A | N/A | 203895 | 203914 | GGGTTTGTTTAGATTTATCC | 19 | 3358 |
| 1055162 | N/A | N/A | 210728 | 210747 | TGTAATACTCCATTTTTCCT | 15 | 3359 |
| 1055167 | N/A | N/A | 210734 | 210753 | CAAATGTGTAATACTCCATT | 16 | 3360 |
| 1055173 | N/A | N/A | 212025 | 212044 | TTAGTCATTTCTCTCTGGCT | 50 | 3361 |
| 1055178 | N/A | N/A | 212032 | 212051 | GTCTATGTTAGTCATTTCTC | 13 | 3362 |
| 1055184 | N/A | N/A | 212041 | 212060 | AAAAATCAAGTCTATGTTAG | 118 | 3363 |
| 1055190 | N/A | N/A | 217281 | 217300 | ATGTTTAAGGTATTTTCATG | 41 | 3364 |
| 1055195 | N/A | N/A | 217287 | 217306 | ACAGTTATGTTTAAGGTATT | 39 | 3365 |
| 1055201 | N/A | N/A | 226199 | 226218 | AAAACAGACTTCGATTTGGA | 70 | 3366 |
| 1055207 | N/A | N/A | 226994 | 227013 | GTTATTTACTCATTCTACCT | 42 | 3367 |
| 1055212 | N/A | N/A | 227000 | 227019 | AACTTGGTTATTTACTCATT | 25 | 3368 |
| 1055218 | N/A | N/A | 233991 | 234010 | AAGTTGGAGAAGTCACCAGC | 103 | 3369 |
| 1055224 | N/A | N/A | 251500 | 251519 | GCATACTTAGCTTTTCAAAT | 6 | 3370 |
| 1055229 | N/A | N/A | 251506 | 251525 | GTGTCAGCATACTTAGCTTT | 27 | 3371 |
| 1055235 | N/A | N/A | 254560 | 254579 | TCTTGGAGGTGACATTTGTG | 55 | 3372 |
| 1055241 | N/A | N/A | 284225 | 284244 | GTTTTTCTGTACAAAGTTCA | 2 | 3373 |
| 1055246 | N/A | N/A | 284232 | 284251 | TGTTTGGTTTTTCTGTACA | 1 | 3374 |
| 1055252 | N/A | N/A | 284241 | 284260 | CTTTAGTTTTGTTTGGGTTT | 2 | 3375 |

TABLE 45-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1055258 | N/A | N/A | 284339 | 284358 | TCAACTAGTTCTTATCACTA | 4 | 3376 |
| 1055263 | N/A | N/A | 284345 | 284364 | ACAATGTCAACTAGTTCTTA | 2 | 3377 |
| 1055269 | N/A | N/A | 291006 | 291025 | TTTTAGTTTTCCTTCTTGTC | 5 | 3378 |
| 1055280 | N/A | N/A | 291022 | 291041 | AGATTAGGTCCTGGGTTTTT | 2 | 3379 |
| 1055286 | N/A | N/A | 297002 | 297021 | TGCATTAAATGACTGTGGTG | 4 | 3380 |
| 1055291 | N/A | N/A | 297008 | 297027 | AGTGTTTGCATTAAATGACT | 5 | 3381 |
| 1055297 | N/A | N/A | 306732 | 306751 | CCACTAAATCTGACCTTCCT | 37 | 3382 |
| 1055303 | N/A | N/A | 306746 | 306765 | TCCATTGGTAAGGGCCACTA | 2 | 3383 |
| 1055309 | N/A | N/A | 318483 | 318502 | TTTGATATTTCTTTTTTTTT | 96 | 3384 |
| 1055314 | N/A | N/A | 318489 | 318508 | AATGTGTTTGATATTTCTTT | 1 | 3385 |
| 1055320 | N/A | N/A | 326832 | 326851 | CAGTTTTGAGATGGTTTGAA | 3 | 3386 |
| 1055326 | N/A | N/A | 332360 | 332379 | AGTATTATAACAATTTGCAT | 22 | 3387 |
| 1055331 | N/A | N/A | 332366 | 332385 | CCAGGGAGTATTATAACAAT | 2 | 3388 |
| 1055337 | N/A | N/A | 347813 | 347832 | CTAGTTTCTGGAAAGTAATG | 36 | 3389 |
| 1055343 | N/A | N/A | 347822 | 347841 | GGTCATTATCTAGTTTCTGG | 1 | 3390 |
| 1055348 | N/A | N/A | 347829 | 347848 | AACAAATGGTCATTATCTAG | 9 | 3391 |
| 1055354 | N/A | N/A | 358326 | 358345 | CCAAATTCCTGGTTGCTGTG | 4 | 3392 |
| 1055360 | N/A | N/A | 397561 | 397580 | AGGGCCTCTTGGATTTTGTT | 130 | 3393 |

TABLE 46

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994314 | 246 | 265 | 10657 | 10676 | TGGTGACTTGATGCACGATG | 12 | 491 |
| 994329 | 590 | 609 | 178200 | 178219 | GTACCATGTGCTTTCATCAC | 5 | 415 |
| 994465 | 6033 | 6052 | 460286 | 460305 | TGTTGGTTTAGTGGATCCAG | 21 | 432 |
| 994467 | 6040 | 6059 | 460293 | 460312 | ATCTTAGTGTTGGTTTAGTG | 20 | 588 |
| 994605 | N/A | N/A | 17726 | 17745 | GTCACCTTTTCTATTTGCAC | 4 | 138 |
| 994700 | N/A | N/A | 203037 | 203056 | TGTTCCTTTCTTCTTTGTTC | 10 | 72 |
| 994761 | N/A | N/A | 347823 | 347842 | TGGTCATTATCTAGTTTCTG | 2 | 469 |
| 1054948 | 108 | 127 | 2618 | 2637 | GCGGCTGCTGTTGCTCTGGC | 57 | 3394 |
| 1054953 | 114 | 133 | 2624 | 2643 | TGTCTTGCGGCTGCTGTTGC | 16 | 3395 |
| 1054970 | 254 | 273 | 10665 | 10684 | GACCACCCTGGTGACTTGAT | 9 | 3396 |
| 1054976 | 559 | 578 | 178169 | 178188 | ATAAGCTATCAGTTCCTTGC | 11 | 3397 |
| 1054981 | 565 | 584 | 178175 | 178194 | AGAACCATAAGCTATCAGTT | 7 | 3398 |

TABLE 46-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1054987 | 582 | 601 | 178192 | 178211 | TGCTTTCATCACAATGGAGA | 62 | 3399 |
| 1054998 | 598 | 617 | N/A | N/A | GGAAAACTGTACCATGTGCT | 4 | 3400 |
| 1055003 | 5495 | 5514 | 459748 | 459767 | TATTTGTTCAGTTTAGTTGC | 9 | 3401 |
| 1055007 | 5501 | 5520 | 459754 | 459773 | GTCAGGTATTTGTTCAGTTT | 9 | 3402 |
| 1055012 | 6024 | 6043 | 460277 | 460296 | AGTGGATCCAGTCAATTCAA | 34 | 3403 |
| 1055027 | 9482 | 9501 | 463735 | 463754 | AGAGATTGTTGTTATTGTAT | 16 | 3404 |
| 1055032 | 9488 | 9507 | 463741 | 463760 | ATTCTTAGAGATTGTTGTTA | 21 | 3405 |
| 1055038 | 10086 | 10105 | 464339 | 464358 | CTGATATTAAAACATCCAGT | 21 | 3406 |
| 1055043 | 10095 | 10114 | 464348 | 464367 | GGTAATGATCTGATATTAAA | 15 | 3407 |
| 1055048 | 10102 | 10121 | 464355 | 464374 | TATGGTGGGTAATGATCTGA | 16 | 3408 |
| 1055054 | 194 | 213 | 9910 | 9929 | TAGTTTTTGTGAGGTAAAAC | 83 | 3409 |
| 1055059 | 200 | 219 | 9916 | 9935 | TTGTAGTAGTTTTGTGAGG | 28 | 3410 |
| 1055062 | N/A | N/A | 17716 | 17735 | CTATTTGCACTAGCTGCCTA | 75 | 3411 |
| 1055068 | N/A | N/A | 17725 | 17744 | TCACCTTTTCTATTTGCACT | 10 | 3412 |
| 1055074 | N/A | N/A | 17734 | 17753 | TCTCAAATGTCACCTTTTCT | 44 | 3413 |
| 1055080 | N/A | N/A | 54036 | 54055 | AACCATATGACATCTCAACA | 33 | 3414 |
| 1055086 | N/A | N/A | 85514 | 85533 | TTGATATGCTATGCTCACAG | 18 | 3415 |
| 1055091 | N/A | N/A | 85520 | 85539 | GTTAGTTTGATATGCTATGC | 36 | 3416 |
| 1055096 | N/A | N/A | 103883 | 103902 | CAACTGAAAATTCTACACAC | 110 | 3417 |
| 1055102 | N/A | N/A | 147181 | 147200 | CAGTAGTCTCCCCATAGCCA | 76 | 3418 |
| 1055108 | N/A | N/A | 179783 | 179802 | TTTAATCATGTTCCCGATAT | 57 | 3419 |
| 1055113 | N/A | N/A | 179790 | 179809 | AGTTATATTTAATCATGTTC | 17 | 3420 |
| 1055118 | N/A | N/A | 179799 | 179818 | CACTAACATAGTTATATTTA | 72 | 3421 |
| 1055124 | N/A | N/A | 184182 | 184201 | AGGTTATATGTATACAATT | 13 | 3422 |
| 1055129 | N/A | N/A | 184188 | 184207 | GTTCTCAGGTTTATATGTAT | 5 | 3423 |
| 1055135 | N/A | N/A | 203029 | 203048 | TCTTCTTTGTTCATAGGAGA | 147 | 3424 |
| 1055146 | N/A | N/A | 203045 | 203064 | CAACCTCTTGTTCCTTTCTT | 52 | 3425 |
| 1055152 | N/A | N/A | 203890 | 203909 | TGTTTAGATTATCCTCAGG | 5 | 3426 |
| 1055157 | N/A | N/A | 210720 | 210739 | TCCATTTTTCCTTCTAGATT | 19 | 3427 |
| 1055163 | N/A | N/A | 210729 | 210748 | GTGTAATACTCCATTTTTCC | 5 | 3428 |
| 1055168 | N/A | N/A | 210736 | 210755 | TACAAATGTGTAATACTCCA | 6 | 3429 |
| 1055174 | N/A | N/A | 212027 | 212046 | TGTTAGTCATTTCTCTCTGG | 23 | 3430 |
| 1055179 | N/A | N/A | 212033 | 212052 | AGTCTATGTTAGTCATTTCT | 24 | 3431 |
| 1055185 | N/A | N/A | 213048 | 213067 | GATGATAAATTAAGGCAGAG | 22 | 3432 |
| 1055191 | N/A | N/A | 217282 | 217301 | TATGTTTAAGGTATTTTCAT | 47 | 3433 |
| 1055196 | N/A | N/A | 217288 | 217307 | AACAGTTATGTTTAAGGTAT | 43 | 3434 |

TABLE 46-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1055202 | N/A | N/A | 226986 | 227005 | CTCATTCTACCTTCAACTCT | 94 | 3435 |
| 1055208 | N/A | N/A | 226995 | 227014 | GGTTATTTACTCATTCTACC | 14 | 3436 |
| 1055213 | N/A | N/A | 227002 | 227021 | TAAACTTGGTTATTTACTCA | 79 | 3437 |
| 1055219 | N/A | N/A | 236034 | 236053 | GAGTGAGCATTAGATGGTCA | 56 | 3438 |
| 1055225 | N/A | N/A | 251501 | 251520 | AGCATACTTAGCTTTTCAAA | 10 | 3439 |
| 1055230 | N/A | N/A | 251507 | 251526 | AGTGTCAGCATACTTAGCTT | 16 | 3440 |
| 1055236 | N/A | N/A | 257663 | 257682 | AGGGAAATGGTCATTTTCTA | 87 | 3441 |
| 1055242 | N/A | N/A | 284227 | 284246 | GGGTTTTTCTGTACAAAGTT | 4 | 3442 |
| 1055247 | N/A | N/A | 284233 | 284252 | TTGTTTGGGTTTTCTGTAC | 3 | 3443 |
| 1055253 | N/A | N/A | 284331 | 284350 | TTCTTATCACTATTCAGTCA | 3 | 3444 |
| 1055259 | N/A | N/A | 284340 | 284359 | GTCAACTAGTTCTTATCACT | 2 | 3445 |
| 1055264 | N/A | N/A | 284347 | 284366 | AAACAATGTCAACTAGTTCT | 12 | 3446 |
| 1055270 | N/A | N/A | 291008 | 291027 | GTTTTTAGTTTTCCTTCTTG | 3 | 3447 |
| 1055275 | N/A | N/A | 291015 | 291034 | GTCCTGGGTTTTTAGTTTTC | 2 | 3448 |
| 1055281 | N/A | N/A | 291024 | 291043 | GAAGATTAGGTCCTGGGTTT | 5 | 3449 |
| 1055287 | N/A | N/A | 297003 | 297022 | TTGCATTAAATGACTGTGGT | 2 | 3450 |
| 1055292 | N/A | N/A | 297009 | 297028 | CAGTGTTTGCATTAAATGAC | 3 | 3451 |
| 1055298 | N/A | N/A | 306734 | 306753 | GGCCACTAAATCTGACCTTC | 54 | 3452 |
| 1055304 | N/A | N/A | 306748 | 306767 | AATCCATTGGTAAGGGCCAC | 4 | 3453 |
| 1055310 | N/A | N/A | 318484 | 318503 | GTTTGATATTTCTTTTTTTT | 2 | 3454 |
| 1055315 | N/A | N/A | 318491 | 318510 | CAAATGTGTTTGATATTTCT | 3 | 3455 |
| 1055321 | N/A | N/A | 332352 | 332371 | AACAATTTGCATAGTCTCTC | 3 | 3456 |
| 1055327 | N/A | N/A | 332361 | 332380 | GAGTATTATAACAATTTGCA | 3 | 3457 |
| 1055332 | N/A | N/A | 332368 | 332387 | TTCCAGGGAGTATTATAACA | 2 | 3458 |
| 1055338 | N/A | N/A | 347815 | 347834 | ATCTAGTTTCTGGAAAGTAA | 22 | 3459 |
| 1055349 | N/A | N/A | 347831 | 347850 | ATAACAAATGGTCATTATCT | 43 | 3460 |
| 1055355 | N/A | N/A | 365965 | 365984 | AATCCAAATCTTGTATTCTT | 9 | 3461 |
| 1055361 | N/A | N/A | 399995 | 400014 | TCTAGAAATGATTTTGATTA | 107 | 3462 |
| 1055366 | N/A | N/A | 439847 | 439866 | TGGGCATTTAAGAAATGCTC | 140 | 3463 |

TABLE 47

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 994448 | 5496 | 5515 | 459749 | 459768 | GTATTTGTTCAGTTTAGTTG | 9 | 352 |
| 994466 | 6034 | 6053 | 460287 | 460306 | GTGTTGGTTTAGTGGATCCA | 21 | 510 |
| 994571 | 10096 | 10115 | 464349 | 464368 | GGGTAATGATCTGATATTAA | 10 | 601 |
| 994598 | 201 | 220 | 9917 | 9936 | CTTGTAGTAGTTTTTGTGAG | 42 | 215 |
| 994605 | N/A | N/A | 17726 | 17745 | GTCACCTTTTCTATTTGCAC | 3 | 138 |
| 994702 | N/A | N/A | 210730 | 210749 | TGTGTAATACTCCATTTTTC | 8 | 228 |
| 994713 | N/A | N/A | 226996 | 227015 | TGGTTATTTACTCATTCTAC | 10 | 463 |
| 994732 | N/A | N/A | 284341 | 284360 | TGTCAACTAGTTCTTATCAC | 3 | 76 |
| 994743 | N/A | N/A | 318485 | 318504 | TGTTTGATATTTCTTTTTTT | 3 | 311 |
| 994756 | N/A | N/A | 332362 | 332381 | GGAGTATTATAACAATTTGC | 1 | 79 |
| 1040299 | 5502 | 5521 | 459755 | 459774 | AGTCAGGTATTTGTTCAGTT | 6 | 2809 |
| 1040631 | 10088 | 10107 | 464341 | 464360 | ATCTGATATTAAAACATCCA | 18 | 1280 |
| 1054949 | 109 | 128 | 2619 | 2638 | TGCGGCTGCTGTTGCTCTGG | 22 | 3464 |
| 1054954 | 115 | 134 | 2625 | 2644 | ATGTCTTGCGGCTGCTGTTG | 10 | 3465 |
| 1054965 | 247 | 266 | 10658 | 10677 | CTGGTGACTTGATGCACGAT | 21 | 3466 |
| 1054971 | 256 | 275 | 10667 | 10686 | TGGACCACCCTGGTGACTTG | 17 | 3467 |
| 1054977 | 560 | 579 | 178170 | 178189 | CATAAGCTATCAGTTCCTTG | 5 | 3468 |
| 1054982 | 566 | 585 | 178176 | 178195 | GAGAACCATAAGCTATCAGT | 11 | 3469 |
| 1054988 | 584 | 603 | 178194 | 178213 | TGTGCTTTCATCACAATGGA | 56 | 3470 |
| 1054993 | 591 | 610 | 178201 | 178220 | TGTACCATGTGCTTTCATCA | 3 | 3471 |
| 1054999 | 600 | 619 | N/A | N/A | TTGGAAAACTGTACCATGTG | 8 | 3472 |
| 1055013 | 6026 | 6045 | 460279 | 460298 | TTAGTGGATCCAGTCAATTC | 31 | 3473 |
| 1055022 | 6042 | 6061 | 460295 | 460314 | CCATCTTAGTGTTGGTTTAG | 23 | 3474 |
| 1055028 | 9483 | 9502 | 463736 | 463755 | TAGAGATTGTTGTTATTGTA | 14 | 3475 |
| 1055033 | 9489 | 9508 | 463742 | 463761 | AATTCTTAGAGATTGTTGTT | 19 | 3476 |
| 1055049 | 10104 | 10123 | 464357 | 464376 | CATATGGTGGGTAATGATCT | 62 | 3477 |
| 1055055 | 195 | 214 | 9911 | 9930 | GTAGTTTTGTGAGGTAAAA | 8 | 3478 |
| 1055063 | N/A | N/A | 17718 | 17737 | TTCTATTTGCACTAGCTGCC | 78 | 3479 |
| 1055069 | N/A | N/A | 17727 | 17746 | TGTCACCTTTTCTATTTGCA | 2 | 3480 |
| 1055075 | N/A | N/A | 17736 | 17755 | CCTCTCAAATGTCACCTTTT | 85 | 3481 |
| 1055081 | N/A | N/A | 85506 | 85525 | CTATGCTCACAGAGAACCTG | 98 | 3482 |
| 1055087 | N/A | N/A | 85515 | 85534 | TTTGATATGCTATGCTCACA | 13 | 3483 |
| 1055092 | N/A | N/A | 85522 | 85541 | CAGTTAGTTTGATATGCTAT | 25 | 3484 |
| 1055097 | N/A | N/A | 103952 | 103971 | TGTGATTTATCGCTGACCTT | 53 | 3485 |
| 1055103 | N/A | N/A | 148568 | 148587 | GAATGGTTCTCTTTTACGGG | 8 | 3486 |
| 1055109 | N/A | N/A | 179785 | 179804 | TATTTAATCATGTTCCCGAT | 19 | 3487 |

TABLE 47-continued

Reduction of ATXN1 RNA by 5-10-5 MOE
gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1055114 | N/A | N/A | 179791 | 179810 | TAGTTATATTTAATCATGTT | 63 | 3488 |
| 1055119 | N/A | N/A | 184174 | 184193 | ATGTATACAATTCTGACAGT | 49 | 3489 |
| 1055125 | N/A | N/A | 184183 | 184202 | CAGGTTTATATGTATACAAT | 5 | 3490 |
| 1055130 | N/A | N/A | 184190 | 184209 | ATGTTCTCAGGTTTATATGT | 5 | 3491 |
| 1055136 | N/A | N/A | 203031 | 203050 | TTTCTTCTTTGTTCATAGGA | 71 | 3492 |
| 1055141 | N/A | N/A | 203038 | 203057 | TTGTTCCTTTCTTCTTTGTT | 46 | 3493 |
| 1055147 | N/A | N/A | 203047 | 203066 | AACAACCTCTTGTTCCTTTC | 13 | 3494 |
| 1055153 | N/A | N/A | 203891 | 203910 | TTGTTTAGATTTATCCTCAG | 6 | 3495 |
| 1055158 | N/A | N/A | 210722 | 210741 | ACTCCATTTTTCCTTCTAGA | 6 | 3496 |
| 1055169 | N/A | N/A | 210738 | 210757 | ATTACAAATGTGTAATACTC | 62 | 3497 |
| 1055175 | N/A | N/A | 212028 | 212047 | ATGTTAGTCATTTCTCTCTG | 20 | 3498 |
| 1055180 | N/A | N/A | 212034 | 212053 | AAGTCTATGTTAGTCATTTC | 31 | 3499 |
| 1055186 | N/A | N/A | 217274 | 217293 | AGGTATTTTCATGGAGTTTC | 3 | 3500 |
| 1055192 | N/A | N/A | 217283 | 217302 | TTATGTTTAAGGTATTTTCA | 60 | 3501 |
| 1055197 | N/A | N/A | 217290 | 217309 | GTAACAGTTATGTTTAAGGT | 8 | 3502 |
| 1055203 | N/A | N/A | 226988 | 227007 | TACTCATTCTACCTTCAACT | 72 | 3503 |
| 1055214 | N/A | N/A | 227004 | 227023 | CATAAACTTGGTTATTTACT | 65 | 3504 |
| 1055220 | N/A | N/A | 248565 | 248584 | CCACTACCACCCCCAAACCA | 53 | 3505 |
| 1055226 | N/A | N/A | 251502 | 251521 | CAGCATACTTAGCTTTTCAA | 16 | 3506 |
| 1055231 | N/A | N/A | 251508 | 251527 | CAGTGTCAGCATACTTAGCT | 20 | 3507 |
| 1055237 | N/A | N/A | 259737 | 259756 | CATGTATTGCTAGGAGCCAG | 46 | 3508 |
| 1055243 | N/A | N/A | 284228 | 284247 | TGGGTTTTTCTGTACAAAGT | 2 | 3509 |
| 1055248 | N/A | N/A | 284234 | 284253 | TTTGTTTGGGTTTTTCTGTA | 2 | 3510 |
| 1055254 | N/A | N/A | 284333 | 284352 | AGTTCTTATCACTATTCAGT | 2 | 3511 |
| 1055265 | N/A | N/A | 284349 | 284368 | CTAAACAATGTCAACTAGTT | 61 | 3512 |
| 1055271 | N/A | N/A | 291010 | 291029 | GGGTTTTTAGTTTTCCTTCT | 2 | 3513 |
| 1055276 | N/A | N/A | 291016 | 291035 | GGTCCTGGGTTTTTAGTTTT | 3 | 3514 |
| 1055282 | N/A | N/A | 296995 | 297014 | AATGACTGTGGTGCAGCCTC | 27 | 3515 |
| 1055288 | N/A | N/A | 297004 | 297023 | TTTGCATTAAATGACTGTGG | 2 | 3516 |
| 1055293 | N/A | N/A | 297011 | 297030 | GCCAGTGTTTGCATTAAATG | 2 | 3517 |
| 1055299 | N/A | N/A | 306736 | 306755 | AGGGCCACTAAATCTGACCT | 118 | 3518 |
| 1055305 | N/A | N/A | 306750 | 306769 | AGAATCCATTGGTAAGGGCC | 6 | 3519 |
| 1055316 | N/A | N/A | 318493 | 318512 | TTCAAATGTGTTTGATATTT | 12 | 3520 |
| 1055322 | N/A | N/A | 332354 | 332373 | ATAACAATTTGCATAGTCTC | 4 | 3521 |
| 1055333 | N/A | N/A | 332370 | 332389 | TTTTCCAGGGAGTATTATAA | 21 | 3522 |
| 1055339 | N/A | N/A | 347817 | 347836 | TTATCTAGTTTCTGGAAAGT | 39 | 3523 |

TABLE 47-continued

Reduction of ATXN1 RNA by 5-10-5 MOE gapmers with mixed PO/PS linkages in A-431 Cells

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN1 (% Control) | SEQ ID NO |
|---|---|---|---|---|---|---|---|
| 1055344 | N/A | N/A | 347824 | 347843 | ATGGTCATTATCTAGTTTCT | 2 | 3524 |
| 1055350 | N/A | N/A | 347833 | 347852 | TGATAACAAATGGTCATTAT | 32 | 3525 |
| 1055356 | N/A | N/A | 372672 | 372691 | CATCAAAATTGTGCACAATT | 81 | 3526 |
| 1055362 | N/A | N/A | 402059 | 402078 | TGAAAACATGTTGTGTGATT | 57 | 3527 |
| 1055367 | N/A | N/A | 453507 | 453526 | TTGTTGGATTCTTTTTTTCT | 27 | 3528 |

TABLE 48

Reduction of ATXN1 RNA by 5-10-5 MOE gapmers with mixed PO/PS linkages in A-431 Cells

| Compound Number | SEQ ID NO: 3 Start Site | SEQ ID NO: 3 Stop Site | Sequence (5' to 3') | ATXN1 (% Control) | SEQ ID NO |
|---|---|---|---|---|---|
| 1054961 | 193 | 212 | GACTTGATGCACGATGCTCT | 8 | 3529 |
| 1054958 | 187 | 206 | ATGCACGATGCTCTGTAAAG | 51 | 3530 |
| 1054959 | 189 | 208 | TGATGCACGATGCTCTGTAA | 42 | 3531 |
| 1054960 | 191 | 210 | CTTGATGCACGATGCTCTGT | 48 | 3532 |

Example 3: Effect of Modified Oligonucleotides on Human ATXN1 RNA In Vitro, Multiple Doses Modified oligonucleotides selected from the examples above were tested at various doses in A-431 cells. Cultured A-431 cells at a density of 10,000 cells per well were treated using free uptake with various concentrations of modified oligonucleotide as specified in the tables below. After a treatment period of approximately 48 hours, total RNA was isolated from the cells and ATXN1 RNA levels were measured by quantitative real-time RTPCR. Human ATXN1 primer probe set RTS37573 was used to measure RNA levels as described above. ATXN1 levels were adjusted according to total RNA content, as measured by RIBOGREEN® fluorescent RNA assay. Results are presented in the tables below as percent reduction of the amount of ATXN1 RNA, relative to untreated control. Where possible, the half maximal inhibitory concentration ($IC_{50}$) of each modified oligonucleotide was calculated using a linear regression on a log/linear plot of the data in excel.

TABLE 49

Dose-dependent percent reduction of human ATXN1 RNA in A-431 cells by modified oligonucleotides

| Compound No. | % Control 125 nM | 500 nM | 2000 nM | 8000 nM | IC50 (μM) |
|---|---|---|---|---|---|
| 994310 | 60 | 32 | 19 | 12 | 0.2 |
| 994316 | 36 | 15 | 9 | 9 | <0.1 |
| 994318 | 46 | 12 | 9 | 7 | <0.1 |
| 994319 | 31 | 13 | 8 | 7 | <0.1 |
| 994392 | 50 | 26 | 13 | 10 | <0.1 |
| 994421 | 16 | 8 | 8 | 10 | <0.1 |
| 994492 | 48 | 25 | 15 | 15 | <0.1 |
| 994542 | 55 | 36 | 25 | 22 | 0.1 |
| 994612 | 22 | 11 | 9 | 9 | <0.1 |
| 994613 | 30 | 23 | 15 | 14 | <0.1 |
| 994623 | 59 | 50 | 40 | 35 | 0.5 |
| 994628 | 21 | 9 | 7 | 9 | <0.1 |
| 994631 | 42 | 25 | 12 | 10 | <0.1 |
| 994645 | 90 | 78 | 68 | 56 | >8.0 |
| 994646 | 64 | 39 | 28 | 21 | 0.3 |
| 994652 | 24 | 11 | 9 | 9 | <0.1 |
| 994653 | 35 | 21 | 13 | 11 | <0.1 |
| 994812 | 31 | 13 | 9 | 8 | <0.1 |

TABLE 50

Dose-dependent percent reduction of human ATXN1 RNA in A-431 cells by modified oligonucleotides

| Compound No. | % Control 125 nM | 500 nM | 2000 nM | 8000 nM | IC50 (μM) |
|---|---|---|---|---|---|
| 994315 | 7 | 6 | 6 | 7 | <0.1 |
| 994320 | 11 | 7 | 4 | 5 | <0.1 |
| 994321 | 42 | 25 | 13 | 6 | <0.1 |
| 994395 | 41 | 27 | 21 | 12 | <0.1 |
| 994609 | 18 | 9 | 8 | 7 | <0.1 |
| 994610 | 94 | 95 | 79 | 63 | >8.0 |
| 994612 | 23 | 11 | 9 | 10 | <0.1 |
| 994616 | 70 | 51 | 40 | 27 | 0.7 |
| 994618 | 60 | 25 | 16 | 14 | 0.1 |
| 994619 | 53 | 32 | 18 | 10 | <0.1 |
| 994642 | 52 | 26 | 16 | 11 | <0.1 |
| 994643 | 56 | 35 | 23 | 17 | 0.2 |
| 994649 | 39 | 23 | 19 | 18 | <0.1 |
| 994651 | 21 | 9 | 7 | 6 | <0.1 |
| 994656 | 62 | 35 | 20 | 14 | 0.2 |
| 994696 | 34 | 17 | 12 | 9 | <0.1 |
| 994698 | 82 | 58 | 51 | 36 | 1.9 |
| 994770 | 46 | 23 | 12 | 11 | <0.1 |
| 994913 | 48 | 30 | 18 | 12 | <0.1 |

TABLE 51

Dose-dependent percent reduction of human ATXN1 RNA by modified oligonucleotides

| Compound No. | % Control 125 nM | % Control 500 nM | % Control 2000 nM | % Control 8000 nM | IC50 (μM) |
|---|---|---|---|---|---|
| 994328 | 115 | 120 | 134 | 116 | >8.0 |
| 994597 | 57 | 24 | 11 | 10 | <0.1 |
| 994599 | 55 | 36 | 30 | 22 | 0.1 |
| 994612 | 28 | 12 | 8 | 12 | <0.1 |
| 994630 | 68 | 43 | 26 | 15 | 0.4 |
| 994638 | 76 | 40 | 22 | 15 | 0.4 |
| 994693 | 78 | 55 | 35 | 17 | 0.8 |
| 994700 | 12 | 5 | 4 | 4 | <0.1 |
| 994701 | 63 | 36 | 19 | 16 | 0.2 |
| 994702 | 50 | 27 | 16 | 12 | <0.1 |
| 994703 | 66 | 43 | 29 | 16 | 0.4 |
| 994717 | 11 | 8 | 9 | 6 | <0.1 |
| 994732 | 21 | 11 | 9 | 9 | <0.1 |
| 994734 | 9 | 4 | 2 | 2 | <0.1 |
| 994735 | 49 | 21 | 15 | 14 | <0.1 |
| 994740 | 67 | 37 | 20 | 15 | 0.3 |
| 994743 | 23 | 11 | 9 | 11 | <0.1 |
| 994756 | 39 | 21 | 13 | 12 | <0.1 |
| 994918 | 63 | 41 | 24 | 15 | 0.3 |

TABLE 52

Dose-dependent percent reduction of human ATXN1 RNA by modified oligonucleotides

| Compound No. | % Control 125 nM | % Control 500 nM | % Control 2000 nM | % Control 8000 nM | IC50 (μM) |
|---|---|---|---|---|---|
| 994313 | 63 | 31 | 15 | 9 | 0.2 |
| 994314 | 41 | 19 | 10 | 15 | <0.1 |
| 994329 | 18 | 7 | 5 | 5 | <0.1 |
| 994346 | 17 | 8 | 6 | 8 | <0.1 |
| 994449 | 28 | 9 | 8 | 10 | <0.1 |
| 994466 | 103 | 104 | 79 | 79 | >8.0 |
| 994474 | 36 | 14 | 13 | 11 | <0.1 |
| 994497 | 16 | 9 | 9 | 10 | <0.1 |
| 994561 | 34 | 17 | 12 | 10 | <0.1 |
| 994571 | 95 | 77 | 76 | 73 | >8.0 |
| 994612 | 26 | 12 | 10 | 9 | <0.1 |
| 994690 | 87 | 60 | 42 | 40 | 1.9 |
| 994697 | 23 | 10 | 6 | 5 | <0.1 |
| 994706 | 12 | 7 | 5 | 5 | <0.1 |
| 994713 | 79 | 61 | 24 | 11 | 0.7 |
| 994731 | 65 | 31 | 18 | 16 | 0.2 |
| 994761 | 57 | 25 | 14 | 14 | <0.1 |
| 994835 | 75 | 36 | 21 | 19 | 0.4 |
| 994848 | 61 | 33 | 22 | 16 | 0.2 |

Example 4: Design of Modified Oligonucleotides Complementary to a Human ATXN1 Nucleic Acid Modified oligonucleotides were designed and synthesized as indicated in the tables below.

The compounds in table 53 are 5-10-5 MOE gapmers with mixed internucleoside linkages. The gapmers are 20 nucleosides in length, wherein the central gap segment consists of ten 2'-β-D-deoxynucleosides, the 5' wing segment consists of five 2'-MOE nucleosides, and the 3' wing segment consists of five 2'-MOE nucleosides. The sugar motif of the gapmers is (from 5' to 3'): eeeeedddddddddddeeeee; wherein 'd' represents a 2'-β-D-deoxyribosyl sugar moiety, and 'e' represents a 2'-MOE sugar moiety. The gapmers have an internucleoside linkage motif of (from 5' to 3'): sooosssssssssssooss; wherein "s" represents a phosphorothioate internucleoside linkage and "o" represents a phosphodiester internucleoside linkage. All cytosine residues are 5-methylcytosines.

TABLE 53

5-10-5 MOE gapmers with mixed PO/PS internucleoside linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1342029 | TGATTGTGTTCCATTGTAAA | 7023 | 7042 | 461276 | 461295 | 3533 |
| 1342030 | GAGTTGTCCATAGTCATGAA | 4432 | 4451 | 458685 | 458704 | 3534 |
| 1342031 | CGAGTTGTCCATAGTCATGA | 4433 | 4452 | 458686 | 458705 | 3535 |
| 1342033 | TGCACTTTTGTTTCTACAGC | N/A | N/A | 441087 | 441106 | 3536 |
| 1342034 | AGGCCTTGCACTTTTGTTTC | N/A | N/A | 441093 | 441112 | 3537 |
| 1342035 | AAGTGGCACCCGAGTTGTCC | 4443 | 4462 | 458696 | 458715 | 3538 |
| 1342036 | GCCTTGCACTTTTGTTTCTA | N/A | N/A | 441091 | 441110 | 3539 |
| 1342037 | GATTGTGTTCCATTGTAAAC | 7022 | 7041 | 461275 | 461294 | 3540 |
| 1342039 | GTGGATCCAGTCAATTCAAT | 6023 | 6042 | 460276 | 460295 | 3541 |
| 1342040 | AATAGCAGCTATTTCATGAC | N/A | N/A | 439446 | 439465 | 3542 |
| 1342044 | TGGATCCAGTCAATTCAATA | 6022 | 6041 | 460275 | 460294 | 3543 |

TABLE 53-continued 5-10-5 MOE gapmers with mixed PO/PS internucleoside
linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1342045 | TCAATTCAATACTCGAAGTA | 6013 | 6032 | 460266 | 460285 | 3544 |
| 1342046 | GGATCCAGTCAATTCAATAC | 6021 | 6040 | 460274 | 460293 | 3545 |
| 1342050 | CAATGACTCTTCACTCATGT | N/A | N/A | 440235 | 440254 | 3546 |
| 1342051 | ACTATTTTCAACTCAAGCTG | N/A | N/A | 439428 | 439447 | 3547 |
| 1342052 | GACTCTTCACTCATGTTTAT | N/A | N/A | 440231 | 440250 | 3548 |
| 1342053 | GGTACTGGCTCATCAGTTGT | N/A | N/A | 444368 | 444387 | 3549 |
| 1342054 | AATGACTCTTCACTCATGTT | N/A | N/A | 440234 | 440253 | 3550 |
| 1342055 | AGCAATGACTCTTCACTCAT | N/A | N/A | 440237 | 440256 | 3551 |
| 1342057 | AAGCAATGACTCTTCACTCA | N/A | N/A | 440238 | 440257 | 3552 |
| 1342060 | AACCAATCTATCACACCAAT | N/A | N/A | 444348 | 444367 | 3553 |
| 1342063 | AGCCATCCAAGTAAGAATAT | 5475 | 5494 | 459728 | 459747 | 3554 |
| 1342065 | ACCAATCTATCACACCAATG | N/A | N/A | 444347 | 444366 | 3555 |
| 1342066 | CAATCTATCACACCAATGCA | N/A | N/A | 444345 | 444364 | 3556 |
| 1342068 | CAGCCATCCAAGTAAGAATA | 5476 | 5495 | 459729 | 459748 | 3557 |
| 1342069 | TATTGTCACATACTAGTTCA | 4755 | 4774 | 459008 | 459027 | 3558 |
| 1342070 | CTGACTAATTTCTTGGTGAT | 7039 | 7058 | 461292 | 461311 | 3559 |
| 1342074 | GTGGTCATTTATTGTCACAT | 4764 | 4783 | 459017 | 459036 | 3560 |
| 1342075 | GTCACATACTAGTTCATAAT | 4751 | 4770 | 459004 | 459023 | 3561 |
| 1342076 | TTATTGTCACATACTAGTTC | 4756 | 4775 | 459009 | 459028 | 3562 |
| 1342032 | CCCGAGTTGTCCATAGTCAT | 4435 | 4454 | 458688 | 458707 | 3563 |
| 1342038 | CATTGTAAACGCAAAAGGCC | 7012 | 7031 | 461265 | 461284 | 3564 |
| 1342041 | CAGTCAATTCAATACTCGAA | 6016 | 6035 | 460269 | 460288 | 3565 |
| 1342042 | GTCCATAGTCATGAACTATA | 4427 | 4446 | 458680 | 458699 | 3566 |
| 1342043 | ATAGCAGCTATTTCATGACT | N/A | N/A | 439445 | 439464 | 3567 |
| 1342047 | GTCAATTCAATACTCGAAGT | 6014 | 6033 | 460267 | 460286 | 3568 |
| 1342048 | GATCCAGTCAATTCAATACT | 6020 | 6039 | 460273 | 460292 | 3569 |
| 1342049 | TAACCAATCTATCACACCAA | N/A | N/A | 444349 | 444368 | 3570 |
| 1342056 | ATGACTCTTCACTCATGTTT | N/A | N/A | 440233 | 440252 | 3571 |
| 1342058 | GACTATTTCAACTCAAGCT | N/A | N/A | 439429 | 439448 | 3572 |
| 1342059 | CTTGGTGGTCATTTATTGTC | 4768 | 4787 | 459021 | 459040 | 3573 |
| 1342061 | GGTGGTCATTTATTGTCACA | 4765 | 4784 | 459018 | 459037 | 3574 |
| 1342062 | TAGTTGCAGCCATCCAAGTA | 5482 | 5501 | 459735 | 459754 | 3575 |
| 1342064 | TGGTGGTCATTTATTGTCAC | 4766 | 4785 | 459019 | 459038 | 3576 |
| 1342067 | GTTCAGTTAGTTGCAGCCA | 5490 | 5509 | 459743 | 459762 | 3577 |
| 1342071 | CATACTAGTTCATAATTCAC | 4747 | 4766 | 459000 | 459019 | 3578 |

TABLE 53-continued 5-10-5 MOE gapmers with mixed PO/PS internucleoside linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1342072 | TCGCCCTGACTAATTTCTTG | 7044 | 7063 | 461297 | 461316 | 3579 |
| 1342073 | CCCTGACTAATTTCTTGGTG | 7041 | 7060 | 461294 | 461313 | 3580 |
| 1342077 | GCCCTGACTAATTTCTTGGT | 7042 | 7061 | 461295 | 461314 | 3581 |

The compounds in table 54 are 5-10-5 MOE gapmers with mixed internucleoside linkages. The gapmers are 20 nucleosides in length, wherein the central gap segment consists of ten 2'-β-D-deoxynucleosides, the 5' wing segment consists of five 2'-MOE nucleosides, and the 3' wing segment consists of five 2'-MOE nucleosides. The sugar motif of the gapmers is (from 5' to 3'): eeeeedddddddddeeeee; wherein 'd' represents a 2'-β-D-deoxyribosyl sugar moiety, and 'e' represents a 2'-MOE sugar moiety. The gapmers have an internucleoside linkage motif of (from 5' to 3'): sssosssssssssssosss; wherein "s" represents a phosphorothioate internucleoside linkage and "o" represents a phosphodiester internucleoside linkage. All cytosine residues are 5-methylcytosines.

TABLE 54

5-10-5 MOE gapmers with mixed PO/PS internucleoside linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1364280 | ACCCGAGTTGTCCATAGTCA | 4436 | 4455 | 458689 | 458708 | 582 |
| 1364281 | CCACGCTTTTATTTTCTGAT | N/A | N/A | 439093 | 439112 | 2074 |
| 1364282 | GCCTTTATAACTTTTCTTTC | N/A | N/A | 446680 | 446699 | 2552 |
| 1364283 | GGTCATTTATTGTCACATAC | 4762 | 4781 | 459015 | 459034 | 194 |
| 1364285 | ATTTTCTTTTTTCTGTGCCT | N/A | N/A | 452653 | 452672 | 488 |
| 1367569 | TTCCTCTTACCATCAAAGGC | 5906 | 5925 | 460159 | 460178 | 2502 |
| 1367572 | CGTGGGTGTTCGCTCTCTCC | 4256 | 4275 | 458509 | 458528 | 3582 |
| 1367573 | GCGTGGGTGTTCGCTCTCTC | 4257 | 4276 | 458510 | 458529 | 3583 |
| 1367575 | CTCTTACCATCAAAGGCTAA | 5903 | 5922 | 460156 | 460175 | 3584 |
| 1367576 | CCTCTTACCATCAAAGGCTA | 5904 | 5923 | 460157 | 460176 | 2425 |
| 1367577 | TCCTCTTACCATCAAAGGCT | 5905 | 5924 | 460158 | 460177 | 431 |
| 1367580 | CAGCCCGTATTCCTCTTACC | 5915 | 5934 | 460168 | 460187 | 509 |
| 1367581 | TGTGGCAGCCCGTATTCCTC | 5920 | 5939 | 460173 | 460192 | 3585 |
| 1367586 | GGGTGTTCGCTCTCTCCCTC | 4253 | 4272 | 458506 | 458525 | 3586 |
| 1367588 | GTGGGTGTTCGCTCTCTCCC | 4255 | 4274 | 458508 | 458527 | 3587 |
| 1367589 | CCGTATTCCTCTTACCATCA | 5911 | 5930 | 460164 | 460183 | 3588 |
| 1367590 | GTATTCCTCTTACCATCAAA | 5909 | 5928 | 460162 | 460181 | 3589 |
| 1367591 | CCCGTATTCCTCTTACCATC | 5912 | 5931 | 460165 | 460184 | 3590 |
| 1394153 | CCCGAGTTGTCCATAGTCAT | 4435 | 4454 | 458688 | 458707 | 3563 |
| 1394154 | GCACCCGAGTTGTCCATAGT | 4438 | 4457 | 458691 | 458710 | 3605 |
| 1394155 | CACCCGAGTTGTCCATAGTC | 4437 | 4456 | 458690 | 458709 | 3593 |
| 1394156 | GTCAGGTATTTGTTCAGTTT | 5501 | 5520 | 459754 | 459773 | 3402 |
| 1394157 | TGTTCAGTTTAGTTGCAGCC | 5491 | 5510 | 459744 | 459763 | 274 |

TABLE 54-continued 5-10-5 MOE gapmers with mixed PO/PS internucleoside linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1394158 | TTGTTCAGTTTAGTTGCAGC | 5492 | 5511 | 459745 | 459764 | 3655 |
| 1394159 | GTTCAGTTTAGTTGCAGCCA | 5490 | 5509 | 459743 | 459762 | 3577 |
| 1394160 | TCAGGTATTTGTTCAGTTTA | 5500 | 5519 | 459753 | 459772 | 3331 |
| 1394161 | GCCCGTATTCCTCTTACCAT | 5913 | 5932 | 460166 | 460185 | 2579 |
| 1394507 | GGTGGTCATTTATTGTCACA | 4765 | 4784 | 459018 | 459037 | 3574 |
| 1394508 | GTGATTGTGTTCCATTGTAA | 7024 | 7043 | 461277 | 461296 | 201 |
| 1394510 | CCTTGCACTTTTGTTTCTAC | N/A | N/A | 441090 | 441109 | 321 |
| 1394511 | GTGGTCATTTATTGTCACAT | 4764 | 4783 | 459017 | 459036 | 3560 |
| 1394512 | ATGTGTTCTTAAATTCTCTA | 8210 | 8229 | 462463 | 462482 | 1583 |
| 1394513 | GCACGGTATTAGTGTCTTCA | 7892 | 7911 | 462145 | 462164 | 126 |
| 1394514 | GCTTCTCAAATCAGGTGTAC | 8481 | 8500 | 462734 | 462753 | 1045 |
| 1394515 | TGATTGTGTTCCATTGTAAA | 7023 | 7042 | 461276 | 461295 | 3533 |
| 1394516 | GTTTGTTGGTTTCTTATTAA | 7083 | 7102 | 461336 | 461355 | 46 |
| 1394517 | CTGTATATTTATTACTTGAT | 8228 | 8247 | 462481 | 462500 | 1891 |
| 1394518 | TGGTCATTTATTGTCACATA | 4763 | 4782 | 459016 | 459035 | 3038 |

The compounds in table 55 are 6-10-4 MOE gapmers with mixed internucleoside linkages. The gapmers are 20 nucleosides in length, wherein the central gap segment consists of ten 2'-β-D-deoxynucleosides, the 5' wing segment consists of six 2'-MOE nucleosides, and the 3' wing segment consists of four 2'-MOE nucleosides. The sugar motif of the gapmers is (from 5' to 3'): eeeeeedddddddddddeeee; wherein 'd' represents a 2'-β-D-deoxyribosyl sugar moiety, and 'e' represents a 2'-MOE sugar moiety. The gapmers have an internucleoside linkage motif of (from 5' to 3'): sooooossssssssssoss; wherein "s" represents a phosphorothioate internucleoside linkage and "o" represents a phosphodiester internucleoside linkage. All cytosine residues are 5-methylcytosines.

TABLE 55

6-10-4 MOE gapmers with mixed PO/PS internucleoside linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1371806 | GTTCGCTCTCTCCCTCTCCC | 4249 | 4268 | 458502 | 458521 | 114 |
| 1371807 | TTTTCTTTTCGCCCTGACTA | 7052 | 7071 | 461305 | 461324 | 3591 |
| 1371808 | TCATTTATTGTCACATACTA | 4760 | 4779 | 459013 | 459032 | 3592 |
| 1371809 | CACCCGAGTTGTCCATAGTC | 4437 | 4456 | 458690 | 458709 | 3593 |
| 1371810 | GTCATTTATTGTCACATACT | 4761 | 4780 | 459014 | 459033 | 3594 |
| 1371811 | TTTTTTCTTTTCGCCCTGAC | 7054 | 7073 | 461307 | 461326 | 3595 |
| 1371812 | GTTGTCCATAGTCATGAACT | 4430 | 4449 | 458683 | 458702 | 3596 |
| 1371813 | TAATTCACATTCATCCCTTT | 4735 | 4754 | 458988 | 459007 | 3597 |
| 1371814 | CCCTGACTAATTTCTTGGTG | 7041 | 7060 | 461294 | 461313 | 3580 |
| 1371815 | ATAATTCACATTCATCCCTT | 4736 | 4755 | 458989 | 459008 | 2268 |

TABLE 55-continued 6-10-4 MOE gapmers with mixed PO/PS internucleoside linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1371816 | TGGTCATTTATTGTCACATA | 4763 | 4782 | 459016 | 459035 | 3038 |
| 1371817 | TTGTCCATAGTCATGAACTA | 4429 | 4448 | 458682 | 458701 | 2421 |
| 1371818 | AGTTGCAGCCATCCAAGTAA | 5481 | 5500 | 459734 | 459753 | 2655 |
| 1371819 | GTTCATAATTCACATTCATC | 4740 | 4759 | 458993 | 459012 | 2499 |
| 1371820 | GCCCCCAAACCCATTTTCTT | N/A | N/A | 452665 | 452684 | 1026 |
| 1371821 | CAGCCATCCAAGTAAGAATA | 5476 | 5495 | 459729 | 459748 | 3557 |
| 1371822 | TTCATAATTCACATTCATCC | 4739 | 4758 | 458992 | 459011 | 2422 |
| 1371823 | GAGAACAAAGTCTATGTGGC | 5934 | 5953 | 460187 | 460206 | 2733 |
| 1371824 | CCCGAGTTGTCCATAGTCAT | 4435 | 4454 | 458688 | 458707 | 3563 |
| 1371825 | AGCCCGTATTCCTCTTACCA | 5914 | 5933 | 460167 | 460186 | 2656 |
| 1371826 | TCCTAACACTGCACAGAAAC | 4279 | 4298 | 458532 | 458551 | 3598 |
| 1371827 | TCAGGTATTTGTTCAGTTTA | 5500 | 5519 | 459753 | 459772 | 3331 |
| 1371828 | TCCATAGTCATGAACTATAA | 4426 | 4445 | 458679 | 458698 | 3599 |
| 1371829 | GTCAGGTATTTGTTCAGTTT | 5501 | 5520 | 459754 | 459773 | 3402 |
| 1371830 | GTGATTGTGTTCCATTGTAA | 7024 | 7043 | 461277 | 461296 | 201 |
| 1371831 | CCATAGTCATGAACTATAAA | 4425 | 4444 | 458678 | 458697 | 3600 |
| 1371832 | TTTTTCTGTGCCTCCTGACC | N/A | N/A | 452646 | 452665 | 795 |
| 1371833 | TGATTGTGTTCCATTGTAAA | 7023 | 7042 | 461276 | 461295 | 3533 |
| 1371834 | CCTGACTAATTTCTTGGTGA | 7040 | 7059 | 461293 | 461312 | 2350 |
| 1371835 | CATAGTCATGAACTATAAAC | 4424 | 4443 | 458677 | 458696 | 3601 |
| 1371836 | GAGTTGTCCATAGTCATGAA | 4432 | 4451 | 458685 | 458704 | 3534 |
| 1371837 | AAAGAAAAGTCAGGTATTTG | 5509 | 5528 | 459762 | 459781 | 3332 |
| 1371838 | GCCCTGACTAATTTCTTGGT | 7042 | 7061 | 461295 | 461314 | 3581 |
| 1371839 | ACAGAAACCAGCGTGGGTGT | 4267 | 4286 | 458520 | 458539 | 3602 |
| 1371840 | CTGACTAATTTCTTGGTGAT | 7039 | 7058 | 461292 | 461311 | 3559 |
| 1371841 | CCTCTTACCATCAAAGGCTA | 5904 | 5923 | 460157 | 460176 | 2425 |
| 1371842 | GCCCGTATTCCTCTTACCAT | 5913 | 5932 | 460166 | 460185 | 2579 |
| 1371843 | GCAGCCATCCAAGTAAGAAT | 5477 | 5496 | 459730 | 459749 | 2578 |
| 1371844 | TCATAATTCACATTCATCCC | 4738 | 4757 | 458991 | 459010 | 2345 |
| 1371845 | AGTTCATAATTCACATTCAT | 4741 | 4760 | 458994 | 459013 | 2576 |
| 1371846 | GTGTTCCATTGTAAACGCAA | 7018 | 7037 | 461271 | 461290 | 123 |
| 1371847 | ATTTTCTTTTTCTGTGCCT | N/A | N/A | 452653 | 452672 | 488 |
| 1371848 | GGTCATTTATTGTCACATAC | 4762 | 4781 | 459015 | 459034 | 194 |
| 1371849 | TCCTCTTACCATCAAAGGCT | 5905 | 5924 | 460158 | 460177 | 431 |
| 1371850 | TGGGTGTTCGCTCTCTCCCT | 4254 | 4273 | 458507 | 458526 | 270 |
| 1371851 | ACCCGAGTTGTCCATAGTCA | 4436 | 4455 | 458689 | 458708 | 582 |

TABLE 55-continued 6-10-4 MOE gapmers with mixed PO/PS internucleoside linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1371852 | CTGCACAGAAACCAGCGTGG | 4271 | 4290 | 458524 | 458543 | 3603 |
| 1371853 | CATAATTCACATTCATCCCT | 4737 | 4756 | 458990 | 459009 | 3604 |
| 1371854 | GCACCCGAGTTGTCCATAGT | 4438 | 4457 | 458691 | 458710 | 3605 |
| 1371855 | TTTTTCTTTTCGCCCTGACT | 7053 | 7072 | 461306 | 461325 | 3606 |
| 1371856 | ACTGCACAGAAACCAGCGTG | 4272 | 4291 | 458525 | 458544 | 3607 |
| 1371857 | TGTGTTCCATTGTAAACGCA | 7019 | 7038 | 461272 | 461291 | 3608 |
| 1371858 | CCTAACACTGCACAGAAACC | 4278 | 4297 | 458531 | 458550 | 3609 |
| 1371859 | TTTTATCCCAGTCATTGGCC | N/A | N/A | 452682 | 452701 | 3610 |
| 1371860 | CCAGTCATTGGCCCCCAAAC | N/A | N/A | 452675 | 452694 | 3611 |
| 1371861 | GGGTGTTCGCTCTCTCCCTC | 4253 | 4272 | 458506 | 458525 | 3586 |
| 1371862 | TTTTCTGTGCCTCCTGACCT | N/A | N/A | 452645 | 452664 | 3612 |
| 1371863 | GACCTCTACCCTTGTGAGCA | N/A | N/A | 452630 | 452649 | 3613 |
| 1371864 | CACTGCACAGAAACCAGCGT | 4273 | 4292 | 458526 | 458545 | 3614 |
| 1371865 | TTAATGAGAACAAAGTCTAT | 5939 | 5958 | 460192 | 460211 | 3615 |
| 1371866 | CATCCAAGTAAGAATATTTA | 5472 | 5491 | 459725 | 459744 | 3616 |
| 1371867 | AACACTGCACAGAAACCAGC | 4275 | 4294 | 458528 | 458547 | 3617 |
| 1371868 | AATGAGAACAAAGTCTATGT | 5937 | 5956 | 460190 | 460209 | 3618 |
| 1371869 | GCCATCCAAGTAAGAATATT | 5474 | 5493 | 459727 | 459746 | 3619 |
| 1371870 | TGTGGCAGCCCGTATTCCTC | 5920 | 5939 | 460173 | 460192 | 3585 |
| 1371871 | GTTGCAGCCATCCAAGTAAG | 5480 | 5499 | 459733 | 459752 | 3620 |
| 1371872 | CCGAGTTGTCCATAGTCATG | 4434 | 4453 | 458687 | 458706 | 3621 |
| 1371873 | CAAAGTCTATGTGGCAGCCC | 5929 | 5948 | 460182 | 460201 | 3622 |
| 1371874 | TAACACTGCACAGAAACCAG | 4276 | 4295 | 458529 | 458548 | 3623 |
| 1371875 | CCCGTATTCCTCTTACCATC | 5912 | 5931 | 460165 | 460184 | 3590 |
| 1371876 | CAGTTTAGTTGCAGCCATCC | 5487 | 5506 | 459740 | 459759 | 3624 |
| 1371877 | GTATTCCTCTTACCATCAAA | 5909 | 5928 | 460162 | 460181 | 3589 |
| 1394164 | TGTTCAGTTTAGTTGCAGCC | 5491 | 5510 | 459744 | 459763 | 274 |
| 1394165 | CCGTATTCCTCTTACCATCA | 5911 | 5930 | 460164 | 460183 | 3588 |
| 1394166 | TTCAGTTTAGTTGCAGCCAT | 5489 | 5508 | 459742 | 459761 | 3190 |
| 1394167 | TTGTTCAGTTTAGTTGCAGC | 5492 | 5511 | 459745 | 459764 | 3655 |
| 1394168 | GTTCAGTTTAGTTGCAGCCA | 5490 | 5509 | 459743 | 459762 | 3577 |
| 1394522 | GCCTTTATAACTTTTCTTTC | N/A | N/A | 446680 | 446699 | 2552 |
| 1394523 | GGTGGTCATTTATTGTCACA | 4765 | 4784 | 459018 | 459037 | 3574 |
| 1394524 | CAGCCCGTATTCCTCTTACC | 5915 | 5934 | 460168 | 460187 | 509 |
| 1394525 | GCTTCTCAAATCAGGTGTAC | 8481 | 8500 | 462734 | 462753 | 1045 |
| 1394526 | CCACGCTTTTATTTTCTGAT | N/A | N/A | 439093 | 439112 | 2074 |

TABLE 55-continued 6-10-4 MOE gapmers with mixed PO/PS internucleoside linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1394527 | GTGGTCATTTATTGTCACAT | 4764 | 4783 | 459017 | 459036 | 3560 |
| 1394528 | ATGTGTTCTTAAATTCTCTA | 8210 | 8229 | 462463 | 462482 | 1583 |
| 1394529 | GCACGGTATTAGTGTCTTCA | 7892 | 7911 | 462145 | 462164 | 126 |
| 1394530 | GTTTGTTGGTTTCTTATTAA | 7083 | 7102 | 461336 | 461355 | 46 |
| 1394531 | CTGTATATTTATTACTTGAT | 8228 | 8247 | 462481 | 462500 | 1891 |
| 1394532 | CCTTGCACTTTTGTTTCTAC | N/A | N/A | 441090 | 441109 | 321 |

The compounds in table 56 are 5-8-4 mixed MOE/cEt gapmers with mixed internucleoside linkages. The gapmers are 17 nucleosides in length, wherein the central gap segment consists of eight 2'-β-D-deoxynucleosides, the 5' wing segment consists of five 2'-MOE nucleosides, and the 3' wing segment consists of two cEt nucleosides and two 2'-MOE nucleosides. The sugar motif of the gapmers is (from 5' to 3'): eeeeeddddddddkkee; wherein 'd' represents a 2'-β-D-deoxyribosyl sugar moiety, 'k' represents a cEt sugar moiety, and 'e' represents a 2'-MOE sugar moiety. The gapmers have an internucleoside linkage motif of (from 5' to 3'): sssosssssssssoss; wherein "s" represents a phosphorothioate internucleoside linkage and "o" represents a phosphodiester internucleoside linkage. All cytosine residues are 5-methylcytosines.

TABLE 56

5-8-4 MOE/cEt mixed wing gapmers with mixed PO/PS internucleoside linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1365254 | CACGCTTTTATTTTCTG | N/A | N/A | 439095 | 439111 | 3625 |
| 1365255 | CCACGCTTTTATTTTCT | N/A | N/A | 439096 | 439112 | 3626 |
| 1365258 | TTTATAACTTTTCTTTC | N/A | N/A | 446680 | 446696 | 3627 |
| 1365259 | CTTTATAACTTTTCTTT | N/A | N/A | 446681 | 446697 | 3628 |
| 1365260 | CCTTTATAACTTTTCTT | N/A | N/A | 446682 | 446698 | 3629 |
| 1365261 | GCCTTTATAACTTTTCT | N/A | N/A | 446683 | 446699 | 3630 |
| 1365262 | TCATTTATTGTCACATA | 4763 | 4779 | 459016 | 459032 | 3631 |
| 1365263 | CATTTATTGTCACATAC | 4762 | 4778 | 459015 | 459031 | 3632 |
| 1365264 | GTCATTTATTGTCACAT | 4764 | 4780 | 459017 | 459033 | 3633 |
| 1365265 | GGTCATTTATTGTCACA | 4765 | 4781 | 459018 | 459034 | 3634 |
| 1365267 | CCGAGTTGTCCATAGTC | 4437 | 4453 | 458690 | 458706 | 3635 |
| 1365268 | CCCGAGTTGTCCATAGT | 4438 | 4454 | 458691 | 458707 | 3636 |
| 1365270 | ACCCGAGTTGTCCATAG | 4439 | 4455 | 458692 | 458708 | 3637 |
| 1365271 | TCAGTTTAGTTGCAGCC | 5491 | 5507 | 459744 | 459760 | 3638 |
| 1365272 | CAGTTTAGTTGCAGCCA | 5490 | 5506 | 459743 | 459759 | 3639 |
| 1365274 | TTCAGTTTAGTTGCAGC | 5492 | 5508 | 459745 | 459761 | 3640 |
| 1365275 | TTCTTTTTTCTGTGCCT | N/A | N/A | 452653 | 452669 | 3641 |

The compounds in table 57 are 5-8-4 mixed gapmers with mixed internucleoside linkages. The mixed gapmers have mixed cEt/MOE wings and a 2'-OMe modified nucleoside at position 2 of the gap. The gapmers are 17 nucleosides in length, wherein the 5' wing segment consists of five 2'-MOE nucleosides, the 3' wing segment consists of two cEt nucleosides and two 2'-MOE nucleosides. The gap is eight nucleosides in length, and has a nucleoside comprising a 2'-β-D-deoxyribosyl sugar moiety at positions 1, 3, 4, 5, 6, 7, and 8 of the gap (counting from the 5' end) and 2'-OMe nucleoside at position 2 of the gap (counting from the 5' end). The sugar motif of the mixed gapmers is (from 5' to 3'): eeeeedydddddkkee; wherein 'd' represents a 2'-β-D-deoxyribosyl sugar moiety, 'y' represents a 2'-O-methyl ribose sugar moiety, 'k' represents a cEt sugar moiety, and 'e' represents a 2'-MOE sugar moiety. The gapmers have an internucleoside linkage motif of (from 5' to 3'): sssosssssss-soss; wherein "s" represents a phosphorothioate internucleoside linkage and "o" represents a phosphodiester internucleoside linkage. All cytosine residues are 5-methylcytosines.

The compounds in table 58 are 5-8-4 MOE gapmers with mixed internucleoside linkages. The gapmers are 17 nucleosides in length, wherein the central gap segment consists of eight 2'-β-D-deoxynucleosides, the 5' wing segment consists of five 2'-MOE nucleosides, and the 3' wing segment consists of four 2'-MOE nucleosides. The sugar motif of the gapmers is (from 5' to 3'): eeeeedddddddeeee; wherein 'd' represents a 2'-β-D-deoxyribosyl sugar moiety, and 'e' represents a 2'-MOE sugar moiety. The gapmers have an internucleoside linkage motif of (from 5' to 3'): sssosssssss-soss; wherein "s" represents a phosphorothioate internucleoside linkage and "o" represents a phosphodiester internucleoside linkage. All cytosine residues are 5-methylcytosines.

TABLE 57

5-8-4 MOE/cEt mixed gapmers with mixed PO/PS internucleoside linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1365278 | CGCTTTUATTTTCTGAT | N/A | N/A | 439093 | 439109 | 3642 |
| 1365281 | CCACGCUTTTATTTTCT | N/A | N/A | 439096 | 439112 | 3643 |
| 1365282 | TTTATAACTTTTCTTTC | N/A | N/A | 446680 | 446696 | 3627 |
| 1365283 | CCTTTAUAACTTTTCTT | N/A | N/A | 446682 | 446698 | 3644 |
| 1365284 | GCCTTTATAACTTTTCT | N/A | N/A | 446683 | 446699 | 3630 |
| 1365285 | CATTTAUTGTCACATAC | 4762 | 4778 | 459015 | 459031 | 3645 |
| 1365286 | TCATTTATTGTCACATA | 4763 | 4779 | 459016 | 459032 | 3631 |
| 1365287 | CTTTATAACTTTTCTTT | N/A | N/A | 446681 | 446697 | 3628 |
| 1365288 | GTCATTUATTGTCACAT | 4764 | 4780 | 459017 | 459033 | 3646 |
| 1365289 | GGTCATUTATTGTCACA | 4765 | 4781 | 459018 | 459034 | 3647 |
| 1365290 | CCGAGTUGTCCATAGTC | 4437 | 4453 | 458690 | 458706 | 3648 |
| 1365291 | CGAGTTGTCCATAGTCA | 4436 | 4452 | 458689 | 458705 | 3649 |
| 1365292 | ACCCGAGTTGTCCATAG | 4439 | 4455 | 458692 | 458708 | 3637 |
| 1365293 | TTTCTTUTTTCTGTGCC | N/A | N/A | 452654 | 452670 | 3650 |
| 1365294 | CAGTTTAGTTGCAGCCA | 5490 | 5506 | 459743 | 459759 | 3639 |
| 1365297 | TTCTTTUTTCTGTGCCT | N/A | N/A | 452653 | 452669 | 3651 |
| 1365298 | CCCGAGUTGTCCATAGT | 4438 | 4454 | 458691 | 458707 | 3652 |
| 1365299 | TTCAGTUTAGTTGCAGC | 5492 | 5508 | 459745 | 459761 | 3653 |
| 1365300 | TCAGTTUAGTTGCAGCC | 5491 | 5507 | 459744 | 459760 | 3654 |

TABLE 58

5-8-4 MOE gapmers with mixed PO/PS internucleoside linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1385293 | TCAGTTTAGTTGCAGCC | 5491 | 5507 | 459744 | 459760 | 3638 |
| 1385294 | GGTCATTTATTGTCACA | 4765 | 4781 | 459018 | 459034 | 3634 |
| 1385295 | CCGAGTTGTCCATAGTC | 4437 | 4453 | 458690 | 458706 | 3635 |
| 1394533 | CAGTTTAGTTGCAGCCA | 5490 | 5506 | 459743 | 459759 | 3639 |
| 1394534 | CGAGTTGTCCATAGTCA | 4436 | 4452 | 458689 | 458705 | 3649 |
| 1394537 | GCACCCGAGTTGTCCAT | 4441 | 4457 | 458694 | 458710 | 3656 |
| 1394538 | CAGCCCGTATTCCTCTT | 5918 | 5934 | 460171 | 460187 | 3657 |
| 1394539 | CACCCGAGTTGTCCATA | 4440 | 4456 | 458693 | 458709 | 3658 |
| 1394540 | GAGTTGTCCATAGTCAT | 4435 | 4451 | 458688 | 458704 | 3659 |
| 1394541 | CCCGTATTCCTCTTACC | 5915 | 5931 | 460168 | 460184 | 3660 |
| 1394543 | AGCCCGTATTCCTCTTA | 5917 | 5933 | 460170 | 460186 | 3661 |
| 1394544 | AGTTTAGTTGCAGCCAT | 5489 | 5505 | 459742 | 459758 | 3662 |
| 1394545 | GTATTCCTCTTACCATC | 5912 | 5928 | 460165 | 460181 | 3663 |
| 1394546 | TTCAGTTTAGTTGCAGC | 5492 | 5508 | 459745 | 459761 | 3640 |
| 1394547 | CCCGAGTTGTCCATAGT | 4438 | 4454 | 458691 | 458707 | 3636 |
| 1394548 | CGTATTCCTCTTACCAT | 5913 | 5929 | 460166 | 460182 | 3664 |
| 1394549 | TGTTCAGTTTAGTTGCA | 5494 | 5510 | 459747 | 459763 | 3665 |
| 1394550 | TATTCCTCTTACCATCA | 5911 | 5927 | 460164 | 460180 | 3666 |
| 1394551 | CCGTATTCCTCTTACCA | 5914 | 5930 | 460167 | 460183 | 3667 |
| 1394552 | GCCCGTATTCCTCTTAC | 5916 | 5932 | 460169 | 460185 | 3668 |
| 1394553 | TTGTTCAGTTTAGTTGC | 5495 | 5511 | 459748 | 459764 | 3669 |

The compounds in table 59 are 5-10-5 MOE gapmers with mixed internucleoside linkages. The gapmers are 20 nucleosides in length wherein the central gap segment consists of ten 2'-β-D-deoxynucleosides, the 5' wing segment consists of five 2'-MOE nucleosides, and the 3' wing segment consists of five 2'-MOE nucleosides. The sugar motif of the gapmers is (from 5' to 3'): eeeeeddddddddddeeeee; wherein 'd' represents a 2'-β-D-deoxyribosyl sugar moiety, and 'e' represents a 2'-MOE sugar moiety. The gapmers have an internucleoside linkage motif of (from 5' to 3'): sooosssssssssssooss; wherein "s" represents a phosphorothioate internucleoside linkage and "o" represents a phosphodiester internucleoside linkage. All cytosine residues are 5-methylcytosines.

TABLE 59

5-10-5 MOE gapmers with mixed PO/PS internucleoside linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1371311 | CCCGTATTCCTCTTACCATC | 5912 | 5931 | 460165 | 460184 | 3590 |
| 1371320 | TGTGGCAGCCCGTATTCCTC | 5920 | 5939 | 460173 | 460192 | 3585 |
| 1371322 | CACCCGAGTTGTCCATAGTC | 4437 | 4456 | 458690 | 458709 | 3593 |

TABLE 59-continued 5-10-5 MOE gapmers with mixed PO/PS internucleoside
linkages complementary to human ATXN1

| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1371325 | GCACCCGAGTIGTCCATAGT | 4438 | 4457 | 458691 | 458710 | 3605 |
| 1394162 | TTGTTCAGTTTAGTTGCAGC | 5492 | 5511 | 459745 | 459764 | 3655 |
| 1394163 | CCGTATTCCTCTTACCATCA | 5911 | 5930 | 460164 | 460183 | 3588 |

Example 5: Tolerability of Modified Oligonucleotides Complementary to Human ATXN1 in Rats, Long-Term Assessment In separate studies run under the same conditions, modified oligonucleotides described above were tested in Sprague Dawley rats to assess the long-term tolerability of the oligonucleotides. Sprague Dawley rats each received a single intrathecal (IT) delivered dose of 3 mg of oligonucleotide or PBS. Each animal was weighed and evaluated weekly by a trained observer for adverse events. Adverse events were defined as neurological dysfunction not typical in PBS-treated control animals, including, but not limited to: abnormal limb splay, abnormal gait, tremors, abnormal respiration, paralysis, and spasticity. Animals treated with Compound No. 994509, Compound No. 1040500, Compound No. 1041927, Compound No. 1055001, Compound No. 1371311, or Compound No. 1385293 achieved no adverse events for the duration of the study.

Example 6: Activity of Modified Oligonucleotides Complementary to Human ATXN1 in Transgenic Mice A transgenic mouse model was developed in the laboratories of Drs. Harry Orr and Michael Koob at the University of Minnesota. The construct contains human Atxn1 exon 8, intron 8 and exon 9 including the entire 3' UTR (Banfi et al. Nat. Genet. 7: 513-520, 1994) (including nucleosides 435531-464889 of SEQ ID NO:2) flanked by Frt sites for FLP recombinase and the selection marker Hygro flanked by LoxN sites for CRE recombinase. The construct was injected into mouse blastocysts. The human sequence of exon 8, intron 8 and exon 9 replace the mouse Atxn1 exon 7, intron 7, and exon 8. The Hygro cassette was removed via recombination to generate chimeric mice expressing human coding sequence exon 8 and exon 9. Human RNA expression is found in brain and spinal cord in this model. There is a one base deletion causing a stop codon at amino acid 190, so protein is not generated.

Transgenic mice described above were used to test activity of modified oligonucleotides described above.
Treatment
ATXN1 transgenic mice were treated with a single ICV bolus of 300 µg of modified oligonucleotide. A group of 3-4 mice received PBS as a negative control on each treatment day, and the PCR values were normalized to the PBS control group for mice treated on the same day. In some cases, individual mice treated with a given modified oligonucleotide were treated on different days, and the reported results for each modified oligonucleotide in the table below represent the average across 1-3 independent experiments representing 1-5 treated mice for each modified oligonucleotide.

RNA Analysis
Two weeks post treatment, mice were sacrificed, and RNA was extracted from cortical brain tissue for real-time qPCR analysis of RNA expression of ATXN1 using primer probe set RTS37573 (described herein above). Results are presented as percent change of RNA, relative to PBS control, normalized to mouse cyclophilin A. Data indicated as "n.d." (no data) means that no data are available for that tissue for that compound.
As shown in the table below, treatment with modified oligonucleotides resulted in reduction of ATXN1 RNA in comparison to the PBS control.

TABLE 60

Reduction of human ATXN1 RNA in transgenic mice

| Compound Number | ATXN1 RNA (% control) |
|---|---|
| 994334 | 88 |
| 994341 | 80 |
| 994346 | 74 |
| 994351 | 51 |
| 994366 | 99 |
| 994367 | 83 |
| 994374 | 82 |
| 994375 | 88 |
| 994398 | 30 |
| 994408 | 72 |
| 994409 | 80 |
| 994413 | 18 |
| 994417 | 95 |
| 994418 | 54 |
| 994419 | 28 |
| 994421 | 15 |
| 994424 | 62 |
| 994429 | 63 |
| 994430 | 36 |
| 994434 | 63 |
| 994437 | 22 |
| 994442 | 76 |
| 994443 | 62 |
| 994447 | 52 |
| 994448 | 62 |
| 994449 | 58 |
| 994453 | 58 |
| 994458 | 24 |
| 994459 | 36 |
| 994460 | 50 |
| 994464 | 49 |
| 994465 | 65 |
| 994467 | 59 |
| 994468 | 43 |
| 994469 | 32 |
| 994484 | 50 |
| 994485 | 90 |
| 994486 | 37 |
| 994491 | 51 |
| 994492 | 37 |

TABLE 60-continued

Reduction of human ATXN1 RNA in transgenic mice

| Compound Number | ATXN1 RNA (% control) |
|---|---|
| 994493 | 19 |
| 994494 | 26 |
| 994495 | 48 |
| 994501 | 69 |
| 994502 | 67 |
| 994503 | 63 |
| 994506 | 56 |
| 994507 | 73 |
| 994508 | 81 |
| 994509 | 33 |
| 994517 | 89 |
| 994518 | 45 |
| 994520 | 48 |
| 994522 | 55 |
| 994526 | 36 |
| 994527 | 38 |
| 994539 | 63 |
| 994540 | 44 |
| 994541 | 82 |
| 994543 | 91 |
| 994545 | 59 |
| 994559 | 84 |
| 994561 | 65 |
| 994562 | 57 |
| 994564 | 73 |
| 994567 | 81 |
| 994569 | 46 |
| 994571 | 75 |
| 994809 | 57 |
| 994810 | 50 |
| 994811 | 43 |
| 994813 | 66 |
| 994819 | 46 |
| 994823 | 42 |
| 994829 | 86 |
| 994831 | 91 |
| 994836 | 94 |
| 994840 | 71 |
| 994841 | 67 |
| 994854 | 89 |
| 994856 | 72 |
| 994857 | 73 |
| 994859 | 78 |
| 994874 | 88 |
| 994876 | 81 |
| 994877 | 42 |
| 994878 | 92 |
| 994885 | 61 |
| 994887 | 71 |
| 994895 | 52 |
| 994904 | 33 |
| 994906 | 68 |
| 994913 | 18 |
| 994921 | 51 |
| 994925 | 91 |
| 1040083 | 83 |
| 1040084 | 39 |
| 1040085 | 48 |
| 1040092 | 62 |
| 1040107 | 104 |
| 1040109 | 59 |
| 1040146 | 55 |
| 1040151 | 64 |
| 1040170 | 56 |
| 1040173 | 94 |
| 1040180 | 93 |
| 1040191 | 108 |
| 1040198 | 107 |
| 1040199 | 69 |
| 1040203 | 75 |
| 1040207 | 75 |
| 1040213 | 85 |
| 1040223 | 60 |
| 1040227 | 80 |
| 1040231 | 56 |
| 1040236 | 91 |
| 1040237 | 59 |
| 1040238 | 79 |
| 1040239 | 72 |
| 1040248 | 82 |
| 1040297 | 63 |
| 1040299 | 48 |
| 1040328 | 17 |
| 1040329 | 32 |
| 1040334 | 84 |
| 1040335 | 90 |
| 1040337 | 51 |
| 1040338 | 66 |
| 1040389 | 92 |
| 1040413 | 81 |
| 1040435 | 81 |
| 1040438 | 75 |
| 1040442 | 85 |
| 1040472 | 93 |
| 1040475 | 44 |
| 1040479 | 27 |
| 1040500 | 38 |
| 1040502 | 84 |
| 1040512 | 49 |
| 1040514 | 74 |
| 1040597 | 92 |
| 1040601 | 72 |
| 1041318 | 49 |
| 1041319 | 88 |
| 1041326 | 82 |
| 1041328 | 51 |
| 1041334 | 90 |
| 1041339 | 90 |
| 1041345 | 87 |
| 1041355 | 63 |
| 1041366 | 71 |
| 1041390 | 41 |
| 1041398 | 48 |
| 1041400 | 72 |
| 1041406 | 98 |
| 1041409 | 37 |
| 1041413 | 62 |
| 1041425 | 69 |
| 1041429 | 65 |
| 1041433 | 73 |
| 1041434 | 103 |
| 1041438 | 85 |
| 1041439 | 66 |
| 1041441 | 86 |
| 1041443 | 101 |
| 1041455 | 77 |
| 1041469 | 75 |
| 1041471 | 48 |
| 1041486 | 48 |
| 1041489 | 101 |
| 1041498 | 43 |
| 1041527 | 95 |
| 1041532 | 85 |
| 1041537 | 87 |
| 1041548 | 98 |
| 1041550 | 114 |
| 1041557 | 83 |
| 1041567 | 71 |
| 1041575 | 103 |
| 1041597 | 119 |
| 1041603 | 96 |
| 1041605 | 82 |
| 1041608 | 76 |
| 1041623 | 64 |
| 1041636 | 70 |
| 1041649 | 94 |

TABLE 60-continued

Reduction of human ATXN1 RNA in transgenic mice

| Compound Number | ATXN1 RNA (% control) |
|---|---|
| 1041653 | 84 |
| 1041676 | 91 |
| 1041679 | 88 |
| 1041682 | 103 |
| 1041699 | 75 |
| 1041729 | 79 |
| 1041733 | 113 |
| 1041736 | 72 |
| 1041746 | 42 |
| 1041757 | 66 |
| 1041768 | 63 |
| 1041769 | 47 |
| 1041776 | 99 |
| 1041777 | 86 |
| 1041927 | 37 |
| 1042257 | 105 |
| 1042471 | 60 |
| 1055001 | 27 |
| 1055004 | 34 |
| 1055006 | 46 |
| 1055007 | 34 |
| 1055012 | 63 |
| 1055013 | 76 |
| 1055014 | 50 |
| 1055017 | 92 |
| 1055020 | 71 |
| 1055025 | 95 |
| 1055027 | 73 |
| 1055035 | 68 |
| 1055046 | 98 |
| 1055050 | 73 |
| 1342029 | 49 |
| 1342030 | 107 |
| 1342031 | 80 |
| 1342032 | 48 |
| 1342033 | 77 |
| 1342034 | 92 |
| 1342035 | 89 |
| 1342036 | 60 |
| 1342037 | 89 |
| 1342038 | 63 |
| 1342039 | 86 |
| 1342040 | 117 |
| 1342041 | 58 |
| 1342042 | 80 |
| 1342043 | 95 |
| 1342044 | 78 |
| 1342045 | 101 |
| 1342046 | 83 |
| 1342047 | 86 |
| 1342048 | 64 |
| 1342049 | 88 |
| 1342050 | 107 |
| 1342051 | 80 |
| 1342052 | 98 |
| 1342053 | 87 |
| 1342054 | 106 |
| 1342055 | 97 |
| 1342056 | 86 |
| 1342057 | 99 |
| 1342058 | 55 |
| 1342059 | 97 |
| 1342060 | 107 |
| 1342061 | 86 |
| 1342062 | 73 |
| 1342063 | 68 |
| 1342064 | 68 |
| 1342065 | 76 |
| 1342066 | 98 |
| 1342067 | 25 |
| 1342068 | 58 |
| 1342069 | 83 |
| 1342070 | 94 |
| 1342071 | 88 |
| 1342072 | 82 |
| 1342073 | 77 |
| 1342074 | 74 |
| 1342075 | 43 |
| 1342076 | 86 |
| 1342077 | 69 |
| 1364280 | 36 |
| 1364281 | 48 |
| 1364282 | 41 |
| 1364283 | 26 |
| 1364285 | 29 |
| 1365254 | 65 |
| 1365255 | 62 |
| 1365258 | 123 |
| 1365259 | 121 |
| 1365260 | 94 |
| 1365261 | 49 |
| 1365262 | 76 |
| 1365263 | 69 |
| 1365264 | 43 |
| 1365265 | 34 |
| 1365267 | 44 |
| 1365268 | 44 |
| 1365270 | 49 |
| 1365271 | 28 |
| 1365272 | 38 |
| 1365274 | 46 |
| 1365275 | 51 |
| 1365278 | 81 |
| 1365281 | 71 |
| 1365282 | 92 |
| 1365283 | 83 |
| 1365284 | 92 |
| 1365285 | 76 |
| 1365286 | 79 |
| 1365287 | 61 |
| 1365288 | 71 |
| 1365289 | 72 |
| 1365290 | 69 |
| 1365291 | 55 |
| 1365292 | 45 |
| 1365293 | 94 |
| 1365294 | 65 |
| 1365297 | 96 |
| 1365298 | 53 |
| 1365299 | 75 |
| 1365300 | 51 |
| 1367569 | 80 |
| 1367572 | 53 |
| 1367573 | 44 |
| 1367575 | 99 |
| 1367576 | 89 |
| 1367577 | 52 |
| 1367580 | 46 |
| 1367581 | 42 |
| 1367586 | 66 |
| 1367588 | 59 |
| 1367589 | 19 |
| 1367590 | 80 |
| 1367591 | 21 |
| 1371311 | 24 |
| 1371320 | 66 |
| 1371322 | 79 |
| 1371325 | 48 |
| 1371806 | 52 |
| 1371807 | 70 |
| 1371808 | 78 |
| 1371809 | 62 |
| 1371810 | 50 |
| 1371811 | 74 |
| 1371812 | 89 |
| 1371813 | 112 |

TABLE 60-continued

Reduction of human ATXN1 RNA in transgenic mice

| Compound Number | ATXN1 RNA (% control) |
|---|---|
| 1371814 | 70 |
| 1371815 | 76 |
| 1371816 | 51 |
| 1371817 | 62 |
| 1371818 | 35 |
| 1371819 | 49 |
| 1371820 | 68 |
| 1371821 | 62 |
| 1371822 | 60 |
| 1371823 | 90 |
| 1371824 | 60 |
| 1371825 | 29 |
| 1371826 | 70 |
| 1371827 | 59 |
| 1371828 | 63 |
| 1371829 | 32 |
| 1371830 | 60 |
| 1371831 | 86 |
| 1371832 | 84 |
| 1371833 | 81 |
| 1371834 | 89 |
| 1371835 | 92 |
| 1371836 | 111 |
| 1371837 | 96 |
| 1371838 | 90 |
| 1371839 | 81 |
| 1371840 | 87 |
| 1371841 | 83 |
| 1371842 | 29 |
| 1371843 | 71 |
| 1371844 | 59 |
| 1371845 | 73 |
| 1371846 | 62 |
| 1371847 | 82 |
| 1371848 | 38 |
| 1371849 | 72 |
| 1371850 | 78 |
| 1371851 | 49 |
| 1371852 | 89 |
| 1371853 | 66 |
| 1371854 | 37 |
| 1371855 | 36 |
| 1371856 | 77 |
| 1371857 | 76 |
| 1371858 | 104 |
| 1371859 | 94 |
| 1371860 | 98 |
| 1371861 | 86 |
| 1371862 | 75 |
| 1371863 | 68 |
| 1371864 | 81 |
| 1371865 | 87 |
| 1371866 | 58 |
| 1371867 | 83 |
| 1371868 | 85 |
| 1371869 | 70 |
| 1371870 | 46 |
| 1371871 | 60 |
| 1371872 | 56 |
| 1371873 | 78 |
| 1371874 | 77 |
| 1371875 | 17 |
| 1371876 | 39 |
| 1371877 | 48 |
| 1385293 | 31 |
| 1385294 | 25 |
| 1385295 | 27 |
| 1394153 | 41 |
| 1394154 | 65 |
| 1394155 | 49 |
| 1394156 | 40 |
| 1394157 | 30 |
| 1394158 | 33 |
| 1394159 | 24 |
| 1394160 | 30 |
| 1394161 | 29 |
| 1394162 | 45 |
| 1394163 | 35 |
| 1394164 | 42 |
| 1394165 | 43 |
| 1394166 | 43 |
| 1394167 | 28 |
| 1394168 | 33 |
| 1394507 | 46 |
| 1394508 | 63 |
| 1394510 | 66 |
| 1394511 | 77 |
| 1394512 | 54 |
| 1394513 | 38 |
| 1394514 | 73 |
| 1394515 | 87 |
| 1394516 | 72 |
| 1394517 | 91 |
| 1394518 | 73 |
| 1394522 | 40 |
| 1394523 | 86 |
| 1394524 | 32 |
| 1394525 | 43 |
| 1394526 | 8 |
| 1394527 | 68 |
| 1394528 | 71 |
| 1394529 | 38 |
| 1394530 | 38 |
| 1394531 | 65 |
| 1394532 | 42 |
| 1394533 | 38 |
| 1394534 | 66 |
| 1394537 | 45 |
| 1394538 | 54 |
| 1394539 | 58 |
| 1394540 | 59 |
| 1394541 | 67 |
| 1394543 | 46 |
| 1394544 | 43 |
| 1394545 | 66 |
| 1394546 | 26 |
| 1394547 | 53 |
| 1394548 | 88 |
| 1394549 | 51 |
| 1394550 | 92 |
| 1394551 | 48 |
| 1394552 | 33 |
| 1394553 | 85 |

Example 7: Activity of Modified Oligonucleotides Complementary to Human ATXN1 in Transgenic Mice, Multiple Doses Modified oligonucleotides described above were tested in the ATXN1 transgenic mice described herein above.

Treatment

ATXN1 transgenic mice were divided into groups of 3-4 mice each. Each mouse received a single ICV bolus of modified oligonucleotide at the doses described in the tables below and were sacrificed two weeks later. A group of 4 mice received PBS as a negative control for each experiment. Each table represents a separate experiment.

RNA Analysis

After two weeks, mice were sacrificed, and RNA was extracted from cortical brain tissue for real-time PCR analysis of measurement of RNA expression of ATXN1 using primer probe set RTS37573. Results are presented as percent change of RNA, relative to PBS control, normalized to mouse cyclophilin A (measured by primer-probe set m_cyclo24 described herein above). ED50 values were calculated in GraphPad Prism. N/A means that an ED50 value could not be reliably calculated for that experiment.

As shown in the tables below, treatment with modified oligonucleotides resulted in dose-dependent reduction of ATXN1 RNA in comparison to the PBS control.

TABLE 61

Dose-dependent percent reduction of human ATXN1 RNA in the cortex of transgenic mice

| Compound ID | Dose (µg) | ATXN1 RNA (% control) | ED50 (µg) |
|---|---|---|---|
| 1040479 | 10 | 97 | 669.1 |
|  | 30 | 86 |  |
|  | 100 | 87 |  |
|  | 300 | 59 |  |
|  | 700 | 51 |  |
| 1040500 | 10 | 87 | 126.2 |
|  | 30 | 83 |  |
|  | 100 | 59 |  |
|  | 300 | 44 |  |
|  | 700 | 22 |  |
| 1367591 | 10 | 80 | 40.59 |
|  | 30 | 66 |  |
|  | 100 | 32 |  |
|  | 300 | 23 |  |
|  | 700 | 22 |  |
| 1371311 | 10 | 76 | 36.11 |
|  | 30 | 57 |  |
|  | 100 | 45 |  |
|  | 300 | 19 |  |
|  | 700 | 14 |  |
| 1371875 | 10 | 70 | 30.41 |
|  | 30 | 67 |  |
|  | 100 | 25 |  |
|  | 300 | 12 |  |
|  | 700 | 9 |  |
| 1394161 | 10 | 71 | 36.04 |
|  | 30 | 68 |  |
|  | 100 | 35 |  |
|  | 300 | 18 |  |
|  | 700 | 8 |  |

TABLE 62

Dose-dependent percent reduction of human ATXN1 RNA in transgenic mice

| | | Cortex | |
|---|---|---|---|
| Compound ID | Dose (µg) | ATXN1 RNA (% control) | ED50 (µg) |
| 1041409 | 10 | 94 | 277.3 |
|  | 30 | 88 |  |
|  | 100 | 78 |  |
|  | 300 | 56 |  |
|  | 700 | 34 |  |
| 1055001 | 10 | 91 | 144 |
|  | 30 | 89 |  |
|  | 100 | 75 |  |
|  | 300 | 23 |  |
|  | 700 | 18 |  |
| 1055007 | 10 | 104 | 156.9 |
|  | 30 | 88 |  |
|  | 100 | 75 |  |
|  | 300 | 31 |  |
|  | 700 | 22 |  |
| 1371827 | 10 | 92 | 87.95 |
|  | 30 | 77 |  |
|  | 100 | 50 |  |

TABLE 62-continued

Dose-dependent percent reduction of human ATXN1 RNA in transgenic mice

| | | Cortex | |
|---|---|---|---|
| Compound ID | Dose (µg) | ATXN1 RNA (% control) | ED50 (µg) |
|  | 300 | 34 |  |
|  | 700 | 22 |  |

TABLE 63

Dose-dependent percent reduction of human ATXN1 RNA in transgenic mice

| | | Cortex | |
|---|---|---|---|
| Compound ID | Dose (µg) | ATXN1 RNA (% control) | ED50 (µg) |
| 994823 | 10 | 110 | 308.3 |
|  | 30 | 96 |  |
|  | 100 | 72 |  |
|  | 300 | 64 |  |
|  | 700 | 32 |  |
| 1385293 | 10 | 90 | 93.14 |
|  | 30 | 75 |  |
|  | 100 | 63 |  |
|  | 300 | 25 |  |
|  | 700 | 15 |  |

TABLE 64

Dose-dependent percent reduction of human ATXN1 RNA in transgenic mice

| | | Cortex | |
|---|---|---|---|
| Compound ID | Dose (µg) | ATXN1 RNA (% control) | ED50 (µg) |
| 994492 | 10 | 78 | 72.25 |
|  | 30 | 72 |  |
|  | 100 | 52 |  |
|  | 300 | 41 |  |
|  | 700 | 22 |  |
| 994509 | 10 | 80 | 27.84 |
|  | 30 | 53 |  |
|  | 100 | 30 |  |
|  | 300 | 20 |  |
|  | 700 | 17 |  |

TABLE 65

Dose-dependent percent reduction of human ATXN1 RNA in transgenic mice

| | | Cortex | |
|---|---|---|---|
| Compound ID | Dose (µg) | ATXN1 RNA (% control) | ED50 (µg) |
| 1041927 | 10 | 72 | 52.22 |
|  | 30 | 71 |  |
|  | 100 | 41 |  |
|  | 300 | 29 |  |
|  | 700 | 33 |  |
| 994419 | 10 | 83 | 50.14 |
|  | 30 | 65 |  |
|  | 100 | 46 |  |
|  | 300 | 22 |  |
|  | 700 | 17 |  |

TABLE 65-continued

Dose-dependent percent reduction of human ATXN1 RNA in transgenic mice

| Compound ID | Dose (µg) | Cortex ATXN1 RNA (% control) | ED50 (µg) |
|---|---|---|---|
| 1394155 | 10 | 72 | 105.4 |
| | 30 | 70 | |
| | 100 | 60 | |
| | 300 | 41 | |
| | 700 | 40 | |

SEQUENCE LISTING

The patent contains a lengthy sequence listing. A copy of the sequence listing is available in electronic form from the USPTO web site (https://seqdata.uspto.gov/?pageRequest=docDetail&DocID=US12180479B2). An electronic copy of the sequence listing will also be available from the USPTO upon request and payment of the fee set forth in 37 CFR 1.19(b)(3).

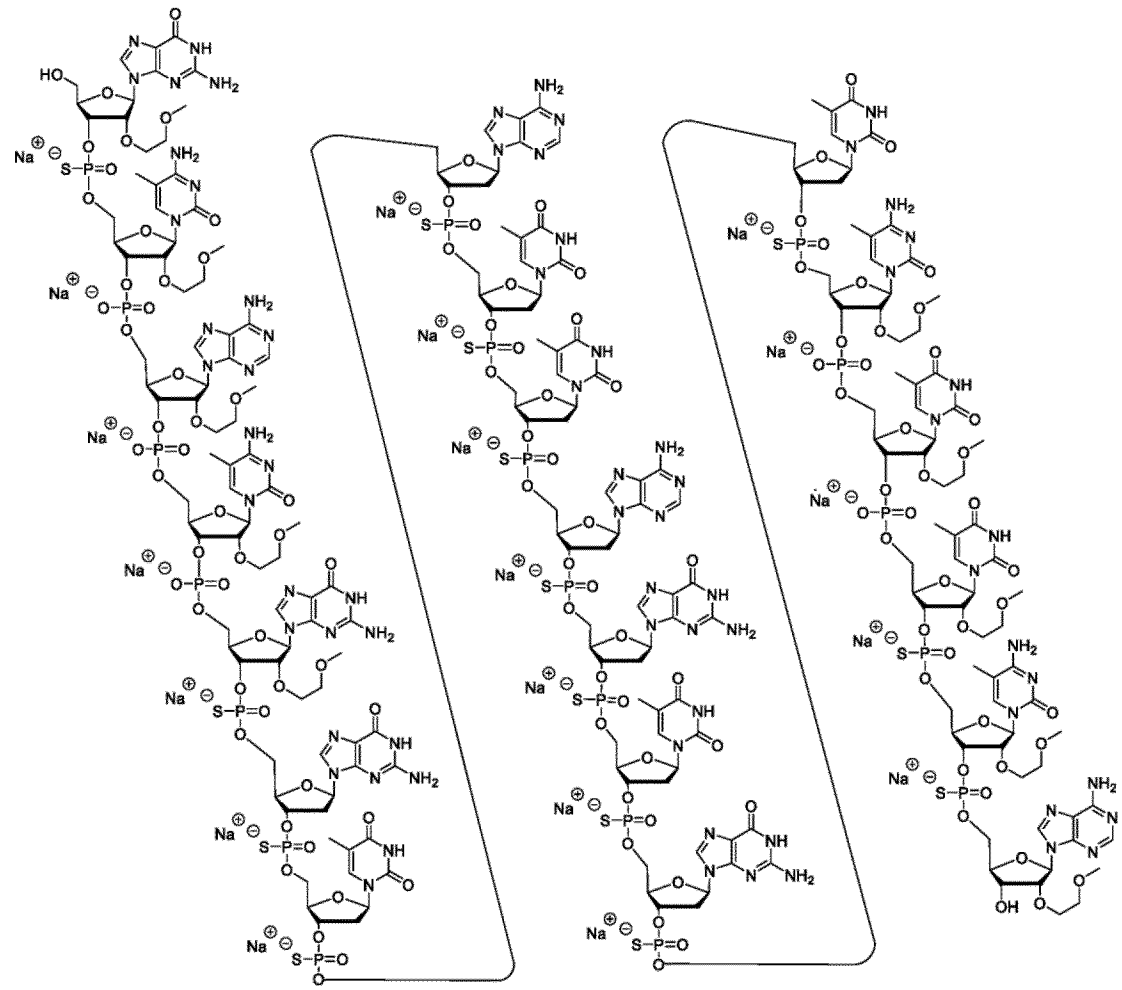

The invention claimed is:

1. A modified oligonucleotide according to the following chemical structure:

(SEQ ID NO: 3671)

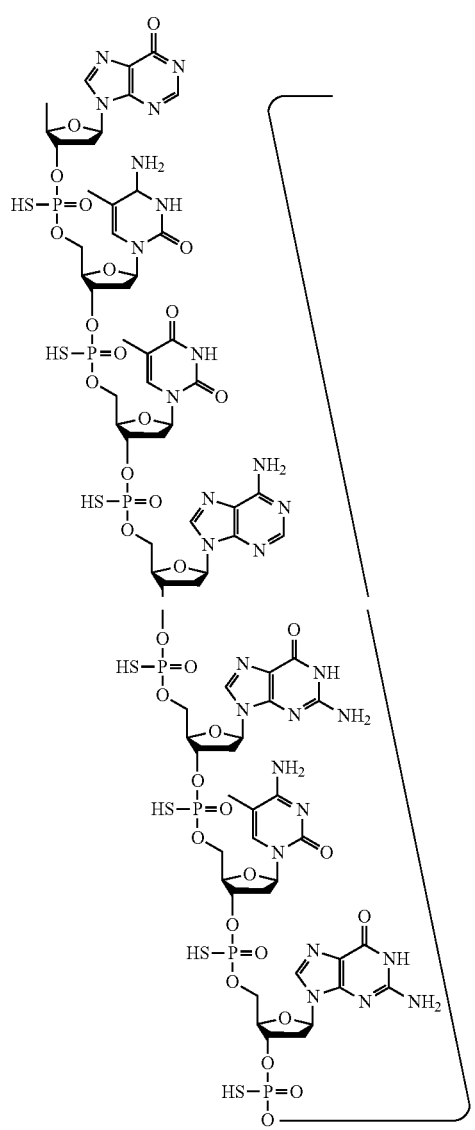
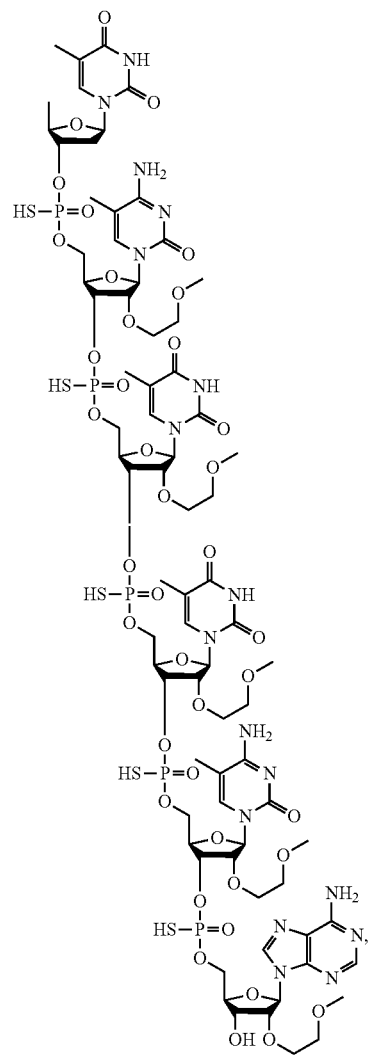
or a salt thereof.
2. A modified oligonucleotide according to the following chemical structure:

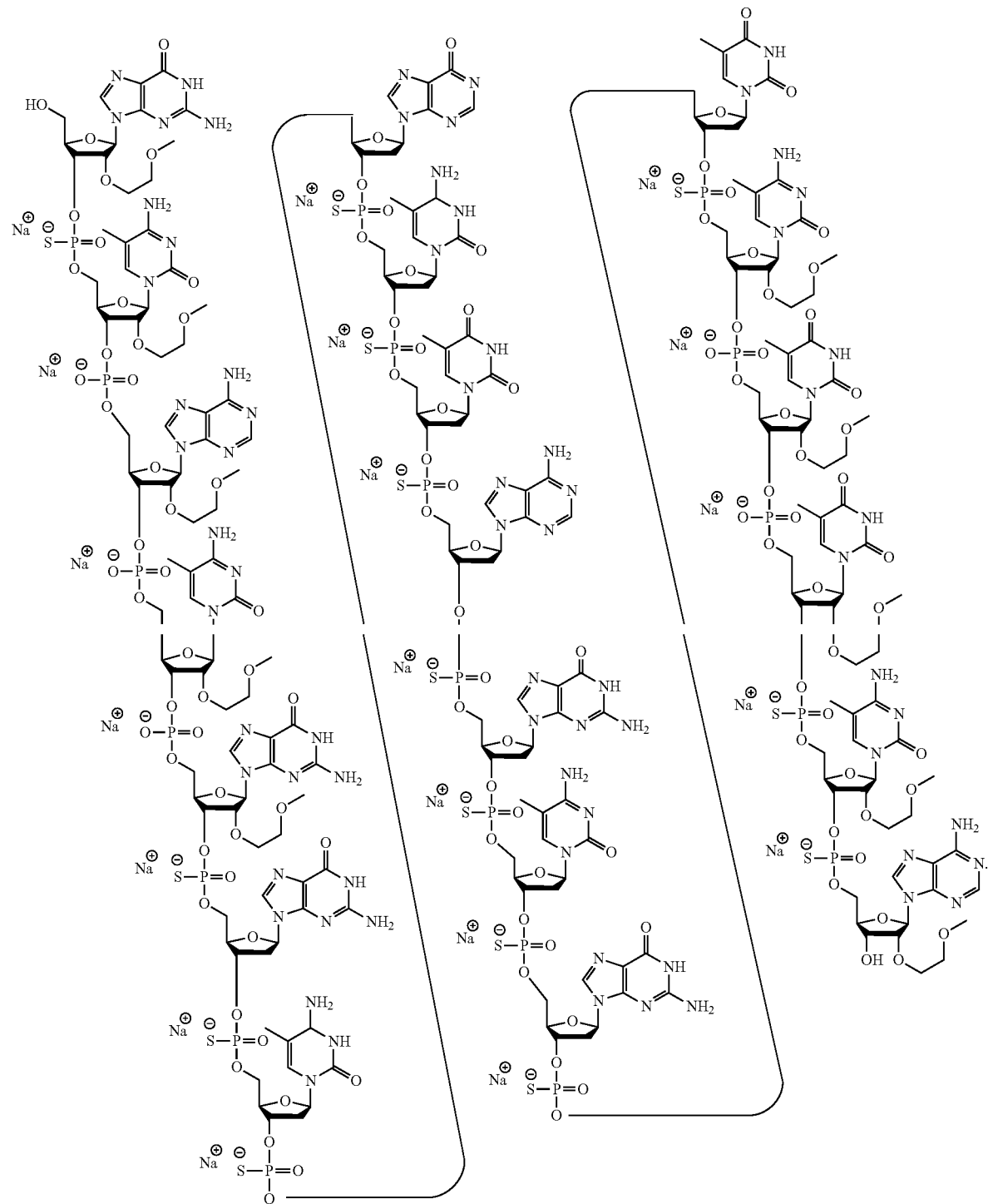
(SEQ ID NO: 3671)

3. An oligomeric compound comprising a modified oligonucleotide according to the following chemical notation:

(SEQ ID NO: 3671)
Ges ᵐCeo Aeo ᵐCeo Ges Gds Tds Ads Tds Tds Ads

Gds Tds Gds Tds ᵐCeo Teo Tes ᵐCes Ae, wherein,
- A=an adenine nucleobase,
- ᵐC=a 5-methylcytosine nucleobase,
- G=a guanine nucleobase,
- T=a thymine nucleobase,
- e=a 2'-MOE sugar moiety,
- d=a 2'-β-D deoxyribosyl sugar moiety,
- s=a phosphorothioate internucleoside linkage, and
- o=a phosphodiester internucleoside linkage.

4. The modified oligonucleotide of claim 1, which is a sodium salt or a potassium salt.

5. A population of modified oligonucleotides of claim 1, wherein all of the phosphorothioate internucleoside linkages of the modified oligonucleotides are stereorandom.

6. A population of modified oligonucleotides of claim 4, wherein all of the phosphorothioate internucleoside linkages of the modified oligonucleotides are stereorandom.

7. A population of modified oligonucleotides of claim 2, wherein all of the phosphorothioate internucleoside linkages of the modified oligonucleotides are stereorandom.

8. A population of oligomeric compounds of claim 3, wherein all of the phosphorothioate internucleoside linkages of the modified oligonucleotides are stereorandom.

9. A pharmaceutical composition comprising the modified oligonucleotide of claim 1, and a pharmaceutically acceptable diluent.

10. The pharmaceutical composition of claim 9, wherein the pharmaceutically acceptable diluent is phosphate-buffered saline (PBS) or artificial cerebrospinal fluid.

11. The pharmaceutical composition of claim 10, wherein the pharmaceutical composition consists essentially of the modified oligonucleotide and artificial cerebrospinal fluid.

12. The pharmaceutical composition of claim 10, wherein the pharmaceutical composition consists essentially of the modified oligonucleotide and PBS.

13. A pharmaceutical composition comprising the modified oligonucleotide of claim 4, and a pharmaceutically acceptable diluent.

14. The pharmaceutical composition of claim 13, wherein the pharmaceutically acceptable diluent is phosphate-buffered saline (PBS) or artificial cerebrospinal fluid.

15. The pharmaceutical composition of claim 14, wherein the pharmaceutical composition consists essentially of the modified oligonucleotide and artificial cerebrospinal fluid.

16. The pharmaceutical composition of claim 14, wherein the pharmaceutical composition consists essentially of the modified oligonucleotide and PBS.

17. A pharmaceutical composition comprising the modified oligonucleotide of claim 2, and a pharmaceutically acceptable diluent.

18. The pharmaceutical composition of claim 17, wherein the pharmaceutically acceptable diluent is phosphate-buffered saline (PBS) or artificial cerebrospinal fluid.

19. The pharmaceutical composition of claim 18, wherein the pharmaceutical composition consists essentially of the modified oligonucleotide and artificial cerebrospinal fluid.

20. The pharmaceutical composition of claim 18, wherein the pharmaceutical composition consists essentially of the modified oligonucleotide and PBS.

21. A pharmaceutical composition comprising the oligomeric compound of claim 3, and a pharmaceutically acceptable diluent.

22. The pharmaceutical composition of claim 21, wherein the pharmaceutically acceptable diluent is phosphate-buffered saline (PBS) or artificial cerebrospinal fluid.

23. The pharmaceutical composition of claim 22, wherein the pharmaceutical composition consists essentially of the oligomeric compound and artificial cerebrospinal fluid.

24. The pharmaceutical composition of claim 22, wherein the pharmaceutical composition consists essentially of the oligomeric compound and PBS.

25. A pharmaceutical composition comprising the population of modified oligonucleotides of claim 5, and a pharmaceutically acceptable diluent.

26. The pharmaceutical composition of claim 25, wherein the pharmaceutically acceptable diluent is phosphate-buffered saline (PBS) or artificial cerebrospinal fluid.

27. A pharmaceutical composition comprising the population of modified oligonucleotides of claim 7, and a pharmaceutically acceptable diluent.

28. The pharmaceutical composition of claim 27, wherein the pharmaceutically acceptable diluent is phosphate-buffered saline (PBS) or artificial cerebrospinal fluid.

29. A pharmaceutical composition comprising the population of oligomeric compounds of claim 8, and a pharmaceutically acceptable diluent.

30. The pharmaceutical composition of claim 29, wherein the pharmaceutically acceptable diluent is phosphate-buffered saline (PBS) or artificial cerebrospinal fluid.

* * * * *

UNITED STATES PATENT AND TRADEMARK OFFICE
CERTIFICATE OF CORRECTION

PATENT NO. : 12,180,479 B2
APPLICATION NO. : 18/047973
DATED : December 31, 2024
INVENTOR(S) : Susan M. Freier Page 1 of 38

It is certified that error appears in the above-identified patent and that said Letters Patent is hereby corrected as shown below:

In the Specification

In Columns 13-16, the structure should read:

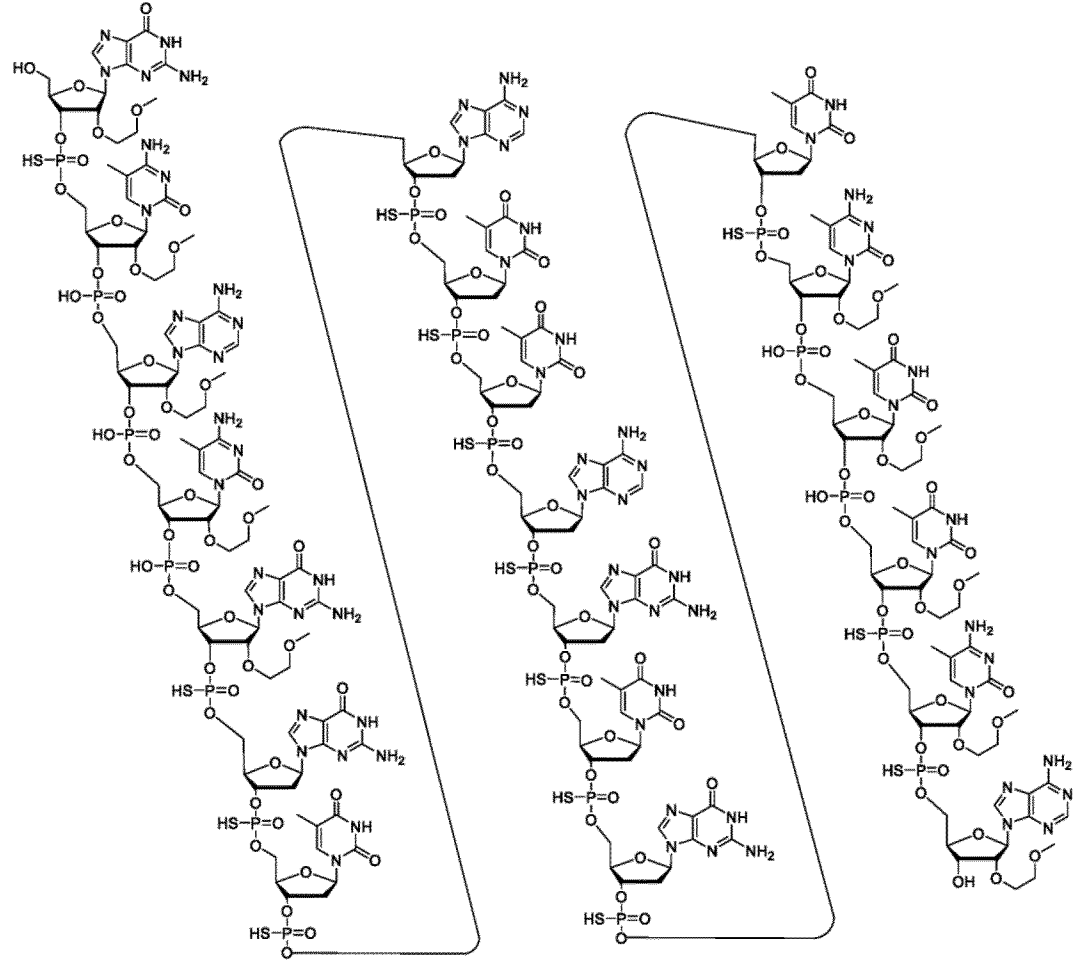

Signed and Sealed this
First Day of April, 2025

Coke Morgan Stewart
*Acting Director of the United States Patent and Trademark Office*

In Columns 15-18, the structure should read:
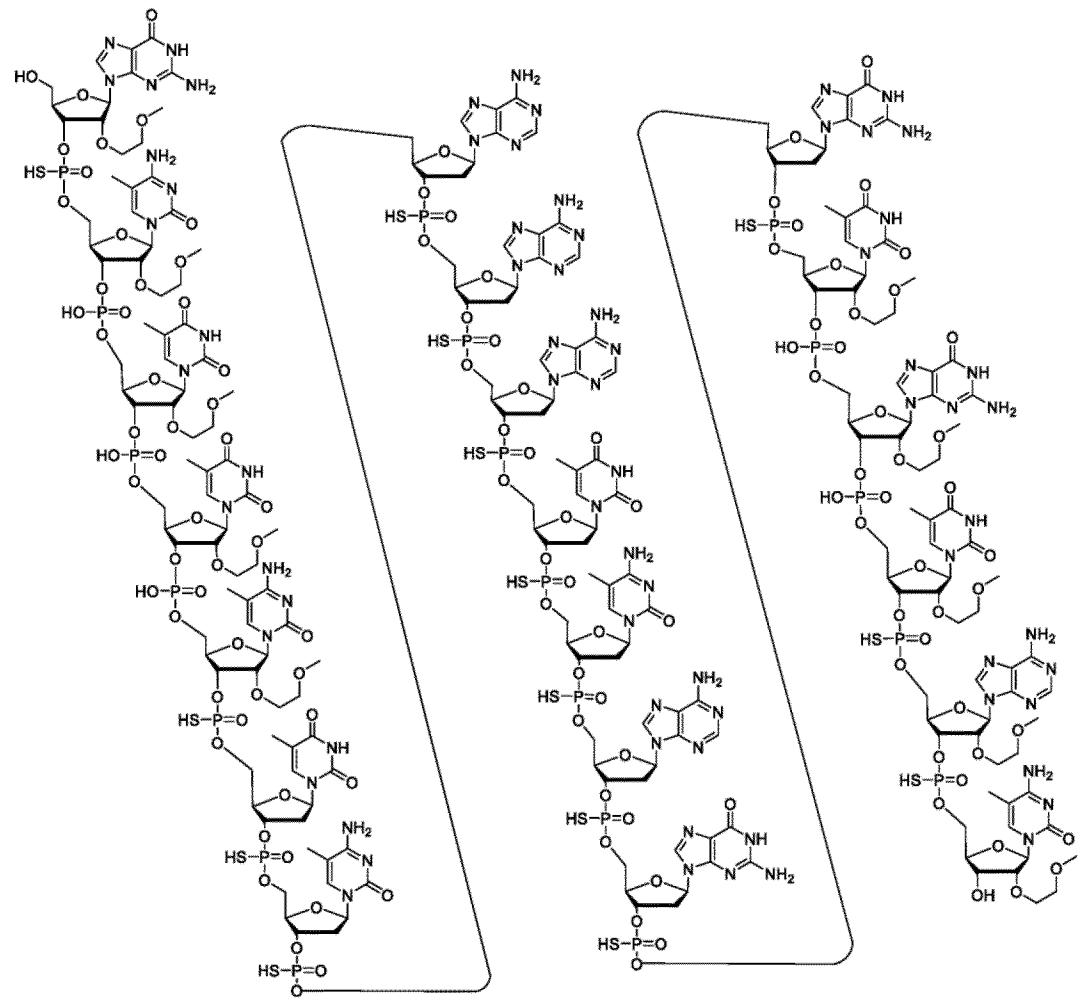

CERTIFICATE OF CORRECTION (continued)
U.S. Pat. No. 12,180,479 B2

In Columns 17-20, the structure should read:

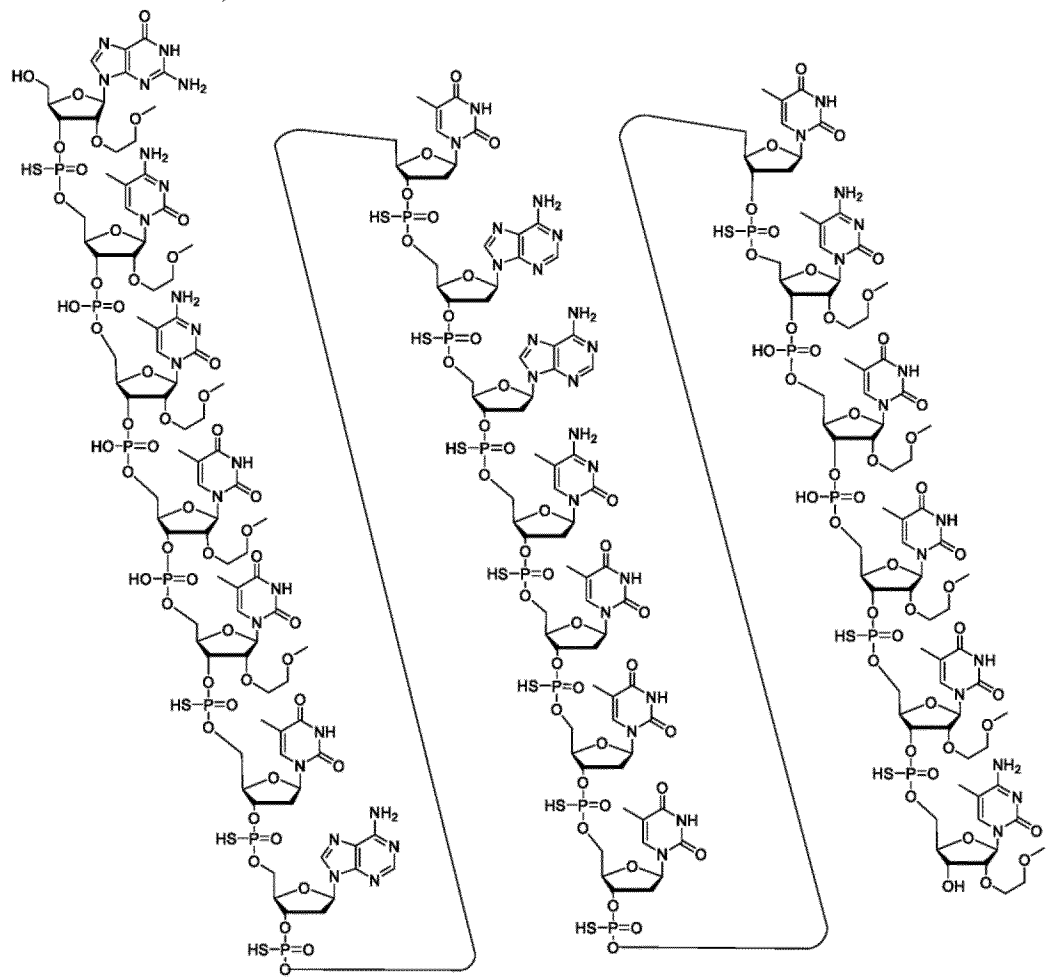

In Columns 19-22, the structure should read:
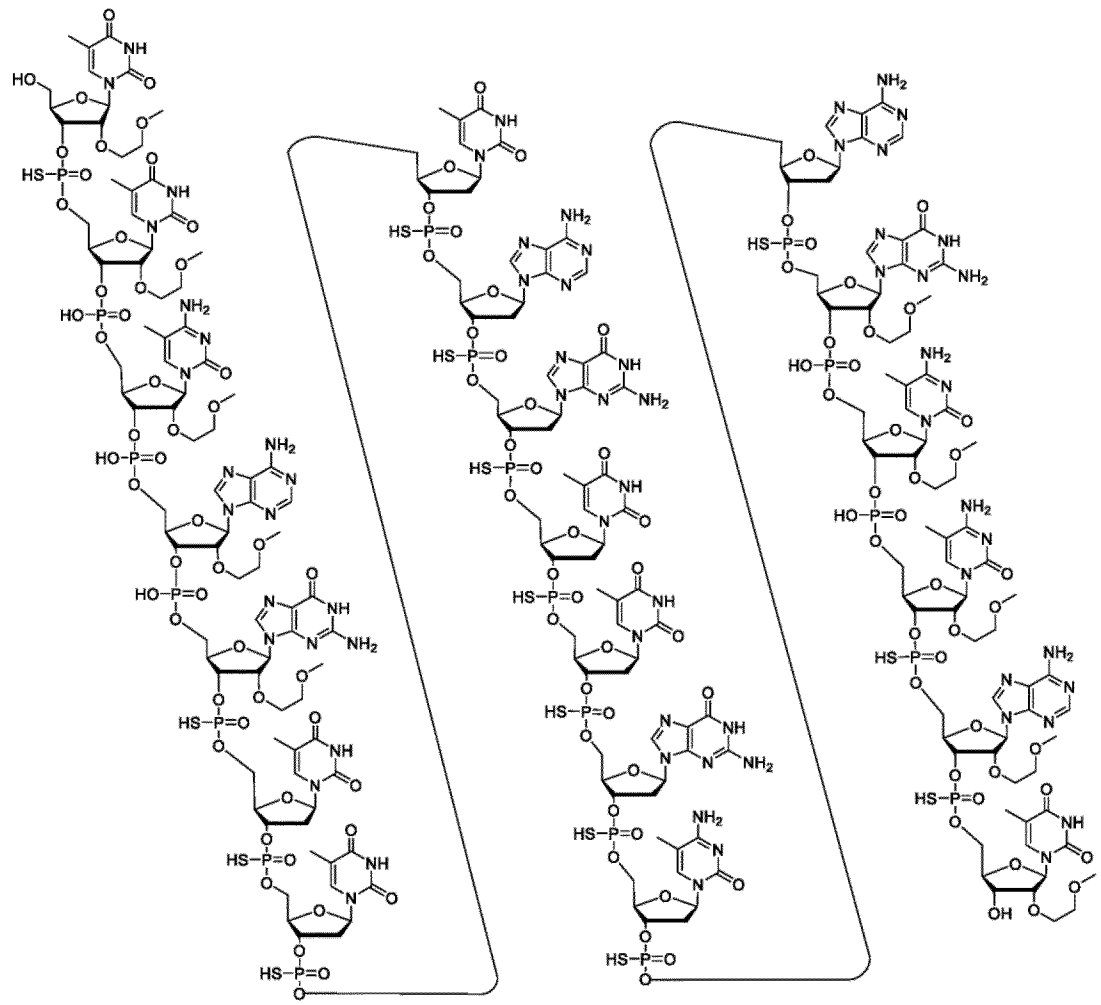

CERTIFICATE OF CORRECTION (continued)
U.S. Pat. No. 12,180,479 B2

In Columns 21-24, the structure should read:

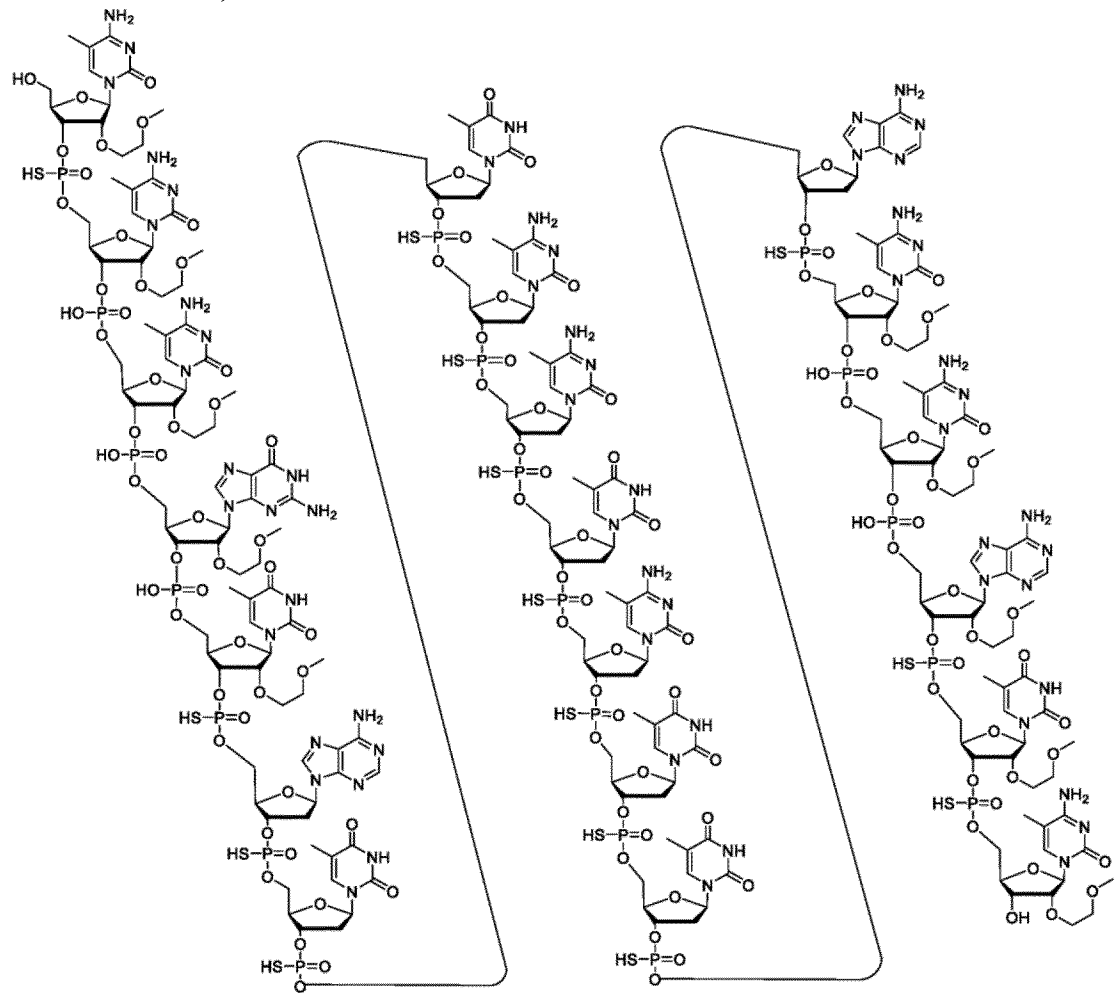

In Columns 23-26, the structure should read:
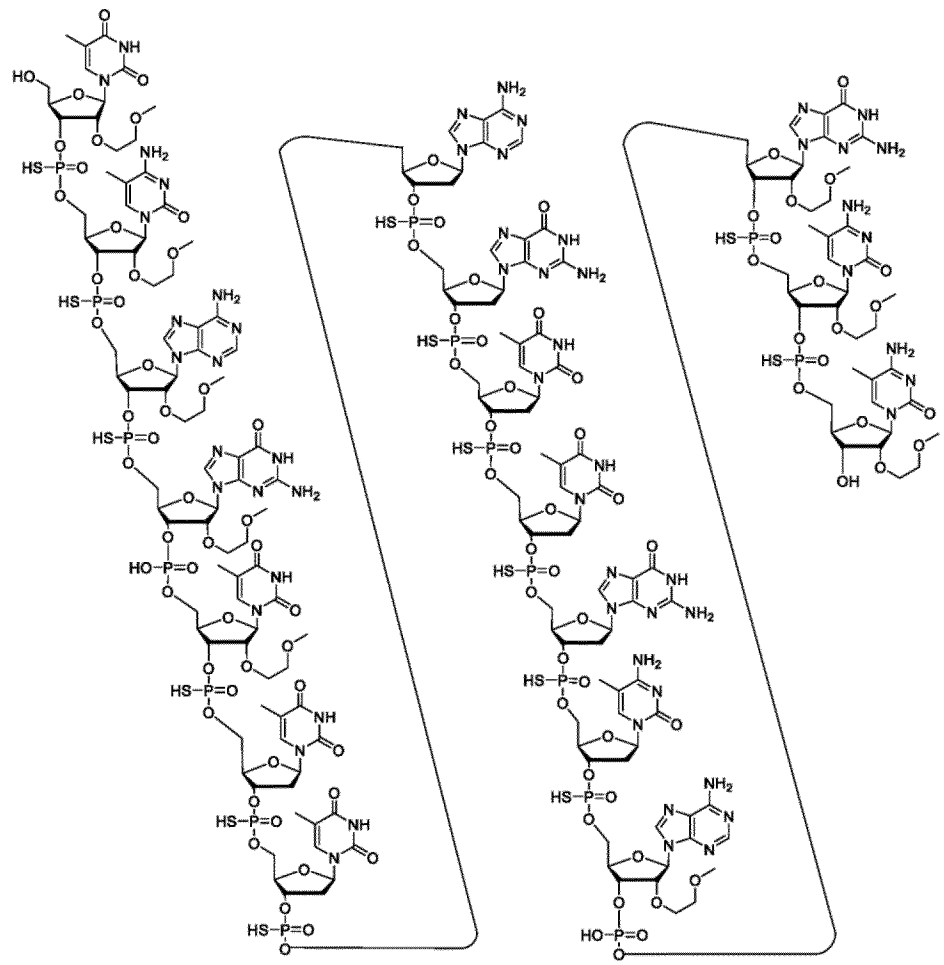

CERTIFICATE OF CORRECTION (continued)
U.S. Pat. No. 12,180,479 B2

In Columns 25-28, the structure should read:

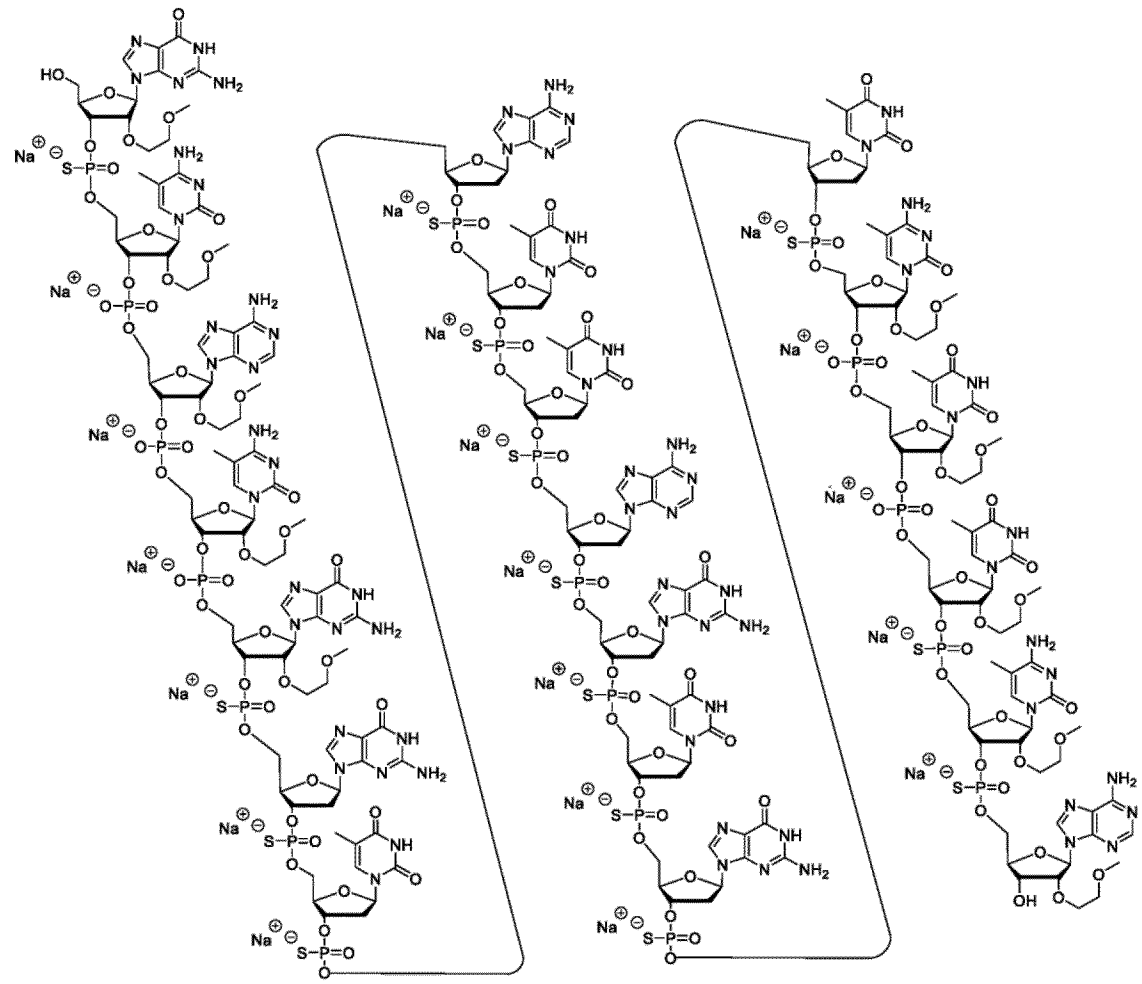

CERTIFICATE OF CORRECTION (continued)
U.S. Pat. No. 12,180,479 B2

In Columns 27-30, the structure should read:

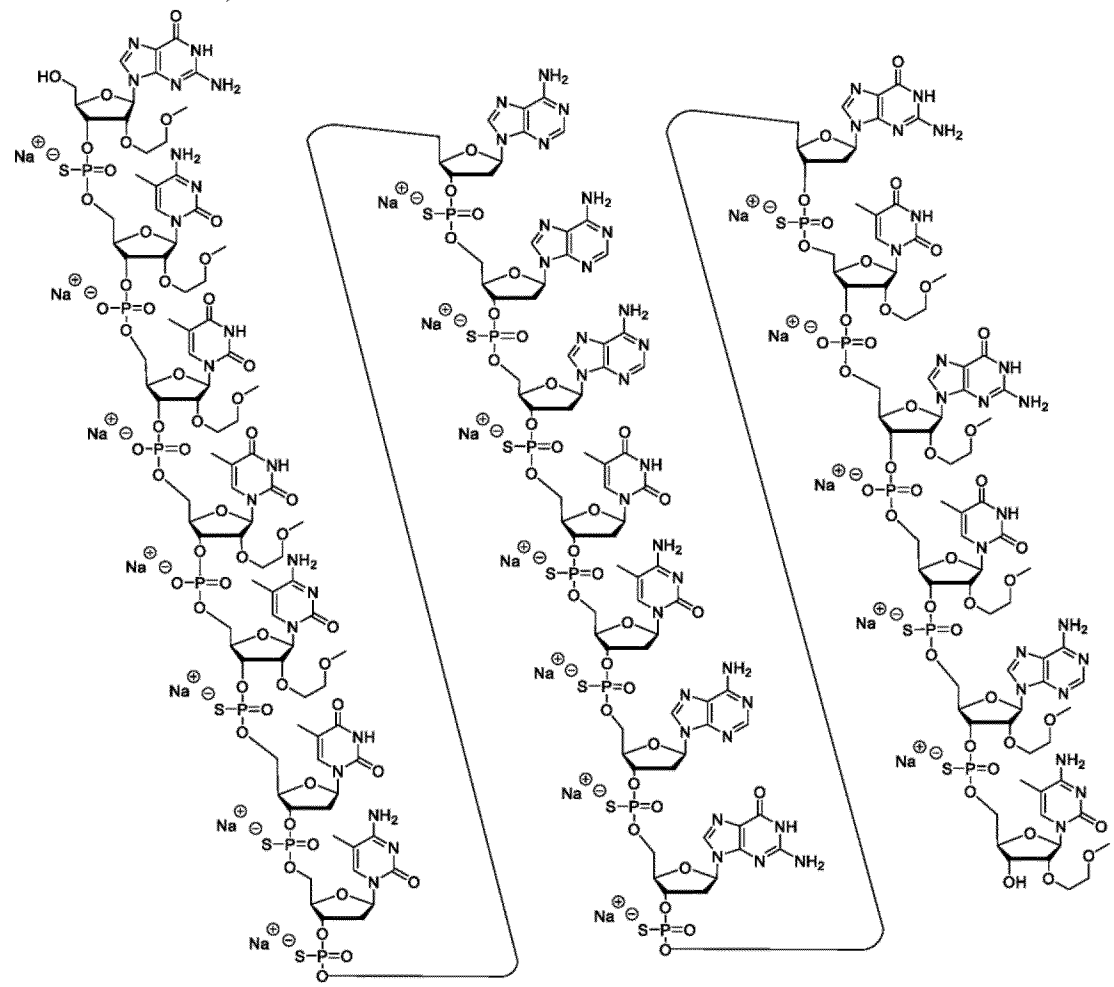

CERTIFICATE OF CORRECTION (continued)
U.S. Pat. No. 12,180,479 B2

In Columns 29-32, the structure should read:

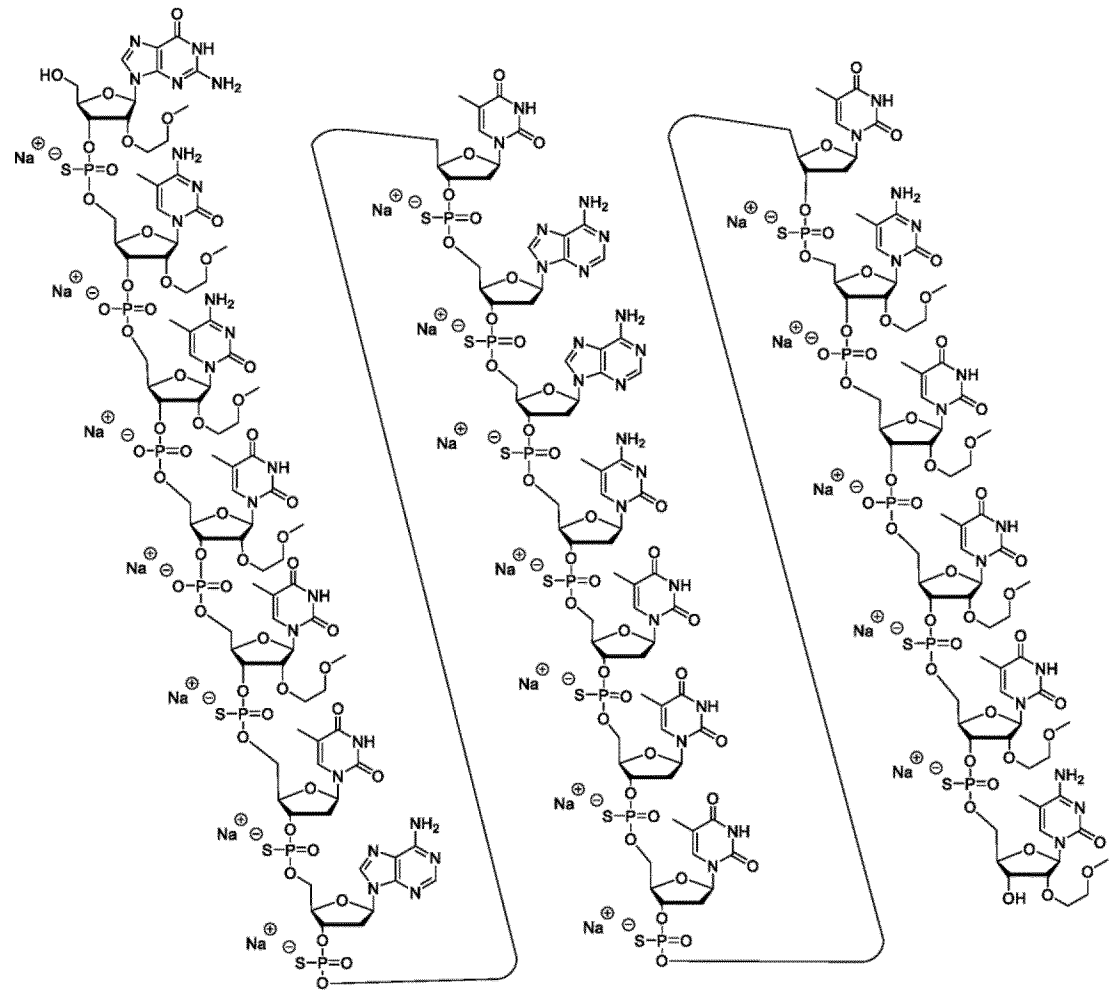

CERTIFICATE OF CORRECTION (continued)
U.S. Pat. No. 12,180,479 B2

In Columns 31-34, the structure should read:

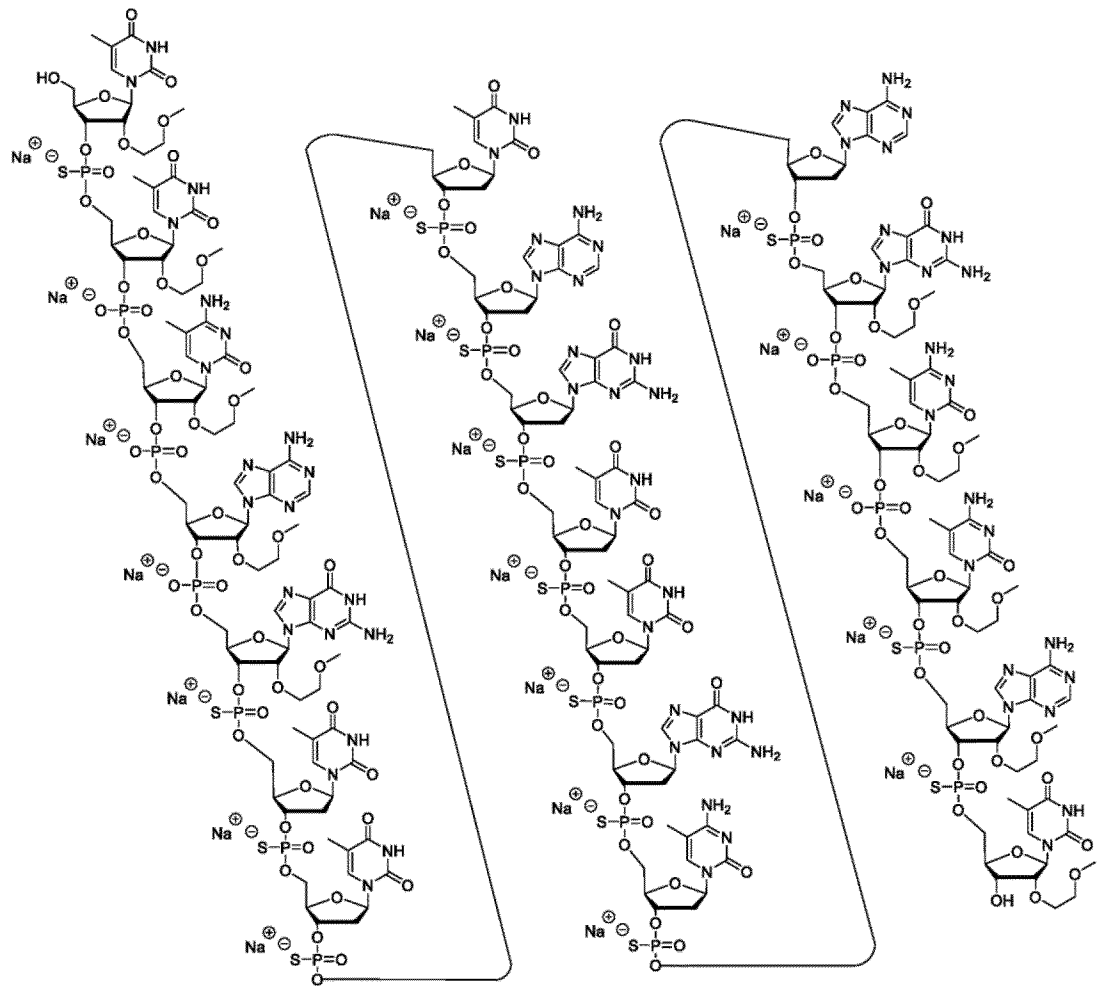

CERTIFICATE OF CORRECTION (continued)
U.S. Pat. No. 12,180,479 B2

In Columns 33-36, the structure should read:

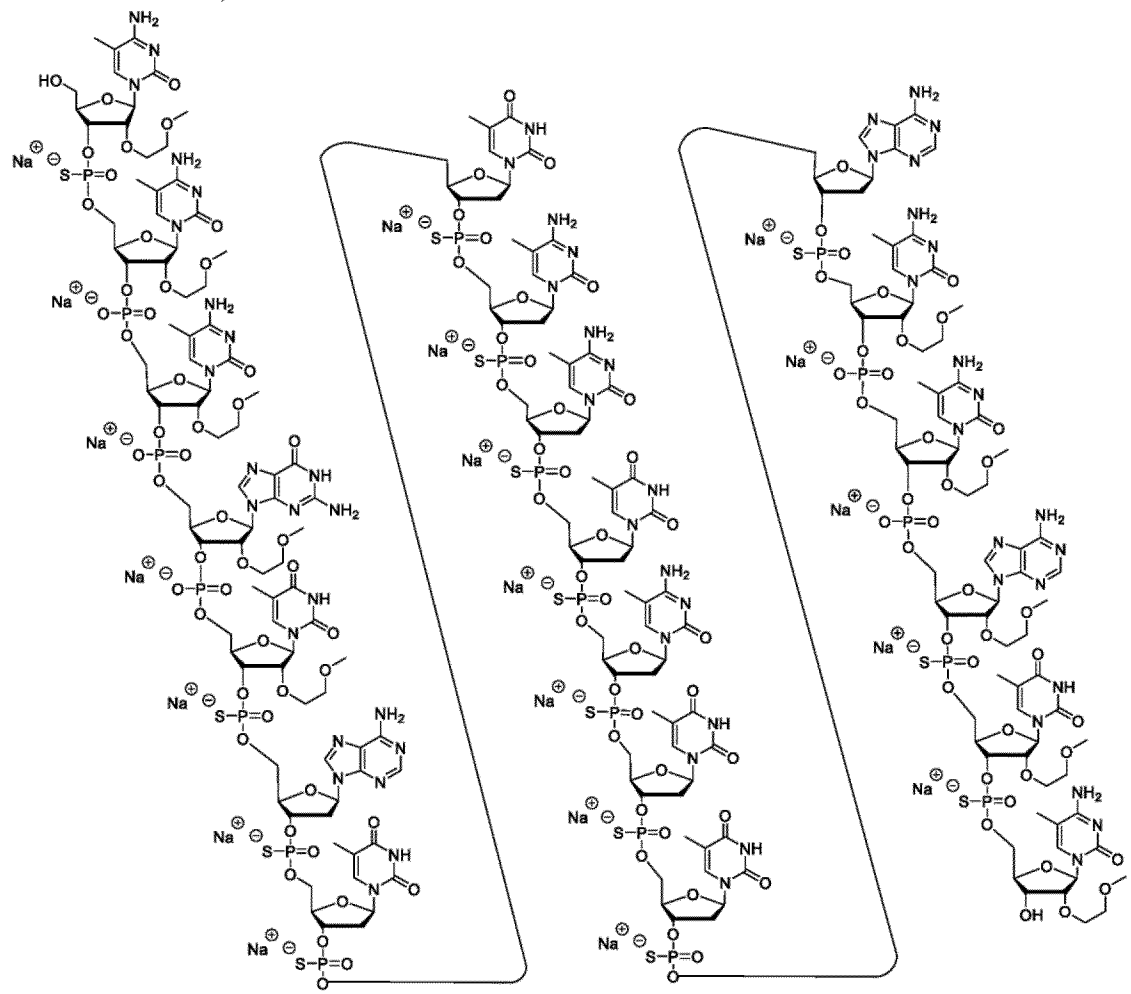

CERTIFICATE OF CORRECTION (continued)
U.S. Pat. No. 12,180,479 B2

In Columns 35-36, the structure should read:

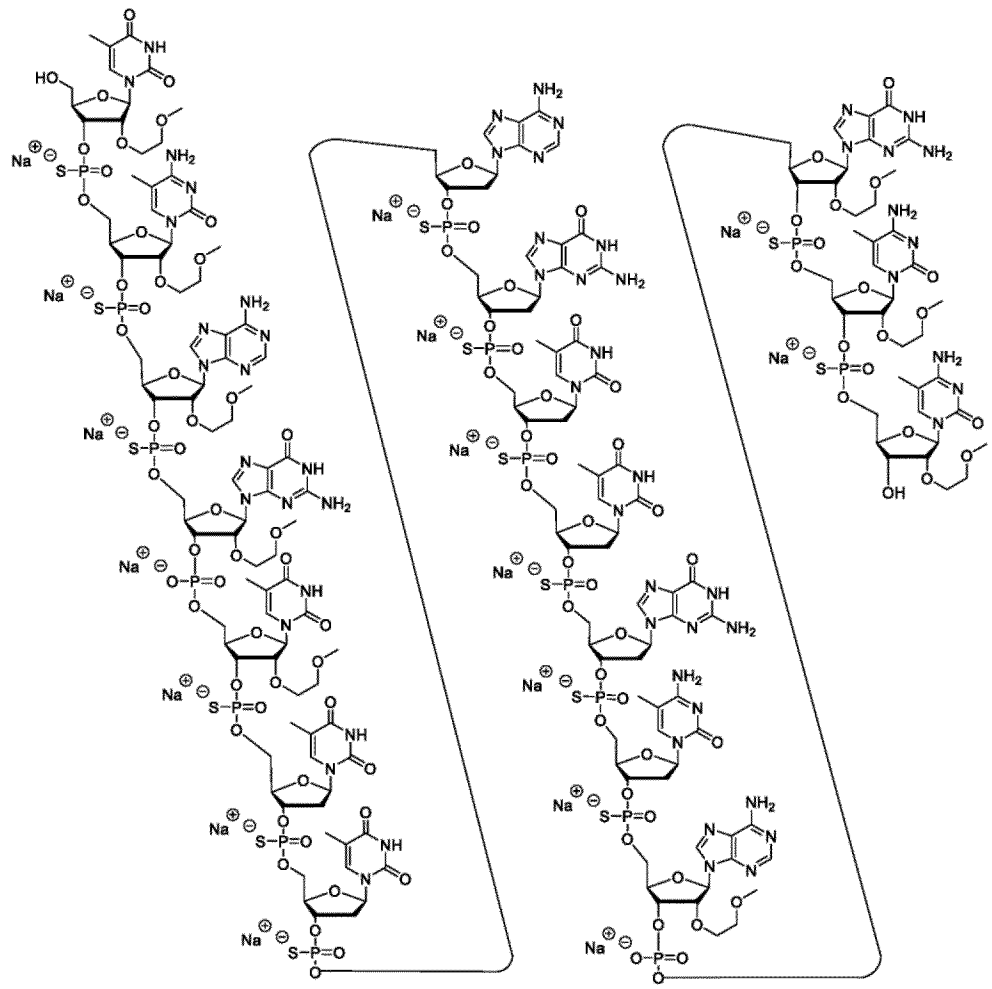

CERTIFICATE OF CORRECTION (continued)
U.S. Pat. No. 12,180,479 B2

In Columns 45-48, the structure should read:

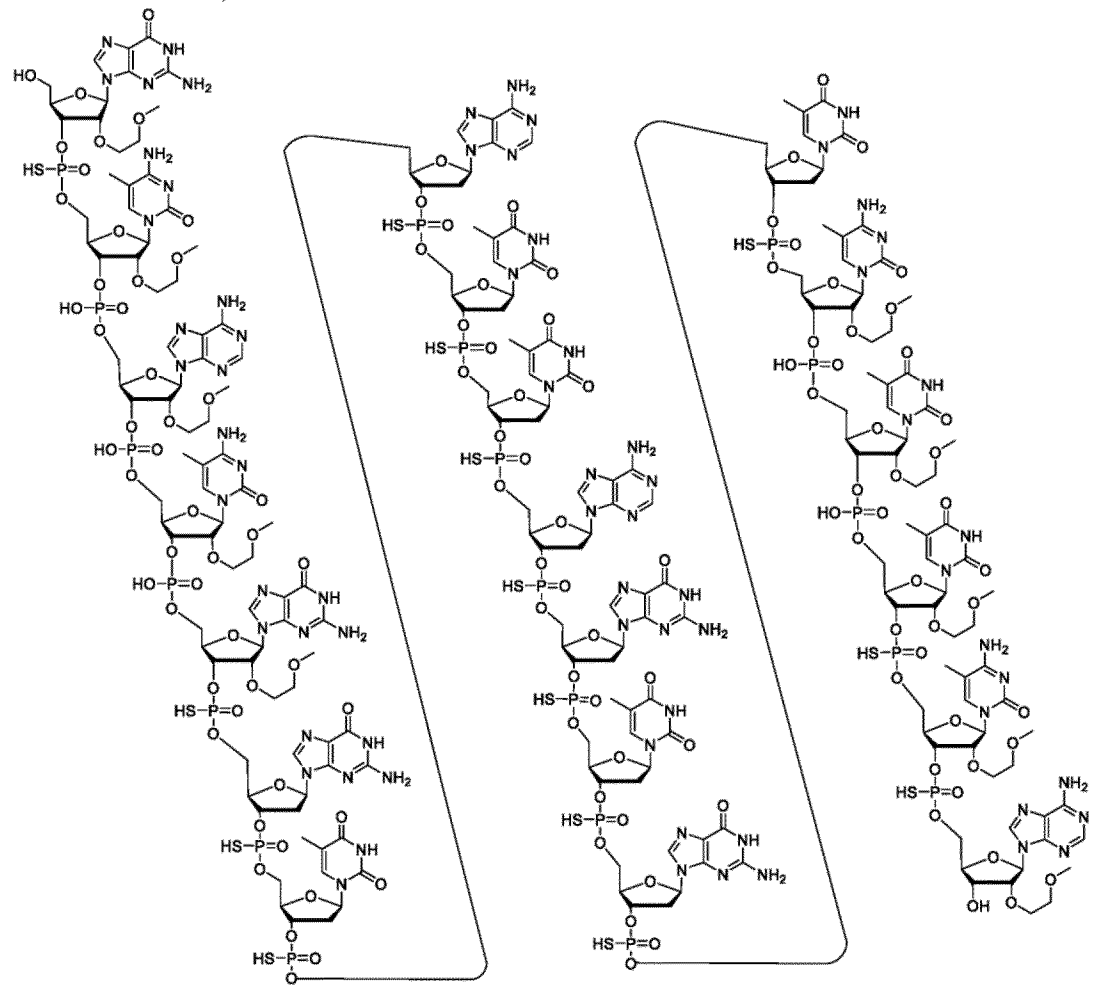

In Columns 47-50, the structure should read:
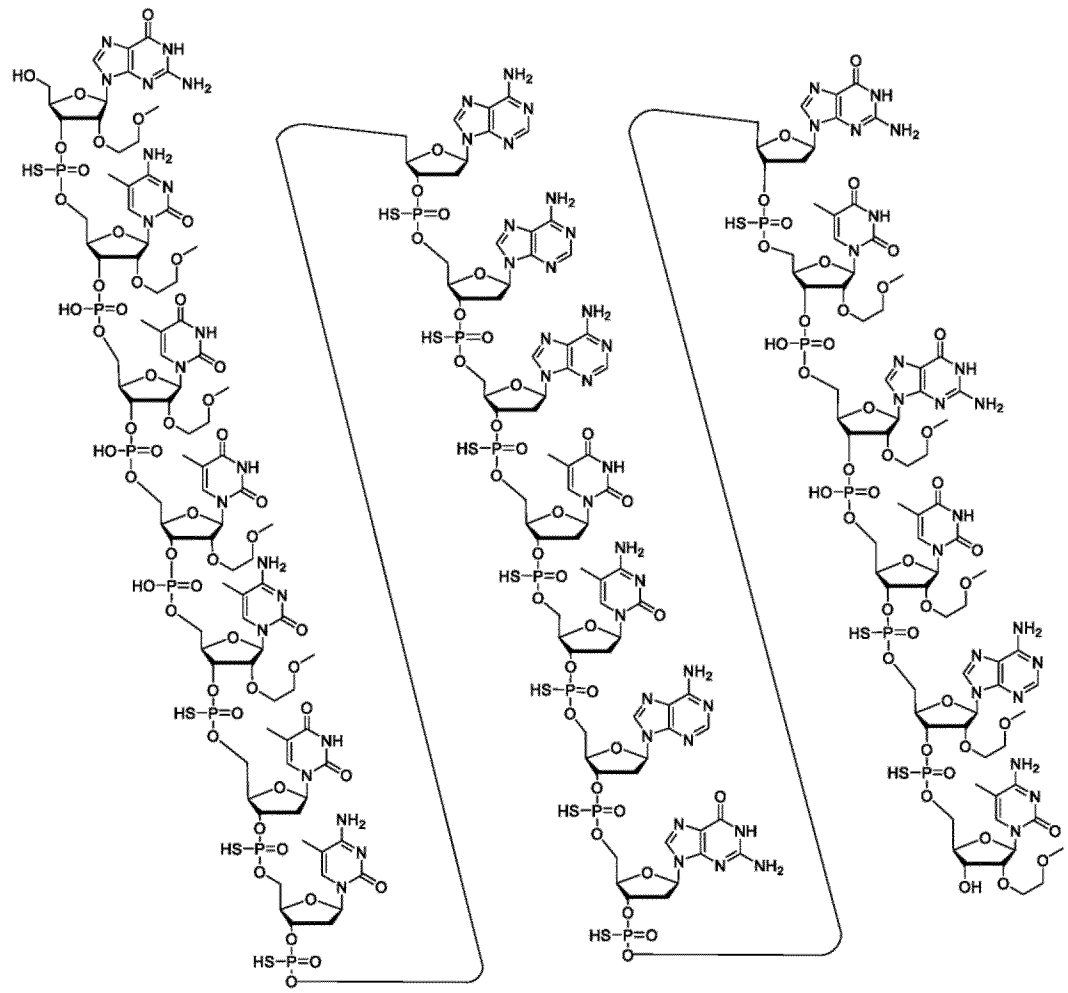

CERTIFICATE OF CORRECTION (continued)
U.S. Pat. No. 12,180,479 B2

In Columns 49-52, the structure should read:

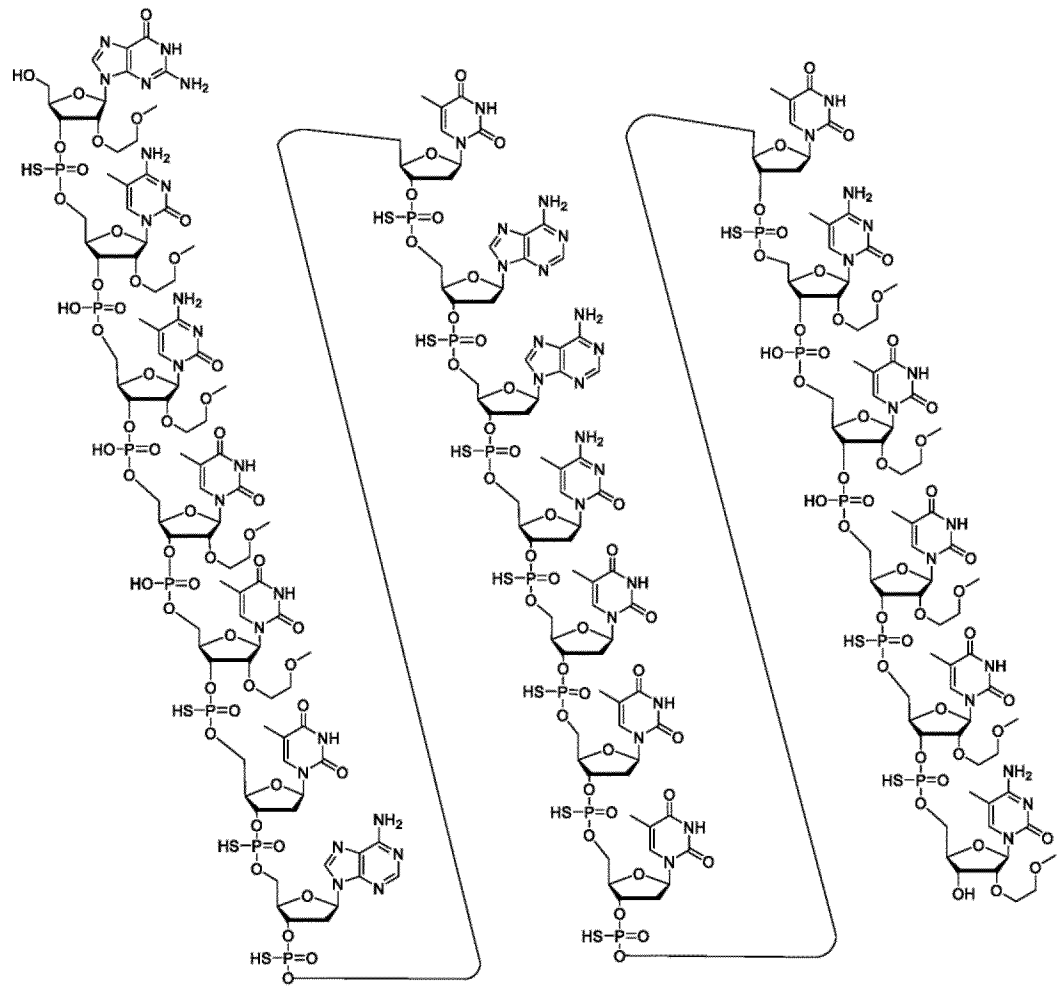

CERTIFICATE OF CORRECTION (continued)
U.S. Pat. No. 12,180,479 B2

In Columns 51-54, the structure should read:

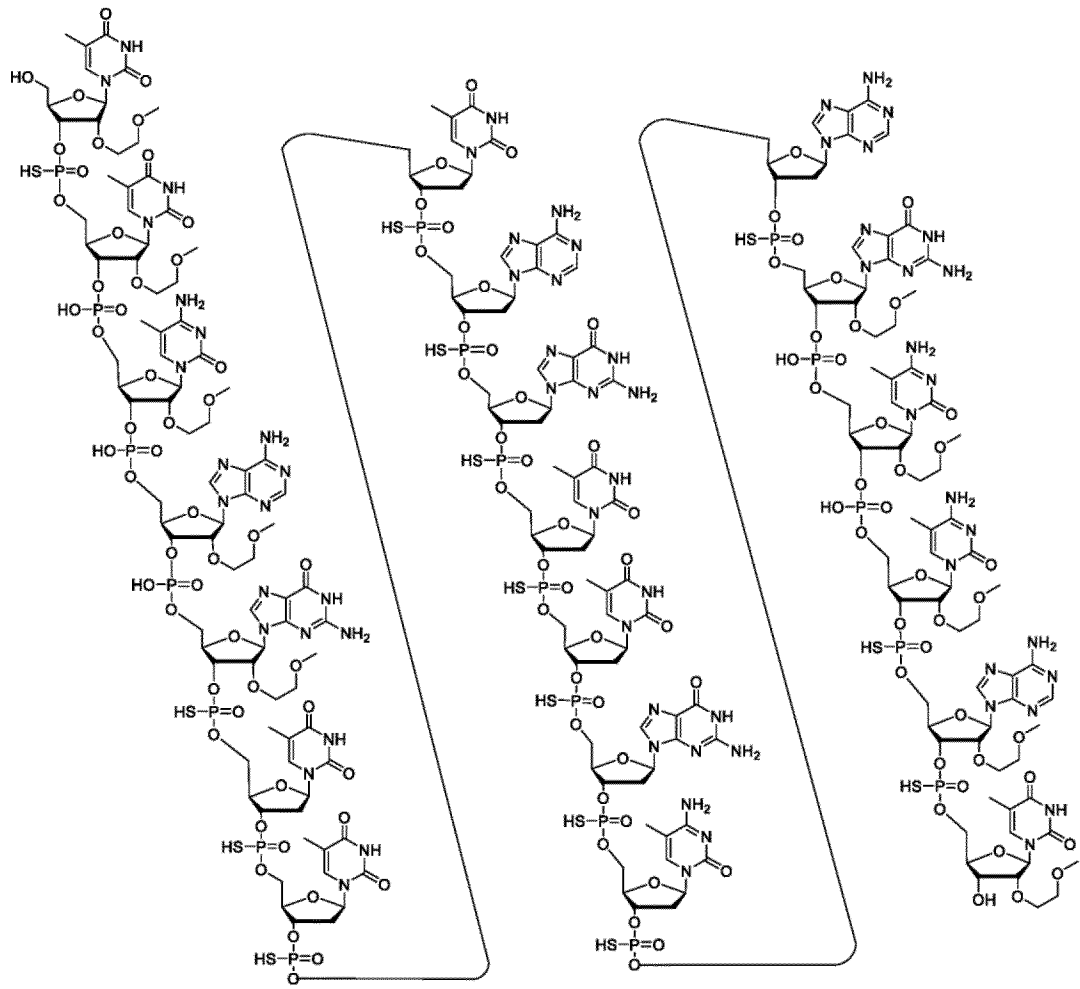

CERTIFICATE OF CORRECTION (continued)
U.S. Pat. No. 12,180,479 B2

In Columns 53-56, the structure should read:

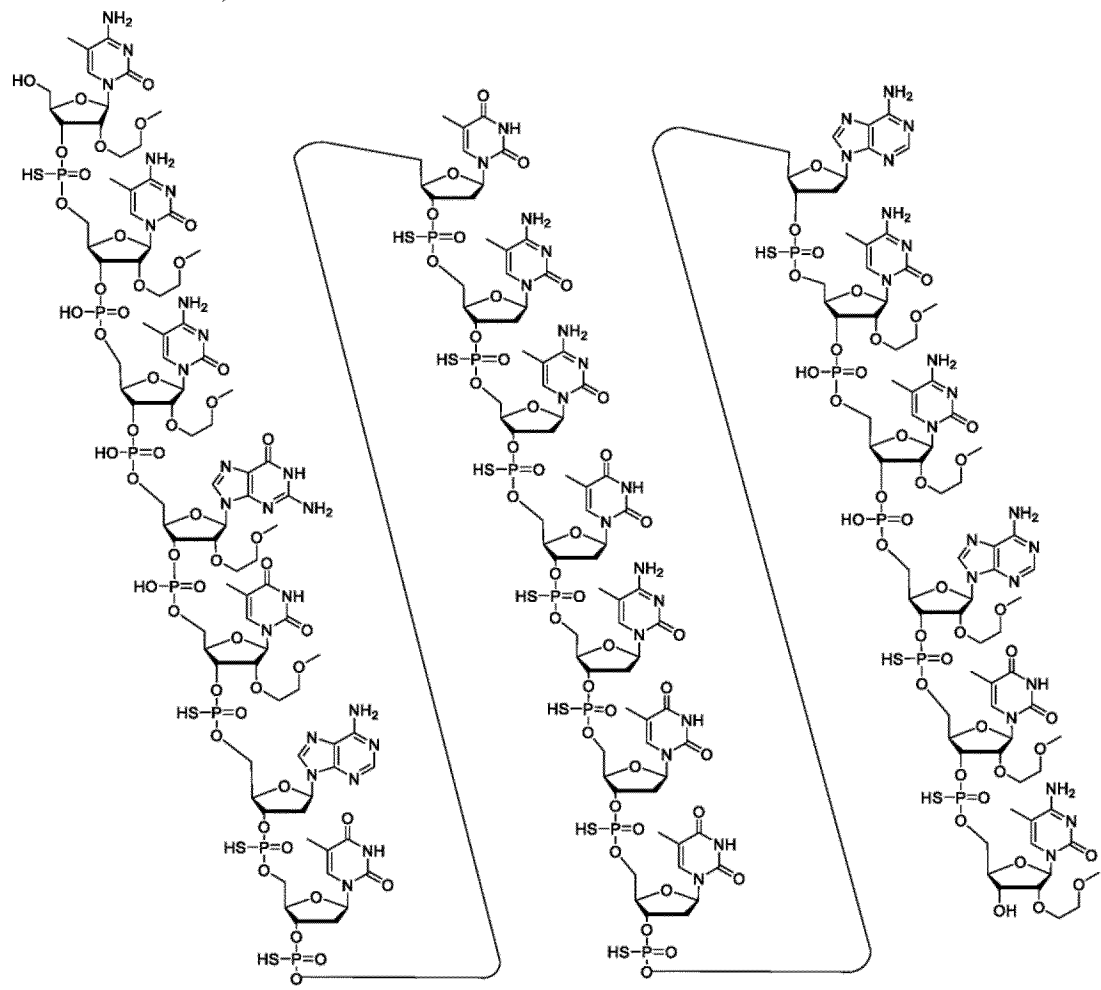

CERTIFICATE OF CORRECTION (continued)
U.S. Pat. No. 12,180,479 B2

In Columns 55-58, the structure should read:

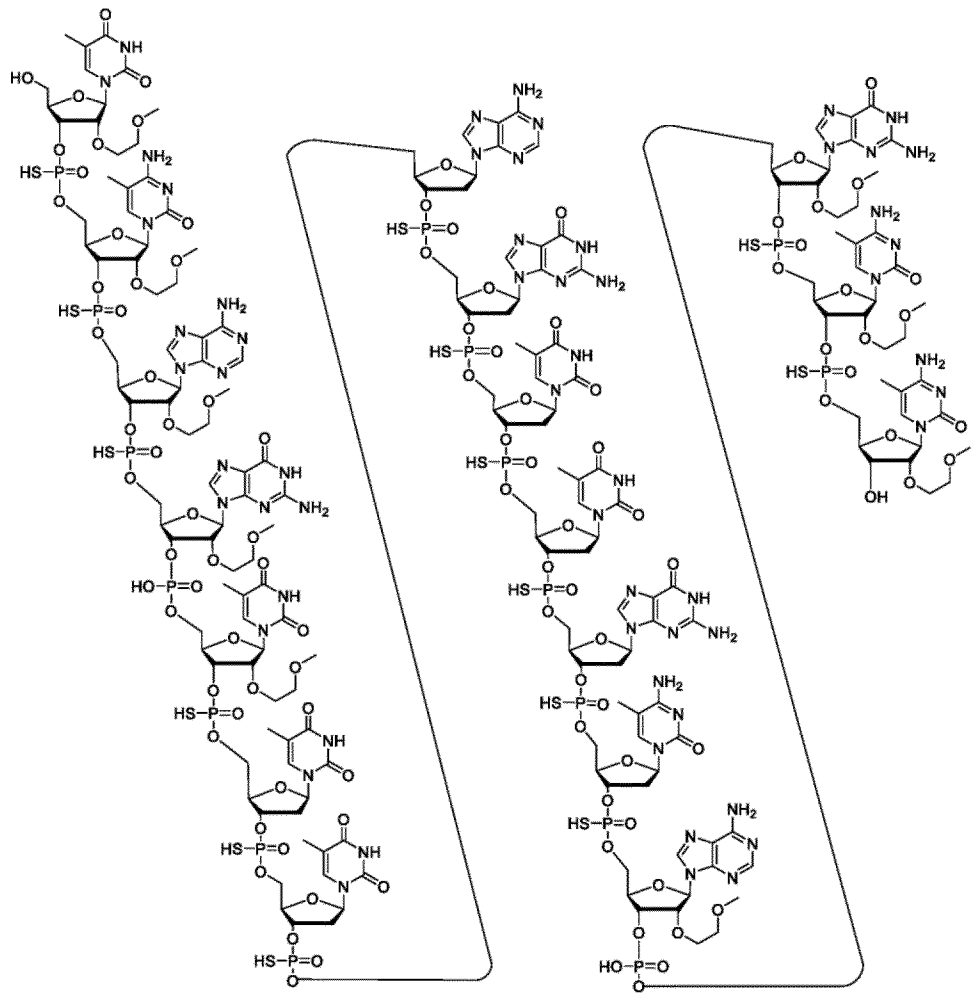

CERTIFICATE OF CORRECTION (continued)
U.S. Pat. No. 12,180,479 B2

In Columns 57-60, the structure should read:

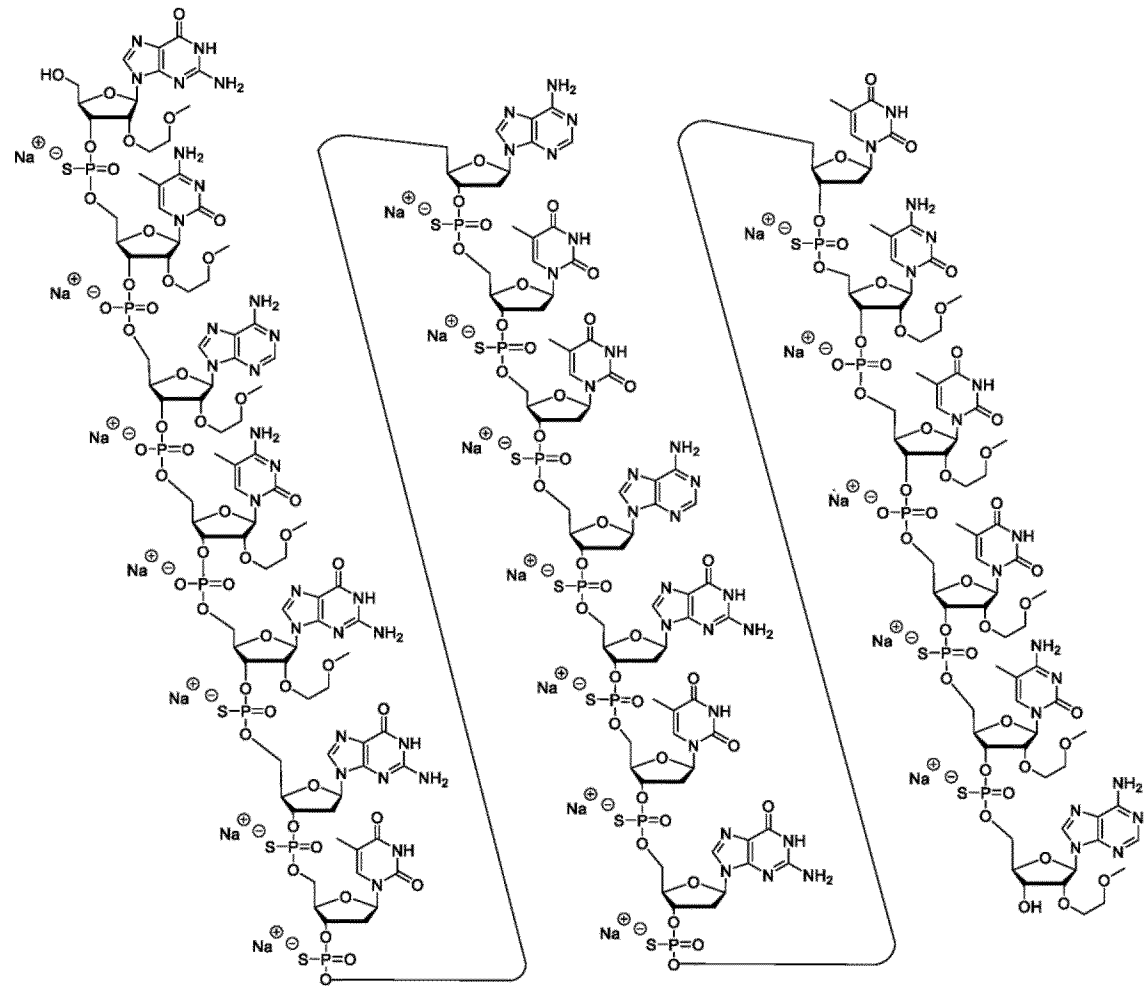

CERTIFICATE OF CORRECTION (continued)
U.S. Pat. No. 12,180,479 B2

In Columns 59-62, the structure should read:

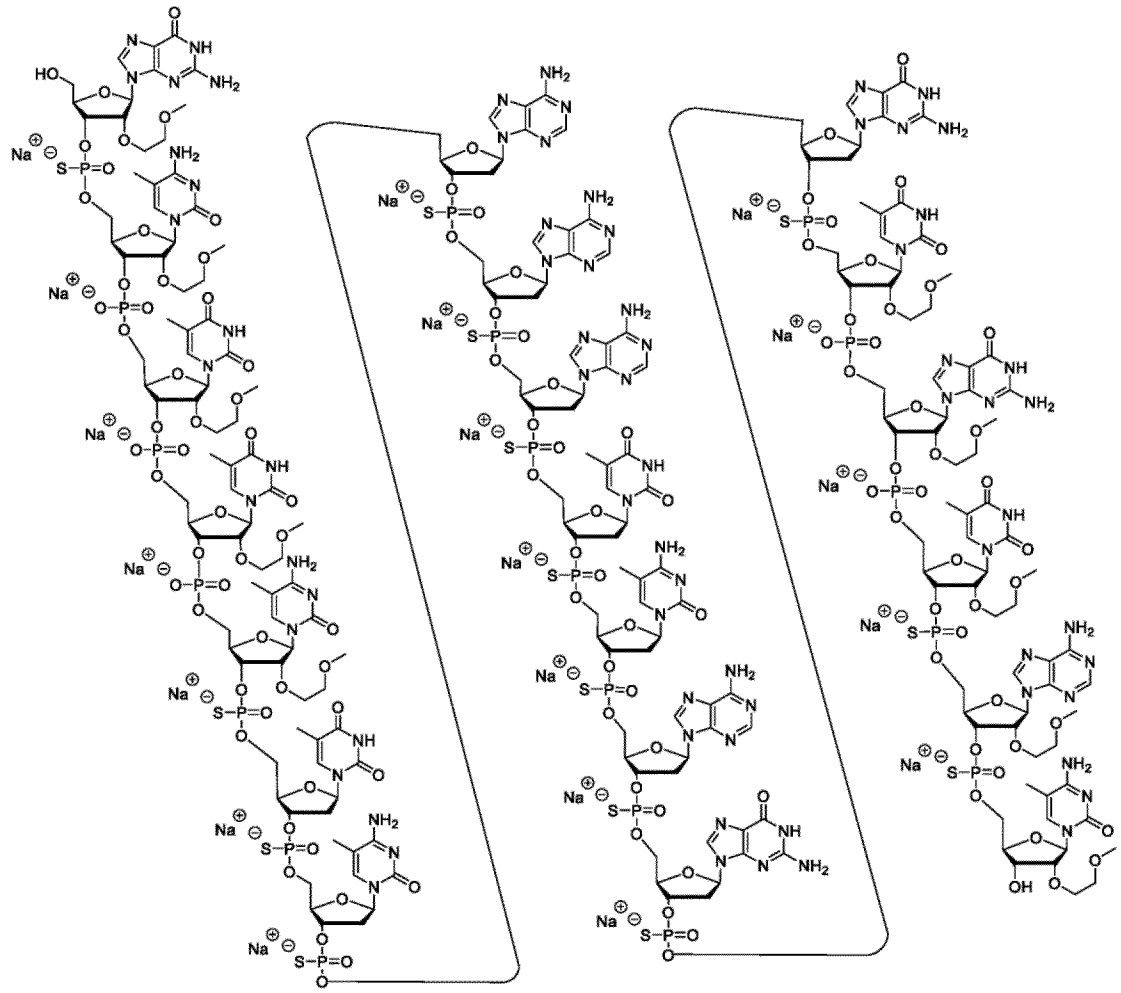

CERTIFICATE OF CORRECTION (continued)
U.S. Pat. No. 12,180,479 B2

In Columns 61-64, the structure should read:

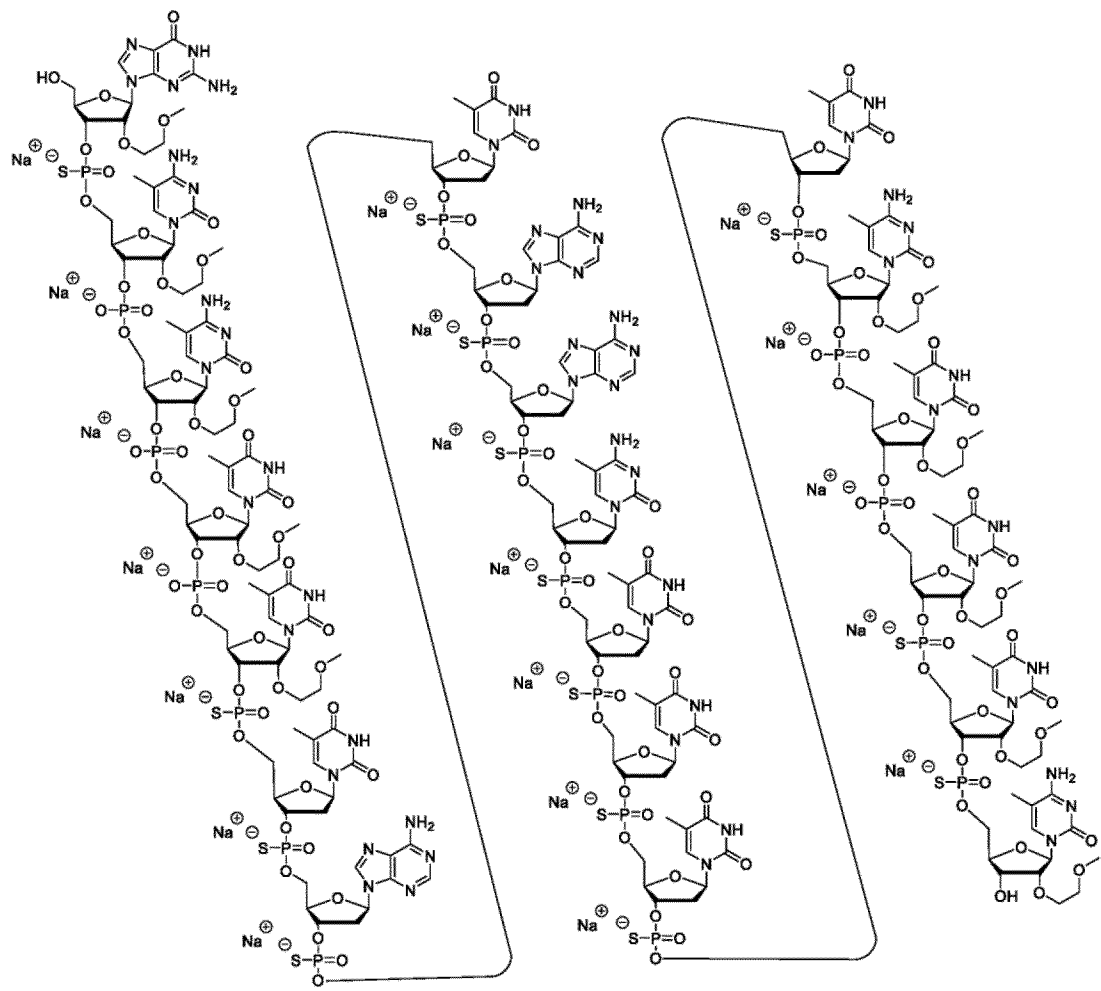

CERTIFICATE OF CORRECTION (continued)
U.S. Pat. No. 12,180,479 B2

In Columns 63-66, the structure should read:

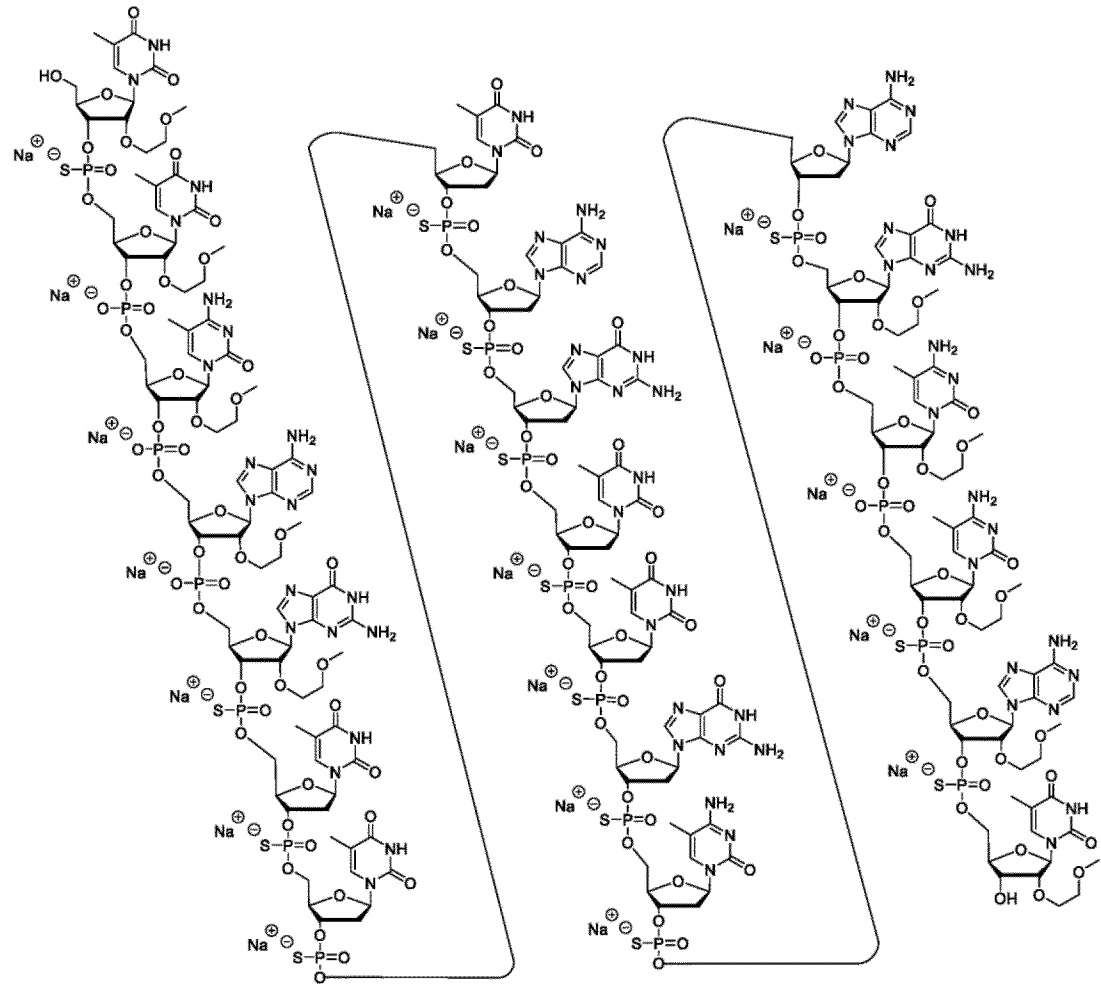

CERTIFICATE OF CORRECTION (continued)
U.S. Pat. No. 12,180,479 B2

In Columns 65-68, the structure should read:

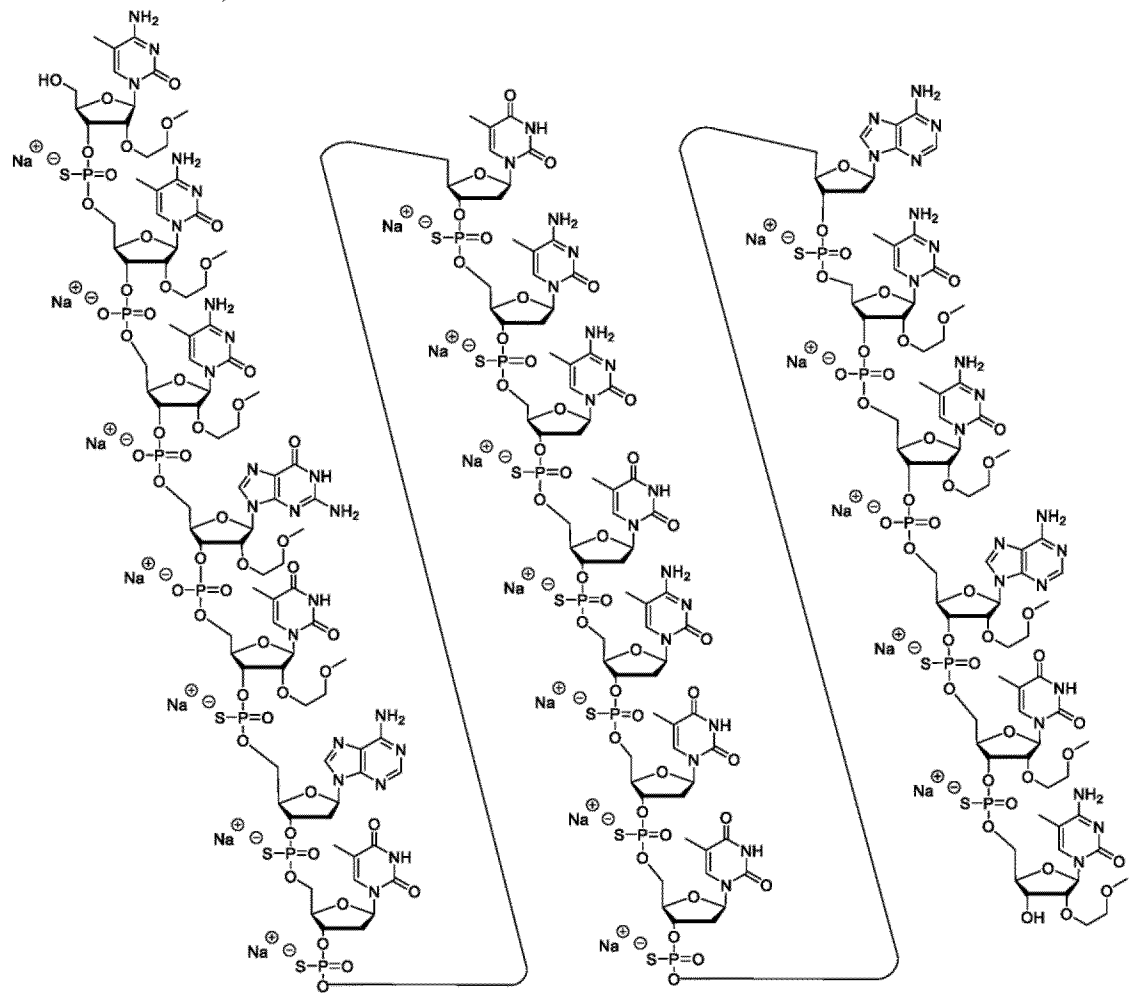

In Columns 67-70, the structure should read:
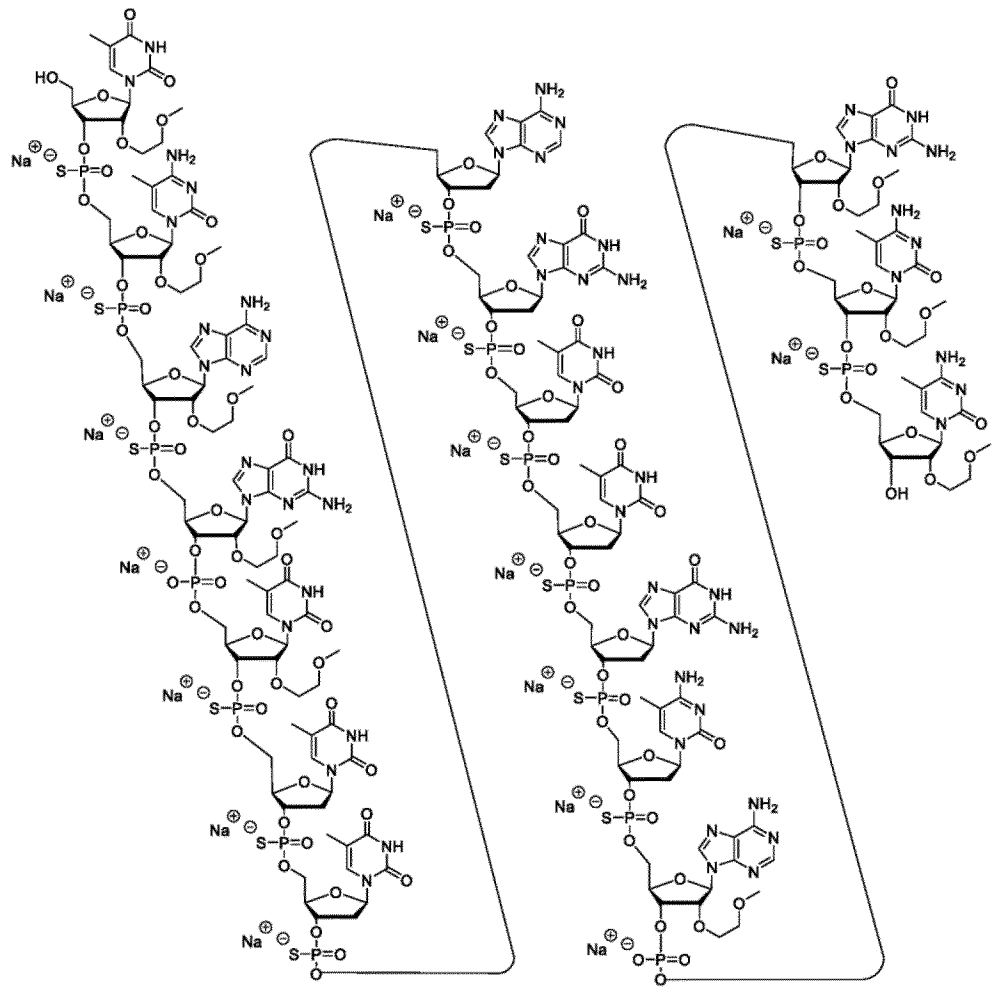

CERTIFICATE OF CORRECTION (continued)
U.S. Pat. No. 12,180,479 B2

In Columns 95-98, the structure should read:

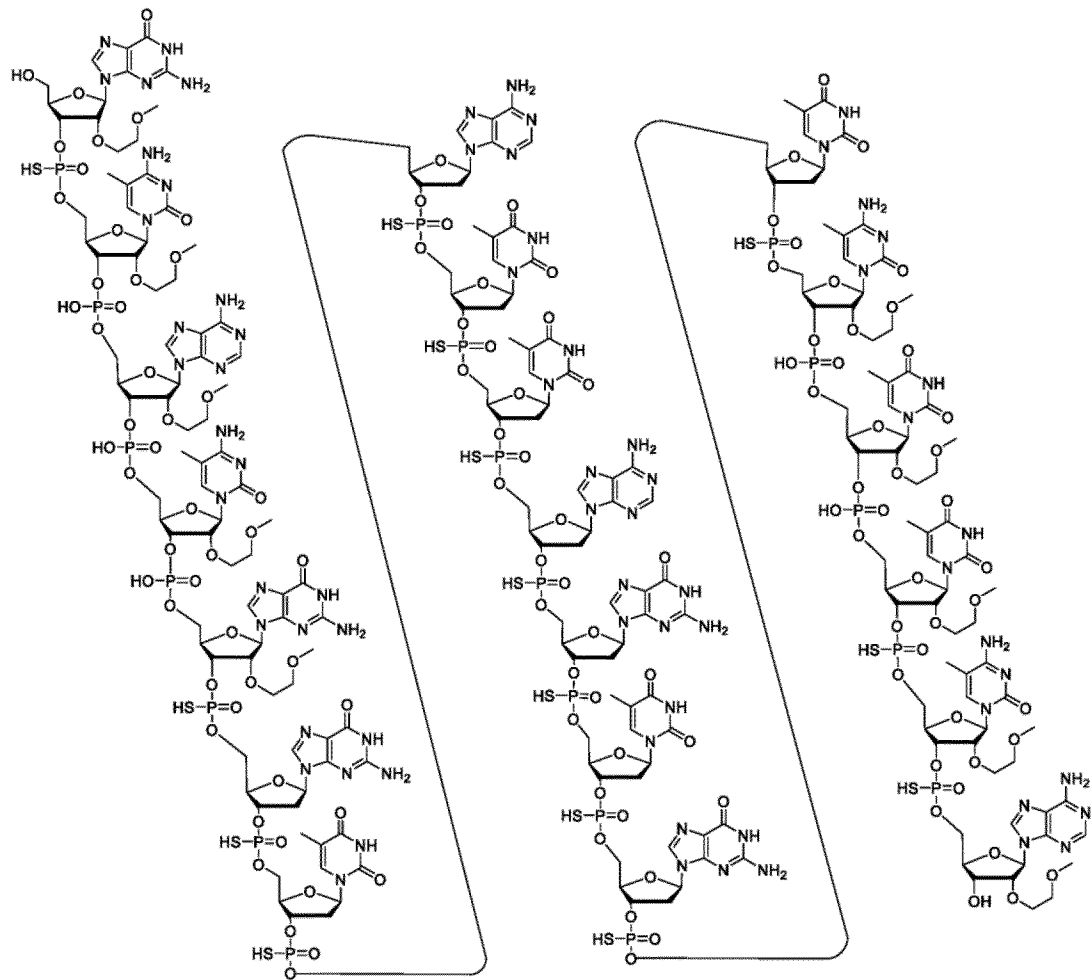

CERTIFICATE OF CORRECTION (continued)
U.S. Pat. No. 12,180,479 B2

In Columns 97-100, the structure should read:

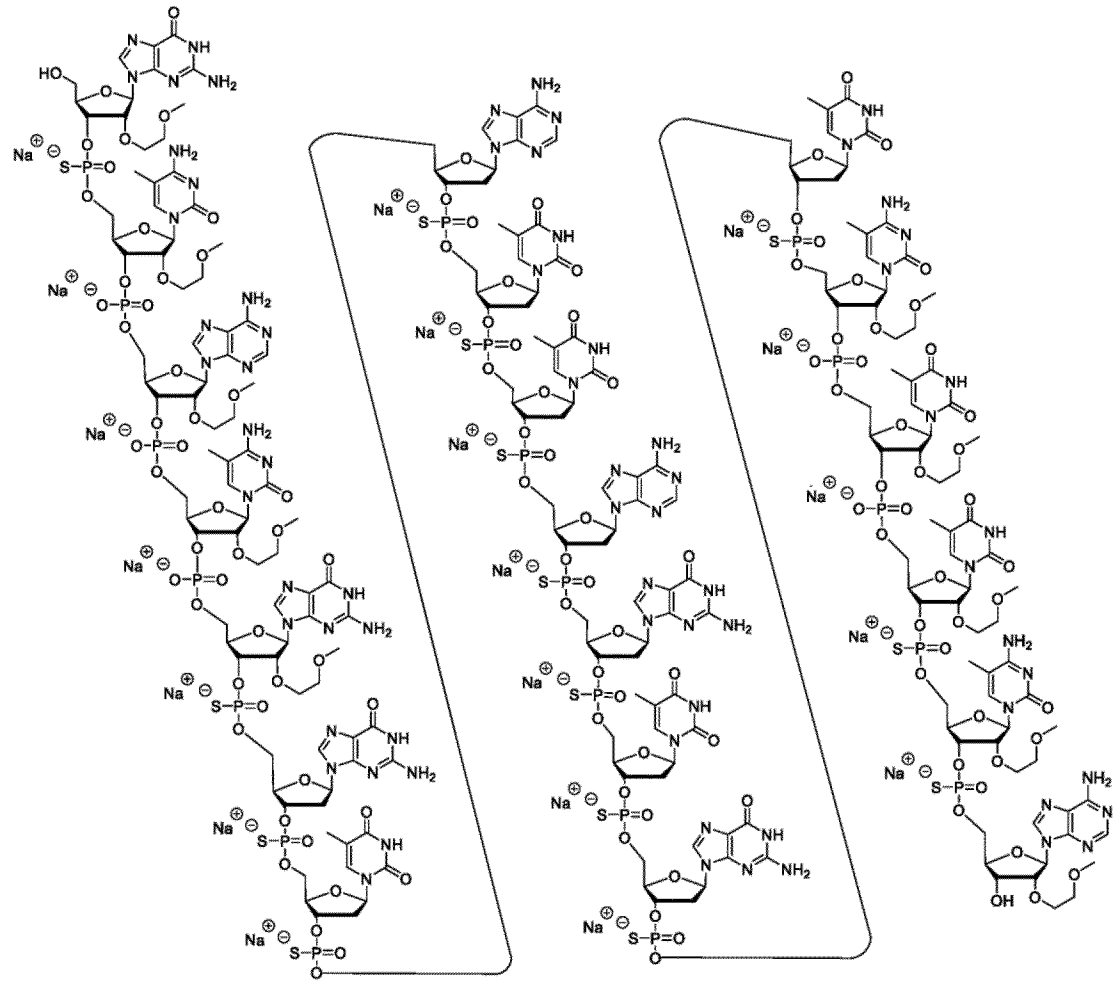

CERTIFICATE OF CORRECTION (continued)
U.S. Pat. No. 12,180,479 B2

In Columns 101-102, the structure should read:

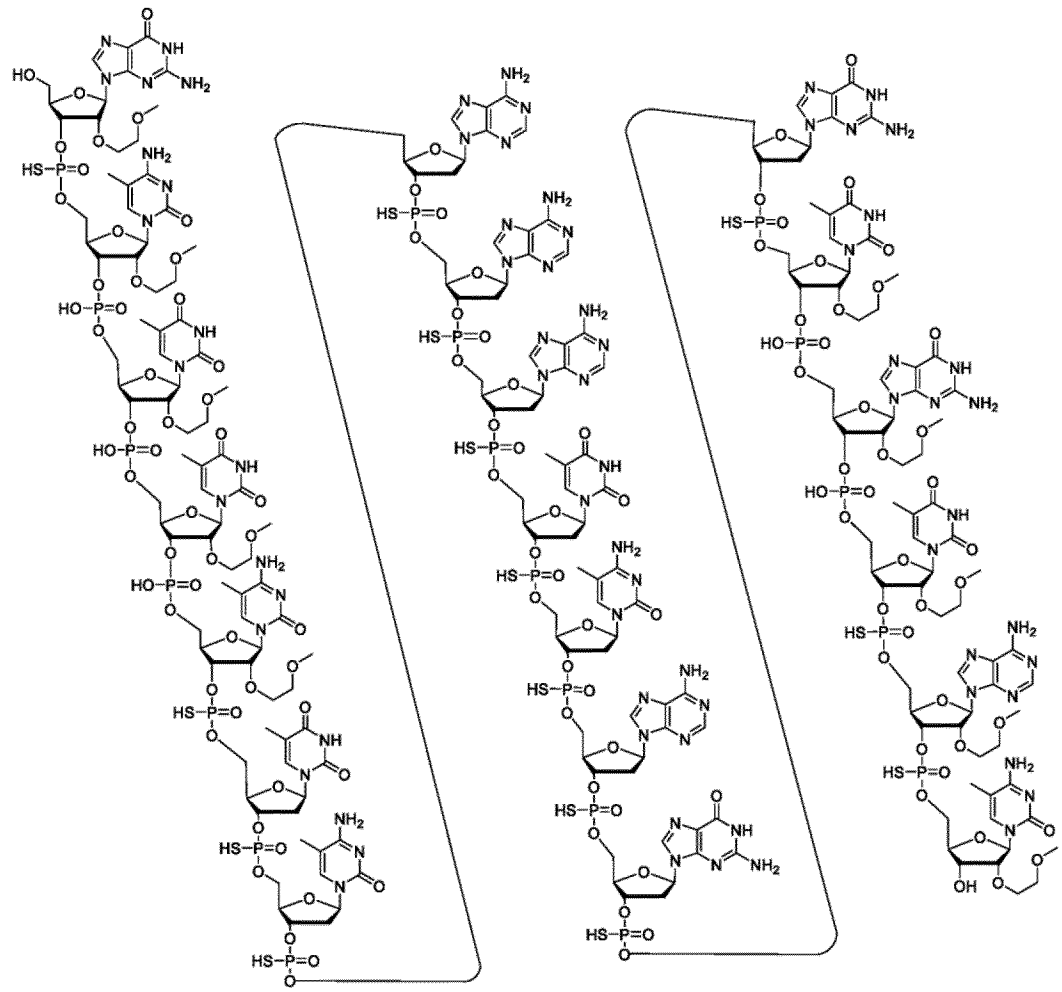

CERTIFICATE OF CORRECTION (continued)
U.S. Pat. No. 12,180,479 B2

In Columns 103-104, the structure should read:

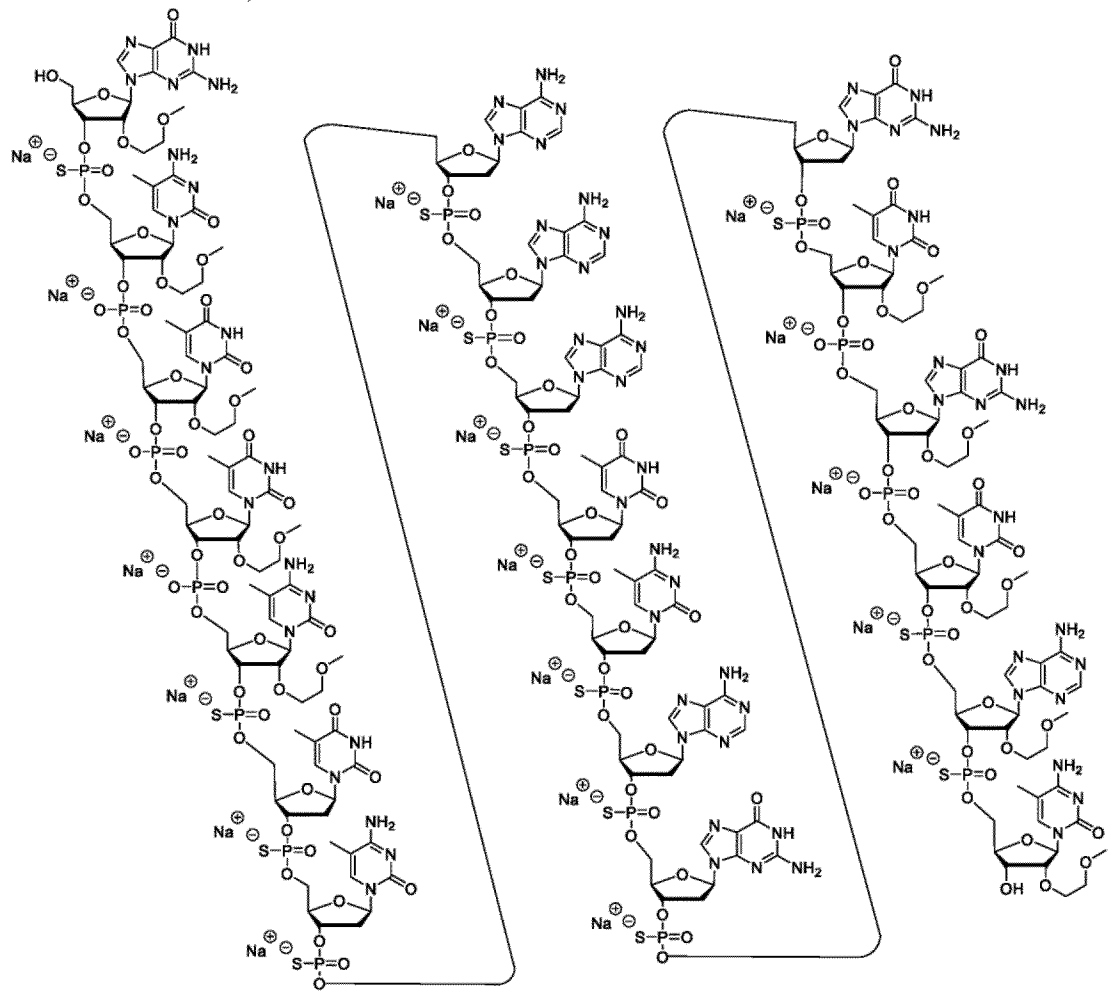

In Columns 105-106, the structure should read:
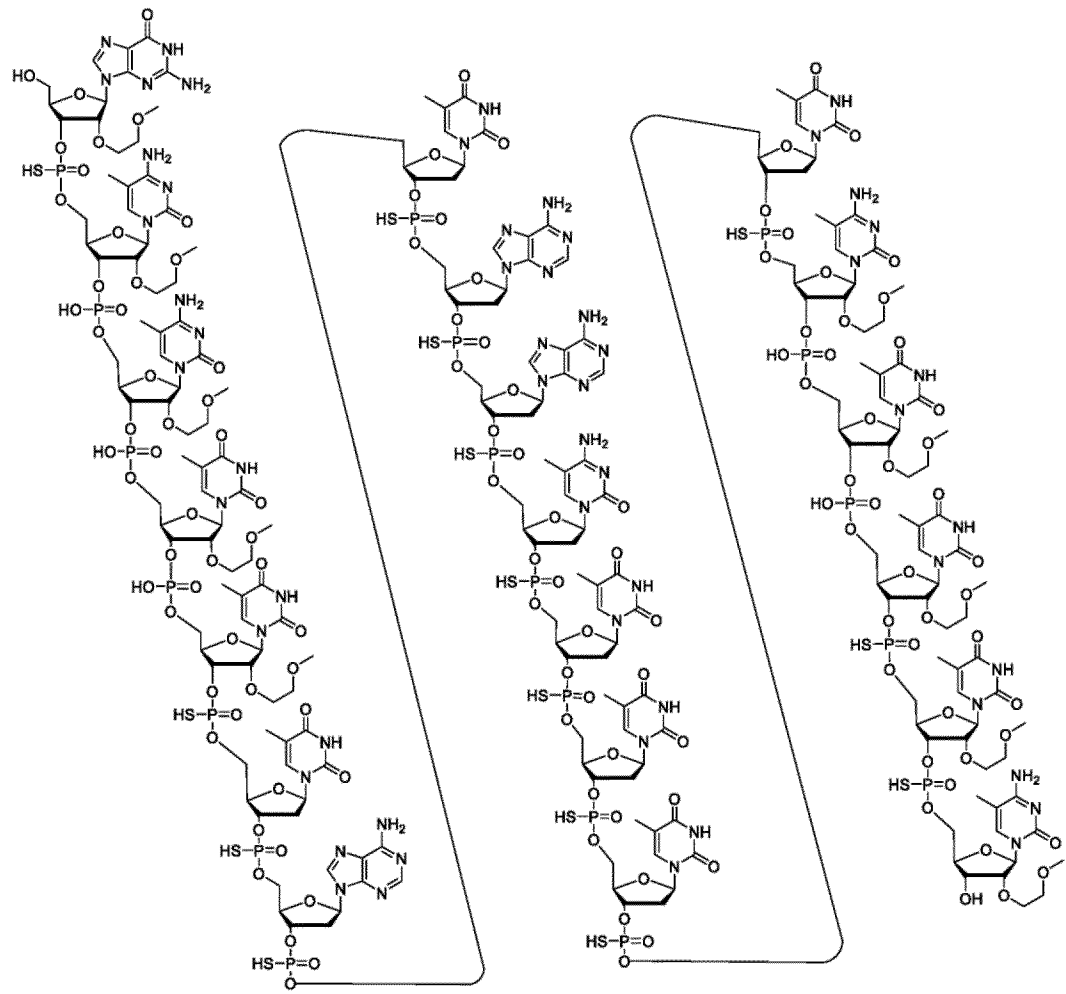

CERTIFICATE OF CORRECTION (continued)
U.S. Pat. No. 12,180,479 B2

In Columns 107-108, the structure should read:

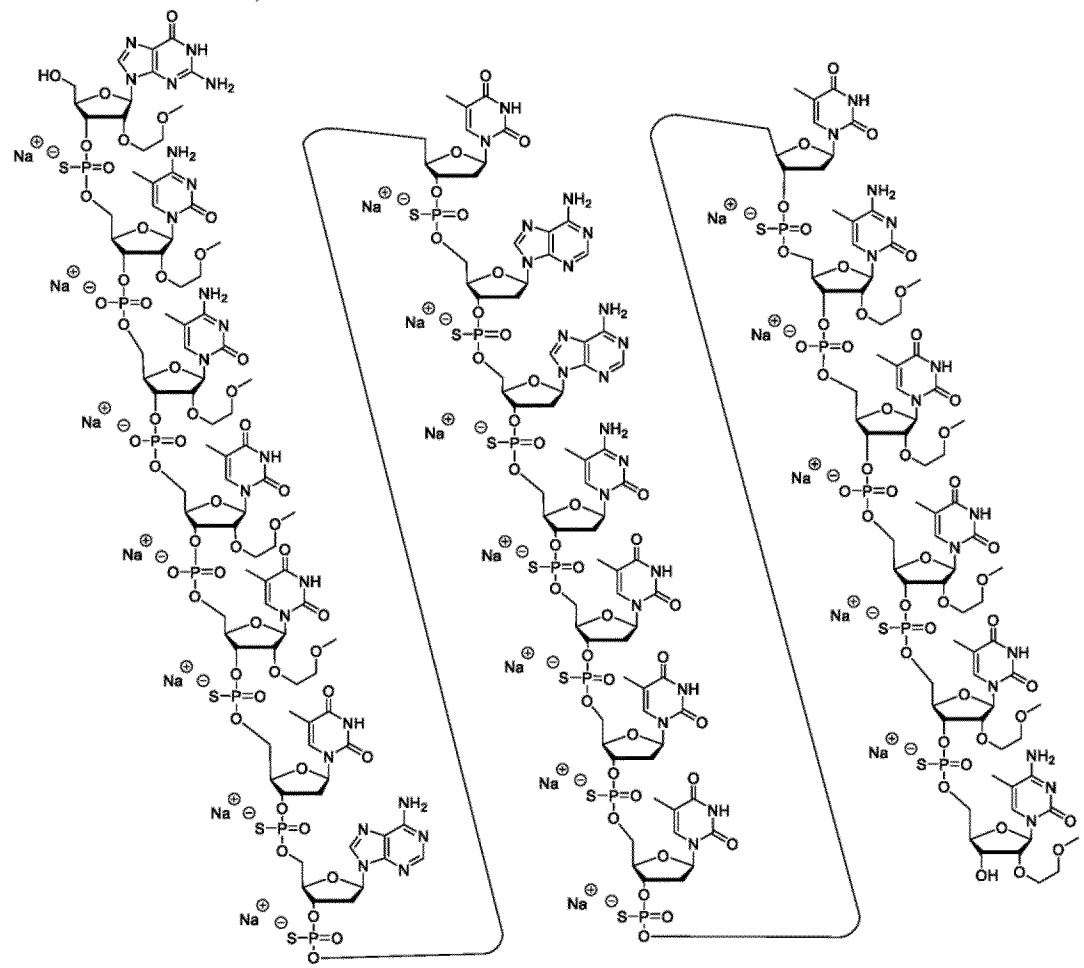

CERTIFICATE OF CORRECTION (continued)
U.S. Pat. No. 12,180,479 B2

In Columns 109-110, the structure should read:

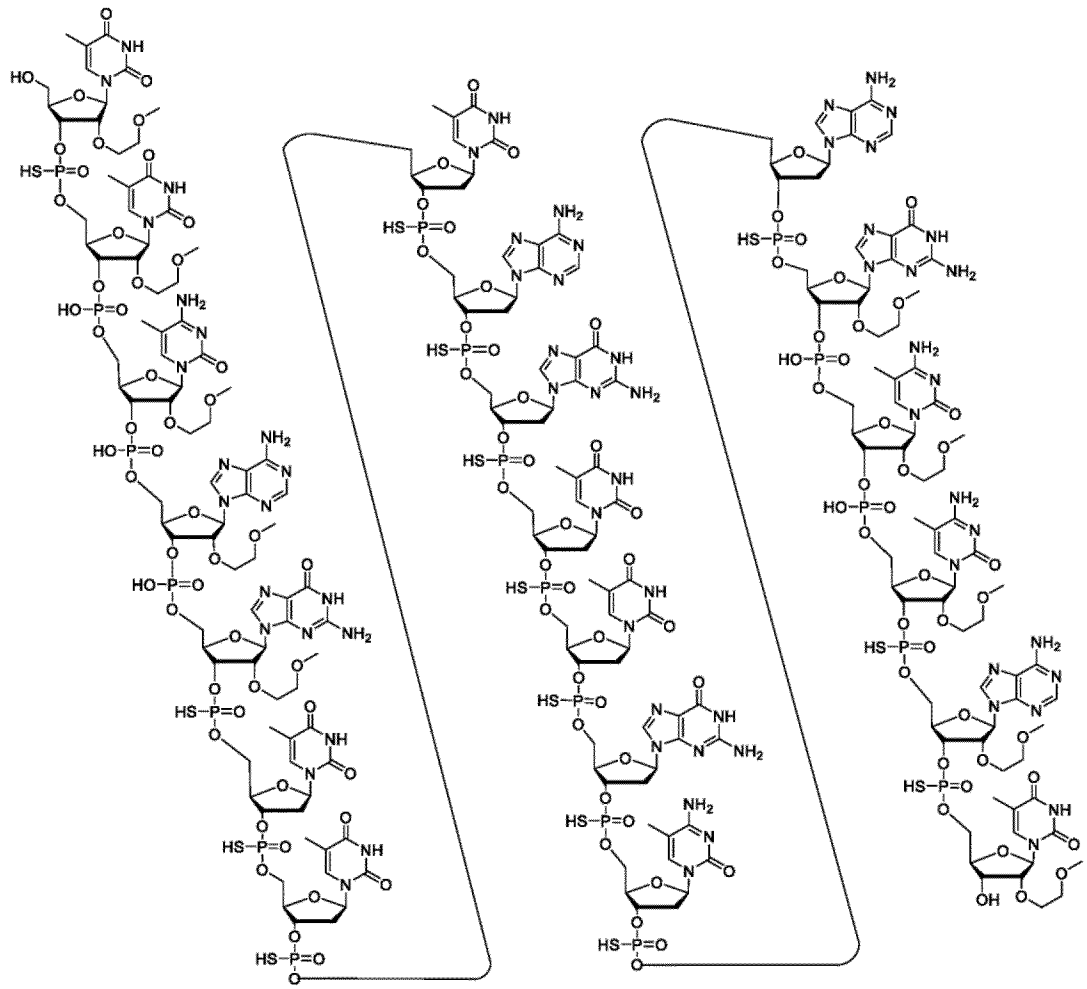

In Columns 111-112, the structure should read:
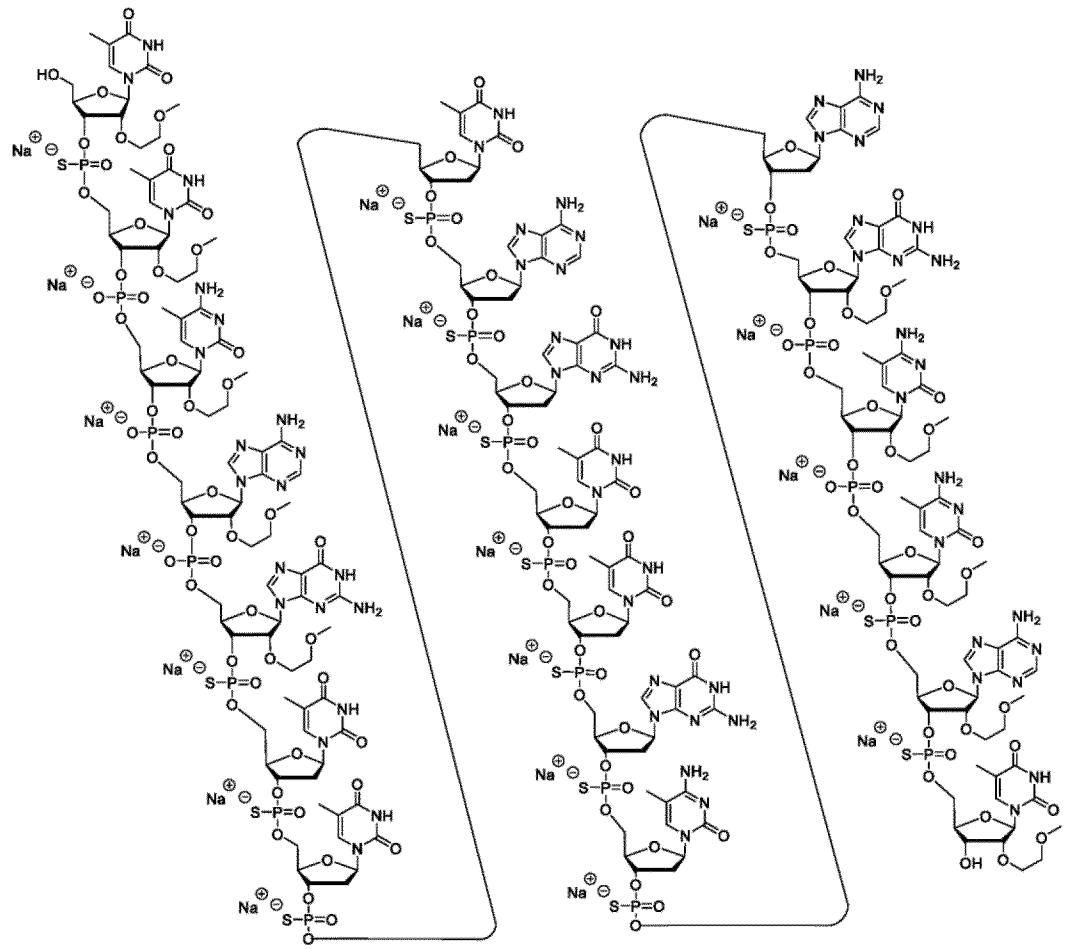

CERTIFICATE OF CORRECTION (continued)
U.S. Pat. No. 12,180,479 B2

In Columns 113-114, the structure should read:

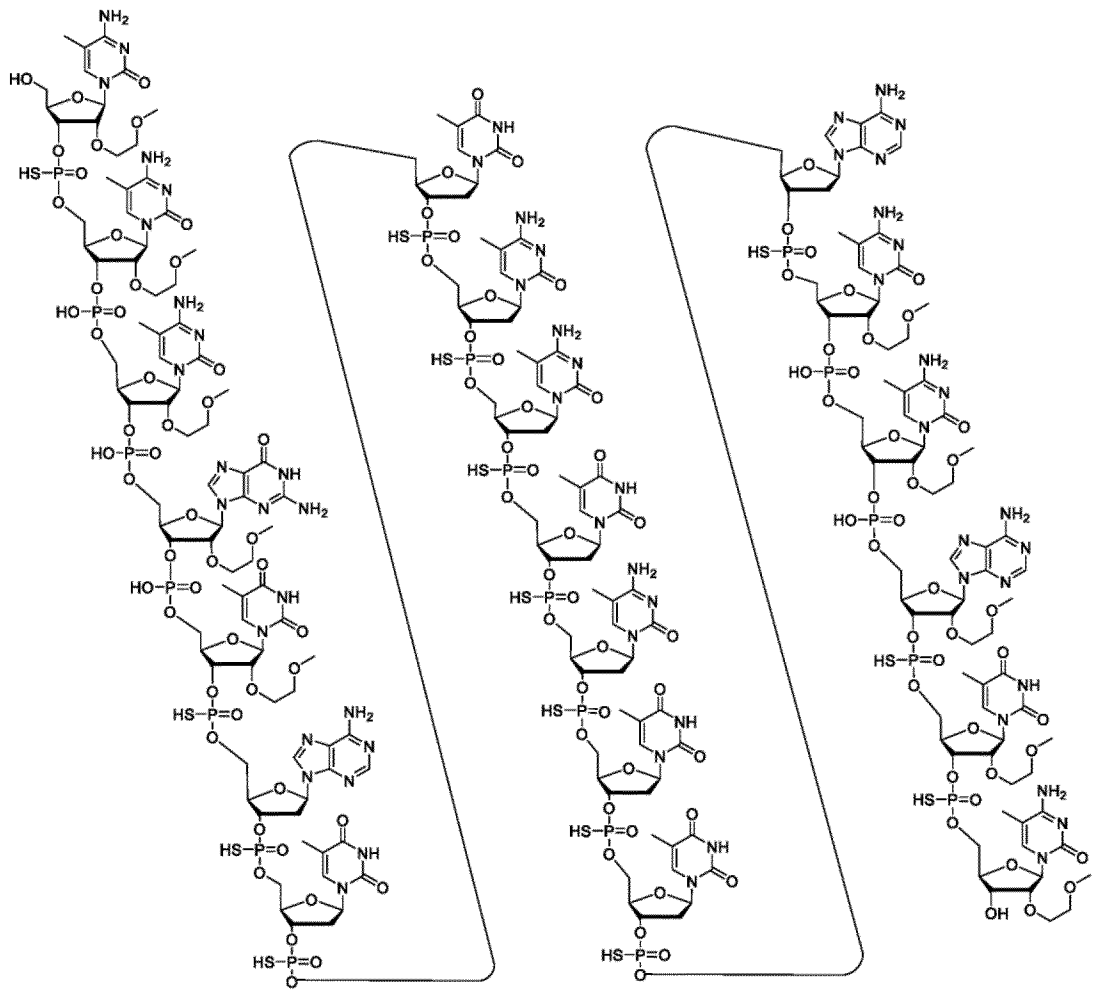

In Columns 115-116, the structure should read:
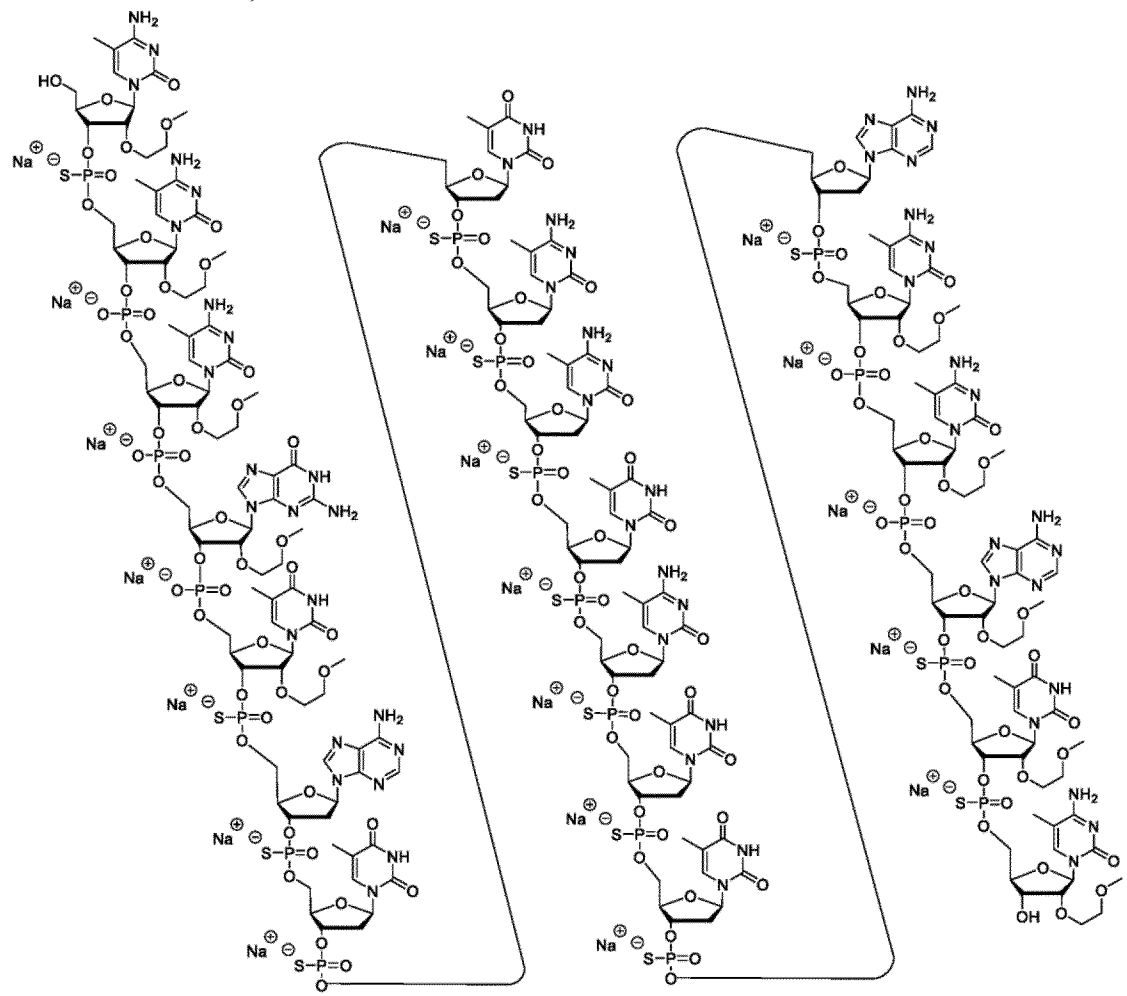

CERTIFICATE OF CORRECTION (continued)
U.S. Pat. No. 12,180,479 B2

In Columns 117-118, the structure should read:

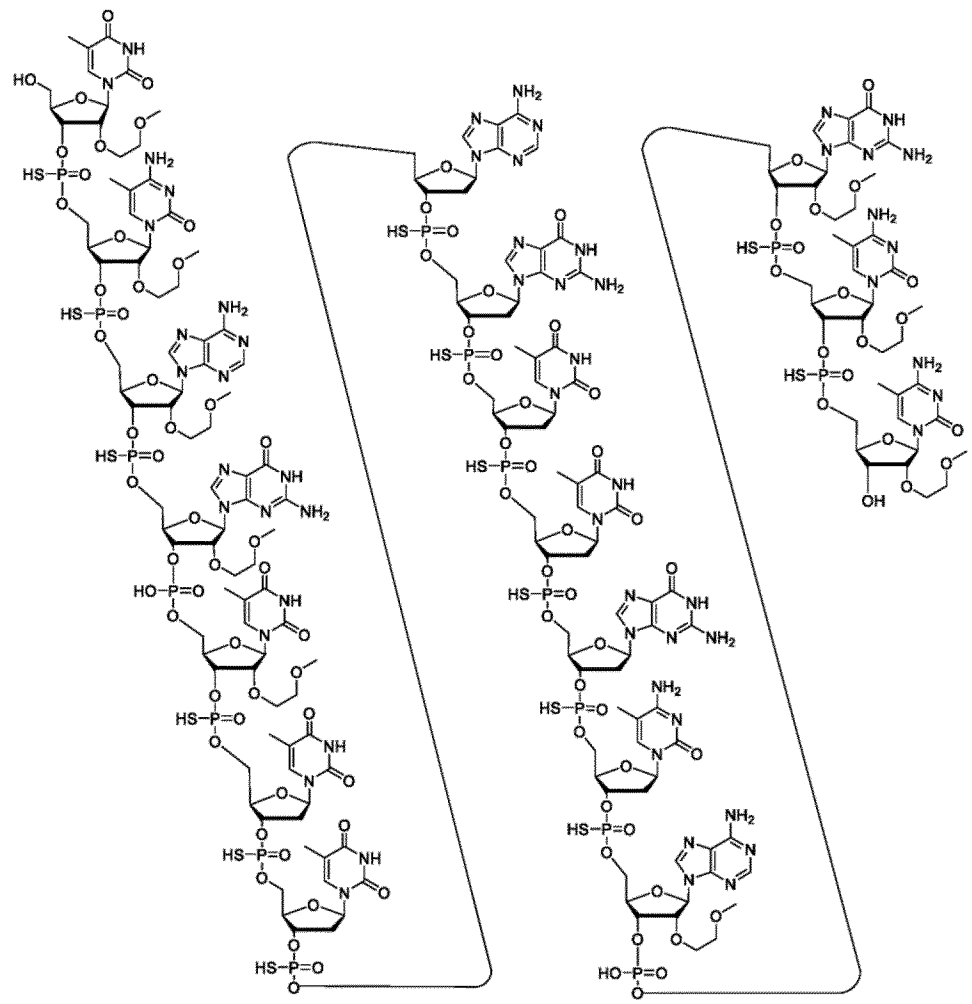

CERTIFICATE OF CORRECTION (continued)
U.S. Pat. No. 12,180,479 B2

In Columns 119-120, the structure should read:

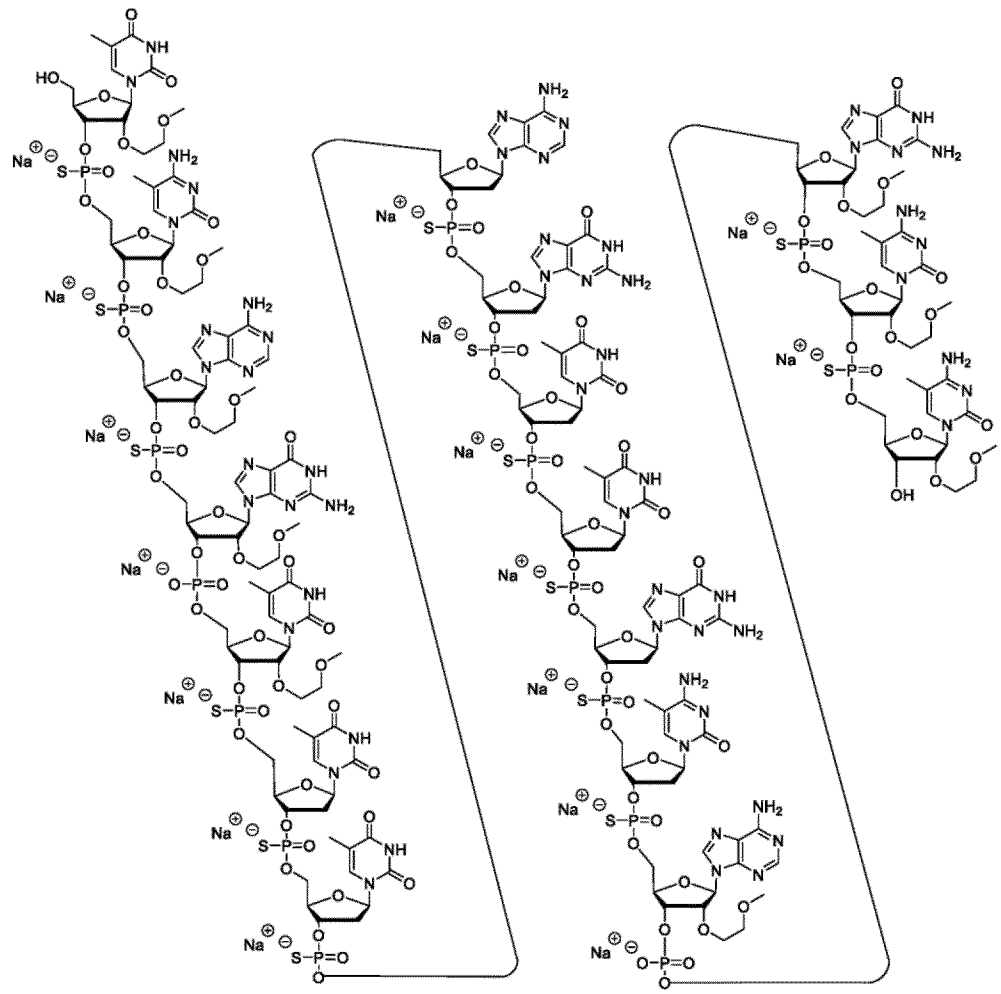

CERTIFICATE OF CORRECTION (continued)
U.S. Pat. No. 12,180,479 B2

In the Claims

In Claim 1, Columns 383-386, the structure should read:

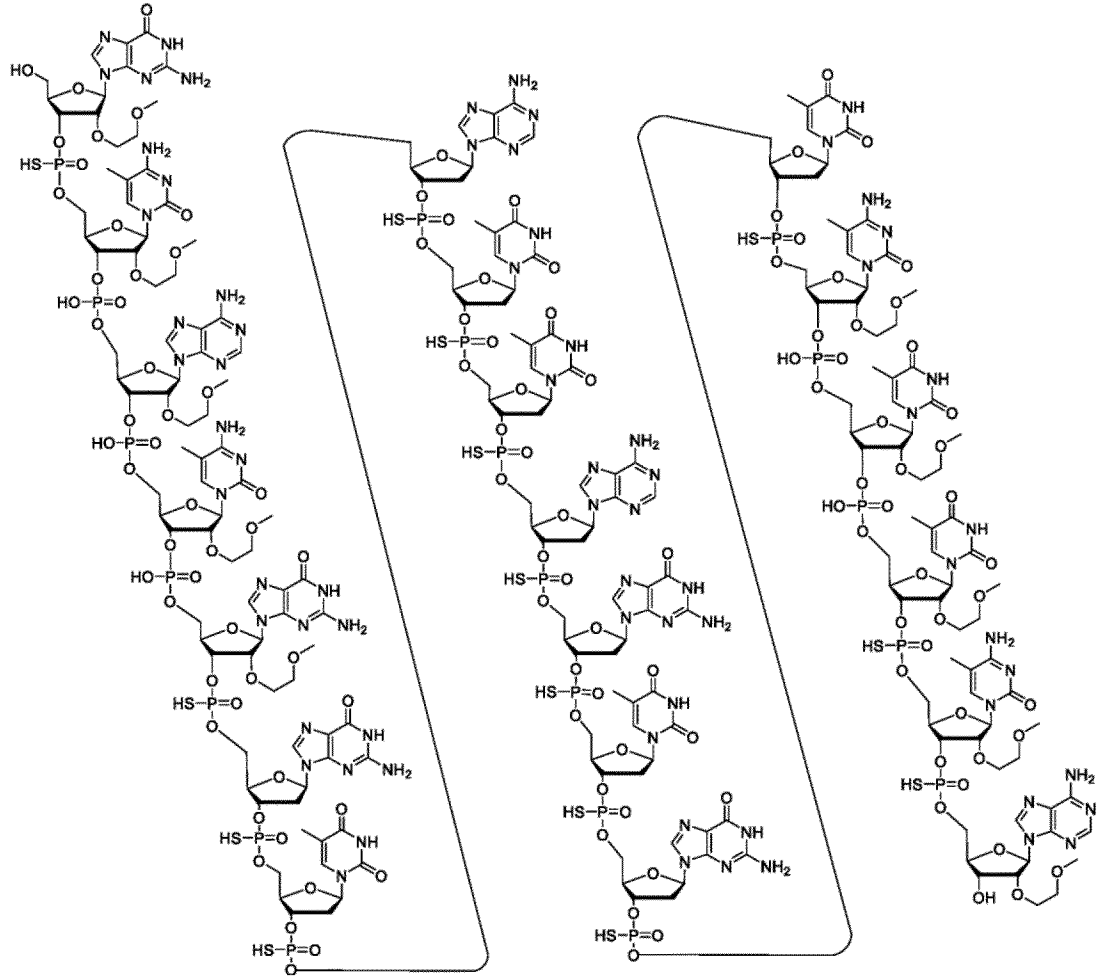

CERTIFICATE OF CORRECTION (continued)

In Claim 2, Columns 387-388, the structure should read: